US012698347B2

(12) United States Patent
Nielsen et al.

(10) Patent No.: US 12,698,347 B2
(45) Date of Patent: Aug. 4, 2026

(54) BI-SPECIFIC FUSION PROTEINS

(71) Applicant: Silver Creek Pharmaceuticals, Inc., San Francisco, CA (US)

(72) Inventors: Ulrik Nielsen, Quincy, MA (US); Thomas Wickham, Groton, MA (US); Birgit Schoeberl, Cambridge, MA (US); Brian Harms, Roslindale, MA (US); Bryan Linggi, Richland, WA (US); Matthew Onsum, El Cerrito, CA (US); Byron DeLaBarre, Cambridge, MA (US); Shaun M. Lippow, San Francisco, CA (US)

(73) Assignee: Silver Creek Pharmaceuticals, Inc., San Francisco, CA (US)

( * ) Notice: Subject to any disclaimer, the term of this patent is extended or adjusted under 35 U.S.C. 154(b) by 26 days.

(21) Appl. No.: 18/483,308

(22) Filed: Oct. 9, 2023

(65) Prior Publication Data

US 2024/0101713 A1     Mar. 28, 2024

Related U.S. Application Data

(60) Continuation of application No. 17/212,270, filed on Mar. 25, 2021, now Pat. No. 11,814,443, which is a division of application No. 16/524,451, filed on Jul. 29, 2019, now Pat. No. 10,988,547, which is a continuation of application No. 15/618,478, filed on Jun. 9, 2017, now Pat. No. 10,407,512, which is a continuation of application No. 14/967,980, filed on Dec. 14, 2015, now Pat. No. 9,718,892, which is a division of application No. 13/068,808, filed on May 20, 2011, now Pat. No. 9,238,080.

(60) Provisional application No. 61/347,040, filed on May 21, 2010.

(51) Int. Cl.
| | |
|---|---|
| *A61K 47/66* | (2017.01) |
| *A61K 45/06* | (2006.01) |
| *A61K 47/68* | (2017.01) |
| *B82Y 5/00* | (2011.01) |
| *C07K 14/47* | (2006.01) |
| *C07K 14/475* | (2006.01) |
| *C07K 14/485* | (2006.01) |
| *C07K 14/65* | (2006.01) |
| *C07K 16/44* | (2006.01) |
| *C07K 16/46* | (2006.01) |
| *C12N 15/62* | (2006.01) |
| *A61K 38/00* | (2006.01) |

(52) U.S. Cl.
CPC .............. *C07K 16/46* (2013.01); *A61K 45/06* (2013.01); *A61K 47/66* (2017.08); *A61K 47/6811* (2017.08); *A61K 47/6891* (2017.08); *B82Y 5/00* (2013.01); *C07K 14/47* (2013.01); *C07K 14/475* (2013.01); *C07K 14/485* (2013.01); *C07K 14/65* (2013.01); *C07K 16/44* (2013.01); *C12N 15/62* (2013.01); *A61K 38/00* (2013.01); *C07K 2317/31* (2013.01); *C07K 2317/76* (2013.01); *C07K 2319/00* (2013.01); *C07K 2319/80* (2013.01)

(58) Field of Classification Search
CPC ........................... A61K 47/6811; A61K 38/16
See application file for complete search history.

(56) References Cited

U.S. PATENT DOCUMENTS

| | | | |
|---|---|---|---|
| 5,273,966 A | 12/1993 | Sknottner-Lundin et al. | |
| 5,632,986 A | 5/1997 | Tait et al. | |
| 5,679,771 A | 10/1997 | Ballard et al. | |
| 6,387,663 B1 | 5/2002 | Hall et al. | |
| 6,541,610 B1 * | 4/2003 | Smith .................... | C07K 14/71 |
| | | | 435/69.7 |
| 6,566,098 B1 | 5/2003 | Chan et al. | |
| 7,226,907 B1 | 6/2007 | Zhou | |
| 7,396,918 B2 | 7/2008 | Glass et al. | |
| 7,459,541 B2 | 12/2008 | Hall et al. | |
| 7,521,211 B2 | 4/2009 | Glass | |
| 7,531,318 B2 | 5/2009 | Srivastava et al. | |
| 7,576,186 B2 | 8/2009 | Lum et al. | |
| 7,612,164 B2 | 11/2009 | Zhou | |
| 7,786,074 B2 | 8/2010 | Gourdie et al. | |
| 7,837,999 B2 | 11/2010 | Glass et al. | |
| 8,067,357 B2 | 11/2011 | Reutelingsperger et al. | |
| 8,158,581 B2 | 4/2012 | Glass et al. | |
| 8,445,434 B2 | 5/2013 | Glass et al. | |
| 8,691,771 B2 | 4/2014 | Nielsen et al. | |

(Continued)

FOREIGN PATENT DOCUMENTS

| | | |
|---|---|---|
| AU | 2008-200706 | 3/2008 |
| AU | 2015-204540 | 8/2016 |

(Continued)

OTHER PUBLICATIONS

Osborn et al., Eur. J. Pharmacol. (2002), 456(1-3), pp. 149-158.*

(Continued)

*Primary Examiner* — Prema M Mertz
(74) *Attorney, Agent, or Firm* — Greenberg Traurig LLP; Natalie Salem

(57) ABSTRACT

Bi-specific fusion proteins with therapeutic uses are provided, as well as pharmaceutical compositions comprising such fusion proteins, and methods for using such fusion proteins to repair or regenerate damaged or diseased tissue. The bi-specific fusion proteins generally comprise: (a) a targeting polypeptide domain that binds to a target molecule; and (b) an activator domain that detectably modulates tissue regeneration.

6 Claims, 37 Drawing Sheets

Specification includes a Sequence Listing.

(56)                References Cited

U.S. PATENT DOCUMENTS

|  |  |  |  |  |
|---|---|---|---|---|
| 8,748,380 | B2 | 6/2014 | Plumridge et al. | |
| 9,238,080 | B2 | 1/2016 | Nielsen et al. | |
| 9,718,892 | B2 | 8/2017 | Nielsen et al. | |
| 9,982,060 | B2 | 5/2018 | Nielsen et al. | |
| 10,040,840 | B2 | 8/2018 | Antipov et al. | |
| 10,407,512 | B2 | 9/2019 | Nielsen et al. | |
| 10,633,425 | B2 | 4/2020 | Antipov et al. | |
| 10,858,450 | B2 | 12/2020 | Nielsen et al. | |
| 10,988,547 | B2 | 4/2021 | Nielsen et al. | |
| 11,155,593 | B2 | 10/2021 | Antipov et al. | |
| 11,673,970 | B2 | 6/2023 | Nielsen et al. | |
| 11,879,002 | B2 | 1/2024 | Antipov et al. | |
| 12,122,819 | B2 | 10/2024 | Antipov et al. | |
| 2003/0153490 | A1 | 8/2003 | Tchelingerian | |
| 2004/0213738 | A1 | 10/2004 | Croll-Kalish et al. | |
| 2005/0043236 | A1 | 2/2005 | Daly et al. | |
| 2005/0164926 | A1 | 7/2005 | Wun | |
| 2005/0287151 | A1 | 12/2005 | Glass | |
| 2006/0018897 | A1 | 1/2006 | Lee et al. | |
| 2006/0223753 | A1 | 10/2006 | Glass | |
| 2006/0228299 | A1 | 10/2006 | Thorpe et al. | |
| 2006/0275254 | A1 | 12/2006 | Kim et al. | |
| 2007/0048282 | A1* | 3/2007 | Rosen .................... | C12N 15/62 |
| | | | | 435/69.51 |
| 2007/0054851 | A1 | 3/2007 | Lin et al. | |
| 2007/0110733 | A1 | 5/2007 | Lum | |
| 2007/0172811 | A1 | 7/2007 | Srivastava et al. | |
| 2007/0224119 | A1 | 9/2007 | McTavish | |
| 2008/0039341 | A1 | 2/2008 | Schellenberger et al. | |
| 2008/0050370 | A1 | 2/2008 | Glaser et al. | |
| 2008/0069823 | A1 | 3/2008 | Allison | |
| 2008/0071063 | A1 | 3/2008 | Allan et al. | |
| 2008/0241118 | A1 | 10/2008 | LeBowitz | |
| 2009/0068181 | A1 | 3/2009 | Lee et al. | |
| 2009/0093407 | A1 | 4/2009 | Hall et al. | |
| 2009/0214507 | A1 | 8/2009 | Srivastava et al. | |
| 2010/0055115 | A1 | 3/2010 | Lum et al. | |
| 2010/0197890 | A1 | 8/2010 | McTavish | |
| 2010/0291080 | A1 | 11/2010 | Lee et al. | |
| 2011/0045007 | A1 | 2/2011 | Schuurman et al. | |
| 2011/0059076 | A1 | 3/2011 | McDonagh et al. | |
| 2011/0274658 | A1 | 11/2011 | Silver et al. | |
| 2011/0293579 | A1 | 12/2011 | Nielsen et al. | |
| 2012/0177652 | A1 | 7/2012 | Nielsen et al. | |
| 2012/0244163 | A1 | 9/2012 | Schoeberl et al. | |
| 2014/0178380 | A1 | 6/2014 | Nielsen et al. | |
| 2014/0315817 | A1 | 10/2014 | Schmidt et al. | |
| 2016/0168269 | A1 | 6/2016 | Nielsen et al. | |
| 2017/0335015 | A1 | 11/2017 | Nielsen et al. | |
| 2018/0237540 | A1 | 8/2018 | Nielsen et al. | |
| 2020/0048368 | A1 | 2/2020 | Nielsen et al. | |
| 2021/0214463 | A1 | 7/2021 | Nielsen et al. | |

FOREIGN PATENT DOCUMENTS

| | | |
|---|---|---|
| CA | 2286264 | 10/1998 |
| CA | 2768621 | 1/2011 |
| CA | 2902744 | 10/2014 |
| EP | 854884 | 7/1998 |
| EP | 1141015 | 10/2001 |
| EP | 1436316 | 7/2004 |
| EP | 2 275 446 | 1/2011 |
| EP | 2900255 | 8/2014 |
| WO | WO 1992/008495 | 5/1992 |
| WO | WO 1994/028133 | 12/1994 |
| WO | WO 1995/032003 | 11/1995 |
| WO | WO 1996/033698 | 10/1996 |
| WO | WO 2000/002587 | 1/2000 |
| WO | WO 2002/017951 | 3/2002 |
| WO | WO 2005/117973 | 12/2005 |
| WO | WO 2006/003488 | 1/2006 |
| WO | WO 2006/004910 | 1/2006 |
| WO | WO 2006/076525 | 7/2006 |
| WO | WO 2006/079120 | 7/2006 |

| | | |
|---|---|---|
| WO | WO 2006/091209 | 8/2006 |
| WO | WO 2006/128125 | 11/2006 |
| WO | WO 2007/021494 | 2/2007 |
| WO | WO 2007/044887 | 4/2007 |
| WO | WO 2007/095338 | 8/2007 |
| WO | WO 2008/063424 | 5/2008 |
| WO | WO 2008/089567 | 7/2008 |
| WO | WO 2008/091209 | 8/2008 |
| WO | WO 2008/096158 | 8/2008 |
| WO | WO 2008/151005 | 12/2008 |
| WO | WO 2008/155134 | 12/2008 |
| WO | WO 2009/030720 | 3/2009 |
| WO | WO 2009/126920 | 10/2009 |
| WO | WO2009/126920 A2 * | 10/2009 |
| WO | WO 2010/059315 | 5/2010 |
| WO | WO 2011/011071 | 1/2011 |
| WO | WO 2011/146902 | 11/2011 |
| WO | WO 2012/078153 | 6/2012 |
| WO | WO 2013/075066 | 11/2012 |
| WO | WO 2013/086785 | 6/2013 |

OTHER PUBLICATIONS

Kineman et al (2018) J. Mol. Endocrinol. 61(1):T187-T198.*

Bork. Powers and Pitfalls in Sequence Analysis: The 70% Hurdle. Genome Research, 2000, 10:398-400 (Year: 2000).*

Greenspan et al. 1999. Defining epitopes: It's not as easy as it seems; Nature Biotechnology, 17:936-937 (Year: 1999).*

Bowie et al. Deciphering the Message in Protein Sequences: Tolerance to Amino Acid Substitutions. Science, 1990, 247:1306-1310 (Year: 1990).*

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine ResidueJ. Cell Biol. 111:2129-2138, 1990 (Year: 1990).*

Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*

Botusan et al (2018), https://journals.plos.org/plosone/article/?id= 10.1371/journal.pone.0193084.*

Adderson, E., et al., "Molecular analysis of polyreactive monoclonal antibodies from rheumatic carditis: human anti-N-acetylglucosamine/ anti-myosin antibody V region genes," J Immunol., 161(4):2020- 2031, (Aug. 15, 1998).

Andrades, et al., "Engineering, expression, and renaturation of a collagen-targeted human bFGF fusion protein," Growth Factors, 18:261-275, (Aug. 1999).

Askari, et al., "Effect of stromal-cell-derived factor 1 on stem-cell homing and tissue regeneration in ischaemic cardiomyopathy," Mechanisms of Disease, 362: 697-703, (Aug. 30, 2003).

Bai et al., "Tracking long-term survival of intramyocardially delivered human adipose tissue-derived stem cells using bioluminescence imaging," Molecular Imaging and Biology, 13 pages (2010).

Barbas, S., et al., "Human autoantibody recognition of DNA," Proc Natl Acad Sci U S A, 92(7):2529-2533, (Mar. 28, 1995).

Bauwens, C., et al., "Geometric control of cardiomyogenic induction in human pluripotent stem cells", Tissue Eng., Part A, (Apr. 25, 2011).

Bayne, Marvin et al., "The Roles of Tyrosines 24,31, and 60 in the High Affinity Binding of Insulin-like Growth Factor-I to the Type 1 Insulin-like Growth Factor Receptor", The Journal of Biological Chemistry, vol. 265, No. 26, Issue of Sep. 15, pp. 15648-15652, 1990.

Bersell, et al., "Neuregulin1/ErbB4 signaling induces cardiomyocyte proliferation and repair of heart injury," Cell, 138:257-270, (Jul. 24, 2009).

Black, S., "In vivo models of myocardial ischemia and reperfusion injury: application to drug discovery and evaluation," J. Pharmacol. Toxicol. Methods 43(2):153-167, (Mar.-Apr. 2000).

Bock-Marquette, et al., "Thymosin B4 activates integrin-linked kinase and promotes cardiac cell migration, survival and cardiac repair," Nature, 432:466-472, (Nov. 25, 2004).

(56)            References Cited

OTHER PUBLICATIONS

Buerke, et al., "Cardioprotective effect of insulin-like growth factor I in myocardial ischemia followed by reperfusion," Proc. Natl. Acad. Sci. USA, 92: 8031-8035, (Aug. 1995).

Bujak, 2007, Cardiovascular Research, vol. 74, Issue 2, pp. 184-195.

Burchfield, et al., "Interleukin-10 from transplanted bone marrow mononuclear cells contributes to cardiac protection after myocardial infarction," Circulation Research, 15 pages, (Mar. 23, 2011).

Burchfield, et al., "Role of paracrine factors in stem and progenitor cell mediated cardiac repair and tissue fibrosis," Fibrogenesis and Tissue Repair, 1(4):1-11, (2008).

Burchfield, et al., "The cytoprotective effects of tumor necrosis factor are conveyed through tumor necrosis factor receptor-associated factor 2 in the heart," Circulation Heart Failure, 16 pages, (Jan. 2010).

Burrill, Devin et al., "Targeted erythropoietin selectively stimulates red blood cell expansion in vivo", Proceedings of the National Academy of Sciences of the United States of America (PNAS), vol. 113, No. 19, pp. 5245-5250, May 10, 2016.

Chen, et al. "Effects of receptor binding on plasma half-life of bifunctional transferrin fusion proteins,"Molecular Pharmaceutics 8: 457-65 (2011).

Chen, et al., "Localization of monoclonal antibody TNT-1 in experimental kidney infarction of the mouse," FASEB J., 4(12):3033-3039, (Sep. 1, 1990).

Chimenti, et al., "Myocardial infarction: animal models," Methods. Mol. Med., 98:217-226, (2004).

Christman, et al., "Enhanced neovasculature formation in ischemic myocardium following delivery of pleiotrophin plasmid in a biopolymer,"Biomaterials, 26:1139-1144 (2005).

Cironi, Pablo et al., "Enhancement of Cell Type Specificity by Quantitative Modulation of Chimeric Ligand", The Journal of Biological Chemistry, vol. 283, No. 13, pp. 8460-8476, Mar. 28, 2008.

Davis, "Local myocardial insulin-like growth factor 1 (IGF-1) delivery with biotinylated peptide nanofibers improves cell therapy for myocardial infarction," Proc. Natl. Acad. Sci USA, 103(21):8155-8160, (May 23, 2006).

Davletov, A. & Sudhof, T., "A single C2 domain from synaptotagmin I is sufficient for high affinity Ca2+/phospholipid binding," J. Biol. Chem., 268(35):26386-2690, (Dec. 15, 1993).

Doldan-Martelli et al., "A Mathematical Model for the Rational Design of Chimeric Ligands in Selective Drug Therapies," CPT: Pharmacometrics & Systems Pharmacology (2013), 2, e26, Feb. 13, 2013.

Dorn II, M.D., "Periostin and myocardial repair, regeneration, and recovery," The New England Journal of Medicine, 357(15):1552-1554, (Oct. 11, 2007).

Dubaquie, Y. et al. "Total Alanine-Scanning Mutagenesis of Insulin-Like Growth Factor I (IGF-I) Identifies Differential Binding Epitopes for IGFBP-1 and IGFBP-3", Biochemistry, 1999, 38, 6386-6396.

Dumont, et al., "Cardiomyocyte Death Induced by Myocardial Ischemia and Reperfusion: Measurement With Recombinant Human Annexin-V in a Mouse Model ," Circulation 102(13):1564-1568, (Sep. 26, 2000).

Engel, et al., "FGF1/p38 MAP kinase inhibitor therapy induces cardiomyocyte mitosis, reduces scarring, and rescues function after myocardial infarction," PNAS, 103(42):15546-15551, (Oct. 17, 2006).

Epa, V.C. et al., "Model for the Complex between the insulin-like growth factor 1 and its receptors: towards designing antagonists for the IGF-1 receptor", Protein Engineering, Design & Selection, vol. 19, No. 8, pp. 377-384, 2006.

Francis, G.L., et al., "Novel recombinant fusion protein analogues of insulin-like growth factor (IGF)-I indicate the relative importance of IGF-binding protein and receptor binding for enhanced biological potency", Journal of Molecular Endocrinology (1992), 8, pp. 213-223.

GenBank: BAA78418.1, vascular endothelial growth factor isoform VEGF165 [*Homo sapiens*], NCBI Protein Database, GenBank: BAA78418.1 (Jun. 3, 1999), also available at http://www.ncbi.nlm.nih.gov/protein/BAA78418.1 (last visited Apr. 21, 2016).

George, et al., "Typhostin AG-556 reduces myocardial infarct size and improves cardiac performance in the rat," Experimental and Molecular Pathology, 74:314-318 (2003).

Gnecchi, et al., "Evidence supporting paracrine hypothesis for Akt-modified mesenchymal stem cell-mediated cardiac protection and functional improvement," The FASEB Journal, 20:661-669, (Apr. 2006).

Gnecchi, et al., "Paracrine mechanisms in adult stem cell signaling and therapy," Adult Stem Cells and Paracrine Effects, 1204-1219, (Nov. 2008).

Greenberg, et al., "Chapter 7. Mouse models of ischemic angiogenesis and ischemia-reperfusion injury," Methods Enzymol., 444:159-174, (2008).

Gripenberg, et al., "A Solid Phase Enzyme-linked Immunosorbent Assay (ELISA) for the Demonstration of Antibodies against Dena-tured, Single-stranded DNA in Patient Sera," Scand. J. Immunol., 7(2):151-157, (Feb. 1978).

Han, et al., "Refolding of a recombinant collagen-targeted TGF-B2 fusion protein expressed in *Escherichia coli*," Protein Expression and Purification, 11:169-178 (1997).

Hashino, K., et al., "A 31-kDa Recombinant Fibronectin Cell-Binding Domain Fragment: Its Binding to Receptor, Cell Adhesive Activity, and Fusion Proteins," J. Biochem., 119(4):604-609, (Apr. 4, 1996).

Hausenloy et al., "Cardioprotective growth factors," Cardiovascular Research, 83: 179-194, (2009).

Hefta, et al., "Measuring Affinity Using Biosensors", in "Antibody engineering: a Practical Approach", pp. 99-116, Oxford University Press, 1996, Edited by McCafferty et al., (Hames B.D.eds).

Henson, 2006, Cellular Signaling, vol. 18, pp. 2089-2097.

Hinkel et al., "Thymosin B4 is an essential paracrine factor of embryonic endothelial progenitor cell-mediated cardioprotection," Circulation, 2232-2240 (Apr. 29, 2008).

Hoberg, E., et al., "Monoclonal antibodies specific for human cardiac myosin: selection, characterization and experimental myocardial infarct imaging," Eur Heart J., 9(3):328-236, (Mar. 1988).

Hofstra, et al., "Visualisation of cell death in vivo in patients with acute myocardial infarction," The Lancet, 356(9225):209-212, (2000).

Hsieh et al., "Local controlled intramyocardial delivery of plateet-derived growth factor improves postinfarction ventricular function without pulmonary toxicity," Circulation, 637-644, (Aug. 15, 2006).

Hu et al., Stromal cell-derived factor-1a confers protection against myocardial ischemia/reperfusion injury, Molecular Cardiology, 654-663, (Aug. 7, 2007).

Ieda, et al., "Cardiac fibroblasts regulate myocardial proliferation through B1 integrin signaling," Developmental Cell, 16: 233-244 (Feb. 17, 2009).

Igarashi, K., et al., "Specific binding of a synthetic peptide derived from an antibody complementarity determining region to phosphatidylserine," J Biochem., 117(2):452-457, (Feb. 1995).

Ishikawa, et al., "Production of biologically active epidermal growth factor fusion protein with high collagen affinity," J. Biochem., 129(4): 627-633 (2001).

Jeon, et al., "Long-term and zero-order release of basic fibroblast growth factor from heparin-conjugated poly(L-lactide-co-glycolide) nanospheres and fibrin gel," Biomaterials, 27:1598-1607 (2006).

Kanashiro-Takeuchi, et al., "Cardioprotective effects of growth hormone-releasing hormone agonist after myocardial infarction," PNAS, 107(6):2604-2609, (Feb. 9, 2010).

Kardami, et al., "Fibroblast growth factor-2 and cardioprotection," Heart Fail Rev., 12:267-277 (2007).

Kawase Y. et al. "Construction and characterization of a fusion protein with epidermal growth factor and the cell-binding domain of fibronectin" FEBS letters, 298(2-3): 126-128, 1992.

Kenis et al., "Annexin A5: shifting from a diagnostic towards a therapeutic realm", Cellular Molecular Life Sciences, vol. 64, pp. 2859-2862, ePub Sep. 17, 2007.

(56)        References Cited

OTHER PUBLICATIONS

Kenis, H., et al., "Annexin A5 uptake in ischemic myocardium: demonstration of reversible phosphatidylserine externalization and feasibility of radionuclide imaging" J. Nucl Med., 51(2):259-67, (Feb. 2010).

Kenis, H., et al., "Cell surface-expressed phosphatidylserine and annexin A5 open a novel portal of cell entry," J Biol Chem., 279(50):52623-52629, Epub Sep. 20, 2004, (Dec. 10, 2004).

Khaw, B., et al., "Monoclonal antibody to cardiac myosin: imaging of experimental myocardial infarction," Hybridoma, 3(1):11-23, (1984).

King et al., "Production and characterization of recombinant insulin-like growth factor-I (IGF-I) and potent analogues of IGF-I, with Gly or Arg substituted for Glu3, following their expression in *Escherichia colu* as fusion proteins", Journal of Molecular Endocrinology, (1992) 8, pp. 29-41.

Klopsch, et al., "Intracardiac injection of erythropoietin induces stem cell recruitment and improves cardiac functions in a rat myocardial infarction model," J. Cell. Mol. Med. 13(4): 664-679, (2009).

Ko, Y., et al., "Gene delivery into ischemic myocardium by double-targeted lipoplexes with anti-myosin antibody and TAT peptide," Gene Ther., 16(1):52-9. Epub Aug. 14, 2008, (Jan. 2009).

Kobayashi, et al., "Effect of atrial natriuretic peptide on ischemia-reperfusion injury in a porcine total hepatic vascular exclusion model," World J. Gastroenterol., 13(25):3487-3492, (Jul. 7, 2007).

Kuhn, et al., "Periostin induces proliferation of differentiated cardiomyocytes and promotes cardiac repair," Nature Medicine, 13(8):962-969, (Aug. 2007).

Kuramochi, "Cardiac Endothelial Cells Regulate Reactive Oxygen Species-induced Cardiomyocyte Apoptosis through Neuregulin-1_/ erbB4 Signaling," J. Biol. Chem., 279(49): 51141-51147, (2004).

Laajoki, L. et al. Solution Structure and Backbone Dynamics of Long-[ARG3] Insulin-like Growth Factor-I; Journal of Biological Chemistry, vol. 275, No. 14, pp. 10009-10015, Apr. 7, 2000.

Laroche-Traineau, J., et al., "A human monoclonal antibody obtained from EBV-transformed B cells with specificity for myosin," Br J Haematol., 91(4):951-962, (Dec. 1995).

Laroche-Traineau, J., et al., "Analysis of the V genes coding for a monospecific human antibody to myosin and functional expression of single chain Fv fragments," FEBS Lett., 460(1):86-92, (Oct. 22, 1999).

Laroche-Traineau, J., et al., "Three-step purification of bacterially expressed human single-chain Fv antibodies for clinical applications," J Chromatogr B Biomed Sci Appl., 737(1-2):107-117, (Jan. 14, 2000).

Liang, W., et al., "ATP-containing immunoliposomes specific for cardiac myosin," Curr Drug Deliv., 1(1):1-7, (Jan. 2004).

Liu, et al., "Neuregulin-1/erbB-activation improves cardiac function and survival in models of ischemic, dilated, and viral cardiomyopathy," Journal of the American College of Cardiology, 48(7):1438-1447, (Oct. 3, 2006).

Loddick, S. et al., "Displacement of insulin-like growth factors from their binding proteins as a potential treatment for stroke", PNAS, vol. 95, pp. 1894-1898, Feb. 1998.

Lorts, et al., "Genetic manipulation of periostin expression in the heart does not affect myocyte content, cell cycle activity, or cardiac repair," UltraRapid Communication, e1-e7, (Jan. 2, 2009).

Marshall, K.W. & Marks, J.D. "Engineering and characterization of a novel fusion protein incorporating B7.2 and an anti-ErbB-2 single-chain antibody fragment for the activation of Jurkat T cells," Journal of Immunotherapy. Hagerstown, Md. : 1997) 24: 27-36 (2001).

Mihardja, et al., "Targeted in vivo extracellular matrix formation promotes neovascularization in a rodent model of myocardial infarction," PLoS One, 5(4):e10384 (8 pages), (Apr. 2010).

Mira, et al., "Inhibition of cytosolic phospholipase A2 by annexin V in differentiated permeabilized HL-60 cells. Evidence of crucial importance of domain I type II Ca2+-binding site in the mechanism of inhibition," J. Biol Chem., 272(16):10474-10482, (Apr. 18, 1997).

Miranda, et al., "Endothelium-dependent and -independent hepatic artery vasodilatation is not impaired in a canine model of liver ischemia-reperfusion injury," Braz. J. Med. Biol. Res., 40(6):857-865, (Jun. 2007).

Murray and Brown, "Measurement of association constants in ELISA. Reactions between solid-phase antibody and fluid-phase biotinylated antigen," J. Immunol. Methods., 127(1):25-28 (Feb. 20, 1990).

Nedelman, M., et al., "Rapid infarct imaging with a technetium-99m-labeled antimyosin recombinant single-chain Fv: evaluation in a canine model of acute myocardial infarction," J Nucl Med., 34(2):234-241, (Feb. 1993).

Nelson, P., et al. "Characterization of anti-myosin monoclonal antibodies," Hybridoma (Larchmt), 24(6):314-318, (Dec. 2005).

Nimni, "Polypeptide growth factors: targeted delivery systems," Biomaterials, 18(18):1201-1225, (1997).

Nishi, et al., "Collagen-binding growth factors: Production and characterization of functional fusion proteins having a collagen-binding domain," Proc. Natl. Acad. Sci. USA, 95:7018-7023, (Jun. 1998).

Novo Nordisk Pharmatech A/S "How Insulin and IGF-1 Bind to the receptors" retrieved from http://novonordiskpharmatech.com/how-insulin0and-igf-1-bind-to-their-receptors/ ; retrieved Dec. 16, 2016.

O' Sullivan et al., "Potent Long-Term Cardioprotective Effects of Single Low-Dose Insulin-Like Growth Factor-1 Treatment Postmyocardial Infarction", American Heart Association— Circulation: Cardiovascular Interventions, 4:327-335, Jun. 28, 2011.

Pak, K., et al., "An instant kit method for labeling antimyosin Fab' with technetium-99m: evaluation in an experimental myocardial infarct model," J. Nucl Med., 33(1):144-149, (Jan. 1992).

Peter, K., et al., "Construction and functional evaluation of a single-chain antibody fusion protein with fibrin targeting and thrombin inhibition after activation by factor Xa," Circulation, 101(10):1158-1164, (Mar. 14, 2000).

Pietronave, et al., "Agonist monoclonal antibodies against HGF receptor protect cardiac muscle cells from apoptosis," Am J Physiol Heart circ Physiol, 298:H1155-H1165, (2010).

Prior, et al. "Cytotoxic Activity of a Recombinant Fusion Protein between Insulin-like Growth Factor I and Pseudomonas Exotoxin," Cancer, 174-180 (1991).

Rosenthal, et al., "Growth factor enhancement of cardiac regeneration," Cell Transplantation, 15(1):S41-S45, (2006).

Saxena, et al., "Stromal cell-derived factor-la is cardioprotective after mocardial infarction," Molecular Cardiology, 2224-2231, (2008).

Schutters, K. & Reutelingsperger, C.P.M. "Phosphatidylserine targeting for diagnosis and treatment of human diseases," Apoptosis: an International Journal on Programmed Cell Death. 15:1072-82, (2010).

Scott, R.C. et al. "Targeted Delivery of Antibody Conjugated Liposomal Drug Carriers to Rat Myocardial Infarction," Biotechnology, 96:795-802, (2007).

Scott, et al. "Aiming for the heart: targeted delivery of drugs to diseased cardiac tissue," Expert Opinion on Drug Delivery, 5:459-70, (2008).

Scott, et al., "Targeting VEGF-encapsulated immunoliposomes to MI heart improves vascularity and cardiac function", The FASEB Journal: Research Communication, vol. 23, pp. 3361-3367, (Oct. 2009).

Segers, et al., "Protein therapeutics for cardiac regeneration after myocradial infarction," J. of Cardiovasc. Trans. Res., 9 pages, (Jul. 7, 2010).

Shan, et al., "Overexpression of TRPC3 increases apoptosis but not necrosis in response to ischemia-reperfusion in adult mouse cardiomyocytes," Am. J. Physiol. Cell. Physiol., 294(3):833-841, (Mar. 2008).

Shin, S.U. & Morrison, S.L., "Expression and characterization of an antibody binding specificity joined to insulin-like growth factor 1: potential applications for cellular targeting," Proceedings of the National Academy of Sciences of the United States of America, 87:5322-6, (1990).

(56) References Cited

OTHER PUBLICATIONS

Shin, et al. "Functional properties of antibody insulin-like growth factor fusion proteins," The Journal of Biological Chemistry, 269: 4979-8,5 (1994).

Simeonova, P., et al., "Identification of human ventricular myosin heavy chain fragments with monoclonal antibody 2F4 in human sera after myocardial necrosis," Clin Chim Acta., 201(3):207-221, (Sep. 30, 1991).

Stamm et al., Human ortholog to mouse gene imap38 encoding an ER-localized G-protein belongs to the gene family clustered on chromosome 7q32-36, Gene vol. 282: 159-167, 2003.

Stokes, et al., "A simple, rapid ELISA method for the detection of DNA antibodies," J. Clin. Pathol., 35(5):566-573, (May 1982).

Stowe, et al., Engineering Growth Factors for Cardiomyocyte Survival and Regeneration Following Ischemic Injury. American Heart Association Basic Cardiovascular Science [online Jul. 15, 2014 [retrieved Dec. 5, 2016].

Suleiman, et al., "Apoptosis and the cardiac action of insulin-like growth factor I," Pharmacology and Therapeutics, 114:278-294, (2007).

Sutton, R., et al., "Structure of the first C2 domain of synaptotagmin I: a novel Ca2+/phospholipid-binding fold," Cell, 80(6):929-938, (Mar. 24, 1995).

Tomas, F.M. et al., "IGF-I variants which bind poorly to IGF-binding proteins show more potent and prolonged hypoglycemic action that native IGF-I in pigs and marmoset monkeys", Journal of Endocrinology (1997), 155, 377-386.

Tuan et al., "Engineering, expression and renaturation of targeted TGF-beta fusion proteins"; Connect Tissue Res. 1996; 34(1):1-9.

Ueda, et al., "A potential cardioprotective role of hepatocyte growth factor in myocardial infarction in rats," Cardiovascular Research, 51:41-50, (2001).

Umeda, M., et al., "Effective production of monoclonal antibodies against phosphatidylserine: stereo-specific recognition of phosphatidylserine by monoclonal antibody," J Immunol., 143(7):2273-2279, (Oct. 1, 1989).

Ungethum, et al., "Engineered annexin A5 variants have impaired cell entry for molecular imaging of apoptosis using pretargeting strategies," J Biol Chem., 286(3):1903-10. Epub Nov. 15, 2010, (Jan. 21, 2011).

Urbanek K et al., "Myocardial regeneration by activation of multipotent cardiac stem cells in ischemic heart failure," Proc. Natl. Acad. Sci. USA, 102(24):8692-8697, (Jun. 14, 2005).

Wang, et al., "Degradable PLGA scaffolds with basic fibroblast growth factor," Texas Heart Institute Journal, 89-97, (2009).

Wassaf, et al., "High-throughput affinity ranking of antibodies using surface plasmon resonance microarrays," Anal. Biochem., 351(2):241-253, (Apr. 15, 2006).

Winter, et al. "A new bioassay for the immunocytokine L19-IL2 for simultaneous analysis of both functional moieties," Journal of Pharmaceutical and Biomedical Analysis, 54:81-6 (2011).

Yang L. et al., "Human cardiovascular progenitor cells develop from a KDR+ embryonic-stem-cell-derived population", Nature. May 22, 2008, 453(7194):524-8. Epub Apr. 23, 2008.

Yeghiazarians, et al., "Injection of bone marrow cell extract into infarcted hearts results in functional improvement comparable to intact cell therapy," The American Society of Gene Therapy, 17(7):1250-1256, (Jul. 2009).

Zaruba, et al., "Synergy between CD26/DPP-IV inhibition and G-CSF improves cardiac function after acute myocardial infarction," Cell Stem Cell, 4:313-323, (Apr. 3, 2009).

Zbinden, et al., "Interanimal variability in preexisting collaterals is a major factor determining outcome in experimental angiogenesis trials," Am. J. Physiol. Heart Circ. Physiol., 292(4): H1891-H1897, (Apr. 2007).

Zentilin, et al., "Cardiomyocyte VEGFR-1 activation by VEGF-B induces compensatory hypertrophy and preserves cardiac function after myocardial infarction," The FASEB Journal, 24:1467-1478, (May 2010).

Zhang et al., "Collagen-Targeting Vascular Endothelial Growth Factor Improves Cardiac Performance After Myocardial Infarction", Circulation, vol. 119, No. (13), pp. 1776-1784, epub Mar. 23, 2009.

Zhao, et al., "Neuregulins promote survival and growth of cardiac myocytes," The Journal of Biological Chemistry, 273(17):0261-10269, (Apr. 24, 1998).

Zhao, Ming, et al., 99m Tc-Labeled C2A Domain of Synaptotagmin I as a Target-Specific Molecular Probe for Noninvasive Imaging of Acute Myocardial Infarction, The Journal of Nuclear Medicine, vol. 47, No. 8, Aug. 2006, pp. 1367-1374.

Zhao, et al., "Recruitment of endogenous stem cells for tissue repair," Macromolecular Bioscience, 8:836-842, (2008).

Ziegler m. et al., "The bispecific SDF1-GPVI fusion protein preserves myocardial function after transient ischemia in mice" Circulation Feb. 7, 2012; 125(5): 685-96. Doi: 10.1161/Circulation. 111.070508.Epub Jan. 5, 2012.

International Search Report based on PCT/2011/037459, mailed Aug. 30, 2011.

Forsberg et al., "Separation and characterization of modified variants of recombinant human insulin-like growth factor I derived from a fusion protein secreted from *Escherichia coli*.", Biochem J., vol. 271, No. , pp. 357-363., Oct. 15, 1990.

Gadgil et al., "Affinity purification of DNA-binding proteins", J Biochem Biophys Methods, vol. 49 (1-3), pp. 607-624, Oct. 30, 2001.

Park et al., "Crystal structure of single-domain VL of an anti-DNA binding antibody 3D8 scFv and its active site revealed by complex structures of a small molecule and metals.", Proteins, vol. 71, No. 4, pp. 2091-2096, Jun. 2008.

Rivadeneyra-Espinoza et al., "Cell-penetrating anti-native DNA antibodies trigger apoptosis through both the neglect and programmed pathways.", J Autoimmun., vol. 26, No. 1, pp. 52-56, Feb. 2006.

* cited by examiner

PS Targeting with Annexin V or Synaptotagmin

IGF1_mHSA_Syt1 (SEQ ID 152)
IGF1_mHSA_AnxV (SEQ ID 136)

DNA Targeting
FIG. 20A
FIG. 20B
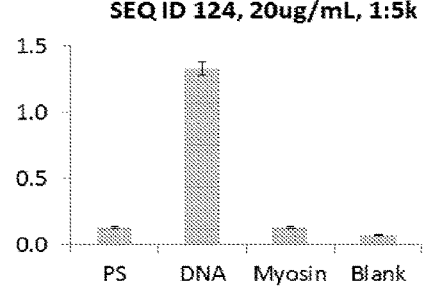
SEQ ID 124, 20ug/mL, 1:5k
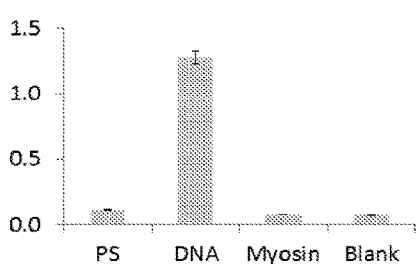
SEQ ID 126, 20ug/mL, 1:50k
FIG. 20C    SEQ ID 154, 0.8ug/mL, 1:5k
aDNASI1_mHSA_FGF2 (SEQ ID 124)
aDNASI1_mHSA_NRG1b(EGF) (SEQ ID 126)
IGF1_mHSA_aDNASI1 (SEQ ID 154)

Heart dissection - option 2

LV

1st cut

A

Ligation site

B1

2nd cut

B2

Infarct

Tissues to collect:

A
B1 - remote
B1 - infarct
B2

B1

FIG. 30A                                             FIG. 30B
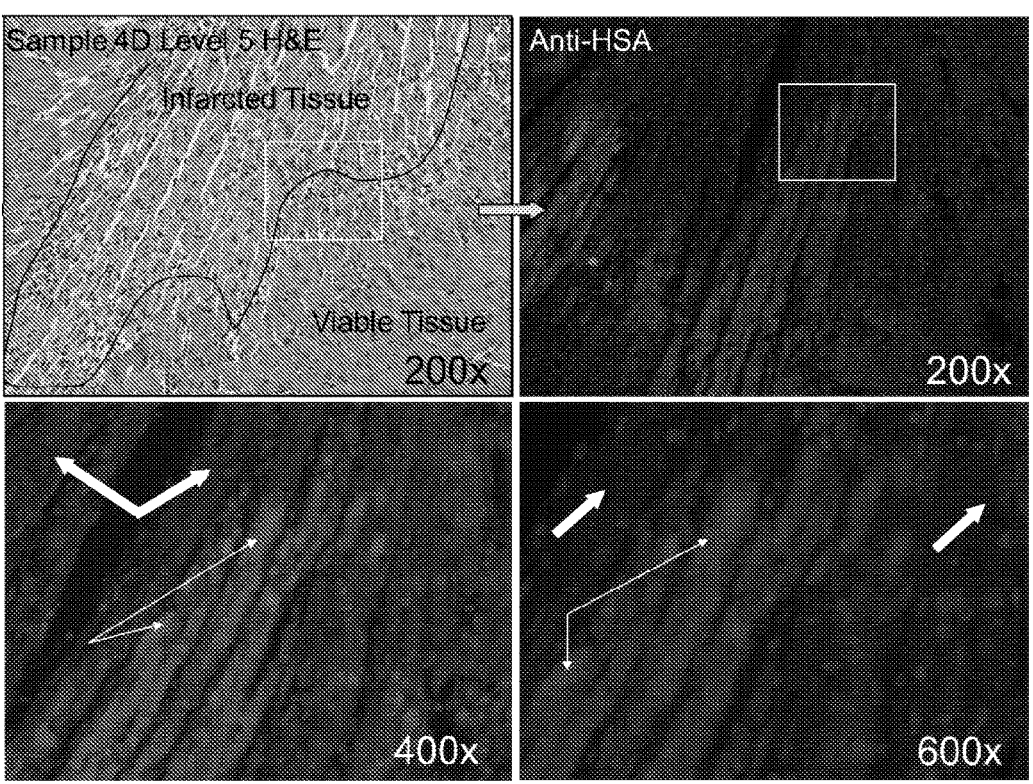
FIG. 30C                                             FIG. 30D FIG. 31A                                                         FIG. 31B
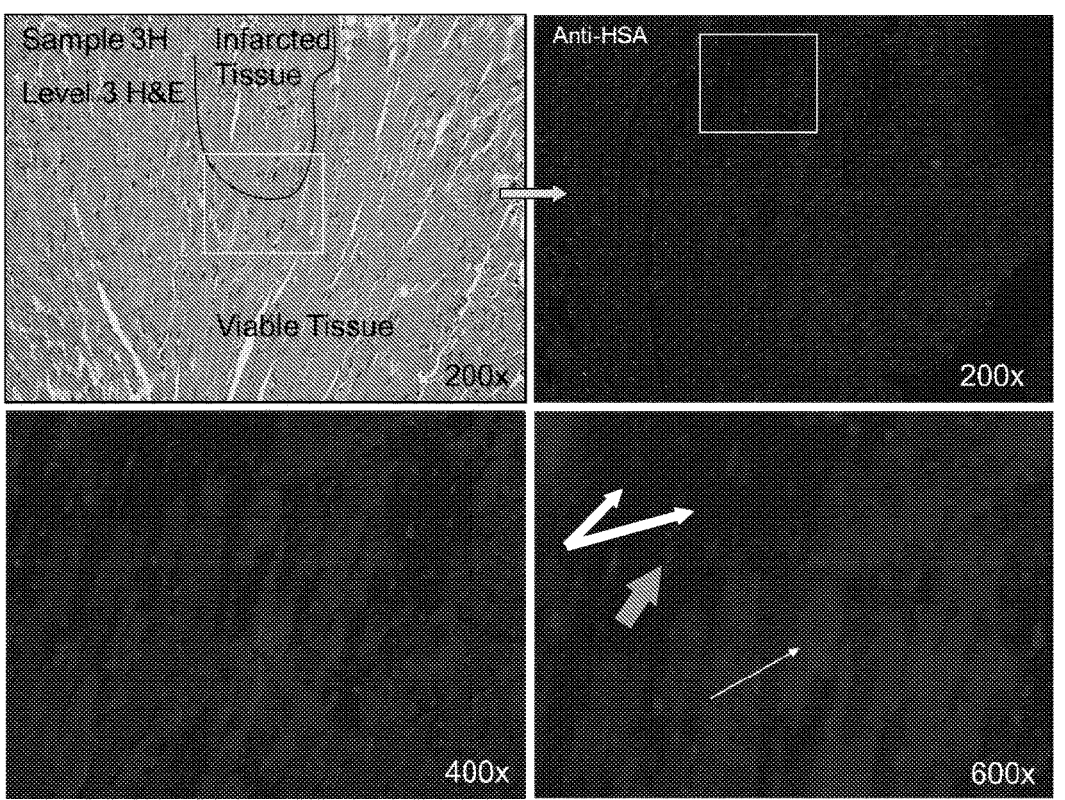
FIG. 31C                                                         FIG. 31D

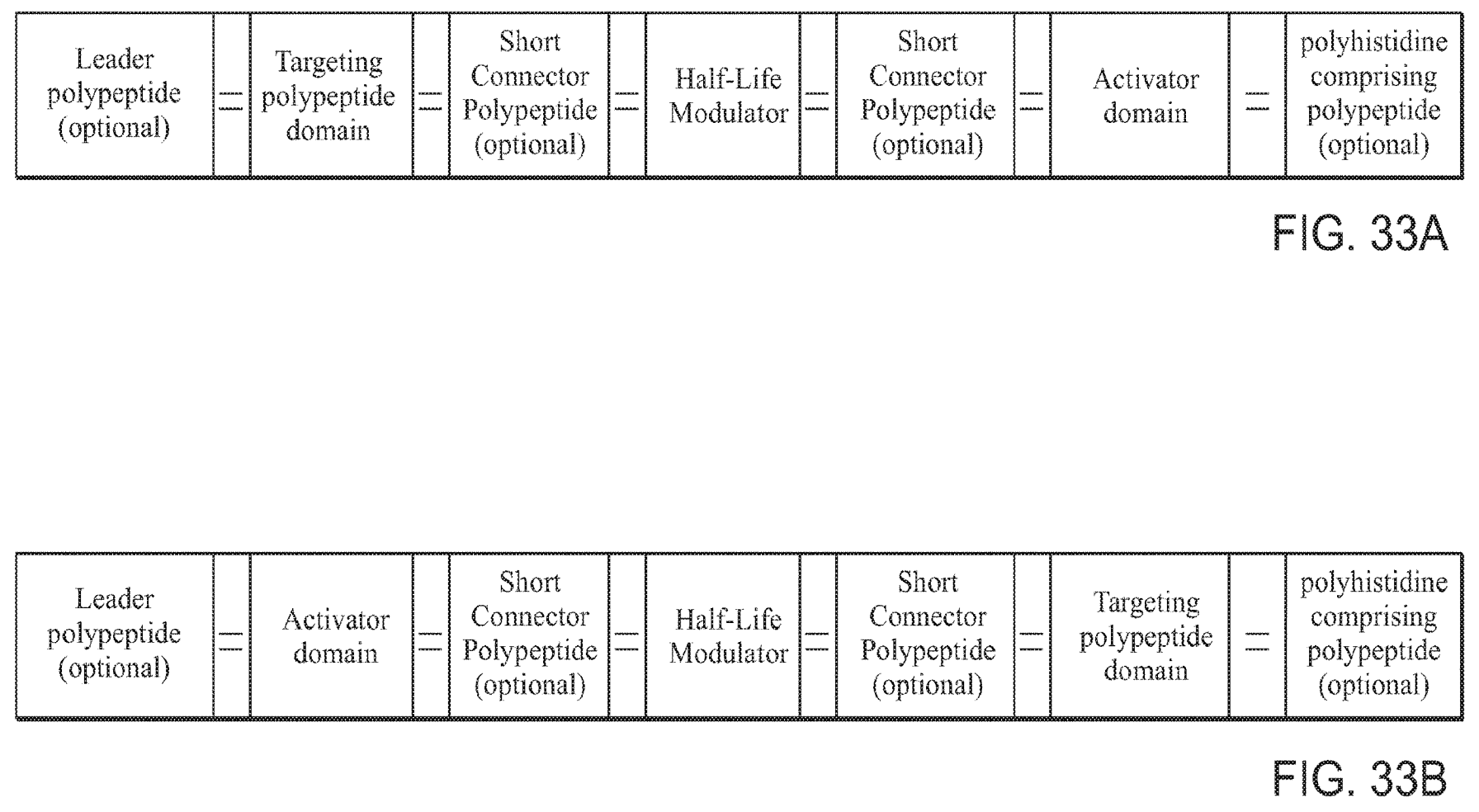

| Leader polypeptide (optional) | = | Targeting polypeptide domain | = | Short Connector Polypeptide (optional) | = | Half-Life Modulator | = | Short Connector Polypeptide (optional) | = | Activator domain | = | polyhistidine comprising polypeptide (optional) |
|---|---|---|---|---|---|---|---|---|---|---|---|---|

FIG. 33A

| Leader polypeptide (optional) | = | Activator domain | = | Short Connector Polypeptide (optional) | = | Half-Life Modulator | = | Short Connector Polypeptide (optional) | = | Targeting polypeptide domain | = | polyhistidine comprising polypeptide (optional) |
|---|---|---|---|---|---|---|---|---|---|---|---|---|

FIG. 33B

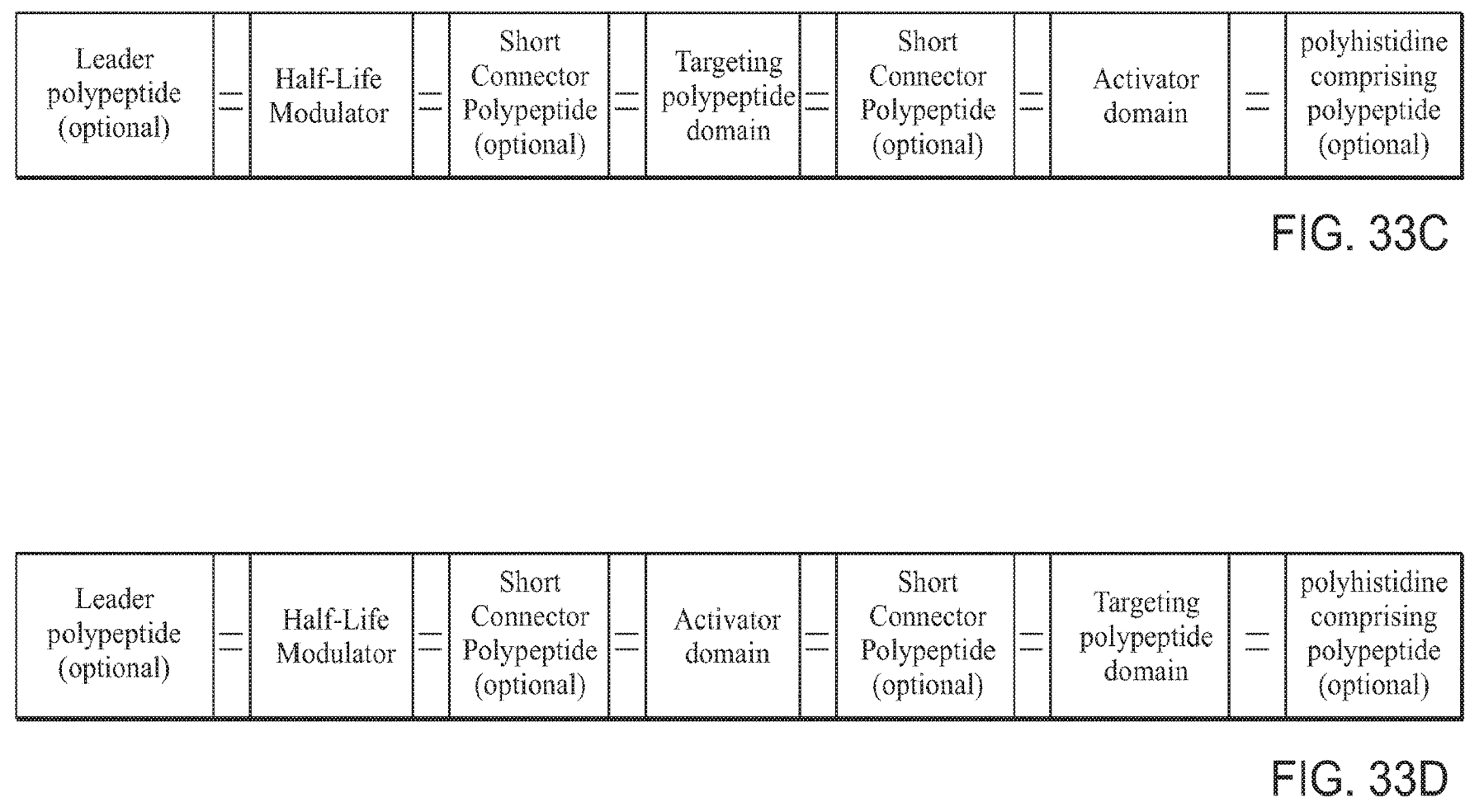

| Leader polypeptide (optional) | = | Half-Life Modulator | = | Short Connector Polypeptide (optional) | = | Targeting polypeptide domain | = | Short Connector Polypeptide (optional) | = | Activator domain | = | polyhistidine comprising polypeptide (optional) |
|---|---|---|---|---|---|---|---|---|---|---|---|---|

FIG. 33C

| Leader polypeptide (optional) | = | Half-Life Modulator | = | Short Connector Polypeptide (optional) | = | Activator domain | = | Short Connector Polypeptide (optional) | = | Targeting polypeptide domain | = | polyhistidine comprising polypeptide (optional) |
|---|---|---|---|---|---|---|---|---|---|---|---|---|

FIG. 33D

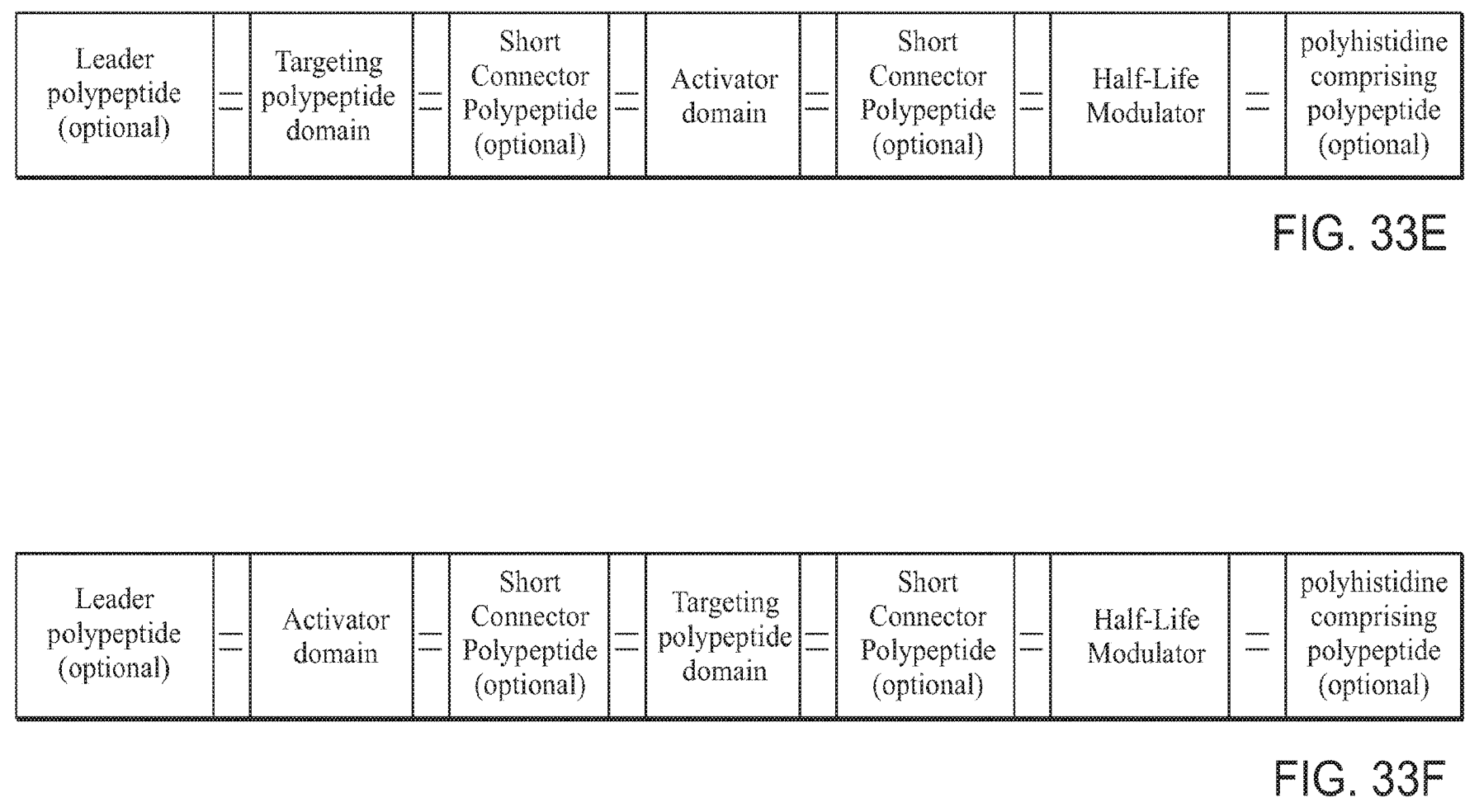

| Leader polypeptide (optional) | = | Targeting polypeptide domain | = | Short Connector Polypeptide (optional) | = | Activator domain | = | Short Connector Polypeptide (optional) | = | Half-Life Modulator | = | polyhistidine comprising polypeptide (optional) |
|---|---|---|---|---|---|---|---|---|---|---|---|---|

FIG. 33E

| Leader polypeptide (optional) | = | Activator domain | = | Short Connector Polypeptide (optional) | = | Targeting polypeptide domain | = | Short Connector Polypeptide (optional) | = | Half-Life Modulator | = | polyhistidine comprising polypeptide (optional) |
|---|---|---|---|---|---|---|---|---|---|---|---|---|

FIG. 33F

SEQUENCE LISTING

Sequence total quantity: 277
SEQ ID NO: 1             moltype = AA   length = 249
FEATURE                  Location/Qualifiers
REGION                   1..249
                         note = Synthetic construct
source                   1..249
                         mol_type = protein
                         organism = synthetic construct
SEQUENCE: 1
LESGGGLVQP GGSLRLSCAG SGFTFSSYAM SWVRQAPGKG LEWVSSISGS GGSTYYADSV  60
KGRFTISRDN SKKTLYLQMN SLRAEDTAVY YCARKRGRTT VSWGLVYFDY WGQGTVVTVS 120
SGGGGSGGGG SGGGGSGGGG SGGSELTQSP GTLSLSPGER ATLSCRASHS VSRAYLAWYQ 180
QKPGQAPRLL IYGTSSRATG IPDRFSGSGS GTDFTLTISR LEPEDFAVYY CQQYGGSPWF 240
GQGTKVELK                                                        249

SEQ ID NO: 2             moltype = AA   length = 251
FEATURE                  Location/Qualifiers
REGION                   1..251
                         note = Synthetic construct
source                   1..251
                         mol_type = protein
                         organism = synthetic construct
SEQUENCE: 2
LEQSGGGVVQ PGGSLRLSCT ASGFTFSSYG MHWVRQAPGK GLEWVTFIRY DGSSKYSADS  60
VKGRFTISRD NSKNTLFLQM NSLRAEDTAV YYCARARWRD YYYYMDVWGK GTTVTVSSGG 120
GGSGGGGSGG GGSGGGGSGG SELTQEPSVS GAPGQRVTIS CTGSSSNIGA GYDVHWYQQL 180
PGTAPKLLIY GNSNRPSGVP DRFSGSKSGT SASLAITGLQ AEDEADYYCQ SYDSSLSGVV 240
FGGGTKLTVL G                                                     251

SEQ ID NO: 3             moltype = AA   length = 70
FEATURE                  Location/Qualifiers
source                   1..70
                         mol_type = protein
                         organism = Homo sapiens
SEQUENCE: 3
GPETLCGAEL VDALQFVCGD RGFYFNKPTG YGSSSRRAPQ TGIVDECCFR SCDLRRLEMY  60
CAPLKPAKSA                                                        70

SEQ ID NO: 4             moltype = AA   length = 70
FEATURE                  Location/Qualifiers
REGION                   1..70
                         note = Synthetic construct
source                   1..70
                         mol_type = protein
                         organism = synthetic construct
SEQUENCE: 4
GPETLCGAEL VAALQFVCGD RGFYFNKPTG YGSSSRRAPQ TGIVDECCFR SCDLRRLEMY  60
CAPLKPAKSA                                                        70

SEQ ID NO: 5             moltype = AA   length = 70
FEATURE                  Location/Qualifiers
REGION                   1..70
                         note = Synthetic construct
source                   1..70
                         mol_type = protein
                         organism = synthetic construct
SEQUENCE: 5
GPETLCGAAL VDALQFVCGD RGFYFNKPTG YGSSSRRAPQ TGIVDECCFR SCDLRRLEMY  60
CAPLKPAKSA                                                        70

SEQ ID NO: 6             moltype = AA   length = 179
FEATURE                  Location/Qualifiers
REGION                   1..179
                         note = Synthetic construct
source                   1..179
                         mol_type = protein
                         organism = synthetic construct
SEQUENCE: 6
QRKRRNTIHE FKKSAKTTLI KIDPALKIKT KKVNTADQCA NRCTRNKGLP FTCKAFVFDK  60
ARKQCLWFPF NSMSSGVKKE FGHEFDLYEN KDYIRNCIIG KGRSYKGTVS ITKSGIKCQP 120
WSSMIPHEHS FLPSSYRGKD LQENYCRNPR GEEGGPWCFT SNPEVRYEVC DIPQCSEVE  179

SEQ ID NO: 7             moltype = AA   length = 88
FEATURE                  Location/Qualifiers
REGION                   1..88
                         note = Synthetic construct
source                   1..88
                         mol_type = protein -continued

```
                          organism = synthetic construct
SEQUENCE: 7
DYIRNCIIGK GRSYKGTVSI TKSGIKCQPW SSMIPHEHSF LPSSYRGKDL QENYCRNPRG   60
EEGGPWCFTS NPEVRYEVCD IPQCSEVE                                       88

SEQ ID NO: 8             moltype = AA  length = 193
FEATURE                  Location/Qualifiers
REGION                   1..193
                         note = HGF alpha chain N-K2 fusion
source                   1..193
                         mol_type = protein
                         organism = synthetic construct
SEQUENCE: 8
QRKRRNTIHE FKKSAKTTLI KIDPALKIKT KKVNTADQCA NRCTRNKGLP FTCKAFVFDK   60
ARKQCLWFPF NSMSSGVKKE FGHEFDLYEN KDYIRNSEVE CMTCNGESYR GLMDHTESGK  120
ICQRWDHQTP HRHKFLPERY PDKGFDDNYC RNPDGQPRPW CYTLDPHTRW EYCAIKTCAD  180
NTMDTDVPLE TTE                                                      193

SEQ ID NO: 9             moltype = AA  length = 97
FEATURE                  Location/Qualifiers
REGION                   1..97
                         note = Synthetic construct
source                   1..97
                         mol_type = protein
                         organism = synthetic construct
SEQUENCE: 9
SEVECMTCNG ESYRGLMDHT ESGKICQRWD HQTPHRHKFL PERYPDKGFD DNYCRNPDGQ   60
PRPWCYTLDP HTRWEYCAIK TCADNTMDTD VPLETTE                            97

SEQ ID NO: 10            moltype = AA  length = 585
FEATURE                  Location/Qualifiers
REGION                   1..585
                         note = Synthetic construct
source                   1..585
                         mol_type = protein
                         organism = synthetic construct
SEQUENCE: 10
DAHKSEVAHR FKDLGEENFK ALVLIAFAQY LQQSPFEDHV KLVNEVTEFA KTCVADESAE   60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFQAETFTFH ADICTLSEKE RQIKKQTALV ELVKHKPKAT  540
KEQLKAVMDD FAAFVEKCCK ADDKETCFAE EGKKLVAASQ AALGL                  585

SEQ ID NO: 11            moltype = DNA  length = 1755
FEATURE                  Location/Qualifiers
misc_feature             1..1755
                         note = Synthetic construct
source                   1..1755
                         mol_type = other DNA
                         organism = synthetic construct
SEQUENCE: 11
gacgctcaca agagcgaagt ggcacatagg ttcaaagatc tgggcgaaga gaactttaag   60
gccctcgtcc tgatcgcttt cgcacagtac ctccagcagt ctccctttga agatcacgtg  120
aaactggtca atgaggtgac cgaatttgcc aagacatgcg tggctgatga gagtgcagaa  180
aactgtgaca aatcactgca tactctcttt ggagataagc tgtgcaccgt cgccacactc  240
agagagactt atgggggaaat ggctgactgt tgcgcaaaac aggagcctga acggaatgag  300
tgtttcctcc agcacaagga tgacaaccca aatctgcccc gcctcgtgcg acctgaggtc  360
gatgtgatgt gcaccgcctt tcatgacaac gaagagacat tcctgaagaa atacctgtat  420
gaaattgctc gtaggcaccc atacttttat gccccccagg tcctgttctt tgcaaagaga  480
tacaaagctg ccttcactga atgttgccag gcagctgata aggccgcatg tctcctgcct  540
aaactggacg agctccggga tgaaggtaag gcttccagcg ccaaacagcg cctgaagtgc  600
gcttctctcc agaagtttgg cgagcgagca ttcaaagcct gggctgtggc ccgtctcagt  660
cagaggtttc caaaggcaga atttgctgag gtctcaaaac tggtgaccga cctcacaaag  720
gtccatactg agtgttgcca cggagatctg ctggaatgtg ccgacgatag agcagacctc  780
gctaaatata tctgcgagaa tcaggattcc attagctcta agctgaaaga atgttgcgag  840
aagcccctcc tggaaaagag tcattgtatc gccgaggtgg aaaacgacga gatgccagca  900
gatctgccat cactcgctgc cgactttgtg aatccaaag atgtctgcaa gaattacgca  960
gaggctaaag acgtgttcct ggggatgttt ctgtatgagt acgcccggcg tcaccccgat 1020
tatagcgtcg tgctcctgct ccgactggca aagacctacg aaacaactct ggagaaatgt 1080
tgcgctgccg cagaccctca tgaatgttat gctaaggtgt tcgatgagtt taagccactc 1140
gtcgaagagc cccagaacct gattaaacag aattgcgaac tgttcgagca gctcggtgaa 1200
tacaagtttc agaacgccct gctcgtgcgt ataccaaaa aggtccctca ggtgtctaca 1260
ccaactctgg tggaggtcag taggaatctg ggcaaagtgg gatcaaagtg ttgcaaacac 1320
cccgaggcaa agagaatgcc ttgtgctgaa gattacctct ccgtcgtgct gaaccagctc 1380
```

-continued

```
tgcgtgctgc atgaaaagac cccagtcagc gatcgggtga caaaatgttg caccgaatct   1440
ctggtcaatc gccgaccctg tttcagtgcc ctcgaagtgg acgaaactta tgtgcctaag   1500
gagtttcagg ctgaaacatt caccttttcac gccgatatct gcactctgtc cgagaaagaa   1560
aggcagatta agaaacagac agcactggtc gagctcgtga agcataaacc aaaggctacc   1620
aaggagcagc tgaaagccgt catgacgat ttcgcagctt ttgtggaaaa gtgttgcaaa   1680
gccgacgata aggagacttg tttcgcagaa gagggggaaa agctcgtggc tgccagccag   1740
gcagctctgg gtctg                                                    1755
```

```
SEQ ID NO: 12          moltype = AA  length = 585
FEATURE                Location/Qualifiers
source                 1..585
                       mol_type = protein
                       organism = Homo sapiens
SEQUENCE: 12
DAHKSEVAHR FKDLGEENFK ALVLIAFAQY LQQCPFEDHV KLVNEVTEFA KTCVADESAE   60
NCDKSLHTLF GDKLCTVATL RETYGEMADC CAKQEPERNE CFLQHKDDNP NLPRLVRPEV   120
DVMCTAFHDN EETFLKKYLY EIARRHPYFY APELLFFAKR YKAAFTECCQ AADKAACLLP   180
KLDELRDEGK ASSAKQRLKC ASLQKFGERA FKAWAVARLS QRFPKAEFAE VSKLVTDLTK   240
VHTECCHGDL LECADDRADL AKYICENQDS ISSKLKECCE KPLLEKSHCI AEVENDEMPA   300
DLPSLAADFV ESKDVCKNYA EAKDVFLGMF LYEYARRHPD YSVVLLLRLA KTYETTLEKC   360
CAAADPHECY AKVFDEFKPL VEEPQNLIKQ NCELFEQLGE YKFQNALLVR YTKKVPQVST   420
PTLVEVSRNL GKVGSKCCKH PEAKRMPCAE DYLSVVLNQL CVLHEKTPVS DRVTKCCTES   480
LVNRRPCFSA LEVDETYVPK EFNAETFTFH ADICTLSEKE RQIKKQTALV ELVKHKPKAT   540
KEQLKAVMDD FAAFVEKCCK ADDKETCFAE EGKKLVAASQ AALGL               585
```

```
SEQ ID NO: 13          moltype = DNA  length = 1755
FEATURE                Location/Qualifiers
source                 1..1755
                       mol_type = unassigned DNA
                       organism = Homo sapiens
SEQUENCE: 13
gatgcacaca agagtgaggt tgctcatcgg tttaaagatt tgggagaaga aaatttcaaa   60
gccttggtgt tgattgcctt tgctcagtat cttcagcagt gtccatttga agatcatgta   120
aaattagtga atgaagtaac tgaatttgca aaaacatgtg tagctgatga gtcagctgaa   180
aattgtgaca aatcacttca tacccttttt ggagacaaat tatgcacagt tgcaactctt   240
cgtgaaacct atggtgaaat ggctgactgc tgtgcaaaac aagaacctga gagaaatgaa   300
tgcttcttgc aacacaaaga tgacaaccca aacctccccc gattggtgag accagaggtt   360
gatgtgatgt gcactgcttt tcatgacaat gaagagacat ttttgaaaaa atacttatat   420
gaaattgcca gaagacatcc ttactttttat gccccggaac tccttttctt tgctaaaagg   480
tataaagctg cttttacaga atgttgccaa gctgctgata agctgcctg cctgttgcca   540
aagctcgatg aacttcggga tgaagggaag gcttcgtctg ccaaacagag actcaaatgt   600
gccagtctcc aaaaatttgg agaaagagct ttcaaagcat gggcagtggc tcgcctgagc   660
cagagatttc ccaaagctga gtttgcagaa gtttccaagt tagtgacaga tcttaccaaa   720
gtccacacgg aatgctgcca tggagatctg cttgaatgtg ctgatgacag ggcggacctt   780
gccaagtata tctgtgaaaa tcaggattcg atctccagta aactgaagga atgctgtgaa   840
aaacctctgt tggaaaaatc ccactgcatt gccgaagtgg aaaatgatga gatgcctgct   900
gacttgcctt cattagctgc tgattttgtt gaaagtaagg atgtttgcaa aaactatgct   960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taacctcctt   1140
gtggaagagc ctcagaattt aatcaaacaa aactgtgagc tttttaagca gcttggaagg   1200
tacaaattcc agaatgcgct attagttcgt tacaccaaga aagtacccca agtgtcaact   1260
ccaactcttg tagaggtctc aagaaaccta ggaaaagtgg gcagcaaatg ttgtaaacat   1320
cctgaagcaa aagaatgcc ctgtgcagaa gactatctat ccgtggtcct gaaccagtta   1380
tgtgtgttgc atgagaaaac gccagtaagt gacagagtca caaatgctg cacagagtcc   1440
ttggtgaaca ggcgaccatg cttttcagct ctggaagtcg atgaaacata cgttcccaaa   1500
gagtttaatg ctgaaacatt caccttccat gcagatatat gcacacttc tgagaaggag   1560
agacaaatca agaaacaaac tgcacttgtt gagcttgtga aacacaagcc caggcaaca   1620
aaaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gctta                                                    1755
```

```
SEQ ID NO: 14          moltype = AA  length = 588
FEATURE                Location/Qualifiers
REGION                 1..588
                       note = Synthetic construct
source                 1..588
                       mol_type = protein
                       organism = synthetic construct
SEQUENCE: 14
AASDAHKSEV AHRFKDLGEE NFKALVLIAF AQYLQQSPFE DHVKLVNEVT EFAKTCVADE   60
SAENCDKSLH TLFGDKLCTV ATLRETYGEM ADCCAKQEPE RNECFLQHKD DNPNLPRLVR   120
PEVDVMCTAF HDNEETFLKK YLYEIARRHP YFYAPELLFF AKRYKAAFTE CCQAADKAAC   180
LLPKLDELRD EGKASSAKQR LKCASLQKFG ERAFKAWAVA RLSQRFPKAE FAEVSKLVTD   240
LTKVHTECCH GDLLECADDR ADLAKYICEN QDSISSKLKE CCEKPLLEKS HCIAEVENDE   300
MPADLPSLAA DFVESKDVCK NYAEAKDVFL GMFLYEYARR HPDYSVVLLL RLAKTYETTL   360
EKCCAAADPH ECYAKVFDEF KPLVEEPQNL IKQNCELFEQ LGEYKFQNAL LVRYTKKVPQ   420
VSTPTLVEVS RNLGKVGSKC CKHPEAKRMP CAEDYLSVVL NQLCVLHEKT PVSDRVTKCC   480
TESLVNRRPC FSALEVDETY VPKEFQAETF TFHADICTLS EKERQIKKQT ALVELVKHKP   540
```

```
KATKEQLKAV MDDFAAFVEK CCKADDKETC FAEEGKKLVA ASQAALGL                588

SEQ ID NO: 15            moltype = AA   length = 588
FEATURE                  Location/Qualifiers
REGION                   1..588
                         note = Synthesized
source                   1..588
                         mol_type = protein
                         organism = synthetic construct
SEQUENCE: 15
AAQDAHKSEV AHRFKDLGEE NFKALVLIAF AQYLQQSPFE DHVKLVNEVT EFAKTCVADE    60
SAENCDKSLH TLFGDKLCTV ATLRETYGEM ADCCAKQEPE RNECFLQHKD DNPNLPRLVR    120
PEVDVMCTAF HDNEETFLKK YLYEIARRHP YFYAPELLFF AKRYKAAFTE CCQAADKAAC    180
LLPKLDELRD EGKASSAKQR LKCASLQKFG ERAFKAWAVA RLSQRFPKAE FAEVSKLVTD    240
LTKVHTECCH GDLLECADDR ADLAKYICEN QDSISSKLKE CCEKPLLEKS HCIAEVENDE    300
MPADLPSLAA DFVESKDVCK NYAEAKDVFL GMFLYEYARR HPDYSVVLLL RLAKTYETTL    360
EKCCAAADPH ECYAKVFDEF KPLVEEPQNL IKQNCELFEQ LGEYKFQNAL LVRYTKKVPQ    420
VSTPTLVEVS RNLGKVGSKC CKHPEAKRMP CAEDYLSVVL NQLCVLHEKT PVSDRVTKCC    480
TESLVNRRPC FSALEVDETY VPKEFQAETF TFHADICTLS EKERQIKKQT ALVELVKHKP    540
KATKEQLKAV MDDFAAFVEK CCKADDKETC FAEEGKKLVA ASQAALGL                588

SEQ ID NO: 16            moltype = AA   length = 589
FEATURE                  Location/Qualifiers
REGION                   1..589
                         note = Synthetic construct
source                   1..589
                         mol_type = protein
                         organism = synthetic construct
SEQUENCE: 16
DAHKSEVAHR FKDLGEENFK ALVLIAFAQY LQQSPFEDHV KLVNEVTEFA KTCVADESAE    60
NCDKSLHTLF GDKLCTVATL RETYGEMADC CAKQEPERNE CFLQHKDDNP NLPRLVRPEV    120
DVMCTAFHDN EETFLKKYLY EIARRHPYFY APELLFFAKR YKAAFTECCQ AADKAACLLP    180
KLDELRDEGK ASSAKQRLKC ASLQKFGERA FKAWAVARLS QRFPKAEFAE VSKLVTDLTK    240
VHTECCHGDL LECADDRADL AKYICENQDS ISSKLKECCE KPLLEKSHCI AEVENDEMPA    300
DLPSLAADFV ESKDVCKNYA EAKDVFLGMF LYEYARRHPD YSVVLLLRLA KTYETTLEKC    360
CAAADPHECY AKVFDEFKPL VEEPQNLIKQ NCELFEQLGE YKFQNALLVR YTKKVPQVST    420
PTLVEVSRNL GKVGSKCCKH PEAKRMPCAE DYLSVVLNQL CVLHEKTPVS DRVTKCCTES    480
LVNRRPCFSA LEVDETYVPK EFQAETFTFH ADICTLSEKE RQIKKQTALV ELVKHKPKAT    540
KEQLKAVMDD FAAFVEKCCK ADDKETCFAE EGKKLVAASQ AALGLAAAL               589

SEQ ID NO: 17            moltype = AA   length = 592
FEATURE                  Location/Qualifiers
REGION                   1..592
                         note = Synthetic construct
source                   1..592
                         mol_type = protein
                         organism = synthetic construct
SEQUENCE: 17
AASDAHKSEV AHRFKDLGEE NFKALVLIAF AQYLQQSPFE DHVKLVNEVT EFAKTCVADE    60
SAENCDKSLH TLFGDKLCTV ATLRETYGEM ADCCAKQEPE RNECFLQHKD DNPNLPRLVR    120
PEVDVMCTAF HDNEETFLKK YLYEIARRHP YFYAPELLFF AKRYKAAFTE CCQAADKAAC    180
LLPKLDELRD EGKASSAKQR LKCASLQKFG ERAFKAWAVA RLSQRFPKAE FAEVSKLVTD    240
LTKVHTECCH GDLLECADDR ADLAKYICEN QDSISSKLKE CCEKPLLEKS HCIAEVENDE    300
MPADLPSLAA DFVESKDVCK NYAEAKDVFL GMFLYEYARR HPDYSVVLLL RLAKTYETTL    360
EKCCAAADPH ECYAKVFDEF KPLVEEPQNL IKQNCELFEQ LGEYKFQNAL LVRYTKKVPQ    420
VSTPTLVEVS RNLGKVGSKC CKHPEAKRMP CAEDYLSVVL NQLCVLHEKT PVSDRVTKCC    480
TESLVNRRPC FSALEVDETY VPKEFQAETF TFHADICTLS EKERQIKKQT ALVELVKHKP    540
KATKEQLKAV MDDFAAFVEK CCKADDKETC FAEEGKKLVA ASQAALGLAA AL           592

SEQ ID NO: 18            moltype = AA   length = 592
FEATURE                  Location/Qualifiers
REGION                   1..592
                         note = Synthetic construct
source                   1..592
                         mol_type = protein
                         organism = synthetic construct
SEQUENCE: 18
AAQDAHKSEV AHRFKDLGEE NFKALVLIAF AQYLQQSPFE DHVKLVNEVT EFAKTCVADE    60
SAENCDKSLH TLFGDKLCTV ATLRETYGEM ADCCAKQEPE RNECFLQHKD DNPNLPRLVR    120
PEVDVMCTAF HDNEETFLKK YLYEIARRHP YFYAPELLFF AKRYKAAFTE CCQAADKAAC    180
LLPKLDELRD EGKASSAKQR LKCASLQKFG ERAFKAWAVA RLSQRFPKAE FAEVSKLVTD    240
LTKVHTECCH GDLLECADDR ADLAKYICEN QDSISSKLKE CCEKPLLEKS HCIAEVENDE    300
MPADLPSLAA DFVESKDVCK NYAEAKDVFL GMFLYEYARR HPDYSVVLLL RLAKTYETTL    360
EKCCAAADPH ECYAKVFDEF KPLVEEPQNL IKQNCELFEQ LGEYKFQNAL LVRYTKKVPQ    420
VSTPTLVEVS RNLGKVGSKC CKHPEAKRMP CAEDYLSVVL NQLCVLHEKT PVSDRVTKCC    480
TESLVNRRPC FSALEVDETY VPKEFQAETF TFHADICTLS EKERQIKKQT ALVELVKHKP    540
KATKEQLKAV MDDFAAFVEK CCKADDKETC FAEEGKKLVA ASQAALGLAA AL           592

SEQ ID NO: 19            moltype = AA   length = 588
```

-continued

```
FEATURE          Location/Qualifiers
REGION           1..588
                 note = Synthetic construct
source           1..588
                 mol_type = protein
                 organism = synthetic construct
SEQUENCE: 19
AASDAHKSEV AHRFKDLGEE NFKALVLIAF AQYLQQCPFE DHVKLVNEVT EFAKTCVADE   60
SAENCDKSLH TLFGDKLCTV ATLRETYGEM ADCCAKQEPE RNECFLQHKD DNPNLPRLVR  120
PEVDVMCTAF HDNEETFLKK YLYEIARRHP YFYAPELLFF AKRYKAAFTE CCQAADKAAC  180
LLPKLDELRD EGKASSAKQR LKCASLQKFG ERAFKAWAVA RLSQRFPKAE FAEVSKLVTD  240
LTKVHTECCH GDLLECADDR ADLAKYICEN QDSISSKLKE CCEKPLLEKS HCIAEVENDE  300
MPADLPSLAA DFVESKDVCK NYAEAKDVFL GMFLYEYARR HPDYSVVLLL RLAKTYETTL  360
EKCCAAADPH ECYAKVFDEF KPLVEEPQNL IKQNCELFEQ LGEYKFQNAL LVRYTKKVPQ  420
VSTPTLVEVS RNLGKVGSKC CKHPEAKRMP CAEDYLSVVL NQLCVLHEKT PVSDRVTKCC  480
TESLVNRRPC FSALEVDETY VPKEFNAETF TFHADICTLS EKERQIKKQT ALVELVKHKP  540
KATKEQLKAV MDDFAAFVEK CCKADDKETC FAEEGKKLVA ASQAALGL               588

SEQ ID NO: 20        moltype = AA   length = 588
FEATURE          Location/Qualifiers
REGION           1..588
                 note = Synthesized
source           1..588
                 mol_type = protein
                 organism = synthetic construct
SEQUENCE: 20
AAQDAHKSEV AHRFKDLGEE NFKALVLIAF AQYLQQCPFE DHVKLVNEVT EFAKTCVADE   60
SAENCDKSLH TLFGDKLCTV ATLRETYGEM ADCCAKQEPE RNECFLQHKD DNPNLPRLVR  120
PEVDVMCTAF HDNEETFLKK YLYEIARRHP YFYAPELLFF AKRYKAAFTE CCQAADKAAC  180
LLPKLDELRD EGKASSAKQR LKCASLQKFG ERAFKAWAVA RLSQRFPKAE FAEVSKLVTD  240
LTKVHTECCH GDLLECADDR ADLAKYICEN QDSISSKLKE CCEKPLLEKS HCIAEVENDE  300
MPADLPSLAA DFVESKDVCK NYAEAKDVFL GMFLYEYARR HPDYSVVLLL RLAKTYETTL  360
EKCCAAADPH ECYAKVFDEF KPLVEEPQNL IKQNCELFEQ LGEYKFQNAL LVRYTKKVPQ  420
VSTPTLVEVS RNLGKVGSKC CKHPEAKRMP CAEDYLSVVL NQLCVLHEKT PVSDRVTKCC  480
TESLVNRRPC FSALEVDETY VPKEFNAETF TFHADICTLS EKERQIKKQT ALVELVKHKP  540
KATKEQLKAV MDDFAAFVEK CCKADDKETC FAEEGKKLVA ASQAALGL               588

SEQ ID NO: 21        moltype = AA   length = 589
FEATURE          Location/Qualifiers
REGION           1..589
                 note = Synthetic construct
source           1..589
                 mol_type = protein
                 organism = synthetic construct
SEQUENCE: 21
DAHKSEVAHR FKDLGEENFK ALVLIAFAQY LQQCPFEDHV KLVNEVTEFA KTCVADESAE   60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGLAAAL              589

SEQ ID NO: 22        moltype = AA   length = 592
FEATURE          Location/Qualifiers
REGION           1..592
                 note = Synthetic construct
source           1..592
                 mol_type = protein
                 organism = synthetic construct
SEQUENCE: 22
AASDAHKSEV AHRFKDLGEE NFKALVLIAF AQYLQQCPFE DHVKLVNEVT EFAKTCVADE   60
SAENCDKSLH TLFGDKLCTV ATLRETYGEM ADCCAKQEPE RNECFLQHKD DNPNLPRLVR  120
PEVDVMCTAF HDNEETFLKK YLYEIARRHP YFYAPELLFF AKRYKAAFTE CCQAADKAAC  180
LLPKLDELRD EGKASSAKQR LKCASLQKFG ERAFKAWAVA RLSQRFPKAE FAEVSKLVTD  240
LTKVHTECCH GDLLECADDR ADLAKYICEN QDSISSKLKE CCEKPLLEKS HCIAEVENDE  300
MPADLPSLAA DFVESKDVCK NYAEAKDVFL GMFLYEYARR HPDYSVVLLL RLAKTYETTL  360
EKCCAAADPH ECYAKVFDEF KPLVEEPQNL IKQNCELFEQ LGEYKFQNAL LVRYTKKVPQ  420
VSTPTLVEVS RNLGKVGSKC CKHPEAKRMP CAEDYLSVVL NQLCVLHEKT PVSDRVTKCC  480
TESLVNRRPC FSALEVDETY VPKEFNAETF TFHADICTLS EKERQIKKQT ALVELVKHKP  540
KATKEQLKAV MDDFAAFVEK CCKADDKETC FAEEGKKLVA ASQAALGLAA AL          592

SEQ ID NO: 23        moltype = AA   length = 592
FEATURE          Location/Qualifiers
REGION           1..592
                 note = Synthetic construct
```

```
source                    1..592
                          mol_type = protein
                          organism = synthetic construct
SEQUENCE: 23
AAQDAHKSEV AHRFKDLGEE NFKALVLIAF AQYLQQCPFE DHVKLVNEVT EFAKTCVADE   60
SAENCDKSLH TLFGDKLCTV ATLRETYGEM ADCCAKQEPE RNECFLQHKD DNPNLPRLVR  120
PEVDVMCTAF HDNEETFLKK YLYEIARRHP YFYAPELLFF AKRYKAAFTE CCQAADKAAC  180
LLPKLDELRD EGKASSAKQR LKCASLQKFG ERAFKAWAVA RLSQRFPKAE FAEVSKLVTD  240
LTKVHTECCH GDLLECADDR ADLAKYICEN QDSISSKLKE CCEKPLLEKS HCIAEVENDE  300
MPADLPSLAA DFVESKDVCK NYAEAKDVFL GMFLYEYARR HPDYSVVLLL RLAKTYETTL  360
EKCCAAADPH ECYAKVFDEF KPLVEEPQNL IKQNCELFEQ LGEYKFQNAL LVRYTKKVPQ  420
VSTPTLVEVS RNLGKVGSKC CKHPEAKRMP CAEDYLSVVL NQLCVLHEKT PVSDRVTKCC  480
TESLVNRRPC FSALEVDETY VPKEFNAETF TFHADICTLS EKERQIKKQT ALVELVKHKP  540
KATKEQLKAV MDDFAAFVEK CCKADDKETC FAEEGKKLVA ASQAALGLAA AL          592

SEQ ID NO: 24           moltype = AA  length = 197
FEATURE                 Location/Qualifiers
REGION                  1..197
                        note = Synthetic construct
source                  1..197
                        mol_type = protein
                        organism = synthetic construct
SEQUENCE: 24
DAHKSEVAHR FKDLGEENFK ALVLIAFAQY LQQSPFEDHV KLVNEVTEFA KTCVADESAE   60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQR                                                 197

SEQ ID NO: 25           moltype = AA  length = 197
FEATURE                 Location/Qualifiers
REGION                  1..197
                        note = Synthetic construct
source                  1..197
                        mol_type = protein
                        organism = synthetic construct
SEQUENCE: 25
GKASSAKQRL KCASLQKFGE RAFKAWAVAR LSQRFPKAEF AEVSKLVTDL TKVHTECCHG   60
DLLECADDRA DLAKYICENQ DSISSKLKEC CEKPLLEKSH CIAEVENDEM PADLPSLAAD  120
FVESKDVCKN YAEAKDVFLG MFLYEYARRH PDYSVVLLLR LAKTYETTLE KCCAAADPHE  180
CYAKVFDEFK PLVEEPQ                                                 197

SEQ ID NO: 26           moltype = AA  length = 205
FEATURE                 Location/Qualifiers
REGION                  1..205
                        note = Synthetic construct
source                  1..205
                        mol_type = protein
                        organism = synthetic construct
SEQUENCE: 26
VEEPQNLIKQ NCELFEQLGE YKFQNALLVR YTKKVPQVST PTLVEVSRNL GKVGSKCCKH   60
PEAKRMPCAE DYLSVVLNQL CVLHEKTPVS DRVTKCCTES LVNRRPCFSA LEVDETYVPK  120
EFQAETFTFH ADICTLSEKE RQIKKQTALV ELVKHKPKAT KEQLKAVMDD FAAFVEKCCK  180
ADDKETCFAE EGKKLVAASQ AALGL                                        205

SEQ ID NO: 27           moltype = AA  length = 197
FEATURE                 Location/Qualifiers
REGION                  1..197
                        note = Synthetic construct
source                  1..197
                        mol_type = protein
                        organism = synthetic construct
SEQUENCE: 27
DAHKSEVAHR FKDLGEENFK ALVLIAFAQY LQQCPFEDHV KLVNEVTEFA KTCVADESAE   60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQR                                                 197

SEQ ID NO: 28           moltype = AA  length = 205
FEATURE                 Location/Qualifiers
REGION                  1..205
                        note = Synthetic construct
source                  1..205
                        mol_type = protein
                        organism = synthetic construct
SEQUENCE: 28
VEEPQNLIKQ NCELFEQLGE YKFQNALLVR YTKKVPQVST PTLVEVSRNL GKVGSKCCKH   60
PEAKRMPCAE DYLSVVLNQL CVLHEKTPVS DRVTKCCTES LVNRRPCFSA LEVDETYVPK  120
EFNAETFTFH ADICTLSEKE RQIKKQTALV ELVKHKPKAT KEQLKAVMDD FAAFVEKCCK  180
ADDKETCFAE EGKKLVAASQ AALGL                                        205
```

-continued

```
SEQ ID NO: 29              moltype = AA  length = 609
FEATURE                    Location/Qualifiers
source                     1..609
                           mol_type = protein
                           organism = Homo sapiens
SEQUENCE: 29
MKWVESIFLI FLLNFTESRT LHRNEYGIAS ILDSYQCTAE ISLADLATIF FAQFVQEATY  60
KEVSKMVKDA LTAIEKPTGD EQSSGCLENQ LPAFLEELCH EKEILEKYGH SDCCSQSEEG  120
RHNCFLAHKK PTPASIPLFQ VPEPVTSCEA YEEDRETFMN KFIYEIARRH PFLYAPTILL  180
WAARYDKIIP SCCKAENAVE CFQTKAATVT KELRESSLLN QHACAVMKNF GTRTFQAITV  240
TKLSQKFTKV NFTEIQKLVL DVAHVHEHCC RGDVLDCLQD GEKIMSYICS QQDTLSNKIT  300
ECCKLTTLER GQCIIHAEND EKPEGLSPNL NRFLGDRDFN QFSSGEKNIF LASFVHEYSR  360
RHPQLAVSVI LRVAKGYQEL LEKCFQTENP LECQDKGEEE LQKYIQESQA LAKRSCGLFQ  420
KLGEYYLQNA FLVAYTKKAP QLTSSELMAI TRKMAATAAT CCQLSEDKLL ACGEGAADII  480
IGHLCIRHEM TPVNPGVGQC CTSSYANRRP CFSSLVVDET YVPPAFSDDK FIFHKDLCQA  540
QGVALQTMKQ EFLINLVKQK PQITEEQLEA VIADFSGLLE KCCQGQEQEV CFAEEGQKLI  600
SKTRAALGV                                                         609

SEQ ID NO: 30              moltype = AA  length = 245
FEATURE                    Location/Qualifiers
REGION                     1..245
                           note = Synthetic construct
source                     1..245
                           mol_type = protein
                           organism = synthetic construct
SEQUENCE: 30
EVQLQQSGPE LVKPGASMKI SCKASGYSFT GYTMKWVKQS HGKNLEWIGL INPYNGGTSY  60
NQKFKGKATL TVDKSSSTAY MELLSLTSDD SAVYYCAREG DYDGAMDYWG QGTSVTVSGG  120
GGSGGGGSGG GGSGGGGSGG SDIQMTQSPS SLSASLGGKV TITCKSSQDI NKYIAWYQHK  180
PGKGPGLLIH YTSTLQPGIP SRFSGSGSGR DYSFSISNLD PENIAAYYCL QYDNLYTFGG  240
GTRLE                                                             245

SEQ ID NO: 31              moltype = AA  length = 319
FEATURE                    Location/Qualifiers
source                     1..319
                           mol_type = protein
                           organism = Homo sapiens
SEQUENCE: 31
AQVLRGTVTD FPGFDERADA ETLRKAMKGL GTDEESILTL LTSRSNAQRQ EISAAFKTLF  60
GRDLLDDLKS ELTGKFEKLI VALMKPSRLY DAYELKHALK GAGTNEKVLT EIIASRTPEE  120
LRAIKQVYEE EYGSSLEDDV VGDTSGYYQR MLVVLLQANR DPDAGIDEAQ VEQDAQALFQ  180
AGELKWGTDE EKFITIFGTR SVSHLRKVFD KYMTISGFQI EETIDRETSG NLEQLLLAVV  240
KSIRSIPAYL AETLYYAMKG AGTDDHTLIR VMVSRSEIDL FNIRKEFRKN FATSLYSMIK  300
GDTSGDYKKA LLLLCGEDD                                              319

SEQ ID NO: 32              moltype = AA  length = 175
FEATURE                    Location/Qualifiers
REGION                     1..175
                           note = Synthetic construct
source                     1..175
                           mol_type = protein
                           organism = synthetic construct
SEQUENCE: 32
QRKRRNTIHE FKKSAKTTLI KIDPALKIKT KKVNTADQCA NRCTRNKGLP FTCKAFVFDK  60
ARKQCLWFPF NSMSSGVKKE FGHEFDLYEN KDYIRNCIIG KGRSYKGTVS ITKSGIKCQP  120
WSSMIPHEHS FLPSSYRGKD LQENYCRNPR GEEGGPWCFT SNPEVRYEVC DIPQC       175

SEQ ID NO: 33              moltype = AA  length = 88
FEATURE                    Location/Qualifiers
REGION                     1..88
                           note = Synthetic construct
source                     1..88
                           mol_type = protein
                           organism = synthetic construct
SEQUENCE: 33
DYIRNCIIGK GRSYKGTVSI TKSGIKCQPW SSMIPHEHSF LPSSYRGKDL QENYCRNPRG  60
EEGGPWCFTS NPEVRYEVCD IPQCSEVE                                     88

SEQ ID NO: 34              moltype = AA  length = 193
FEATURE                    Location/Qualifiers
REGION                     1..193
                           note = Synthetic construct
source                     1..193
                           mol_type = protein
                           organism = synthetic construct
SEQUENCE: 34
QRKRRNTIHE FKKSAKTTLI KIDPALKIKT KKVNTADQCA NRCTRNKGLP FTCKAFVFDK  60
ARKQCLWFPF NSMSSGVKKE FGHEFDLYEN KDYIRNSEVE CMTCNGESYR GLMDHTESGK  120
```

```
ICQRWDHQTP HRHKFLPERY PDKGFDDNYC RNPDGQPRPW CYTLDPHTRW EYCAIKTCAD   180
NTMDTDVPLE TTE                                                       193

SEQ ID NO: 35            moltype = AA  length = 97
FEATURE                  Location/Qualifiers
REGION                   1..97
                         note = Synthetic construct
source                   1..97
                         mol_type = protein
                         organism = synthetic construct
SEQUENCE: 35
SEVECMTCNG ESYRGLMDHT ESGKICQRWD HQTPHRHKFL PERYPDKGFD DNYCRNPDGQ    60
PRPWCYTLDP HTRWEYCAIK TCADNTMDTD VPLETTE                             97

SEQ ID NO: 36            moltype = AA  length = 206
FEATURE                  Location/Qualifiers
REGION                   1..206
                         note = Synthetic construct
source                   1..206
                         mol_type = protein
                         organism = synthetic construct
SEQUENCE: 36
APMAEGGGQN HHEVVKFMDV YQRSYCHPIE TLVDIFQEYP DEIEYIFKPS CVPLMRCGGC    60
CNDEGLECVP TEESNITMQI MRIKPHQGQH IGEMSFLQHN KCECRPKKDR ARQEKKSVRG    120
KGKGQKRKRK KSRYKSWSVY VGARCCLMPW SLPGPHPCGP CSERRKHLFV QDPQTCKCSC    180
KNTDSRCKAR QLELNERTCR CDKPRR                                         206

SEQ ID NO: 37            moltype = AA  length = 430
FEATURE                  Location/Qualifiers
REGION                   1..430
                         note = Synthetic construct
source                   1..430
                         mol_type = protein
                         organism = synthetic construct
SEQUENCE: 37
APMAEGGGQN HHEVVKFMDV YQRSYCHPIE TLVDIFQEYP DEIEYIFKPS CVPLMRCGGC    60
CNDEGLECVP TEESNITMQI MRIKPHQGQH IGEMSFLQHN KCECRPKKDR ARQEKKSVRG    120
KGKGQKRKRK KSRYKSWSVY VGARCCLMPW SLPGPHPCGP CSERRKHLFV QDPQTCKCSC    180
KNTDSRCKAR QLELNERTCR CDKPRRASTG GGGSGGGGSG GGGSAPMAEG GGQNHHEVVK    240
FMDVYQRSYC HPIETLVDIF QEYPDEIEYI FKPSCVPLMR CGGCCNDEGL ECVPTEESNI    300
TMQIMRIKPH QGQHIGEMSF LQHNKCECRP KKDRARQEKK SVRGKGKGQK RKRKKSRYKS    360
WSVYVGARCC LMPWSLPGPH PCGPCSERRK HLFVQDPQTC KCSCKNTDSR CKARQLELNE    420
RTCRCDKPRR                                                          430

SEQ ID NO: 38            moltype = AA  length = 146
FEATURE                  Location/Qualifiers
REGION                   1..146
                         note = Synthetic construct
source                   1..146
                         mol_type = protein
                         organism = synthetic construct
SEQUENCE: 38
PALPEDGGSG AFPPGHFKDP KRLYCKNGGF FLRIHPDGRV DGVREKSDPH IKLQLQAEER    60
GVVSIKGVCA NRYLAMKEDG RLLASKCVTD ECFFFERLES NNYNTYRSRK YTSWYVALKR    120
TGQYKLGSKT GPGQKAILFL PMSAKS                                        146

SEQ ID NO: 39            moltype = AA  length = 65
FEATURE                  Location/Qualifiers
REGION                   1..65
                         note = Synthetic construct
source                   1..65
                         mol_type = protein
                         organism = synthetic construct
SEQUENCE: 39
SHLVKCAEKE KTFCVNGGEC FMVKDLSNPS RYLCKCQPGF TGARCTENVP MKVQNQEKAE    60
ELYQK                                                               65

SEQ ID NO: 40            moltype = AA  length = 222
FEATURE                  Location/Qualifiers
source                   1..222
                         mol_type = protein
                         organism = Homo sapiens
SEQUENCE: 40
SGKKPESAAG SQSPALPPRL KEMKSQESAA GSKLVLRCET SSEYSSLRFK WFKNGNELNR    60
KNKPQNIKIQ KKPGKSELRI NKASLADSGE YMCKVISKLG NDSASANITI VESNEIITGM    120
PASTEGAYVS SESPIRISVS TEGANTSSST STSTTGTSHL VKCAEKEKTF CVNGGECFMV    180
KDLSNPSRYL CKCQPGFTGA RCTENVPMKV QNQEKAEELY QK                       222

SEQ ID NO: 41            moltype = AA  length = 19
```

```
FEATURE                 Location/Qualifiers
REGION                  1..19
                        note = Synthetic construct
source                  1..19
                        mol_type = protein
                        organism = synthetic construct
SEQUENCE: 41
MGWSLILLFL VAVATRVLS                                                          19

SEQ ID NO: 42           moltype = AA  length = 21
FEATURE                 Location/Qualifiers
REGION                  1..21
                        note = Synthetic construct
source                  1..21
                        mol_type = protein
                        organism = synthetic construct
SEQUENCE: 42
MAWRLWWLLL LLLLLWPMVW A                                                       21

SEQ ID NO: 43           moltype = AA  length = 9
FEATURE                 Location/Qualifiers
REGION                  1..9
                        note = Synthetic construct
source                  1..9
                        mol_type = protein
                        organism = synthetic construct
SEQUENCE: 43
GGSHHHHHH                                                                      9

SEQ ID NO: 44           moltype = AA  length = 11
FEATURE                 Location/Qualifiers
REGION                  1..11
                        note = Synthetic construct
source                  1..11
                        mol_type = protein
                        organism = synthetic construct
SEQUENCE: 44
GGSGGHHHHH H                                                                  11

SEQ ID NO: 45           moltype = AA  length = 588
FEATURE                 Location/Qualifiers
REGION                  1..588
                        note = Synthetic construct
source                  1..588
                        mol_type = protein
                        organism = synthetic construct
SEQUENCE: 45
DAHKSEVAHR FKDLGEENFK ALVLIAFAQY LQQSPFEDHV KLVNEVTEFA KTCVADESAE   60
NCDKSLHTLF GDKLCTVATL RETYGEMADC CAKQEPERNE CFLQHKDDNP NLPRLVRPEV   120
DVMCTAFHDN EETFLKKYLY EIARRHPYFY APELLFFAKR YKAAFTECCQ AADKAACLLP   180
KLDELRDEGK ASSAKQRLKC ASLQKFGERA FKAWAVARLS QRFPKAEFAE VSKLVTDLTK   240
VHTECCHGDL LECADDRADL AKYICENQDS ISSKLKECCE KPLLEKSHCI AEVENDEMPA   300
DLPSLAADFV ESKDVCKNYA EAKDVFLGMF LYEYARRHPD YSVVLLLRLA KTYETTLEKC   360
CAAADPHECY AKVFDEFKPL VEEPQNLIKQ NCELFEQLGE YKFQNALLVR YTKKVPQVST   420
PTLVEVSRNL GKVGSKCCKH PEAKRMPCAE DYLSVVLNQL CVLHEKTPVS DRVTKCCTES   480
LVNRRPCFSA LEVDETYVPK EFQAETFTFH ADICTLSEKE RQIKKQTALV ELVKHKPKAT   540
KEQLKAVMDD FAAFVEKCCK ADDKETCFAE EGKKLVAASQ AALGLAAA              588

SEQ ID NO: 46           moltype = AA  length = 592
FEATURE                 Location/Qualifiers
REGION                  1..592
                        note = Synthetic construct
source                  1..592
                        mol_type = protein
                        organism = synthetic construct
SEQUENCE: 46
GADAHKSEVA HRFKDLGEEN FKALVLIAFA QYLQQSPFED HVKLVNEVTE FAKTCVADES   60
AENCDKSLHT LFGDKLCTVA TLRETYGEMA DCCAKQEPER NECFLQHKDD NPNLPRLVRP   120
EVDVMCTAFH DNEETFLKKY LYEIARRHPY FYAPELLFFA KRYKAAFTEC CQAADKAACL   180
LPKLDELRDE GKASSAKQRL KCASLQKFGE RAFKAWAVAR LSQRFPKAEF AEVSKLVTDL   240
TKVHTECCHG DLLECADDRA DLAKYICENQ DSISSKLKEC CEKPLLEKSH CIAEVENDEM   300
PADLPSLAAD FVESKDVCKN YAEAKDVFLG MFLYEYARRH PDYSVVLLLR LAKTYETTLE   360
KCCAAADPHE CYAKVFDEFK PLVEEPQNLI KQNCELFEQL GEYKFQNALL VRYTKKVPQV   420
STPTLVEVSR NLGKVGSKCC KHPEAKRMPC AEDYLSVVLN QLCVLHEKTP VSDRVTKCCT   480
ESLVNRRPCF SALEVDETYV PKEFQAETFT FHADICTLSE KERQIKKQTA LVELVKHKPK   540
ATKEQLKAVM DDFAAFVEKC CKADDKETCF AEEGKKLVAA SQAALGLAAA LQ           592

SEQ ID NO: 47           moltype = AA  length = 592
FEATURE                 Location/Qualifiers
```

```
REGION                  1..592
                        note = Synthetid construct
source                  1..592
                        mol_type = protein
                        organism = synthetic construct
SEQUENCE: 47
GADAHKSEVA HRFKDLGEEN FKALVLIAFA QYLQQSPFED HVKLVNEVTE FAKTCVADES      60
AENCDKSLHT LFGDKLCTVA TLRETYGEMA DCCAKQEPER NECFLQHKDD NPNLPRLVRP     120
EVDVMCTAFH DNEETFLKKY LYEIARRHPY FYAPELLFFA KRYKAAFTEC CQAADKAACL     180
LPKLDELRDE GKASSAKQRL KCASLQKFGE RAFKAWAVAR LSQRFPKAEF AEVSKLVTDL     240
TKVHTECCHG DLLECADDRA DLAKYICENQ DSISSKLKEC CEKPLLEKSH CIAEVENDEM     300
PADLPSLAAD FVESKDVCKN YAEAKDVFLG MFLYEYARRH PDYSVVLLLR LAKTYETTLE     360
KCCAAADPHE CYAKVFDEFK PLVEEPQNLI KQNCELFEQL GEYKFQNALL VRYTKKVPQV     420
STPTLVEVSR NLGKVGSKCC KHPEAKRMPC AEDYLSVVLN QLCVLHEKTP VSDRVTKCCT     480
ESLVNRRPCF SALEVDETYV PKEFQAETFT FHADICTLSE KERQIKKQTA LVELVKHKPK     540
ATKEQLKAVM DDFAAFVEKC CKADDKETCF AEEGKKLVAA SQAALGLAAA TG            592

SEQ ID NO: 48           moltype = AA  length = 592
FEATURE                 Location/Qualifiers
REGION                  1..592
                        note = Synthetic construct
source                  1..592
                        mol_type = protein
                        organism = synthetic construct
SEQUENCE: 48
ASDAHKSEVA HRFKDLGEEN FKALVLIAFA QYLQQSPFED HVKLVNEVTE FAKTCVADES      60
AENCDKSLHT LFGDKLCTVA TLRETYGEMA DCCAKQEPER NECFLQHKDD NPNLPRLVRP     120
EVDVMCTAFH DNEETFLKKY LYEIARRHPY FYAPELLFFA KRYKAAFTEC CQAADKAACL     180
LPKLDELRDE GKASSAKQRL KCASLQKFGE RAFKAWAVAR LSQRFPKAEF AEVSKLVTDL     240
TKVHTECCHG DLLECADDRA DLAKYICENQ DSISSKLKEC CEKPLLEKSH CIAEVENDEM     300
PADLPSLAAD FVESKDVCKN YAEAKDVFLG MFLYEYARRH PDYSVVLLLR LAKTYETTLE     360
KCCAAADPHE CYAKVFDEFK PLVEEPQNLI KQNCELFEQL GEYKFQNALL VRYTKKVPQV     420
STPTLVEVSR NLGKVGSKCC KHPEAKRMPC AEDYLSVVLN QLCVLHEKTP VSDRVTKCCT     480
ESLVNRRPCF SALEVDETYV PKEFQAETFT FHADICTLSE KERQIKKQTA LVELVKHKPK     540
ATKEQLKAVM DDFAAFVEKC CKADDKETCF AEEGKKLVAA SQAALGLAAA LQ            592

SEQ ID NO: 49           moltype = AA  length = 592
FEATURE                 Location/Qualifiers
REGION                  1..592
                        note = Synthetic construct
source                  1..592
                        mol_type = protein
                        organism = synthetic construct
SEQUENCE: 49
ASDAHKSEVA HRFKDLGEEN FKALVLIAFA QYLQQSPFED HVKLVNEVTE FAKTCVADES      60
AENCDKSLHT LFGDKLCTVA TLRETYGEMA DCCAKQEPER NECFLQHKDD NPNLPRLVRP     120
EVDVMCTAFH DNEETFLKKY LYEIARRHPY FYAPELLFFA KRYKAAFTEC CQAADKAACL     180
LPKLDELRDE GKASSAKQRL KCASLQKFGE RAFKAWAVAR LSQRFPKAEF AEVSKLVTDL     240
TKVHTECCHG DLLECADDRA DLAKYICENQ DSISSKLKEC CEKPLLEKSH CIAEVENDEM     300
PADLPSLAAD FVESKDVCKN YAEAKDVFLG MFLYEYARRH PDYSVVLLLR LAKTYETTLE     360
KCCAAADPHE CYAKVFDEFK PLVEEPQNLI KQNCELFEQL GEYKFQNALL VRYTKKVPQV     420
STPTLVEVSR NLGKVGSKCC KHPEAKRMPC AEDYLSVVLN QLCVLHEKTP VSDRVTKCCT     480
ESLVNRRPCF SALEVDETYV PKEFQAETFT FHADICTLSE KERQIKKQTA LVELVKHKPK     540
ATKEQLKAVM DDFAAFVEKC CKADDKETCF AEEGKKLVAA SQAALGLAAA TG            592

SEQ ID NO: 50           moltype = AA  length = 157
FEATURE                 Location/Qualifiers
REGION                  1..157
                        note = Synthetic construct
source                  1..157
                        mol_type = protein
                        organism = synthetic construct
SEQUENCE: 50
GTMAAGSITT LPALPEDGGS GAFPPGHFKD PKRLYCKNGG FFLRIHPDGR VDGVREKSDP      60
HIKLQLQAEE RGVVSIKGVC ANRYLAMKED GRLLASKCVT DECFFFERLE SNNYNTYRSR     120
KYTSWYVALK RTGQYKLGSK TGPGQKAILF LPMSAKS                             157

SEQ ID NO: 51           moltype = AA  length = 463
FEATURE                 Location/Qualifiers
REGION                  1..463
                        note = Synthetic construct
source                  1..463
                        mol_type = protein
                        organism = synthetic construct
SEQUENCE: 51
QRKRRNTIHE FKKSAKTTLI KIDPALKIKT KKVNTADQCA NRCTRNKGLP FTCKAFVFDK      60
ARKQCLWFPF NSMSSGVKKE FGHEFDLYEN KDYIRNCIIG KGRSYKGTVS ITKSGIKCQP     120
WSSMIPHEHS FLPSSYRGKD LQENYCRNPR GEEGGPWCFT SNPEVRYEVC DIPQCSEVEC     180
MTCNGESYRG LMDHTESGKI CQRWDHQTPH RHKFLPERYP DKGFDDNYCR NPDGQPRPWC     240
```

```
YTLDPHTRWE YCAIKTCADN TMNDTDVPLE TTECIQGQGE GYRGTVNTIW NGIPCQRWDS    300
QYPHEHDMTP ENFKCKDLRE NYCRNPDGSE SPWCFTTDPN IRVGYCSQIP NCDMSHGQDC    360
YRGNGKNYMG NLSQTRSGLT CSMWDKNMED LHRHIFWEPD ASKLNENYCR NPDDDAHGPW    420
CYTGNPLIPW DYCPISRCEG DTTPTIVNLD HPVISCAKTK QLR                     463

SEQ ID NO: 52              moltype = AA   length = 84
FEATURE                    Location/Qualifiers
REGION                     1..84
                           note = Synthetic construct
source                     1..84
                           mol_type = protein
                           organism = synthetic construct
SEQUENCE: 52
DYIRNCIIGK GRSYKGTVSI TKSGIKCQPW SSMIPHEHSF LPSSYRGKDL QENYCRNPRG    60
EEGGPWCFTS NPEVRYEVCD IPQC                                          84

SEQ ID NO: 53              moltype = AA   length = 178
FEATURE                    Location/Qualifiers
REGION                     1..178
                           note = Synthetic construct
source                     1..178
                           mol_type = protein
                           organism = synthetic construct
SEQUENCE: 53
QRKRRNTIHE FKKSAKTTLI KIDPALKIKT KKVNTADQCA NRCTRNKGLP FTCKAFVFDK    60
ARKQCLWFPF NSMSSGVKKE FGHEFDLYEN KDYIRNSEVE CMTCNGESYR GLMDHTESGK    120
ICQRWDHQTP HRHKFLPERY PDKGFDDNYC RNPDGQPRPW CYTLDPHTRW EYCAIKTC     178

SEQ ID NO: 54              moltype = AA   length = 82
FEATURE                    Location/Qualifiers
REGION                     1..82
                           note = Synthetic construct
source                     1..82
                           mol_type = protein
                           organism = synthetic construct
SEQUENCE: 54
SEVECMTCNG ESYRGLMDHT ESGKICQRWD HQTPHRHKFL PERYPDKGFD DNYCRNPDGQ    60
PRPWCYTLDP HTRWEYCAIK TC                                           82

SEQ ID NO: 55              moltype = AA   length = 245
FEATURE                    Location/Qualifiers
REGION                     1..245
                           note = Synthetic constrruct
source                     1..245
                           mol_type = protein
                           organism = synthetic construct
SEQUENCE: 55
SERKEGRGKG KGKKKERGSG KKPESAAGSQ SPALPPRLKE MKSQESAAGS KLVLRCETSS    60
EYSSLRFKWF KNGNELNRKN KPQNIKIQKK PGKSELRINK ASLADSGEYM CKVISKLGND    120
SASANITIVE SNEIITGMPA STEGAYVSSE SPIRISVSTE GANTSSSTST STTGTSHLVK    180
CAEKEKTFCV NGGECFMVKD LSNPSRYLCK CPNEFTGDRC QNYVMASFYK HLGIEFMEAE    240
ELYQK                                                              245

SEQ ID NO: 56              moltype = AA   length = 71
FEATURE                    Location/Qualifiers
REGION                     1..71
                           note = Synthetic construct
source                     1..71
                           mol_type = protein
                           organism = synthetic construct
SEQUENCE: 56
TSHLVKCAEK EKTFCVNGGE CFMVKDLSNP SRYLCKCPNE FTGDRCQNYV MASFYKHLGI    60
EFMEAEELYQ K                                                       71

SEQ ID NO: 57              moltype = AA   length = 815
FEATURE                    Location/Qualifiers
source                     1..815
                           mol_type = protein
                           organism = Homo sapiens
SEQUENCE: 57
NNHYDKILAH SRIRGRDQGP NVCALQQILG TKKKYFSTCK NWYKKSICGQ KTTVLYECCP    60
GYMRMEGMKG CPAVLPIDHV YGTLGIVGAT TTQRYSDASK LREEIEGKGS FTYFAPSNEA    120
WDNLDSDIRR GLESNVNVEL LNALHSHMIN KRMLTKDLKN GMIIPSMYNN LGLFINHYPN    180
GVVTVNCARI IHGNQIATNG VVHVIDRVLT QIGTSIQDFI EAEDDLSSFR AAAITSDILE    240
ALGRDGHFTL FAPTNEAFEK LPRGVLERIM GDKVASEALM KYHILNTLQC SESIMGGAVF    300
ETLEGNTIEI GCDGDSITVN GIKMVNKKDI VTNNGVIHLI DQVLIPDSAK QVIELAGKQQ    360
TTFTDLVAQL GLASALRPDG EYTLLAPVNN AFSDDTLSMD QRLLKLILQN HILKVKVGLN    420
ELYNGQILET IGGKQLRVFV YRTAVCIENS CMEKGSKQGR NGAIHIFREI IKPAEKSLHE    480
KLKQDKRFST FLSLLEAADL KELLTQPGDW TLFVPTNDAF KGMTSEEKEI LIRDKNALQN    540
```

-continued

```
IILYHLTPGV FIGKGFEPGV TNILKTTQGS KIFLKEVNDT LLVNELKSKE SDIMTTNGVI  600
HVVDKLLYPA DTPVGNDQLL EILNKLIKYI QIKFVRGSTF KEIPVTVYTT KIITKVVEPK  660
IKVIEGSLQP IIKTEGPTLT KVKIEGEPEF RLIKEGETIT EVIHGEPIIK KYTKIIDGVP  720
VEITEKETRE ERIITGPEIK YTRISTGGGE TEETLKKLLQ EEVTKVTKFI EGGDGHLFED  780
EEIKRLLQGD TPVRKLQANK KVQGSRRRLR EGRSQ                              815

SEQ ID NO: 58              moltype = AA  length = 648
FEATURE                   Location/Qualifiers
REGION                    1..648
                          note = Synthetic construct
source                    1..648
                          mol_type = protein
                          organism = synthetic construct
SEQUENCE: 58
NNHYDKILAH SRIRGRDQGP NVCALQQILG TKKKYFSTCK NWYKKSICGQ KTTVLYECCP  60
GYMRMEGMKG CPAVLPIDHV YGTLGIVGAT TTQRYSDASK LREEIEGKGS FTYFAPSNEA  120
WDNLDSDIRR GLESNVNVEL LNALHSHMIN KRMLTKDLKN GMIIPSMYNN LGLFINHYPN  180
GVVTVNCARI IHGNQIATNG VVHVIDRVLT QIGTSIQDFI EAEDDLSSFR AAAITSDILE  240
ALGRDGHFTL FAPTNEAFEK LPRGVLERIM GDKVASEALM KYHILNTLQC SESIMGGAVF  300
ETLEGNTIEI GCDGDSITVN GIKMVNKKDI VTNNGVIHLI DQVLIPDSAK QVIELAGKQQ  360
TTFTDLVAQL GLASALRPDG EYTLLAPVNN AFSDDTLSMD QRLLKLILQN HILKVKVGLN  420
ELYNGQILET IGGKQLRVFV YRTAVCIENS CMEKGSKQGR NGAIHIFREI IKPAEKSLHE  480
KLKQDKRFST FLSLLEAADL KELLTQPGDW TLFVPTNDAF KGMTSEEKEI LIRDKNALQN  540
IILYHLTPGV FIGKGFEPGV TNILKTTQGS KIFLKEVNDT LLVNELKSKE SDIMTTNGVI  600
HVVDKLLYPA DTPVGNDQLL EILNKLIKYI QIKFVRGSTF KEIPVTVY              648

SEQ ID NO: 59              moltype = AA  length = 114
FEATURE                   Location/Qualifiers
REGION                    1..114
                          note = Synthetic construct
source                    1..114
                          mol_type = protein
                          organism = synthetic construct
SEQUENCE: 59
QAKHKQRKRL KSSCKRHPLY VDFSDVGWND WIVAPPGYHA FYCHGECPFP LADHLNSTNH  60
AIVQTLVNSV NSKIPKACCV PTELSAISML YLDENEKVVL KNYQDMVVEG CGCR        114

SEQ ID NO: 60              moltype = AA  length = 223
FEATURE                   Location/Qualifiers
REGION                    1..223
                          note = Synthetic construct
source                    1..223
                          mol_type = protein
                          organism = synthetic construct
SEQUENCE: 60
KSSCKRHPLY VDFSDVGWND WIVAPPGYHA FYCHGECPFP LADHLNSTNH AIVQTLVNSV  60
NSKIPKACCV PTELSAISML YLDENEKVVL KNYQDMVVEG CGCRGGGSGG GSGGGSGGGK  120
SSCKRHPLYV DFSDVGWNDW IVAPPGYHAF YCHGECPFPL ADHLNSTNHA IVQTLVNSVN  180
SKIPKACCVP TELSAISMLY LDENEKVVLK NYQDMVVEGC GCR                   223

SEQ ID NO: 61              moltype = AA  length = 188
FEATURE                   Location/Qualifiers
REGION                    1..188
                          note = Synthetic construct
source                    1..188
                          mol_type = protein
                          organism = synthetic construct
SEQUENCE: 61
MSPLLRRLLL AALLQLAPAQ APVSQPDAPG HQRKVVSWID VYTRATCQPR EVVVPLTVEL  60
MGTVAKQLVP SCVTVQRCGG CCPDDGLECV PTGQHQVRMQ ILMIRYPSSQ LGEMSLEEHS  120
QCECRPKKKD SAVKPDSPRP LCPRCTQHHQ RPDPRTCRRR CRRRSFLRCQ GRGLELNPDT  180
CRCRKLRR                                                           188

SEQ ID NO: 62              moltype = AA  length = 167
FEATURE                   Location/Qualifiers
REGION                    1..167
                          note = Synthetic construct
source                    1..167
                          mol_type = protein
                          organism = synthetic construct
SEQUENCE: 62
PVSQPDAPGH QRKVVSWIDV YTRATCQPRE VVVPLTVELM GTVAKQLVPS CVTVQRCGGC  60
CPDDGLECVP TGQHQVRMQI LMIRYPSSQL GEMSLEEHSQ CECRPKKKDS AVKPDSPRPL  120
CPRCTQHHQR PDPRTCRRRC RRRSFLRCQG RGLELNPDTC RCRKLRR               167

SEQ ID NO: 63              moltype = AA  length = 131
FEATURE                   Location/Qualifiers
REGION                    1..131
                          note = Synthetic construct
```

```
source                  1..131
                        mol_type = protein
                        organism = synthetic construct
SEQUENCE: 63
MSPLLRRLLL AALLQLAPAQ APVSQPDAPG HQRKVVSWID VYTRATCQPR EVVVPLTVEL   60
MGTVAKQLVP SCVTVQRCGG CCPDDGLECV PTGQHQVRMQ ILMIRYPSSQ LGEMSLEEHS  120
QCECRPKKKD S                                                        131

SEQ ID NO: 64           moltype = AA  length = 110
FEATURE                 Location/Qualifiers
REGION                  1..110
                        note = Synthetic construct
source                  1..110
                        mol_type = protein
                        organism = synthetic construct
SEQUENCE: 64
PVSQPDAPGH QRKVVSWIDV YTRATCQPRE VVVPLTVELM GTVAKQLVPS CVTVQRCGGC   60
CPDDGLECVP TGQHQVRMQI LMIRYPSSQL GEMSLEEHSQ CECRPKKKDS             110

SEQ ID NO: 65           moltype = AA  length = 205
FEATURE                 Location/Qualifiers
REGION                  1..205
                        note = Synthetic construct
source                  1..205
                        mol_type = protein
                        organism = synthetic construct
SEQUENCE: 65
GEEPQNLIKQ NCELFEQLGE YKFQNALLVR YTKKVPQVST PTLVEVSRNL GKVGSKCCKH   60
PEAKRMPCAE DYLSVVLNQL CVLHEKTPVS DRVTKCCTES LVNRRPCFSA LEVDETYVPK  120
EFNAETFTFH ADICTLSEKE RQIKKQTALV ELVKHKPKAT KEQLKAVMDD FAAFVEKCCK  180
ADDKETCFAE EGKKLVAASQ AALGL                                        205

SEQ ID NO: 66           moltype = AA  length = 458
FEATURE                 Location/Qualifiers
REGION                  1..458
                        note = Synthetic construct
source                  1..458
                        mol_type = protein
                        organism = synthetic construct
SEQUENCE: 66
LERGRDYEKN KVCKEFSHLG KEDFTSLSLV LYSRKFPSGT FEQVSQLVKE VVSLTEACCA   60
EGADPDCYDT RTSALSAKSC ESNSPFPVHP GTAECCTKEG LERKLCMAAL KHQPQEFPTY  120
VEPTNDEICE AFRKDPKEYA NQFMWEYSTN YGQAPLSLLV SYTKSYLSMV GSCCTSASPT  180
VCFLKERLQL KHLSLLTTLS NRVCSQYAAY GEKKSRLSNL IKLAQKVPTA DLEDVLPLAE  240
DITNILSKCC ESASEDCMAK ELPEHTVKLC DTLSTKNSKF EDCCQEKTAM DVFVCTYFMP  300
AAQLPELPDV ELPTNKDVCD PGNTKVMDKY TFELSRRTHL PEVFLSKVLE PTLKSLGECC  360
DVEDSTTCFN AKGPLLKKEL SSFIDKGQEL CADYSENTFT EYKKKLAERL KAKLPDATPK  420
ELAKLVNKRS DFASNCCSIN SPPLYCDSEI DAELKNIL                          458

SEQ ID NO: 67           moltype = AA  length = 205
FEATURE                 Location/Qualifiers
REGION                  1..205
                        note = Synthetic construct
source                  1..205
                        mol_type = protein
                        organism = synthetic construct
SEQUENCE: 67
GEEPQNLIKQ NCELFEQLGE YKFQNALLVR YTKKVPQVST PTLVEVSRNL GKVGSKCCKH   60
PEAKRMPCAE DYLSVVLNQL CVLHEKTPVS DRVTKCCTES LVNRRPCFSA LEVDETYVPK  120
EFQAETFTFH ADICTLSEKE RQIKKQTALV ELVKHKPKAT KEQLKAVMDD FAAFVEKCCK  180
ADDKETCFAE EGKKLVAASQ AALGL                                        205

SEQ ID NO: 68           moltype = AA  length = 591
FEATURE                 Location/Qualifiers
REGION                  1..591
                        note = Synthetic construct
source                  1..591
                        mol_type = protein
                        organism = synthetic construct
SEQUENCE: 68
RTLHRNEYGI ASILDSYQCT AEISLADLAT IFFAQFVQEA TYKEVSKMVK DALTAIEKPT   60
GDEQSSGCLE NQLPAFLEEL CHEKEILEKY GHSDCCSQSE EGRHNCFLAH KKPTPASIPL  120
FQVPEPVTSC EAYEEDRETF MNKFIYEIAR RHPFLYAPTI LLWAARYDKI IPSCCKAENA  180
VECFQTKAAT VTKELRESSL LNQHACAVMK NFGTRTFQAI TVTKLSQKFT KVNFTEIQKL  240
VLDVAHVHEH CCRGDVLDCL QDGEKIMSYI CSQQDTLSNK ITECCKLTTL ERGQCIIHAE  300
NDEKPEGLSP NLNRFLGDRD FNQFSSGEKN IFLASFVHEY SRRHPQLAVS VILRVAKGYQ  360
ELLEKCFQTE NPLECQDKGE EELQKYIQES QALAKRSCGL FQKLGEYYLQ NAFLVAYTKK  420
APQLTSSELM AITRKMAATA ATCCQLSEDK LLACGEGAAD IIIGHLCIRH EMTPVNPGVG  480
QCCTSSYANR RPCFSSLVVD ETYVPPAFSD DKFIFHKDLC QAQGVALQTM KQEFLINLVK  540
```

```
QKPQITEEQL EAVIADFSGL LEKCCQGQEQ EVCFAEEGQK LISKTRAALG V          591

SEQ ID NO: 69              moltype = AA   length = 591
FEATURE                    Location/Qualifiers
REGION                     1..591
                           note = Synthetic construct
source                     1..591
                           mol_type = protein
                           organism = synthetic construct
SEQUENCE: 69
RTLHRNEYGI ASILDSYQCT AEISLADLAT IFFAQFVQEA TYKEVSKMVK DALTAIEKPT  60
GDEQSSGCLE NQLPAFLEEL CHEKEILEKY GHSDCCSQSE EGRHNCFLAH KKPTPASIPL  120
FQVPEPVTSC EAYEEDRETF MNKFIYEIAR RHPFLYAPTI LLWAARYDKI IPSCCKAENA  180
VECFQTKAAT VTKELRESSL LNQHACAVMK NFGTRTFQAI TVTKLSQKFT KVQFTEIQKL  240
VLDVAHVHEH CCRGDVLDCL QDGEKIMSYI CSQQDTLSNK ITECCKLTTL ERGQCIIHAE  300
NDEKPEGLSP NLNRFLGDRD FNQFSSGEKN IFLASFVHEY SRRHPQLAVS VILRVAKGYQ  360
ELLEKCFQTE NPLECQDKGE EELQKYIQES QALAKRSCGL FQKLGEYYLQ NAFLVAYTKK  420
APQLTSSELM AITRKMAATA ATCCQLSEDK LLACGEGAAD IIIGHLCIRH EMTPVNPGVG  480
QCCTSSYANR RPCFSSLVVD ETYVPPAFSD DKFIFHKDLC QAQGVALQTM KQEFLINLVK  540
QKPQITEEQL EAVIADFSGL LEKCCQGQEQ EVCFAEEGQK LISKTRAALG V          591

SEQ ID NO: 70              moltype = AA   length = 107
FEATURE                    Location/Qualifiers
REGION                     1..107
                           note = Synthetic construct
source                     1..107
                           mol_type = protein
                           organism = synthetic construct
SEQUENCE: 70
DIQMTQSPSS LSASVGDRVT ITCRASQWIG SQLSWYQQKP GKAPKLLIMW RSSLQSGVPS  60
RFSGSGSGTD FTLTISSLQP EDFATYYCAQ GAALPRTFGQ GTKVEIK              107

SEQ ID NO: 71              moltype = AA   length = 482
FEATURE                    Location/Qualifiers
REGION                     1..482
                           note = Synthetic construct
source                     1..482
                           mol_type = protein
                           organism = synthetic construct
SEQUENCE: 71
EPKSSDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GGGGGSGGGG  240
SGGGGSGGGG SEPKSSDKTH TCPPCPAPEL LGGPSVFLFP PKPKDTLMIS RTPEVTCVVV  300
DVSHEDPEVK FNWYVDGVEV HNAKTKPREE QYQSTYRVVS VLTVLHQDWL NGKEYKCKVS  360
NKALPAPIEK TISKAKGQPR EPQVYTLPPS RDELTKNQVS LTCLVKGFYP SDIAVEWESN  420
GQPENNYKTT PPVLDSDGSF FLYSKLTVDK SRWQQGNVFS CSVMHEALHN HYTQKSLSLS  480
PG                                                               482

SEQ ID NO: 72              moltype = AA   length = 128
FEATURE                    Location/Qualifiers
REGION                     1..128
                           note = Synthetic construct
source                     1..128
                           mol_type = protein
                           organism = synthetic construct
SEQUENCE: 72
EKLGKLQYSL DYDFQNNQLL VGIIQAAELP ALDMGGTSDP YVKVFLLPDK KKKFETKVHR  60
KTLNPVFNEQ FTFKVPYSEL GGKTLVMAVY DFDRFSKHDI IGEFKVPMNT VDFGHVTEEW  120
RDLQSAEK                                                          128

SEQ ID NO: 73              moltype = AA   length = 244
FEATURE                    Location/Qualifiers
REGION                     1..244
                           note = Synthetic construct
source                     1..244
                           mol_type = protein
                           organism = synthetic construct
SEQUENCE: 73
LESGGGLVQP GGSLRLSCAG SGFTFSSYAM SWVRQAPGKG LEWVSSISGS GGSTYYADSV  60
KGRFTISRDN SKKTLYLQMN SLRAEDTAVY YCARKRGRTT VSWGLVYFDY WGQGTVVTVS  120
SGGGGSGGGG SGGGGSGGSE LTQSPGTLSL SPGERATLSC RASHSVSRAY LAWYQQKPGQ  180
APRLLIYGTS SRATGIPDRF SGSGSGTDFT LTISRLEPED FAVYYCQQYG GSPWFGQGTK  240
VELK                                                             244

SEQ ID NO: 74              moltype = AA   length = 128
FEATURE                    Location/Qualifiers
REGION                     1..128
```

```
                              note = Synthetic construct
source                        1..128
                              mol_type = protein
                              organism = synthetic construct
SEQUENCE: 74
EKLGKLQYSL DYDFQNNQLL VGIIQAAELP ALDMGGTSNP YVKVFLLPDK KKKFETKVHR  60
KTLNPVFNEQ FTFKVPYSEL GGKTLVMAVY NFDRFSKHDI IGEFKVPMNT VDFGHVTEEW  120
RDLQSAEK                                                            128

SEQ ID NO: 75                 moltype = AA   length = 254
FEATURE                       Location/Qualifiers
REGION                        1..254
                              note = Synthetic construct
source                        1..254
                              mol_type = protein
                              organism = synthetic construct
SEQUENCE: 75
QVQLVQSGAE VKKPGESLKI SCKGSGYSFT SYWIAWVRQM PGKGLEYMGL IYPGDSDTKY  60
SPSFQGQVTI SVDKSVSTAY LQWSSLKPSD SAVYFCARAD VGYCTDRTCA KAPAWLGVWG  120
QGTLVTVSSG GGGSSGGGSG GGGSQSVLTQ PPSVSAAPGQ KVTISCSGSS SNIGNNYVSW  180
YQQLPGTAPK LLIYDHTNRP AGVPDRFSGS KSGTSASLAI SGFRSEDEAD YYCASWDYTL  240
SGWVFGGGTK LTVL                                                    254

SEQ ID NO: 76                 moltype = AA   length = 252
FEATURE                       Location/Qualifiers
REGION                        1..252
                              note = Synthetic construct
source                        1..252
                              mol_type = protein
                              organism = synthetic construct
SEQUENCE: 76
EVQLVESGGG LVQPGGSLRL SCSASGFTFS SYAMHWVRQA PGKGLEYVSA ISSNGGSTYY  60
ADSVKGRFTI SRDNSKNTLY LQMSSLRAED TAVYYCVKIT GAYSSSWYYD NWFDPWGQGT  120
LVTVSSGGGG SGGGGSGGGG SGGSSYELTQ PPSVSVSPGQ TASITCSGDK LGDKYACWYQ  180
QKPGQSPVLV IYQDSKRPSG IPERFSGSNS GNTATLTISG TQAMDEADYY CQAWDSSTAV  240
FGGGTKLTVL GQ                                                      252

SEQ ID NO: 77                 moltype = AA   length = 247
FEATURE                       Location/Qualifiers
REGION                        1..247
                              note = Synthetic construct
source                        1..247
                              mol_type = protein
                              organism = synthetic construct
SEQUENCE: 77
EVQLVESGGG VVQPGGSLRL FCAASGFTFD GYAMHWVRQA PGKGLEWVSL ISGDGGSTYY  60
ADSVKGRFTI SRDNSKNSLY LQMNSLRAED TALYYCAKGK VTTIYDRFDI WGQGTMVTVS  120
SGGGGSGGGG SGGGGSGGSD IQMTQSPSSL SASVGDRVTI TCRASQGISN YLAWYQQKPG  180
KVPKSLIYAA STLQSGVPSR FSGSGSGTDF TLTISSLQPE DVATYYCQKY NSAPRTFGPG  240
TKLEIKR                                                            247

SEQ ID NO: 78                 moltype = AA   length = 243
FEATURE                       Location/Qualifiers
REGION                        1..243
                              note = Synthetic construct
source                        1..243
                              mol_type = protein
                              organism = synthetic construct
SEQUENCE: 78
EVQLVESGGG LVQPGGSLRL SCAASGFTFS SYSMNWVRQA PGKGLEWVSY ISSTIITIYY  60
ADSVKGRFTI SRDNAKNSLY LQMNSLRAED TAVYYCARGD SSEAFDIWGQ GTMVTVSLGG  120
GGSGGGGSGG GGSGGSSYEL TQPSSVSVSP GQTARITCSG DLLAKKYARW FQQKPGQAPI  180
LVIFKDTERP SGIPERFSGS SSGTTVTLTI SGAQVEDEAD YYCYSASDNN GRVFGGGTKL  240
TVL                                                                243

SEQ ID NO: 79                 moltype = AA   length = 256
FEATURE                       Location/Qualifiers
REGION                        1..256
                              note = Synthetic construct
source                        1..256
                              mol_type = protein
                              organism = synthetic construct
SEQUENCE: 79
EVQLVESGGG LVKPGGSLRL SCAASGFTFS KAWMSWVRQA PGKGLEWVGR IKSKTDGGTT  60
DYAAPVKGRL TISRDSSKNT LYLRMNSLKT EDTAVYYCTT GITMIIVVIT TSSKRTSFEY  120
WGQGTLVTVS SGGGGSGGGG SGGGGSGGSD IQMTQSPSSL SASVGDRVTI TCRASQSISN  180
YLNWYQQKPG KAPNLLIYAA SSLQSGVPSR FSGSGSGTDF TLTISGLQAE DFATYYCQQS  240
YSALTFGPGT KVDIRR                                                  256
```

-continued

```
SEQ ID NO: 80            moltype = AA  length = 229
FEATURE                  Location/Qualifiers
REGION                   1..229
                         note = Synthetic construct
source                   1..229
                         mol_type = protein
                         organism = synthetic construct
SEQUENCE: 80
GLVKPSQTLS LTCAISGDSV SSNSAAWNCI RPVPSRGLEW LGRTTYRSKW YNDYAVSVKS  60
RITINPDTSK NQFSLQLNSV TPEDTAVYYC ASTTLNWGYE KDDAFDIWGQ GTMVTVSSGG  120
GGSGGGGSGG GGSGGGSQAVL TQPASLSASP GASASLTCTL RSGINVCTPR IYWQGSGVPS  180
RFSGSKNASA NAGILLISGL QSEDEADYYC MIWHSSALVF GGGTKLTVL              229

SEQ ID NO: 81            moltype = AA  length = 319
FEATURE                  Location/Qualifiers
REGION                   1..319
                         note = Synthetic construct
source                   1..319
                         mol_type = protein
                         organism = synthetic construct
SEQUENCE: 81
AQVLRGTVTD FPGFDERADA ETLRKAMKGL GTDEESILTL LTSRSNAQRQ EISAAFKTLF  60
GRDLLDDLKS ELTGKFEKLI VALMKPSRLY DAYELKHALK GAGTNEKVLT EIIASRTPEE  120
LRAIKQVYEE EYGSSLEDDV VGDTSGYYQR MLVVLLQANR DPDAGIDEAQ VEQDAQALFQ  180
AGELKWGTDE EKFITIFGTR SVSHLRKVFD KYMTISGFQI EETIDRETSG NLEQLLLAVV  240
KSIRSIPAYL AETLYYAMKG AGTDDHTLIR VMVSRSEIDL FNIRKEFRKN FATSLYSMIK  300
GDTSGDYKKA LLLLSGEDD                                               319

SEQ ID NO: 82            moltype = AA  length = 319
FEATURE                  Location/Qualifiers
REGION                   1..319
                         note = Synthetic construct
source                   1..319
                         mol_type = protein
                         organism = synthetic construct
SEQUENCE: 82
AQVLRGTVTD FPGFDERADA ETLRKAMKGL GTDEESILTL LTSRSNAQRQ EISAAFKTLF  60
GRDLLDDLKS ELTGKFEKLI VALMKPSRLY DAYELKHALK GAGTNEKVLT EIIASRTPEE  120
LRAIKQVYEE EYGSSLEDDV VGDTSGYYQR MLVVLLQANR DPDAGIDEAQ VEQDAQALFQ  180
AGELKWGTDE EKFITIFGTR SVSHLRKVFD KYMTISGFQI EETIDRATSG NLEQLLLAVV  240
KSIRSIPAYL AETLYYAMKG AGTDDHTLIR VMVSRSEIDL FNIRKEFRKN FATSLYSMIK  300
GDTSGDYKKA LLLLCGEDD                                               319

SEQ ID NO: 83            moltype = AA  length = 319
FEATURE                  Location/Qualifiers
REGION                   1..319
                         note = Synthetic construct
source                   1..319
                         mol_type = protein
                         organism = synthetic construct
SEQUENCE: 83
AQVLRGTVTD FPGFDERADA ETLRKAMKGL GTDEESILTL LTSRSNAQRQ EISAAFKTLF  60
GRDLLDDLKS ELTGKFEKLI VALMKPSRLY DAYELKHALK GAGTNEKVLT EIIASRTPEE  120
LRAIKQVYEE EYGSSLEDDV VGNTSGYYQR MLVVLLQANR DPDAGIDEAQ VEQDAQALFQ  180
AGELKWGTDE EKFITIFGTR SVSHLRKVFD KYMTISGFQI EETIDRATSG NLEQLLLAVV  240
KSIRSIPAYL AETLYYAMKG AGTDDHTLIR VMVSRSEIDL FNIRKEFRKN FATSLYSMIK  300
GDTSGDYKKA LLLLCGEDD                                               319

SEQ ID NO: 84            moltype = AA  length = 319
FEATURE                  Location/Qualifiers
REGION                   1..319
                         note = Synthetic construct
source                   1..319
                         mol_type = protein
                         organism = synthetic construct
SEQUENCE: 84
AQVLRGTVTD FPGFDERADA ETLRKAMKGL GTDEESILTL LTSRSNAQRQ EISAAFKTLF  60
GRDLLDDLKS DLTGKFEKLI VALMKPSRLY DAYELKHALK GAGTNEKVLT EIIASRTPEE  120
LRAIKQVYEE EYGSSLEDDV VGNTSGYYQR MLVVLLQANR DPDAGIDEAQ VEQDAQALFQ  180
AGELKWGTDE EKFITIFGTR SVSHLRKVFD KYMTISGFQI EETIDRATSG NLEQLLLAVV  240
KSIRSIPAYL AETLYYAMKG AGTDDHTLIR VMVSRSEIDL FNIRKEFRKN FATSLYSMIK  300
GNTSGDYKKA LLLLCGEDD                                               319

SEQ ID NO: 85            moltype = AA  length = 364
FEATURE                  Location/Qualifiers
REGION                   1..364
                         note = Synthetic construct
source                   1..364
                         mol_type = protein
```

```
                              organism = synthetic construct
SEQUENCE: 85
LDICSKNPCH NGGLCEEISQ EVRGDVFPSY TCTCLKGYAG NHCETKCVEP LGMENGNIAN   60
SQIAASSVRV TFLGLQHWVP ELARLNRAGM VNAWTPSSND DNPWIQVNLL RRMWVTGVVT  120
QGASRLASHE YLKAFKVAYS LNGHEFDFIH DVNKKHKEFV GNWNKNAVHV NLFETPVEAQ  180
YVRLYPTSCH TACTLRFELL GCELNGCANP LGLKNNSIPD KQITASSSYK TWGLHLFSWN  240
PSYARLDKQG NFNAWVAGSY GNDQWLQVDL GSSKEVTGII TQGARNFGSV QFVASYKVAY  300
SNDSANWTEY QDPRTGSSKI FPGNWDNHSH KKNLFETPIL ARYVRILPVA WHNRIALRLE  360
LLGC                                                              364

SEQ ID NO: 86            moltype = AA   length = 186
FEATURE                  Location/Qualifiers
REGION                   1..186
                         note = Synthetic construct
source                   1..186
                         mol_type = protein
                         organism = synthetic construct
SEQUENCE: 86
AQYVRLYPTS CHTACTLRFE LLGCELNGCA NPLGLKNNSI PDKQITASSS YKTWGLHLFS   60
WNPSYARLDK QGNFNAWVAG SYGNDQWLQV DLGSSKEVTG IITQGARNFG SVQFVASYKV  120
AYSNDSANWT EYQDPRTGSS KIFPGNWDNH SHKKNLFETP ILARYVRILP VAWHNRIALR  180
LELLGC                                                            186

SEQ ID NO: 87            moltype = AA   length = 86
FEATURE                  Location/Qualifiers
REGION                   1..86
                         note = Synthetic construct
PEPTIDE                  1..86
source                   1..86
                         mol_type = protein
                         organism = synthetic construct
SEQUENCE: 87
MMRFPSIFTA VLFAASSALA APVNTTTEDE TAQIPAEAVI GYSDLEGDFD VAVLPFSNST   60
NNGLLFINTT IASIAAKEEG VSLDKR                                       86

SEQ ID NO: 88            moltype = AA   length = 85
FEATURE                  Location/Qualifiers
REGION                   1..85
                         note = Synthetic construct
PEPTIDE                  1..85
source                   1..85
                         mol_type = protein
                         organism = synthetic construct
SEQUENCE: 88
MRFPSIFTAV LFAASSALAA PANTTTEDET AQIPAEAVID YSDLEGDFDA AALPLSNSTN   60
NGLSSTNTTI ASIAAKEEGV QLDKR                                        85

SEQ ID NO: 89            moltype = AA   length = 18
FEATURE                  Location/Qualifiers
REGION                   1..18
                         note = Synthetic construct
PEPTIDE                  1..18
source                   1..18
                         mol_type = protein
                         organism = synthetic construct
SEQUENCE: 89
MQLLRCFSIF SVIASVLA                                                18

SEQ ID NO: 90            moltype = AA   length = 20
FEATURE                  Location/Qualifiers
REGION                   1..20
                         note = Synthetic construct
PEPTIDE                  1..20
source                   1..20
                         mol_type = protein
                         organism = synthetic construct
SEQUENCE: 90
MMLLQAFLFL LAGFAAKISA                                              20

SEQ ID NO: 91            moltype = AA   length = 38
FEATURE                  Location/Qualifiers
REGION                   1..38
                         note = Synthetic construct
PEPTIDE                  1..38
source                   1..38
                         mol_type = protein
                         organism = synthetic construct
SEQUENCE: 91
MKVLIVLLAI FAALPLALAQ PVISTTVGSA AEGSLDKR                          38
```

```
SEQ ID NO: 92            moltype = AA  length = 14
FEATURE                 Location/Qualifiers
REGION                  1..14
                        note = Synthetic construct
PEPTIDE                 1..14
source                  1..14
                        mol_type = protein
                        organism = synthetic construct
SEQUENCE: 92
GGSGGSGGHH HHHH                                                            14

SEQ ID NO: 93            moltype = AA  length = 14
FEATURE                 Location/Qualifiers
REGION                  1..14
                        note = Synthetic construct
PEPTIDE                 1..14
source                  1..14
                        mol_type = protein
                        organism = synthetic construct
SEQUENCE: 93
GGSGGCGGHH HHHH                                                            14

SEQ ID NO: 94            moltype = AA  length = 14
FEATURE                 Location/Qualifiers
REGION                  1..14
                        note = Synthetic construct
PEPTIDE                 1..14
source                  1..14
                        mol_type = protein
                        organism = synthetic construct
SEQUENCE: 94
GGAGGSGGHH HHHH                                                            14

SEQ ID NO: 95            moltype = AA  length = 4
FEATURE                 Location/Qualifiers
REGION                  1..4
                        note = Synthetic construct
REGION                  1..4
                        note = Synthetic construct
source                  1..4
                        mol_type = protein
                        organism = synthetic construct
SEQUENCE: 95
GAAS                                                                        4

SEQ ID NO: 96            moltype = AA  length = 4
FEATURE                 Location/Qualifiers
REGION                  1..4
                        note = Synthetic construct
REGION                  1..4
                        note = Synthetic construct
source                  1..4
                        mol_type = protein
                        organism = synthetic construct
SEQUENCE: 96
ASAQ                                                                        4

SEQ ID NO: 97            moltype = AA  length = 12
FEATURE                 Location/Qualifiers
REGION                  1..12
                        note = Synthetic construct
PEPTIDE                 1..12
source                  1..12
                        mol_type = protein
                        organism = synthetic construct
SEQUENCE: 97
GAQGGGSGGS AG                                                              12

SEQ ID NO: 98            moltype = AA  length = 15
FEATURE                 Location/Qualifiers
REGION                  1..15
                        note = Synthetic construct
PEPTIDE                 1..15
source                  1..15
                        mol_type = protein
                        organism = synthetic construct
SEQUENCE: 98
GGAGAQGGGS GGSAG                                                           15
```

-continued

```
SEQ ID NO: 99          moltype = AA  length = 5
FEATURE                Location/Qualifiers
REGION                 1..5
                       note = Synthetic construct
PEPTIDE                1..5
source                 1..5
                       mol_type = protein
                       organism = synthetic construct
SEQUENCE: 99
AAALQ                                                                5

SEQ ID NO: 100         moltype = AA  length = 5
FEATURE                Location/Qualifiers
REGION                 1..5
                       note = Synthetic construct
PEPTIDE                1..5
source                 1..5
                       mol_type = protein
                       organism = synthetic construct
SEQUENCE: 100
AAATG                                                                5

SEQ ID NO: 101         moltype = AA  length = 6
FEATURE                Location/Qualifiers
REGION                 1..6
                       note = Synthetic construct
PEPTIDE                1..6
source                 1..6
                       mol_type = protein
                       organism = synthetic construct
SEQUENCE: 101
AAATGS                                                               6

SEQ ID NO: 102         moltype = AA  length = 12
FEATURE                Location/Qualifiers
REGION                 1..12
                       note = Synthetic construct
PEPTIDE                1..12
source                 1..12
                       mol_type = protein
                       organism = synthetic construct
SEQUENCE: 102
GSTGGGSGGG TG                                                        12

SEQ ID NO: 103         moltype = AA  length = 15
FEATURE                Location/Qualifiers
REGION                 1..15
                       note = Sythetic constrict
PEPTIDE                1..15
source                 1..15
                       mol_type = protein
                       organism = synthetic construct
SEQUENCE: 103
GGGGSGGGGS GGGGS                                                     15

SEQ ID NO: 104         moltype = AA  length = 20
FEATURE                Location/Qualifiers
REGION                 1..20
                       note = Synthetic construct
PEPTIDE                1..19
source                 1..20
                       mol_type = protein
                       organism = synthetic construct
SEQUENCE: 104
GGGGSGGGGS GGGGSGGGGS                                                20

SEQ ID NO: 105         moltype = AA  length = 20
FEATURE                Location/Qualifiers
REGION                 1..20
                       note = Synthetic construct
source                 1..20
                       mol_type = protein
                       organism = synthetic construct
SEQUENCE: 105
ASPAAPAPAS PAAPAPSAPA                                                20

SEQ ID NO: 106         moltype = AA  length = 922
FEATURE                Location/Qualifiers
```

```
REGION                    1..922
                          note = Synthetic construct
source                    1..922
                          mol_type = protein
                          organism = synthetic construct
SEQUENCE: 106
LESGGGLVQP GGSLRLSCAG SGFTFSSYAM SWVRQAPGKG LEWVSSISGS GGSTYYADSV   60
KGRFTISRDN SKKTLYLQMN SLRAEDTAVY YCARKRGRTT VSWGLVYFDY WGQGTVVTVS  120
SGGGGSGGGG SGGGGSGGGG SGGSELTQSP GTLSLSPGER ATLSCRASHS VSRAYLAWYQ  180
QKPGQAPRLL IYGTSSRATG IPDRFSGSGS GTDFTLTISR LEPEDFAVYY CQQYGGSPWF  240
GQGTKVELKG AASDAHKSEV AHRFKDLGEE NFKALVLIAF AQYLQQSPFE DHVKLVNEVT  300
EFAKTCVADE SAENCDKSLH TLFGDKLCTV ATLRETYGEM ADCCAKQEPE RNECFLQHKD  360
DNPNLPRLVR PEVDVMCTAF HDNEETFLKK YLYEIARRHP YFYAPELLFF AKRYKAAFTE  420
CCQAADKAAC LLPKLDELRD EGKASSAKQR LKCASLQKFG ERAFKAWAVA RLSQRFPKAE  480
FAEVSKLVTD LTKVHTECCH GDLLECADDR ADLAKYICEN QDSISSKLKE CCEKPLLEKS  540
HCIAEVENDE MPADLPSLAA DFVESKDVCK NYAEAKDVFL GMFLYEYARR HPDYSVVLLL  600
RLAKTYETTL EKCCAAADPH ECYAKVFDEF KPLVEEPQNL IKQNCELFEQ LGEYKFQNAL  660
LVRYTKKVPQ VSTPTLVEVS RNLGKVGSKC CKHPEAKRMP CAEDYLSVVL NQLCVLHEKT  720
PVSDRVTKCC TESLVNRRPC FSALEVDETY VPKEFQAETF TFHADICTLS EKERQIKKQT  780
ALVELVKHKP KATKEQLKAV MDDFAAFVEK CCKADDKETC FAEEGKKLVA ASQAALGLAA  840
ALQGPETLCG AELVDALQFV CGDRGFYFNK PTGYGSSSRR APQTGIVDEC CFRSCDLRRL  900
EMYCAPLKPA KSAGGSHHHH HH                                          922

SEQ ID NO: 107           moltype = DNA   length = 2772
FEATURE                  Location/Qualifiers
misc_feature             1..2772
                         note = Synthetic construct
source                   1..2772
                         mol_type = other DNA
                         organism = synthetic construct
SEQUENCE: 107
ctggagagcg ggggtggcct ggtccaacca ggcggatctc tgagactcag ttgtgcaggg    60
agcggattta ccttcagctc ctatgctatg tcttgggtgc gccaggcacc cgggaagggg   120
ctggagtggg tcagtagcat cagtggcagc ggcggaagca cctactatgc tgatagtgtt   180
aagggaaggt tcacgatcag ccgcgacaat tccaaaaaga cccttttatct ccaaatgaac   240
tcactgcgcg ccgaagatac ggccgtctac tactgtgcac ggaaaagagg cagaaccacc   300
gtgtcctggg gcctggttta cttcgattac tggggtcagg gcaccgtagt gactgtgagc   360
agcggaggcg ggggttctgg tggcggagga tcaggcggcg gaggaagtgg tgggggcggc   420
tccggtgggg gcgagctgac tcagtctccg ggaactctta gtttgtctcc cggcgagcga   480
gcgacactct cttgccgagc gtcccactcc gtgtctcgag cctatctggc ctggtatcaa   540
cagaaacctg ggcaggcacc ccggctgctg atttacggga cttcctcacg ggctacaggt   600
atccctgaca ggttttccgg cagtggctcc gggacagact tcaccctgac tatatcaagg   660
ctggaaccag aagactttgc cgtgtattac tgccagcagt acggagggtc accttggttc   720
gggcagggaa caaaggtgga gcttaagggc gccgcctccg acgctcacaa gagcgaagtg   780
gcacataggt tcaaagatct gggcgaagag aactttaagg ccctcgtcct gatcgctttc   840
gcacagtacc tccagcagtc tccctttgaa gatcacgtga aactggtcaa tgaggtgacc   900
gaatttgcca agacatgcgt ggctgatgag agtgcagaaa actgtgacaa atcactgcat   960
actctctttg gagataagct gtgcaccgtc gccacactca gagagactta tggggaaatg  1020
gctgactgtt gcgcaaaaca ggagcctgaa cggaatgagt gtttcctcca gcacaaggat  1080
gacaaccaa atctgccccg cctcgtgcga cctgaggtcg atgtgatgtg caccgccttt  1140
catgacaacg aagagacatt cctgaagaaa tacctgtatg aaattgctcg taggcaccca  1200
tactttatg ccccccgagct cctgttcttt gcaaagagat acaaagctgc cttcactgaa  1260
tgttgccagg cagctgataa ggccgcatgt ctcctgccta aactggacga gctccgggat  1320
gaaggtaagg cttccagcgc caaacagcgc ctgaagtgcg cttctctcca gaagtttggc  1380
gagcgagcat tcaaagcctg ggctgtggcc cgtctcagtc agaggtttcc aaaggcagaa  1440
tttgctgagg tctcaaaact ggtgaccgac ctcacaaagg tccatactga gtgttgccac  1500
ggagatctgc tggaatgtgc cgacgataga gcagacctcg ctaaatatat ctgcgagaat  1560
caggattcca ttagctctaa gctgaaagaa tgttgcgaga gcccctcct ggaaaagagt  1620
cattgtatcg ccgaggtgga aaacgacgag atgccagcac atctgccatc actcgctgcc  1680
gactttgtgg aatccaaaga tgtctgcaag aattacgcag aggctaaaga cgtgttcctg  1740
gggatgtttc tgtatgagta cgcccggcgt caccccgatt atagcgtcgt gctcctgctc  1800
cgactggcaa agacctacga aacaactctg gagaaatgtt gcgctgccgc agaccctcat  1860
gaatgttatg ctaaggtgtt cgatgagttt aagccactcg tcgaagagcc ccagaacctg  1920
attaaacaga attgcgaact gttcgaacag ctcggtgaat acaagtttca gaacgccctg  1980
ctcgtgcgtt ataccaaaaa ggtccctcag gtgtctacac caactctggt ggaggtcagt  2040
aggaatctgg gcaaagtggg atcaaagtgt tgcaaacacc ccgaggcaaa gagaatgcct  2100
tgtgctgaag attacctctc cgtcgtgctg aaccagctct gcgtgctgca tgaaaagacc  2160
ccagtcagcg accgggtgac aaaatgttgc accgaatctc tggtcaatcg ccgaccctgt  2220
ttcagtgccc tcgaagtgga cgaaacttat gtgcctaagg agtttcaggc tgaaacattc  2280
acctttcacg ccgatatctg cactctgtcc gagaaagaaa ggcagattaa gaaacagaca  2340
gcactggtcg agctcgtgaa gcataaacca aaggctacca aggagcagct gaaagccgtc  2400
atggacgatt tcgcagcttt tgtggaaaag tgttgcaaag ccgacgataa ggagacttgt  2460
ttcgcagaag aggggaaaaa gctcgtggct gccagccagg cagctctggg tctggccgca  2520
gctctgcagg gcccagaaac actttgtgga gccgaactgg tggatgctct ccaattcgtt  2580
tgcggcgacc gcggattcta ctttaacaag cccaccggtt acgggtcttc aagccggagg  2640
gcccccgcaga ctggcatcgt cgacgagtgc tgtttttagaa gctgcgatct gcgacggttg  2700
gagatgtatt gtgcacctct gaagcccgcg aaaagtgctg ggggctccca ccatcaccat  2760
caccactagt ga                                                     2772
```

-continued

```
SEQ ID NO: 108         moltype = AA   length = 918
FEATURE                Location/Qualifiers
REGION                 1..918
                       note = Synthetic construct
source                 1..918
                       mol_type = protein
                       organism = synthetic construct
SEQUENCE: 108
EVQLQQSGPE LVKPGASMKI SCKASGYSFT GYTMKWVKQS HGKNLEWIGL INPYNGGTSY    60
NQKFKGKATL TVDKSSSTAY MELLSLTSDD SAVYYCAREG DYDGAMDYWG QGTSVTVSGG   120
GGSGGGGSGG GGSGGGGSGG SDIQMTQSPS SLSASLGGKV TITCKSSQDI NKYIAWYQHK   180
PGKGPGLLIH YTSTLQPGIP SRFSGSGSGR DYSFSISNLD PENIAAYYCL QYDNLYTFGG   240
GTRLEGAASD AHKSEVAHRF KDLGEENFKA LVLIAFAQYL QQSPFEDHVK LVNEVTEFAK   300
TCVADESAEN CDKSLHTLFG DKLCTVATLR ETYGEMADCC AKQEPERNEC FLQHKDDNPN   360
LPRLVRPEVD VMCTAFHDNE ETFLKKYLYE IARRHPYFYA PELLFFAKRY KAAFTECCQA   420
ADKAACLLPK LDELRDEGKA SSAKQRLKCA SLQKFGERAF KAWAVARLSQ RFPKAEFAEV   480
SKLVTDLTKV HTECCHGDLL ECADDRADLA KYICENQDSI SSKLKECCEK PLLEKSHCIA   540
EVENDEMPAD LPSLAADFVE SKDVCKNYAE AKDVFLGMFL YEYARRHPDY SVVLLLRLAK   600
TYETTLEKCC AAADPHECYA KVFDEFKPLV EEPQNLIKQN CELFEQLGEY KFQNALLVRY   660
TKKVPQVSTP TLVEVSRNLG KVGSKCCKHP EAKRMPCAED YLSVVLNQLC VLHEKTPVSD   720
RVTKCCTESL VNRRPCFSAL EVDETYVPKE FQAETFTFHA DICTLSEKER QIKKQTALVE   780
LVKHKPKATK EQLKAVMDDF AAFVEKCCKA DDKETCFAEE GKKLVAASQA ALGLAAALQG   840
PETLCGAELV DALQFVCGDR GFYFNKPTGY GSSSRRAPQT GIVDECCFRS CDLRRLEMYC   900
APLKPAKSAG GSHHHHHH                                                 918

SEQ ID NO: 109         moltype = DNA   length = 2760
FEATURE                Location/Qualifiers
misc_feature           1..2760
                       note = Synthetic construct
source                 1..2760
                       mol_type = other DNA
                       organism = synthetic construct
SEQUENCE: 109
gaagtgcagc ttcagcagag cgggcctgaa ctggttaaac caggtgccag catgaagatt    60
tcctgtaagg cttctgggta cagtttcacc gggtacacca tgaaatgggt gaagcaaagc   120
cacggaaaga accttgagtg gattggattg atcaacccct ataatggggg aactagctat   180
aaccagaagt tcaaggggaa ggctactctg acggtggaca agtcatcaag caccgcatat   240
atggagctcc tctccctgac ttctgacgac agcgcagtat actattgcgc cagagagggg   300
gactacgatg gggctatgga ctactggggc caggggacag cgtcactgt ctccggtgga    360
ggtggctccg gtggcggcgg aagcggcggt ggaggctcag ggggcggagg ctctggcggc   420
tcagacatcc agatgaccca atccccgtct tccctctctg cctccttggg cgggaaggtg   480
acaatcacgt gcaaaagttc ccaggatatc aataaataca tcgcctggta ccaacacaaa   540
ccaggcaaag gccctggact gctgatacat taccagta ccttgcagcc cggcatacco    600
tctcggttca gcggcagtgg atcaggtcgc gattacagtt ttagtatttc aaatctggat   660
cctgagaata ttgcagcgta ttactgtctc cagtatgata acctgtacac atttggaggg   720
ggaacaaggc tggaaggcgc cgcctccgac gctcacaaga gcgaagtggc acataggttc   780
aaagatctgg gcgaagagaa ctttaaggcc ctcgtcgtta cagtacctc acagtacctc    840
cagcagtctc cctttgaaga tcacgtgaaa ctggtcaatg aggtgaccga atttgccaag   900
acatgcgtgg ctgatgagag tgcagaaaac tgtgacaaat cactgcatac tctctttgga   960
gataagctgt gcaccgtcgc cacactcaga gagacttatg gggaaatggc tgactgttgc  1020
gcaaaacagg agcctgaacg gaatgagtgt ttcctccagc acaaggatgt caacccaaat  1080
ctgcccccgcc tcgtgcgacc tgaggtcgat gtgatgtgca ccgcctttca tgacaacgaa  1140
gagacattcc tgaagaaata cctgtatgaa attgctcgta ggcacccata cttttatgcc  1200
cccgagctcc tgttctttgc aaagagatac aaagctgcct tcactgaatg ttgccaggca  1260
gctgataagg ccgcatgtct cctgcctaaa ctggacgagc tgaggtaagg ct           1320
tccagcgcca aacagcgcct gaagtgcgct tctctccaga agtttggcga gcgagcattc  1380
aaagcctggg ctgtggcccg tctcagtcag aggtttccaa aggcagaatt gctgaggtc    1440
tcaaaactgg tgaccgacct cacaaaggtc catactgagt gttgccacgg agatctgctg  1500
gaatgtgccg acgatagagc agacctcgct aaatatatct gcgagaatca ggattccatt  1560
agctctaagc tgaaagaatg ttgcgagaag cccctcctgg aaaagagtca ttgtatcgcc  1620
gaggtggaaa acgacgagat gccagcagat ctgccatcac tcgctgccga ctttgtggaa  1680
tccaaagatg tctgcaagaa ttacgcagag gctaaagacg tgttcctggg gatgtttctg  1740
tatgagtacg cccggcgtca ccccgattat agcgtcgtgc tcctgctccg actggcaaag  1800
acctacgaaa caactctgga gaaatgttgc gctgcccgaa accctcatga atgttatgct  1860
aaggtgttcg atgagtttaa gccactcgtc gaagagcccc agaacctgat aaaacagaat  1920
tgcgaactgt tcgagcagct cggtgaatac aagtttcaga acgccctgct cgtgcgttat  1980
accaaaaagg tccctcaggt gtctacacca actctggtgg aggtcagtag gaatctgggc  2040
aaagtgggat caaagtgttg caaacacccc gaggcaaaga gaatgccttg tgctgaagat  2100
tacctctccg tcgtgctgaa ccagctctgc gtgctgcatg aaaagacccc agtcagcgac  2160
cgggtgacaa aatgttgcac cgaatctctg gtcaatcgcc gaccctgttt cagtgccctc  2220
gaagtggacg aaacttatgt gcctaaggag tttcaggctg aaacattcac ctttcacgcc  2280
gatatctgca ctctgtccga aaagaaagg cagattaaga acagacagc actggtcgag    2340
ctcgtgaagc ataaaccaaa ggctaccaag gagcagctga agccgtcat ggacgatttc    2400
gcagcttttg tggaaaagtg ttgcaaagcc gacgataagg agacttgttt cgcagaagag  2460
gggaaaaagc tcgtggctgc cagccaggca gctctgggtc tggccgcagc tctgcagggc  2520
ccagaaacac tttgtggagc cgaactggtg gatgctctcc aattcgtttg cggcgaccgc  2580
ggattctact taacaagcc caccggttac gggtcttcaa gccggagggc cccgcagact    2640
ggcatcgtcg acgagtgctg ttttagaagc tgcgatctgc gacggttgga gatgtattgt  2700
gcacctctga agcccgcgaa aagtgctggg ggctcccacc atcaccatca ccactagtga  2760
```

```
SEQ ID NO: 110          moltype = AA  length = 1027
FEATURE                 Location/Qualifiers
REGION                  1..1027
                        note = Synthetic construct
source                  1..1027
                        mol_type = protein
                        organism = synthetic construct
SEQUENCE: 110
LESGGGLVQP GGSLRLSCAG SGFTFSSYAM SWVRQAPGKG LEWVSSISGS GGSTYYADSV     60
KGRFTISRDN SKKTLYLQMN SLRAEDTAVY YCARKRGRTT VSWGLVYFDY WGQGTVVTVS    120
SGGGGSGGGG SGGGGSGGGG SGGSELTQSP GTLSLSPGER ATLSCRASHS VSRAYLAWYQ    180
QKPGQAPRLL IYGTSSRATG IPDRFSGSGS GTDFTLTISR LEPEDFAVYY CQQYGGSPWF    240
GQGTKVELKG AASDAHKSEV AHRFKDLGEE NFKALVLIAF AQYLQQSPFE DHVKLVNEVT    300
EFAKTCVADE SAENCDKSLH TLFGDKLCTV ATLRETYGEM ADCCAKQEPE RNECFLQHKD    360
DNPNLPRLVR PEVDVMCTAF HDNEETFLKK YLYEIARRHP YFYAPELLFF AKRYKAAFTE    420
CCQAADKAAC LLPKLDELRD EGKASSAKQR LKCASLQKFG ERAFKAWAVA RLSQRFPKAE    480
FAEVSKLVTD LTKVHTECCH GDLLECADDR ADLAKYICEN QDSISSKLKE CCEKPLLEKS    540
HCIAEVENDE MPADLPSLAA DFVESKDVCK NYAEAKDVFL GMFLYEYARR HPDYSVVLLL    600
RLAKTYETTL EKCCAAADPH ECYAKVFDEF KPLVEEPQNL IKQNCELFEQ LGEYKFQNAL    660
LVRYTKKVPQ VSTPTLVEVS RNLGKVGSKC CKHPEAKRMP CAEDYLSVVL NQLCVLHEKT    720
PVSDRVTKCC TESLVNRRPC FSALEVDETY VPKEFQAETF TFHADICTLS EKERQIKKQT    780
ALVELVKHKP KATKEQLKAV MDDFAAFVEK CCKADDKETC FAEEGKKLVA ASQAALGLAA    840
ALQQRKRRNT IHEFKKSAKT TLIKIDPALK IKTKKVNTAD QCANRCTRNK GLPFTCKAFV    900
FDKARKQCLW FPFNSMSSGV KKEFGHEFDL YENKDYIRNC IIGKGRSYKG TVSITKSGIK    960
CQPWSSMIPH EHSFLPSSYR GKDLQENYCR NPRGEEGGPW CFTSNPEVRY EVCDIPQCGG   1020
SHHHHHH                                                            1027

SEQ ID NO: 111          moltype = DNA  length = 3087
FEATURE                 Location/Qualifiers
misc_feature            1..3087
                        note = Synthetic construct
source                  1..3087
                        mol_type = other DNA
                        organism = synthetic construct
SEQUENCE: 111
ctggagagcg ggggtggcct ggtccaacca ggcggatctc tgagactcag ttgtgcaggg     60
agcggattta ccttcagctc ctatgctatg tcttgggtgc gccaggcacc cgggaagggg    120
ctggagtggg tcagtagcat cagtggcagc ggcggaagca cctactatgc tgatagtgtt    180
aagggaaggt tcacgatcag ccgcgacaat tccaaaaaga ccctttatct ccaaatgaac    240
tcactgcgcg ccgaagatac ggccgtctac tactgtgcac ggaaaagagg cagaaccacc    300
gtgtcctggg gcctggttta cttcgattac tggggtcagg gcaccgtagt gactgtgagc    360
agcggaggcg ggggttctgg tggcggagga tcaggcgggg gaggaagtgg tgggggcggc    420
tccggtggga gcgagctgac tcagtctccg ggaactctta gtttgtctcc cggcgagcga    480
gcgacactct cttgccgagc gtcccactcc gtgtctcgag cctatctggc ctggtatcaa    540
cagaaacctg gcaggcacc ccggctgctg atttacggga cttcctcacg ggctacaggt    600
atccctgaca ggttttccgg cagtggctcc gggacagact tcaccctgac tatatcaagg    660
ctggaaccag aagactttgc cgtgtattac tgccagcagt acggagggtc accttggttc    720
gggcagggaa caaaggtgga gcttaagggc gccgcctccg acgctcacaa gagcgaagtg    780
gcacataggt tcaaagatct gggcgaagag aactttaagg ccctcgtcct gatcgctttc    840
gcacagtacc tccagcagtc tccctttgaa gatcacgtga aactggtcaa tgaggtgacc    900
gaatttgcca agacatgcgt ggctgatgag agtgcagaaa actgtgacaa atcactgcat    960
actctctttg gagataagct gtgcaccgtc gccacactca gagagactta tggggaaatg   1020
gctgactgtt gcgcaaaaca ggagcctgaa cggaatgagt gtttcctcca gcacaaggat   1080
gacaacccaa atctgcccg cctcgtgcga cctgaggtcg atgtgatgtg caccgccttt   1140
catgacaacg aagagacatt cctgaagaaa tacctgtatg aaattgctcg taggcaccca   1200
tacttttatg cccccgagct cctgttcttt gcaaagagat acaaagctgc cttcactgaa   1260
tgttgccagg cagctgataa ggccgcatgt ctcctgccta aactggacga gctccgggat   1320
gaaggtaagg cttccagcgc caaacagcgc ctgaagtgcg cttctctcca gaagtttggc   1380
gagcgagcat tcaaagcctg ggctgtggcc cgtctcagtc agaggtttcc aaaggcagaa   1440
tttgctgagg tctcaaaact ggtgaccgac ctcacaaagg tccatactga gtgttgccac   1500
ggagatctgc tggaatgtgc cgacgataga gcagacctcg ctaaatatat ctgcgagaat   1560
caggattcca ttagctctaa gctgaaagaa tgttgcgaga gcccctcct ggaaaagagt   1620
cattgtatcg ccgaggtgga aaacgacgag atgccagcac actcgctgcc actgcctct  1680
gactttgtgg aatccaaaga tgtctgcaag aattacgcag aggctaaaga cgtgttcctg   1740
gggatgtttc tgtatgagta cgcccggcgt caccccgatt atagcgtcgt gctcctgctc   1800
cgactggcaa agacctacga aacaactctg gagaaatgtt gcgctgccgc agaccctcat   1860
gaatgttatg ctaaggtgtt cgatgagttt aagcccactcg tcgaagagcc ccagaacctg   1920
attaaacaga attgcgaact gttcgagcag ctcggtgaat acaagtttca gaacgccctg   1980
ctcgtgcgtt ataccaaaaa ggtccctcag gtgtctacac caactctggt ggaggtcagt   2040
aggaatctgg gcaaagtggg atcaaagtgt tgcaaacacc ccgaggcaaa gagaatgcct   2100
tgtgctgaag attacctctc cgtcgtgctg aaccagctct gcgtgctgca tgaaaagacc   2160
ccagtcagcg accgggtgac aaaatgttgc accgaatctc tggtcaatcg ccgacccgt   2220
ttcagtgccc tcgaagtgga cgaaacttat gtgcctaagg agtttcaggc tgaaacattc   2280
accttcacg ccgatatctg cactctgtcc gagaaagaaa ggcagattaa gaaacagaca   2340
gcactggtcg agctcgtgaa gcataaacca aaggctacca aggagcagct gaaagccgtc   2400
atggacgatt tcgcagcttt tgtggaaaag tgttgcaaag ccgacgataa ggagacttgt   2460
ttcgcagaag agggggaaaa gctcgtggct gccagccagg cagctctggg tctggccgca   2520
gctctgcagc agcggaaaag gagaaacacc attcacgagt ttaagaagtc cgcgaagacc   2580
```

-continued

```
acactgatta agattgatcc cgcccttaaa atcaagacaa agaaggtgaa cacggctgac   2640
cagtgtgcta atcgctgcac aaggaataaa ggactgccat ttacttgtaa agcctttgta   2700
ttcgataagg cacgcaagca gtgcctctgg ttccctttca attctatgag cagtggtgtt   2760
aagaaagagt ttggccatga attcgacttg tacgaaaaca aagattatat ccggaactgc   2820
attatcggga aaggccggtc ttacaaaggc accgtcttca taaccaagag tggcatcaaa   2880
tgtcaaccct ggagctcaat gatcccacat gaacactcct tcctcccaag ttcataccgg   2940
ggcaaggacc tgcaagagaa ctattgcaga aatccgcgag gggaagaggg agggccttgg   3000
tgtttcactt ctaatcccga ggtgaggtat gaggtgtgcg acatacctca gtgcggtgga   3060
agccaccatc accaccacca ttagtga                                       3087
```

SEQ ID NO: 112          moltype = AA   length = 1023
FEATURE                 Location/Qualifiers
REGION                  1..1023
                        note = Synthetic construct
source                  1..1023
                        mol_type = protein
                        organism = synthetic construct
SEQUENCE: 112

```
EVQLQQSGPE LVKPGASMKI SCKASGYSFT GYTMKWVKQS HGKNLEWIGL INPYNGGTSY   60
NQKFKGKATL TVDKSSSTAY MELLSLTSDD SAVYYCAREG DYDGAMDYWG QGTSVTVSGG   120
GGSGGGGSGG GGSGGGGSGG SDIQMTQSPS SLSASLGGKV TITCKSSQDI NKYIAWYQHK   180
PGKGPGLLIH YTSTLQPGIP SRFSGSGSGR DYSFSISNLD PENIAAYYCL QYDNLYTFGG   240
GTRLEGAASD AHKSEVAHRF KDLGEENFKA LVLIAFAQYL QQSPFEDHVK LVNEVTEFAK   300
TCVADESAEN CDKSLHTLFG DKLCTVATLR ETYGEMADCC AKQEPERNEC FLQHKDDNPN   360
LPRLVRPEVD VMCTAFHDNE ETFLKKYLYE IARRHPYFYA PELLFFAKRY KAAFTECCQA   420
ADKAACLLPK LDELRDEGKA SSAKQRLKCA SLQKFGERAF KAWAVARLSQ RFPKAEFAEV   480
SKLVTDLTKV HTECCHGDLL ECADDRADLA KYICENQDSI SSKLKECCEK PLLEKSHCIA   540
EVENDEMPAD LPSLAADFVE SKDVCKNYAE AKDVFLGMFL YEYARRHPDY SVVLLLRLAK   600
TYETTLEKCC AAADPHECYA KVFDEFKPLV EEPQNLIKQN CELFEQLGEY KFQNALLVRY   660
TKKVPQVSTP TLVEVSRNLG KVGSKCCKHP EAKRMPCAED YLSVVLNQLC VLHEKTPVSD   720
RVTKCCTESL VNRRPCFSAL EVDETYVPKE FQAETFTFHA DICTLSEKER QIKKQTALVE   780
LVKHKPKATK EQLKAVMDDF AAFVEKCCKA DDKETCFAEE GKKLVAASQA ALGLAAALQQ   840
RKRRNTIHEF KKSAKTTLIK IDPALKIKTK KVNTADQCAN RCTRNKGLPF TCKAFVFDKA   900
RKQCLWFPFN SMSSGVKKEF GHEFDLYENK DYIRNCIIGK GRSYKGTVSI TKSGIKCQPW   960
SSMIPHEHSF LPSSYRGKDL QENYCRNPRG EEGGPWCFTS NPEVRYEVCD IPQCGGSHHH   1020
HHH                                                                 1023
```

SEQ ID NO: 113          moltype = DNA   length = 3075
FEATURE                 Location/Qualifiers
misc_feature            1..3075
                        note = Synthetic construct
source                  1..3075
                        mol_type = other DNA
                        organism = synthetic construct
SEQUENCE: 113

```
gaagtgcagc ttcagcagag cgggcctgaa ctggttaaac caggtgccag catgaagatt   60
tcctgtaagg cttctgggta cagtttcacc gggtacacca tgaaatgggt gaagcaaagc   120
cacggaaaga accttgagtg gattggattg atcaacccct ataatggggg aactagctat   180
aaccagaagt tcaaggggaa ggctactctg acggtggaca agtcatcaag caccgcatat   240
atggagctcc tctccctgac ttctgacgac agcgcagtat actattgcgc cagagagggg   300
gactacgatg gggctatgga ctactggggc caggggacaa gcgtcactgt ctccggtgga   360
ggtggctccg gtggcggcgg aagcggcggt ggaggctcag ggggcggagg ctctggcggc   420
tcagacatcc agatgaccca atcccccgtct tccctctctg cctccttggg cgggaaggtg   480
acaatcacgt gcaaaagttc ccaggatatc aataaataca tcgcctggta ccaacacaaa   540
ccaggcaaag gccctggact gctgatacat tataccagta ccttgcagcc cggcataccc   600
tctcggttca gcggcagtgg atcaggtcgc gattacagtt ttagtatttc aaatctggat   660
cctgagaata ttgcagcgta ttactgtctc cagtatgata acctgtacac atttggaggg   720
ggaacaaggc tggaaggcgc cgcctccgac gctcacaaga gcgaagtggc acataggttc   780
aaagatctgg gcgaagagaa ctttaaggcc ctcgtcctga ttgctttcgc acagtacctc   840
cagcagtctc cctttgaaga tcacgtgaaa ctggtcaatg aggtgaccga atttgccaag   900
acatgcgtgg ctgatgagag tgcagaaaac tgtgacaaat cactgcatac tctctttgga   960
gataagctgt gcaccgtcgc cacactcaga gagacttatg gggaaatggc tgactgttgc   1020
gcaaacagg agcctgaacg gaatgagtgt ttcctccagc acaaggatga caacccaaat   1080
ctgcccgcc tcgtgcgacc tgaggtcgat gtgatgtgca ccgcctttca tgacaacgaa   1140
gagacattcc tgaagaaata cctgtatgaa attgctcgta ggcacccata cttttatgcc   1200
cccgagctcc tgttctttgc aaagagatac aaagctgcct tcactgaatg ttgccaggca   1260
gctgataagg ccgcatgtct cctgcctaaa ctggacgagc tccgggatga aggtaaggct   1320
tccagcgcca aacagcgcct gaagtgcgct tctctccaga agtttggcga gcgagcattc   1380
aaagcctggg ctgtggcccg tctcagtcag aggtttccaa aggcagaatt tgctgaggtc   1440
tcaaaactgg tgaccgacct cacaaaggtc catactgagt gttgccacgg agatctgctg   1500
gaatgtgccg acgatagagc agacctcgct aaatatatct gcgagaatca ggattccatt   1560
agctctaagc tgaaagaatg ttgcgagaag ccccctcctgg aaaagagtca ttgtatcgcc   1620
gaggtggaaa acgacgagat gccagcagat ctgcctcac tcgctgccga ctttgtggaa   1680
tccaaagtgt tctgcaagaa ttacgcagag gctaaagacg ttttcctggg gatgtttcta   1740
tatgagtacg cccggcgtca ccccgattat agcgtcgtgc tcctgctccg actggcaaag   1800
acctacgaaa caactctgga aatgttgc gctgccgcag cccctcatga atgttatgct   1860
aaggtgttcg atgagtttaa gccactcgtc gaagagcccc agaacctgat taacagaat   1920
tgcgaactgt tcgagcagct cggtgaatac aagtttcaga cgccctgct cgtgcgttat   1980
accaaaaagg tccctcaggt gtctacacca actctggtgg aggtcagtag gaatctgggc   2040
```

-continued

```
aaagtgggat caaagtgttg caaacacccc gaggcaaaga gaatgccttg tgctgaagat   2100
tacctctccg tcgtgctgaa ccagctctgc gtgctgcatg aaaagacccc agtcagcgac   2160
cgggtgacaa aatgttgcac cgaatctctg gtcaatcgcc gaccctgttt cagtgccctc   2220
gaagtggacg aaacttatgt gcctaaggag tttcaggctg aaacattcac ctttcacgcc   2280
gatatctgca ctctgtccga gaaagaaagg cagattaaga aacagacagc actggtcgag   2340
ctcgtgaagc ataaaccaaa ggctaccaag gagcagctga aagccgtcat ggacgatttc   2400
gcagcttttg tggaaaagtg ttgcaaagcc gacgataagg agacttgttt cgcagaaagg   2460
gggaaaaagc tcgtggctgc cagccaggca gctctgggtc tggccgcagc tctgcagcag   2520
cggaaaaagga gaaacaccat tcacgagttt aagaagtccg cgaagaccac actgattaag   2580
attgatcccg cccttaaaat caagacaaag aaggtgaaca cggctgacca gtgtgctaat   2640
cgctgcacaa ggaataaagg actgccattt acttgtaaag cctttgtatt cgataaggca   2700
cgcaagcagt gcctctggtt cccttttcaat tctatgagca gtggtgttaa gaaagagttt   2760
ggccatgaat tcgacttgta cgaaaacaaa gattatatcc ggaactgcat tatcgggaaa   2820
ggccggtctt acaaaggcac cgtctccata accaagagtg gcatcaaatg tcaaccctgg   2880
agctcaatga tcccacatga acactccttc ctcccaagtt cataccgggg caaggacctg   2940
caagagaact attgcagaaa tccgcgaggg gaagagggag ggccttggtg tttcacttct   3000
aatcccgagg tgaggtatga ggtgtgcgac atacctcagt gcggtggaag ccaccatcac   3060
caccaccatt agtga                                                     3075
```

SEQ ID NO: 114        moltype = AA   length = 990
FEATURE               Location/Qualifiers
REGION                1..990
                      note = Synthetic construct
source                1..990
                      mol_type = protein
                      organism = synthetic construct
SEQUENCE: 114
AQVLRGTVTD FPGFDERADA ETLRKAMKGL GTDEESILTL LTSRSNAQRQ EISAAFKTLF   60
GRDLLDDLKS DLTGKFEKLI VALMKPSRLY DAYELKHALK GAGTNEKVLT EIIASRTPEE   120
LRAIKQVYEE EYGSSLEDDV VGNTSGYYQR MLVVLLQANR DPDAGIDEAQ VEQDAQALFQ   180
AGELKWGTDE EKFITIFGTR SVSHLRKVFD KYMTISGFQI EETIDRATSG NLEQLLLAVV   240
KSIRSIPAYL AETLYYAMKG AGTDDHTLIR VMVSRSEIDL FNIRKEFRKN FATSLYSMIK   300
GNTSGDYKKA LLLLCGEDDA SDAHKSEVAH RFKDLGEENF KALVLIAFAQ YLQQSPFEDH   360
VKLVNEVTEF AKTCVADESA ENCDKSLHTL FGDKLCTVAT LRETYGEMAD CCAKQEPERN   420
ECFLQHKDDN PNLPRLVRPE VDVMCTAFHD NEETFLKKYL YEIARRHPYF YAPELLFFAK   480
RYKAAFTECC QAADKAACLL PKLDELRDEG KASSAKQRLK CASLQKFGER AFKAWAVARL   540
SQRFPKAEFA EVSKLVTDLT KVHTECCHGD LLECADDRAD LAKYICENQD SISSKLKECC   600
EKPLLEKSHC IAEVENDEMP ADLPSLAADF VESKDVCKNY AEAKDVFLGM FLYEYARRHP   660
DYSVVLLLRL AKTYETTLEK CCAAADPHEC YAKVFDEFKP LVEEPQNLIK QNCELFEQLG   720
EYKFQNALLV RYTKKVPQVS TPTLVEVSRN LGKVGSKCCK HPEAKRMPCA EDYLSVVLNQ   780
LCVLHEKTPV SDRVTKCCTE SLVNRRPCFS ALEVDETYVP KEFQAETFTF HADICTLSEK   840
ERQIKKQTAL VELVKHKPKA TKEQLKAVMD DFAAFVEKCC KADDKETCFA EEGKKLVAAS   900
QAALGLAAAT GGPETLCGAE LVDALQFVCG DRGFYFNKPT GYGSSSRRAP QTGIVDECCF   960
RSCDLRRLEM YCAPLKPAKS AGGSHHHHHH                                    990

SEQ ID NO: 115        moltype = DNA   length = 2976
FEATURE               Location/Qualifiers
misc_feature          1..2976
                      note = Synthetic construct
source                1..2976
                      mol_type = other DNA
                      organism = synthetic construct
SEQUENCE: 115
gctcaagtgc taaggggaac tgttactgat tttccaggtt ttgatgaaag agcagatgct   60
gagactttaa ggaaagctat gaaaggattg ggtacagacg aggaatccat tttgacacta   120
ttgacatcac gaagtaacgc ccagagacaa gagatctcag cagctttcaa aaccctgttc   180
ggaagagatt tgcttgacga tttgaagtct gatttgactg gtaagtttga aaaactaata   240
gttgccctga tgaagccttc cagactttat gatgcttacg aacttaagca cgctttgaaa   300
ggggctggaa caaatgaaaa agtttttact gagataatcg catcacgtac ccctgaggaa   360
ctaagagcca ttaagcaggt atatgaagag gaatacggta gttccttaga ggacgacgtc   420
gttggtaaca catctggtta ctatcagagg atgttggttg tcttgttgca agctaatagg   480
gatcctgatg ctggcatcga tgaagcccaa gtagagcagg acgcccaagc cctgtttcaa   540
gcaggcgaat tgaagtgggg aacggacgaa gagaagttta tcaccatctt cggaactcgt   600
tctgtatctc atcttagaaa agtattcgac aaatacatga ctttctgg tttttcaaatt   660
gaggagacta ttgatagagc tacgtctgga aacttagaac agcttttgct tgccgtcgtt   720
aagtctataa ggagtattcc agcctactta gctgaaacct tgtactacgc catgaaggggt   780
gctggaactg atgatcatac cttgatacga gttatggtaa gtcgatcaga gattgatttg   840
tttaacatta ggaaggagtt caggaaaaac tttgctacct cattgtattc catgataaag   900
ggtaacactt caggtgatta caaaaaggct ctgcttttgc tgtgtggcga ggacgatgct   960
agcgatgctc acaaatctga agtcgctcat cgtttcaaag acttgggtga ggaaaacttt   1020
aaggctttag ttctgattgc tttttgcccaa tatcttcaac aatcaccatt cgaagatcat   1080
gtgaaacttg ttaacgaagt taccgaattt gcaaaacgt gtgtggcaga cgaaagtgcc   1140
gaaaactgtg acaaatcatt acacactttg ttcggtgaca agtatgcac tgttgcaacc   1200
ctacgtgaga catatggaga aatggcagac tgttgcgcca aacaagagcc tgaacgaaat   1260
gaatgctttc tgcagcacaa agacgataat ccaaatcttc cccgattagt tcgtcccgaa   1320
gtagacgtaa tgtgcacagc ctttcatgat aatgaagaga ctttcctgaa aaagtacttg   1380
tacgaaattg caagacgtca cccatacttc tatgctcccg agttactgtt tttcgccaaa   1440
cgatacaagg cagcctttac agaatgttgc caagcagctg acaaggctgc atgtcttttta   1500
cctaagttag atgagttaag agacgaaggt aaggcttcct cagcaaaaca gagacttaag   1560
```

```
tgcgcatccc ttcaaaagtt tggtgagaga gctttcaagg cttgggctgt cgccagactg 1620
tctcagagat ttcctaaggc tgaattcgca gaagtctcta agctagtaac tgacttgact 1680
aaagttcata ctgagtgctg tcatgggat ttgttggaat gcgcagatga tcgtgcagac 1740
ttagcaaagt acatctgcga gaaccaagac tctatttcca gtaagttaaa ggaatgttgc 1800
gaaaagccac tacttgagaa gtcccactgt attgctgaag tcgaaaatga tgaaatgcct 1860
gctgaccttc catctttggc cgctgatttc gttgagtcca aggatgtgtg caaaaactat 1920
gctgaagcaa aagatgtgtt cctagggatg ttcctgtatg aatatgctcg tcgacatccc 1980
gactattccg ttgtccttt actgagattg gctaagacct acgagacaac cttggagaag 2040
tgttgtgctg ccgcagatcc tcacgagtgt tacgcaaaag tgtttgatga gttcaaacca 2100
ttggttgaag agccacaaaa tctaatcaag cagaactgtg aactgtttga acaattgggc 2160
gaatacaaat tccaaaatgc tctgttagtg agatacacca aaaaggtccc acaagtttcc 2220
accccaactc tagtcgaggt gtccagaaat ctaggaaaag ttggatctaa gtgttgtaag 2280
catccagaag ctaagaggat gccttgcgct gaggattact tgtctgtggt tttgaaccag 2340
ttatgtgttc tacacgagaa aactcctgtc tccgacaagt ttactaagtg ctgcacagag 2400
tctttggtca atagaaggcc ttgtttcagt gccctggaag tcgatgaaac ttatgtgcct 2460
aaagagttcc aagccgaaac gttcacttt cacgctgaca tttgtactct ttctgagaag 2520
gaacgtcaga tcaaaaagca gacagcattg gtggaattgg taaagcataa accaaaggct 2580
acaaaagagc agctgaaggc tgttatggat gattttgtag ctttcgtgaa aaagtgttgt 2640
aaagccgatg ataaagagac ttgttttgca gaggaggggga aaaagctggt tgctgcatca 2700
caagctgccc taggtcttgc agccgctacc ggtggacctg aaaccttatg tggagctgaa 2760
cttgtggatg ctctacaatt tgtttgtggc gatagagggg tctacttcaa caaacccact 2820
ggatatggta gttcctcaag acgagctcct cagacagtta ttgtcgacga gtgttgtttt 2880
aggtcttgcg acttgcgtag actggagatg tactgcgcac cattgaagcc agcaaagtct 2940
gccggtggtt cacatcacca ccatcaccat tagtga 2976
```

SEQ ID NO: 116          moltype = AA  length = 992
FEATURE                 Location/Qualifiers
REGION                  1..992
                        note = Synthetic construct
source                  1..992
                        mol_type = protein
                        organism = synthetic construct
SEQUENCE: 116
AQVLRGTVTD FPGFDERADA ETLRKAMKGL GTDEESILTL LTSRSNAQRQ EISAAFKTLF    60
GRDLLDDLKS DLTGKFEKLI VALMKPSRLY DAYELKHALK GAGTNEKVLT EIIASRTPEE   120
LRAIKQVYEE EYGSSLEDDV VGNTSGYYQR MLVVLLQANR DPDAGIDEAQ VEQDAQALFQ   180
AGELKWGTDE EKFITIFGTR SVSHLRKVFD KYMTISGFQI EETIDRATSG NLEQLLLAVV   240
KSIRSIPAYL AETLYYAMKG AGTDDHTLIR VMVSRSEIDL FNIRKEFRKN FATSLYSMIK   300
GNTSGDYKKA LLLLCGEDDA SDAHKSEVAH RFKDLGEENF KALVLIAFAQ YLQQSPFEDH   360
VKLVNEVTEF AKTCVADESA ENCDKSLHTL FGDKLCTVAT LRETYGEMAD CCAKQEPERN   420
ECFLQHKDDN PNLPRLVRPE VDVMCTAFHD NEETFLKKYL YEIARRHPYF YAPELLFFAK   480
RYKAAFTECC QAADKAACLL PKLDELRDEG KASSAKQRLK CASLQKFGER AFKAWAVARL   540
SQRFPKAEFA EVSKLVTDLT KVHTECCHGD LLECADDRAD LAKYICENQD SISSKLKECC   600
EKPLLEKSHC IAEVENDEMP ADLPSLAADF VESKDVCKNY AEAKDVFLGM FLYEYARRHP   660
DYSVVLLLRL AKTYETTLEK CCAAADPHEC YAKVFDEFKP LVEEPQNLIK QNCELFEQLG   720
EYKFQNALLV RYTKKVPQVS TPTLVEVSRN LGKVGSKCCK HPEAKRMPCA EDYLSVVLNQ   780
LCVLHEKTPV SDRVTKCCTE SLVNRRPCFS ALEVDETYVP KEFQAETFTF HADICTLSEK   840
ERQIKKQTAL VELVKHKPKA TKEQLKAVMD DFAAFVEKCC KADDKETCFA EEGKKLVAAS   900
QAALGLAAAT GSTSHLVKCA EKEKTFCVNG GECFMVKDLS NPSRYLCKCP NEFTGDRCQN   960
YVMASFYKHL GIEFMEAEEL YQKGGSHHHH HH                               992

SEQ ID NO: 117          moltype = DNA  length = 2982
FEATURE                 Location/Qualifiers
misc_feature            1..2982
                        note = Synthetic construct
source                  1..2982
                        mol_type = other DNA
                        organism = synthetic construct
SEQUENCE: 117
gctcaagtgc taaggggaac tgttactgat tttccaggtt ttgatgaaag agcagatgct    60
gagactttaa ggaaagctat gaaaggattg ggtacagacg aggaatccat tttgacacta   120
ttgacatcac gaagtaacgc ccagagacaa gagatctcag cagctttcaa aaccctgttc   180
ggaagagatt tgcttgacga tttgaagtct gatttgactg gtaagtttga aaaactaata   240
gttgccctga tgaagccttc cagactttat gatgcttacg aacttaagca cgctttgaaa   300
ggggctggaa caaatgaaaa agttttgact gagataatcg catcacgtac ccctgaggaa   360
ctaagagcca ttaagcaggt atatgaagag gaataccgta gttccttaga ggacgacgtc   420
gttggtaaca catctggtta ctatcagagg atgttggttg tcttgttgca agctaatagg   480
gatcctgatg ctggcatcga tgaagcccaa gtagagcagg acgcccaagc cctgtttcaa   540
gcaggcgaat tgaagtgggg aacggacgaa gagaagttta tcaccatctt cggaactcgt   600
tctgtatctc atcttagaaa agtattcgac aaatacatga gatttctgg ttttcaaatt   660
gaggagacta ttgatagagc tacgtctgga aacttagaac agcttttgct tgccgtcgtt   720
aagtctataa ggagtattcc agcctactta gctgaaacct tgtactacgc catgaagggt   780
gctggaactg atgatcatac cttgatacga gttatggtaa gtcgatcaga gattgatttg   840
tttaacatta ggaaggattt caggaaaaac tttgctacct cattgtattc catgataaag   900
ggtaacactt caggtgatta caaaaaggct ctgctttttg tgtgtggcga ggacgatgct   960
agcgatgctc acaaatctga agtcgctcat cgtttcaaag acttgggtga ggaaaacttt  1020
aaggctttag ttctgattgc ttttgcccaa tatcttcaac aatcaccatt cgaagatcat  1080
gtgaaacttg ttaacgaagt taccgaattt gcaaaaacgt gtgtggcaga cgaaagtgcc  1140
gaaaactgtg acaaatcatt acacactttg ttcggtgaca agttatgcac tgttgcaacc  1200
```

```
ctacgtgaga catatggaga aatggcagac tgttgcgcca aacaagagcc tgaacgaaac   1260
gaatgctttc tgcagcacaa agacgataat ccaaatcttc cccgattagt tcgtcccgaa   1320
gtagacgtaa tgtgcacagc ctttcatgat aatgaagaga ctttcctgaa aaagtacttg   1380
tacgaaattg caagacgtca cccatacttc tatgctcccg agttactgtt tttcgccaaa   1440
cgatacaagg cagcctttac agaatgttgc caagcagctg acaaggctgc atgtcttttt   1500
cctaagttag atgagttaag agacgaaggt aaggcttcct cagcaaaaca gagacttaag   1560
tgcgcatccc ttcaaaagtt tggtgagaga gctttcaagg cttgggctgt cgccagactg   1620
tctcagagat ttcctaaggc tgaattcgca gaagtctcta agctagtaac tgacttgact   1680
aaagttcata ctgagtgctg tcatggggat ttgttggaat gcgcagatga tcgtgcagac   1740
ttagcaaagt acatctgcga gaaccaagac tctatttcca gtaagttaaa ggaatgttgc   1800
gaaaagccac tacttgagaa gtcccactgt attgctgaag tcgaaaatga tgaaatgcct   1860
gctgaccttc catctttggc cgctgatttc gttgagtcca aggatgtgtg caaaaactat   1920
gctgaagcaa aagatgtgtt cctagggatg ttcctgtatg aatatgctcg tcgacatccc   1980
gactattccg ttgtcctttt actgagattg gctaagacct cttggagaag cctttgatga   2040
tgttgtgctg ccgcagatcc tcacgagtgt tacgcaaaag tgtttgatga gttcaaacca   2100
ttggttgaag agccacaaaa tctaatcaag cagaactgtg aactgtttga caattgggc    2160
gaatacaaat tccaaaatgc tctgttagtg agatacacca aaaaggtccc acaagtttcc   2220
accccaactc tagtcgaggt gtccagaaat ctaggaaaag ttggatctaa gtgttgtaag   2280
catccagaag ctaagaggat gccttgcgct gaggattact tgtctgtggt ttgaaccag    2340
ttatgtgttc tacacgagaa aactcctgtc tccgacagag ttactaagtg ctgcacagag   2400
tctttggtca atagaaggcc ttgtttcagt gccctgaag tcgatgaaac ttatgtgcct     2460
aaagagttcc aagccgaaac gttcacttt cacgctgaca tttgtactct ttctgagaag    2520
gaacgtcaga tcaaaaagca gacagcattg gtggaattgg taaagcataa accaaaggct   2580
acaaaagagc agctgaaggc tgttatggat gattttgcag ctttcgtgga aaagtgttgt    2640
aaagccgatg ataaagagac ttgttttgca gaggagggga aaaagctggt tgctgcatca   2700
caagctgccc taggtcttgc agccgctacc ggttctactt cccatttggt gaagtgtgca   2760
gaaaaggaaa agacattttg tgtaaacggt ggggagtgct ttatggttaa ggacttgagt   2820
aatccttcaa gatatctttg caaatgtcca aatgagttta ccggagatcg ttgtcaaaac   2880
tacgtcatgg cctccttcta caaacactta ggtattgaat tcatggaagc tgaggaactg   2940
tatcagaaag gaggctctca tcaccaccat caccattagt ga                     2982
```

```
SEQ ID NO: 118               moltype = AA   length = 1066
FEATURE                      Location/Qualifiers
REGION                       1..1066
                             note = Synthetic construct
source                       1..1066
                             mol_type = protein
                             organism = synthetic construct
SEQUENCE: 118
AQVLRGTVTD FPGFDERADA ETLRKAMKGL GTDEESILTL LTSRSNAQRQ EISAAFKTLF    60
GRDLLDDLKS ELTGKFEKLI VALMKPSRLY DAYELKHALK GAGTNEKVLT EIIASRTPEE    120
LRAIKQVYEE EYGSSLEDDV VGDTSGYYQR MLVVLLQANR DPDAGIDEAQ VEQDAQALFQ    180
AGELKWGTDE EKFITIFGTR SVSHLRKVFD KYMTISGFQI EETIDRETSG NLEQLLLAVV    240
KSIRSIPAYL AETLYYAMKG AGTDDHTLIR VMVSRSEIDL FNIRKEFRKN FATSLYSMIK    300
GDTSGDYKKA LLLLCGEDDA SDAHKSEVAH RFKDLGEENF KALVLIAFAQ YLQQSPFEDH    360
VKLVNEVTEF AKTCVADESA ENCDKSLHTL FGDKLCTVAT LRETYGEMAD CCAKQEPERN    420
ECFLQHKDDN PNLPRLVRPE VDVMCTAFHD NEETFLKKYL YEIARRHPYF YAPELLFFAK    480
RYKAAFTECC QAADKAACLL PKLDELRDEG KASSAKQRLK CASLQKFGER AFKAWAVARL    540
SQRFPKAEFA EVSKLVTDLT KVHTECCHGD LLECADDRAD LAKYICENQD SISSKLKECC    600
EKPLLEKSHC IAEVENDEMP ADLPSLAADF VESKDVCKNY AEAKDVFLGM FLYEYARRHP    660
DYSVVLLLRL AKTYETTLEK CCAAADPHEC YAKVFDEFKP LVEEPQNLIK QNCELFEQLG    720
EYKFQNALLV RYTKKVPQVS TPTLVEVSRN LGKVGSKCCK HPEAKRMPCA EDYLSVVLNQ    780
LCVLHEKTPV SDRVTKCCTE SLVNRRPCFS ALEVDETYVP KEFQAETFTF HADICTLSEK    840
ERQIKKQTAL VELVKHKPKA TKEQLKAVMD DFAAFVEKCC KADDKETCFA EEGKKLVAAS    900
QAALGLAAAT GPALPEDGGS GAFPPGHFKD PKRLYCKNGD FFLRIHPDGR VDGVREKSDP    960
HIKLQLQAEE RGVVSIKGVC ANRYLAMKED GRLLASKCVT DECFFFERLE SNNYNTYRSR   1020
KYTSWYVALK RTGQYKLGSK TGPGQKAILF LPMSAKSGGS HHHHHH                  1066
```

```
SEQ ID NO: 119               moltype = DNA   length = 3204
FEATURE                      Location/Qualifiers
misc_feature                 1..3204
                             note = Synthetic construct
source                       1..3204
                             mol_type = other DNA
                             organism = synthetic construct
SEQUENCE: 119
gctcaagtgc taaggggaac tgttactgat tttccaggtt ttgatgaaag agcagatgct    60
gagactttaa ggaaagctat gaaaggattg ggtacagacg aggaatccat tttgacacta   120
ttgacatcac gaagtaacgc ccagagacaa gagatctcag cagctttcaa aaccctgttc   180
ggaagagatt tgcttgacga tttgaagtct gagttgactg gtaagtttga aaaactaata   240
gttgccctga tgaagccttc cagactttat gatgcttacg aacttaagca cgctttgaaa   300
ggggctggaa caaatgaaaa agttttgact gagataatcg catcacgtac ccctgaggaa   360
ctaagagcca ttaagcaggt atatgaagag aatacggta gttccttaga ggacgacgtc    420
gttggtgaca catctggtta ctatcagagg atgttggttg tcttgttgca agctaatagg   480
gatcctgatg ctggcatcga tgaagcccaa gtagagcagg acgcccaagc cctgtttcaa   540
gcaggcgaat gaagtggggg aacggacgaa gagaagttta tcaccatctt cggaactcgt   600
tctgtatctc atcttagaaa agtattcgac aaatacatga cgatttctgg ttttcaaatt   660
gaggagacta ttgatagaga gacgtctgga aacttagaac agcttttgct tgccgtcgtt   720
aagtctataa ggagtattcc agcctactta gctgaaacct tgtactacgc catgaagggt   780
```

```
gctggaactg atgatcatac cttgatacga gttatggtaa gtcgatcaga gattgatttg    840
tttaacatta ggaaggagtt caggaaaaac tttgctacct cattgtattc catgataaag    900
ggtgatactt caggtgatta caaaaaggct ctgctttttgc tgtgtggcga ggacgatgct   960
agcgatgctc acaaatctga agtcgctcat cgtttcaaag acttgggtga ggaaaacttt   1020
aaggctttag ttctgattgc ttttgcccaa tatcttcaac aatcaccatt cgaagatcat   1080
gtgaaacttg ttaacgaagt taccgaattt gcaaaaacgt gtgtggcaga cgaaagtgcc   1140
gaaaactgtg acaaatcatt acacactttg ttcggtgaca agttatgcac tgttgcaacc   1200
ctacgtgaga catatggaga aatggcagac tgttgcgcca aacaagagcc tgaacgaaac   1260
gaatgctttc tgcagcacaa agacgataat ccaaatcttc cccgattagt tcgtcccgaa   1320
gtagacgtaa tgtgcacagc ctttcatgat aatgaagaga ctttcctgaa aaagtacttg   1380
tacgaaattg caagacgtca cccatacttc tatgctcccg agttactgtt tttcgccaaa   1440
cgatacaagg cagcctttac agaatgttgc caagcagctg acaaggctgc atgtctttta   1500
cctaagttag atgagttaag agacgaaggt aaggcttcct cagcaaaaca gagacttaag   1560
tgcgcatccc ttcaaaagtt tggtgagaga gctttcaagg cttgggctgt cgccagactg   1620
tctcagagat ttcctaaggc tgaattcgca gaagtctcta agctagtaac tgacttgact   1680
aaagttcata ctgagtgctg tcatggggat ttgttggaat gcgcagatga tcgtgcagac   1740
ttagcaaagt acatctgcga gaaccaagac tctatttcca gtaagttaaa ggaatgttgc   1800
gaaaagccac tacttgagaa gtcccactgt attgctgaag tcgaaaatga tgaaatgcct   1860
gctgaccttc catctttggc cgctgatttc gttgagtcca aggatgtgtg caaaaactat   1920
gctgaagcaa aagatgtgtt cctagggatg ttcctgtatg aatatgctcg tcgacatccc   1980
gactattccg ttgtccttttt actgagattg gctaagacct acgagacaac cttggagaag   2040
tgttgtgctg ccgcagatcc tcacgagtgt tacgcaaagt gtttgatga gttcaaacca    2100
ttggttgaag agccacaaaa tctaatcaag cagaactgtg aactgtttga caattgggc    2160
gaatacaaat tccaaatgc tctgttagtg agatacacca aaaaggtccc acaagtttcc    2220
accccaactc tagtcgaggt gtccagaaat ctaggaaaag ttggatctaa gtgttgtaag    2280
catccagaag ctaagaggat gccttgcgct gaggattgct tgtctgtgt tttgaaccag     2340
ttatgtgttc tacacgagaa aactcctgtc tccgacagag ttactaagtg ctgcacagag   2400
tctttggtca atagaaggcc ttgtttcagt gccctggaag tcgatgaaac ttatgtgcct   2460
aaagagttcc aagccgaaac gttcacttttt cacgctgaca tttgtactct ttctgagaag   2520
gaacgtcaga tcaaaaagca gacagccattg gtggaattgg taaagcataa accaaaggct   2580
acaaaagagc agctgaaggc tgttatggat gattttgcag ctttcgtgga aaagtgttgt   2640
aaagccgatg ataaagagac ttgttttgca gaggagggga aaaagctggt tgctgcatca   2700
caagctgccc taggtcttgc agccgctacc ggtcccgcct tgccagagga tggcggttct   2760
ggagctttttc ctccaggtca cttcaaagat ccaaaaaagt tgtattgcaa aaacggtggg    2820
tttttccttc gaatacatcc tgacggtaga gttgacgggg taagagaaaa gagtgaccca   2880
catatcaagc tacagttaca agccgaggaa agaggagttg tctcaatcaa gggcgtttgt   2940
gctaacagat acttggctat gaaggaagat ggtagactgc ttgctagtaa gtgtgtcact   3000
gatgaatgtt tcttttttcga aagattggag tccaataact ataacacgta caggtcacgt   3060
aagtatacga gttggtacgt ggctctgaaa cgtacaggcc agtataagtt aggttcaaaa   3120
actggacccg gacagaaagc tatcttattc ctacccatgt ctgcaaagtc tggcggtagt   3180
caccatcacc atcatcatta gtga                                         3204
```

```
SEQ ID NO: 120         moltype = AA  length = 992
FEATURE                Location/Qualifiers
REGION                 1..992
                       note = Synthetic construct
source                 1..992
                       mol_type = protein
                       organism = synthetic construct
SEQUENCE: 120
AQVLRGTVTD FPGFDERADA ETLRKAMKGL GTDEESILTL LTSRSNAQRQ EISAAFKTLF    60
GRDLLDDLKS ELTGKFEKLI VALMKPSRLY DAYELKHALK GAGTNEKVLT EIIASRTPEE    120
LRAIKQVYEE EYGSSLEDDV VGDTSGYYQR MLVVLLQANR DPDAGIDEAQ VEQDAQALFQ    180
AGELKWGTDE EKFITIFGTR SVSHLRKVFD KYMTISGFQI EETIDRETSG NLEQLLLAVV    240
KSIRSIPAYL AETLYYAMKG AGTDDHTLIR VMVSRSEIDL FNIRKEFRKN FATSLYSMIK    300
GDTSGDYKKA LLLLCGEDDA SDAHKSEVAH RFKDLGEENF KALVLIAFAQ YLQQSPFEDH    360
VKLVNEVTEF AKTCVADESA ENCDKSLHTL FGDKLCTVAT LRETYGEMAD CCAKQEPERN    420
ECFLQHKDDN PNLPRLVRPE VDVMCTAFHD NEETFLKKYL YEIARRHPYF YAPELLFFAK    480
RYKAAFTECC QAADKAACLL PKLDELRDEG KASSAKQRLK CASLQKFGER AFKAWAVARL    540
SQRFPKAEFA EVSKLVTDLT KVHTECCHGD LLECADDRAD LAKYICENQD SISSKLKECC    600
EKPLLEKSHC IAEVENDEMP ADLPSLAADF VESKDVCKNY AEAKDVFLGM FLYEYARRHP    660
DYSVVLLLRL AKTYETTLEK CCAAADPHEC YAKVFDEFKP LVEEPQNLIK QNCELFEQLG    720
EYKFQNALLV RYTKKVPQVS TPTLVEVSRN LGKVGSKCCK HPEAKRMPCA EDYLSVVLNQ    780
LCVLHEKTPV SDRVTKCCTE SLVNRRPCFS ALEVDETYVP KEFQAETFTF HADICTLSEK    840
ERQIKKQTAL VELVKHKPKA TKEQLKAVMD DFAAFVEKCC KADDKETCFA EEGKKLVAAS    900
QAALGLAAAT GSTSHLVKCA EKEKTFCVNG GECFMVKDLS NPSRYLCKCP NEFTGDRCQN    960
YVMASFYKHL GIEFMEAEEL YQKGGSHHHH HH                                  992
```

```
SEQ ID NO: 121         moltype = DNA  length = 2982
FEATURE                Location/Qualifiers
misc_feature           1..2982
                       note = Synthetic construct
source                 1..2982
                       mol_type = other DNA
                       organism = synthetic construct
SEQUENCE: 121
gctcaagtgc taaggggaac tgttactgat tttccaggtt ttgatgaaag agcagatgct    60
gagactttaa ggaaagctat gaaaggattg ggtacagacg aggaatccat tttgacacta    120
ttgacatcac gaagtaacgc ccagagacaa gagatctcag cagcttttcaa aacccctgttc   180
```

```
ggaagagatt tgcttgacga tttgaagtct gagttgactg gtaagtttga aaaactaata  240
gttgccctga tgaagccttc cagactttat gatgcttacg aacttaagca cgctttgaaa  300
ggggctggaa caaatgaaaa agttttgact gagataatcg catcacgtac ccctgaggaa  360
ctaagagcca ttaagcaggt atatgaagag gaatacggta gttccttaga ggacgacgtc  420
gttggtgaca catctggtta ctatcagagg atgttggttg tcttgttgca agctaatagg  480
gatcctgatg ctggcatcga tgaagcccaa gtagagcagg acgcccaagc cctgtttcaa  540
gcaggcgaat tgaagtgggg aacggacgaa gagaagttta tcaccatctt cggaactcgt  600
tctgtatctc atcttagaaa agtattcgac aaatacatga cgatttctgg ttttcaaatt  660
gaggagacta ttgatagaga gacgtctgga aacttagaac agctttttgct tgccgtcgtt  720
aagtctataa ggagtattcc agcctactta gctgaaacct tgtactacgc catgaagggt  780
gctggaactg atgatcatac cttgatacga gttatggtaa gtcgatcaga gattgatttg  840
tttaacatta ggaaggagtt caggaaaaac tttgctacct cattgtattc catgataaag  900
ggtgatactt caggtgatta caaaaaggct ctgctttgc tgtgtggcga ggacgatgct  960
agcgatgctc acaaatcgga agtcgctcat cgtttcaaag acttgggtga ggaaaacttt  1020
aaggctttag ttctgattgc ttttgcccaa tatcttcaac aatcaccatt cgaagatcat  1080
gtgaaacttg ttaacgaagt taccgaattt gcaaaaacgt gtgtggcaga cgaaagtgcc  1140
gaaaactgtg acaaatcatt acacactttg ttcggtgaca agttatgcac tgttgcaacc  1200
ctacgtgaga catatggaga aatggcagac tgttgcgcca aacaagagcc tgaacgaaac  1260
gaatgctttc tgcagcacaa agacgataat ccaaatcttc cccgattagt tcgtcccgaa  1320
gtagacgtaa tgtgcacagc ctttcatgat aatgaagaga ctttcctgaa aaagtacttg  1380
tacgaaattg caagacgtca cccatacttc tatgctcccg agttactgtt tttcgccaaa  1440
cgatacaagg cagcctttac agaatgttgc caagcagctg acaagatggc atgtcttta  1500
cctaagttag atgagttaag agacgaaggt aaggcttcct cagcaaaaca gagacttaag  1560
tgcgcatccc ttcaaaagtt tggtgagaga gctttcaagg cttgggctgt cgccagactg  1620
tctcagagat ttcctaaggc tgaattcgca gaagtctcta agctagtaac tgacttgact  1680
aaagttcata ctgagtgctg tcatgggat ttgttggaat gcgcagatga tcgtgcaaac  1740
ttagcaaagt acatctgcga gaaccaagac tctatttcca gtaagttaaa ggaatgttgc  1800
gaaaagccac tacttgagaa gtcccactgt attgctgaag tcgaaatga tgaaatgcct  1860
gctgacctC catctttggc cgctgattC gttgagtcca aggatgtgtg caaaaactat  1920
gctgaagcaa aagatgtgtt cctagggatg ttcctgtatg aatatgctcg tcgacatccc  1980
gactattccg ttgtccttt actgagattg gctaagacct acgagacaac cttggagaag  2040
tgttgtgctg ccgcagatcc tcacgagtgt tacgcaaaag tgtttgatga gttcaaacca  2100
ttggttgaag agccacaaaa tctaatcaag cagaactgtg aactgtttga caattgggc  2160
gaatacaaat tccaaaatgc tctgttagtg agatacacca aaaaggtccc acaagtttcc  2220
accccaactc tagtcgaggt gtccagaaat ctaggaaaag ttggatctaa gtgttgtaag  2280
catccagaag ctaagaggat gccttgcgct gaggattact tgtctgtggt tttgaaccag  2340
ttatgtgttc tacacgagaa aactcctgtc tccgacagag ttactaagtg ctgcacagag  2400
tctttggtca atagaaggcc ttgtttcagt gccctggaag tcgatgaaac ttatgtgcct  2460
aaagagttcc aagccgaaac gttcactttt cacgctgactct ttctgagaag  2520
gaacgtcaga tcaaaaagca gacagcattg gtgtgaattgg taaagcataa accaaaggct  2580
acaaaagagc agctgaaggc tgttatggat gattttgcag ctttcgtgga aaagtgttgt  2640
aaagccgatg ataaagagac ttgtttttgca gaggaggggga aaaagctggt tgctgcatca  2700
caagctgccc taggtcttgc agccgctacc ggttctactt cacatcttgt gaaatgcgcc  2760
gaaaaagaga aaacattttg tgtgaatggt ggagagtgct ttatggttaa agatttgtct  2820
aaccctagta gataccgtgtg caaatgtccc aatgaattca caggtgacag atgtcagaac  2880
tatgttatgg ctagtttcta caaacatctg ggcattgagt tcatggaagc cgaggaattg  2940
tatcaaaaag gtggatccca ccatcaccac catcattagt ga                      2982
```

SEQ ID NO: 122          moltype = AA  length = 1068
FEATURE                 Location/Qualifiers
REGION                  1..1068
                        note = Synthetic construct
source                  1..1068
                        mol_type = protein
                        organism = synthetic construct
SEQUENCE: 122
```
PALPEDGGSG AFPPGHFKDP KRLYCKNGGF FLRIHPDGRV DGVREKSDPH IKLQLQAEER  60
GVVSIKGVCA NRYLAMKEDG RLLASKCVTD ECFFFERLES NNYNTYRSRK YTSWYVALKR  120
TGQYKLGSKT GPGQKAILFL PMSAKSGAAS DAHKSEVAHR FKDLGEENFK ALVLIAFAQY  180
LQQSPFEDHV KLVNEVTEFA KTCVADESAE NCDKSLHTLF GDKLCTVATL RETYGEMADC  240
CAKQEPERNE CFLQHKDDNP NLPRLVRPEV DVMCTAFHDN EETFLKKYLY EIARRHPYFY  300
APELLFFAKR YKAAFTECCQ AADKAACLLP KLDELRDEGK ASSAKQRLKC ASLQKFGERA  360
FKAWAVARLS QRFPKAEFAE VSKLVTDLTK VHTECCHGDL LECADDRADL AKYICENQDS  420
ISSKLKECCE KPLLEKSHCI AEVENDEMPA DLPSLAADFV ESKDVCKNYA EAKDVFLGMF  480
LYEYARRHPD YSVVLLLRLA KTYETTLEKC CAAADPHECY AKVFDEFKPL VEEPQNLIKQ  540
NCELFEQLGE YKFQNALLVR YTKKVPQVST PTLVEVSRNL GKVGSKCCKH PEAKRMPCAE  600
DYLSVVLNQL CVLHEKTPVS DRVTKCCTES LVNRRPCFSA LEVDETYVPK EFQAETFTFH  660
ADICTLSEKE RQIKKQTALV ELVKHKPKAT KEQLKAVMDD FAAFVEKCCK ADDKETCFAE  720
EGKKLVAASQ AALGLAAATG AQVLRGTVTD FPGFDERADA ETLRKAMKGL GTDEESILTL  780
LTSRSNAQRQ EISAAFKTLF GRDLLDDLKS DLTGKFEKLI VALMKPSRLY DAYELKHALK  840
GAGTNEKVLT EIIASRTPEE LRAIKQVYEE EYGSSLEDDV VGNTSGYYQR MLVVLLQANR  900
DPDAGIDEAQ VEQDAQALFQ AGELKWGTDE EKFITIFGTR SVSHLRKVFD KYMTISGFQI  960
EETIDRATSG NLEQLLLAVV KSIRSIPAYL AETLYYAMKG AGTDDHTLIR VMVSRSEIDL  1020
FNIRKEFRKN FATSLYSMIK GNTSGDYKKA LLLLCGEDDG GSHHHHHH             1068
```

SEQ ID NO: 123          moltype = DNA  length = 3210
FEATURE                 Location/Qualifiers
misc_feature            1..3210
                        note = Synthetic construct -continued

```
source                 1..3210
                       mol_type = other DNA
                       organism = synthetic construct
SEQUENCE: 123
ccagctttgc ctgaggatgg aggctctggt gcttttcctc ctggtcattt caaagaccca   60
aaaagactgt attgcaaaaa cggtgggttt ttcctgagga ttcatccaga tgggagggtc  120
gatggagtta gagagaaatc agacccccac attaagcttc aactacaggc tgaggaacgt  180
ggtgttgtct ccatcaaggg tgtttgtgca aatcgatact tagctatgaa agaggacggc  240
agattacttg ccagtaagtg tgtaactgat gaatgtttct ttttcgaaag actagaatcc  300
aataactaca atacttaccg ttctcgtaag tatacatcat ggtacgtggc cttgaagaga  360
acgggacaat acaaattggg ttctaagacc ggaccaggac agaaagcaat cttgtttttg  420
cccatgtcag ctaagagtgg agctgcaagt gacgctcata agtctgaagt tgctcacaga  480
ttcaaagacc taggtgaaga gaactttaag gctcttgtac ttatagcatt tgctcagtat  540
ctgcaacaga gtcccttcga agatcatgtc aagctgatga atgaggtaac cgaattcgcc  600
aagacttgtg tggctgatga atccgccgaa aactgtgaca aatctttaca cacattgttc  660
ggagataaac tatgcacagt agcaacttta cgtgaaactt atggtgagat ggcagattgt  720
tgtgctaaac aggagcctga gagaaatgaa tgctttttgc aacacaagga cgacaatcct  780
aaccttccca gattggttag acccgaggtt gacgttatgt gtaccgcctt ccacgacaat  840
gaggaaacat ttctgaaaaa gtacttgtac gaaattgcac gacgtcaccc atacttctat  900
gcacctgagc ttttgttttt cgccaaaaga tacaaggcag ctttcactga gtgctgtcaa  960
gcagccgata aggctgcttg tctattacct aaacttgatg agcttagaga tgagggtaaa 1020
gcatcctccg ctaaacagag gttgaaatgt gccagtttgc agaagtttgg tgaacgtgct 1080
ttcaaggcat gggctgttgc tagattatct caaagatttc ctaaggccga atttgctgag 1140
gtgtcaaagt tggtgacgga tttgactaag gtccacactg agtgttgcca tggtgatctt 1200
ttggaatgtg ctgacgatag agccgacctg gccaagtata tctgtgaaaa ccaagattct 1260
atcagtagta agctgaagga atgttgcgaa aaacctctac tagagaaatc tcattgcaat 1320
gcagaagttg aaaacgatga aatgccagcc gacttgccca gtctggctgc tgatttcgtc 1380
gagtcaaaag atgtttgcaa aaactatgcc gaagcaaagg atgtcttttt gggcatgttt 1440
ctgtacgaat atgctcgtcg tcatcctgac tattccgttg tcctgttgct aagactagct 1500
aaaacgtatg aaacgacctt ggaaaagtgt tgcgctgcag ctgatcccca cgagtgttat 1560
gcaaaagttt tcgatgagtt taagccactt gtagaagagc cacagaactt gatcaaacag 1620
aattgtgagc ttttcgagca attaggtgag tataagtttc aaaacgcttt gctggttaga 1680
tataccaaaa aggtcccaca agtgtcaacc cctaccctgg tagaagtgag tagaaatcta 1740
ggaaaagtcg gatctaagtg ctgcaagcat ccagaagcta agaatgcc ttgcgctgag 1800
gattacttgt cagtagtttt gaatcagttg tgcgtcctac atgaaaagac acccgtttct 1860
gatagagtca ctaagtgttg tactgagtct ctagtaaaca gaaggccttg tttctctgca 1920
ttagaagtag atgaaaccta tgtcccaaag gagttccaag ctgaaacctt acatttcac 1980
gccgacattt gtacgctatc tgagaaggag cgtcagatca aaaagcaaac agcccttgtt 2040
gagcttgtga agcacaagcc aaaagctaca aaggagcaat tgaaagccgt catggacgat 2100
ttcgccgcat ttgttgagaa gtgttgcaag gcagatgata aggaaacttg ttttgctgaa 2160
gagggcaaaa agcttgttgc cgcctctcaa gctgctttgg gactagccgc tgctaccggt 2220
gctcaagttt tgaggggaac cgttaccgac ttcccaggtt ttgacgaaag agccgacgca 2280
gaaacattaa ggaaagccat gaagggctta ggcaccgatg aggagtccat tctgacactg 2340
ttgacttccc gatccaatgc ccaaaggcag gagatttcag ccgctttcaa gactttgttt 2400
ggtagagatc ttctggacga cctgaaatca gatctgactg gaaagtttga gaaacttatt 2460
gttgctttga tgaagccttc aagactatat gacgcatacg agttgaaaca tgcattgaaa 2520
ggtgcggaa ctaatgaaaa agtgttaact gagatcgttg cttccagaac accagaaag 2580
cttcgtgcta tcaaacaagt gtatgaagag gaatacggat caagtctgga agatgacgtt 2640
gttggtaata cctcagggta ttaccaaagg atgcttgtcg ttctattaca agctaatcga 2700
gatcctgacg ccggaatcga tgaagctcaa gttgaacaag atgctcaggc tcttttcaa 2760
gccggtgaat tgaagtgggg gactgatgag gaaaagttta tcacgatctt tggtactaga 2820
tctgttagtc atttgagaaa agtatttgac aaatacatga ccattctgg ctttcaaata 2880
gaagagacta ttgataggc cacttccggt aacttggaac aactgttgtt agctgtggtc 2940
aagagtataa gatcaattcc agcttactta gctgaaactc tgtattacgc aatgaaagga 3000
gcaggcacag acgatcacac gttgatccga gtcatggttt ccagatcaga gattgacttg 3060
ttcaatatca ggaaggaatt caggaaaaac tttgcaacct ctttgtactc catgatcaaa 3120
ggtaatactt ccggtgatta caaaaaggct ttgttgttgt tatgtggaga ggatgacgga 3180
ggttcacatc accatcatca ccattagtga                                  3210

SEQ ID NO: 124       moltype = AA  length = 991
FEATURE              Location/Qualifiers
REGION               1..991
                     note = Synthetic construct
source               1..991
                     mol_type = protein
                     organism = synthetic construct
SEQUENCE: 124
LESGGGLVQP GGSLRLSCAG SGFTFSSYAM SWVRQAPGKG LEWVSSISGS GGSTYYADSV   60
KGRFTISRDN SKKTLYLQMN SLRAEDTAVY YCARKRGRTT VSWGLVYFDY WGQGTVVTVS  120
SGGGGSGGGG SGGGGSGGSE LTQSPGTLSL SPGERATLSC RASHSVSRAY LAWYQQKPGQ  180
APRLLIYGTS SRATGIPDRF SGSGSGTDFT LTISRLEPED FAVYYCQQYG GSPWFGQGTK  240
VELKASDAHK SEVAHRFKDL GEENFKALVL IAFAQYLQQS PFEDHVKLVN EVTEFAKTCV  300
ADESAENCDK SLHTLFGDKL CTVATLRETY GEMADCCAKQ EPERNECFLQ HKDDNPNLPR  360
LVRPEVDVMC TAFHDNEETF LKKYLYEIAR RHPYFYAPEL LFFAKRYKAA FTECCQAADK  420
AACLLPKLDE LRDEGKASSA KQRLKCASLQ KFGERAFKAW AVARLSQRFP KAEFAEVSKL  480
VTDLTKVHTE CCHGDLLECA DDRADLAKYI CENQDSISSK LKECCEKPLL EKSHCIAEVE  540
NDEMPADLPS LAADFVESKD VCKNYAEAKD VFLGMFLYEY ARRHPDYSVV LLLRLAKTYE  600
TTLEKCCAAA DPHECYAKVF DEFKPLVEEP QNLIKQNCEL FEQLGEYKFQ NALLVRYTKK  660
VPQVSTPTLV EVSRNLGKVG SKCCKHPEAK RMPCAEDYLS VVLNQLCVLH EKTPVSDRVT  720
```

```
KCCTESLVNR RPCFSALEVD ETYVPKEFQA ETFTFHADIC TLSEKERQIK KQTALVELVK   780
HKPKATKEQL KAVMDDFAAF VEKCCKADDK ETCFAEEGKK LVAASQAALG LAAATGPALP   840
EDGGSGAFPP GHFKDPKRLY CKNGGFFLRI HPDGRVDGVR EKSDPHIKLQ LQAEERGVVS   900
IKGVCANRYL AMKEDGRLLA SKCVTDECFF FERLESNNYN TYRSRKYTSW YVALKRTGQY   960
KLGSKTGPGQ KAILFLPMSA KSGGSHHHHH H                                  991

SEQ ID NO: 125          moltype = DNA  length = 2979
FEATURE                 Location/Qualifiers
misc_feature            1..2979
                        note = Synthetic construct
source                  1..2979
                        mol_type = other DNA
                        organism = synthetic construct
SEQUENCE: 125
ttggagagtg ggggtggctt ggttcaaccc ggtggatctt tgagattgtc atgtgccggt    60
tctggtttta cctttagttc ctatgctatg tcttgggtcc gtcaagcccc aggcaaagga   120
cttgaatggg tatcatcaat ctccgggtca ggtggtagta cgtattacgc agattctgtg   180
aaaggtaggt ttaccatttc cagagataac tccaaaaaga cattgtactt gcaaatgaat   240
agtctgagag ctgaggatac tgccgtctat tactgtgccc gaaaaagagg cagaactaca   300
gttagttggg gtcttgtcta cttttgactac tggggtcagg ggacggtcgt taccgtatct   360
tccggtggag ggggttctgg aggaggagga tctggtggtg gtggaagtgg aggttctgaa   420
ttgacccaat ctcctggtac tctgtctcta agtccaggag aacgagccac gttgtcatgt   480
agggcctcac attcagtttc aagagcttat cttgcctggt atcaacagaa acctggacag   540
gccccacgtt tgttgatata cggcaccagt tccagggcta caggaatacc agataggttt   600
tctggatctg gctcaggaac ggatttcact ttgacaattt caagactaga gccagaggac   660
tttgccgtat actactgtca acaatatgga ggatcacctt ggttcggaca ggtactaaa    720
gttgaactta aagctagcga tgctcacaaa tctgaagtcg ctcatcgttt caaagacttg   780
ggtgaggaaa actttaaggc tttagttctg attgcttttg cccaatatct tcaacaatca   840
ccattcgaag atcatgtgaa acttgttaac gaagttaccg aatttgcaaa aacgtgtgtg   900
gcagcagaaa gtgccgaaaa ctgtgacaaa tcattcacaca ctttgttcgg tgacaagtta   960
tgcactgttg caaccctacg tgagacatat ggagaaatgg cagactgttg cgccaaacaa  1020
gagcctgaac gaaacgaatg ctttctgcag cacaaagacg ataatccaaa tcttccccga  1080
ttagttcgtc ccgaagtaga cgtaatgtgc acagcctttc atgataatga agagactttc  1140
ctgaaaaagt acttgtacga aattgcaaga cgtcacccat acttctatgc tcccgagtta  1200
ctgtttttcg ccaaacgata caaggcagcc tttacagaat gttgccaagc agctgacaag  1260
gctgcatgtc ttttacctaa gttagatgag ttaagagacg aaggtaaggc ttcctcagca  1320
aaacagagac ttaagtgcgc atcccttcaa aagtttggtg agagagcttt caaggcttgg  1380
gctgtcgcca gactgtctca gagatttcct aaggctgaat tcgcagaagt ctctaagcta  1440
gtaactgact tgactaaagt tcatactgag tgctgtcatg gggatttgtt ggaatgcgca  1500
gatgatcgtg cagacttagc aaaagtacatc tgcgagaacc aagactctat ttccagtaag  1560
ttaaaggaat gttgcgaaaa gccactactt gagaagtccc actgtattgc tgaagtcgaa  1620
aatgatgaaa tgcctgctga ccttccatct ttggccgctg atttcgttga gtccaaggat  1680
gtgtgcaaaa actatgctga agcaaaagat gtgttcctag gggatgttcct gtatgaatat  1740
gctcgtcgac atcccgacta ttccgttgtc cttttactga gattggctaa gacctacagg  1800
acaaccttgg agaagtgttg tgctgccgca gatcctcacg agtgttacgc aaaagtgttt  1860
gatgagttca aaccattggt tgaagagcca caaaatctaa tcaagcagaa ctgtgaactg  1920
tttgaacaat tgggcgaata caaattccaa aatgctctgt tagtgagata caccaaaaag  1980
gtcccacaag tttccacccc aactctagtc gaggtgtcca gaaatctagg aaaagttgga  2040
tctaagtgtt gtaagcatcc agaagctaag aggatgcctt gcgctgagga ttacttgtct  2100
gtggttttga accagttatg tgttctacac gagaaaactc ctgtctccga cagagttact  2160
aagtgctgca cagagtcttt ggtcaataga aggccttgtt tcagtgccct ggaagtcgat  2220
gaaacttatg tgcctaaaga gttccaagcc gaaacgttca cttttcacgc tgacatttgt  2280
actctttctg agaaggaacg tcagatcaaa aagcagacag cattggtgga attggtaaag  2340
cataaaccaa aggctacaaa agagcagctg aaggctgtta tggatgattt tgcagctttc  2400
gtggaaaagt gttgtaaagc cgatgataaa gagacttgtt ttgcagagga ggggaaaaag  2460
ctggttgctg catcacaagc tgccctaggt cttgcagccg ctaccggtcc cgccttgcca  2520
gaggatggcg gttctggagc ttttcctcca ggtcacttca aagatccaaa aagattgtat  2580
tgcaaaaacg gtgggttttt ccttcgaata catcctgacg gtagagttga cggggtaaga  2640
gaaaagagtg acccacatat caagctacag ttacaagccg aggaaagagg agttgtctca  2700
atcaagggcg tttgtgctaa cagatacttg gctatgaagg aagatggtag actgcttgct  2760
agtaagtgtg tcactgatga atgtttcttt ttcgaaagat tggagtccaa taactataac  2820
acgtacaggt cacgtaagta tacgagttgg tacgtggctc tgaaacgtac aggccagtat  2880
aagttaggtt caaaaactgg acccggacag aaagctatct tattcctacc catgtctgca  2940
aagtctggcg gtagtcacca tcaccatcat cattagtga                         2979

SEQ ID NO: 126          moltype = AA  length = 917
FEATURE                 Location/Qualifiers
REGION                  1..917
                        note = Synthetic construct
source                  1..917
                        mol_type = protein
                        organism = synthetic construct
SEQUENCE: 126
LESGGGLVQP GGSLRLSCAG SGFTFSSYAM SWVRQAPGKG LEWVSSISGS GGSTYYADSV    60
KGRFTISRDN SKKTLYLQMN SLRAEDTAVY YCARKRGRTT VSWGLVYFDY WGQGTVVTVS   120
SGGGGSGGGG SGGGGSGGSE LTQSPGTLSL SPGERATLSC RASHSVSRAY LAWYQQKPGQ   180
APRLLIYGTS SRATGIPDRF SGSGSGTDFT LTISRLEPED FAVYYCQQYG GSPWFGQGTK   240
VELKASDAHK SEVAHRFKDL GEENFKALVL IAFAQYLQQS PFEDHVKLVN EVTEFAKTCV   300
ADESAENCDK SLHTLFGDKL CTVATLRETY GEMADCCAKQ EPERNECFLQ HKDDNPNLPR   360
```

```
LVRPEVDVMC TAFHDNEETF LKKYLYEIAR RHPYFYAPEL LFFAKRYKAA FTECCQAADK   420
AACLLPKLDE LRDEGKASSA KQRLKCASLQ KFGERAFKAW AVARLSQRFP KAEFAEVSKL   480
VTDLTKVHTE CCHGDLLECA DDRADLAKYI CENQDSISSK LKECCEKPLL EKSHCIAEVE   540
NDEMPADLPS LAADFVESKD VCKNYAEAKD VFLGMFLYEY ARRHPDYSVV LLLRLAKTYE   600
TTLEKCCAAA DPHECYAKVF DEFKPLVEEP QNLIKQNCEL FEQLGEYKFQ NALLVRYTKK   660
VPQVSTPTLV EVSRNLGKVG SKCCKHPEAK RMPCAEDYLS VVLNQLCVLH EKTPVSDRVT   720
KCCTESLVNR RPCFSALEVD ETYVPKEFQA ETFTFHADIC TLSEKERQIK KQTALVELVK   780
HKPKATKEQL KAVMDDFAAF VEKCCKADDK ETCFAEEGKK LVAASQAALG LAAATGSTSH   840
LVKCAEKEKT FCVNGGECFM VKDLSNPSRY LCKCPNEFTG DRCQNYVMAS FYKHLGIEFM   900
EAEELYQKGG SHHHHHH                                                 917
```

```
SEQ ID NO: 127          moltype = DNA  length = 2757
FEATURE                 Location/Qualifiers
misc_feature            1..2757
                        note = Synthetic construct
source                  1..2757
                        mol_type = other DNA
                        organism = synthetic construct
SEQUENCE: 127
ttggagagtg ggggtggctt ggttcaaccc ggtggatctt tgagattgtc atgtgccggt   60
tctggtttta cctttagttc ctatgctatg tcttgggtcc gtcaagcccc aggcaaagga   120
cttgaatggg tatcatcaat ctccgggtca ggtggtagta gattctgtg aaaggtaggt   180
aaaggtaggt ttaccatttc cagagataac tccaaaaaga cattgtactt gcaaatgaat   240
agtctgagag ctgaggatac tgccgtctat tactgtgccc gaaaaagagg cagaactaca   300
gttagttggg gtcttgtcta ctttgactac tggggtcagg ggacggtcgt taccgtatct   360
tccggtggag ggggttctgg aggaggagga tctggtggtg gtggaagtgg aggttctgaa   420
ttgacccaat ctcctggtac tctgtctcta agtccaggag aacgagccac gttgtcatgt   480
agggcctcac attcagtttc aagagcttat cttgcctggt atcaacagaa acctggacag   540
gccccacgtt tgttgatata cggcaccagt tccagggcta caggaatacc agataggttt   600
tctggatctg gctcaggaac ggatttcact ttgacaattt caagactaga gccagaggac   660
tttgccgtat actactgtca acaatatgga ggatcacctt ggttcggaca gggtactaaa   720
gttgaactta aagctagcga tgctcacaaa tctgaagtcg ctcatcgttt caaagacttg   780
ggtgaggaaa actttaaggc tttagttctg attgcttttg cccaatatct tcaacaatca   840
ccattcgaag atcatgtgaa acttgttaac gaagttaccg aatttgcaaa aacgtgtgtg   900
gcagacgaaa gtgccgaaaa ctgtgacaaa tcattcacaca ctttgttcgg tgacaagtta   960
tgcactgttg caaccctacg tgagacatat ggagaaatgg cagactgttg cgccaaacaa   1020
gagcctgaac gaaacgaatg ctttctgcag cacaaagacg ataatccaaa tcttccccga   1080
ttagttcgtc ccgaagtaga cgtaatgtgc acagcctttc atgataatga agagactttc   1140
ctgaaaaagt acttgtacga aattgcaaga cgtcacccat acttctatgc tcccgagtta   1200
ctgttttcg ccaaacgata caaggcagcc tttacagaat gttgccaagc agctgacaag   1260
gctgcatgtc ttttacctaa gttagatgag ttaagagacg aaggtaaggc ttcctcagca   1320
aaacagagac ttaagtgcgc atcccttcaa aagtttggtg agagagcttt caaggcttgg   1380
gctgtcgcca gactgtctca gagatttcct aaggctgaat tcgcagaagt cctaagcta   1440
gtaactgact tgactaaagt tcatactgag tgctgtcatg gggatttgtt ggaatgcgca   1500
gatgatcgtg cagacttagc aaaagtacatc tgcgagaacc aagactctat ttccagtaag   1560
ttaaaggaat gttgcgaaaa gccactactt gagaagtccc actgtattgc tgaagtcgaa   1620
aatgataaa tgcctgctga ccttccatct ttggccgctg atttcgttga gtccaaggat   1680
gtgtgcaaaa actatgctga agcaaaaagat gtgttcctag ggatgttcct gtatgaatat   1740
gctcgtcgac atcccgacta ttccgttgtc cttttactga gattggctaa gacctacgag   1800
acaaccttgg agaagtgttg tgctgccgca gatcctcacg agtgttacgc aaaagtgttt   1860
gatgagttca aaccattggt tgaagagcca caaaatctaa tcaagcagaa ctgtgaactg   1920
tttgaacaat tgggcgaata caaattccaa aatgctctgt tagtgagata caccaaaaag   1980
gtcccacaag tttccacccc aactctagtc gaggtgtcca gaaatctagg aaaagttgga   2040
tctaagtgtt gtaagcatcc agaagctaag aggatgcctt gcgctgagga ttacttgtct   2100
gtggttttga accagttatg tgttctacac gagaaaactc ctgtctccga cagagttact   2160
aagtgctgca cagagtcttt ggtcaataga aggccttgtt tcagtgccct ggaagtcgat   2220
gaaacttatg tgcctaaaga gttccaagcc gaaacgttca cttttcacgc tgacatttgt   2280
actctttctg agaaggaacg tcagatcaaa aagcagacag cattggtgga attggtaaag   2340
cataaaccaa aggctacaaa agagcagcta aaggctgtta tggatgattt tgcagctttc   2400
gtggaaaagt gttgtaaagc cgatgataaa gagacttgtt ttgcagagga ggggaaaaag   2460
ctggttgctg catcacaagc tgccctaggt cttgcagccg ctaccggttc tacttcacat   2520
cttgtgaaat cgcgccgaaaa agagaaaaca ttttgtgtga atggtggaga gtgctttatg   2580
gttaaagatt tgtctaaccc tagtagatac ctgtgcaaat gtccaatga attcacaggt   2640
gacagatgtc agaactatgt tatggctagt ttctacaaac atctgggcat tgagttcatg   2700
gaagccgagg aattgtatca aaaaggtgga tcccaccatc accaccatca ttagtga       2757
```

```
SEQ ID NO: 128          moltype = AA  length = 1051
FEATURE                 Location/Qualifiers
REGION                  1..1051
                        note = Synthetic construct
source                  1..1051
                        mol_type = protein
                        organism = synthetic construct
SEQUENCE: 128
AQVLRGTVTD FPGFDERADA ETLRKAMKGL GTDEESILTL LTSRSNAQRQ EISAAFKTLF   60
GRDLLDDLKS ELTGKFEKLI VALMKPSRLY DAYELKHALK GAGTNEKVLT EIIASRTPEE   120
LRAIKQVYEE EYGSSLEDDV VGDTSGYYQR MLVVLLQANR DPDAGIDEAQ VEQDAQALFQ   180
AGELKWGTDE EKFITIFGTR SVSHLRKVFD KYMTISGFQI EETIDRETSG NLEQLLLAVV   240
KSIRSIPAYL AETLYYAMKG AGTDDHTLIR VMVSRSEIDL FNIRKEFRKN FATSLYSMIK   300
```

```
GDTSGDYKKA LLLLCGEDDA SDAHKSEVAH RFKDLGEENF KALVLIAFAQ YLQQSPFEDH    360
VKLVNEVTEF AKTCVADESA ENCDKSLHTL FGDKLCTVAT LRETYGEMAD CCAKQEPERN    420
ECFLQHKDDN PNLPRLVRPE VDVMCTAFHD NEETFLKKYL YEIARRHPYF YAPELLFFAK    480
RYKAAFTECC QAADKAACLL PKLDELRDEG KASSAKQRLK CASLQKFGER AFKAWAVARL    540
SQRFPKAEFA EVSKLVTDLT KVHTECCHGD LLECADDRAD LAKYICENQD SISSKLKECC    600
EKPLLEKSHC IAEVENDEMP ADLPSLAADF VESKDVCKNY AEAKDVFLGM FLYEYARRHP    660
DYSVVLLLRL AKTYETTLEK CCAAADPHEC YAKVFDEFKP LVEEPQNLIK QNCELFEQLG    720
EYKFQNALLV RYTKKVPQVS TPTLVEVSRN LGKVGSKCCK HPEAKRMPCA EDYLSVVLNQ    780
LCVLHEKTPV SDRVTKCCTE SLVNRRPCFS ALEVDETYVP KEFQAETFTF HADICTLSEK    840
ERQIKKQTAL VELVKHKPKA TKEQLKAVMD DFAAFVEKCC KADDKETCFA EEGKKLVAAS    900
QAALGLAAAT GMSPLLRRLL LAALLQLAPA QAPVSQPDAP GHQRKVVSWI DVYTRATCQP    960
REVVVPLTVE LMGTVAKQLV PSCVTVQRCG GCCPDDGLEC VPTGQHQVRM QILMIRYPSS   1020
QLGEMSLEEH SQCECRPKKK DSGGSHHHHH H                                  1051

SEQ ID NO: 129          moltype = DNA   length = 3159
FEATURE                 Location/Qualifiers
misc_feature            1..3159
                        note = Synthetic construct
source                  1..3159
                        mol_type = other DNA
                        organism = synthetic construct
SEQUENCE: 129
gctcaagtgc taaggggaac tgttactgat tttccaggtt ttgatgaaag agcagatgct     60
gagactttaa ggaaagctat gaaaggattg ggtacagacg aggaatccat tttgacacta    120
ttgacatcac gaagtaacgc ccagagacaa gagatctcag cagcttttca aaccctgttc    180
ggaagagatt tgcttgacga tttgaagtct gagttgactg gtaagtttga aaaactaata    240
gttgccctga tgaagccttc cagacttttat gatgcttacg aacttaagca cgctttgaaa    300
ggggctggaa caaatgaaaa agttttgact gagataatcg catcacgtac ccctgaggaa    360
ctaagagcca ttaagcaggt atatgaagag gaatacggta gttccttaga ggacgacgtc    420
gttggtgaca catctggtta ctatcagagg atgttggttg tcttgttgca agctaatagg    480
gatcctgatg ctggcatcga tgaagcccaa gtagagcagg acgcccaagc cctgtttcaa    540
gcaggcgaat tgaagtgggg aacggacgaa gagaagttta tcaccatctt cggaactcgt    600
tctgtatctc atcttagaaa agtattcgac aaatacatga cgatttctgg ttttcaaatt    660
gaggagacta ttgatagaga gacgtctgga aacttagaac agcttttgct tgccgtcgtt    720
aagtctataa ggagtattcc agcctactta gctgaaacct tgtactacgc catgaagggt    780
gctggaactg atgatcatac cttgatacga gttatggtaa gtcgatcaga gattgatttg    840
tttaacatta ggaaggagtt caggaaaaac tttgctacct cattgtattc catgataaag    900
ggtgatactt caggtgatta caaaaaggct ctgctttgc tgtgtggcga ggacgatgct    960
agcgatgctc acaaatctga agtcgctcat cgtttcaaag acttgggtga ggaaaacttt   1020
aaggctttag ttctgattgc ttttgcccaa tatcttcaac aatcaccatt cgaagatcat   1080
gtgaaacttg ttaacgaagt taccgaattt gcaaaaacgt gtgtggcaga cgaaagtgcc   1140
gaaaactgtg acaaatcatt acacactttg ttcggtgaca agttatgcac tgttgcaacc   1200
ctacgtgaga catatggaga aatggcagac tgttgcgcca aacaagagcc tgaacgaaac   1260
gaatgctttc tgcagcacaa agacgataat ccaaatcttc cccgattagt tcgtcccgaa   1320
gtagacgtaa tgtgcacagc ctttcatgat aatgaagaga ctttcctgaa aaagtacttg   1380
tacgaaattg caagacgtca cccatacttc tatgctcccg agttactgtt tttcgccaaa   1440
cgatacaagg cagcctttac agaatgttgc caagcagctg acaaggctgc atgtcttta   1500
cctaagttag atgagttaag agacgaaggt aaggcttcct cagcaaaaca gagacttaag   1560
tgcgcatccc ttcaaaagtt tggtgagaga gctttcaagg cttgggctgt cgccagactg   1620
tctcagagat ttcctaaggc tgaattcgca gaagtctcta agctagtaac tgacttgact   1680
aaagttcata ctgagtgctg tcatgggat ttgttggaat gcgcagatga tcgtgcgac   1740
ttagcaaagt acatctgcga gaaccaagac tctatttcca gtaagttaaa ggaatgttgc   1800
gaaaagccac tacttgagaa gtcccactgt attgctgaag tcgaaatga tgaaatgcct   1860
gctgaccttc catctttggc cgctgatttc gttgagtcca aggatgtgtg caaaaactat   1920
gctgaagcaa aagatgtgtt cctaggatg ttcctgtatg aatatgctcg tcgacatcct   1980
gactattccg ttgtcctttt actgagattg gctaagacct acgagacaac cttggagaag   2040
tgttgtgctg ccgcagatcc tcacgagtgt tacgcaaaag tgtttgatga gttcaaacca   2100
ttggttgaag agccacaaaa tctaatcaag cagaactgtg aactgtttga caattgggc   2160
gaatacaaat tccaaaatgc tctgttagtg agatacacca aaaaggtccc acaagtttcc   2220
accccaactc tagtcgaggt gtccagaaat ctaggaaaag ttggatctaa gtgttgtaag   2280
catccagaag ctaagaggat gccttgcgct gaggattact tgtctgtggt tttgaaccag   2340
ttatgtgttc tacacgagaa aactcctgtc tccgacagag ttactaagtg ctgcacagag   2400
tctttggtca atagaaggcc ttgtttcagt gccctggaag tcgatgaaac ttatgtgcct   2460
aaagagttcc aagccgaaac gttcactttt cacgctgactct ttctgagaag   2520
gaacgtcaga tcaaaaagca gacagcattg gtggaattgg taaagcataa accaaaggct   2580
acaaaagagc agctgaaggc tgttatggat gattttgcag ctttcgtgga aaagtgttgt   2640
aaagccgatg ataaagagac ttgtttttgca gaggaggga aaaagctggt tgctgcatca   2700
caagctgccc taggtcttgc agccgctacc ggtatgagtc ctttgttgag aaggttgcta   2760
ttagctgcat tgttacagtt agctcctgct caggccccag tttctcagcc agacgcccct   2820
ggtcatcaac gtaaggttgt gtcttggatt gacgtataca cgagagcaac atgccaacca   2880
agggaagtcg ttgttcccct tactgttgag ttgatgggga ctgtggctaa gcagctggtc   2940
ccttcatgtg tcaccgtaca gagatgtgga ggttgttgcc cagacgatgg actagaatgt   3000
gttcaacag gacaacatca ggtgagaatg caaatactgt tgatcagata tccatcttca   3060
caacttggcg aaatgtccct ggaagagcac tctcaatgcg agtgtcgacc caaaaagaaa   3120
gatagtggtg gttcccatca ccaccatcat cattagtga                         3159

SEQ ID NO: 130          moltype = AA   length = 1108
FEATURE                 Location/Qualifiers
REGION                  1..1108
```

```
                        note = Synthetic construct
source                  1..1108
                        mol_type = protein
                        organism = synthetic construct
SEQUENCE: 130
AQVLRGTVTD FPGFDERADA ETLRKAMKGL GTDEESILTL LTSRSNAQRQ EISAAFKTLF    60
GRDLLDDLKS ELTGKFEKLI VALMKPSRLY DAYELKHALK GAGTNEKVLT EIIASRTPEE   120
LRAIKQVYEE EYGSSLEDDV VGDTSGYYQR MLVVLLQANR DPDAGIDEAQ VEQDAQALFQ   180
AGELKWGTDE EKFITIFGTR SVSHLRKVFD KYMTISGFQI EETIDRETSG NLEQLLLAVV   240
KSIRSIPAYL AETLYYAMKG AGTDDHTLIR VMVSRSEIDL FNIRKEFRKN FATSLYSMIK   300
GDTSGDYKKA LLLLCGEDDA SDAHKSEVAH RFKDLGEENF KALVLIAFAQ YLQQSPFEDH   360
VKLVNEVTEF AKTCVADESA ENCDKSLHTL FGDKLCTVAT LRETYGEMAD CCAKQEPERN   420
ECFLQHKDDN PNLPRLVRPE VDVMCTAFHD NEETFLKKYL YEIARRHPYF YAPELLFFAK   480
RYKAAFTECC QAADKAACLL PKLDELRDEG KASSAKQRLK CASLQKFGER AFKAWAVARL   540
SQRFPKAEFA EVSKLVTDLT KVHTECCHGD LLECADDRAD LAKYICENQD SISSKLKECC   600
EKPLLEKSHC IAEVENDEMP ADLPSLAADF VESKDVCKNY AEAKDVFLGM FLYEYARRHP   660
DYSVVLLLRL AKTYETTLEK CCAAADPHEC YAKVFDEFKP LVEEPQNLIK QNCELFEQLG   720
EYKFQNALLV RYTKKVPQVS TPTLVEVSRN LGKVGSKCCK HPEAKRMPCA EDYLSVVLNQ   780
LCVLHEKTPV SDRVTKCCTE SLVNRRPCFS ALEVDETYVP KEFQAETFTF HADICTLSEK   840
ERQIKKQTAL VELVKHKPKA TKEQLKAVMD DFAAFVEKCC KADDKETCFA EEGKKLVAAS   900
QAALGLAAAT GMSPLLRRLL LAALLQLAPA QAPVSQPDAP GHQRKVVSWI DVYTRATCQP   960
REVVVPLTVE LMGTVAKQLV PSCVTVQRCG GCCPDDGLEC VPTGQHQVRM QILMIRYPSS  1020
QLGEMSLEEH SQCECRPKKK DSAVKPDSPR PLCPRCTQHH QRPDPRTCRR RCRRRSFLRC  1080
QGRGLELNPD TCRCRKLRRG GSHHHHHH                                     1108

SEQ ID NO: 131         moltype = DNA   length = 3330
FEATURE                Location/Qualifiers
misc_feature           1..3330
                       note = Synthetic construct
source                 1..3330
                       mol_type = other DNA
                       organism = synthetic construct
SEQUENCE: 131
gctcaagtgc taaggggaac tgttactgat tttccaggtt ttgatgaaag agcagatgct    60
gagactttaa ggaaagctat gaaaggattg ggtacagacg aggaatccat tttgacacta   120
ttgacatcac gaagtaacgc ccagagacaa gagatctcag cagctttcaa aaccctgttc   180
ggaagagatt tgcttgacga tttgaagtct gagttgactg gtaagtttga aaaactaata   240
gttgccctga tgaagccttc cagactttat gatgcttacg aacttaagca cgctttgaaa   300
ggggctggaa caaatgaaaa agtttttgact gagataatcg catcacgtac ccctgaggaa   360
ctaagagcca ttaagcaggt atatgaagag gaatacggta gttccttaga ggacgacgtc   420
gttggtgaca catctggtta ctatcagagg atgttggttg tcttgttgca agctaatagg   480
gatcctgatg ctggcatcga tgaagcccaa gtagagcagg acgcccaagc cctgtttcaa   540
gcaggcgaat tgaagtgggg aacggacgaa gagaagttta tcaccatctt cggaactcgt   600
tctgtatctc atcttagaaa agtattcgac aaatacatga cgattctgg ttttttcaaatt   660
gaggagacta ttgatagaga gacgtctgga aacttagaac agcttttgct tgccgtcgtt   720
aagtctataa ggagtattcc agcctactta gctgaaacct tgtactacgc catgaaggg t   780
gctggaactg atgatcatac cttgatacga gttatggtaa gtcgatcaga gattgatttg   840
tttaacatta ggaaggagtt caggaaaaac tttgctacct cattgtattc catgataaag   900
ggtgatactt caggtgatta caaaaaggct ctgcttttgc tgtgtggcga ggacgatgct   960
agcgatgctc acaaatctga agtcgctcat cgtttcaaag acttgggtga ggaaaacttt  1020
aaggctttag ttctgattgc ttttgcccaa tatcttcaac aatcaccatt cgaagatcat  1080
gtgaaacttg ttaacgaagt taccgaattt gcaaaaacgt gtgtggcaga cgaaagtgcc  1140
gaaaactgtg acaaatcatt acacactttg ttcggtgaca agttatgcac tgttgcaacc  1200
ctacgtgaga catatggaga aatggcagac tgttgcgcca acaagagcc tgaacgaaac  1260
gaatgctttc tgcagcacaa agacgataat ccaaatcttc ccgattagt tcgtcccgaa  1320
gtagacgtaa tgtgcacagc cttcatgat aatgaagaga cttttcctga aaaagtacttg  1380
tacgaaattg caagacgtca cccatacttc tatgctcccg agttactgtt tttcgccaaa  1440
cgatacaagg cagcctttac agaatgttgc caagcagctg acaaggctgc atgtcttta  1500
cctaagttag atgagttaag agacgaaggt aaggcttcct cagcaaaaca gagacttaag  1560
tgcgcatccc ttcaaaagtt tggtgagaga gctttcaagg cttgggctgt cgccagactg  1620
tctcagagat ttcctaaggc tgaattcgca gaagtctcta agctagtaac tgacttgact  1680
aaagttcata ctgagtgctg tcatgggat ttgttggaat gcgcagatga tcgtgcagac  1740
ttagcaaagt acatctgcga gaaccaagac tctatttcca gtaagttaaa ggaatgttgc  1800
gaaaagccac tacttgaaaa gtcccactgt attgctgaag tcgaaaatga tgaaatgcct  1860
gctgaccttc catctttggc cgctgatttc gttgagtcca aggatgtgtg caaaaactat  1920
gctgaagcaa aagatgtgtt cctagggatg ttcctgtatg aatatgctcg tcgacatccc  1980
gactattccg ttgtcctttt actgagattg gctaagacct acgagacaac cttggagaag  2040
tgttgtgctg ccgcagatcc tcacgatgt tacgcaaaag tgtttgatga gttcaaacca  2100
ttggttgaag agccacaaaa tctaatcaag cagaactgtg aactgtttga acaattgggc  2160
gaatacaaat tccaaaatgc tctgttagtc agatacacca aaaaggtccc acaagtttcc  2220
accccaactc tagtcgaggt gtccagaaat ctaggaaaag ttggatctaa gtgttgtaag  2280
catccagaag ctaagaggat gccttgcgct gaggattact tgtctgtggt tttgaaccag  2340
ttatgtgttc tacacgagaa aactcctgtc tccgacagag ttactaagtg ctgcacagag  2400
tctttggtca atagaaggcc ttgtttcagt gcctgaag ttgatgaaac ttatgtgcct  2460
aaagagttcc aagccgaaac gttcacttttt cacgctgaca tttgtactct ttctgagaag  2520
gaacgtcaga tcaaaaagca gacagcattg gtggaattgg taaagcataa accaaaggct  2580
acaaagagc agctgaaggc tgttatggat gattttgcag ctttcgtgga aaagtgttgt  2640
aaagccgatg ataaagagac ttgttttgca gaggagggga aaaagctggt tgctgcatca  2700
caagctgccc taggtcttgc agccgctacc ggtatgagtc ctttgcttag aaggttgtta  2760
```

```
ctggccgcac tgcttcaact tgcaccagct caagccccag tctctcaacc tgacgctccc  2820
ggtcatcaga gaaaggtggt atcatggatt gatgtgtata ctcgtgctac atgccaaccc  2880
cgtgaggttg ttgtaccttt gacagtcgaa ttgatgggaa ccgttgccaa gcagttagtt  2940
ccttcctgtg tcacagtgca gagatgtgga ggatgttgtc cagatgatgg tttggagtgt  3000
gtacctactg gccaacatca ggttagaatg cagatcttga tgatacgtta cccatcaagt  3060
caactaggtg aaatgtcttt ggaggaacac tcccagtgcg aatgcagacc caaaaagaaa  3120
gattctgctg ttaaaccaga ctctccaaga ccattatgtc ccagatgcac gcaacaccat  3180
caaagaccag atccaaggac ttgtagacgt agatgcagga ggcgatcctt tttgcgatgc  3240
caaggtagag gcctagagct gaatcctgac acctgtcgat gtcgaaagtt aagacgtggt  3300
gggtcacacc accatcacca tcattagtga                                   3330
```

SEQ ID NO: 132        moltype = AA  length = 1095
FEATURE               Location/Qualifiers
REGION                1..1095
                      note = Synthetic construct
source                1..1095
                      mol_type = protein
                      organism = synthetic construct
SEQUENCE: 132
AQVLRGTVTD FPGFDERADA ETLRKAMKGL GTDEESILTL LTSRSNAQRQ EISAAFKTLF   60
GRDLLDDLKS ELTGKFEKLI VALMKPSRLY DAYELKHALK GAGTNEKVLT EIIASRTPEE  120
LRAIKQVYEE EYGSSLEDDV VGDTSGYYQR MLVVLLQANR DPDAGIDEAQ VEQDAQALFQ  180
AGELKWGTDE EKFITIFGTR SVSHLRKVFD KYMTISGFQI EETIDRETSG NLEQLLLAVV  240
KSIRSIPAYL AETLYYAMKG AGTDDHTLIR VMVSRSEIDL FNIRKEFRKN FATSLYSMIK  300
GDTSGDYKKA LLLLCGEDDA SDAHKSEVAH RFKDLGEENF KALVLIAFAQ YLQQSPFEDH  360
VKLVNEVTEF AKTCVADESA ENCDKSLHTL FGDKLCTVAT LRETYGEMAD CCAKQEPERN  420
ECFLQHKDDN PNLPRLVRPE VDVMCTAFHD NEETFLKKYL YEIARRHPYF YAPELLFFAK  480
RYKAAFTECC QAADKAACLL PKLDELRDEG KASSAKQRLK CASLQKFGER APKAWAVARL  540
SQRFPKAEFA EVSKLVTDLT KVHTECCHGD LLECADDRAD LAKYICENQD SISSKLKECC  600
EKPLLEKSHC IAEVENDEMP ADLPSLAADF VESKDVCKNY AEAKDVFLGM FLYEYARRHP  660
DYSVVLLLRL AKTYETTLEK CCAAADPHEC YAKVFDEFKP LVEEPQNLIK QNCELFEQLG  720
EYKFQNALLV RYTKKVPQVS TPTLVEVSRN LGKVGSKCCK HPEAKRMPCA EDYLSVVLNQ  780
LCVLHEKTPV SDRVTKCCTE SLVNRRPCFS ALEVDETYVP KEFQAETFTF HADICTLSEK  840
ERQIKKQTAL VELVKHKPKA TKEQLKAVMD DFAAFVEKCC KADDKETCFA EEGKKLVAAS  900
QAALGLAAAT GQRKRRNTIH EFKKSAKTTL IKIDPALKIK TKKVNTADQC ANRCTRNKGL  960
PFTCKAFVFD KARKQCLWFP FNSMSSGVKK EFGHEFDLYE NKDYIRNCII GKGRSYKGTV 1020
SITKSGIKCQ PWSSMIPHEH SFLPSSYRGK DLQENYCRNP RGEEGGPWCF TSNPEVRYEV 1080
CDIPQCGGSH HHHH                                                  1095

SEQ ID NO: 133        moltype = DNA  length = 3291
FEATURE               Location/Qualifiers
misc_feature          1..3291
                      note = Synthetic construct
source                1..3291
                      mol_type = other DNA
                      organism = synthetic construct
SEQUENCE: 133
gctcaagtgc taaggggaac tgttactgat tttccaggtt ttgatgaaag agcagatgct   60
gagactttaa ggaaagctat gaaaggattg ggtacagacg aggaatccat tttgacacta  120
ttgacatcac gaagtaacgc ccagagacaa gagatctcag cagctttcaa aaccctgttc  180
ggaagagatt tgcttgacga tttgaagtct gagttgactg gtaagtttga aaaactaata  240
gttgccctga tgaagccttc cagactttat gatgcttacg aacttaagca cgctttgaaa  300
ggggctggaa caaatgaaaa agttttgact gagataatcg catcacgtac ccctgaggaa  360
ctaagagcca ttaagcaggt atatgaagag gaatacggta gttccttaga ggacgacgtc  420
gttggtgaca catctggtta ctatcagagg atgttggttg tcttgttgca agctaatagg  480
gatcctgatg ctggcatcga tgaagcccaa gtagagcagg acgcccaagc cctgtttcaa  540
gcaggcgaat gaagtggggg aacggacgaa gagaagttta tcaccatctt cggaactcgt  600
tctgtatctc atcttagaaa agtattcgac aaatacatga cgatttctgg ttttcaaatt  660
gaggagacta ttgatagaga gacgtctgga aacttagaac agctttttgct tgccgtcgtt  720
aagtctataa ggagtattcc agcctactta gctgaaacct tgtactacgc catgaagggt  780
gctggaactg atgatcatac cttgatacga gttatggtaa gtcgatcaga gattgatttg  840
tttaacatta ggaaggagtt caggaaaaac tttgctacct cattgtattc catgataaag  900
ggtgatactt caggtgatta caaaaaggct ctgcttttgc tgtgtggcga ggacgatgct  960
agcgatgctc acaaatctga agtcgctcat cgtttcaagg acttgggtga ggaaaacttt 1020
aaggctttag ttctgattgc ttttgcccaa tatcttcaac aatcaccatt cgaagatcat 1080
gtgaaacttg ttaacgaagt taccgaattt gcaaaaacgt gtgtggcaga cgaaagtgcc 1140
gaaaactgtg acaaatcatt acacactttg ttcggtgaca agttatgcac tgttgcaacc 1200
ctacgtgaga catatggaga aatggcagac tgttgcgcca aacaagagcc tgaacgaaac 1260
gaatgctttc tgcagcacaa agacgataat ccaaatcttc cccgattagt tcgtcccgaa 1320
gtagacgtaa tgtgcacagc ctttcatgat aatgaagaga ctttcctgaa aaagtacttg 1380
tacgaaattg caagacgtca cccatacttc tatgctcccg agttactgtt tttcgccaaa 1440
cgatacaagc agcctttac agaatgttgc caagcagctg acaaggctgc atgtcttta 1500
cctaagttag atgagttaag agacgaaggt aaggcttcct cagcaaaaca gagacttaag 1560
tgcgcatccc ttcaaaagtt tggtgagaga gctttcaagg cttgggctgc cgtcgcagctg 1620
tctcagagat ttcctaaggc tgaattcgca gaagtctcta agctagtaac tgacttgact 1680
aaagttcata ctgagtgctg tcatgggggat ttgttggaat gcgcagatga tcgtgcagac 1740
ttagcaaagt acatctgcga gaaccaagac tctatttcca gtaagttaaa ggaatgttgc 1800
gaaaagccac tacttgagaa gtcccactgt attgctgaag tcgaaaatga tgaaatgcct 1860
gctgaccttc catctttggc cgctgatttc gttgagtcca aggatgtgtg caaaaactat 1920
```

```
gctgaagcaa aagatgtgtt cctagggatg ttcctgtatg aatatgctcg tcgacatccc   1980
gactattccg ttgtcctttt actgagattg gctaagacct acgagacaac cttgggaaag   2040
tgttgtgctg ccgcagatcc tcacgagtgt tacgcaaaag tgtttgatga gttcaaacca   2100
ttggttgaag agccacaaaa tctaatcaag cagaactgtg aactgtttga caattgggc    2160
gaatacaaat tccaaaatgc tctgttagtg agatacacca aaaaggtccc acaagtttcc   2220
accccaactc tagtcgaggt gtccagaaat ctaggaaaag ttggatctaa gtgttgtaag   2280
catccagaag ctaagaggat gccttgcgct gaggattact tgtctgtggt tttgaaccag   2340
ttatgtgttc tacacgagaa aactcctgtc tccgacagag ttactaagtg ctgcacagag   2400
tctttggtca atagaaggcc ttgtttcagt gccctgaagg tcgatgaaac ttatgtgcct   2460
aaagagttcc aagccgaaac gttcactttt cacgctgaca tttgtactct ttctgagaag   2520
gaacgtcaga tcaaaaagca gacagcattg gtggaattgg taaagcataa accaaaggct   2580
acaaaagagc agctgaaggc tgttatggat gattttgcag ctttcgtgga aaagtgttgt   2640
aaagccgatg ataaagagac ttgttttgca gaggagggga aaaagctggt tgctgcatca   2700
caagctgccc taggtcttgc agccgctacc ggtcaacgta aaagacgaaa tacaattcat   2760
gagttcaaaa agtcagccaa aactacattg attaagattg atcccgctct gaagataaag   2820
accaaaaagg tcaacacagc tgaccagtgc gccaacaggt gtaccaggaa taagggacta   2880
cctttttactt gtaaagcttt cgtattcgac aaagcaagga agcaatgtct gtggttcccc   2940
tttaactcta tgtcatctgg ggtgaaaaag gaatttgacg atgaatttga tttgtatgaa   3000
aacaaagatt acattagaaa ttgcattatc ggcaagggaa gatcatacaa aggtacggtt   3060
tctattacta agtctggaat caagtgccaa ccatggtcat ccatgatccc tcacgagcac   3120
agtttccttc caagttccta ccgtggtaaa gacttacaag agaactattg ccgaaatcct   3180
agaggtgaag agggaggtcc atggtgtttt acctccaacc ctgaagttag atatgaagtc   3240
tgtgatatac ctcagtgtgg cggttctcat catcaccacc accattagtg a           3291
```

```
SEQ ID NO: 134         moltype = AA  length = 990
FEATURE                Location/Qualifiers
REGION                 1..990
                       note = Synthetic construct
source                 1..990
                       mol_type = protein
                       organism = synthetic construct
SEQUENCE: 134
AQVLRGTVTD FPGFDERADA ETLRKAMKGL GTDEESILTL LTSRSNAQRQ EISAAFKTLF   60
GRDLLDDLKS ELTGKFEKLI VALMKPSRLY DAYELKHALK GAGTNEKVLT EIIASRTPEE   120
LRAIKQVYEE EYGSSLEDDV VGDTSGYYQR MLVVLLQANR DPDAGIDEAQ VEQDAQALFQ   180
AGELKWGTDE EKFITIFGTR SVSHLRKVFD KYMTISGFQI EETIDRETSG NLEQLLLAVV   240
KSIRSIPAYL AETLYYAMKG AGTDDHTLIR VMVSRSEIDL FNIRKEFRKN FATSLYSMIK   300
GDTSGDYKKA LLLLCGEDDA SDAHKSEVAH RFKDLGEENF KALVLIAFAQ YLQQSPFEDH   360
VKLVNEVTEF AKTCVADESA ENCDKSLHTL FGDKLCTVAT LRETYGEMAD CCAKQEPERN   420
ECFLQHKDDN PNLPRLVRPE VDVMCTAFHD NEETFLKKYL YEIARRHPYF YAPELLFFAK   480
RYKAAFTECC QAADKAACLL PKLDELRDEG KASSAKQRLK CASLQKFGER AFKAWAVARL   540
SQRFPKAEFA EVSKLVTDLT KVHTECCHGD LLECADDRAD LAKYICENQD SISSKLKECC   600
EKPLLEKSHC IAEVENDEMP ADLPSLAADF VESKDVCKNY AEAKDVFLGM FLYEYARRHP   660
DYSVVLLLRL AKTYETTLEK CCAAADPHEC YAKVFDEFKP LVEEPQNLIK QNCELFEQLG   720
EYKFQNALLV RYTKKVPQVS TPTLVEVSRN LGKVGSKCCK HPEAKRMPCA EDYLSVVLNQ   780
LCVLHEKTPV SDRVTKCCTE SLVNRRPCFS ALEVDETYVP KEFQAETFTF HADICTLSEK   840
ERQIKKQTAL VELVKHKPKA TKEQLKAVMD DFAAFVEKCC KADDKETCFA EEGKKLVAAS   900
QAALGLAAAT GGPETLCGAE LVDALQFVCG DRGFYFNKPT GYGSSSRRAP QTGIVDECCF   960
RSCDLRRLEM YCAPLKPAKS AGGSHHHHHH                                     990
```

```
SEQ ID NO: 135         moltype = DNA  length = 2976
FEATURE                Location/Qualifiers
misc_feature           1..2976
                       note = Synthetic construct
source                 1..2976
                       mol_type = other DNA
                       organism = synthetic construct
SEQUENCE: 135
gctcaagtgc taaggggaac tgttactgat tttccaggtt ttgatgaaag agcagatgct   60
gagactttaa ggaaagctat gaaaggattg ggtacagacg aggaatccat tttgacacta   120
ttgacatcac gaagtaacgc ccagagacaa gagatctcag cagctttcaa aaccctgttc   180
ggaagagatt tgcttgacga tttgaagtct gagttgactg gtaagtttga aaaactaata   240
gttgccctga tgaagccttc cagacttat gatgcttacg aacttaagca cgctttgaaa   300
ggggctggaa caaatgaaaa agtttttact gagataatcg catcacgtac ccctgaggaa   360
ctaagagcca ttaagcaggt atatgaagag aatacggtg gttccttaga ggacgacgtc   420
gttggtgaca catctggtta ctatcagagg atgttggttg tcttgttgca agctaatagg   480
gatcctgatg ctggcatcga tgaagcccaa gtagagcagg acgcccaagc cctgtttcaa   540
gcaggcgaat tgaagtgggg aacggacgaa gagaagttta tcaccatctt cggaactcgt   600
tctgtatctc atcttagaaa agtattcgac aaatacatga cgatttctgg ttttcaaatt   660
gaggagacta ttgatagaga gacgtctgga aacttagaac agcttttgct tgccgtcgtt   720
aagtctataa ggagtattcc agcctactta gctgaacct tgtactacgc catgaagggt   780
gctggaactg atgatcatac cttgatacga gttatggtaa gtcgatcaga gattgatttg   840
tttaacatta ggaaggagtt caggaaaaac tttgctacct cattgtattc catgataaag   900
ggtgatactt caggtgatta caaaaaggct ctgcttttgt gtggtggcga ggacgatgct   960
agcgatgctc acaaatctga agtcgctcat cgtttcaaag acttgggtga ggaaaacttt   1020
aaggctttag ttctgattgc ttttgcccaa tatcttcaac aatcaccatt cgaagatcat   1080
gtgaaacttg ttaacgaagt taccgaattt gcaaaaacgt gtgtggcaga cgaaagtgcc   1140
gaaaactgtg acaaatcatt acacactttg ttcggtgaca agttatgcac tgttgcaacc   1200
ctacgtgaga catatggaga aatggcagac tgttgcgcca acaagagcc tgaacgaaac   1260
```

```
gaatgctttc tgcagcacaa agacgataat ccaaatcttc cccgattagt tcgtcccgaa   1320
gtagacgtaa tgtgcacagc ctttcatgat aatgaagaga ctttcctgaa aaagtacttg   1380
tacgaaattg caagacgtca cccatacttc tatgctcccg agttactgtt tttcgccaaa   1440
cgatacaagg cagcctttac agaatgttgc caagcagctg acaaggctgc atgtctttta   1500
cctaagttag atgagttaag agacgaaggt aaggcttcct cagcaaaaca gagacttaag   1560
tgcgcatccc ttcaaaagtt tggtgagaga gctttcaagg cttgggctgt cgccagactg   1620
tctcagagat ttcctaaggc tgaattcgca gaagtctcta agctagtaac tgacttgact   1680
aaagttcata ctgagtgctg tcatgggat ttgttggaat gcgcagatga tcgtgcagac   1740
ttagcaaagt acatctgcga gaaccaagac tctatttcaa gtaagttaaa ggaatgttgc   1800
gaaaagccac tacttgagaa gtcccactgt attgctgaag tcgaaaatga tgaaatgcct   1860
gctgaccttc catctttggc cgctgatttc gttgagtcca aggatgtgtg caaaaactat   1920
gctgaagcaa aagatgtgtt cctagggatg ttcctgtatg aatatgctcg tcgacatccc   1980
gactattccg ttgtcctttt actgagattg gctaagacct acgagacaac cttggagaag   2040
tgttgtgcag ccgcagatcc tcacgagtgt tacgcaaaag tgtttgatga gttcaaacca   2100
ttggttgaag agccacaaaa tctaatcaag cagaactgtg aactgtttga caattgggc   2160
gaatacaaat tccaaaatgc tctgttagtg agatacacca aaaaggtccc acaagtttcc   2220
accccaactc tagtcgaggt gtccagaaat ctaggaaaag ttggatcaa gtgttgtaag   2280
catccagaag ctaagaggat gccttgcgct gaggattact tgtctgtgt tttgaaccag   2340
ttatgtgttc tacacgagaa aactcctgtc tccgacagag ttactaagtg ctgcacagag   2400
tctttggtca atagaaggcc ttgtttcagt gccctggaag tcgatgaaac ttatgtgcct   2460
aaagagttcc aagccgaaac gttcacttttt cacgctgaca tttgtactct ttctgagaag   2520
gaacgtcaga tcaaaaagca gacagcattg gtggaattgg taaagcataa accaaaggct   2580
acaaaagagc agctgaaggc tgttatggat gattttgcag ctttcgtgga aaagtgttgt   2640
aaagccgatg ataaagagac ttgttttgca gaggagggga aaaagctggt tgctgcatca   2700
caagctgccc taggtcttgc agccgctacc ggtggacctg aaaccttatg tggagctgaa   2760
cttgtgaggta ctctacaatt tgtttgtggc gatagaggt tctacttcaa caaacccact   2820
ggatatggta gttcctcaag acgagctcct cagacaggta ttgtcgacga gtgttgtttt   2880
aggtcttgcg acttgcgtag actggagatg tactgcgcac cattgaagcc agcaaagtct   2940
gccggtggtt cacatcacca ccatcaccat tagtga                          2976
```

SEQ ID NO: 136              moltype = AA   length = 992
FEATURE                     Location/Qualifiers
REGION                      1..992
                            note = Synthetic construct
source                      1..992
                            mol_type = protein
                            organism = synthetic construct
SEQUENCE: 136
GPETLCGAEL VDALQFVCGD RGFYFNKPTG YGSSSRRAPQ TGIVDECCFR SCDLRRLEMY   60
CAPLKPAKSA GAASDAHKSE VAHRFKDLGE ENFKALVLIA FAQYLQQSPF EDHVKLVNEV   120
TEFAKTCVAD ESAENCDKSL HTLFGDKLCT VATLRETYGE MADCCAKQEP ERNECFLQHK   180
DDNPNLPRLV RPEVDVMCTA FHDNEETFLK KYLYEIARRH PYFYAPELLF FAKRYKAAFT   240
ECCQAADKAA CLLPKLDELR DEGKASSAKQ RLKCASLQKF GERAFKAWAV ARLSQRFPKA   300
EFAEVSKLVT DLTKVHTECC HGDLLECADD RADLAKYICE NQDSISSKLK ECCEKPLLEK   360
SHCIAEVEND EMPADLPSLA ADFVESKDVC KNYAEAKDVF LGMFLYEYAR RHPDYSVVLL   420
LRLAKTYETT LEKCCAAADP HECYAKVFDE FKPLVEEPQN LIKQNCELFE QLGEYKFQNA   480
LLVRYTKKVP QVSTPTLVEV SRNLGKVGSK CCKHPEAKRM PCAEDYLSVV LNQLCVLHEK   540
TPVSDRVTKC CTESLVNRRP CFSALEVDET YVPKEFQAET FTFHADICTL SEKERQIKKQ   600
TALVELVKHK PKATKEQLKA VMDDFAAFVE KCCKADDKET CFAEEGKKLV AASQAALGLA   660
AATGAQVLRG TVTDFPGFDE RADAETLRKA MKGLGTDEES ILTLLTSRSN AQRQEISAAF   720
KTLFGRDLLD DLKSELTGKF EKLIVALMKP SRLYDAYELK HALKGAGTNE KVLTEIIASR   780
TPEELRAIKQ VYEEEYGSSL EDDVVGDTSG YYQRMLVVLL QANRDPDAGI DEAQVEQDAQ   840
ALFQAGELKW GTDEEKFITI FGTRSVSHLR KVFDKYMTIS GFQIEETIDR ETSGNLEQLL   900
LAVVKSIRSI PAYLAETLYY AMKGAGTDDH TLIRVMVSRS EIDLFNIRKE FRKNFATSLY   960
SMIKGDTSGD YKKALLLLCG EDDGGSHHHH HH                                992

SEQ ID NO: 137              moltype = DNA   length = 2982
FEATURE                     Location/Qualifiers
misc_feature                1..2982
                            note = Synthetic construct
source                      1..2982
                            mol_type = other DNA
                            organism = synthetic construct
SEQUENCE: 137
```
ggaccagaga cattgtgtgg agcagaactg gtggacgctt acagtttgt gtgtggtgac   60
cgtggtttct acttcaacaa acctacgggt tacgggtcta gttctcgtag agctccacag   120
actgggattt agatgaatg ctgcttcaga tcttgtgacc ttcgacgttt agaaatgtac   180
tgtgcacctc taaaaccagc caaatctgct ggagctgcaa gtgacgctca taagtctgaa   240
gttgctcaca gattcaaaga cctaggtgaa gagaacttta aggctcttgt acttatagca   300
tttgctcagt atctgcaaca gagtcccttc gaagatcatg tcaagctggt gaatgaggta   360
accgaattcg ccaagacttg tgtggctgat gaatccgccg aaaactgtga caaatcttta   420
cacacattgt tcggagataa actatgcaca gtagcaactt acgtgaaac ttatggtgag   480
atggcagatt gttgtgctaa acaggagcct gagagaaatg aatgcttttt gcaacacaag   540
gacgacaatc ctaaccttcc cagattggtt agacccgagg ttgacgttat gtgtaccgcc   600
ttccacgaca atgaggaaac atttctgaaa aagtacttgt acgaaattgc acgacgtcac   660
ccatacttct atgcacctga gcttttgttt ttcgccaaaa gatacaaggc agctttcact   720
gagtgctgtc aagcagccga taaggctgct tgtctattac ctaaacttga tgagcttaga   780
gatgagggta aagcatcctc cgctaaacag aggttgaaat gtgccagttt gcagaagttt   840
ggtgaacgtg cttttcaaggc atgggctgtt gctagattat ctcaaagatt tcctaaggcc   900
```

```
gaatttgctg aggtgtcaaa gttggtgacg gatttgacta aggtccacac tgagtgttgc    960
catggtgatc ttttggaatg tgctgacgat agagccgacc tggccaagta tatctgtgaa    1020
aaccaagatt ctatcagtag taagctgaag gaatgttgcg aaaaacctct actagagaaa    1080
tctcattgca tcgcagaagt tgaaaacgat gaaatgccag ccgacttgcc cagtctggct    1140
gctgatttcg tcgagtcaaa agatgtttgc aaaaactatg ccgaagcaaa ggatgtcttt    1200
ttgggcatgt ttctgtacga atatgctcgt cgtcatcctg actattccgt tgtcctgttg    1260
ctaagactag ctaaaacgta tgaaacgacc ttggaaaagt gttgcgctgc agctgatccc    1320
cacgagtgtt atgcaaaagt tttcgatgag tttaagccac ttgtagaaga gccacagaac    1380
ttgatcaaac agaattgtga gctttttcgag caattaggtg agtataagtt tcaaaacgtt    1440
ttgctggtta gatataccaa aaaggtccca caagtgtcaa cccctaccct ggtagaagtg    1500
agtagaaatc taggaaaagt cggatctaag tgctgcaagc atccagaagc taagagaatg    1560
ccttgcgctg aggattactt gtcagtagtt ttgaatcagt tgtgcgtcct acatgaaaag    1620
acacccgttt ctgatagagt cactaagtgt tgtactgagt ctctagtaaa cagaaggcct    1680
tgtttctctg cattagaagt agatgaaacc tatgtcccaa aggagttcca agctgaaacc    1740
tttacatttc acgccgacat ttgtacgcta tctgagaagg agcgtcagat caaaaagcaa    1800
acagcccttg ttgagcttgt gaagcacaag ccaaaagcta caaaggagca attgaaagcc    1860
gtcatggacg atttcgccgc atttgttgag aagtgttgca aggcagatga taaggaaact    1920
tgttttgctg aagagggcaa aaagcttgtt gccgcctctc aagctgcttt gggactaggc    1980
gctgctaccg gtgctcaagt tttgagggga accgttaccg acttcccagg ttttgacgaa    2040
agagccgacg cagaaacatt aaggaaagcc atgaagggct aggcaccga tgaggagtcc    2100
attctgcac tgttgacttc ccgatccaat gcccaaaggc aggagatttc agccgctttc    2160
aagactttgt ttggtagaga tcttctggac gacctgaaac cagaactgac tggaaagttt    2220
gagaaactta ttgttgcttt gatgaagcct tcaagactat atgacgcata cgagttgaaa    2280
catgcattga aaggtgcagg aactaatgaa aaagtgttaa ctgagatcat tgcttccaga    2340
acaccagaag agcttcgtgc tatcaaacaa gtgtatgaag aggaatacgg atcaagtctg    2400
gaagatgacg ttgttggtga tacctcaggg tattaccaaa ggatgcttgt cgttctatta    2460
caagctaatc gagatcctga cgccggaatc gatgaagctc aagttgaaca agatgctcag    2520
gctcttttc aagccggtga attgaagtgg gggactgatg aggaaaagtt tatcacgatc    2580
tttggtacta gatctgttag tcatttgaga aaagtatttg acaaatacat gaccatttct    2640
ggctttcaaa tagaagagac tattgatagg gaaacttccg gtaacttgga acaactgttg    2700
ttagctgtgg tcaagagtat aagatcaatt ccagcttact tagctgaaac tctgtattac    2760
gcaatgaaag gagcaggcac agacgatcac acgttgatcc gagtcatggt ttccagatca    2820
gagattgact tgttcaatat caggaaggaa ttcaggaaaa actttgcaac ctctttgtac    2880
tccatgatca aaggtgatac ttccggtgat tacaaaaagg ctttgttgtt gttatgtgga    2940
gaggatgacg gaggttcaca tcaccatcat caccattagt ga                      2982
```

```
SEQ ID NO: 138           moltype = AA  length = 992
FEATURE                  Location/Qualifiers
REGION                   1..992
                         note = Synthetic construct
source                   1..992
                         mol_type = protein
                         organism = synthetic construct
SEQUENCE: 138
GPETLCGAEL VDALQFVCGD RGFYFNKPTG YGSSSRRAPQ TGIVDECCFR SCDLRRLEMY   60
CAPLKPAKSA GAASDAHKSE VAHRFKDLGE ENFKALVLIA FAQYLQQSPF EDHVKLVNEV   120
TEFAKTCVAD ESAENCDKSL HTLFGDKLCT VATLRETYGE MADCCAKQEP ERNECFLQHK   180
DDNPNLPRLV RPEVDVMCTA FHDNEETFLK KYLYEIARRH PYFYAPELLF FAKRYKAAFT   240
ECCQAADKAA CLLPKLDELR DEGKASSAKQ RLKCASLQKF GERAFKAWAV ARLSQRFPKA   300
EFAEVSKLVT DLTKVHTECC HGDLLECADD RADLAKYICE NQDSISSKLK ECCEKPLLEK   360
SHCIAEVEND EMPADLPSLA ADFVESKDVC KNYAEAKDVF LGMFLYEYAR RHPDYSVVLL   420
LRLAKTYETT LEKCCAAADP HECYAKVFDE FKPLVEEPQN LIKQNCELFE QLGEYKFQNA   480
LLVRYTKKVP QVSTPTLVEV SRNLGKVGSK CCKHPEAKRM PCAEDYLSVV LNQLCVLHEK   540
TPVSDRVTKC CTESLVNRRP CFSALEVDET YVPKEFQAET FTFHADICTL SEKERQIKKQ   600
TALVELVKHK PKATKEQLKA VMDDFAAFVE KCCKADDKET CFAEEGKKLV AASQAALGLA   660
AATGAQVLRG TVTDFPGFDE RADAETLRKA MKGLGTDEES ILTLLTSRSN AQRQEISAAF   720
KTLFGRDLLD DLKSDLTGKF EKLIVALMKP SRLYDAYELK HALKGAGTNE KVLTEIIASR   780
TPEELRAIKQ VYEEEYGSSL EDDVVGNTSG YYQRMLVVLL QANRDPDAGI DEAQVEQDAQ   840
ALFQAGELKW GTDEEKFITI FGTRSVSHLR KVFDKYMTIS GFQIEETIDR ATSGNLEQLL   900
LAVVKSIRSI PAYLAETLYY AMKGAGTDDH TLIRVMVSRS EIDLFNIRKE FRKNFATSLY   960
SMIKGNTSGD YKKALLLLCG EDDGGSHHHH HH                                 992
```

```
SEQ ID NO: 139           moltype = DNA  length = 2982
FEATURE                  Location/Qualifiers
misc_feature             1..2982
                         note = Synthetic construct
source                   1..2982
                         mol_type = other DNA
                         organism = synthetic construct
SEQUENCE: 139
ggaccagaga cattgtgtgg agcagaactg gtggacgctt tacagtttgt gtgtggtgac    60
cgtggtttct acttcaacaa acctacgggt tacgggtcta gttctcgtag agctccacag    120
actgggattt tagatgaatg ctgcttcaga tcttgtgacc ttcgacgttt agaaatgtac    180
tgtgcacctc taaaaccagc caaatctgct ggagctgcaa gtgacgctca taagtctgaa    240
gttgctcaca gattcaaaga cctaggtgaa gagaacttta aggctcttgt acttatagca    300
tttgctcagt atctgcaaca gagtcccttc gaagatcatg tcaagctggt gaatgaggta    360
accgaattcg ccaagacttg tgtggctgat gaatccgccg aaaactgtga caaatctta    420
cacacattgt tcggagataa actatgcaca gtagcaactt tacgtgaaac ttatggtgag    480
atggcagatt gttgtgctaa acaggagcct gagagaaatg aatgcttttt gcaacacaag    540
```

```
gacgacaatc ctaaccttcc cagattggtt agacccgagg ttgacgttat gtgtaccgcc   600
ttccacgaca atgaggaaac atttctgaaa aagtacttgt acgaaattgc acgacgtcac   660
ccatacttct atgcacctga gcttttgttt ttcgccaaaa gatacaaggc agctttcact   720
gagtgctgtc aagcagccga taaggctgct tgtctattac ctaaacttga tgagcttaga   780
gatgagggta aagcatcctc cgctaaacag aggttgaaca gtgccagttt gcagaagttt   840
ggtgaacgtg ctttcaaggc atgggctgtt gctagattat ctcaaagatt tcctaaggcc   900
gaatttgctg aggtgtcaaa gttggtgacg gatttgacta aggtccacac tgagtgttgc   960
catggtgatc ttttggaatg tgctgacgat agagccgacc tggccaagta tatctgtgaa  1020
aaccaagatt ctatcagtag taagctgaag gaatgttgcg aaaaacctct actagagaaa  1080
tctcattgca tcgcagaagt tgaaaacgat gaaatgccag ccgacttgcc cagtctggct  1140
gctgatttcg tcgagtcaaa agatgtttgc aaaaactatg ccgaagcaaa ggatgtcttt  1200
ttgggcatgt ttctgtacga atatgctcgt cgtcatcctg actattccgt tgtcctgttg  1260
ctaagactag ctaaaacgta tgaaacgacc ttggaaaagt gttgcgctgc agctgatccc  1320
cacgagtgtt atgcaaaagt tttcgatgag tttaagccac ttgtagaaga gccacagaac  1380
ttgatcaaac agaattgtga gcttttcgag caattaggtg agtataagtt tcaaaacgct  1440
ttgctggtta gatataccaa aaaggtccca caagtgtcaa cccctaccct ggtagaagtg  1500
agtagaaatc taggaaaagt cggatctaag tgctgcaagc atccagaagc taagagaatg  1560
ccttgcgctg aggattactt gtcagtagtt ttgaatcagt tgtgcgtcct acatgaaaag  1620
acacccgttt ctgatagagt cactaagtgt tgtactgagt ctctagtaaa cagaaggcct  1680
tgtttctctg cattagaagt agatgaaacc tatgtcccaa aggagttcca agctgaaacc  1740
tttacatttc acgccgacat ttgtacgcta tctgagaagg agcgtcagat caaaaagcaa  1800
acagcccttg ttgagcttgt gaagcacaag ccaaaagcta caaaggagca attgaaagcc  1860
gtcatggacg atttcgccgc atttgttgag aagtgttgca aggcagatga taaggaaact  1920
tgttttgctg aagagggcaa aaagcttgtt gccgcctctc aagctgcttt gggactagcc  1980
gctgctaccg tgtctcaagt tttgagggga accgttaccg acttcccagg ttttgacgaa  2040
agagccgacg cagaaacatt aaggaaagcc atgaaggcgt taggcaccga tgaggagtcc  2100
attctgacac tgttgacttc ccgatccaat gcccaaaggc aggagatttc agccgctttc  2160
aagactttgt ttggtagaga tcttctggac gacctgaaat cagatctgac tggaaagttt  2220
gagaaactta ttgttgcttt gatgaagcct tcaagactat atgacgcata cgagttgaaa  2280
catgcattga aaggtgcagg aactaatgaa aaagtgttaa ctgagatcat tgcttccaga  2340
acaccagaag agcttcgtgc tatcaaacaa gtgtatgaag aggaatacgg atcaagtctg  2400
gaagatgacg ttgttggtaa tacctcaggg tattaccaaa ggatgcttgt cgttctatta  2460
caagctaatc gagatcctga cgccggaatc gatgaagctc aagttgaaca gatgctcag   2520
gctctttttc aagccggtga attgaagtgg gggactgatg aggaaaagtt tatcacgatc  2580
tttggtacta gatctgttag tcatttgaga aaagtatttg acaaatacat gaccatttct  2640
ggctttcaaa tagaagagac tattgatagg gccacttccg gtaacttgga caactgttg   2700
ttagctgtgg tcaagagtat aagatcaatt ccagcttact tagctgaaac tctgtattac  2760
gcaatgaaag gagcaggcac agacgatcac acgttgatcc gagtcatggt ttccagatca  2820
gagattgact tgttcaatat caggaaggaa ttcaggaaaa actttgcaac ctctttgtac  2880
tccatgatca aaggtaatac ttccggtgat tacaaaaagg ctttgttgtt gttatgtgga  2940
gaggatgacg gaggttcaca tcaccatcat caccattagt ga                     2982
```

```
SEQ ID NO: 140          moltype = AA   length = 1097
FEATURE                 Location/Qualifiers
REGION                  1..1097
                        note = Synthetic construct
source                  1..1097
                        mol_type = protein
                        organism = synthetic construct
SEQUENCE: 140
QRKRRNTIHE FKKSAKTTLI KIDPALKIKT KKVNTADQCA NRCTRNKGLP FTCKAFVFDK    60
ARKQCLWFPF NSMSSGVKKE FGHEFDLYEN KDYIRNCIIG KGRSYKGTVS ITKSGIKCQP   120
WSSMIPHEHS FLPSSYRGKD LQENYCRNPR GEEGGPWCFT SNPEVRYEVC DIPQCGAASD   180
AHKSEVAHRK DLGEENFKA LVLIAFAQYL QQSPFEDHVK LVNEVTEFAK TCVADESAEN    240
CDKSLHTLFG DKLCTVATLR ETYGEMADCC AKQEPERNEC FLQHKDDNPN LPRLVRPEVD   300
VMCTAFHDNE ETFLKKYLYE IARRHPFYFA PELLFFAKRY KAAFTECCQA ADKAACLLPK   360
LDELRDEGKA SSAKQRLKCA SLQKFGERAF KAWAVARLSQ RFPKAEFAEV SKLVTDLTKV   420
HTECCHGDLL ECADDRADLA KYICENQDSI SSKLKECCEK PLLEKSHCIA EVENDEMPAD   480
LPSLAADFVE SKDVCKNYAE AKDVFLGMFL YEYARRHPDY SVVLLLRLAK TYETTLEKCC   540
AAADPHECYA KVFDEFKPLV EEPQNLIKQN CELFEQLGEY KFQNALLVRY TKKVPQVSTP   600
TLVEVSRNLG KVGSKCCKHP EAKRMPCAED YLSVVLNQLC VLHEKTPVSD RVTKCCTESL   660
VNRRPCFSAL EVDETYVPKE FQAETFTFHA DICTLSEKER QIKKQTALVE LVKHKPKATK   720
EQLKAVMDDF AAFVEKCCKA DDKETCFAEE GKKLVAASQA ALGLAAATGA QVLRGTVTDF   780
PGFDERADAE TLRKAMKGLG TDEESILTLL TSRSNAQRQE ISAAFKTLFG RDLLDDLKSE   840
LTGKFEKLIV ALMKPSRLYD AYELKHALKG AGTNEKVLTE IIASRTPEEL RAIKQVYEEE   900
YGSSLEDDVV GDTSGYYQRM LVVLLQANRD PDAGIDEAQV EQDAQALFQA GELKWGTDEE   960
KFITIFGTRS VSHLRKVFDK YMTISGFQIE ETIDRETSGN LEQLLLAVVK SIRSIPAYLA  1020
ETLYYAMKGA GTDDHTLIRV MVSRSEIDLF NIRKEFRKNF ATSLYSMIKG DTSGDYKKAL  1080
LLLCGEDDGG SHHHHHH                                                 1097
```

```
SEQ ID NO: 141          moltype = DNA   length = 3297
FEATURE                 Location/Qualifiers
misc_feature            1..3297
                        note = Synthetic construct
source                  1..3297
                        mol_type = other DNA
                        organism = synthetic construct
SEQUENCE: 141
caacgtaagc gtcgaaacac tatccatgag ttcaaaaagt ctgcaaaaac tactttgata    60
```

```
aagatagacc cagctttgaa gataaagacg aaaaaggtca atactgccga ccagtgtgct  120
aatcgatgta ctagaaacaa gggcttaccc tttacttgta aggcttttgt tttcgacaaa  180
gcaaggaagc aatgtttatg gttccccttc aattcaatga gttctggtgt gaaaaaggaa  240
tttggtcatg aatttgattt gtacgagaac aaagattaca ttagaaactg cattatcggc  300
aaaggaagat cttacaaggg gacggtgtct ataacaaaga gtggcataaa gtgtcaacca  360
tggtctagta tgattccaca tgagcactct ttccttccct cctcctatcg aggaaaaagac  420
ctacaagaga actattgtcg aaaccctaga ggagaagagg gaggcccttg gtgctttacg  480
agtaaccctg aggttagata cgaagtttgt gacattccac aatgcggagc tgcaagtgac  540
gctcataagt ctgaagttgc tcacagattc aaagacctag gtgaagagaa ctttaaggct  600
cttgtactta tagcatttgc tcagtatctg caacagagtc ccttcgaaga tcatgtcaag  660
ctggtgaatg aggtaaccga attcgccaag acttgtgtgg ctgatgaatc cgccgaaaac  720
tgtgacaaat ctttacacac attgttcgga gataaactat gcacagtagc aactttacgt  780
gaaacttatg gtgagatggc agattgttgt gctaaacagg agcctgagag aaatgaatgc  840
tttttgcaac acaaggacga caatcctaac cttcccagat tggttagacc cgaggttgac  900
gttatgtgta ccgccttcca cgacaatgag gaaacatttc tgaaaaagta cttgtacgaa  960
attgcacgac gtcacccata cttctatgca cctgagcttt tgttttcgc caaaagatac  1020
aaggcagctt tcactgagtg ctgtcaagca gccgataag ctgcttgtct attacctaaa  1080
cttgatgagc ttagagatga gggtaaagca tcctccgtca aacagaggtt gaaatgtgcc  1140
agtttgcaga agtttggtga acgtgctttc aaggcatggg ctgttgctag attatctcaa  1200
agatttccta aggccgaatt tgctgaggtg tcaaagttgg tgacggattt gactaaggtc  1260
cacactgagt gttgccatgg tgatctttt gaatgtgctg acgatagagc cgacctggcc  1320
aagtatatct gtgaaaacca agattctatc agtagtaagc ttaaggaatg ttgcgaaaaa  1380
cctctactag agaaatctca ttgcatcgca gaagttgaaa acgatgaaat gccagccgac  1440
ttgcccagtc tggctgctga tttcgtcgag tcaaagatg tttgcaaaaa ctatgccgaa  1500
gcaaggatg tctttttggg catgtttctg tacgaatatg ctcgtcgtca tcctgactat  1560
tccgttgtcc tgttgctaag actagctaaa acgtatgaaa cgaccttgga aaagtgttgc  1620
gctgcagctg atccccacga gtgttatgca aaagtttcg atgagtttaa gccacttgta  1680
gaagagccac agaacttgat caaacagaat tgtgagcttt tcgagcaatt aggtgagtat  1740
aagtttcaaa acgctttgct ggttagatat accaaaaagg tcccacaagt gtcaacccct  1800
accctggtag aagtgagtag aaatctagga aagtcggat ctaagtgctg caagcatcca  1860
gaagctaaga gaatgccttg cgctgaggat tacttgtcag tagtttttgaa tcagttgtgc  1920
gtcctacatg aaaagacacc cgtttctgat agagtcacta agtgttgtac tgagtctcta  1980
gtaaacagaa ggccttgttt ctctgcatta gaagtagatg aaacctatgt cccaaaggag  2040
ttccaagctg aaacctttac atttcacgcc gacatttgta cgctatctga gaaggagcgt  2100
cagatcaaaa agcaaacagc ccttgttgag cttgtgaagc acaagccaaa agctacaaag  2160
gagcaattga aagccgtcat ggacgatttc gccgcatttg ttgagaagtg ttgcaaggca  2220
gatgataagg aaacttgttt tgctgaagag ggcaaaaagc ttgttgccgc ctctcaagct  2280
gctttgggac tagccgctgc taccggtgct caagtttga ggggaaccgt taccgacttc  2340
ccaggttttg acgaaagagc cgacgcagaa acattaagga aagccatgaa gggcttaggc  2400
accgatgagg agtccattct gacactgttg acttcccgat ccaatgccca aaggcaggag  2460
atttcagccg ctttcaagac tttgtttggt agagatcttc tggacgacct gaaatcagaa  2520
ctgactggaa agtttgagaa acttattgtt gctttgatga agccttcaag actatatgac  2580
gcatacgagt tgaaacatgc attgaaaggt gcaggaacta atgaaaaagt gttaactgag  2640
atcattgctt ccagaacacc agaagagctt cgtgctatca aacaagtgta tgaagaggaa  2700
tacggatcaa gtctggaaga tgacgttgtt ggtgatacct cagggtatta ccaaaggatg  2760
cttgtcgttc tattacaagc taatcgagat cctgacgccg gaatcgatga agctcaagtt  2820
gaacaagatg ctcaggctct tttttcaagcc ggtgaattga agtgggggac tgatgaggaa  2880
aagtttatca cgatctttgg tactagatct gttagtcatt tgagaaaagt atttgacaaa  2940
tacatgacca tttctggctt tcaaatagaa gagactattg atagggaaac ttccggtaac  3000
ttggaacaac tgttgttagc tgtggtcaag agtataagat caattccagc ttacttagct  3060
gaaactctgt attacgcaat gaaaggagca ggcacagacg atcacacgtt gatccgaatc  3120
atggtttcca gatcagagat tgacttgttc aatatcagga aggaattcag gaaaaacttt  3180
gcaacctctt tgtactccat gatcaaaggt gatacttccg gtgattacaa aaaggctttg  3240
ttgttgttat gtggagagga tgacggaggt tcacatcacc atcatcacca ttagtga  3297
```

SEQ ID NO: 142        moltype = AA   length = 994
FEATURE                 Location/Qualifiers
REGION                  1..994
                          note = Synthetic construct
source                  1..994
                          mol_type = protein
                          organism = synthetic construct
SEQUENCE: 142

```
STSHLVKCAE KEKTFCVNGG ECFMVKDLSN PSRYLCKCPN EFTGDRCQNY VMASFYKHLG  60
IEFMEAEELY QKGAASDAHK SEVAHRFKDL GEENFKALVL IAFAQYLQQS PFEDHVKLVN  120
EVTEFAKTCV ADESAENCDK SLHTLFGDKL CTVATLRETY GEMADCCAKQ EPERNECFLQ  180
HKDDNPNLPR LVRPEVDVMC TAFHDNEETF LKKYLYEIAR RHPYFYAPEL LFFAKRYKAA  240
FTECCQAADK AACLLPKLDE LRDEGKASSA KQRLKCASLQ KFGERAFKAW AVARLSQRFP  300
KAEFAEVSKL VTDLTKVHTE CCHGDLLECA DDRADLAKYI CENQDSISSK LKECCEKPLL  360
EKSHCIAEVE NDEMPADLPS LAADFVESKD VCKNYAEAKD VFLGMFLYEY ARRHPDYSVV  420
LLLRLAKTYE TTLEKCCAAA DPHECYAKVF DEFKPLVEEP QNLIKQNCEL FEQLGEYKFQ  480
NALLVRYTKK VPQVSTPTLV EVSRNLGKVG SKCCKHPEAK RMPCAEDYLS VVLNQLCVLH  540
EKTPVSDRVT KCCTESLVNR RPCFSALEVD ETYVPKEFQA ETFTFHADIC TLSEKERQIK  600
KQTALVELVK HKPKATKEQL KAVMDDFAAF VEKCCKADDK ETCFAEEGKK LVAASQAALG  660
LAAATGAQVL RGTVTDFPGF DERADAETLR KAMKGLGTDE ESILTLLTSR SNAQRQEISA  720
APKTLFGRDL LDDLKSELTG KFEKLIVALM KPSRLYDAYE LKHALKGAGT NEKVLTEIIA  780
SRTPEELRAI KQVYEEEYGS SLEDDVVGDT SGYYQRMLVV LLQANRDPDA GIDEAQVEQD  840
AQALFQAGEL KWGTDEEKFI TIFGTRSVSH LRKVFDKYMT ISGFQIEETI DRETSGNLEQ  900
LLLAVVKSIR SIPAYLAETL YYAMKGAGTD DHTLIRVMVS RSEIDLFNIR KEFRKNFATS  960
```

```
LYSMIKGDTS GDYKKALLLL CGEDDGGSHH HHHH                                994

SEQ ID NO: 143          moltype = DNA   length = 2988
FEATURE                 Location/Qualifiers
misc_feature            1..2988
                        note = Synthetic construct
source                  1..2988
                        mol_type = other DNA
                        organism = synthetic construct
SEQUENCE: 143
tccacttctc atttggtgaa atgcgccgag aaggagaaaa cgttctgcgt gaacggtggt   60
gaatgcttta tggtcaaaga tctgtctaac ccttctcgat atctttgtaa gtgtcccaac   120
gagtttactg gtgatcgatg tcagaactac gttatggctt ccttttacaa acacttgggt   180
atagaattca tggaggccga ggagttgtac caaaaaggag ctgcaagtga cgctcataag   240
tctgaagttg ctcacagatt caaagaccta ggtgaagaga actttaaggc tcttgtactt   300
atagcatttg ctcagtatct gcaacagagt cccttcgaag atcatgtcaa gctggtgaat   360
gaggtaaccg aattcgccaa gacttgtgtg gctgatgaat ccgccgaaaa ctgtgacaaa   420
tctttacaca cattgttcgg agataaacta tgcacagtag caactttacg tgaaacttat   480
ggtgagatgg cagattgttg tgctaaacag gagcctgaga gaaatgaatg cttttttgcaa   540
cacaaggacg acaatcctaa ccttcccaga ttggttagac ccgaggttga cgttatgtgt   600
accgccttcc acgacaatga ggaaacattt ctgaaaaagt acttgtacga aattgcacga   660
cgtcacccat acttctatgc acctgagctt ttgttttcg ccaaaagata caaggcagct   720
ttcactgagt gctgtcaagc agccgataag gctgcttgtc tattacctaa acttgatgag   780
cttagagatg agggtaaagc atcctccgct aaacagaggt tgaaatgtgc cagtttgcag   840
aagtttggtg aacgtgcttt caaggcatgg gctgttgcta gattatctca aagatttcct   900
aaggccgaat ttgctgaggt gtcaaagttg gtgacggatt tgactaagct ccacactgag   960
tgttgccatg gtgatctttt ggaatgtgct gacgatagag ccgacctggc caagtatatc   1020
tgtgaaaacc aagattctat cagtagtaag ctgaaggaat gttgcgaaaa acctctacta   1080
gagaaatctc attcatcgc agaagttgaa aacgatgaaa tgccagccga cttgcccagt   1140
ctggctgctg atttcgtcga gtcaaaagat gtttgcaaaa actatgccga agcaaaggat   1200
gtcttttttgg gcatgtttct gtacgaatat gctcgtcgtc atcctgacta ttccgttgtc   1260
ctgttgctaa gactagctaa aacgtatgaa acgaccttgg aaaagtgttg cgctgcagct   1320
gatccccacg agtgttatgc aaaagttttc gatgagttta gcccacttgt agaagagcca   1380
cagaacttga tcaaacagaa ttgtgagctt ttcgagcaat taggtgagta taagtttcaa   1440
aacgctttgc tggttagata taccaaaaag gtcccacaag tgtcaacccc taccctggta   1500
gaagtgagta gaaatctagg aaaagtcgga tctaagtgct gcaagcatcc agaagctaag   1560
agaatgcctt gcgctgagga ttacttgtca gtagttttga atcagttgtg cgtcctacat   1620
gaaaagacac ccgtttctga tagagtcact aagtgttgta ctgagtctct agtaaacaga   1680
aggccttgtt tctctgcatt agaagtagat gaaacctatg tcccaaagga gttccaagct   1740
gaaacctta cattcacgc cgacatttgt acgctatctg agaaggagcg tcagatcaaa   1800
aagcaaacag cccttgttga gcttgtgaag cacaagccaa aagctacaaa ggagcaattg   1860
aaagccgtca tggacgattt cgccgcattt gttgagaagt gttgcaaggc agatgataag   1920
gaaacttgtt ttgctgaaga gggcaaaaag cttgttgccg cctctcaagc tgctttggga   1980
ctagccgctg ctaccggtgc tcaagtttttg aggggaaccg ttaccgactt cccaggtttt   2040
gacgaaagag ccgacgcaga aacattaagg aaagccatga agggcttagg caccgatgag   2100
gagtccattc tgacactgtt gacttcccga tccaatgccc aaaggcagga gatttcagcc   2160
gctttcaaga ctttgtttgg tagagatctt ctggacgacc tgaaatcaaa actgactgga   2220
aagtttgaga aacttattgt tgctttgatg aagccttcaa gactatatga cgcatacgag   2280
ttgaaacatg cattgaaagg tgcaggaact aatgaaaaag tgttaactga gatcattgct   2340
tccgaacac cagaagagct tcgtgctatc aaacaagtgt atgaagagga atacggatca   2400
agtctggaac atgacgttgt tggtgatacc tcagggtatt accaaaggat gcttgtcggt   2460
ctattacaag ctaatcgaga tcctgacgcc ggaatcgatg aagctcaagt tgaacaagat   2520
gctcaggctc ttttttcaagc cggtgaattg aagtggggga ctgatgagga aaagttttatc   2580
acgatctttg gtactagatc tgttagtcat ttgagaaaag tatttgacaa atacatgacc   2640
atttctggct ttcaaataga agagactatt gatagggaaa cttccggtaa cttggaacaa   2700
ctgttgttag ctgtggtcaa gagtataaga tcaattccag cttacttagc tgaaactctg   2760
tattacgcaa tgaaaggagc aggcacagac gatcacacgt tgatccgagt catggtttcc   2820
agatcagaga ttgacttgtt caatatcagg aaggaattca ggaaaaactt tgcaacctct   2880
ttgtactcca tgatcaaagg tgatacttcc ggtgattaca aaaaggcttt gttgttgtta   2940
tgtggagagg atgacggagg ttcacatcac catcatcacc attagtga            2988

SEQ ID NO: 144          moltype = AA   length = 1068
FEATURE                 Location/Qualifiers
REGION                  1..1068
                        note = Synthetic construct
source                  1..1068
                        mol_type = protein
                        organism = synthetic construct
SEQUENCE: 144
PALPEDGGSG AFPPGHFKDP KRLYCKNGGF FLRIHPDGRV DGVREKSDPH IKLQLQAEER   60
GVVSIKGVCA NRYLAMKEDG RLLASKCVTD ECFFFERLES NNYNTYRSRK YTSWYVALKR   120
TGQYKLGSKT GPGQKAILFL PMSAKSGAAS DAHKSEVAHR FKDLGEENFK ALVLIAFAQY   180
LQQSPFEDHV KLVNEVTEFA KTCVADESAE NCDKSLHTLF GDKLCTVATL RETYGEMADC   240
CAKQEPERNE CFLQHKDDNP NLPRLVRPEV DVMCTAFHDN EETFLKKYLY EIARRHPYFY   300
APELLFFAKR YKAAFTECCQ AADKAACLLP KLDELRDEGK ASSAKQRLKC ASLQKFGERA   360
FKAWAVARLS QRFPKAEFAE VSKLVTDLTK VHTECCHGDL LECADDRADL AKYICENQDS   420
ISSKLKECCE KPLLEKSHCI AEVENDEMPA DLPSLAADFV ESKDVCKNYA EAKDVFLGMF   480
LYEYARRHPD YSVVLLLRLA KTYETTLEKC CAAADPHECY AKVFDEFKPL VEEPQNLIKQ   540
NCELFEQLGE YKFQNALLVR YTKKVPQVST PTLVEVSRNL GKVGSKCCKH PEAKRMPCAE   600
```

```
DYLSVVLNQL CVLHEKTPVS DRVTKCCTES LVNRRPCFSA LEVDETYVPK EFQAETFTFH  660
ADICTLSEKE RQIKKQTALV ELVKHKPKAT KEQLKAVMDD FAAFVEKCCK ADDKETCFAE  720
EGKKLVAASQ AALGLAAATG AQVLRGTVTD FPGFDERADA ETLRKAMKGL GTDEESILTL  780
LTSRSNAQRQ EISAAFKTLF GRDLLDDLKS ELTGKFEKLI VALMKPSRLY DAYELKHALK  840
GAGTNEKVLT EIIASRTPEE LRAIKQVYEE EYGSSLEDDV VGDTSGYYQR MLVVLLQANR  900
DPDAGIDEAQ VEQDAQALFQ AGELKWGTDE EKFITIFGTR SVSHLRKVFD KYMTISGFQI  960
EETIDRETSG NLEQLLLAVV KSIRSIPAYL AETLYYAMKG AGTDDHTLIR VMVSRSEIDL 1020
FNIRKEFRKN FATSLYSMIK GDTSGDYKKA LLLLCGEDDG GSHHHHHH              1068

SEQ ID NO: 145          moltype = DNA  length = 3210
FEATURE                 Location/Qualifiers
misc_feature            1..3210
                        note = Synthetic construct
source                  1..3210
                        mol_type = other DNA
                        organism = synthetic construct SEQUENCE: 145
ccagctttgc ctgaggatgg aggctctggt gcttttcctc ctggtcattt caaagaccca   60
aaaagactgt attgcaaaaa cggtgggttt ttcctgagga ttcatccaga tgggagggtc  120
gatggagtta gagagaaatc agacccccac attaagcttc aactacaggc tgaggaacgt  180
ggtgttgtct ccatcaaggg tgtttgtgca aatcgatact tagctatgaa agaggacggc  240
agattacttg ccagtaagtg tgtaactgat gaatgtttct ttttcgaaag actagaatcc  300
aataactaca atacttaccg ttctcgtaag tatacatcat ggtacgtggc cttgaagaga  360
acgggacaat acaaattggg ttctaagacc ggaccaggac agaaagcaat cttgtttttg  420
cccatgtcag ctaagagtgg agctgcaagt gacgctcata agtctgaagt tgctcacaga  480
ttcaaagacc taggtgaaga gaactttaag gctcttgtac ttatagcatt tgctcagtat  540
ctgcaacaga gtcccttcga agatcatgtc aagctggtga atgaggtaac cgaattcgcc  600
aagacttgtg tggctgatga atccgccgaa aactgtgaca aatctttaca cacattgttc  660
ggagataaac tatgcacagt agcaacttta cgtgaaactt atggtgagat ggcagattgt  720
tgtgctaaac aggagcctga gagaaatgaa tgcttttgtc aacacaagga cgacaatcct  780
aaccttccca gattggttag acccgaggtt gacgttatgt gtaccgcctt ccacgacaat  840
gaggaaacat ttctgaaaaa gtacttgtac gaaattgcac gacgtcaccc atacttctat  900
gcacctgagc ttttgttttt cgccaaaaga tacaaggcag ctttcactga gtgctgtcaa  960
gcagccgata aggctgcttg tctattacct aaacttgatg agcttagaga tgagggtaaa 1020
gcatcctccg ctaaacagag gttgaaatgt gccagtttgc agaagtttgg tgaacgtgct 1080
ttcaaggcat gggctgttgc tagattatct caaagatttc ctaaggccga atttgctgag 1140
gtgtcaaagt tggtgacgga tttgactaag gtccacactg agtgttgcca tggtgatctt 1200
ttggaatgtg ctgacgatag agccgacctg gccaagtata tctgtgaaaa ccaagattct 1260
atcagtagta agctgaagga atgttgcgaa aaacctctac tagagaaatc tcattgcatc 1320
gcagaagttg aaaacgatga aatgccagcc gacttgccca gtctggctgc tgatttcgtc 1380
gagtcaaaag atgtttgcaa aaactatgcc gaagcaaagg atgtcttttt gggcatgttt 1440
ctgtacgaat atgctcgtcg tcatcctgac tattccgttg tcctgttgct aagactagct 1500
aaaacgtatg aaacgacctt ggaaaagtgt tgcgctgcag ctgatcccca cgagtgttat 1560
gcaaaagttt tcgatgagtt taagccactt gtagaagagc cacagaactt gatcaaacag 1620
aattgtgagc ttttcgagca attaggtgag tataagtttc aaaacgcttt gctggttaga 1680
tataccaaaa aggtcccaca agtgtcaacc cctaccctgg tagaagtgag tagaaatcta 1740
ggaaaagtcg gatctaagtg ctgcaagcat ccagaagcta agagaatgcc ttgcgctgag 1800
gattacttgt cagtagtttt gaatcagttg tgcgtcctac atgaaaagac acccgtttct 1860
gatagagtca ctaagtgttg tactgagtct ctagtaaaca gaaggccttg tttctctgca 1920
ttagaagtag atgaaaccta tgtcccaaag gagttccaag ctgaaacctt acatttcac  1980
gccgacattt gtacgctatc tgagaaggag cgtcagatca aaaagcaaac agcccttgct 2040
gagcttgtga agcacaagcc aaaagctaca aaggagcaat tgaaagccgt catggacgat 2100
ttcgccgcat ttgttgagaa gtgttgcaag gcagatgata aggaaacttg ttttgctgaa 2160
gagggcaaaa agcttgttgc cgcctctcaa gctgctttgg gactagccgc tgctaccggt 2220
gctcaagttt tgaggggaac cgttaccgac ttcccaggtt ttgacgaaag accgacgca  2280
gaaacattaa ggaaagccat gaagggctta ggcaccgatg aggagtccat tctgacactg 2340
ttgacttccc gatccaatgc ccaaaggcag gagatttcag ccgctttcaa gactttgttt 2400
ggtagagatc ttctggacga cctgaaatca gaactgactg gaaagtttga gaaacttatt 2460
gttgctttga tgaagccttc aagactatat gacgcatacg agttgaaaca tgcattgaaa 2520
ggtgcaggaa ctaatgaaaa agtgttaact gagatcattg cttccagaac accagaagag 2580
cttcgtgcta tcaaacaagt gtatgaagag gaatacggat caagtctgga agatgacgtt 2640
gttggtgata cctcagggta ttaccaaagg atgcttgtcg ttctattaca agctaatcga 2700
gatcctgacg ccggaatcga tgaagctcaa gttgaacaag atgctcaggc tcttttcaa  2760
gccggtgaat tgaagtgggg gactgatgag gaaaagttta tcacgatctt tggtactaga 2820
tctgttagtc atttgagaaa agtatttgac aaatacatga ccattctgg ctttcaaata  2880
gaagagacta ttgataggga aacttccggt aacttggaac aactgttgtt agctgtggtc 2940
aagagtataa gatcaattcc agcttactta gctgaaactc tgtattacgc aatgaaagga 3000
gcaggcacag acgatcacac gttgatccga gtcatggttt ccagatcaga gattgacttg 3060
ttcaatatca ggaaggaatt caggaaaaac tttgcaacct ctttgtactc catgatcaaa 3120
ggtgatactt ccggtgatta caaaaaggct ttgttgttgt tatgtggaga ggatgacgga 3180
ggttcacatc accatcatca ccattagtga                                  3210

SEQ ID NO: 146          moltype = AA  length = 1110
FEATURE                 Location/Qualifiers
REGION                  1..1110
                        note = Synthetic construct
source                  1..1110
                        mol_type = protein
                        organism = synthetic construct
```

```
SEQUENCE: 146
MSPLLRRLLL AALLQLAPAQ APVSQPDAPG HQRKVVSWID VYTRATCQPR EVVVPLTVEL   60
MGTVAKQLVP SCVTVQRCGG CCPDDGLECV PTGQHQVRMQ ILMIRYPSSQ LGEMSLEEHS  120
QCECRPKKKD SAVKPDSPRP LCPRCTQHHQ RPDPRTCRRR CRRRSFLRCQ GRGLELNPDT  180
CRCRKLRRGA ASDAHKSEVA HRFKDLGEEN FKALVLIAFA QYLQQSPFED HVKLVNEVTE  240
FAKTCVADES AENCDKSLHT LFGDKLCTVA TLRETYGEMA DCCAKQEPER NECFLQHKDD  300
NPNLPRLVRP EVDVMCTAFH DNEETFLKKY LYEIARRHPY FYAPELLFFA KRYKAAFTEC  360
CQAADKAACL LPKLDELRDE GKASSAKQRL KCASLQKFGE RAFKAWAVAR LSQRFPKAEF  420
AEVSKLVTDL TKVHTECCHG DLLECADDRA DLAKYICENQ DSISSKLKEC CEKPLLEKSH  480
CIAEVENDEM PADLPSLAAD FVESKDVCKN YAEAKDVFLG MFLYEYARRH PDYSVVLLLR  540
LAKTYETTLE KCCAAADPHE CYAKVFDEFK PLVEEPQNLI KQNCELFEQL GEYKFQNALL  600
VRYTKKVPQV STPTLVEVSR NLGKVGSKCC KHPEAKRMPC AEDYLSVVLN QLCVLHEKTP  660
VSDRVTKCCT ESLVNRRPCF SALEVDETYV PKEFQAETFT FHADICTLSE KERQIKKQTA  720
LVELVKHKPK ATKEQLKAVM DDFAAFVEKC CKADDKETCF AEEGKKLVAA SQAALGLAAA  780
TGAQVLRGTV TDFPGFDERA DAETLRKAMK GLGTDEESIL TLLTSRSNAQ RQEISAAFKT  840
LFGRDLLDDL KSELTGKFEK LIVALMKPSR LYDAYELKHA LKGAGTNEKV LTEIIASRTP  900
EELRAIKQVY EEEYGSSLED DVVGDTSGYY QRMLVVLLQA NRDPDAGIDE AQVEQDAQAL  960
FQAGELKWGT DEEKFITIFG TRSVSHLRKV FDKYMTISGF QIEETIDRET SGNLEQLLLA 1020
VVKSIRSIPA YLAETLYYAM KGAGTDDHTL IRVMVSRSEI DLFNIRKEFR KNFATSLYSM 1080
IKGDTSGDYK KALLLLCGED DGGSHHHHHH                                  1110

SEQ ID NO: 147           moltype = DNA   length = 3336
FEATURE                  Location/Qualifiers
misc_feature             1..3336
                         note = Synthetic construct
source                   1..3336
                         mol_type = other DNA
                         organism = synthetic construct
SEQUENCE: 147
atgtctcctt tgctgagaag gttactattg gctgcattgt tgcagttagc cccagcccaa   60
gctcccgttt cccaaccaga tgcacctggt catcaacgaa aggtggtttc ctggatcgat  120
gtctacacga gagctacctg tcaaccaagg gaagttgtag ttcccttaac tgtggagctt  180
atgggtacag tagccaagca attagttccc tcatgtgtca ctgttcagcg atgtggaggg  240
tgttgtcctg acgacggcct agagtgcgtc ccaacaggac agcaccaagt gagaatgcaa  300
attctgatga tacgatatcc tagttctcag ttgggtgaaa tgagtttgga ggagcattct  360
caatgcgaat gtagacccaa aaagaaagat tccgctgtca aaccagactc tcctagacca  420
ctatgcccaa gatgcactca acaccaccag cgtcctgatc ctagaacttg taggcgtaga  480
tgtcgtagaa gatcattcct tagatgtcag ggaagaggtc ttgaattgaa tccagacacc  540
tgccgatgtc gtaagctgcg taggggagct gcaagtgacg ctcataagtc tgaagttgct  600
cacagattca aagacctagg tgaagagaac tttaaggctc ttgtacttat agcatttgct  660
cagtatctgc aacagagtcc cttcgaagat catgtcaagc tggtgaatga ggtaaccgaa  720
ttcgccaaga cttgtgtggc tgatgaatcc gccgaaaact gtgacaaatc tttacacaca  780
ttgttcggag ataaactatg cacagtagca actttacgtg aaacttatgg tgagatggca  840
gattgttgtg ctaaacagga gcctgagaga aatgaatgct ttttgcaaca caaggacgac  900
aatcctaacc ttcccagatt ggttagaccc gaggttgacg ttatgtgtac cgccttccac  960
gacaatgagg aaacatttct gaaaaagtac ttgtacgaaa ttgcacgacg tcacccatac 1020
ttctatgcac ctgagctttt gttttttcgcc aaaagataca aggcagcttt cactgagtgc 1080
tgtcaagcag ccgataaggc tgcttgtcta ttacctaaac ttgatgagct tagagatgag 1140
ggtaaagcat cctccgctaa acagaggttg aaatgtgcca gtttgcagaa gtttggtgaa 1200
cgtgctttca aggcatgggc tgttgctaga ttatctcaaa gatttcctaa ggccgaattt 1260
gctgaggtgt caaagttggt gacggatttg actaaggtcc acactgagttg ttgccatggt 1320
gatcttttgg aatgtgctga cgatagagcc gacctggcca agtatatctg tgaaaaccaa 1380
gattctatca gtagtaagct gaaggaatgt tgcgaaaaac tctactagaa gaaatctcat 1440
tgcatcgcag aagttgaaaa cgatgaaatg ccagccgact tgcccagtct ggctgctgat 1500
ttcgtcgagt caaaagatgt ttgcaaaaac tatgccgaag caaaggatgt cttttttgggc 1560
atgtttctgt acgaatatgc tcgtcgtcat cctgactatt ccgttgtcct gttgctaaga 1620
ctagctaaaa cgtatgaaac gaccttggaa aagtgttgcg ctgcagctga tccccacgag 1680
tgttatgcaa aagttttcga tgagtttaag ccacttgtag aagagccaca gaacttgatc 1740
aaacagaatt gtgagctttt cgagcaatta ggtgagtata agttccaaaa cgctttgctg 1800
gttagatata ccaaaaaggt cccacaagtg tcaaccccta ccctggtaga agtgagtaga 1860
aatctaggaa aagtcggatc taagtgctgc aagcatccag aagctaagag aatgccttgc 1920
gctgaggatt acttgtcagt agttttgaat cagttgtgcg tcctacatga aaaagacaccc 1980
gtttctgata gagtcactaa gtgttgtact gagtctctag taaacagaag gccttgtttc 2040
tctgcattag aagtagatga aacctatgtc ccaaaggagt tccaagctga aacctttaca 2100
tttcacgccg acatttgtac gctatctgag aaggagcgtc agatcaaaaa gcaaacagcc 2160
cttgttgagc ttgtgaagca caagccaaaa gctacaaagg agcaattgaa agccgtcatg 2220
gacgatttcg ccgcatttgt tgagaagtgt tgcaaggcag atgataagga aacttgtttt 2280
gctgaagagg gcaaaaagct tgttgccgcc tctcaagctg ctttgggact agccgctgct 2340
accggtgctc aagttttgag gggaaccgtt accgacttcc caggttttga cgaaagagcc 2400
gacgcagaaa cattaaggaa agccatgaag ggcttaggca ccgatgagga gtccattctg 2460
acactgttga cttcccgatc caatgcccaa aggcaggaga tttcagccgc tttcaagact 2520
ttgtttggta gagatcttct ggacgacctg aaatcagaac tgactggaaa gtttgagaaa 2580
cttattgttg cttttgatgaa gccttcaaga ctatatgacg catacgagtt gaaacatgca 2640
ttgaaaggtg caggaactaa tgaaaaagtg ttaactgaga tcattgcttc cagaacaccca 2700
gaagagcttc gtgctatcaa acaagtgtat gaagaggaat acggatcaag tctggaagat 2760
gacgttgttg gtgataccta ggggtattac caaaggatgc ttgtcgttct attacaagct 2820
aatcgagatc ctgacgccgg aatcgatgaa gctcaagttg aacaagatgc tcaggctctt 2880
tttcaagccg tgaattgaa gtgggggact gatgaggaaa agtttatcac gatctttggt 2940
actagatctg ttagtcattt gagaaaagta tttgacaaat acatgaccat ttctggcttt 3000
```

-continued

```
caaatagaag agactattga tagggaaact tccggtaact tggaacaact gttgttagct  3060
gtggtcaaga gtataagatc aattccagct tacttagctg aaactctgta ttacgcaatg  3120
aaaggagcag gcacagacga tcacacgttg atccgagtca tggtttccag atcagagatt  3180
gacttgttca atatcaggaa ggaattcagg aaaaactttg caacctcttt gtactccatg  3240
atcaaaggtg atacttccgg tgattacaaa aaggctttgt tgttgttatg tggagaggat  3300
gacggaggtt cacatcacca tcatcaccat tagtga                              3336
```

SEQ ID NO: 148          moltype = AA   length = 1053
FEATURE                 Location/Qualifiers
REGION                  1..1053
                        note = Synthetic construct
source                  1..1053
                        mol_type = protein
                        organism = synthetic construct
SEQUENCE: 148

```
MSPLLRRLLL AALLQLAPAQ APVSQPDAPG HQRKVVSWID VYTRATCQPR EVVVPLTVEL  60
MGTVAKQLVP SCVTVQRCGG CCPDDGLECV PTGQHQVRMQ ILMIRYPSSQ LGEMSLEEHS  120
QCECRPKKKD SGAASDAHKS EVAHRFKDLG EENFKALVLI AFAQYLQQSP FEDHVKLVNE  180
VTEFAKTCVA DESAENCDKS LHTLFGDKLC TVATLRETYG EMADCCAKQE PERNECFLQH  240
KDDNPNLPRL VRPEVDVMCT AFHDNEETFL KKYLYEIARR HPYFYAPELL FFAKRYKAAF  300
TECCQAADKA ACLLPKLDEL RDEGKASSAK QRLKCASLQK FGERAFKAWA VARLSQRFPK  360
AEFAEVSKLV TDLTKVHTEC CHGDLLECAD DRADLAKYIC ENQDSISSKL KECCEKPLLE  420
KSHCIAEVEN DEMPADLPSL AADFVESKDV CKNYAEAKDV FLGMFLYEYA RRHPDYSVVL  480
LLRLAKTYET TLEKCCAAAD PHECYAKVFD EFKPLVEEPQ NLIKQNCELF EQLGEYKFQN  540
ALLVRYTKKV PQVSTPTLVE VSRNLGKVGS KCCKHPEAKR MPCAEDYLSV VLNQLCVLHE  600
KTPVSDRVTK CCTESLVNRR PCFSALEVDE TYVPKEFQAE TFTFHADICT LSEKERQIKK  660
QTALVELVKH KPKATKEQLK AVMDDFAAFV EKCCKADDKE TCFAEEGKKL VAASQAALGL  720
AAATGAQVLR GTVTDFPGFD ERADAETLRK AMKGLGTDEE SILTLLTSRS NAQRQEISAA  780
FKTLFGRDLL DDLKSELTGK FEKLIVALMK PSRLYDAYEL KHALKGAGTN EKVLTEIIAS  840
RTPEELRAIK QVYEEEYGSS LEDDVVGDTS GYYQRMLVVL LQANRDPDAG IDEAQVEQDA  900
QALFQAGELK WGTDEEKFIT IFGTRSVSHL RKVFDKYMTI SGFQIEETID RETSGNLEQL  960
LLAVVKSIRS IPAYLAETLY YAMKGAGTDD HTLIRVMVSR SEIDLFNIRK EFRKNFATSL  1020
YSMIKGDTSG DYKKALLLLC GEDDGGSHHH HHH                                1053
```

SEQ ID NO: 149          moltype = DNA   length = 3165
FEATURE                 Location/Qualifiers
misc_feature            1..3165
                        note = Synthetic construct
source                  1..3165
                        mol_type = other DNA
                        organism = synthetic construct
SEQUENCE: 149

```
atgagtcctt tgctaagacg tttacttttg gctgccttat tgcagctggc accagcccaa  60
gcaccagtgt cacagccaga tgctcccggt caccagagaa aagtggttag ttggattgat  120
gtttacacga gggctacatg ccaacctaga gaagtagttg tccctctgac agttgaacta  180
atggggaccg ttgctaagca attggtgcct tcctgtgtca ctgttcagcg atgcggagga  240
tgttgtccag acgacggtct ggaatgcgta ccaactggcc aacatcaagt cagaatgcag  300
atcttgatga taagatatcc atcttcccaa ttaggagaaa tgtcacttga ggaacattgt  360
caatgtgagt gtaggcccaa aaagaaggat tctggagctg caagtgacgc tcataagtct  420
gaagttgctc acagattcaa agacctaggt gaagagaact ttaaggctct tgtacttata  480
gcatttgctc agtatctgca acagagtccc ttcgaagatc atgtcaagct ggtgaatgag  540
gtaaccgaat tcgccaagac ttgtgtggct gatgaatccg ccgaaaactg tgacaaatct  600
ttacacacat tgttcggaga taaactatgc acagtagcaa ctttacgtga aacttatggt  660
gagatggcag attgttgtgc taaacaggag cctgagagaa atgaatgctt tttgcaacac  720
aaggacgaca atcctaacct tcccagattg gttagacccg aggttgacgt tatgtgtacc  780
gccttccacg acaatgagga aacatttctg aaaaagtact tgtacgaaat tgcacgacgt  840
cacccatact tctatgcacc tgagcttttt ttttcgcca aaagatacaa ggcagctttc  900
actgagtgct gtcaagcagc cgataaggct gcttgtctat tacctaaact tgatgagctt  960
agagatgagg gtaaagcatc ctccgctaaa cagaggttga aatgtgccag tttgcagaag  1020
tttggtgaac gtgctttcaa ggcatgggct gttgctagat tatctcaaag atttcctaag  1080
gccgaatttg ctgaggtgtc aaagttggtg acggatttga ctaaggtcca cactgagtgt  1140
tgccatggtg atcttttgga atgtgctgac gatagagccg acctggccaa gtatatctgt  1200
gaaaaccaag attctatcag tagtaagctg aaggaatgtt gcgaaaaacc tctactagag  1260
aaatctcatt gcatcgcaga agttgaaaac gatgaaatgc ccgcagatct gcccagtctg  1320
gctgctgatt tcgtcgagtc aaaagatgtt tgcaaaaact atgccgaagc aaaggatgtc  1380
tttttgggca tgtttctgta cgaatatgct cgtcgtcatc ctgactattc cgttgtcctg  1440
ttgctaagac tagctaaaac gtatgaaacg accttggaaa agtgttgcgc tgcagctgat  1500
ccccacgagt gttatgcaaa agttttcgat gagtttaagc cacttgtaga agagccacag  1560
aacttgatca aacagaattg tgagcttttc gagcaattag gtgagtataa gtttcaaaac  1620
gctttgctgg ttagatatac caaaaaggtc cacaagtgt caaccccctac cctggtagaa  1680
gtgagtagaa atctaggaaa agtcggatct aagtgctgca agcatccaga agctaagaga  1740
atgccttgcg ctgaggatta cttgtcagta gttttgaatc agttgtgcgt cctacatgaa  1800
aagacacccg tttctgatag agtcactaag tgttgtactg agtctctagt aaacagaagg  1860
ccttgtttct ctgcattaga agtagatgaa acctatgtcc caaaggagtt caagctgcag  1920
acctttacat ttcacgccga catttgtacg ctatctgaga aggagcgtca gatcaaaaag  1980
caaaacagcc ttgttgagct tgtgaagcac aagccaaaag ctacaaagga gcaattgaaa  2040
gccgtcatgg acgatttcgc cgcatttgtt gagaagtgtt gcaggcaga tgataaggaa  2100
acttgttttg ctgaagaggg caaaaagctt gttgccgcct ctcaagctgc tttgggacta  2160
gccgctgcta ccggtgctca agttttgagg ggaaccgtta ccgacttccc aggttttgac  2220
```

```
gaaagagccg acgcagaaac attaaggaaa gccatgaagg gcttaggcac cgatgaggag  2280
tccattctga cactgttgac ttcccgatcc aatgcccaaa ggcaggagat ttcagccgct  2340
ttcaagactt tgtttggtag agatcttctg gacgacctga aatcagaact gactggaaag  2400
tttgagaaac ttattgttgc tttgatgaag ccttcaagac tatatgacgc atacgagttg  2460
aaacatgcat tgaaaggtgc aggaactaat gaaaaagtgt cattgcttcc  2520
agaacaccag aagagcttcg tgctatcaaa caagtgtatg aagaggaata cggatcaagt  2580
ctggaagatg acgttgttgg tgatacctca gggtattacc aaaggatgct tgtcgttcta  2640
ttacaagcta atcgagatcc tgacgccgga atcgatgaag ctcaagttga acaagatgct  2700
caggctcttt ttcaagccgg tgaattgaag tgggggactg atgatggaaaa gtttatcacg  2760
atctttggta ctagatctgt tagtcatttg agaaaagtat ttgacaaata catgaccatt  2820
tctggctttc aaatagaaga gactattgat agggaaactt ccggtaactt ggaacaactg  2880
ttgttagctg tggtcaagag tataagatca attccagctt acttagctga aactctgtat  2940
tacgcaatga aaggagcagg cacagacgat cacacgttga tccgagtcat ggtttccaga  3000
tcagagattg acttgttcaa tatcaggaag gaattcagca aaaactttgc aacctctttg  3060
tactccatga tcaaaggtga tacttccggt gattacaaaa aggctttgtt gttgttatgt  3120
ggagaggatg acggaggttc acatcaccat catcaccatt agtga  3165
```

SEQ ID NO: 150          moltype = AA   length = 934
FEATURE                 Location/Qualifiers
REGION                  1..934
                        note = Synthetic construct
source                  1..934
                        mol_type = protein
                        organism = synthetic construct
SEQUENCE: 150
GPETLCGAEL VDALQFVCGD RGFYFNKPTG YGSSSRRAPQ TGIVDECCFR SCDLRRLEMY  60
CAPLKPAKSA GAASDAHKSE VAHRFKDLGE ENFKALVLIA FAQYLQQSPF EDHVKLVNEV  120
TEFAKTCVAD ESAENCDKSL HTLFGDKLCT VATLRETYGE MADCCAKQEP ERNECFLQHK  180
DDNPNLPRLV RPEVDVMCTA FHDNEETFLK KYLYEIARRH PYFYAPELLF FAKRYKAAFT  240
ECCQAADKAA CLLPKLDELR DEGKASSAKQ RLKCASLQKF GERAFKAWAV ARLSQRFPKA  300
EFAEVSKLVT DLTKVHTECC HGDLLECADD RADLAKYICE NQDSISSKLK ECCEKPLLEK  360
SHCIAEVEND EMPADLPSLA ADFVESKDVC KNYAEAKDVF LGMFLYEYAR RHPDYSVVLL  420
LRLAKTYETT LEKCCAAADP HECYAKVFDE FKPLVEEPQN LIKQNCELFE QLGEYKFQNA  480
LLVRYTKKVP QVSTPTLVEV SRNLGKVGSK CCKHPEAKRM PCAEDYLSVV LNQLCVLHEK  540
TPVSDRVTKC CTESLVNRRP CFSALEVDET YVPKEFQAET FTFHADICTL SEKERQIKKQ  600
TALVELVKHK PKATKEQLKA VMDDFAAFVE KCCKADDKET CFAEEGKKLV AASQAALGLG  660
STGGGSGGGT GEVQLVESGG GLVQPGGSLR LSCSASGFTF SSYAMHWVRQ APGKGLEYVS  720
AISSNGGSTY YADSVKGRFT ISRDNSKNTL YLQMSSLRAE DTAVYYCVKI TGAYSSSWYY  780
DNWFDPWGQG TLVTVSSGGG GSGGGGSGGG GSGGSSYELT QPPSVSVSPG QTASITCSGD  840
KLGDKYACWY QQKPGQSPVL VIYQDSKRPS GIPERFSGSN SGNTATLTIS GTQAMDEADY  900
YCQAWDSSTA VFGGGTKLTV LGQGGSGGHH HHHH  934

SEQ ID NO: 151          moltype = DNA   length = 2808
FEATURE                 Location/Qualifiers
misc_feature            1..2808
                        note = Synthetic construct
source                  1..2808
                        mol_type = other DNA
                        organism = synthetic construct
SEQUENCE: 151
```
ggaccagaga cattgtgtgg agcagaactg gtggacgctt tacagtttgt gtgtggtgac  60
cgtggtttct acttcaacaa acctacgggt tacgggtcta gttctcgtag agctccacag  120
actgggattg tagatgaatg ctgcttcaga tcttgtgacc ttcgacgttt agaaatgtac  180
tgtgcacctc taaaaccagc caaatctgct ggagctgcaa gtgacgctca taagtctgaa  240
gttgctcaca gattcaaaga cctaggtgaa gagaacttta aggctcttgt acttatagca  300
tttgctcagt atctgcaaca gagtcccttc gaagatcatg tcaagctggt gaatgaggta  360
accgaattcg ccaagacttg tgtggctgat gaatccgccg aaaactgtga caaatcttta  420
cacacattgt tcgagataa actatgcaca gtagcaactt tacgtgaaac ttatggtgag  480
atggcagatt gttgtgctaa acaggagcct gagagaaatg aatgctttt gcaacacaag  540
gacgacaatc ctaaccttcc cagattggtt agacccgagg ttgacgttat gtgtaccgcc  600
ttccacgaca tgaggaaac atttctgaaa aagtacttgt acgaaattgc acgacgtcac  660
ccatacttct atgcacctga gcttttgttt tcgccaaaa gatacaaggc agctttcact  720
gagtgctgtc aagcagccga taaggctgct tgtctattac ctaaacttga tgagcttaga  780
gatgagggta aagcatcctc cgctaaacag aggttgaaat gtgccagttt gcagaagttt  840
ggtgaacgtg ctttcaaggc atgggctgtt gctagattat ctcaaagatt tcctaaggca  900
gaatttgctg aggtgtcaaa gttggtgacg gatttgacta aggtccacac tgagtgttgc  960
catggtgatc ttttggaatg tgctgacgat agagccgacc tggccaagta tatctgtgaa  1020
aaccaagatt ctatcagtag taagctcaag aatgttgcg aaaaacctct actagagaaa  1080
tctcattgca tcgcagaagt tgaaaacgat gaaatgccaa ccgacttgcc cagtctggct  1140
gctgatttcg tcgagtcaaa agatgtttgc aaaaactatg ccgaagcaaa ggatgtcttt  1200
ttgggcatgt ttctgtacga atatgctcgt cgtcatcctg actattccgt tgtcctgttg  1260
ctaagactag ctaaaacgta tgaaacgacc ttggaaaagt gttgcgctgc agctgatccc  1320
cacgagtgtt atgcaaaagt tttcgatgag tttaagccac ttgtagaaga gccacagaac  1380
ttgatcaaac agaattgtga gctttctgag caattaggtg agtataagtt tcaaaacgct  1440
ttgctggtta gatataccaa aaaggtccca caagtgtcaa ccctaccct ggtagaagtg  1500
agtagaaatc taggaaaagt cggatctaag tgctgcaagc atccagaagc taagagaatg  1560
ccttgcgctg aggattactt gtcagtagtt ttgaatcagt tgtgcgtcct acatgaaaag  1620
acacccgttt ctgatagagt cactaagtgt tgtactgagt ctctagtaaa cagaaggcct  1680
tgtttctctg cattagaagt agatgaaacc tatgtcccaa aggagttcca agctgaaacc  1740
```

-continued

```
tttacatttc acgccgacat ttgtacgcta tctgagaagg agcgtcagat caaaaagcaa  1800
acagcccttg ttgagcttgt gaagcacaag ccaaaagcta caaaggagca attgaaagcc  1860
gtcatggacg atttcgccgc atttgttgag aagtgttgca aggcagatga taaggaaact  1920
tgtttttgctg aagagggcaa aaagcttgtt gccgcctctc aagctgcttt gggactaggg  1980
tcgactgggg gagggagcgg tggaggaacc ggtgaggtgc agttggtcga atcaggagga  2040
ggtttagtgc agcccggtgg atcacttagg ctgagttgct ccgcatctgg tttcactttc  2100
tcttcctatg ccatgcattg ggtacgtcag gcaccgggga aaggactaga atacgtatca  2160
gccatatctt ctaatggcgg atcaacctac tatgctgatt cagttaaagg tagattcact  2220
atctcaagag ataactccaa aaacacattg taccttcaaa tgagttcact gcgtgctagg  2280
gacacagctg tctattactg tgtaaagatt actggagcct actctagttc ctggtactac  2340
gacaattggt ttgatccttg gggccaagga accttagtta cggtttccag tggcggtggg  2400
ggatctggcg gaggtgggag tggtggaggg ggttctggtg gatcatctta tgaattgacc  2460
cagccccctt ctgtgtctgt tagccctgga cagactgcca gcattacctg ttccggccgat  2520
aagctaggtg acaagtacgc ttgctggtat caacaaaagc cagggcagtc accagtgctt  2580
gtcatctacc aagattctaa gaggccaagt ggaataccag aacgatttc tggctccaac  2640
agtggcaata cagctaccct gacaatttcc ggtacgcaag caatgggatga ggctgactac  2700
tattgtcagg cctgggattc gtcaactgct gtgtttggtg gtggtactaa actcactgtc  2760
ttgggtcaag gcggatcagg tggtcaccac catcatcacc attagtga            2808
```

SEQ ID NO: 152          moltype = AA  length = 810
FEATURE                 Location/Qualifiers
REGION                  1..810
                        note = Synthetic construct
source                  1..810
                        mol_type = protein
                        organism = synthetic construct
SEQUENCE: 152

```
GPETLCGAEL VDALQFVCGD RGFYFNKPTG YGSSSRRAPQ TGIVDECCFR SCDLRRLEMY  60
CAPLKPAKSA GAASDAHKSE VAHRFKDLGE ENFKALVLIA FAQYLQQSPF EDHVKLVNEV  120
TEFAKTCVAD ESAENCDKSL HTLFGDKLCT VATLRETYGE MADCCAKQEP ERNECFLQHK  180
DDNPNLPRLV RPEVDVMCTA FHDNEETFLK KYLYEIARRH PYFYAPELLF FAKRYKAAFT  240
ECCQAADKAA CLLPKLDELR DEGKASSAKQ RLKCASLQKF GERAFKAWAV ARLSQRFPKA  300
EFAEVSKLVT DLTKVHTECC HGDLLECADD RADLAKYICE NQDSISSKLK ECCEKPLLEK  360
SHCIAEVEND EMPADLPSLA ADFVESKDVC KNYAEAKDVF LGMFLYEYAR RHPDYSVVLL  420
LRLAKTYETT LEKCCAAADP HECYAKVFDE FKPLVEEPQN LIKQNCELFE QLGEYKFQNA  480
LLVRYTKKVP QVSTPTLVEV SRNLGKVGSK CCKHPEAKRM PCAEDYLSVV LNQLCVLHEK  540
TPVSDRVTKC CTESLVNRRP CFSALEVDET YVPKEFQAET FTFHADICTL SEKERQIKKQ  600
TALVELVKHK PKATKEQLKA VMDDFAAFVE KCCKADDKET CFAEEGKKLV AASQAALGLG  660
STGGGSGGGT GEKLGKLQYS LDYDFQNNQL LVGIIQAAEL PALDMGGTSD PYVKVFLLPD  720
KKKKFETKVH RKTLNPVFNE QFTFKVPYSE LGGKTLVMAV YDFDRFSKHD IIGEFKVPMN  780
TVDFGHVTEE WRDLQSAEKG GSGGHHHHHH                                  810
```

SEQ ID NO: 153          moltype = DNA  length = 2436
FEATURE                 Location/Qualifiers
misc_feature            1..2436
                        note = Synthetic construct
source                  1..2436
                        mol_type = other DNA
                        organism = synthetic construct
SEQUENCE: 153

```
ggaccagaga cattgtgtgg agcagaactg gtggacgctt tacagtttgt gtgtggtgac  60
cgtggtttct acttcaacaa acctacgggg tacgggtcta gttctcgtag agctccacag  120
actgggattg tagatgaatg ctgcttcaga tcttgtgacc ttcgacgttt agaaatgtac  180
tgtgcacctc taaaaccagc caaatctgct ggagctgcaa gtgacgctca taagtctgaa  240
gttgctcaca gattcaaaga cctaggtgaa gagaactta aggctcttgt acttatagca  300
tttgctcagt atctgcaaca gagtcccttc gaagatcatg tcaagctggt gaatgaggta  360
accgaattcg ccaagacttg tgtggctgat gaatccgccg aaaactgtga caaatcttta  420
cacacattgt tcggagataa actatgcaca gtagcaactt tacgtgaaac ttatggtgag  480
atggcagatt gttgtgctgca acaggagcct gagagaaatg aatgctttt gcaacacaag  540
gacgacaatc ctaaccttcc cagattggtt agacccgagg ttgacgttat gtgtaccgcc  600
ttccacgaca tgaggaaac atttctgaaa aagtacttgt acgaaattgc acgacgtcac  660
ccatacttct atgcacctga gcttttgttt ttcgccaaaa gatacaaggc agctttcact  720
gagtgctgtc aagcagccga taaggctgct tgtctattac ctaaacttga tgagcttaga  780
gatgagggta aagcatcctc cgctaaacag aggttgaaat gtgccagttt gcagaagttt  840
ggtgaacgtg ctttcaaggc atgggctgtt gctagattat ctcaaagatt tcctaaggcc  900
gaatttgctg aggtgtcaaa gttggtgacg gatttgacta aggtccacac tgagtgttgc  960
catggtgatc ttttggaatg tgctgacgat agagccgacc tggccaagta tatctgtgaa  1020
aaccaagatt ctatcagtag taagctgaag gaatgttgcg aaaaacctct actagagaaa  1080
tctcattgca tcgcagaagt tgaaaacgat gaaatgccaa ccgacttgcc cagtctggct  1140
gctgatttcg tcgagtcaaa agatgtttgc aaaaactatg ccgaagcaaa ggatgtcttt  1200
ttgggcatgt ttctgtacga atatgctcgt cgtcatcctg actattccgt tgtcctgttg  1260
ctaagactag ctaaaacgta tgaaacgacc ttggaaaagt gttgcgctgc agctgatccc  1320
cacgagtgtt atgcaaaagt tttcgatgag tttaagccac ttgtagaaga gccacagaac  1380
ttgatcaaac agaattgtga gctttttcag caattaggtg agtataagtt tcaaaacgct  1440
ttgctggtta gatataccaa aaaggtccca caagtgtcaa ccctacccct ggtagaagtg  1500
agtagaaatc taggaaaagt cggatctaag tgctgcaagc atccagaagc taagagaatg  1560
ccttgcgctg aggattactt gtcagtagtt ttgaatcagt tgtgcgtcct acatgaaaag  1620
acacccgttt ctgatagagt cactaagtgt tgtactgagt ctctagtaaa cagaaggcct  1680
tgtttctctg cattagaagt agatgaaacc tatgtcccaa aggagttcca agctgaaacc  1740
```

```
tttacatttc acgccgacat ttgtacgcta tctgagaagg agcgtcagat caaaaagcaa    1800
acagcccttg ttgagcttgt gaagcacaag ccaaaagcta caaaggagca attgaaagcc    1860
gtcatggacg atttcgccgc atttgttgag aagtgttgca aggcagatga taaggaaact    1920
tgtttttgctg aagagggcaa aaagcttgtt gccgcctctc aagctgcttt gggactaggg    1980
tcgactgggg gagggagcgg tggaggaacc ggtgaaaagc gcaatacagt             2040
ttggactacg atttccaaaa caatcagttg ctcgtcggca ttatccaggc tgccgaattg    2100
ccagctttag atatgggtgg tacatcagat ccctacgtca aagtatttct actgcctgac    2160
aaaaagaaaa agtttgaaac taaggtgcac agaaaaacgc ttaacccagt tttcaacgag    2220
cagtttacat tcaaagttcc ttattctgaa cttggaggaa aaactctagt gatggccgtt    2280
tatgatttcg ataggttttc taagcatgac atcataggg agtttaaggt cccaatgaat    2340
actgttgatt tcggtcatgt gaccgaggaa tggcgtgacc ttcaatccgc agagaaaggc    2400
ggatcaggtg gtcaccacca tcatcaccat tagtga                              2436
```

```
SEQ ID NO: 154           moltype = AA  length = 926
FEATURE                  Location/Qualifiers
REGION                   1..926
                         note = Synthetic construct
source                   1..926
                         mol_type = protein
                         organism = synthetic construct
SEQUENCE: 154
GPETLCGAEL VDALQFVCGD RGFYFNKPTG YGSSSRRAPQ TGIVDECCFR SCDLRRLEMY    60
CAPLKPAKSA GAASDAHKSE VAHRFKDLGE ENFKALVLIA FAQYLQQSPF EDHVKLVNEV    120
TEFAKTCVAD ESAENCDKSL HTLFGDKLCT VATLRETYGE MADCCAKQEP ERNECFLQHK    180
DDNPNLPRLV RPEVDVMCTA FHDNEETFLK KYLYEIARRH PYFYAPELLF FAKRYKAAFT    240
ECCQAADKAA CLLPKLDELR DEGKASSAKQ RLKCASLQKF GERAFKAWAV ARLSQRFPKA    300
EFAEVSKLVT DLTKVHTECC HGDLLLECADD RADLAKYICE NQDSISSKLK ECCEKPLLEK    360
SHCIAEVEND EMPADLPSLA ADFVESKDVC KNYAEAKDVF LGMFLYEYAR RHPDYSVVLL    420
LRLAKTYETT LEKCCAAADP HECYAKVFDE FKPLVEEPQN LIKQNCELFE QLGEYKFQNA    480
LLVRYTKKVP QVSTPTLVEV SRNLGKVGSK CCKHPEAKRM PCAEDYLSVV LNQLCVLHEK    540
TPVSDRVTKC CTESLVNRRP CFSALEVDET YVPKEFQAET FTFHADICTL SEKERQIKKQ    600
TALVELVKHK PKATKEQLKA VMDDFAAFVE KCCKADDKET CFAEEGKKLV AASQAALGLG    660
STGGGSGGGT GLESGGGLVQ PGGSLRLSCA GSGFTFSSYA MSWVRQAPGK GLEWVSSISG    720
SGGSTYYADS VKGRFTISRD NSKKTLYLQM NSLRAEDTAV TYCARKRGRT TVSWGLVYFD    780
YWGQGTVVTV SSGGGGSGGG GSGGGGSGGS ELTQSPGTLS LSPGERATLS CRASHSVSRA    840
YLAWYQQKPG QAPRLLIYGT SSRATGIPDR FSGSGSGTDF TLTISRLEPE DFAVYYCQQY    900
GGSPWFGQGT KVELKGGSGG HHHHHH                                         926
```

```
SEQ ID NO: 155           moltype = DNA  length = 2784
FEATURE                  Location/Qualifiers
misc_feature             1..2784
                         note = Synthetic construct
source                   1..2784
                         mol_type = other DNA
                         organism = synthetic construct
SEQUENCE: 155
ggaccagaga cattgtgtgg agcagaactg gtggacgctt tacagtttgt gtgtggtgac    60
cgtggttctt acttcaacaa acctacgggt tacgggtcta gttctcgtag agctccacag    120
actgggattg tagatgaatg ctgcttcaga tcttgtgacc ttcgacgttt agaaatgtac    180
tgtgcacctc taaaaccagc caaatctgct ggagctgcaa gtgacgctca taagtctgaa    240
gttgctcaca gattcaaaga cctaggtgaa gagaactta aggctcttgt acttatgca    300
tttgctcagt atctgcaaca gagtcccttc gaagatcatg tcaagctggt gaatgaggta    360
accgaattcg ccaagacttg tgtggctgat gaatccgccg aaaactgtga caaatctta    420
cacacattgt tcggagataa actatgcaca gtagcaactt tacgtgaaac ttatggtgag    480
atggcagatt gttgtgctaa acaggagcct gagagaaatg aatgctttt gcaacacaag    540
gacgacaatc ctaaccttcc cagattggtt agacccgagg ttgacgttat gtgtaccgcc    600
ttccacgaca atgaggaaac atttctgaaa aagtacttgt acgaaattgc acgacgtcac    660
ccatacttct atgcacctga gcttttgttt ttcgccaaaa gatacaaggc agctttcact    720
gagtgctgtc aagcagccga taaggctgct tgtctattac ctaaacttga tgagcttaga    780
gatgagggta aagcatcctc cgctaaacag aggttgaaat gtgccagttt gcagaagttt    840
ggtgaacgtg ctttcaaggc atgggctgtt gctagattat ctcaaagatt tcctaaggcc    900
gaatttgctg aggtgtcaaa gttggtgacg gatttgacta aggtccacac tgagtgttgc    960
catggtgatc ttttggaatg tgctgacgat agagccgacc tggccaagta tatctgtgaa    1020
aaccaagatt ctatcagtag taagctgaag gaatgttgca gaaaacctct actagagaaa    1080
tctcattgca tcgcagaagt tgaaacgat gaaatgccag ccgacttgcc cagtctggct    1140
gctgatttcg tcgagtcaaa agatgtttgc aaaaactatg ccgaagcaaa ggatgtcttt    1200
ttgggcatgt ttctgtacga atatgctcgt cgtcatcctg actattccgt tgtcctgttg    1260
ctaagactag ctaaaacgta tgaaacgacc ttggaaaagt gttgcgctgc agctgatccc    1320
cacgagtgtt atgcaaaagt tttcgatgag tttaagccac ttgtagaaga gccacagaac    1380
ttgatcaaac agaattgtga gcttttcgag caattaggtg agtataagtt tcaaaacgct    1440
ttgctggtta gatataccaa aaaggtccca caagtgtcaa cccctacct ggtagaagtg    1500
agtagaaatc taggaaaagt cggatctaag tgctgcaagc atccagaagc taagagaatg    1560
ccttgcgctg aggattactt gtcagtagtt ttgaatcagt tgtgcgtcct acatgaaaag    1620
acacccgttt ctgatagagt cactaagtgt tgtactgagt ctctagtaaa cagaaggcct    1680
tgtttctctg cattagaagt agatgaaacc tatgtcccaa aggagttcca agctgaaacc    1740
tttacatttc acgccgacat ttgtacgcta tctgagaagg agcgtcagat caaaaagcaa    1800
acagcccttg ttgagcttgt gaagcacaag ccaaaagcta caaaggagca attgaaagcc    1860
gtcatggacg atttcgccgc atttgttgag aagtgttgca aggcagatga taaggaaact    1920
tgtttttgctg aagagggcaa aaagcttgtt gccgcctctc aagctgcttt gggactaggg    1980
```

```
tcgactgggg gagggagcgg tggaggaacc ggtttggaga gtgggggtgg cttggttcaa    2040
cccggtggat ctttgagatt gtcatgtgcc ggttctggtt ttacctttag ttcctatgct    2100
atgtcttggg tccgtcaagc cccaggcaaa ggacttgaat gggtatcatc aatctccggg    2160
tcaggtggta gtacgtatta cgcagattct gtgaaaggta ggtttaccat ttccagagat    2220
aactccaaaa agacattgta cttgcaaatg aatagtctga gagctgagga tactgccgtc    2280
tattactgtg cccgaaaaag aggcagaact acagttagtt ggggtcttgt ctactttgac    2340
tactgggtc aggggacggt cgttaccgta tcttccggtg gaggggggttc tggaggagga    2400
ggatctggtg gtggtggaag tggaggttct gaattgaccc aatctcctgg tactctgtct    2460
ctaagtccag gagaacgagc cacgttgtca tgtagggcct cacattcagt ttcaagagct    2520
tatcttgcct ggtatcaaca gaaacctgga caggccccac gtttgttgat atacggcacc    2580
agttccaggg ctacaggaat accagatagg ttttctggat ctggctcagg aacggatttc    2640
actttgacaa tttcaagact agagccagag gactttgccg tatactactg tcaacaatat    2700
ggaggatcac cttggttcgg acagggtact aaagttgaac ttaaaggcgg atcaggtggt    2760
caccaccatc atcaccatta gtga                                          2784
```

SEQ ID NO: 156              moltype = AA   length = 936
FEATURE                     Location/Qualifiers
REGION                      1..936
                            note = Synthetic construct
source                      1..936
                            mol_type = protein
                            organism = synthetic construct
SEQUENCE: 156
STSHLVKCAE KEKTFCVNGG ECFMVKDLSN PSRYLCKCPN EFTGDRCQNY VMASFYKHLG     60
IEFMEAEELY QKGAASDAHK SEVAHRFKDL GEENFKALVL IAFAQYLQQS PFEDHVKLVN    120
EVTEFAKTCV ADESAENCDK SLHTLFGDKL CTVATLRETY GEMADCCAKQ EPERNECFLQ    180
HKDDNPNLPR LVRPEVDVMC TAFHDNEETF LKKYLYEIAR RHPYFYAPEL LFFAKRYKAA    240
FTECCQAADK AACLLPKLDE LRDEGKASSA KQRLKCASLQ KFGERAFKAW AVARLSQRFP    300
KAEFAEVSKL VTDLTKVHTE CCHGDLLECA DDRADLAKYI CENQDSISSK LKECCEKPLL    360
EKSHCIAEVE NDEMPADLPS LAADFVESKD VCKNYAEAKD VFLGMFLYEY ARRHPDYSVV    420
LLLRLAKTYE TTLEKCCAAA DPHECYAKVF DEFKPLVEEP QNLIKQNCEL FEQLGEYKFQ    480
NALLVRYTKK VPQVSTPTLV EVSRNLGKVG SKCCKHPEAK RMPCAEDYLS VVLNQLCVLH    540
EKTPVSDRVT KCCTESLVNR RPCFSALEVD ETYVPKEFQA ETFTFHADIC TLSEKERQIK    600
KQTALVELVK HKPKATKEQL KAVMDDFAAF VEKCCKADDK ETCFAEEGKK LVAASQAALG    660
LGSTGGGSGG GTGEVQLVES GGGLVQPGGS LRLSCSASGF TFSSYAMHWV RQAPGKGLEY    720
VSAISSNGGS TYYADSVKGR FTISRDNSKN TLYLQMSSLR AEDTAVYYCV KITGAYSSSW    780
YYDNWFDPWG QGTLVTVSSG GGGSGGGGSG GGGSGGSSYE LTQPPSVSVS PGQTASITCS    840
GDKLGDKYAC WYQQKPGQSP VLVIYQDSKR PSGIPERFSG SNSGNTATLT ISGTQAMDEA    900
DYYCQAWDSS TAVFGGGTKL TVLGQGGSGG HHHHHH                             936

SEQ ID NO: 157              moltype = DNA   length = 2814
FEATURE                     Location/Qualifiers
misc_feature               1..2814
                            note = Synthetic construct
source                      1..2814
                            mol_type = other DNA
                            organism = synthetic construct
SEQUENCE: 157
tccacttctc atttggtgaa atgcgccgag aaggagaaaa cgttctgcgt gaacggtggt     60
gaatgcttta tggtcaaaga tctgtctaac ccttctcgat atctttgtaa gtgtcccaac    120
gagtttactg gtgatcgatg tcagaactac gttatggctt cctttacaa acacttggt     180
atagaattca tggaggccga ggagttgtac caaaaaggag ctgcaagtga cgctcataag    240
tctgaagttg ctcacagatt caaagaccta ggtgaagaga actttaaggc tcttgtactt    300
atagcatttg ctcagtatct gcaacagagt cccttcgaag atcatgtcaa gctggtgaat    360
gaggtaaccg aattcgccaa gacttgtgtg gctgatgaat ccgccgaaaa ctgtgacaaa    420
tctttacaca cattgttcgg agataaaacta tgcacagtag caactttacg tgaaacttat    480
ggtgagatgg cagattgttg tgctaaacag gagcctgaga gaaatgaatg cttttttgcaa    540
cacaaggacg acaatcctaa ccttcccaga ttggttagac ccgaggttga cgttatgtgt    600
accgccttcc acgacaatga ggaaacattt ctgaaaaagt acttgtacga aattgcacga    660
cgtcacccat acttctatgc acctgagctt ttgtttttcg ccaaaagata caaggcagct    720
ttcactgagt gctgtcaagc agccgataag gctgcttgtc tattacctaa acttgatgag    780
cttagagatg agggtaaagc atcctccgct aaacagaggt tgaaatgtgc cagtttgcag    840
aagtttggtg aacgtgcttt caaggcatgg gctgttgcta gattatctca aagatttcct    900
aaggccgaat ttgctgaggt gtcaaagttg gtgacggatt tgactaaggt ccacactgag    960
tgttgccatg gtgatctttt ggaatgtgct gacgatagac cgacctggc caagtatatc    1020
tgtgaaaacc aagattctat cagtagtaag ctgaaggaat gttgcgaaaa acctctacta    1080
gagaaatctc attgcatcgc agaagttgaa aacgatgaaa tgccagccga cttgcccagt    1140
ctggctgctg atttcgtcga gtcaaaagat gtttgcaaaa actatgccta agcaaaggat    1200
gtcttttttgg gcatgtttct gtacgaatat gctcgtcgtc atcctgacta ttccgttgtc    1260
ctgttgctaa gactagctaa aacgtatgaa acgaccttgg aaaagtgttg cgctgcagct    1320
gatcccacg agtgttatgc aaaagttttc gatgagttta agccacttgt agaagagcca    1380
cagaacttga tcaaacagaa ttgtgagctt ttcgagcaat taggtgagta taagtttcaa    1440
aacgctttgc tggttagata taccaaaaag gtcccacaag tgtcaacccc taccctggta    1500
gaagtgagta gaaatctagg aaaagtcgga tctaagtgct caagcatcc agaagctaag    1560
agaatgcctt gcgctgagga ttacttgtca gtagttttga atcagttgtg cgtcctacat    1620
gaaaagacac ccgttctga tagagtcact aagtgttgta ctgagtctct agtaaacaga    1680
aggccttgtt tctctgcatt agaagtagat gaaacctatg tcccaaagga gttccaagct    1740
gaaacctttta catttcacgc cgacatttgt acgctatctg agaggagcg tcagatcaaa    1800
aagcaaacag cccttgttga gcttgtgaag cacaagccaa aagctacaaa ggagcaattg    1860
```

```
aaagccgtca tggacgattt cgccgcattt gttgagaagt gttgcaaggc agatgataag  1920
gaaacttgtt ttgctgaaga gggcaaaaag cttgttgccg cctctcaagc tgctttggga  1980
ctagggtcga ctgggggagg gagcggtgga ggaaccggtg aggtgcagtt ggtcgaatca  2040
ggaggaggt  tagtgcagcc cggtggatca cttaggctga gttgctccgc atctggtttc  2100
actttctctt cctatgccat gcattgggta cgtcaggcac cgggggaaagg actagaaatac  2160
gtatcagcca tatcttctaa tggcggatca acctactatg ctgattcagt taaaggtaga  2220
ttcactatct caagagataa ctccaaaaac acattgtacc ttcaaatgag ttcactgcgt  2280
gctgaggaca cagctgtcta ttactgtgta aagattactg gagcctactc tagttcctgg  2340
tactacgaca attggtttga tccttggggc caaggaacct tagttacggt ttccagtggc  2400
ggtggggat  ctggcggagg tgggagtggt ggaggggggtt ctggtggatc atcttatgaa  2460
ttgacccagc ccccttctgt gtctgttagc cctggacaga ctgccagcat tacctgttcc  2520
ggcgataagc taggtgacaa gtacgcttgc tggtatcaac aaaagccagg gcagtcacca  2580
gtgcttgtca tctaccaaga ttctaagagg ccaagtggaa taccagaacg attttctggc  2640
tccaacagtg gcaatacagc taccctgaca atttccggta cgcaagcaat ggatgaggct  2700
gactactatt gtcaggcctg ggattcgtca actgctgtgt ttggtggtgg tactaaactc  2760
actgtcttgg gtcaaggcgg atcaggtggt caccaccatc atcaccatta gtga        2814
```

```
SEQ ID NO: 158          moltype = AA  length = 812
FEATURE                 Location/Qualifiers
REGION                  1..812
                        note = Synthetic construct
source                  1..812
                        mol_type = protein
                        organism = synthetic construct
SEQUENCE: 158
STSHLVKCAE KEKTFCVNGG ECFMVKDLSN PSRYLCKCPN EFTGDRCQNY VMASFYKHLG   60
IEFMEAEELY QKGAASDAHK SEVAHRFKDL GEENFKALVL IAFAQYLQQS PFEDHVKLVN  120
EVTEFAKTCV ADESAENCDK SLHTLFGDKL CTVATLRETY GEMADCCAKQ EPERNECFLQ  180
HKDDNPNLPR LVRPEVDVMC TAFHDNEETF LKKYLYEIAR RHPYFYAPEL LFFAKRYKAA  240
FTECCQAADK AACLLPKLDE LRDEGKASSA KQRLKCASLQ KFGERAFKAW AVARLSQRFP  300
KAEFAEVSKL VTDLTKVHTE CCHGDLLECA DDRADLAKYI CENQDSISSK LKECCEKPLL  360
EKSHCIAEVE NDEMPADLPS LAADFVESKD VCKNYAEAKD VFLGMFLYEY ARRHPDYSVV  420
LLLRLAKTYE TTLEKCCAAA DPHECYAKVF DEFKPLVEEP QNLIKQNCEL FEQLGEYKFQ  480
NALLVRYTKK VPQVSTPTLV EVSRNLGKVG SKCCKHPEAK RMPCAEDYLS VVLNQLCVLH  540
EKTPVSDRVT KCCTESLVNR RPCFSALEVD ETYVPKEFQA ETFTFHADIC TLSEKERQIK  600
KQTALVELVK HKPKATKEQL KAVMDDFAAF VEKCCKADDK ETCFAEEGKK LVAASQAALG  660
LGSTGGGSGG GTGEKLGKLQ YSLDYDFQNN QLLVGIIQAA ELPALDMGGT SDPYVKVFLL  720
PDKKKKFETK VHRKTLNPVF NEQFTFKVPY SELGGKTLVM AVYDFDRFSK HDIIGEFKVP  780
MNTVDFGHVT EEWRDLQSAE KGGSGGHHHH HH                                812
```

```
SEQ ID NO: 159          moltype = DNA  length = 2442
FEATURE                 Location/Qualifiers
misc_feature            1..2442
                        note = Synthetic construct
source                  1..2442
                        mol_type = other DNA
                        organism = synthetic construct
SEQUENCE: 159
tccacttctc atttggtgaa atgcgccgag aaggagaaaa cgttctgcgt gaacggtggt   60
gaatgcttta tggtcaaaga tctgtctaac ccttctcgat atctttgtaa gtgtcccaac  120
gagtttactg gtgatcgatg tcagaactac gttatggctt ccttttacaa acacttggtg  180
atagaattca tggaggccga ggagttgtac caaaaaggag ctgcaagtga cgctcataag  240
tctgaagttg ctcacagatt caaagaccta ggtgaagaga actttaaggc tcttgtactt  300
atagcatttg ctcagtatct gcaacagagt ccccttcgaag atcatgtcaa gctggtgaat  360
gaggtaaccg aattcgccaa gacttgtgtg gctgatgaat ccgccgaaaa ctgtgacaaa  420
tctttacaca cattgttcgg agataaaacta tgcacagtag caactttacg tgaaacttat  480
ggtgagatgg cagattgttg tgctaaacag gagcctgaga gaaatgaatg cttttttgcaa  540
cacaaggacg acaatcctaa ccttcccaga ttggttagac ccgaggttga cgttatgtgt  600
accgccttcc acgacaatga ggaaacattt ctgaaaaagt acttgtacga aattgcacga  660
cgtcacccat acttctatgc acctgagctt ttgtttttcg ccaaaagata caaggcagct  720
ttcactgagt gctgtcaagc agccgataag gctgcttgtc tattacctaa acttgatgag  780
cttagagatg agggtaaagc atcctccgct aaacagaggt tgaaatgtgc cagtttgcag  840
aagtttggtg aacgtgcttt caaggcatgg gctgttgcta gattatctca aagatttcct  900
aaggccgaat ttgctgaggt gtcaaagttg gtacgacggatt tgactaaggt ccacactgag  960
tgttgccatg gtgatctttt ggaatgtgct gacgatagag ccgacctggc caagtatatc  1020
tgtgaaaacc aagattctat cagtagtaag ctgaaggaat gttgcgaaaa acctctacta  1080
gagaaatctc attcatcgc agaagttgaa aacgatgaaa tgccagccga cttgcccagt  1140
ctggctgctg atttcgtcga gtcaaaagat gtttgcaaaa actatgccga agcaaaggat  1200
gtcttttggg gcatgtttct gtacgaatat gctcgtcgtc atcctgacta ttccgttgtc  1260
ctgttgctaa gactagctaa aacgtatgaa acgaccttgg aaaagtgttg cgctgcagct  1320
gatccccacg agtgttatgc aaaagttttc gatgagttta gccacttgt agaagagcca  1380
cagaacttga tcaaacagaa ttgtgagctt ttcgagcaat taggtgagta taagtttcaa  1440
aacgctttgc tggttagata taccaaaaag gtcccacaag tgtcaacccc taccctggta  1500
gaagtgagta gaaatctagg aaaagtcgga tctaagtgct gcaagcatcc agaagctaag  1560
agaatgcctt gcgctgagga ttacttgtca gtagttttga atcagttgtg cgtcctacat  1620
gaaaagacac ccgtttctga tagagtcact aagtgttgta ctgagtctct agtaaacaga  1680
aggccttgtt tctctgcatt agaagtagat gaaacctatg tcccaaagga gttccaagct  1740
gaaaccttta catttcacgc cgacatttgt acgtatctg agaaggagcg tcagatcaaa  1800
aagcaaacag ccccttgttga gcttgtgaag cacaagccaa aagctacaaa ggagcaattg  1860
```

```
aaagccgtca tggacgattt cgccgcattt gttgagaagt gttgcaaggc agatgataag    1920
gaaacttgtt ttgctgaaga gggcaaaaag cttgttgccg cctctcaagc tgctttggga    1980
ctagggtcga ctgggggagg gagcggtgga ggaaccggtg aaaagctggg aaagctgcaa    2040
tacagtttgg actacgattt ccaaaacaat cagttgctcg tcggcattat ccaggctgcc    2100
gaattgccag ctttagatat gggtgttaca tcagatccct acgtcaaagt atttctactg    2160
cctgacaaaa agaaaaagtt tgaaactaag gtgcacagaa aaacgcttaa cccagttttc    2220
aacgagcagt ttacattcaa agttccttat tctgaacttg gaggaaaaac tctagtgatg    2280
gccgtttatg atttcgatag gttttctaag catgacatca taggggagtt taaggtccca    2340
atgaatactg ttgatttcgg tcatgtgacc gaggaatggc gtgaccttca atccgcagag    2400
aaaggcggat caggtggtca ccaccatcat caccattagt ga                       2442
```

SEQ ID NO: 160            moltype = AA   length = 928
FEATURE                   Location/Qualifiers
REGION                     1..928
                           note = Synthetic construct
source                     1..928
                           mol_type = protein
                           organism = synthetic construct
SEQUENCE: 160

```
STSHLVKCAE KEKTFCVNGG ECFMVKDLSN PSRYLCKCPN EFTGDRCQNY VMASFYKHLG    60
IEFMEAEELY QKGAASDAHK SEVAHRFKDL GEENFKALVL IAFAQYLQQS PFEDHVKLVN    120
EVTEFAKTCV ADESAENCDK SLHTLFGDKL CTVATLRETY GEMADCCAKQ EPERNECFLQ    180
HKDDNPNLPR LVRPEVDVMC TAFHDNEETF LKKYLYEIAR RHPYFYAPEL LFFAKRYKAA    240
FTECCQAADK AACLLPKLDE LRDEGKASSA KQRLKCASLQ KFGERAFKAW AVARLSQRFP    300
KAEFAEVSKL VTDLTKVHTE CCHGDLLECA DDRADLAKYI CENQDSISSK LKECCEKPLL    360
EKSHCIAEVE NDEMPADLPS LAADFVESKD VCKNYAEAKD VFLGMFLYEY ARRHPDYSVV    420
LLLRLAKTYE TTLEKCCAAA DPHECYAKVF DEFKPLVEEP QNLIKQNCEL FEQLGEYKFQ    480
NALLVRYTKK VPQVSTPTLV EVSRNLGKVG SKCCKHPEAK RMPCAEDYLS VVLNQLCVLH    540
EKTPVSDRVT KCCTESLVNR RPCFSALEVD ETYVPKEFQA ETFTFHADIC TLSEKERQIK    600
KQTALVELVK HKPKATKEQL KAVMDDFAAF VEKCCKADDK ETCFAEEGKK LVAASQAALG    660
LGSTGGGSGG GTGLESGGGL VQPGGSLRLS CAGSGFTFSS YAMSWVRQAP GKGLEWVSSI    720
SGSGGSTYYA DSVKGRFTIS RDNSKKTLYL QMNSLRAEDT AVYYCARKRG RTTVSWGLVY    780
FDYWGQGTVV TVSSGGGGSG GGGSGGGGSG GSELTQSPGT LSLSPGERAT LSCRASHSVS    840
RAYLAWYQQK PGQAPRLLIY GTSSRATGIP DRFSGSGSGT DFTLTISRLE PEDFAVYYCQ    900
QYGGSPWFGQ GTKVELKGGS GGHHHHHH                                       928
```

SEQ ID NO: 161           moltype = DNA   length = 2790
FEATURE                   Location/Qualifiers
misc_feature              1..2790
                           note = Synthetic construct
source                     1..2790
                           mol_type = other DNA
                           organism = synthetic construct
SEQUENCE: 161

```
tccacttctc atttggtgaa atgcgccgag aaggagaaaa cgttctgcgt gaacggtggt    60
gaatgcttta tggtcaaaga tctgtctaac ccttctcgat atctttgtaa gtgtcccaac    120
gagtttactg gtgatcgatg tcagaactac gttatggctt cctttacaa acacttgggt    180
atagaattca tggaggccga ggagttgtac caaaaaggag ctgcaagtga cgctcataag    240
tctgaagttg ctcacagatt caaagaccta ggtgaagaga actttaaggc tcttgtactt    300
atagcatttg ctcagtatct gcaacagagt cccttcgaag atcatgtcaa gctggtgaat    360
gaggtaaccg aattcgccaa gacttgtgtg gctgatgaaa ccgccgaaaa ctgtgacaaa    420
tctttacaca cattgttcgg agataaacta tgcacagtag caactttacg tgaaacttat    480
ggtgagatgg cagattgttg tgctaaacag gagcctgaga gaaatgaatg cttttttgcaa    540
cacaaggacg acaatcctaa ccttcccaga ttggttagac ccgaggttga cgttatgtgt    600
accgccttcc acgacaatga ggaaacattt ctgaaaaagt acttgtacga aattgcacga    660
cgtcacccat acttctatgc acctgagctt ttgtttttcg ccaaaagata caaggcagct    720
ttcactgagt gctgtcaagc agccgataag gctgcttgtc tattacctaa acttgatgag    780
cttagagatg agggtaaagc atcctccgct aaacagaggt tgaaatgtgc cagtttgcag    840
aagtttggtg aacgtgcttt caaggcatgg gctgttgcta gattatctca aagatttcct    900
aaggccgaat ttgctgaggt gtcaaagttg gtgacggatt tgactaaggt ccacactgag    960
tgttgccatg gtgatctttt ggaatgtgct gacgatagag ccgacctggc caagtatatc    1020
tgtgaaaacc aagattctat cagtagtaag ctgaaggaat gttgcgaaaa acctctacta    1080
gagaaatctc attgcatcgc agaagttgaa aacgatgaaa tgccagccga cttgcccagt    1140
ctggctgctg atttcgtcga gtcaaaagat gtttgcaaaa actatgccga agcaaaggat    1200
gtctttttgg gcatgtttct gtacgaatat gctcgtcgtc atcctgacta ttccgttgtc    1260
ctgttgctaa gactagctaa aacgtatgaa acgaccttgg aaaagtgttg cgctgcagct    1320
gatccccacg agtgttatgc aaaagttttc gatgagttta gccacttgt agaagagcca    1380
cagaacttga tcaaacagaa ttgtgagctt ttcgagcaat taggtgagta taagtttcaa    1440
aacgctttgc tggttagata taccaaaaag gtcccacaag tgtcaacccc taccctggta    1500
gaagtgagta gaaatctagg aaaagtcgga tctaagtgct gcaagcatcc agaagctaag    1560
agaatgcctt gcgctgagga ttacttgtca gtagtttga atcagttgtg cgtcctacat    1620
gaaaagacac ccgtttctga tagagtcact aagtgttgta ctgagtctct agtaaacaga    1680
aggccttgtt tctctgcatt agaagtagat gaaacctatg tcccaaagga gttccaagct    1740
gaaacctta catttcacgc cgacatttgt acgctatctg agaaggagcg tcagatcaaa    1800
aagcaaacag cccttgttga gcttgtgaag cacaagccaa aagctacaaa ggagcaattg    1860
aaagccgtca tggacgattt cgccgcattt gttgagaagt gttgcaaggc agatgataag    1920
gaaacttgtt ttgctgaaga gggcaaaaag cttgttgccg cctctcaagc tgctttggga    1980
ctagggtcga ctgggggagg gagcggtgga ggaaccggtt ggagagtggg gggtggcttg    2040
gttcaacccg tggatctttt gagattgtca tgtgccggtt ctggttttac ctttagttcc    2100
```

```
tatgctatgt cttgggtccg tcaagcccca ggcaaaggac ttgaatgggg atcatcaatc   2160
tccgggtcag gtggtagtac gtattacgca gattctgtga aaggtaggtt taccatttcc   2220
agagataact ccaaaaagac attgtacttg caaatgaata gtctgagagc tgaggatact   2280
gccgtctatt actgtgcccg aaaaagaggc agaactacag ttagttgggg tcttgtctac   2340
tttgactact ggggtcaggg gacggtcgtt accgtatctt ccggtggagg gggttctgga   2400
ggaggaggat ctggtggtgg tggaagtgga ggttctgaat tgacccaatc tcctggtact   2460
ctgtctctaa gtccaggaga acgagccacg ttgtcatgta gggcctcaca ttcagtttca   2520
agagcttatc ttgcctggta tcaacagaaa cctggacagg ccccacgttt gttgatatac   2580
ggcaccagtt ccagggctac aggaatacca gataggtttt ctggatctgg ctcaggaacg   2640
gatttcactt tgacaatttc aagactagag ccagaggact ttgccgtata ctactgtcaa   2700
caatatggag gatcaccttg gttcggacag ggtactaaag ttgaacttaa aggcggatca   2760
ggtggtcacc accatcatca ccattagtga                                      2790
```

SEQ ID NO: 162          moltype = AA   length = 1010
FEATURE                 Location/Qualifiers
REGION                  1..1010
                        note = Synthetic construct
source                  1..1010
                        mol_type = protein
                        organism = synthetic construct
SEQUENCE: 162
PALPEDGGSG AFPPGHFKDP KRLYCKNGGF FLRIHPDGRV DGVREKSDPH IKLQLQAEER   60
GVVSIKGVCA NRYLAMKEDG RLLASKCVTD ECFFFERLES NNYNTYRSRK YTSWYVALKR   120
TGQYKLGSKT GPGQKAILFL PMSAKSGAAS DAHKSEVAHR FKDLGEENFK ALVLIAFAQY   180
LQQSPFEDHV KLVNEVTEFA KTCVADESAE NCDKSLHTLF GDKLCTVATL RETYGEMADC   240
CAKQEPERNE CFLQHKDDNP NLPRLVRPEV DVMCTAFHDN EETFLKKYLY EIARRHPYFY   300
APELLFFAKR YKAAFTECCQ AADKAACLLP KLDELRDEGK ASSAKQRLKC ASLQKFGERA   360
FKAWAVARLS QRFPKAEFAE VSKLVTDLTK VHTECCHGDL LECADDRADL AKYICENQDS   420
ISSKLKECCE KPLLEKSHCI AEVENDEMPA DLPSLAADFV ESKDVCKNYA EAKDVFLGMF   480
LYEYARRHPD YSVVLLLRLA KTYETTLEKC CAAADPHECY AKVFDEFKPL VEEPQNLIKQ   540
NCELFEQLGE YKFQNALLVR YTKKVPQVST PTLVEVSRNL GKVGSKCCKH PEAKRMPCAE   600
DYLSVVLNQL CVLHEKTPVS DRVTKCCTES LVNRRPCFSA LEVDETYVPK EFQAETFTFH   660
ADICTLSEKE RQIKKQTALV ELVKHKPKAT KEQLKAVMDD FAAFVEKCCK ADDKETCFAE   720
EGKKLVAASQ AALGLGSTGG GSGGGTGEVQ LVESGGGLVQ PGGSLRLSCS ASGFTFSSYA   780
MHWVRQAPGK GLEYVSAISS NGGSTYYADS VKGRFTISRD NSKNTLYLQM SSLRAEDTAV   840
YYCVKITGAY SSSWYYDNWF DPWGQGTLVT VSSGGGGSGG GGSGGGGSGG SSYELTQPPS   900
VSVSPGQTAS ITCSGDKLGD KYACWYQQKP GQSPVLVIYQ DSKRPSGIPE RFSGSNSGNT   960
ATLTISGTQA MDEADYYCQA WDSSTAVFGG GTKLTVLGQG GSGGHHHHHH             1010

SEQ ID NO: 163          moltype = DNA   length = 3036
FEATURE                 Location/Qualifiers
misc_feature            1..3036
                        note = Synthetic construct
source                  1..3036
                        mol_type = other DNA
                        organism = synthetic construct
SEQUENCE: 163
```
```
ccagctttgc ctgaggatgg aggctctggt gctttcctc ctggtcattt caaagaccca   60
aaaagactgt attgcaaaaa cggtgggttt ttcctgagga ttcatccaga tgggagggtc   120
gatggagtta gagagaaatc agaccccac attaagcttc aactacaggc tgaggaacgt   180
ggtgttgtct ccatcaaggg tgtttgtgca aatcgatact tagctatgaa agaggacgtc   240
agattacttg ccagtaagtg tgtaactgat gaatgtttct tttttcgaaag actagaatcc   300
aataactaca atacttaccg ttctcgtaag tatacatcat ggtacgtggc cttgaagaga   360
acgggacaat acaaattggg ttctaagacc ggaccaggac agaaagcaat cttgtttttg   420
cccatgtcag ctaagagtgg agctgcaagt gacgctcata agtctgaagt tgctcacaga   480
ttcaaagacc taggtgaaga gaactttaag gctcttgtac ttatagcatt tgctcagtat   540
ctgcaacaga gtcccttcga agatcatgtc aagctggtga atgaggtaac cgaattcgcc   600
aagacttgtg tggctgatga atccgccgaa aactgtgaca atctttaca cacattgttc   660
ggagataaac tatgcacagt agcaacttta cgtgaaactt atggtgagat ggcagattgt   720
tgtgctaaac aggagcctga gagaaatgaa tgcttttttgc aacacaagga cgacaatcct   780
aaccttccca gattggttag acccgaggtt gacgttatgt gtaccgcctt ccacgacaat   840
gaggaaacat ttctgaaaaa gtacttgtac gaaattgcac gacgtcaccc atacttctat   900
gcacctgagc tttttgtttt cgccaaaaga tacaaggcag ctttcactga gtgctgtcaa   960
gcagccgata aggctgcttg tctattacct aaacttgatg agcttagaga tgagggtaaa   1020
gcatcctccg ctaaacagag gttgaaatgt gccagtttgc agaagtttgg tgaacgtgct   1080
ttcaaggcat gggctgttgc tagattatct caaagatttc ctaaggccga atttgctgag   1140
gtgtcaaagt tggtgacgga tttgactaag gtccacactg agtgttgcca tggtgatctt   1200
ttggaatgtg ctgacgatag agccgacctg gccaagtata tctgtgaaaa ccaagattct   1260
atcagtagta agctgaagga atgttgcgaa aaacctctac tagagaaatc tcattgcatc   1320
gcagaagttg aaaacgatga aatgccagcc gacttgccca gtctggctgc tgatttcgtc   1380
gagtcaaaag atgtttgcaa aaactatgcc gaagcaaagg atgtcttttt gggcatgttt   1440
ctgtacgaat atgctcgtcg tcatcctgac tattccgttg tcctgttgct aagactagct   1500
aaaacgtatg aaacgacctt ggaaaagtgt tgcgctcag ctgatcccca cgagtgttat   1560
gcaaaagttt tcgatgagtt taagccactt gtagaagagc cacagaactt gatcaaacag   1620
aattgtgagc ttttcgagca attaggtgag tataagtttc aaaacgcttt gctggttaga   1680
tataccaaaa aggtcccaca agtgtcaacc cctaccctgg tagaagtgag tagaaatcta   1740
ggaaaagtcg atctaagtg ctgcaagcat ccagaagcta agagaatgcc ttgcgctgag   1800
gattacttgc agtagtttt gaatcagttg tgcgtcctac atgaaaagac accgtttct   1860
gatagagtca ctaagtgttg tactgagtct ctagtaaaca gaaggccttg tttctctgca   1920
```

```
ttagaagtag atgaaaccta tgtcccaaag gagttccaag ctgaaacctt tacatttcac   1980
gccgacattt gtacgctatc tgagaaggag cgtcagatca aaaagcaaac agcccttgtt   2040
gagcttgtga agcacaagcc aaaagctaca aaggagcaat tgaaagccgt catggacgat   2100
ttcgccgcat ttgttgagaa gtgttgcaag gcagatgata aggaaacttg ttttgctgaa   2160
gagggcaaaa agcttgttgc cgcctctcaa gctgctttgg gactagggtc gactgggggga  2220
gggagcggtg gaggaaccgg tgaggtgcag ttggtcgaat caggaggagg tttagtgcag   2280
cccggtggat cacttaggct gagttgctcc gcatctggtt tcactttctc ttcctatgcc   2340
atgcattggg tacgtcaggc accgggggaaa ggactagaat acgtatcagc catatcttct   2400
aatggcggat caacctacta tgctgattca gttaaaggta gattcactat ctcaagagat   2460
aactccaaaa acacattgta ccttcaaatg agttcactgc gtgctgagga cacagctgtc   2520
tattactgtg taaagattac tggagcctac tctagttcct ggtactacga caattggttt   2580
gatccttggg gccaaggaac cttagttacg gtttccagtg gcggtggggg atctggcgga   2640
ggtgggagtg gtggagggggg ttctggtgga tcatcttatg aattgaccca gcccccttct   2700
gtgtctgtta gccctggaca gactgccagc attacctgtt ccggcgataa gctaggtgac   2760
aagtacgctt gctggtatca acaaaagcca gggcagtcac cagtgcttgt catctaccaa   2820
gattctaaga ggccaagtgg aataccagaa cgatttctg gctccaacag tggcaataca    2880
gctaccctga caatttccgg tacgcaagca atggatgagg ctgactacta ttgtcaggcc   2940
tgggattcgt caactgctgt gtttggtggt ggtactaaac tcactgtctt gggtcaaggc   3000
ggatcaggtg gtcaccacca tcatcaccat tagtga                             3036
```

SEQ ID NO: 164          moltype = AA  length = 886
FEATURE                 Location/Qualifiers
REGION                  1..886
                        note = Synthetic construct
source                  1..886
                        mol_type = protein
                        organism = synthetic construct
SEQUENCE: 164

```
PALPEDGGSG AFPPGHFKDP KRLYCKNGGF FLRIHPDGRV DGVREKSDPH IKLQLQAEER   60
GVVSIKGVCA NRYLAMKEDG RLLASKCVTD ECFFFERLES NNYNTYRSRK YTSWYVALKR   120
TGQYKLGSKT GPGQKAILFL PMSAKSGAAS DAHKSEVAHR FKDLGEENFK ALVLIAFAQY   180
LQQSPFEDHV KLVNEVTEFA KTCVADESAE NCDKSLHTLF GDKLCTVATL RETYGEMADC   240
CAKQEPERNE CFLQHKDDNP NLPRLVRPEV DVMCTAFHDN EETFLKKYLY EIARRHPYFY   300
APELLFFAKR YKAAFTECCQ AADKAACLLP KLDELRDEGK ASSAKQRLKC ASLQKFGERA   360
FKAWAVARLS QRFPKAEFAE VSKLVTDLTK VHTECCHGDL LECADDRADL AKYICENQDS   420
ISSKLKECCE KPLLEKSHCI AEVENDEMPA DLPSLAADFV ESKDVCKNYA EAKDVFLGMF   480
LYEYARRHPD YSVVLLLRLA KTYETTLEKC CAAADPHECY AKVFDEFKPL VEEPQNLIKQ   540
NCELFEQLGE YKFQNALLVR YTKKVPQVST PTLVEVSRNL GKVGSKCCKH PEAKRMPCAE   600
DYLSVVLNQL CVLHEKTPVS DRVTKCCTES LVNRRPCFSA LEVDETYVPK EFQAETFTFH   660
ADICTLSEKE RQIKKQTALV ELVKHKPKAT KEQLKAVMDD FAAFVEKCCK ADDKETCFAE   720
EGKKLVAASQ AALGLGSTGG GSGGGTGEKL GKLQYSLDYD FQNNQLLVGI IQAAELPALD   780
MGGTSDPYVK VFLLPDKKKK FETKVHRKTL NPVFNEQFTF KVPYSELGGK TLVMAVYDFD   840
RFSKHDIIGE FKVPMNTVDF GHVTEEWRDL QSAEKGGSGG HHHHHH                  886
```

SEQ ID NO: 165          moltype = DNA  length = 2664
FEATURE                 Location/Qualifiers
misc_feature            1..2664
                        note = Synthetic construct
source                  1..2664
                        mol_type = other DNA
                        organism = synthetic construct
SEQUENCE: 165

```
ccagctttgc ctgaggatgg aggctctggt gcttttcctc ctggtcattt caaagaccca   60
aaaagactgt attgcaaaaa cggtgggttt ttcctgagga ttcatccaga tgggagggtc   120
gatggagtta gagagaaatc agacccccac attaagcttc aactacaggc tgaggaacgt   180
ggtgttgtct ccatcaaggg tgtttgtgca aatcgatact tagctatgaa agaggacggc   240
agattacttg ccagtaagtg tgtaactgat gaatgtttct ttttcgaaag actagaatcc   300
aataactaca atacttaccg ttctcgtaag tatacatcat ggtacgtggc cttgaagaga   360
acgggacaat acaaattggg ttctaagacc ggaccaggac agaaagcaat cttgttttg    420
cccatgtcag ctaagagtgg agctgcaagt gacgctcata gtctgaagt tgctcacaga    480
ttcaaagacc taggtgaaga gaactttaag gctcttgtac ttatagcatt tgctcagtat   540
ctgcaacaga gtcccttcga agatcatgtc aagctggtga atgaggtaac cgaattcgcc   600
aagacttgtg tggctgatga atccgccgaa aactgtgaca aatctttaca cacattgttc   660
ggagataaac tatgcacagt agcaacttta cgtgaaactt atggtgagat ggcagattgt   720
tgtgctaaac aggagcctga gagaaatgaa tgctttttgc aacacaagga cgacaatcct   780
aaccttccca gattggttag acccgaggtt gacgttatgt gtaccgcctt ccacgacaat   840
gaggaaacat ttctgaaaaa gtacttgtac gaaattgcac gacgtcaccc atacttctat   900
gcacctgagc tttttgtttt cgccaaaaga tacaaggcag ctttcactga gtgctgtcaa   960
gcagccgata aggctgcttg tctattacct aaacttgatg agcttagaga tgagggtaaa   1020
gcatcctccg ctaaacagag gttgaaatgt gccagtttgc agaagtttgg tgaacgtgct   1080
ttcaaggcat gggctgttgc tagattatct caaagatttc ctaaggccga atttgctgag   1140
gtgtcaaagt tggtgacgga tttgactaag gtccacactg agtgttgcca tggtgatctt   1200
ttggaatgtg ctgacgatag agccgacctg gccaagtata tctgtgaaaa ccaagattct   1260
atcagtagta agctgaagga atgttgcgaa aaacctctac tagagaaatc tcattgcatc   1320
gcagaagttg aaaacgatga aatgccagcc gacttgccca gtctggctgc tgatttcgtc   1380
gagtcaaaag atgtttgcaa aaactatgcc gaagcaaagg atgtcttttt gggcatgttt   1440
ctgtacgaat atgctcgtcg tcatcctgac tattccgttg tcctgttgct aagactagct   1500
aaaacgtatg aaacgacctt ggaaagtgt tgcgctgcag ctgatcccca cgagtgttat   1560
gcaaaagttt tcgatgagtt taagccactt gtagaagagc cacagaactt gatcaaacag   1620
```

```
aattgtgagc ttttcgagca attaggtgag tataagtttc aaaacgcttt gctggttaga   1680
tataccaaaa aggtcccaca agtgtcaacc cctaccctgg tagaagtgag tagaaatcta   1740
ggaaaagtcg gatctaagtg ctgcaagcat ccagaagcta agagaatgcc ttgcgctgag   1800
gattacttgt cagtagtttt gaatcagttg tgcgtcctac atgaaaagac acccgtttct   1860
gatagagtca ctaagtgttg tactgagtct ctagtaaaca gaaggccttg tttctctgca   1920
ttagaagtag atgaaaccta tgtcccaaag gagttccaag ctgaaacctt tacatttcac   1980
gccgacattt gtacgctatc tgagaaggag cgtcagatca aaaagcaaac agcccttgtt   2040
gagcttgtga agcacaagcc aaaagctaca aaggagcaat tgaaagccgt catggacgat   2100
ttcgccgcat ttgttgagaa gtgttgcaag gcagatgata aggaaacttg ttttgctgaa   2160
gagggcaaaa agcttgttgc cgcctctcaa gctgctttgg gactagggtc gactgggga   2220
gggagcggtg gaggaaccgg tgaaaagctg ggaaagctgc aatacagttt ggactacgat   2280
ttccaaaaca atcagttgct cgtcggcatt atccaggctg ccgaattgcc agctttagat   2340
atgggtggta catcagatcc ctacgtcaaa gtatttctac tgcctgacaa aaagaaaaag   2400
tttgaaacta aggtgcacag aaaaacgctt aacccagttc tcaacgagca gtttacattc   2460
aaagttcctt attctgaact tggaggaaaa actctagtga tggccgttta tgatttcgat   2520
aggtttttcta agcatgacat cataggggag tttaaggtcc caatgaatac tgttgatttc   2580
ggtcatgtga ccgaggaatg gcgtgacctt caatccgcag agaaaggcgg atcaggtggt   2640
caccaccatc atcaccatta gtga                                          2664
```

```
SEQ ID NO: 166          moltype = AA  length = 1002
FEATURE                 Location/Qualifiers
REGION                  1..1002
                        note = Synthetic construct
source                  1..1002
                        mol_type = protein
                        organism = synthetic construct
SEQUENCE: 166
PALPEDGGSG AFPPGHFKDP KRLYCKNGGF FLRIHPDGRV DGVREKSDPH IKLQLQAEER   60
GVVSIKGVCA NRYLAMKEDG RLLASKCVTD ECFFFERLES NNYNTYRSRK YTSWYVALKR   120
TGQYKLGSKT GPGQKAILFL PMSAKSGAAS DAHKSEVAHR FKDLGEENFK ALVLIAFAQY   180
LQQSPFEDHV KLVNEVTEFA KTCVADESAE NCDKSLHTLF GDKLCTVATL RETYGEMADC   240
CAKQEPERNE CFLQHKDDNP NLPRLVRPEV DVMCTAFHDN EETFLKKYLY EIARRHPYFY   300
APELLFFAKR YKAAFTECCQ AADKAACLLP KLDELRDEGK ASSAKQRLKC ASLQKFGERA   360
FKAWAVARLS QRFPKAEFAE VSKLVTDLTK VHTECCHGDL LECADDRADL AKYICENQDS   420
ISSKLKECCE KPLLEKSHCI AEVENDEMPA DLPSLAADFV ESKDVCKNYA EAKDVFLGMF   480
LYEYARRHPD YSVVLLLRLA KTYETTLEKC CAAADPHECY AKVFDEFKPL VEEPQNLIKQ   540
NCELFEQLGE YKFQNALLVR YTKKVPQVST PTLVEVSRNL GKVGSKCCKH PEAKRMPCAE   600
DYLSVVLNQL CVLHEKTPVS DRVTKCCTES LVNRRPCFSA LEVDETYVPK EFQAETFTFH   660
ADICTLSEKE RQIKKQTALV ELVKHKPKAT KEQLKAVMDD FAAFVEKCCK ADDKETCFAE   720
EGKKLVAASQ AALGLGSTGG GSGGGTGLES GGGLVQPGGS LRLSCAGSGF TFSSYAMSWV   780
RQAPGKGLEW VSSISGSGGS TYYADSVKGR FTISRDNSKK TLYLQMNSLR AEDTAVYYCA   840
RKRGRTTVSW GLVYFDYWGQ GTVVTVSSGG GGSGGGGSGG GGSGGSELTQ SPGTLSLSPG   900
ERATLSCRAS HSVSRAYLAW YQQKPGQAPR LLIYGTSSRA TGIPDRFSGS GSGTDFTLTI   960
SRLEPEDFAV YYCQQYGGSP WFGQGTKVEL KGGSGGHHHH HH                      1002
```

```
SEQ ID NO: 167          moltype = DNA  length = 3012
FEATURE                 Location/Qualifiers
misc_feature            1..3012
                        note = Synthetic construct
source                  1..3012
                        mol_type = other DNA
                        organism = synthetic construct
SEQUENCE: 167
ccagctttgc ctgaggatgg aggctctggt gcttttcctc ctggtcattt caaagaccca   60
aaaagactgt attgcaaaaa cggtgggttt ttcctgagga ttcatccaga tgggagggtc   120
gatggagtta gagagaaatc agacccccac attaagcttc aactacaggc tgaggaacgt   180
ggtgttgtct ccatcaaggg tgtttgtgca aatcgatact tagctatgaa agaggacggc   240
agattacttg ccagtaagtg tgtaactgat gaatgtttct ttttcgaaag actagaatcc   300
aataactaca tacttaccg ttctcgtaag tatacatcat ggtacgtggc cttgaagaga   360
acgggacaat acaaattggg ttctaagacc ggaccaggac agaaagcaat cttgtttttg   420
cccatgtcag ctaagagtgg agctgcaagt gacgctcata agtctgaagt tgctcacaga   480
ttcaaagacc taggtgaaga gaactttaag gctcttgtac ttatagcatt tgctcagtat   540
ctgcaacaga gtcccttcga agatcatgtc aagctggtga atgaggtaac cgaattcgcc   600
aagacttgtg tggctgatga atccgccgaa aactgtgaca aatctttaca cacattgttc   660
ggagataaac tatgcacagt agcaacttta cgtgaaactt atggtgagat ggcagattgc   720
tgtgctaaac aggagcctga gagaaatgaa tgctttttgc aacacaagga cgacaatcct   780
aaccttccca gattggttag acccgaggtt gacgttatgt gtaccgcctt ccacgacaat   840
gaggaaacat ttctgaaaaa gtacttgtac gaaattgcac gacgtcaccc atacttctat   900
gcacctgagc tttttgtttt cgccaaaaga tacaaggcag ctttcactga gtgctgtcaa   960
gcagccgata aggctgcttg tctattacct aaacttgatg agcttagaga tgagggtaaa   1020
gcatcctccg ctaaacagag gttgaaatgt gccagtttgc agaagtttgg tgaacgtgct   1080
ttcaaggcat gggctgttgc tagattatct caaagatttc ctaaggccga atttgctgag   1140
gtgtcaaagt tggtgacgga tttgactaag gtccacactg agtgttgcca tggtgatctt   1200
ttggaatgtg ctgacgatag agccgacctg gccaagtata tctgtgaaaa ccaagattct   1260
atcagtagta agctgaagga atgttgcgaa aaacctctac tagagaaatc tcattgcatc   1320
gcagaagttg aaaacgatga aatgccagcc gacttgccca gtctggctgc tgatttcgtc   1380
gagtcaaaag atgtttgcaa aaactatgcc gaagcaaagg atgtctttt gggcatgttt   1440
ctgtacgaat atgctcgtcg tcatcctgac tattccgttg tcctgttgct aagactagct   1500
aaaacgtatg aaacgacctt ggaaaagtgt tgcgctgcag ctgatcccca cgagtgttat   1560
```

```
gcaaaagttt tcgatgagtt taagccactt gtagaagagc cacagaactt gatcaaacag    1620
aattgtgagc ttttcgagca attaggtgag tataagtttc aaaacgcttt gctggttaga    1680
tataccaaaa aggtcccaca agtgtcaacc cctaccctgg tagaagtgag tagaaatcta    1740
ggaaaagtcg gatctaagtg ctgcaagcat ccagaagcta agagaatgcc ttgcgctgag    1800
gattacttgt cagtagtttt gaatcagttg tgcgtcctac atgaaaagac acccgtttct    1860
gatagagtca ctaagtgttg tactgagtct ctagtaaaca gaaggccttg tttctctgca    1920
ttagaagtag atgaaaccta tgtcccaaag gagttccaag ctgaaacctt acatttcac     1980
gccgacattt gtacgctatc tgagaaggag cgtcagatca aaaagcaaac agcccttgtt    2040
gagcttgtga agcacaagcc aaaagctaca aaggagcaat tgaaagccgt catggacgat    2100
ttcgccgcat ttgttgagaa gtgttgcaag gcagtgata aggaaacttg ttttgctgaa     2160
gagggcaaaa agcttgttgc cgcctctcaa gctgctttgg gactagggtc gactggggga    2220
gggagcggtg gaggaaccgg tttggagagt gggggtggct tggttcaacc cggtggatct    2280
ttgagattgt catgtgccgg ttctggtttt acctttagtt cctatgctat gtcttgggtc    2340
cgtcaagccc caggcaaagg gtatcatcaa tctccgggtc aggtggtagt               2400
acgtattacg cagattctgt gaaaggtagg tttaccattt ccagagataa ctccaaaaag    2460
acattgtact tgcaaatgaa tagtctgaga gctgaggata ctgccgtcta ttactgtgcc    2520
cgaaaaagag gcagaactac agttagttgg ggtcttgtct actttgacta ctggggtcag    2580
gggacggtcg ttccggtgga gggggttctg gaggaggagg atctggtagt               2640
ggtggaagtg gaggttctga attgacccaa tctcctggta ctctgtctct aagtccagga    2700
gaacgagcca cgttgtcatg tagggcctca cattcagttt caagagctta tcttgcctgg    2760
tatcaacaga aacctggaca ggcccccacgt ttgttgatat acggcaccag ttccaggggct   2820
acaggaaatac cagataggtt ttctggatct ggctcaggaa cggatttcac tttgacaatt    2880
tcaagactag agccagagga ctttgccgta tactactgtc aacaatatgg aggatcacct    2940
tggttcggac agggtactaa agttgaactt aaaggcggat caggtggtca ccaccatcat    3000
caccattagt ga                                                         3012
```

SEQ ID NO: 168               moltype = AA  length = 933
FEATURE                      Location/Qualifiers
REGION                       1..933
                             note = Synthetic construct
source                       1..933
                             mol_type = protein
                             organism = synthetic construct
SEQUENCE: 168
EVQLVESGGG LVQPGGSLRL SCSASGFTFS SYAMHWVRQA PGKGLEYVSA ISSNGGSTYY    60
ADSVKGRFTI SRDNSKNTLY LQMSSLRAED TAVYYCVKIT GAYSSSWYYD NWFDPWGQGT    120
LVTVSSGGGG SGGGGSGGGG SGGSSYELTQ PPSVSVSPGQ TASITCSGDK LGDKYACWYQ    180
QKPGGQSPVLV IYQDSKRPSG IPERFSGSNS GNTATLTISG TQAMDEADYY CQAWDSSTAV    240
FGGGTKLTVL GQGAQGGGSG GSAGDAHKSE VAHRFKDLGE ENFKALVLIA FAQYLQQSPF    300
EDHVKLVNEV TEFAKTCVAD ESAENCDKSL HTLFGDKLCT VATLRETYGE MADCCAKQEP    360
ERNECFLQHK DDNPNLPRLV RPEVDVMCTA FHDNEETFLK KYLYEIARRH PYFYAPELLF    420
FAKRYKAAFT ECCQAADKAA CLLPKLDELR DEGKASSAKQ RLKCASLQKF GERAFKAWAV    480
ARLSQRFPKA EFAEVSKLVT DLTKVHTECC HGDLLECADD RADLAKYICE NQDSISSKLK    540
ECCEKPLLEK SHCIAEVEND EMPADLPSLA ADFVESKDVC KNYAEAKDVF LGMFLYEYAR    600
RHPDYSVVLL LRLAKTYETT LEKCCAAADP HECYAKVFDE FKPLVEEPQN LIKQNCELFE    660
QLGEYKFQNA LLVRYTKKVP QVSTPTLVEV SRNLGKVGSK CCKHPEAKRM PCAEDYLSVV    720
LNQLCVLHEK TPVSDRVTKC CTESLVNRRP CFSALEVDET YVPKEFQAET FTFHADICTL    780
SEKERQIKKQ TALVELVKHK PKATKEQLKA VMDDFAAFVE KCCKADDKET CFAEEGKKLV    840
AASQAALGLA AATGGPETLC GAELVDALQF VCGDRGFYFN KPTGYGSSSR RAPQTGIVDE    900
CCFRSCDLRR LEMYCAPLKP AKSAGGSHHH HHH                                 933

SEQ ID NO: 169               moltype = DNA  length = 2805
FEATURE                      Location/Qualifiers
misc_feature                 1..2805
                             note = Synthetic construct
source                       1..2805
                             mol_type = other DNA
                             organism = synthetic construct
SEQUENCE: 169
gaggtgcagt tggtcgaatc aggaggaggt ttagtgcagc ccggtggatc acttaggctg    60
agttgctccg catctggttt cactttctct tcctatgcca tgcattgggt acgtcaggca    120
ccggggaaag gactagaata cgtatcagcc atatcttcta atggcggatc aacctactat    180
gctgattcag ttaaaggtag attcactatc tcaagagata actccaaaaa cacattgtac    240
cttcaaatga gttcactgcg tgctgaggac acagctgtct attactgtgt aaagattact    300
ggagcctact ctagttcctg gtactacgac aattggtttg atccttgggg ccaaggaacc    360
ttagttacgg tttccagtgg cggtggggga tctggcggag gtgggagtgg tggagggggt    420
tctggtggat catcttatga attgacccag cccccttctg tgtctgttag ccctggacag    480
actgccagca ttacctgttc cggcgataag ctaggtgaca agtacgcttg ctggtatcaa    540
caaaagccag ggcagtcacc agtgcttgtc atctaccaag attctaagca gccaagtgga    600
ataccagaac gattttctgg ctccaacagt ggcaatacag ctaccctgac aatttccggt    660
acgcaagcaa tggatgaggc tgactactat tgtcaggcct gggattcgtc aactgctgtg    720
tttggtggtg gtactaaact cactgtcttg ggtcaagggg cccaaggagg tggatcagga    780
ggctctcag gtgatgctca aaatctgaa gtcgctcatc gtttcaaaga cttgggtgag     840
gaaaacttta aggcttagt tctgattgct tttgcccaat atcttcaaca atcaccattc    900
gaagatcatg tgaaacttgt taacgaagtt accgaatttg caaaaacgtg tgtggcagac    960
gaaagtgccg aaaactgtga caaatcatta cacactttgt tcggtgacaa gttatgcact    1020
gttgcaaccc tacgtgagac atatggagaa atggcagact gttgcgccaa acaagagcct    1080
gaacgaaacg aatgctttct gcagcacaaa gacgataatc caaatcttcc ccgattagtt   1140
cgtcccgaag tagacgtaat gtgcacagcc tttcatgata atgaagagac tttcctgaaa    1200
```

```
aagtacttgt acgaaattgc aagacgtcac ccatacttct atgctcccga gttactgttt    1260
ttcgccaaac gatacaaggc agcctttaca gaatgttgcc aagcagctga caaggctgca    1320
tgtctttttac ctaagttaga tgagttaaga gacgaaggta aggcttcctc agcaaaacag    1380
agacttaagt gcgcatccct tcaaaagttt ggtgagagag ctttcaaggc ttgggctgtc    1440
gccagactgt ctcagagatt tcctaaggct gaattcgaca aagtctctaa gctagtaact    1500
gacttgacta aagttcatac tgagtgctgt catgggggatt tgttggaatg cgcagatgat    1560
cgtgcagact tagcaaagta catctgcgag aaccaagact ctatttccag taagttaaag    1620
gaatgttgcg aaaagccact acttgagaag tcccactgta ttgctgaagt cgaaaatgat    1680
gaaatgcctg ctgaccttcc atctttggcc gctgatttcg ttgagtccaa ggatgtgtgc    1740
aaaaactatg ctgaagcaaa agatgtgttc ctagggatgt tcctgtatga atatgctcgt    1800
cgacatcccg actattccgt tgtcctttta ctgagattgg ctaagaccta cgagacaacc    1860
ttggagaagt gttgtgctgc cgcagatcct cacgagtgtt acgcaaaagt gtttgatgag    1920
ttcaaaccat tggttgaaga gccacaaaat ctaatcaagc agaactgtga actgtttgaa    1980
caattgggcg aatacaaatt ccaaaatgct ctgttagtga gataccaccaa aaaggtccca    2040
caagtttcca ccccaactct agtcgaggtg tccagaaatc taggaaaagt tggatctaag    2100
tgttgtaagc atccagaagc taagaggatg ccttgcgctg aggattactt gtctgtggtt    2160
ttgaaccagt tatgtgttct cacgagaaa actcctgtct ccgacagagt tactaagtgc    2220
tgcacagagt ctttggtcaa tagaaggcct tgtttcagtg ccctggaagt cgatgaaact    2280
tatgtgccta aagagttcca agccgaaacg ttcacttttc acgctgacat ttgtactctt    2340
tctgagaagg aacgtcagat caaaaagcag acagcattgg tggaattggt aaaagcataaa    2400
ccaaaggcta caaaagagca gctgaaggct gttatgtgatg attttgcagc tttcgttgaa    2460
aagtgttgta aagccgatga taaagagact tgtttttgcag ggaggggggaa aaagctggtt    2520
gctgcatcac aagctgccct aggtcttgca gccgctaccg gtggacctga aaccttatgt    2580
ggagctgaac ttgtggatgc tctacaattt gtttgtggcg atagagggtt ctacttcaac    2640
aaacccactg gatatggtag ttcctcaaga cgagctcctc agacaggtat tgtcgacgag    2700
tgttgttttta ggtcttgcga cttgcgtaga ctggagatgt actgcgcacc attgaagcca    2760
gcaaagtctg ccggtggttc acatcaccac catcaccatt agtga            2805
```

```
SEQ ID NO: 170           moltype = AA  length = 809
FEATURE                  Location/Qualifiers
REGION                   1..809
                         note = Synthetic construct
source                   1..809
                         mol_type = protein
                         organism = synthetic construct
SEQUENCE: 170
EKLGKLQYSL DYDFQNNQLL VGIIQAAELP ALDMGGTSDP YVKVFLLPDK KKKFETKVHR    60
KTLNPVFNEQ FTFKVPYSEL GGKTLVMAVY DFDRFSKHDI IGEFKVPMNT VDFGHVTEEW    120
RDLQSAEKGA QGGGSGGSAG DAHKSEVAHR FKDLGEENFK ALVLIAFAQY LQQSPFEDHV    180
KLVNEVTEFA KTCVADESAE NCDKSLHTLF GDKLCTVATL RETYGEMADC CAKQEPERNE    240
CFLQHKDDNP NLPRLVRPEV DVMCTAFHDN EETFLKKYLY EIARRHPYFY APELLFFAKR    300
YKAAFTECCQ AADKAACLLP KLDELRDEGK ASSAKQRLKC ASLQKFGERA FKAWAVARLS    360
QRFPKAEFAE VSKLVTDLTK VHTECCHGDL LECADDRADL AKYICENQDS ISSKLKECCE    420
KPLLEKSHCI AEVENDEMPA DLPSLAADFV ESKDVCKNYA EAKDVFLGMF LYEYARRHPD    480
YSVVLLLRLA KTYETTLEKC CAAADPHECY AKVFDEFKPL VEEPQNLIKQ NCELFEQLGE    540
YKFQNALLVR YTKKVPQVST PTLVEVSRNL GKVGSKCCKH PEAKRMPCAE DYLSVVLNQL    600
CVLHEKTPVS DRVTKCCTES LVNRRPCFSA LEVDETYVPK EFQAETFTFH ADICTLSEKE    660
RQIKKQTALV ELVKHKPKAT KEQLKAVMDD FAAFVEKCCK ADDKETCFAE EGKKLVAASQ    720
AALGLAAATG GPETLCGAEL VDALQFVCGD RGFYFNKPTG YGSSSRRAPQ TGIVDECCFR    780
SCDLRRLEMY CAPLKPAKSA GGSHHHHHH                                      809
```

```
SEQ ID NO: 171           moltype = DNA  length = 2433
FEATURE                  Location/Qualifiers
misc_feature             1..2433
                         note = Synthetic construct
source                   1..2433
                         mol_type = other DNA
                         organism = synthetic construct
SEQUENCE: 171
gaaaagctgg gaaagctgca atacagtttg gactacgatt tccaaaacaa tcagttgctc    60
gtcggcatta tccaggctgc cgaattgcca gctttagata tgggtggtac atcagatccc    120
tacgtcaaag tatttctact gcctgacaaa aagaaaaagt ttgaaactaa ggtgcacaga    180
aaaacgctta acccagtttt caacgagcag tttacattca agttccttta ttctgaactt    240
ggaggaaaaa ctctagtgat ggccgtttat gatttcgata ggtttttctaa gcatgacatc    300
ataggggagt ttaaggtccc aatgaatact gttgatttcg gtcatgtgac cgaggaatgc    360
cgtgaccttc aatccgcaga gaaggggggcc caaggaggtg gatcaggagg ctctgcaggt    420
gatgctcaca atctgaagt cgctcatcgt ttcaaagact ggggtgagga aaactttaag    480
gctttagttc tgattgcttt tgcccaatat cttcaacaat caccattcga agatcatgtg    540
aaacttgtta acgaagttac cgaatttgca aaaacgtgtg tggcagacga aagtgccgaa    600
aactgtgaca atcattaca cactttgttc ggtgacaagt tatgcactgt tgcaaccctaa    660
cgtgagacat atggagaaat ggcagactgt tgcgccaaac aagagcctga acgaaacgaa    720
tgctttctgc agcacaaaga cgataatcca atcttcccc gattagttcg tcccgaagta    780
gacgtaatgt gcacagcctt tcatgataat gaagagactt tcctgaaaaa gtacttgtac    840
gaaattgcaa gacgtcaccc atacttctat cgcccgagt tactgtttt cgccaaacatc    900
tacaaggcag cctttacaga atgttgccaa gcagctgaca aggctgcatg tcttttacct    960
aagttagatg agttaagaga cgaaggtaag gcttcctcag caaaacagag acttaagtgc    1020
gcatcccttc aaaagtttgg tgagagagct ttcaaggctt gggctgtcgc cagactgtct    1080
cagagattc ctaaggctga attcgacaaa gtctctaagc tagtaactga cttgactaaa    1140
gttcatactg agtgctgtca tgggggattg ttggaatgcg cagatgatcg tgcagactta    1200
```

```
gcaaagtaca tctgcgagaa ccaagactct atttccagta agttaaagga atgttgcgaa   1260
aagccactac ttgagaagtc ccactgtatt gctgaagtcg aaaatgatga aatgcctgct   1320
gaccttccat cttttggccgc tgatttcgtt gagtccaagg atgtgtgcaa aaactatgct   1380
gaagcaaaag atgtgttcct agggatgttc ctgtatgaat atgctcgtcg acatcccgac   1440
tattccgttg tccttttact gagattggct aagacctacg gagacaacctt ggagaagtgt   1500
tgtgctgccg cagatcctca cgagtgttac gcaaaagtgt ttgatgagtt caaaccattg   1560
gttgaagagc cacaaaatct aatcaagcag aactgtgaac tgtttgaaca attgggcgaa   1620
tacaaattcc aaaatgctct gttagtgaga tacaccaaaa aggtcccaca agtttccacc   1680
ccaactctag tcgaggtgtc cagaaatcta ggaaaagttg gatctaagtg ttgtaagcat   1740
ccagaagcta gaggatgcc ttgcgctgag gattacttgt ctgtggtttt gaaccagtta   1800
tgtgttctac acgagaaaac tcctgtctcc gacagagtta ctaagtgctg cacagagtct   1860
ttggtcaata gaaggccttg tttcagtgcc ctggaagtcg atgaaactta tgtgcctaaa   1920
gagttccaag ccgaaacgtt cactttcac gctgacattg tgactctttc tgagaaggaa   1980
cgtcagatca aaaagcagac agcattggtg gaattggtaa agcataaacc aaaggctaca   2040
aaagagcagc tgaaggctgt tatggatgat tttgcagctt tcgtggaaaa gtgttgtaaa   2100
gccgatgata aagagacttg ttttgcagag gaggggaaa agctggttgc tgcatcacaa   2160
gctgccctag gtcttgcagc cgctaccggt ggacctgaaa cctatgtgg agctgaactt   2220
gtggatgctc tacaatttgt ttgtggcgat agagggttct acttcaacaa acccactgga   2280
tatggtagtt cctcaagacg agctcctcag acaggtattg tcgacgagtg ttgtttttagg   2340
tcttgcgact tgcgtagact ggagatgtac tgcgcaccat tgaagccagc aaagtctgcc   2400
ggtggttcac atcaccacca tcaccattag tga                                2433
```

SEQ ID NO: 172            moltype = AA  length = 925
FEATURE                   Location/Qualifiers
REGION                    1..925
                          note = Synthetic construct
source                    1..925
                          mol_type = protein
                          organism = synthetic construct
SEQUENCE: 172
```
LESGGGLVQP GGSLRLSCAG SGFTFSSYAM SWVRQAPGKG LEWVSSISGS GGSTYYADSV   60
KGRFTISRDN SKKTLYLQMN SLRAEDTAVY YCARKRGRTT VSWGLVYFDY WGQGTVVTVS   120
SGGGGSGGGG SGGGGSGGSE LTQSPGTLSL SPGERATLSC RASHSVSRAY LAWYQQKPGQ   180
APRLLIYGTS SRATGIPDRF SGSGSGTDFT LTISRLEPED FAVYYCQQYG GSPWFGQGTK   240
VELKGAQGGG SGGSAGDAHK SEVAHRFKDL GEENFKALVL IAFAQYLQQS PFEDHVKLVN   300
EVTEFAKTCV ADESAENCDK SLHTLFGDKL CTVATLRETY GEMADCCAKQ EPERNECFLQ   360
HKDDNPNLPR LVRPEVDVMC TAFHDNEETF LKKYLYEIAR RHPYFYAPEL LFFAKRYKAA   420
FTECCQAADK AACLLPKLDE LRDEGKASSA KQRLKCASLQ KFGERAFKAW AVARLSQRFP   480
KAEFAEVSKL VTDLTKVHTE CCHGDLLECA DDRADLAKYI CENQDSISSK LKECCEKPLL   540
EKSHCIAEVE NDEMPADLPS LAADFVESKD VCKNYAEAKD VFLGMFLYEY ARRHPDYSVV   600
LLLRLAKTYE TTLEKCCAAA DPHECYAKVF DEFKPLVEEP QNLIKQNCEL FEQLGEYKFQ   660
NALLVRYTKK VPQVSTPTLV EVSRNLGKVG SKCCKHPEAK RMPCAEDYLS VVLNQLCVLH   720
EKTPVSDRVT KCCTESLVNR RPCFSALEVD ETYVPKEFQA ETFTFHADIC TLSEKERQIK   780
KQTALVELVK HKPKATKEQL KAVMDDFAAF VEKCCKADDK ETCFAEEGKK LVAASQAALG   840
LAAATGGPET LCGAELVDAL QFVCGDRGFY FNKPTGYGSS SRRAPQTGIV DECCFRSCDL   900
RRLEMYCAPL KPAKSAGGSH HHHH                                          925
```

SEQ ID NO: 173            moltype = DNA  length = 2781
FEATURE                   Location/Qualifiers
misc_feature              1..2781
                          note = Synthetic construct
source                    1..2781
                          mol_type = other DNA
                          organism = synthetic construct
SEQUENCE: 173
```
ttggagagtg ggggtggctt ggttcaaccc ggtggatctt tgagattgtc atgtgccggt   60
tctggtttta cctttagttc ctatgctatg tcttgggtcc gtcaagcccc aggcaaagga   120
cttgaatggg tatcatcaat ctccgggtca ggtggtagta cgtattacgc agattctgtg   180
aaaggtaggt ttaccatttc cagagataac tccaaaaaga cattgtactt gcaaatgaat   240
agtctgagag ctgaggatac tgccgtctat tactgtgcc gaaaaagagg cagaactaca   300
gttagttggg gtcttgtcta ctttgactac tggggtcagg ggacggtcgt taccgtatct   360
tccggtggag ggggttctgg aggaggagga tctggtggtg gtggaagtgg aggttctgaa   420
ttgacccaat ctcctggtac tctgtctcta agtccaggaa acgagccac gttgtcatgt   480
agggcctcac attcagtttc aagagcttat cttgcctggt atcaacagaa acctggacag   540
gccccacgtt tgttgatata cggcaccagt tccaggggcta caggaatacc agataggttt   600
tctggatctg gctcaggaac ggatttcact ttgacaattt caagactaga gccagaggac   660
tttgccgtat actactgtca acaatatgga ggatcacctt ggttcggaca gggtactaaa   720
gttgaactta agggggccca aggaggtgga tcaggaggc ctgcaggtga tgctcacaaa   780
tctgaagtcg ctcatcgttt caaagacttg ggtgaggaaa actttaaggc tttagttctg   840
attgctttg cccaatatct tcaacaatca ccattcgaag atcatgtgaa acttgttaac   900
gaagttaccg aatttgcaaa aacgtgtgtg gcagacgaaa gtgccgaaaa ctgtgacaaa   960
tcattacaca ctttgttcgg tgacaagtta tgcactgttg caaccctacg tgagacatat   1020
ggagaaatgg cagactgttg cgccaaacaa gagcctgaac gaaacgaatg ctttctgcag   1080
cacaaagacg ataatccaaa tcttccccga ttagttcgtc ccgaagtaga cgtaatgtgc   1140
acagcctttc atgataatga gagactttc ctgaaaaagt acttgtacga aattgcaaga   1200
cgtcacccat acttctatgc tcccgagtta ctgtttttcg ccaaacgata caaggcagcc   1260
tttacagaat gttgccaagc agctgacaag gctgcatgtc ttttacctaa gttagatgag   1320
ttaagagacg aaggtaaggc ttcctcagca aaacagagac ttaagtgcgc atcccttcaa   1380
aagtttggtg agagagcttt caaggcttgg gctgtcgcca gactgtctca gagatttcct   1440
```

```
aaggctgaat  tcgcagaagt  ctctaagcta  gtaactgact  tgactaaagt  tcatactgag  1500
tgctgtcatg  gggatttgtt  ggaatgcgca  gatgatcgtg  cagacttagc  aaagtacatc  1560
tgcgagaacc  aagactctat  ttccagtaag  ttaaaggaat  gttgcgaaaa  gccactactt  1620
gagaagtccc  actgtattgc  tgaagtcgaa  aatgatgaaa  tgcctgctga  ccttccatct  1680
ttggccgctg  atttcgttga  gtccaaggat  gtgtgcaaaa  actatgctga  agcaaaagat  1740
gtgttcctag  ggatgttcct  gtatgaatat  gctcgtcgac  atcccgacta  ttccgttgtc  1800
cttttactga  gattggctaa  gacctacgag  acaaccttgg  agaagtgttg  tgctgccgca  1860
gatcctcacg  agtgttacgc  aaaagtgttt  gatgagttca  aaccattggt  tgaagagcca  1920
caaaatctaa  tcaagcagaa  ctgtgaactg  tttgaacaat  tgggcgaata  caaattccaa  1980
aatgctctgt  tagtgagata  caccaaaaag  gtcccacaag  tttccacccc  aactctagtc  2040
gaggtgtcca  gaaatctagg  aaaagttgga  tctaagtgtt  gtaagcatcc  agaagctaag  2100
aggatgcctt  gcgctgagga  ttacttgtct  gtggttttga  accagttatg  tgttctacac  2160
gagaaaactc  ctgtctccga  cagagttact  aagtgctgca  cagagtcttt  ggtcaataga  2220
aggccttgtt  tcagtgccct  ggaagtcgat  gaaacttatg  tgcctaaaga  gttccaagcc  2280
gaaacgttca  cttttcacgc  tgacatttgt  actctttctg  agaaggaacg  tcagatcaaa  2340
aagcagacag  cattggtgga  attggtaaag  cataaaccaa  aggctacaaa  agagcagctg  2400
aaggctgtta  tggatgattt  tgcagctttc  gtggaaaagt  gttgtaaagc  cgatgataaa  2460
gagacttgtt  ttgcagagga  ggggaaaaag  ctggttgctg  catcacaagc  tgccctaggt  2520
cttgcagccg  ctaccggtgg  acctgaaacc  ttatgtggag  ctgaacttgt  ggatgctcta  2580
caatttgttt  gtggcgatag  agggttctac  ttcaacaaac  ccactggata  tggtagttcc  2640
tcaagacgag  ctcctcagac  aggtattgtc  gacgagtgtt  gttttaggtc  ttgcgacttg  2700
cgtagactgg  agatgtactg  cgcaccattg  aagccagcaa  agtctgccgg  tggttcacat  2760
caccaccatc  accattagtg  a                                              2781
```

```
SEQ ID NO: 174          moltype = AA   length = 935
FEATURE                 Location/Qualifiers
REGION                  1..935
                        note = Synthetic construct
source                  1..935
                        mol_type = protein
                        organism = synthetic construct
SEQUENCE: 174
EVQLVESGGG  LVQPGGSLRL  SCSASGFTFS  SYAMHWVRQA  PGKGLEYVSA  ISSNGGSTYY   60
ADSVKGRFTI  SRDNSKNTLY  LQMSSLRAED  TAVYYCVKIT  GAYSSSWYYD  NWFDPWGQGT  120
LVTVSSGGGG  SGGGGSGGGG  SGGSSYELTQ  PPSVSVSPGQ  TASITCSGDK  LGDKYACWYQ  180
QKPGQSPVLV  IYQDSKRPSG  IPERFSGSNS  GNTATLTISG  TQAMDEADYY  CQAWDSSTAV  240
FGGGTKLTVL  GQGAQGGGSG  GSAGDAHKSE  VAHRFKDLGE  ENFKALVLIA  FAQYLQQSPF  300
EDHVKLVNEV  TEFAKTCVAD  ESAENCDKSL  HTLFGDKLCT  VATLRETYGE  MADCCAKQEP  360
ERNECFLQHK  DDNPNLPRLV  RPEVDVMCTA  FHDNEETFLK  KYLYEIARRH  PYFYAPELLF  420
FAKRYKAAFT  ECCQAADKAA  CLLPKLDELR  DEGKASSAKQ  RLKCASLQKF  GERAFKAWAV  480
ARLSQRFPKA  EFAEVSKLVT  DLTKVHTECC  HGDLLECADD  RADLAKYICE  NQDSISSKLK  540
ECCEKPLLEK  SHCIAEVEND  EMPADLPSLA  ADFVESKDVC  KNYAEAKDVF  LGMFLYEYAR  600
RHPDYSVVLL  LRLAKTYETT  LEKCCAAADP  HECYAKVFDE  FKPLVEEPQN  LIKQNCELFE  660
QLGEYKFQNA  LLVRYTKKVP  QVSTPTLVEV  SRNLGKVGSK  CCKHPEAKRM  PCAEDYLSVV  720
LNQLCVLHEK  TPVSDRVTKC  CTESLVNRRP  CFSALEVDET  YVPKEFQAET  FTFHADICTL  780
SEKERQIKKQ  TALVELVKHK  PKATKEQLKA  VMDDFAAFVE  KCCKADDKET  CFAEEGKKLV  840
AASQAALGLA  AATGSTSHLV  KCAEKEKTFC  VNGGECFMVK  DLSNPSRYLC  KCPNEFTGDR  900
CQNYVMASFY  KHLGIEFMEA  EELYQKGGSH  HHHH                                935
```

```
SEQ ID NO: 175          moltype = DNA   length = 2811
FEATURE                 Location/Qualifiers
misc_feature            1..2811
                        note = Synthetic construct
source                  1..2811
                        mol_type = other DNA
                        organism = synthetic construct
SEQUENCE: 175
gaggtgcagt  tggtcgaatc  aggaggaggt  ttagtgcagc  ccggtggatc  acttaggctg   60
agttgctccg  catctggttt  cacttttctct  tcctatgcca  tgcattgggt  acgtcaggca  120
ccggggaaag  gactagaata  cgtatcagcc  atatcttcta  atggcggatc  aacctactat  180
gctgattcag  ttaaaggtag  attcactatc  tcaagagata  actccaaaaa  cacattgtac  240
cttcaaatga  gttcactgcg  tgctgaggac  acagctgtct  attactgtgt  aaagattact  300
ggagcctact  ctagttcctg  gtactacgac  aattggtttg  atccttgggg  ccaaggaacc  360
ttagttacgg  tttccagtgg  cggtggggga  tctggcggag  gtggaggtgg  ttccagttac  420
tctggtggat  catcttatga  attgacccag  cccccttctg  tgtctgttag  ccctggacag  480
actgccagca  ttacctgttc  cggcgataag  ctaggtgaca  agtacgcttg  ctggtatcaa  540
caaaagccag  gcagtcacc   agtgcttgtc  atctaccaag  attctaagag  gccaagtgga  600
ataccagaac  gattttctgg  ctccaacagt  ggcaatacag  ctaccctgac  aatttccggt  660
acgcaagcaa  tggatgaggc  tgactactat  tgtcaggcct  gggattcgtc  aactgctgtg  720
tttggtggtg  gtactaaact  cactgtcttg  ggtcaagggg  cccaaggagg  tggatcagga  780
ggctctgcag  gtgatgctca  caaatctgaa  gtcgctcatc  gtttcaaaga  cttgggtgag  840
gaaaacttta  aggctttagt  tctgattgct  tttgcccaat  atcttcaaca  atcaccattc  900
gaagatcatg  tgaaacttgt  taacgaagtt  accgaatttg  caaaaacgtg  tgtggcagac  960
gaaagtgcga  aaaactgtga  caaatcatta  cacactttgt  tcggtgacaa  gttatgcact  1020
gttcaaccc   tacgtgagac  atatggagaa  atggcagact  gttgcgccaa  acaagagcct  1080
gaacgaaacg  aatgctttct  gcagcacaaa  gacgataatc  caaatcttcc  ccgattagtt  1140
cgtcccgaag  tagacgtaat  gtgcacagcc  tttcatgata  atgaagagac  tttcctgaaa  1200
aagtacttgt  acgaaattgc  aagacgtcac  ccatacttct  atgctcccga  gttactgttt  1260
ttcgccaaac  gatacaaggc  agcctttaca  gaatgttgcc  aagcagctga  caaggctgca  1320
```

```
tgtcttttac ctaagttaga tgagttaaga gacgaaggta aggcttcctc agcaaaacag   1380
agacttaagt gcgcatccct tcaaaagttt ggtgagagag ctttcaaggc ttgggctgtc   1440
gccagactgt ctcagagatt tcctaaggct gaattcgcag aagtctctaa gctagtaact   1500
gacttgacta aagttcatac tgagtgctgt catgggggatt tgttggaatg cgcagatgat   1560
cgtgcagact tagcaaagta catctgcgag aaccaagact ctatttccag taagttaaag   1620
gaatgttgcg aaaagccact acttgagaag tcccactgta ttgctgaagt cgaaaatgat   1680
gaaatgcctg ctgaccttcc atctttggcc gctgatttcg ttgagtccaa ggatgtgtgc   1740
aaaaactatg ctgaagcaaa agatgtgttc ctagggatgt tcctgtatga atatgctcgt   1800
cgacatcccg actattccgt tgtccttta ctgagattgg ctaagaccta cgagacaacc   1860
ttggagaagt gttgtgctgc cgcagatcct cacgagtgtt acgcaaaagt gtttgatgag   1920
ttcaaaccat tggttgaaga gccacaaaat ctaatcaagc agaactgtga actgtttgaa   1980
caattgggcg aatacaaatt ccaaaatgct ctgttagtga gatacaccaa aaaggtccca   2040
caagtttcca ccccaactct agtcgaggtg tccagaaatc taggaaaagt tggatctaag   2100
tgttgtaagc atccagaagc taagaggatg ccttgcgctg aggattactt gtctgtggtt   2160
ttgaaccagt tatgtgttct acacgagaaa actcctgtct ccgacagagt tactaagtgc   2220
tgcacagagt ctttggtcaa tagaaggcct tgtttcagtg ccctggaagt cgatgaaact   2280
tatgtgccta aagagttcca agccgaaacg ttcacttttc acgctgacat ttgtactctt   2340
tctgaagaga aacgtcagat caaaaagcag acagcattgg tggaattggt aaagcataaa   2400
ccaaaggcta caaaagagca gctgaaggct gttatggatg attttgcagc tttcgttggaa   2460
aagtgttgta aagccgatga taaagagact tgttttgcag aggaggggaa aaagctggtt   2520
gctgcatcac aagctgccct aggtcttgca gccgctaccg ttctacttc acatcttgtg    2580
aaatgcgccg aaaaagagaa aacattttgt gtgaatggtg gaggtgctt tatggttaaa    2640
gatttgtcta accctagtag ataccotgtgc aaatgtccca atgaattcac aggtgacaga   2700
tgtcagaact atgttatggc tagtttctac aaacatctgg gcattgagtt catggaagcc   2760
gaggaattgt atcaaaaagg tggatcccac catcaccacc atcattagtg a             2811
```

```
SEQ ID NO: 176          moltype = AA  length = 811
FEATURE                 Location/Qualifiers
REGION                  1..811
                        note = Synthetic construct
source                  1..811
                        mol_type = protein
                        organism = synthetic construct
SEQUENCE: 176
EKLGKLQYSL DYDFQNNQLL VGIIQAAELP ALDMGGTSDP YVKVFLLPDK KKKFETKVHR   60
KTLNPVFNEQ FTFKVPYSEL GGKTLVMAVY DFDRFSKHDI IGEFKVPMNT VDFGHVTEEW   120
RDLQSAEKGA QGGGSGGSAG DAHKSEVAHR FKDLGEENFK ALVLIAFAQY LQQSPFEDHV   180
KLVNEVTEFA KTCVADESAE NCDKSLHTLF GDKLCTVATL RETYGEMADC CAKQEPERNE   240
CFLQHKDDNP NLPRLVRPEV DVMCTAFHDN EETFLKKYLY EIARRHPYFY APELLFFAKR   300
YKAAFTECCQ AADKAACLLP KLDELRDEGK ASSAKQRLKC ASLQKFGERA FKAWAVARLS   360
QRFPKAEFAE VSKLVTDLTK VHTECCHGDL LECADDRADL AKYICENQDS ISSKLKECCE   420
KPLLEKSHCI AEVENDEMPA DLPSLAADFV ESKDVCKNYA EAKDVFLGMF LYEYARRHPD   480
YSVVLLLRLA KTYETTLEKC CAAADPHECY AKVFDEFKPL VEEPQNLIKQ NCELFEQLGE   540
YKFQNALLVR YTKKVPQVST PTLVEVSRNL GKVGSKCCKH PEAKRMPCAE DYLSVVLNQL   600
CVLHEKTPVS DRVTKCCTES LVNRRPCFSA LEVDETYVPK EFQAETFTFH ADICTLSEKE   660
RQIKKQTALV ELVKHKPKAT KEQLKAVMDD FAAFVEKCCK ADDKETCFAE EGKKLVAASQ   720
AALGLAAATG STSHLVKAE KEKTFCVNGG ECFMVKDLSN PSRYLCKCPN EFTGDRCQNY    780
VMASFYKHLG IEFMEAEELY QKGGSHHHHH H                                   811
```

```
SEQ ID NO: 177          moltype = DNA  length = 2439
FEATURE                 Location/Qualifiers
misc_feature            1..2439
                        note = Synthetic construct
source                  1..2439
                        mol_type = other DNA
                        organism = synthetic construct
SEQUENCE: 177
gaaaagctgg gaaagctgca atacagtttg gactacgatt tccaaaacaa tcagttgctc   60
gtcggcatta tccaggctgc cgaattgcca gctttagata tgggtggtac atcagatccc   120
tacgtcaaag tatttctact gcctgacaaa aagaaaaagt ttgaaactaa ggtgcacaga   180
aaaacgctta acccagtttt caacgagcag tttacattca aagttcctta ttctgaactt   240
ggaggaaaaa ctctagtgat ggccgtttat gatttcgata ggtttctaa gcatgacatc     300
ataggggagt ttaaggtccc aatgaatact gttgatttcg gtcatgtgac cgaggaatgg    360
cgtgaccttc aatccgcaga gaaaggggcc caaggaggtg gatcaggagg ctctgcaggt    420
gatgctcaca aatctgaagt cgctcatcgt ttcaaagact ggggtgagga aaactttaag   480
gctttagttc tgattgcttt tgcccaatat cttcaacaat caccattcga agatcatgtg    540
aaacttgtta cgaagttac cgaatttgca aaaacgtgtg tggcagacga agtgccgaa     600
aactgtgaca atcattaca cactttgttc ggtgacaagt tatgcactgt tgcaaccgta    660
cgtgagacat atggagaaat ggcagactgt tgcgccaaac aagagcctga acgaaacgaa    720
tgctttctgc agcacaaaga cgataatcca aatcttcccc gattagttcg tcccgaagta    780
gacgtaatgt gcacagcctt tcatgataat aagagagctt tcctgaaaaa gtacttgtac    840
gaaattgcaa gacgtcaccc atacttctat gctcccgagt actgttttt cgccaaacga     900
tacaaggcag ccttttacaga atgttgccaa gcagctgaca aggctgcatg tctttttacct   960
aagttagatg agttaagaga cgaaggtaag gcttcctcag caaaacagag acttaagtgc   1020
gcatcccttc aaaagtttgg tgagagagct tcaaggctt gggctgtcgc cagactgtct    1080
cagagatttc ctaaggctga attcgcagaa gtctctaagc tagtaactga cttgactaaa   1140
gttcatactg agtgctgtca tggggatttg ttggaatgcg cagatgatcg tgcagactta   1200
gcaaagtaca tctgcgagaa ccaagactct atttccagta gttaaagga atgttgcgaa     1260
aagccactac ttgagaagtc ccactgtatt gctgaagtcg aaaatgatga aatgcctgct   1320
```

```
gaccttccat ctttggccgc tgatttcgtt gagtccaagg atgtgtgcaa aaactatgct 1380
gaagcaaaag atgtgttcct agggatgttc ctgtatgaat atgctcgtcg acatcccgac 1440
tattccgttg tccttttact gagattggct aagacctacg agacaacctt ggagaagtgt 1500
tgtgctgccg cagatcctca cgagtgttac gcaaaagtgt ttgatgagtt caaaccattg 1560
gttgaagagc cacaaaatct aatcaagcag aactgtgaac tgtttgaaca attgggcgaa 1620
tacaaattcc aaaatgctct gttagtgaga tacaccaaaa aggtcccaca agtttccacc 1680
ccaactctag tcgaggtgtc cagaaatcta ggaaaagttg gatctaagtg ttgtaagcat 1740
ccagaagcta agaggatgcc ttgcgctgag gattacttgt ctgtggtttt gaaccagtta 1800
tgtgttctac acgagaaaac tcctgtctcc gacagagtta ctaagtgctg cacagagtct 1860
ttggtcaata gaaggccttg tttcagtgcc ctggaagtcg atgaaactta tgtgcctaaa 1920
gagttccaag ccgaaacgtt cactttttcac gctgacattt gtactctttc tgagaaggaa 1980
cgtcagatca aaaagcagac agcattggtg gaattggtaa agcataaacc aaaggctaca 2040
aaagagcagc tgaaggctgt tatggatgat tttgcagctt tcgtggaaaa gtgttgtaaa 2100
gccgatgata aagagacttg ttttgcagag gaggggaaaa agctggttgc tgcatcacaa 2160
gctgccctag tcttgcagc cgctaccggt tctacttcac atcttgtgaa atgcgccgaa 2220
aaagagaaaa cattttgtgt gaatggtgga gagtgcttta tggttaaaga tttgtctaac 2280
cctagtagat aacctgtgcaa atgtcccaat gaattcacag gtgacagatg tcagaactat 2340
gttatggcta gtttctacaa acatctgggc attgagttca tggaagccga ggaattgtat 2400
caaaaaggtg gatcccacca tcaccaccat cattagtga 2439
```

```
SEQ ID NO: 178           moltype = AA   length = 1009
FEATURE                  Location/Qualifiers
REGION                   1..1009
                         note = Synthetic construct
source                   1..1009
                         mol_type = protein
                         organism = synthetic construct
SEQUENCE: 178
EVQLVESGGG LVQPGGSLRL SCSASGFTFS SYAMHWVRQA PGKGLEYVSA ISSNGGSTYY 60
ADSVKGRFTI SRDNSKNTLY LQMSSLRAED TAVYYCVKIT GAYSSSWYYD NWFDPWGQGT 120
LVTVSSGGGG SGGGGSGGGG SGGSSYELTQ PPSVSVSPGQ TASITCSGDK LGDKYACWYQ 180
QKPGQSPVLV IYQDSKRPSG IPERFSGSNS GNTATLTISG TQAMDEADYY CQAWDSSTAV 240
FGGGTKLTVL GQGAQGGGSG GSAGDAHKSE VAHRFKDLGE ENFKALVLIA FAQYLQQSPF 300
EDHVKLVNEV TEFAKTCVAD ESAENCDKSL HTLFGDKLCT VATLRETYGE MADCCAKQEP 360
ERNECFLQHK DDNPNLPRLV RPEVDVMCTA FHDNEETFLK KYLYEIARRH PYFYAPELLF 420
FAKRYKAAFT ECCQAADKAA CLLPKLDELR DEGKASSAKQ RLKCASLQKF GERAFKAWAV 480
ARLSQRFPKA EFAEVSKLVT DLTKVHTECC HGDLLECADD RADLAKYICE NQDSISSKLK 540
ECCEKPLLEK SHCIAEVEND EMPADLPSLA ADFVESKDVC KNYAEAKDVF LGMFLYEYAR 600
RHPDYSVVLL LRLAKTYETT LEKCCAAADP HECYAKVFDE FKPLVEEPQN LIKQNCELFE 660
QLGEYKFQNA LLVRYTKKVP QVSTPTLVEV SRNLGKVGSK CCKHPEAKRM PCAEDYLSVV 720
LNQLCVLHEK TPVSDRVTKC CTESLVNRRP CFSALEVDET YVPKEFQAET FTFHADICTL 780
SEKERQIKKQ TALVELVKHK PKATKEQLKA VMDDFAAFVE KCCKADDKET CFAEEGKKLV 840
AASQAALGLA AATGPALPED GGSGAFPPGH FKDPKRLYCK NGGFFLRIHP DGRVDGVREK 900
SDPHIKLQLQ AEERGVVSIK GVCANRYLAM KEDGRLLASK CVTDECFFFE RLESNNYNTY 960
RSRKYTSWYV ALKRTGQYKL GSKTGPGQKA ILFLPMSAKS GGSHHHHHH 1009
```

```
SEQ ID NO: 179           moltype = DNA   length = 3033
FEATURE                  Location/Qualifiers
misc_feature             1..3033
                         note = Synthetic construct
source                   1..3033
                         mol_type = other DNA
                         organism = synthetic construct
SEQUENCE: 179
gaggtgcagt tggtcgaatc aggaggaggt ttagtgcagc ccggtggatc acttaggctg 60
agttgctccg catctggttt cactttctct tcctatgcca tgcattgggt acgtcaggca 120
ccggggaaag gactagaata cgtatcagcc atatcttcta atggcggatc aacctactat 180
gctgattcag ttaaaggtag attcactatc tcaagagata actccaaaaa cacattgtac 240
cttcaaatga gttcactgcg tgctgaggac acagctgtct attactgtgt aaagattact 300
ggagcctact ctagttcctg gtactacgac aattggtttg atccttgggg ccaaggaacc 360
ttagttacgg tttccagtgg cggtggggga tctggcggag gtgggagtgg tggaggggggg 420
tctggtggat catcttatga attgacccag ccccccttctg tgtctgttag ccctggacag 480
actgccagca ttacctgttc cggcgataag ctaggtgaca agtacgcttg ctggtatcaa 540
caaaagccag ggcagtcacc agtgcttgtc atctaccaag attctaagga gccaagtgga 600
ataccagaac gattttctgg ctccaacagt ggcaatacag ctaccctgac aatttccggt 660
acgcaagcaa tggatgaggc tgactactat tgtcaggcct gggattcgtc aactgctgtg 720
tttggtggtg gtactaaact cactgtcttg ggtcaagggg cccaaggagg tggatcagga 780
ggctctcag gtgatgctca caaatctgaa gtcgctcatc gtttcaaaga cttgggtgag 840
gaaaactta aggcttttagt tctgattgct tttgcccaat atcttcaaca atcaccattc 900
gaagatcatg tgaaacttgt taacgaagtt accgaatttg caaaaacgtg tgtggcagac 960
gaaagtgccg aaaactgtga caaatcatta cacactttgt tcggtgacaa gttatgcact 1020
gttgcaaccc tacgtgagac atatggagaa atggcagact gttgcgccaa acaagagcct 1080
gaacgaaacg aatgctttct gcagcacaaa gacgataatc caaatcttcc ccgattagtt 1140
cgtcccgaag tagacgtaat gtgcacagcc tttcatgata atgaagaaac tttcctgaaa 1200
aagtacttgt acgaaattgc aagacgtcac ccatacttct atgctcccga gttactgttt 1260
ttcgccaaac gatacaaggc agcctttaca gaatgttgcc aagcagctga caaggctgca 1320
tgtctttac ctaagttaga tgagttaaga gacgaaggta aggcttcctc agcaaaacag 1380
agacttaagt gcgcatccct tcaaaagttt ggtgagagag ctttcaaggc ttgggctgtc 1440
gccagactgt ctcagagatt tcctaaggct gaattcgcag aagtctctaa gctagtaact 1500
```

```
gacttgacta aagttcatac tgagtgctgt catggggatt tgttggaatg cgcagatgat 1560
cgtgcagact tagcaaagta catctgcgag aaccaagact ctatttccag taagttaaag 1620
gaatgttgcg aaaagccact acttgagaag tcccactgta ttgctgaagt cgaaaatgat 1680
gaaatgcctg ctgaccttcc atctttggcc gctgatttcg ttgagtccaa ggatgtgtgc 1740
aaaaactatg ctgaagcaaa agatgtgttc ctagggatgt tcctgtatga atatgctcgt 1800
cgacatcccg actattccgt tgtcctttta ctgagattgg ctaagaccta cgagacaacc 1860
ttggagaagt gttgtgctgc cgcagatcct cacgagtgtt acgcaaaagt gtttgatgag 1920
ttcaaaccat tggttgaaga gccacaaaat ctaatcaagc agaactgtga actgtttgaa 1980
caattgggcg aatacaaatt ccaaaatgct ctgttagtga gatacaccaa aaaggtccca 2040
caagtttcca ccccaactct agtcgaggtg tccagaaatc taggaaaagt tggatctaag 2100
tgttgtaagc atccagaagc taagaggatg ccttgcgctg aggattactt gtctgtggtt 2160
ttgaaccagt tatgtgttct acacgagaaa actcctgtct ccgacagagt tactaagtgc 2220
tgcacagagt ctttggtcaa tagaaggcct tgtttcagtg ccctggaagt cgatgaaact 2280
tatgtgccta aagagttcca agccgaaacg ttcacttttc acgctgacat ttgtactctt 2340
tctgagaagg aacgtcagat caaaaagcag acagcattgg tggaattggt aaagcataaa 2400
ccaaaggcta caaaagagca gctgaaggct gttatggatg attttgcagc tttcgtggaa 2460
aagtgttgta aagccgatga taaagagact tgttttgcag aggaggggaa aaagctggtt 2520
gctgcatcac aagctgccct aggtcttgca gccgctaccg gtcccgcctt gccagaggat 2580
ggcggttctg gagcttttcc tccaggtcac ttcaaagatc caaaaagatt gtattgcaaa 2640
aacggtgggt ttttccttcg aatacatcct gacggtagag ttgacggggt aagagaaaag 2700
agtgacccac atatcaagct acagttacaa gccgaggaaa gaggagttgt ctcaatcaag 2760
ggcgtttgtg ctaacagata cttggctatg aaggaagatg gtagactgct tgctagtaag 2820
tgtgtcactg atgaatgttt cttttttcgaa agattggagt ccaataacta taacacgtac 2880
aggtcacgta agtatacgag ttggtacgtg gctctgaaac gtacaggcca gtataagtta 2940
ggttcaaaaa ctggacccgg acagaaagct atcttattcc tacccatgtc tgcaaagtct 3000
ggcggtagtc accatcacca tcatcattag tga 3033
```

```
SEQ ID NO: 180            moltype = AA   length = 885
FEATURE                   Location/Qualifiers
REGION                    1..885
                          note = Synthetic construct
source                    1..885
                          mol_type = protein
                          organism = synthetic construct
SEQUENCE: 180
EKLGKLQYSL DYDFQNNQLL VGIIQAAELP ALDMGGTSDP YVKVFLLPDK KKKFETKVHR   60
KTLNPVFNEQ FTFKVPYSEL GGKTLVMAVY DFDRFSKHDI IGEFKVPMNT VDFGHVTEEW  120
RDLQSAEKGA QGGGSGGSAG DAHKSEVAHR FKDLGEENFK ALVLIAFAQY LQQSPFEDHV  180
KLVNEVTEFA KTCVADESAE NCDKSLHTLF GDKLCTVATL RETYGEMADC CAKQEPERNE  240
CFLQHKDDNP NLPRLVRPEV DVMCTAFHDN EETFLKKYLY EIARRHPYFY APELLFFAKR  300
YKAAFTECCQ AADKAACLLP KLDELRDEGK ASSAKQRLKC ASLQKFGERA FKAWAVARLS  360
QRFPKAEFAE VSKLVTDLTK VHTECCHGDL LECADDRADL AKYICENQDS ISSKLKECCE  420
KPLLEKSHCI AEVENDEMPA DLPSLAADFV ESKDVCKNYA EAKDVFLGMF LYEYARRHPD  480
YSVVLLLRLA KTYETTLEKC CAAADPHECY AKVFDEFKPL VEEPQNLIKQ NCELFEQLGE  540
YKFQNALLVR YTKKVPQVST PTLVEVSRNL GKVGSKCCKH PEAKRMPCAE DYLSVVLNQL  600
CVLHEKTPVS DRVTKCCTES LVNRRPCFSA LEVDETYVPK EFQAETFTFH ADICTLSEKE  660
RQIKKQTALV ELVKHKPKAT KEQLKAVMDD FAAFVEKCCK ADDKETCFAE EGKKLVAASQ  720
AALGLAAATG PALPEDGGSG AFPPGHFKDP KRLYCKNGGF FLRIHPDGRV DGVREKSDPH  780
IKLQLQAEER GVVSIKGVCA NRYLAMKEDG RLLASKCVTD ECFFFERLES NNYNTYRSRK  840
YTSWYVALKR TGQYKLGSKT GPGQKAILFL PMSAKSGGSH HHHH          885
```

```
SEQ ID NO: 181            moltype = DNA   length = 2661
FEATURE                   Location/Qualifiers
misc_feature              1..2661
                          note = Synthetic construct
source                    1..2661
                          mol_type = other DNA
                          organism = synthetic construct
SEQUENCE: 181
gaaaagctgg aaagctgca atacagtttg gactacgatt tccaaaacaa tcagttgctc   60
gtcggcatta tccaggctgc cgaattgcca gctttagata tgggtggtac atcagatccc  120
tacgtcaaag tatttctact gcctgacaaa aagaaaagt ttgaaactaa ggtgcacaga  180
aaaacgctta acccagtttt caacgagcag tttacattca aagttcctta ttctgaactt  240
ggaggaaaaa ctctagtgat ggccgtttat gatttcgata ggttttctaa tgcatgacatc  300
ataggggagt ttaaggtccc aatgaatact gttgatttcg gtcatgtgac cgaggaatgg  360
cgtgaccttc aatccgcaga gaaaggggcc caaggaggtg gatcaggagg ctctgcaggt  420
gatgctcaca atctgaagt cgctcatcgt ttcaaagact gggtgaggca aaactttaag  480
gctttagttc tgattgcttt tgcccaatat cttcaacaat caccattcga agatcatgtg  540
aaacttgtta acgaagttac gaatttgca aaaacgtgtg tggcagacga aagtgccgaa  600
aactgtgaca atcattaca cactttgttc ggtgacaagt tatgcactgt tgcaaccta  660
cgtgagacat atggagaaat ggcagactgt tgcgccaaac aagagcctga acgaaacgaa  720
tgctttctgc agcacaaaga cgataatcca aatcttcccc gattagttcg tcccgaagta  780
gacgtaatgt gcacagcctt tcatgataat gaagagactt tcctgaaaaa gtacttgtac  840
gaaattgcaa gacgtcaccc atacttctat gctcccgagt tactgttttt cgccaaacga  900
tacaaggcag cctttacaga atgttgccaa gcagctgaca aggctgcatg tcttttacct  960
aagttagatg agttaagaga cgaaggtaag gcttcctcag caaaacagag acttaagtgc 1020
gcatcccttc aaaagtttgg tgagagagct ttcaaggctt gggctgtcgc cagactgtct 1080
cagagatttc ctaaggctga attcgcagaa gtctctaagc tagtaactga cttgactaaa 1140
gttcatactg agtgctgtca tggggatttg ttggaatgcg cagatgatcg tgcagactta 1200
```

```
gcaaagtaca tctgcgagaa ccaagactct atttccagta agttaaagga atgttgcgaa   1260
aagccactac ttgagaagtc ccactgtatt gctgaagtcg aaaatgatga aatgcctgct   1320
gaccttccat cttttggccgc tgatttcgtt gagtccaagg atgtgtgcaa aaactatgct   1380
gaagcaaaag atgtgttcct agggatgttc ctgtatgaat atgctcgtcg acatcccgac   1440
tattccgttg tcctttttact gagattggct aagacctacg agacaacctt ggagaagtgt   1500
tgtgctgccg cagatcctca cgagtgttac gcaaaagtgt ttgatgagtt caaaccattg   1560
gttgaagagc cacaaaatct aatcaagcag aactgtgaac tgtttgaaca attgggcgaa   1620
tacaaattcc aaaatgctct gttagtgaga tacaccaaaa aggtcccaca agtttccacc   1680
ccaactctag tcgaggtgtc cagaaatcta ggaaaagttg gatctaagtg ttgtaagcat   1740
ccagaagcta agaggatgcc ttgcgctgag gattacttgt ctgtggtttt gaaccagtta   1800
tgtgttctac acgagaaaac tcctgtctcc gacagagtta ctaagtgctg cacagagtct   1860
ttggtcaata gaaggccttg tttcagtgcc ctggaagtcg atgaaactta tgtgcctaaa   1920
gagttccaag ccgaaacgtt cacttttcac gctgacattt gtactctttc tgagaaggaa   1980
cgtcagatca aaaagcagac agcattggtg gaattggtaa agcataaacc aaaggctaca   2040
aaagagcagc tgaaggctgt tatggatgat tttgcagctt tcgtggaaaa gtgttgtaaa   2100
gccgatgata aagagacttg ttttgcagag gaggggaaaa agctggttgc tgcatcacaa   2160
gctgccctag tcttgcagc cgctaccggt cccgccttgc cagaggatgg cggttctgga   2220
gcttttcctc caggtcactt caaagatcca aaaagttgt attgcaaaaa cggtgggttt   2280
ttccttcgaa tacatcctga cggtagagtt gacggggtaa gagaaaagag tgacccacat   2340
atcaagctac agttacaagc cgaggaaaga ggagttgtct caatcaaggg cgtttgtgct   2400
aacagatact tggctatgaa ggaagatggt agactgcttg ctagtaagtg tgtcactgat   2460
gaatgtttct ttttcgaaag attggagtcc aataactata acaggccagt ataagttagg   2520
tatacgagtt ggtacgtggc tctgaaacgt acaggccagt ataagttagg ttcaaaaact   2580
ggacccggac agaaagctat cttattccta cccatgtctg caaagtctgg cggtagtcac   2640
catcaccatc atcattagtg a                                            2661
```

SEQ ID NO: 182          moltype = AA  length = 18
FEATURE                Location/Qualifiers
REGION                 1..18
                         note = Synthetic construct
PEPTIDE               1..18
source                 1..18
                         mol_type = protein
                         organism = synthetic construct
SEQUENCE: 182
GGGGSGGGGS GGGGSGGS                               18

SEQ ID NO: 183          moltype = AA  length = 5
FEATURE                Location/Qualifiers
REGION                 1..5
                         note = Synthetic construct
PEPTIDE               1..5
source                 1..5
                         mol_type = protein
                         organism = synthetic construct
SEQUENCE: 183
GGGGS                                        5

SEQ ID NO: 184          moltype = AA  length = 23
FEATURE                Location/Qualifiers
REGION                 1..23
                         note = Synthetic construct
PEPTIDE               1..23
source                 1..23
                         mol_type = protein
                         organism = synthetic construct
SEQUENCE: 184
GGGGSGGGGS GGGGSGGGGS GGS                         23

SEQ ID NO: 185          moltype = AA  length = 810
FEATURE                Location/Qualifiers
REGION                 1..810
                         note = Synthetic construct
source                 1..810
                         mol_type = protein
                         organism = synthetic construct
SEQUENCE: 185

```
GPETLCGAEL VDALQFVCGD RGFYFNKPTG YGSSSRRAPQ TGIVDECCFR SCDLRRLEMY   60
CAPLKPAKSA GAASDAHKSE VAHRFKDLGE ENFKALVLIA FAQYLQQSPF EDHVKLVNEV  120
TEFAKTCVAD ESAENCDKSL HTLFGDKLCT VATLRETYGE MADCCAKQEP ERNECFLQHK  180
DDNPNLPRLV RPEVDVMCTA FHDNEETFLK KYLYEIARRH PYFYAPELLF FAKRYKAAFT  240
ECCQAADKAA CLLPKLDELR DEGKASSAKQ RLKCASLQKF GERAFKAWAV ARLSQRFPKA  300
EFAEVSKLVT DLTKVHTECC HGDLLECADD RADLAKYICE NQDSISSKLK ECCEKPLLEK  360
SHCIAEVEND EMPADLPSLA ADFVESKDVC KNYAEAKDVF LGMFLYEYAR RHPDYSVVLL  420
LRLAKTYETT LEKCCAAADP HECYAKVFDE FKPLVEEPQN LIKQNCELFE QLGEYKFQNA  480
LLVRYTKKVP QVSTPTLVEV SRNLGKVGSK CCKHPEAKRM PCAEDYLSVV LNQLCVLHEK  540
TPVSDRVTKC CTESLVNRRP CFSALEVDET YVPKEFQAET FTFHADICTL SEKERQIKKQ  600
TALVELVKHK PKATKEQLKA VMDDFAAFVE KCCKADDKET CFAEEGKKLV AASQAALGLG  660
STGGGSGGGG GEKLGKLQYS LDYDFQNNQL LVGIIQAAEL PALDMGGTSD PYVKVFLLPD  720
```

```
KKKKFETKVH RKTLNPVFNE QFTFKVPYSE LGGKTLVMAV YDFDRFSKHD IIGEFKVPMN  780
TVDFGHVTEE WRDLQSAEKG GSGGHHHHHH                                    810

SEQ ID NO: 186              moltype = DNA   length = 2823
FEATURE                     Location/Qualifiers
misc_feature                1..2823
                            note = Synthetic construct
source                      1..2823
                            mol_type = other DNA
                            organism = synthetic construct
SEQUENCE: 186
ggaccagaga cattgtgtgg agcagaactg gtggacgctt tacagtttgt gtgtggtgac   60
cgtggtttct acttcaacaa acctacgggt tacgggtcta gttctcgtag agctccacag  120
actgggattg tagatgaatg ctgcttcaga tcttgtgacc ttcgacgttt agaaatgtac  180
tgtgcacctc taaaaccagc caaatctgct ggagctgcaa gtgacgctca taagtctgaa  240
gttgctcaca gattcaaaga cctaggtgaa gagaacttta aggctcttgt acttatagca  300
tttgctcagt atctgcaaca gagtcccttc gaagatcatg tcaagctggt gaatgaggta  360
accgaattcg ccaagacttg tgtggctgat gaatccgccg aaaactgtga caaatcttta  420
cacacattgt tcggagataa actatgcaca gtagcaactt tacgtgaaac ttatggtgag  480
atggcagatt gttgtgctaa acaggagcct gagagaaatg aatgcttttt gcaacacaag  540
gacgacaatc ctaaccttcc cagattggtt agacccgagg ttgacgttat gtgtaccgcc  600
ttccacgaca atgaggaaac atttctgaaa aagtacttgt acgaaattgc acgacgtcac  660
ccatacttct atgcacctga gcttttgttt ttcgccaaaa gatacaaggc agctttcact  720
gagtgctgtc aagcagccga taaggctgct tgtctattac ctaaacttga tgagcttaga  780
gatgagggta aagcatcctc cgctaaacag aggttgaaat gtgccagttt gcagaagttt  840
ggtgaacgtg ctttcaaggc atgggctgtt gctagattat ctcaaagatt tcctaaggcc  900
gaatttgctg aggtgtcaaa gttggtgacg gatttgacta aggtccacac tgagtgttgc  960
catggtgatc ttttggaatg tgctgacgat agagccgacc tggccaagta tatctgtgaa 1020
aaccaagatt ctatcagtag taagctgaag gaatgttgcg aaaaacctct actagagaaa 1080
tctcattgca tcgcagaagt tgaaaacgat gaaatgccag ccgacttgcc cagtctggct 1140
gctgatttcg tcgagtcaaa agatgtttgc aaaaactatg ccgaagcaaa ggatgtcttt 1200
ttgggcatgt ttctgtacga atatgctcgt cgtcatcctg actattccgt tgtcctgttg 1260
ctaagactag ctaaaacgta tgaaacgacc ttggaaaagt gttgcgctgc agctgatccc 1320
cacgagtgtt atgcaaaagt tttcgatgag tttaagccac ttgtagaaga gccacagaac 1380
ttgatcaaac agaattgtga gcttttcgag caattaggtg agtataagtt tcaaaacgct 1440
ttgctggtta gatataccaa aaaggtccca caagtgtcaa cccctaccct ggtagaagtg 1500
agtagaaatc taggaaaagt cggatctaag tgctgcaagc atccagaagc taagagaatg 1560
ccttgcgctg aggattactt gtcagtagtt ttgaatcagt tgtgcgtcct acatgaaaag 1620
acacccgttt ctgatagagt cactaagtgt tgtactgagt ctctagtaaa cagaaggcct 1680
tgtttctctg cattagaagt agatgaaacc tatgtcccaa aggagttcca agctgaaacc 1740
tttacatttc acgccgacat ttgtacgcta tctgagaagg agcgtcagat caaaaagcaa 1800
acagcccttg ttgagcttgt gaagcacaag ccaaaagcta caaaggagca attgaaagcc 1860
gtcatggacg atttcgccgc atttgttgag aagtgttgca aggcagatga taaggaaact 1920
tgttttgctg aagagggcaa aaagcttgtt gccgcctctc aagctgcttt gggactaggg 1980
tcgactgggg gagggagcgg tggaggaacc ggtcaagtcc agctggtcca gtcagggggca 2040
gaagtcaaaa agcctggtga atctctgaaa atctcatgta aaggctctgg atatagtttt 2100
acctcatatt ggatagcttg ggttcgtcaa atgcctggta aaggtttgga gtacatgggt 2160
ctaatctacc caggcgattc ggatacaaag tactctccct cttttcaagg tcaagtcact 2220
atatccgtag ataagtccgt atccaccgca tacctacaat ggtcatcttt gaagccttct 2280
gattctgccg tctacttctg cgctagggct gatgttggtt attgtaccga taggacatgt 2340
gctaaggctc ccgcttggct gggggtgtgg ggtcaaggca ccttggttac agtgtcctct 2400
ggcggaggtg gttcgtcagg aggcggttct ggtggtggcg ctcccaatc agtattgacc 2460
cagcccctt ctgtctccgc tgctccaggg caaaaggtca ccatcagttg ctctggtagt 2520
tcctctaaca ttggtaacaa ttacgtcagc tggtatcagc agttaccagg tactgcacca 2580
aagctgttga tctacgacca caccaacaga cccgctggtg tcccagatag gttttctgga 2640
tcaaaatctg gcacttcagc tagtcttgct atctctggat ttcgttccga ggatgaagcc 2700
gattactact cgcgcttcatg ggattacact ctatccaggc gggtgtttgg cggaggcact 2760
aaactgacag tgcttggagg cgcaggcgga tcaggtggtc accaccatca tcaccattag 2820
tga                                                               2823

SEQ ID NO: 187              moltype = DNA   length = 438
FEATURE                     Location/Qualifiers
misc_feature                1..438
                            note = Synthetic construct
source                      1..438
                            mol_type = other DNA
                            organism = synthetic construct
SEQUENCE: 187
cccgcgttgc ccgaggacgg aggttcaggg gcctttccgc cgggtcactt taaggacccg   60
aaaaggctgt attgcaagaa tggagggttc ttccttcgta tccacccaga cggccgagtc  120
gatggagtga gggagaagag cgatccccat atcaaattgc agcttcaagc agaagaaagg  180
ggtgtagtgt cgatcaaagg agtttgtgcg aatcgttatc tcgccatgaa agaggacggg  240
cggttgttgg cgtcgaaatg tgtgactgat gaatgcttct tctttgaaag acttgagagc  300
aataactata acacataccg atctcgcaag tacacgtcct ggtacgtcgc cctcaaacgc  360
acggggcagt acaaactggg gagtaaaacc ggccccggac aaaaggctat tctctttctg  420
cctatgtcgg caaagtca                                                438

SEQ ID NO: 188              moltype = DNA   length = 438
FEATURE                     Location/Qualifiers
```

-continued

```
misc_feature            1..438
                        note = Synthetic construct
source                  1..438
                        mol_type = other DNA
                        organism = synthetic construct
SEQUENCE: 188
cccgccttgc cagaggatgg cggttctgga gcttttcctc caggtcactt caaagatcca   60
aaaagattgt attgcaaaaa cggtgggttt ttccttcgaa tacatcctga cggtagagtt  120
gacggggtaa gagaaaagag tgacccacat atcaagctac agttacaagc cgaggaaaga  180
ggagttgtct caatcaaggg cgtttgtgct aacagatact tggctatgaa ggaagatgct  240
agactgcttg ctagtaagtg tgtcactgat gaatgtttct ttttcgaaag attggagtcc  300
aataactata acacgtacag gtcacgtaag tatacgagtt ggtacgtggc tctgaaacgt  360
acaggccagt ataagttagg ttcaaaaact ggacccggac agaaagctat cttattccta  420
cccatgtctg caaagtct                                                 438

SEQ ID NO: 189          moltype = DNA   length = 438
FEATURE                 Location/Qualifiers
misc_feature            1..438
                        note = Synthetic construct
source                  1..438
                        mol_type = other DNA
                        organism = synthetic construct
SEQUENCE: 189
ccagcactgc cagaggatgg cggatctggt gctttcccac ctggacactt caaggatcct   60
aaaaggttat actgcaaaaa cggtgggttt ttccttagaa ttcaccctga tggcagagtc  120
gacggtgttc gtgaaaagag tgacccacat atcaagttac agttacaagc caagagcgta  180
ggagtagttt ccatcaaagg cgtctgtgct aacagatatc tagctatgaa ggaggatgga  240
agattgttgg cctctaagtg tgttaccgac gaatgctttt tctttgaaag gttggagtcc  300
aacaattaca atacttatcg ttcacgaaag tatacgtctt ggtacgtggc tttgaagaga  360
acaggacagt acaaattggg ttccaaaact ggtcctggtc aaaaagctat acttttttcta  420
cccatgtctg caaaatca                                                 438

SEQ ID NO: 190          moltype = DNA   length = 438
FEATURE                 Location/Qualifiers
misc_feature            1..438
                        note = Synthetic construct
source                  1..438
                        mol_type = other DNA
                        organism = synthetic construct
SEQUENCE: 190
ccagctttgc ctgaggatgg aggctctggt gctttcctc ctggtcattt caaagaccca   60
aaaagactgt attgcaaaaa cggtgggttt ttcctgagga ttcatccaga tgggagggtc  120
gatggagtta gagagaaatc agaccccac attaagcttc aactacaggc tgaggaacgt  180
ggtgttgtct ccatcaaggg tgtttgtgca aatcgatact tagctatgaa agaggacggc  240
agattacttg ccagtaagtg tgtaactgat gaatgtttct ttttcgaaag actagaatcc  300
aataactaca atacttaccg ttctcgtaag tatacatcat ggtacgtggc cttgaagaga  360
acgggacaat acaaattggg ttctaagacc ggaccaggac agaaagcaat cttgtttttg  420
cccatgtcag ctaagagt                                                 438

SEQ ID NO: 191          moltype = DNA   length = 525
FEATURE                 Location/Qualifiers
misc_feature            1..525
                        note = Synthetic construct
source                  1..525
                        mol_type = other DNA
                        organism = synthetic construct
SEQUENCE: 191
caacgtaaga ggagaaacac tatccatgag ttcaaaaaga gtgccaagac aacccttata   60
aagatagatc cagcgttgaa gatcaaaact aagaaagtaa ataccgctga ccaatgcgct  120
aataggtgta cgaggaataa aggtctacca tttacttgta aagcatttgt ttttgataaa  180
gcacgtaaac aatgcttgtg gtttccattt aattctatgt caagcggtgt gaaaaaggaa  240
tttgggcacg agttcgatct gtacgaaaac aaggattaca ttagaaactg cattataggt  300
aagggtagat cctataaagg tacagtttca attactaaat ctggcattaa atgccagccc  360
tggagttcca tgattccgca tgaacattcg ttcttacctt ctagctatcg tggaaaagat  420
ttacaggaaa actactgtag aaatccaaga ggagaagaag gaggccttg gtgtttcaca  480
tctaatcccg aagttagata tgaggtctgt gacatccctc aatgt                  525

SEQ ID NO: 192          moltype = DNA   length = 525
FEATURE                 Location/Qualifiers
misc_feature            1..525
                        note = Synthetic construct
source                  1..525
                        mol_type = other DNA
                        organism = synthetic construct
SEQUENCE: 192
cagcggaaaa ggagaaacac cattcacgag tttaagaagt ccgcgaagac cacactgatt   60
aagattgatc ccgcccttaa aatcaagaca aagaaggtga acacggctga ccagtgtgct  120
aatcgctgca caaggaataa aggactgcca tttacttgta aagcctttgt attcgataag  180
gcacgcaagc agtgcctctg gttccctttc aattctatga gcagtggtgt taagaaagag  240
```

```
tttggccatg aattcgactt gtacgaaaac aaagattata tccggaactg cattatcggg  300
aaaggccggt cttacaaagg caccgtctcc ataaccaaga gtggcatcaa atgtcaaccc  360
tggagctcaa tgatcccaca tgaacactcc ttcctcccaa gttcataccg gggcaaggac  420
ctgcaagaga actattgcag aaatccgcga ggggaagagg gagggccttg gtgtttcact  480
tctaatcccg aggtgaggta tgaggtgtgc gacatacctc agtgc             525

SEQ ID NO: 193          moltype = DNA   length = 525
FEATURE                 Location/Qualifiers
misc_feature            1..525
                        note = Synthetic construct
source                  1..525
                        mol_type = other DNA
                        organism = synthetic construct
SEQUENCE: 193
caacgtaaaa gacgaaatac aattcatgag ttcaaaaagt cagccaaaac tacattgatt  60
aagattgatc ccgctctgaa gataaagacc aaaaaggtca acacagctga ccagtgcgcc  120
aacaggtgta ccaggaataa gggactacct tttacttgta aagctttcgt attcgacaaa  180
gcaaggaagc aatgtctgtg gttccccttt aactctatgt catctggggt gaaaaaggaa  240
tttggccatg aatttgattt gtatgaaaac aaagattaca ttagaaattg cattatcggc  300
aagggaagat catacaaagg tacggtttct attactaagt ctggaatcaa gtgccaacca  360
tggtcatcca tgatccctca cgagcacagt ttccttccaa gttcctaccg tggtaaagac  420
ttacaagaga actattgccg aaatcctaga ggtgaagagg gaggtccatg gtgtttttacc  480
tccaaccctg aagttagata tgaagtctgt gatatacctc agtgt             525

SEQ ID NO: 194          moltype = DNA   length = 525
FEATURE                 Location/Qualifiers
misc_feature            1..525
                        note = Synthetic construct
source                  1..525
                        mol_type = other DNA
                        organism = synthetic construct
SEQUENCE: 194
caacgtaagc gtcgaaacac tatccatgag ttcaaaaagt ctgcaaaaac tactttgata  60
aagatagacc cagctttgaa gataaagacg aaaaaggtca atactgccga ccagtgtgct  120
aatcgatgta ctagaaacaa gggcttaccc tttacttgta aggcttttgt tttcgacaaa  180
gcaaggaagc aatgtttatg gttcccccttc aattcaatga gttctggtgt gaaaaaggaa  240
tttggtcatg aatttgattt gtacgagaac aaagattaca ttagaaactg cattatcggc  300
aaaggaagat cttacaaggg gacggtgtct ataacaaaga gtggcataaa gtgtcaacca  360
tggtcctagta tgattccaca tgagcactct ttccttccct cctcctatcg aggaaaagac  420
ctacaagaga actattgtcg aaaccctaga ggagaagagg gaggcccttg gtgctttacg  480
agtaaccctg aggttagata cgaagtttgt gacattccac aatgc             525

SEQ ID NO: 195          moltype = DNA   length = 210
FEATURE                 Location/Qualifiers
misc_feature            1..210
                        note = Synthetic construct
source                  1..210
                        mol_type = other DNA
                        organism = synthetic construct
SEQUENCE: 195
ggcccagaaa cactttgtgg agccgaactg gtggatgctc tccaattcgt ttgcggcgac  60
cgcggattct actttaacaa gcccaccggt tacgggtctt caagccggag ggccccgcag  120
actggcatcg tcgacgagtg ctgtttttaga agctgcgatc tgcgacggtt ggagatgtat  180
tgtgcacctc tgaagcccgc gaaaagtgct                            210

SEQ ID NO: 196          moltype = DNA   length = 210
FEATURE                 Location/Qualifiers
misc_feature            1..210
                        note = Synthetic construct
source                  1..210
                        mol_type = other DNA
                        organism = synthetic construct
SEQUENCE: 196
ggacctgaaa ccttatgtgg agctgaactt gtggatgctc tacaatttgt ttgtggcgat  60
agagggttct acttcaacaa acccactgga tatggtagtt cctcaagacg agctcctcag  120
acaggtattg tcgacgagtg ttgttttagg tcttgcgact tgcgtagact ggagatgtac  180
tgcgcaccat tgaagccagc aaagtctgcc                            210

SEQ ID NO: 197          moltype = DNA   length = 210
FEATURE                 Location/Qualifiers
misc_feature            1..210
                        note = Synthetic construct
source                  1..210
                        mol_type = other DNA
                        organism = synthetic construct
SEQUENCE: 197
ggaccagaga cattgtgtgg agcagaactg gtggacgctt tacagtttgt gtgtggtgac  60
cgtggtttct acttcaacaa acctacgggt tacgggtcta gttctcgtag agctccacag  120
actgggattg tagatgaatg ctgcttcaga tcttgtgacc ttcgacgttt agaaatgtac  180
```

```
tgtgcacctc taaaaccagc caaatctgct                                           210

SEQ ID NO: 198        moltype = DNA   length = 666
FEATURE               Location/Qualifiers
misc_feature          1..666
                      note = Synthetic construct
source                1..666
                      mol_type = other DNA
                      organism = synthetic construct
SEQUENCE: 198
tcggggaaga aacccgaatc cgctgccggt tcgcaatcgc ccgccttgcc tccgcgtttg   60
aaggagatga aaagccagga gagcgcagca ggaagcaaac tcgtcctccg gtgtgaaacc  120
tcgagcgaat acagttccct gaggtttaag tggttcaaga atgggaatga gcttaatcgg  180
aagaacaaac cgcaaaacat caaaatccag aagaaaccgg ggaaatccga actccgcatt  240
aacaaagcgt cgcttgccga tagcggggag tacatgtgca aagtgatctc gaaactgggc  300
aatgattcgg cgtctgcgaa cattacaatc gtagaatcca atgagattat cacgggggatg  360
cccgcgtcaa ctgagggagc atatgtatcg tccgaatccc caattagaat ctccgtgtcg  420
acagagggtg cgaacacgtc gtcatcgact tcaacatcaa cgacgggcac cagtcacctt  480
gtcaaatgcg ccgagaagga aaagacgttt tgcgtgaatg gaggagaatg cttcatggtc  540
aaggacttgt cgaacccttc acgatatctg tgtaagtgtc aacccggttt caccggagct  600
cgatgtacag aaaatgttcc gatgaaagtg caaaatcagg agaaagcgga agagctctac  660
cagaaa                                                                    666

SEQ ID NO: 199        moltype = DNA   length = 195
FEATURE               Location/Qualifiers
misc_feature          1..195
                      note = Synthetic construct
source                1..195
                      mol_type = other DNA
                      organism = synthetic construct
SEQUENCE: 199
agccaccttg tgaaatgtgc ggagaaagaa aagacattct gtgttaatgg cggggagtgc   60
ttcatggtaa aagacctgtc gaatccgtca agatatctct gcaaatgcca gcccggtttt  120
acgggagccc gatgtaccga gaacgtgcct atgaaagtcc aaaaccagga aaaggcagaa  180
gaattgtacc aaaag                                                          195

SEQ ID NO: 200        moltype = DNA   length = 213
FEATURE               Location/Qualifiers
misc_feature          1..213
                      note = Synthetic construct
source                1..213
                      mol_type = other DNA
                      organism = synthetic construct
SEQUENCE: 200
acttcacatc ttgtgaaatg cgccgaaaaa gagaaaacat tttgtgtgaa tggtggagag   60
tgctttatgg ttaaagattt gtctaaccct agtagatacc tgtgcaaatg tcccaatgaa  120
ttcacaggtg acagatgtca gaactatgtt atggctagtt tctacaaaca tctgggcatt  180
gagttcatgg aagccgagga attgtatcaa aaa                                      213

SEQ ID NO: 201        moltype = DNA   length = 213
FEATURE               Location/Qualifiers
misc_feature          1..213
                      note = Synthetic construct
source                1..213
                      mol_type = other DNA
                      organism = synthetic construct
SEQUENCE: 201
acttcccatt tggtgaagtg tgcagaaaag gaaaagacat tttgtgtaaa cggtgggggag   60
tgctttatgg ttaaggactt gagtaatcct tcaagatatc tttgcaaatg tccaaatgag  120
tttaccggag atcgttgtca aaactacgtc atggcctcct tctacaaaca cttaggtatt  180
gaattcatgg aagctgagga actgtatcag aaa                                      213

SEQ ID NO: 202        moltype = DNA   length = 213
FEATURE               Location/Qualifiers
misc_feature          1..213
                      note = Synthetic construct
source                1..213
                      mol_type = other DNA
                      organism = synthetic construct
SEQUENCE: 202
acttctcatt tggtgaaatg cgccgagaag gagaaaacgt tctgcgtgaa cggtggtgaa   60
tgctttatgt tcaaagatct gtctaaccct tctcgatatc tttgtaagtg tcccaacgag  120
tttactggtg atcgatgtca gaactacgtt atggcttcct tttacaaaca cttgggtata  180
gaattcatgg aggccgagga gttgtaccaa aaa                                      213

SEQ ID NO: 203        moltype = DNA   length = 1944
FEATURE               Location/Qualifiers
misc_feature          1..1944
                      note = Synthetic construct
```

```
source                  1..1944
                        mol_type = other DNA
                        organism = synthetic construct
SEQUENCE: 203
aacaatcact atgacaagat tctggcacat agccgaatca ggggcaggga ccagggaccc    60
aatgtatgcg ctttacaaca aattctgggc accaagaaaa agtatttctc tacatgcaaa   120
aactggtaca aaaagtcaat ttgcggtcaa aagaccacgg ttctgtacga gtgttgtcca   180
ggctatatga gaatggaggg tatgaaggga tgtccagcag ttttgccaat cgaccacgtg   240
tatgggactc tcggcattgt tggagctact accactcaga ggtactctga tgcttccaag   300
ctgagggagg aaattgaggg taaaggctct tttacctact tcgctcctag taacgaggca   360
tgggataatc tggacagcga tatccgtagg gggttggaat ctaatgttaa tgtcgaattg   420
ctgaatgcct tgcactccca catgattaac aaacgaatgc taacaaaaga tttgaaaaac   480
ggaatgatta tcccttcaat gtacaacaac ttaggtcttt tcattaacca ttacccgaat   540
ggtgtggtca ctgtcaattg tgctagaatc atccacggta atcaaatcgc tacaaacggg   600
gtagtccatg taatcgatag agtgctaacg cagataggaa cgtccattca agatttcatt   660
gaagccgagg acgatctgtc tagtttttaga gctgccgcaa taacgtcaga cattttggag   720
gctttaggaa gggatggcca ctttaccttg tttgctccaa ctaatgaagc atttgagaag   780
ttgcctagag gtgttttgga aaggataatg ggtgacaaag tcgccagtga ggccttaatg   840
aaataccata tactaaacac gctgcaatgt agtgaatcca tcatgggagg ggcagttttt   900
gaaacactgg aaggaaacac tattgaaatc ggatgcgatg gtgattccat tacagttaac   960
ggaatcaaaa tggtcaacaa aaaggacatt gttaccaaca acggtgttat tcatttgatt  1020
gatcaggtgc ttattccaga ttccgccaag caggtaatag aacttgctgg aaagcagcaa  1080
actactttta ctgacctggt tgcccaacta ggcttggcct cggctcttag acccgatggt  1140
gaatacacat tacttgctcc tgtcaacaat gcattttccg acgatacctt gagtatggac  1200
cagagactac tgaaactgat actgcaaaac catatcttaa aggttaaagt gggattgaat  1260
gagttgtaca atggacaaat cttggagact attggcagca aacagttacg tgtctttgtg  1320
tatcgaaccg cagtgtgtat agagaatagt tgtatggaaa agggttcaaa gcagggtaga  1380
aatggagcta tccacatatt cagagagatt atcaaaccag ctgagaaatc cctccacgaa  1440
aagctgaaac aggacaaacg ttttagtacc ttcctttctc tattggaggc agctgacttg  1500
aaggaacttc tcactcaacc cggagattgg acacttttcg tcccaacaaa tgatgccttc  1560
aagggaatga cctcagagga aaaggaaata cttatcaggg acaaaaacgc attacagaac  1620
attatcttat accatttgac accaggggtt ttcattggta aaggttttga acccggtgtg  1680
actaacattc taaagactac tcaaggatct aagatctttt tgaaagaggt caatgacact  1740
ttgttggtga atgaacttaa gtctaaagag tccgatatca tgacaacaaa tggtgtaatc  1800
catgtagttg ataagttact ttatcctgcc gacacaccag ttgggaacga tcaactgctt  1860
gagattttga acaaactaat caagtacatt cagattaagt tcgttcgtgg atctaccttc  1920
aaggaaattc ctgttactgt ttat                                         1944

SEQ ID NO: 204        moltype = DNA   length = 342
FEATURE               Location/Qualifiers
misc_feature         1..342
                      note = Synthetic construct
source               1..342
                      mol_type = other DNA
                      organism = synthetic construct
SEQUENCE: 204
caggctaaac acaagcagcg aaagagattg aagtctagtt gcaaaaggca cccactgtac    60
gttgatttct ccgatgtggg gtggaatgat tggattgttg ctccacctgg ttaccacgcc   120
ttctattgtc atggcgagtg tccctttcct ctagccgacc atctgaactc aactaaccat   180
gcaatagtgc aaaccctagt taactccgtc aattctaaga ttcccaaggc ttgttgtgta   240
ccaacagaac ttagtgcaat ctctatgctt tacttagacg aaaatgagaa ggtcgttttg   300
aaaaactatc aagcatggcg cgtagaagga tgcggttgca ga                      342

SEQ ID NO: 205        moltype = DNA   length = 669
FEATURE               Location/Qualifiers
misc_feature         1..669
                      note = Synthetic construct
source               1..669
                      mol_type = other DNA
                      organism = synthetic construct
SEQUENCE: 205
aagtccagtt gcaaaagaca tccactttat gttgactttt cagacgttgg ttggaatgat    60
tggatagtgg ctcctcctgg ctatcacgca ttctattgtc atggtgaatg cccctttcca   120
ttagccgatc acttgaactc tactaatcat gcaatagttc agacgctggt aactccgtg    180
aattctaaga ttcccaaggc ttgttgtgtt cctaccgaac tttctgccat ttcgatgcta   240
tatctggacg aaaacgagaa agtcgtgttg aaaaactatc aagacatggt tgttgagggt   300
tgtggatgca ggggtggtgg aagtggggga ggctcaggcg gagggtctgg tggcgggaag   360
tctagctgca agcgacaccc tttgtacgtc gatttctccg acgtgggttg gaacgattgg   420
atcgtagctc cgccaggtta ccatgcattc tactgccacg gcgagtgcct ttttcccctt   480
gctgatcatc tgaattccac aaatcatgct attgtgcaga ccctagttaa ctcagttaac   540
tctaagatcc ctaaagcctg ttgtgtccca actgaactca gtgctatttc tatgttatac   600
ttagatgaaa atgaaaaggt cgtcttgaaa aactaccaag atatggtagt agagggatgc   660
ggatgtcgt                                                           669

SEQ ID NO: 206        moltype = DNA   length = 618
FEATURE               Location/Qualifiers
misc_feature         1..618
                      note = Synthetic construct
source               1..618
```

-continued

```
                       mol_type = other DNA
                       organism = synthetic construct
SEQUENCE: 206
gctccgatgg cagagggtgg aggtcaaaat catcatgagg tggtgaagtt tatggatgta   60
tatcaacgat cctactgtca ccccatcgaa acattggtcg atatcttcca agaatatccc  120
gacgaaattg aatacatctt taagccctcg tgtgtacctc ttatgaggtg tggaggttgc  180
tgcaatgatg aaggcctgga atgtgtcccg acggaagagt caaacattac aatgcagatt  240
atgcgaatca aaccccacca agggcagcac atcggagaga tgtcgtttct ccagcacaac  300
aaatgtgagt gcagacccaa gaaagataga gcgaggcagg aaaagaaaag cgtcgcgga   360
aaagggaaag gacaaaagcg taaacggaag aaatcccggt ataagtcgtg gagtgtgtac  420
gttggggcca gatgttgttt gatgccttgg tcgctgcctg ggccgcaccc atgcgggcca  480
tgctctgaga ggcgtaaaca tctcttcgtc caagacccgc agacgtgcaa atgctcatgc  540
aagaatactg acagccgttg taaagcgcgg cagcttgagc ttaacgagag gacctgccga  600
tgtgacaaac cgcgccgc                                                618

SEQ ID NO: 207          moltype = DNA   length = 1290
FEATURE                 Location/Qualifiers
misc_feature            1..1290
                        note = Synthetic construct
source                  1..1290
                        mol_type = other DNA
                        organism = synthetic construct
SEQUENCE: 207
gcgccgatgg ctgagggcgg agggcagaac catcacgagg tcgtgaaatt catggacgtg   60
taccagagga gttattgtca tcctatcgaa acacttgtcg acattttcca agagtacccc  120
gatgagatcg agtatatctt taagccctcg tgcgtgccac ttatgcgctg cggaggctgt  180
tgcaatgatg aaggcctgga gtgtgtacca actgaagagt caaacattac catgcagatc  240
atgagaatca aaccgcacca agggcaacac atcggggaga tgtcattctt gcaacacaac  300
aaatgcgaat gccgaccgaa gaaagaccgt gcacgacagg agaagaaatc ggtccgggga  360
aaagggaaag ggcagaaaag gaaaaggaag aaatctcgct ataagtcgtg gtccgtcac   420
gtgggtgcgc gttgttgttt gatgccgtgg agcctgccgg gaccccatcc ttgtgggccg  480
tgttctgaac ggcgaaaaca tctctttgta caagatccgc agacttgcaa atgttcgtgc  540
aagaatactg actccagatg taaagccagg caattggagc tcaatgagag gacgtgccga  600
tgtgacaaac ccagaagggc atcaacgggt ggaggtggat caggtggcgg cggttctggt  660
ggaggaggat ccgccccgat ggcggaggga ggtggacaaa atcaccatga agtggtaaag  720
tttatggacg tttatcagag atcgtattgt caccccattg aaacactggt agatatcttt  780
caagaatacc ccgacgaaat tgaatacatt ttcaaaccta gctgtgtgcc actgatgcgg  840
tgcggtgggt gctgcaacga cgaagggctc gagtgtgtgc caacggagga gtccaatatc  900
acaatgcaaa tcatgcgcat caagcnccat caaggacagc acattgggga aatgtcgttt  960
ctccagcaca ataagtgtga atgtcgcccc aagaaagata gagcgcgaca ggaaaagaaa  1020
agcgtgcgag ggaaggggaa gggacaaaag aggaaacgca agaaatcgag atacaaaagt  1080
tggtccgttt acgtcggagc ccgttgctgc cttatgccgt ggtcactgcc cggtcctcat  1140
ccctgtggac cttgcagcga gcgccggaaa cacctttcg tccaagatcc tcagacgtgc  1200
aagtgctcgt gtaagaatac cgattcacgg tgcaaagcgc gtcagttgga actcaacgaa  1260
agaacatgta gatgcgataa accacgtcga                                  1290

SEQ ID NO: 208          moltype = DNA   length = 564
FEATURE                 Location/Qualifiers
misc_feature            1..564
                        note = Synthetic construct
source                  1..564
                        mol_type = other DNA
                        organism = synthetic construct
SEQUENCE: 208
atgagtcctt tgcttagaag gttgttactg gccgcactgc ttcaacttgc accagctcaa   60
gccccagtct ctcaacctga cgctcccggt catcagagaa aggtggtatc atggattgat  120
gtgtatactc gtgctacatg ccaaccccgt gaggttgttg tacctttgac agtcgaattg  180
atgggaaccg ttgccaagca gttagttcct tcctgtgtca cagtgcagag atgtggagga  240
tgttgtccag atgatggttt ggagtgtgta cctactggcc aacatcaggt tagaatgcag  300
atcttgatga tacgttaccc atcaagtcaa ctaggtgaaa tgtctttgga ggaacactcc  360
cagtgcgaat gcagacccaa aaagaaagat tctgctgtta aaccagactc tccaagacca  420
ttatgtccca gatgcacgca acaccatcaa agaccagatc caaggacttg tagacgtaga  480
tgcaggaggc gatcctttt gcgatgccaa ggtagaggcc tagagctgaa tcctgacacc  540
tgtcgatgtc gaaagttaag acgt                                        564

SEQ ID NO: 209          moltype = DNA   length = 564
FEATURE                 Location/Qualifiers
misc_feature            1..564
                        note = Synthetic construct
source                  1..564
                        mol_type = other DNA
                        organism = synthetic construct
SEQUENCE: 209
atgtctcctt tgctgagaag gttactattg gctgcattgt tgcagttagc cccagcccaa   60
gctcccgttt cccaaccaga tgcacctggt catcaacgaa aggtggtttc ctggatcgat  120
gtctacacga gagctacctg tcaaccaagg gaagttgtag ttcccttaac tgtggagctt  180
atgggtacag tagccaagca attagttccc tcatgtgtca ctgttcagcg atgtggaggg  240
tgttgtcctg acgacggcct agagtgcgtc ccaacaggac agcaccaagt gagaatgcaa  300
attctgatga tacgatatcc tagttctcag ttgggtgaaa tgagtttgga ggagcattct  360
```

```
caatgcgaat gtagacccaa aaagaaagat tccgctgtca aaccagactc tcctagacca   420
ctatgcccaa gatgcactca acaccaccag cgtcctgatc ctagaacttg taggcgtaga   480
tgtcgtagaa gatcattcct tagatgtcag ggaagaggtc ttgaattgaa tccagacacc   540
tgccgatgtc gtaagctgcg tagg                                          564

SEQ ID NO: 210          moltype = DNA   length = 393
FEATURE                 Location/Qualifiers
misc_feature            1..393
                        note = Synthetic construct
source                  1..393
                        mol_type = other DNA
                        organism = synthetic construct
SEQUENCE: 210
atgagtcctt tgttgagaag gttgctatta gctgcattgt tacagttagc tcctgctcag    60
gccccagttt ctcagccaga cgccctggt catcaacgta aggttgtgtc ttggattgac    120
gtatacacga gagcaacatg ccaaccaagg gaagtcgttg ttcccttac tgttgagttg    180
atggggactg tggctaagca gctggtccct tcatgtgtca ccgtacagag atgtggaggt    240
tgttgcccag acgatggact agaatgtgtt ccaacaggac aacatcaggt gagaatgcaa    300
atactgatga tcagatatcc atcttcacaa cttggcgaaa tgtccctgga agagcactct    360
caatgcgagt gtcgacccaa aaagaaagat agt                                393

SEQ ID NO: 211          moltype = DNA   length = 393
FEATURE                 Location/Qualifiers
misc_feature            1..393
                        note = Synthetic construct
source                  1..393
                        mol_type = other DNA
                        organism = synthetic construct
SEQUENCE: 211
atgagtcctt tgctaagacg tttacttttg gctgccttat tgcagctggc accagcccaa    60
gcaccagtgt cacagccaga tgctcccggt caccagagaa aagtggttag ttggattgat    120
gtttacacga gggctacatg ccaacctaga gaagtagttg tccctctgac agttgaacta    180
atggggaccg ttgctaagca attggtgcct tcctgtgtca ctgttcagcg atgcggagga    240
tgttgtccag acgacggtct ggaatgcgta ccaactggcc aacatcaagt cagaatgcag    300
atcttgatga taagatatcc atcttcccaa ttaggagaaa tgtcacttga ggaacattct    360
caatgtgagt gtaggcccaa aaagaaggat tct                                393

SEQ ID NO: 212          moltype = DNA   length = 1755
FEATURE                 Location/Qualifiers
misc_feature            1..1755
                        note = Synthetic construct
source                  1..1755
                        mol_type = other DNA
                        organism = synthetic construct
SEQUENCE: 212
gacgctcaca agagcgaagt ggcacatagg ttcaaagatc tgggcgaaga gaactttaag    60
gccctcgtcc tgatcgcttt cgcacagtac ctccagcagt ctcccttttga agatcacgtg   120
aaactggtca atgaggtgac cgaatttgcc aagacatgcg tggctgatga gagtgcagaa   180
aactgtgaca aatcactgca tactctcttt ggagataagc tgtgcaccgt cgccacactc   240
agagagactt atggggaaat ggctgactgt tgcgcaaaac aggagcctga acggaatgag   300
tgtttcctcc agcacaagga tgacaaccca aatctgcccc gcctcgtgcg acctgaggtc   360
gatgtgatgt gcaccgcctt tcatgacaac gaagagacat tcctgaagaa atacctgtat   420
gaaattgctc gtaggcaccc atactttat gcccccgagc tcctgttctt tgcaaagaga   480
tacaaagctg ccttcactga atgttgccag gcagctgata aggccgcatg tctcctgcct   540
aaactggacg agtccggga tgaaggtaag gcttccagcg ccaaacagcg cctgaagtgc   600
gcttctctcc agaagtttgg cgagcgagca ttcaaagcct gggctgtggc ccgtctcagt   660
cagaggtttc caaaggcaga atttgctgag gtctcaaaac tggtgaccga cctcacaaag   720
gtccatactg agtgttgcca cggagatctg ctggaatgtg ccgacgatag agcagacctc   780
gctaaatata tctgcgagaa tcaggattcc attagctcta agctgaaaga atgttgcgag   840
aagcccctcc tggaaaagag tcattgtatc gccgaggtgg aaaacgacga gatgccagca   900
gatctgccat cactcgctgc cgactttgtg gaatccaaag atgtctgcaa gaattacgca   960
gaggctaaag acgtgttcct ggggatgttt ctgtatgagt acgcccggcg tcaccccgat   1020
tatagcgtcg tgctcctgct ccgactggca aagacctacg aaacaactct ggagaaatgt   1080
tgcgctgccg cagaccctca tgaatgttat gctaaggtgt tcgatgagtt taagccactc   1140
gtcgaagagc cccagaacct gattaaacag aattgcgaac tgttcgagca gctcggtgaa   1200
tacaagtttc agaacgccct gctcgtgcgt tataccaaaa aggtccctca ggtgtctaca   1260
ccaactctgt tggaggtcag taggaatctg ggcaaagtgg gatcaaagtg ttgcaaacac   1320
cccgaggcaa agagaatgcc ttgtgctgaa gattacctct ccgtcgtgct gaaccagctc   1380
tgcgtgctgc atgaaaagac cccagtcagc gaccgggtga caaatgttg caccgaatct   1440
ctggtcaatc gccgacctg tttcagtgcc ctcgaagtgg acgaaactta tgtgcctaag   1500
gagtttcagg ctgaccatt caccttcac gccgatatct gcactctgtc cgagaaagaa   1560
aggcagatta agaacagac agcactggtc gagctcgtga agcataaacc aaaggctacc   1620
aaggagcagc tgaaagccgt catggacgat ttcgcagctt ttgtggaaaa gtgttgcaaa   1680
gccgacgata aggagacttg tttcgcagaa gagggggaaa agctcgtggc tgccagccag   1740
gcagctctgg gtctg                                                   1755

SEQ ID NO: 213          moltype = DNA   length = 1755
FEATURE                 Location/Qualifiers
misc_feature            1..1755
```

```
                           note = Synthetic construct
source                     1..1755
                           mol_type = other DNA
                           organism = synthetic construct
SEQUENCE: 213
gatgctcaca aatctgaagt cgctcatcgt ttcaaagact tgggtgagga aaactttaag   60
gctttagttc tgattgcttt tgcccaatat cttcaacaat caccattcga agatcatgtg   120
aaacttgtta acgaagttac cgaatttgca aaaacgtgtg tggcagacga aagtgccgaa   180
aactgtgaca aatcattaca cactttgttc ggtgacaagt tatgcactgt tgcaacccta   240
cgtgagacat atggagaaat ggcagactgt tgcgccaaac aagagcctga acgaaacgaa   300
tgctttctgc agcacaaaga cgataatcca aatcttcccc gattagttcg tcccgaagta   360
gacgtaatgt gcacagcctt tcatgataat gaagagactt tcctgaaaaa gtacttgtac   420
gaaattgcaa gacgtcaccc atacttctat gctcccgagt tactgttttt cgccaaacga   480
tacaaggcag cctttacaga atgttgccaa gcagctgaca aggctgcatg tcttttacct   540
aagttagatg agttaagaga cgaaggtaag gcttcctcag caaaacagag acttaagtgc   600
gcatcccttc aaaagtttgg tgagagagct ttcaaggctt gggctgtcgc cagactgtct   660
cagagatttc ctaaggctga attcgcagaa gtctctaagc tagtaactga cttgactaaa   720
gttcatactg agtgctgtca tgggatttg ttggaatgcg cagatgatcg tgcagactta   780
gcaaagtaca tctgcgagaa ccaagactct atttccagta agttaaagga atgttgcgaa   840
aagccactac ttgagaagtc ccactgtatt gctgaagtcg aaaatgatga aatgcctgct   900
gaccttccat cttttggccg ctgatttcgtt gagtccaagg atgtgtgcaa aaactatgct   960
gaagcaaaag atgtgttcct agggatgttc ctgtatgaat atgctcgtcg acatcccgac   1020
tattccgttg tccttttact gagattggct aagacctacg agacaacctt ggagaagtgt   1080
tgtgctgccg cagatcctca cgagtgttac gcaaaagtgt ttgatgagtt caaaccattg   1140
gttgaagagc cacaaaatct aatcaagcag aactgtgaac tgtttgaaca attgggcgaa   1200
tacaaattcc aaaatgctct gttagtgaga tacaccaaaa aggtcccaca agtttccacc   1260
ccaactctag tcgaggtgtc cagaaatcta ggaaaagttg gatctaagtg ttgtaagcat   1320
ccagaagcta agaggatgcc ttgcgctgag gattacttgt ctgtggtttt gaaccagtta   1380
tgtgttctac acgagaaaac tcctgtctcc gacagagtta ctaagtgctg cacagagtct   1440
ttggtcaata gaaggccttg tttcagtgcc ctggaagtcg atgaaactta tgtgcctaaa   1500
gagttccaag ccgaaacgtt cacttttcac gctgacattt gtactctttc tgagaaggaa   1560
cgtcagatca aaaagcagac agcattggtg gaattggtaa agcataaacc aaaggctaca   1620
aaagagcagc tgaaggctgt tatggatgat tttgcagctt cgtgtgaaaa gtgttgtaaa   1680
gccgatgata aagagacttg ttttgcagag gaggggaaaa agctggttgc tgcatcacaa   1740
gctgccctag gtctt                                                   1755

SEQ ID NO: 214             moltype = DNA  length = 1755
FEATURE                    Location/Qualifiers
misc_feature              1..1755
                           note = Synthetic construct
source                     1..1755
                           mol_type = other DNA
                           organism = synthetic construct
SEQUENCE: 214
gacgctcata agtctgaagt tgctcacaga ttcaaagacc taggtgaaga gaactttaag   60
gctcttgtac ttatagcatt tgctcagtat ctgcaacaga gtcccttcga agatcatgtc   120
aagctgtga atgaggtaac cgaattcgcc aagacttgtg tggctgatga atccgccgaa   180
aactgtgaca aatctttaca cacattgttc ggagataaac tatgcacagt agcaacttta   240
cgtgaaactt atggtgagat ggcagattgt tgtgctaaac aggagcctga gagaaatgaa   300
tgcttttgc aacacaagga cgacaatcct aaccttccca gattggttag acccgaggtt   360
gacgttatgt gtaccgcctt ccacgacaat gaggaaacat ttctgaaaaa gtacttgtac   420
gaaattgcac gacgtcaccc atacttctat gcacctgagc ttttgttttt cgccaaaaga   480
tacaaggcag ctttcactga gtgctgtcaa gcagccgata aggctgcttg tctattacct   540
aaacttgatg agcttagaga tgaggtaaa gcatcctccg ctaaacagag gttgaaatgt   600
gccagtttgc agaagtttgg tgaacgtgct ttcaaggcat gggctgttgc tagattatct   660
caaagatttc ctaaggccga atttgctgag gtgtcaaagt tggtgacgga tttgactaag   720
gtccacactg agtgttgcca tggtgatctt ttggaatgtg ctgacgatag agccgacctg   780
gccaagtata tctgtgaaaa ccaagattct atcagtagta agctgaagga atgttgcgaa   840
aaacctctac tagagaaatc tcattgcatc gcagaagttg aaaacgatga aatgccagcc   900
gacttgccca gtctggctgc tgatttcgtc gagtcaaaag atgtttgcaa aaactatgcc   960
gaagcaaagg atgtctttt gggcatgttc ctgtacgaat atgctcgtcg tcatcctgac   1020
tattccgttg tcctgttgct aagactagct aaaacgtatg aaacgacctt ggaaaagtgt   1080
tgcgctgcag ctgatcccca cgagtgttat gcaaaagttt tcgatgagtt taagccactt   1140
gtagaagagc cacagaactt gatcaaacag aattgtgagc ttttcgagca attaggtgag   1200
tataagtttc aaaacgcttt gctggttaga tataccaaaa aggtcccaca agtgtcaacc   1260
cctaccctgg tagaagtgag tagaaatcta ggaaaagtcg gatctaagtg ctgcaagcat   1320
ccagaagcta agagaatgcc ttgcgctgag gattacttgt cagtagtttt gaatcagttg   1380
tgcgtcctac atgaaaagac acccgtttct gatagagtaa ctaagtgttg tactgagtct   1440
ctagtaaaca gaaggccttg tttctctgca ttagaagtag atgaaactta tgtcccaaag   1500
gagttccaag ctgaaacctt tacatttcac gccgacattt gtacgctatc tgagaaggag   1560
cgtcagatca aaaagcaaac agcccttgtt gagcttgtga agcacaagcc aaaagctaca   1620
aaggagcaat tgaaagccgt catggacgat ttcgccgcat ttgttgagaa gtgttgcaag   1680
gcagatgata aggaaacttg ttttgctgaa gagggcaaaa agcttgttgc cgcctctcaa   1740
gctgctttgg gacta                                                   1755

SEQ ID NO: 215             moltype = DNA  length = 615
FEATURE                    Location/Qualifiers
misc_feature              1..615
                           note = Synthetic construct
```

-continued

```
source                  1..615
                        mol_type = other DNA
                        organism = synthetic construct
SEQUENCE: 215
ggtgaggaac cacagaatct gatcaaacag aactgcgaac tattcgaaca actgggcgag   60
tacaagtttc aaaatgccct gcttgtgagg tataccaaaa aggttcctca agtgtccact  120
cccaccttag ttgaggtatc tagaaatctt ggaaaggtgg gttccaaatg ttgcaaacat  180
ccagaagcta aaaggatgcc ttgtgccgag gactatttgt cagtcgtgtt gaaccagctt  240
tgtgtcttac acgaaaagac acctgttagt gacagagtta cgaaatgctg tacagagtca  300
cttgtaaacc gtagaccatg tttttctgct ttggaagttg acgagactta cgtaccaaaa  360
gagttccaag ccgaaacttt tacgtttcat gccgacattt gcactttgtc tgagaaggaa  420
cgacagatca aaaagcaaac cgctctggtt gaactggtta agcacaagcc caaagctaca  480
aaggaacagc taaaggcagt catggatgat ttcgcagctt ttgtcgagaa atgttgtaag  540
gctgatgata aggagacatg cttcgctgaa gagggcaaaa agttggtcgc agctagtcag  600
gctgctctag gtttg                                                    615

SEQ ID NO: 216           moltype = DNA  length = 1773
FEATURE                  Location/Qualifiers
misc_feature             1..1773
                         note = Synthetic construct
source                   1..1773
                         mol_type = other DNA
                         organism = synthetic construct
SEQUENCE: 216
agaaccttgc atagaaacga atatggcata gcatccattt tggactctta tcagtgtacc   60
gctgaaatca gtctggctga tctagccacc atcttttcg cccagtttgt acaagaggct   120
acgtataagg aggtttccaa gatggttaag gatgcattaa ctgcaattga aaaaccaaca   180
ggtgatgaac aatctagcgg ttgtcttgaa aatcaacttc cagccttttt ggaggagctt   240
tgtcacgaaa aggaaatcct tgagaagtac gggcactccg attgttgctc acaatccgag   300
gagggcgac ataactgttt tctggctcac aaaaagccta cacccgccag tattcccctt   360
tttcaagtcc cagaaccagt gacctcatgt gaagcctatg aggaggatag agaaacctt   420
atgaataagt tcatatacga gatcgccagg aggcacctt tcctatacgc tccaacaatc   480
ttgctatggg cagctcgata tgacaagatc attccctctt gctgtaaagc tgaaaatgct   540
gtagagtgct tccaaaccaa ggctgccact gttaccaagg aactgcgaga atctagtctt   600
ttgaaccagc acgcttgcgc tgtaatgaaa aactttggaa ccagaacatt tcaagccatt   660
actgtcacaa aactgtctca aaagttcact aaagtacagt ttactgaaat tcagaaattg   720
gtgttggacg tcgcccatgt ccatgaacat tgttgtaggg gagatgtact ggattgcctc   780
caagacggcg agaagattat gtcctacatt tgctcacagc aggatacgtt gtccaacaag   840
atcaccgaat gttgcaaact cactacattg gaaagaggtc agtgtatcat tcacgctgaa   900
aacgacgaga aaccagaagg actatcacct aatctaaacc gattccttgg tgatagagac   960
ttcaatcaat tctcttctgg cgagaaaaac atattccttg cttcatttgt tcacgagtac  1020
tcccgtcgtc atccacaact ggccgttagt gtgatcttga gagttgccaa aggctaccag  1080
gaactgctgg aaaagtgttt tcagactgag aatcctctgg agtgccaaga taagggtgaa  1140
gaagagttac agaagtacat tcaagagtca caagcattag caaaaaggtc atgcggtctg  1200
tttcagaagt tgggagaata ctatcttcaa aatgccttcc tggtcgctta cacgaaaaag  1260
gctcctcaac taacgtccag tgagcttatg gctattacaa ggaaaatggc agccaccgct  1320
gctacatgtt gccaactgtc cgaagataag ttattggcat gtggtgaagg agccgctgac  1380
ataatcattg gtcatctgtg cattagacat gaaatgactc cggtcaatcc cggagtgggt  1440
cagtgttgta cttcatctta tgctaaccgt aggccttgtt tctcttcgct ggtgggtgac  1500
gaaacctatg ttccaccagc tttctctgat gacaagttca tctttcacaa agacttatgt  1560
caggcacaag gagttgcatt gcaaactatg aaacaggaat tccttatcaa tctagtgaag  1620
cagaaaccac agattactga agagcagtta gaagcagtga ttgctgattt ctctggtttg  1680
ctagaaaagt gctgccaggg ccaggagcag gaagtgtgct ttgcagagga aggacagaag  1740
ttaatcagta agacaagagc tgctcttgga gtg                                1773

SEQ ID NO: 217           moltype = DNA  length = 321
FEATURE                  Location/Qualifiers
misc_feature             1..321
                         note = Synthetic construct
source                   1..321
                         mol_type = other DNA
                         organism = synthetic construct
SEQUENCE: 217
gatatacaga tgacgcagtc tccatcatcc ctgtctgctt cagttggtga ccgagtaact   60
attacatgta gagccagtca gtggataggt tcacaattgt cctggtatca acagaagccc  120
ggaaaggctc ctaaacttct aatcatgtgg agatcctctt tacagtctgg agtcccatct  180
aggttctccg gcagtggctc cggtactgac ttcaccttga ccattagttc actgcaacca  240
gaagattttg ccacctacta ttgcgcacag ggtgctgctc ttcctcgtac ttttggtcaa  300
ggcacaaaag tggagattaa g                                              321

SEQ ID NO: 218           moltype = DNA  length = 1446
FEATURE                  Location/Qualifiers
misc_feature             1..1446
                         note = Synthetic construct
source                   1..1446
                         mol_type = other DNA
                         organism = synthetic construct
SEQUENCE: 218
gaaccaaaat caagcgacaa aacccacacc tgccctccgt gtccagcccc agagttacta   60
```

```
ggtggtccat ccgttttttct cttcccacca aagccaaaag ataccctgat gattagccga   120
acgcctgaag tcacatgtgt tgtcgttgac gtttcccacg aggacccctga ggtaaagttt   180
aactggtacg tagacggcgt agaagtccac aatgctaaaa caaagccaag ggaagagcaa   240
tacaactcta cttatagggt cgtgagtgtc ttaaccgtgc tacaccagga ctggttgaat   300
ggtaaagagt acaagtgcaa ggtgtctaac aaagcactac ctgccccaat agaaaagaca   360
atcagtaagg caaaaggtca gcccagagaa ccccaagtgt atactctgcc cccatctaga   420
gatgagctta cgaaaaacca ggtttctctc acgtgtctgg ttaaaggatt ctatccttct   480
gatatcgccg ttgagtggga gtcgaatgga cagcccgaaa acaattacaa aactacccca   540
ccagtccttg attccgacgg ctccttttttc ctttactcta agttgacagt tgacaaatcc   600
agatggcaac aaggtaatgt gttctcttgt tcagtgatgc atgaggcttt gcataaccac   660
tatacccaga aatcccttag tttatcccct ggtggaggtg ggggtagtgg cggtggtgga   720
tcaggaggtg gtggctcagg gggaggcggt tcggaaccca agtccagtga taagactcat   780
acttgtccac cctgtcctgc ccctgagctt ttgggaggtc cgagtgtctt tttgtttccg   840
cctaagccta aagacaccct tatgatttca aggacacgag aggttacatg cgtggtcgtc   900
gatgtctctc acgaggaccc tgaggtgaaa ttcaattggt acgtggatgg cgtggaagtt   960
cataacgcta agacgaaacc cagagaggaa caatatcaga gtacttatcg tgtggtttcc   1020
gttctgactg tactgcatca ggattggctg aatggaaagg agtacaaatg taaggtttct   1080
aacaaggctc tacctgctcc aattgaaaag actatatcta aggctaaggg acaaccaagg   1140
gaacctcaag tatacacatt gcctcctagt agagatgaat tgaccaaaaa ccaagtatct   1200
ttaacctgcc tagttaaagg cttctaccca tccgacattg ctgtagaatg ggagtcaaat   1260
gggcagccag aaaacaacta taagactaca cccccagtgt tggattctga cggctccttt   1320
ttcctatact ctaaactgac tgtagataag tcacgttggc aacagggaaa tgtctttttca   1380
tgctctgtta tgcatgaagc attgcacaat cactacactc agaaaagtct gtcactttca   1440
cctggt                                                               1446

SEQ ID NO: 219        moltype = DNA  length = 1374
FEATURE               Location/Qualifiers
misc_feature         1..1374
                     note = Synthetic construct
source               1..1374
                     mol_type = other DNA
                     organism = synthetic construct
SEQUENCE: 219
ctagaaaggg gtcgagacta tgagaaaaac aaagtgtgta aagagtttag tcatcttggg   60
aaggaggact tcacaagtct ttctctggtg ttatacagta ggaagtttcc atctggcaca   120
tttgaacaag tctcacagtt ggtgaaggaa gttgtgtctt taactgaagc ctgttgtgcc   180
gagggtgccg atccagattg ctatgacacc agaaccagtg ctttatccgc taagtcttgt   240
gaaagtaata gtccatttcc agtccatccc ggtactgccg aatgctgtac aaaagaggga   300
ttggagagaa agttgtgtat ggctgctcta aagcatcagc ctcaagagtt tccaacgtac   360
gtagaaccca cgaatgacga gatttgtgag gctttccgta aagaccctaa agagtatgct   420
aatcagttca tgtgggaata ctcaacgaat tacggtcaag ctcccttgag cctgttagtt   480
tcctatacca aatcatatct gtcaatggtc ggatcatgtt gtacctctgc atcacctaca   540
gtttgctttc taaaggaaag attacagctt aagcacttgt ctttgttgac tactctatct   600
aaccgtgttt gttctcaata tgcagcctat ggtgagaaaa agtccaggct atccaatctt   660
atcaaactgg cacaaaaggt ccctacggcc gatcttgagg atgttctgcc actggccgaa   720
gatatcacca acatcctttc caagtgctgt gaatccgctt cagaagattg tatggcaaag   780
gagttgccag agcacactgt gaaactatgc gacactctaa gtaccaaaaa ctcaaagttc   840
gaggactgct gccaggaaaa gaccgctatg gacgtttttg tttgcactta ctttatgcct   900
gccgcacagc tgcctgaact gcctgatgtg gagttaccaa ctaacaaaga cgtgtgcgat   960
cccggcaata ccaaagtcat ggacaagtac actttcgaat tgtccagaag gacacacctc   1020
cctgagtttt tcctctctaa ggtattggaa cccaccctga agtctttagg cgagtgttgc   1080
gatgttgagg actcgacaac atgcttcaat gcaaagggac ctctattgaa aaaggagctt   1140
tcctctttca ttgataaagg ccaggaactt tgtgcagatt actcagaaaa cacattcact   1200
gaatacaaaa agaagctggc tgagagattg aaagctaagc tgccagacgc tactccaaag   1260
gaactagcta aactggtcaa taagcgaagt gatttcgcct ctaactgttg ctccataaac   1320
tctccgcctc tttactgcga ttctgagatc gatgccgaat gaaaaacat tttg           1374

SEQ ID NO: 220        moltype = DNA  length = 732
FEATURE               Location/Qualifiers
misc_feature         1..732
                     note = Synthetic construct
source               1..732
                     mol_type = other DNA
                     organism = synthetic construct
SEQUENCE: 220
cttgaatcag gaggcgggct tgtgcaacca gggggatcct tgagactttc gtgcgccgga   60
agtggtttca cgttttcgtc gtatgcgatg agctgggtga gacaggcccc tggtaaagga   120
cttgagtggg tatcgtccat ttccgggtct ggaggatca catactacgc cgattctgtt   180
aagggccgct ttaccatctc ccgcgacaac agcaaaaaga cgctgtacct ccaaatgaac   240
tcgttgcggg cagaagatac ggcggtgtat tactgcgcaa gaaaacgcgg gagaacgaca   300
gtgagttggg gactggtata ctttgactac tggggggcagg gtactgtggt aacggtttct   360
tcgggaggtg gcgggtcagg gggtggggga tcggagggg gaggtagcgg aggttctgag   420
ctgacgcaat cgcccggtac attgagtctc tcgcctggcg agcgagcaac gctgtcatgt   480
agagcgagac actcagtttc gagggcgtat ctggcgtgat accagcagaa acccggtcag   540
gcccccagac ttttgatcta tgggacttca agtcgagcga ccgggatccc cgataggttt   600
tcggggtccg gctcgggaac ggactttacc ctcaccattt cgaggctgga gccagaagat   660
ttcgccgtgt actactgcca acagtacggc gggagcccgt ggtttggaca gggaactaag   720
gtggaactta aa                                                        732
```

-continued

```
SEQ ID NO: 221            moltype = DNA   length = 732
FEATURE                   Location/Qualifiers
misc_feature              1..732
                          note = Synthetic construct
source                    1..732
                          mol_type = other DNA
                          organism = synthetic construct
SEQUENCE: 221
ttggagagtg ggggtggctt ggttcaaccc ggtggatctt tgagattgtc atgtgccggt   60
tctggtttta cctttagttc ctatgctatg tcttgggtcc gtcaagcccc aggcaaagga   120
cttgaatggg tatcatcaat ctccgggtca ggtggtagta cgtattacgc agattctgtg   180
aaaggtaggt ttaccatttc cagagataac tccaaaaaga cattgtactt gcaaatgaat   240
agtctgagag ctgaggatac tgccgtctat tactgtgccc gaaaaagagg cagaactaca   300
gttagttggg gtcttgtcta ctttgactac tggggtcagg ggacggtcgt taccgtatct   360
tccggtggag ggggttctgg aggaggagga tctggtggtg gtggaagtgg aggttctgaa   420
ttgacccaat ctcctggtac tctgtctcta agtccaggag aacgagccac gttgtcatgt   480
agggcctcac attcagtttc aagagcttat cttgcctggt atcaacagaa acctggacag   540
gccccacgtt tgttgatata cggcaccagt tccagggcta cggaataccc agataggttt   600
tctggatctg gctcaggaac ggatttcact ttgacaattt caagactaga gccagaggac   660
tttgccgtat actactgtca acaatatgga ggatcacctt ggttcggaca gggtactaaa   720
gttgaactta aa                                                       732

SEQ ID NO: 222            moltype = DNA   length = 747
FEATURE                   Location/Qualifiers
misc_feature              1..747
                          note = Synthetic construct
source                    1..747
                          mol_type = other DNA
                          organism = synthetic construct
SEQUENCE: 222
ctggagagcg ggggtggcct ggtccaacca ggcggatctc tgagactcag ttgtgcaggg   60
agcggattta ccttcagctc ctatgctatg tcttgggtgc gccaggcacc cgggaagggg   120
ctggagtggg tcagtagcat cagtggcagc ggcggaagca cctactatgc tgatagtgtt   180
aagggaaggt tcacgatcag ccgcgacaat tccaaaaaga ccctttatct ccaaatgaac   240
tcactgcgcg ccgaagatac ggccgtctac tactgtgcac ggaaaagagg cagaaccacc   300
gtgtcctggg gcctggttta cttcgattac tggggtcagg gcaccgtagt gactgtgagc   360
agcggaggcg ggggttctgg tggcggagga tcaggcggcg gaggaagtgg tggggcggc    420
tccggtggga gcgagctgac tcagtctccg ggaactctta gtttgtctcc cggcgagcga   480
gcgacactct cttgccgagc gtcccactcc gtgtctcgag cctatctggc ctggtatcaa   540
cagaaacctg gcaggcacc ccggctgctg atttacggga cttcctcacg gctacaggt    600
atccctgaca ggtttccgg cagtggctcc gggacagact tcaccctgac tatatcaagg   660
ctggaaccag aagactttgc cgtgtattac tgccagcagt acggagggtc accttggttc   720
gggcagggaa caaaggtgga gcttaag                                       747

SEQ ID NO: 223            moltype = DNA   length = 756
FEATURE                   Location/Qualifiers
misc_feature              1..756
                          note = Synthetic construct
source                    1..756
                          mol_type = other DNA
                          organism = synthetic construct
SEQUENCE: 223
gaggtgcagt tggtcgaatc aggaggaggt ttagtgcagc ccggtggatc acttaggctg   60
agttgctccg catctggttt cactttctct tcctatgcca tgcattgggt acgtcaggca   120
ccgggaaag gactagaata cgtatcagcc atatcttcta atggcggatc aacctactat   180
gctgattcag ttaaaggtag attcactatc tcaagagata actccaaaaa cacattgtac   240
cttcaaatga gttcactgcg tgctgaggac acagctgtct attactgtgt aaagattact   300
ggagcctact ctagttcctg gtactacgac aattggtttg atccttgggg ccaaggaacc   360
ttagttacgg tttccagtgg cggtggggga tctggcggag gtgggagtgg tggaggggt    420
tctggtggat catcttatga attgacccag ccccttctg tgtctgttag cctggaccag   480
actgccagca ttaccgttc cggcgataag ctaggtgaca gtacgcttg ctggtatcaa    540
caaaagccag ggcagtcacc agtgcttgtc atctaccaag attctaagag gccaagtgga   600
ataccagaac gattttctgg ctccaacagt ggcaatacag ctaccctgac aatttccggt   660
acgcaagcaa tggatgaggc tgactactat tgtcaggcct gggattcgtc aactgctgtg   720
tttggtggtg gtactaaact cactgtcttg ggtcaa                             756

SEQ ID NO: 224            moltype = DNA   length = 735
FEATURE                   Location/Qualifiers
misc_feature              1..735
                          note = Synthetic construct
source                    1..735
                          mol_type = other DNA
                          organism = synthetic construct
SEQUENCE: 224
gaagtgcagc ttcagcagag cgggcctgaa ctggttaaac caggtgccag catgaagatt   60
tcctgtaagg cttctgggta cagtttcacc gggtacacca tgaaatgggt gaagcaaagc   120
cacgaaaga accttgagtg gattggattg atcaacccct ataatggggg aactagctat   180
aaccagaagt tcaaggggaa ggctactctg acggtggaca agtcatcaag caccgcatat   240
atggagctcc tctccctgac ttctgacgac agcgcagtat actattgcgc cagagagggg   300
```

```
gactacgatg gggctatgga ctactggggc caggggacaa gcgtcactgt ctccggtgga    360
ggtggctccg gtggcggcgg aagcggcggg ggaggctcag ggggcggagg ctctggcggc    420
tcagacatcc agatgaccca atccccgtct tccctctctg cctccttggg cgggaaggtg    480
acaatcacgt gcaaaagttc ccaggatatc aataaataca tcgcctggta ccaacacaaa    540
ccaggcaaag gccctggact gctgatacat tataccagta ccttgcagcc cggcataccc    600
tctcggttca gcggcagtgg atcaggtcgc gattacagtt ttagtatttc aaatctggat    660
cctgagaata ttgcagcgta ttactgtctc cagtatgata acctgtacac atttggaggg    720
ggaacaaggc tggaa                                                     735
```

SEQ ID NO: 225          moltype = DNA   length = 957
FEATURE                 Location/Qualifiers
misc_feature            1..957
                        note = Synthetic construct
source                  1..957
                        mol_type = other DNA
                        organism = synthetic construct
SEQUENCE: 225

```
gcgcaagtct tgcgtggtac ggtgacagac ttcccaggct tcgatgaaag agcggacgcg    60
gaaacacttc gaaaggcgat gaaagggctc ggtactgacg aagagtccat tttgaccctt    120
cttacgagca ggtcaaacgc tcagaggcaa gaaatctctg cagcctttaa gacactcttt    180
ggacgtgacc ttcttgatga cctcaaatct gagctgacgg gaaagtttga gaaactcatc    240
gtagctttga tgaagcccag ccgattgtat gatgcttacg aactgaaaca cgccctgaaa    300
ggagcgggaa cgaacgagaa agtttttgact gagatcatcg catcgcggac cccggaagag    360
ctcagagcca tcaaacaagt ctacgaggag gagtacggat cgtcattgga agatgacgtg    420
gtgggggata cgtcgggtta ctaccaacga atgcttgtcg tgcttttgca ggcaaatcgc    480
gacccggatg cggggatcga cgaggcccaa gtggagcaag atgcgcaagc actcttccag    540
gccggtgaac tcaaatgggg gaccgatgaa gagaagttta tcaccatctt ggcacgagg    600
agtgtaagtc atctgcgtaa agtattcgat aagtatatga caatctcagg gtttcagatt    660
gaggagacaa ttgacaggga aacctccggt aacttggagc agctcttgct tgccgtcgtc    720
aagtccattc gctcgatccc tgcgtatctg gctgaaacac tgtattacgc catgaaaggg    780
gcaggcactg atgaccacac cttgattaga gttatggtgt cgcgatcaga aattgacttg    840
ttcaatatcc ggaaagagtt ccggaagaat ttcgcaacga gcctctatag catgatcaaa    900
ggggacactt cgggagatta caagaaagcg ttgctccttc tttgtggaga ggatgac      957
```

SEQ ID NO: 226          moltype = DNA   length = 957
FEATURE                 Location/Qualifiers
misc_feature            1..957
                        note = Synthetic construct
source                  1..957
                        mol_type = other DNA
                        organism = synthetic construct
SEQUENCE: 226

```
gctcaagtgc taaggggaac tgttactgat tttccaggtt ttgatgaaag agcagatgct    60
gagactttaa ggaaagctat gaaaggattg ggtacagacg aggaatccat tttgacacta    120
ttgcatcac gaagtaacgc ccagagacaa gagatctcag cagctttcaa aaccctgttc    180
ggaagagatt tgcttgacga tttgaagtct gagttgactg gtaagtttga aaaactaata    240
gttgccctga tgaagccttc cagactttat gatgcttacg aacttaagca cgctttgaaa    300
ggggctggaa caaatgaaaa agttttgact gagataatcg catcacgtac ccctgaggaa    360
ctaagagcca ttaagcaggt atatgaagag gaatacggta gttccttaga ggacgacgtc    420
gttggtgaca catctggtta ctatcagagg atgttggttg tcttgttgca agctaatagg    480
gatcctgatg ctggcatcga tgaagcccaa gtagagcagg acgcccaagc cctgtttcaa    540
gcaggcgaat tgaagtgggg aacggacgaa gagaagttta tcaccatctt cggaactcgt    600
tctgtatctc atcttagaaa agtattcgac aaatacatga cgatttctgg ttttcaaatt    660
gaggagacta ttgatagaga gacgtctgga aacttagaac agcttttgct tgccgtcgtt    720
aagtctataa ggagtattcc agcctactta gctgaaacct tgtactacgc catgaagggt    780
gctggaactg atgatcatac cttgatacga gttatggtaa gtcgatcaga gattgatttg    840
tttaacatta ggaaggagtt caggaaaaac tttgctacct cattgtattc catgataaag    900
ggtgatactt caggtgatta caaaaaggct ctgctttgc tgtgtggcga ggacgat       957
```

SEQ ID NO: 227          moltype = DNA   length = 957
FEATURE                 Location/Qualifiers
misc_feature            1..957
                        note = Synthetic construct
source                  1..957
                        mol_type = other DNA
                        organism = synthetic construct
SEQUENCE: 227

```
gctcaagttt tgaggggaac cgttaccgac ttcccaggtt ttgacgaaag agccgacgca    60
gaaacattaa ggaaagccat gaagggctta ggcaccgatg aggagtccat tctgacactg    120
ttgacttccc gatccaatgc ccaaaggcag gagatttcag ccgctttcaa gactttgttt    180
ggtagagatc ttctggacga cctgaaatca gaactgactg gaaagtttga gaaacttatt    240
gttgctttga tgaagccttc aagactatat gacgcatacg agttgaaaca tgcattgaaa    300
ggtgcaggaa ctaatgaaaa agtgttaact gagatcattg cttccagaac accagaagag    360
cttcgtgcta tcaaacaagt gtatgaagag gaatacggat caagtctgga agatgacgtt    420
gttggtgata cctcagggta ttaccaaagg atgcttgtcg ttctattaca agctaatcga    480
gatcctgacg ccggaatcga tgaagctcaa gttgaacaag atgctcaggc tcttttttcaa    540
gccggtgaat tgaagtgggg gactgatgag gaaaagttta tcacgatctt tggtactaga    600
tctgttagtc atttgagaaa agtatttgac aaatacatga ccatttctgg ctttcaaata    660
gaagagacta ttgataggga aacttccggt aacttggaac aactgttgtt agctgtggtc    720
```

```
aagagtataa gatcaattcc agcttactta gctgaaactc tgtattacgc aatgaaagga   780
gcaggcacag acgatcacac gttgatccga gtcatggttt ccagatcaga gattgacttg   840
ttcaatatca ggaaggaatt caggaaaaac tttgcaacct ctttgtactc catgatcaaa   900
ggtgatactt ccggtgatta caaaaaggct ttgttgttgt tatgtggaga ggatgac      957

SEQ ID NO: 228         moltype = DNA  length = 957
FEATURE                Location/Qualifiers
misc_feature           1..957
                       note = Synthetic construct
source                 1..957
                       mol_type = other DNA
                       organism = synthetic construct
SEQUENCE: 228
gcgcaagtct tgcgtggtac ggtgacagac ttcccaggct tcgatgaaag agcggacgcg   60
gaaacacttc gaaaggcgat gaaagggctc ggtactgacg aagagtccat tttgaccctt   120
cttacgagca ggtcaaacgc tcagaggcaa gaaatctctg cagcctttaa gacactcttt   180
ggacgtgacc ttcttgatga cctcaaatct gagctgacgg gaaagtttga gaaactcatc   240
gtagctttga tgaagcccag ccgattgtat gatgcttacg aactgaaaca cgccctgaaa   300
ggagcgggaa cgaacgagaa agttttgact gagatcatcg catcgcggac cccggaagag   360
ctcagagcca tcaaacaagt ctacgaggag gagtacggat cgtcattgga agatgacgtg   420
gtgggggata cgtcgggtta ctaccaacga atgcttgtcg tgcttttgca ggcaaatcgc   480
gacccggatg cggggatcga cgaggcccaa gtggagcaag atcgcgaagc actcttccag   540
gccggtgaac tcaaatgggg gaccgatgaa gagaagttta tcaccatctt ggcacgagg    600
agtgtaagtc atctgcgtaa agtattcgat aagtatatga caatctcagg gtttcagatt   660
gaggagacaa ttgacaggga aacctccggt aacttggagc agctcttgct tgccgtcgtc   720
aagtccattc gctcgatccc tgcgtatctg gctgaaacac tgtattacga catgaaaggt   780
gcaggcactg atgaccacac cttgattaga gttatggtgt cgcgatcaga aattgacttg   840
ttcaatatcc ggaaagagtt ccggaagaat ttcgcaacga gcctctatag catgatcaaa   900
ggggacactt cgggagatta caagaaagcg ttgctccttc tttcaggaga ggatgac      957

SEQ ID NO: 229         moltype = DNA  length = 957
FEATURE                Location/Qualifiers
misc_feature           1..957
                       note = Synthetic construct
source                 1..957
                       mol_type = other DNA
                       organism = synthetic construct
SEQUENCE: 229
gctcaagtgc taaggggaac tgttactgat tttccaggtt ttgatgaaag agcagatgct   60
gagactttaa ggaaagctat gaaaggattg ggtacagacg aggaatccat tttgacacta   120
ttgcatcac gaagtaacgc ccagagacaa gagatctcag cagctttcaa aaccctgttc    180
ggaagagatt tgcttgacga tttgaagtct gagttgactg gtaagtttga aaaactaata   240
gttgccctga tgaagccttc cagactttat gatgcttacg aacttaagca cgctttgaaa   300
ggggctggaa caaatgaaaa agttttgact gagataatcg catcacgtac ccctgaggaa   360
ctaagagcca ttaagcaggt atatgaagag gaatacggta gttccttaga ggacgacgtc   420
gttggtgaca catctggtta ctatcagagg atgttggttg tcttgttgca agctaatagg   480
gatcctgatg ctggcatcga tgaagcccaa gtagagcaag acgcccaagc cctgtttcaa   540
gcaggcgaat tgaagtgggg aacggacgaa gagaagttta tcaccatctt cggaactcgt   600
tctgtatctc atcttagaaa agtattcgac aaatacatga cgatttctgg tttttcaaatt  660
gaggagacta ttgatagagc tacgtctgga aacttagaac agcttttgct tgccgtcgtt   720
aagtctataa ggagtattcc agcctactta gctgaaacct tgtactacgc catgaaaggt   780
gctggaactg atgatcatac cttgatacga gttatggtaa gtcgatcaga gattgatttg   840
tttaacatta ggaaggagtt caggaaaaac tttgctacct cattgtattc catgataaag   900
ggtgatactt caggtgatta caaaaaggct ctgctttgc tgtgtggcga ggacgat       957

SEQ ID NO: 230         moltype = DNA  length = 957
FEATURE                Location/Qualifiers
misc_feature           1..957
                       note = Synthetic construct
source                 1..957
                       mol_type = other DNA
                       organism = synthetic construct
SEQUENCE: 230
gctcaagttt tgaggggaac cgttaccgac ttcccaggtt ttgacgaaag agccgacgca   60
gaaacattaa ggaaagccat gaagggctta ggcaccgatg aggagtccat tctgacactg   120
ttgacttccc gatccaatgc ccaaaggcag gagatttcag ccgctttcaa gactttgttt   180
ggtagagatc ttctggacga cctgaaatca gaactgactg gaaagtttga gaaacttatt   240
gttgctttga tgaagccttc aagactatat gacgcatacg agttgaaaca tgcattgaaa   300
ggtgcaggaa ctaatgaaaa agtgttaact gagatcattg cttccagaac accagaagag   360
cttcgtgcta tcaaacaagt gtatgaagag gaatacggat caagtctgga agatgacgtt   420
gttggtgata cctcagggta ttaccaaagg atgcttgtcg ttctattaca gctaatcga   480
gatcctgacg ccggaatcga tgaagctcaa gttgaacaag atgctcaggc tctttttcaa   540
gccggtgaat tgaagtgggg gactgatgag gaaaagttta tcacgatctt tggtactaga   600
tctgttagtc atttgagaaa agtatttgac aaatacatga catttctgg ctttcaaata    660
gaagagacta ttgatagggc cacttccggt aacttggaac aactgttgtt agctgtggtc   720
aagagtataa gatcaattcc agcttactta gctgaaactc tgtattacgc aatgaaagga   780
gcaggcacag acgatcacac gttgatccga gtcatggttt ccagatcaga gattgacttg   840
ttcaatatca ggaaggaatt caggaaaaac tttgcaacct ctttgtactc catgatcaaa   900
ggtgatactt ccggtgatta caaaaaggct ttgttgttgt tatgtggaga ggatgac      957
```

-continued

```
SEQ ID NO: 231          moltype = DNA  length = 957
FEATURE                 Location/Qualifiers
misc_feature            1..957
                        note = Synthetic construct
source                  1..957
                        mol_type = other DNA
                        organism = synthetic construct
SEQUENCE: 231
gctcaagtgc taaggggaac tgttactgat tttccaggtt ttgatgaaag agcagatgct  60
gagactttaa ggaaagctat gaaaggattg ggtacagacg aggaatccat tttgacacta  120
ttgacatcac gaagtaacgc ccagagacaa gagatctcag cagctttcaa aaccctgttc  180
ggaagagatt tgcttgacga tttgaagtct gagttgactg gtaagtttga aaaactaata  240
gttgccctga tgaagccttc cagactttat gatgcttacg aacttaagca cgctttgaaa  300
ggggctggaa caaatgaaaa agtttttgact gagataatcg catcacgtac ccctgaggaa  360
ctaagagcca ttaagcaggt atatgaagag gaatacggta gttccttaga ggacgacgtc  420
gttggtaaca catctggtta ctatcagagg atgttggttg tcttgttgca agctaatagg  480
gatcctgatg ctggcatcga tgaagcccaa gtagagcagg acgcccaagc cctgtttcaa  540
gcaggcgaat tgaagtgggg aacggacgaa gagaagttta tcaccatctt cggaactcgt  600
tctgtatctc atcttagaaa agtattcgac aaatacatga cgatttctgg ttttcaaatt  660
gaggagacta ttgatagagc tacgtctgga aacttagaac agcttttgct tgccgtcgtt  720
aagtctataa ggagtattcc agcctactta gctgaaacct tgtactacgc catgaagggt  780
gctggaactg atgatcatac cttgatacga gttatggtaa gtcgatcaga gattgatttg  840
tttaacatta ggaaggagtt caggaaaaac tttgctacct cattgtattc catgataaag  900
ggtgatactt caggtgatta caaaaaggct ctgctttttgc tgtgtggcga ggacgat      957

SEQ ID NO: 232          moltype = DNA  length = 957
FEATURE                 Location/Qualifiers
misc_feature            1..957
                        note = Synthetic construct
source                  1..957
                        mol_type = other DNA
                        organism = synthetic construct
SEQUENCE: 232
gctcaagttt tgaggggaac cgttaccgac ttcccaggtt ttgacgaaag agccgacgca  60
gaaacattaa ggaaagccat gaagggctta ggcaccgatg aggagtccat tctgacactg  120
ttgacttccc gatccaatgc ccaaaggcag gagatttcag ccgctttcaa gactttgttt  180
ggtagagatc ttctggacga cctgaaatca gaactgactg gaaagtttga gaaacttatt  240
gttgctttga tgaagccttc aagactatat gacgcatacg agttgaaaca tgcattgaaa  300
ggtgcaggaa ctaatgaaaa agtgttaact gagatcattg cttccagaac accagaaagg  360
cttcgtgcta tcaaacaagt gtatgaagag gaatacggat caagtctgga agatgacgtt  420
gttggtaata cctcagggta ttaccaaagg atgcttgtcg ttctattaca agctaatcga  480
gatcctgacg ccggaatcga tgaagctcaa gttgaacaag atgctcaggc tcttttttcaa  540
gccggtgaat tgaagtgggg gactgatgag gaaaagttta tcacgatctt tggtactaga  600
tctgttagtc atttgagaaa agtatttgac aaatacatga ccatttctgg ctttcaaata  660
gaagagacta ttgataggggc cacttccggt aacttggaac aactgttgtt agctgtggtc  720
aagagtataa gatcaattcc agcttactta gctgaaacct tgtattacgc aatgaaaagga  780
gcaggcacag acgatcacac gttgatccga gtcatggttt ccagatcaga gattgacttg  840
ttcaatatca ggaaggaatt caggaaaaac tttgcaacct ctttgtactc catgatcaaa  900
ggtgatactt ccggtgatta caaaaaggct ttgttgttgt tatgtggaga ggatgac      957

SEQ ID NO: 233          moltype = DNA  length = 957
FEATURE                 Location/Qualifiers
misc_feature            1..957
                        note = Synthetic construct
source                  1..957
                        mol_type = other DNA
                        organism = synthetic construct
SEQUENCE: 233
gctcaagtgc taaggggaac tgttactgat tttccaggtt ttgatgaaag agcagatgct  60
gagactttaa ggaaagctat gaaaggattg ggtacagacg aggaatccat tttgacacta  120
ttgacatcac gaagtaacgc ccagagacaa gagatctcag cagctttcaa aaccctgttc  180
ggaagagatt tgcttgacga tttgaagtct gatttgactg gtaagtttga aaaactaata  240
gttgccctga tgaagccttc cagactttat gatgcttacg aacttaagca cgctttgaaa  300
ggggctggaa caaatgaaaa agtttttgact gagataatcg catcacgtac ccctgaggaa  360
ctaagagcca ttaagcaggt atatgaagag gaatacggta gttccttaga ggacgacgtc  420
gttggtaaca catctggtta ctatcagagg atgttggttg tcttgttgca agctaatagg  480
gatcctgatg ctggcatcga tgaagcccaa gtagagcagg acgcccaagc cctgtttcaa  540
gcaggcgaat tgaagtgggg aacggacgaa gagaagttta tcaccatctt cggaactcgt  600
tctgtatctc atcttagaaa agtattcgac aaatacatga cgatttctgg ttttcaaatt  660
gaggagacta ttgatagagc tacgtctgga aacttagaac agcttttgct tgccgtcgtt  720
aagtctataa ggagtattcc agcctactta gctgaacct tgtactacgc catgaagggt  780
gctggaactg atgatcatac cttgatacga gttatggtaa gtcgatcaga gattgatttg  840
tttaacatta ggaaggagtt caggaaaaac tttgctacct cattgtattc catgataaag  900
ggtaacactt caggtgatta caaaaaggct ctgctttttgc tgtgtggcga ggacgat      957

SEQ ID NO: 234          moltype = DNA  length = 957
FEATURE                 Location/Qualifiers
misc_feature            1..957
```

-continued

```
                              note = Synthetic construct
source                        1..957
                              mol_type = other DNA
                              organism = synthetic construct
SEQUENCE: 234
gctcaagttt tgaggggaac cgttaccgac ttcccaggtt ttgacgaaag agccgacgca  60
gaaacattaa ggaaagccat gaagggctta ggcaccgatg aggagtccat tctgacactg  120
ttgacttccc gatccaatgc ccaaaggcag gagatttcag ccgctttcaa gactttgttt  180
ggtagagatc ttctggacga cctgaaatca gatctgactg gaaagtttga gaaacttatt  240
gttgctttga tgaagccttc aagactatat gacgcatacg agttgaaaca tgcattgaaa  300
ggtgcaggaa ctaatgaaaa agtgttaact gagatcattg cttccagaac accagaagag  360
cttcgtgcta tcaaacaagt gtatgaagag gaatacggat caagtctgga agatgacgtt  420
gttggtaata cctcagggta ttaccaaagg atgcttgtcg ttctattaca agctaatcga  480
gatcctgacg ccggaatcga tgaagctcaa gttgaacaag atgctcaggc tcttttttcaa  540
gccggtgaat tgaagtgggg gactgatgag gaaaagttta tcacgatctt tggtactaga  600
tctgttagtc atttgagaaa agtatttgac aaatacatga ccatttctgg ctttcaaata  660
gaagagacta ttgatagggc cacttccggt aacttggaac aactgttgtt agctgtggtc  720
aagagtataa gatcaattcc agcttactta gctgaaactc tgtattacgc aatgaaagga  780
gcaggcacag acgatcacac gttgatccga gtcatggttt ccagatcaga gattgacttg  840
ttcaatatca ggaaggaatt caggaaaaac tttgcaacct ctttgtactc catgatcaaa  900
ggtaatactt ccggtgatta caaaaaggct ttgttgttgt tatgtggaga ggatgac     957

SEQ ID NO: 235             moltype = DNA   length = 384
FEATURE                    Location/Qualifiers
misc_feature               1..384
                           note = Synthetic construct
source                     1..384
                           mol_type = other DNA
                           organism = synthetic construct
SEQUENCE: 235
gaaaagctgg gaaagctgca atacagtttg gactacgatt tccaaaacaa tcagttgctc  60
gtcggcatta tccaggctgc cgaattgcca gctttagata tgggtggtac atcagatccc  120
tacgtcaaag tatttctact gcctgacaaa aagaaaaagt ttgaaactaa ggtgcacaga  180
aaaacgctta acccagtttt caacgagcag tttacattca aagttcctta ttctgaactt  240
ggaggaaaaa ctctagtgat ggccgtttat gatttcgata ggttttctaa gcatgacatc  300
ataggggagt ttaaggtccc aatgaatact gttgatttcg gtcatgtgac cgaggaatgg  360
cgtgaccttc aatccgcaga gaaa                                         384

SEQ ID NO: 236             moltype = DNA   length = 762
FEATURE                    Location/Qualifiers
misc_feature               1..762
                           note = Synthetic construct
source                     1..762
                           mol_type = other DNA
                           organism = synthetic construct
SEQUENCE: 236
caggtgcagc tcgtccagag cggcgccgag gtgaagaagc caggcgagtc cctgaagatc  60
tcctgtaagg gctccggcta cagcttcacc tcctactgga tcgcttgggt gaggcagatg  120
ccaggaaagg gactggagta catgggcctg atctaccctg gcgactccga caccaagtac  180
tccccatcct tccagggcca ggtgaccatc agcgtggaca agtccgtgtc taccgcctac  240
ctgcaatggt cctccctgaa gccttctgac tctgccgtgt actttgtgc cggggccgtt  300
gtgggctact gcaccgaccg gacatgtgcc aaggcccccg cgtggctggg agtgtgggga  360
caggaaacac tggtgacagt gagttctggc ggtggcggct cttccggcgg tggctctggt  420
ggcggcggat ctcagagcgt gctgacacag ccacctagcg tgtccgctgc ccctggccag  480
aaggtgacaa tcagctgctc cggcagctct tccaacaacg gcaacaacta cgtgtcttgg  540
tatcagcagc tgcccggaac agctccaaaa ctgctgatct atgaccacac caatcggcct  600
gccggcgtgc cagatcggtt ctctggctct aagagcggca cctccgccag cctggctatc  660
tctggcttca gatctgagga tgaggctgac tactattgtg cctcctggga ctacaccctg  720
tctggctggg tgttcggcgg tggcaccaag ctgacagtcc tg                    762

SEQ ID NO: 237             moltype = DNA   length = 762
FEATURE                    Location/Qualifiers
misc_feature               1..762
                           note = Synthetic construct
source                     1..762
                           mol_type = other DNA
                           organism = synthetic construct
SEQUENCE: 237
caagtccagc tggtccagtc aggggcagaa gtcaaaaagc ctggtgaatc tctgaaaatc  60
tcatgtaaag gctctggata tagtttttacc tcatattgga tagcttgggt tcgtcaaatg  120
cctggtaaag gtttggagta catgggtcta atctacccag gcgattcgga tacaaagtac  180
tctccctctt ttcaaggtca agtcactata tccgtagata agtccgtatc caccgcatac  240
ctacaatggt catctttgaa gccttctgat tctgccgtct acttctgcgc tagggctgat  300
gttggttatt gtaccgatag gacatgtgct aaggctcccg cttggctggg ggtgtggggt  360
caaggcacct ggttacagt gtcctctggc ggaggtggtt cgtcaggagg cggttctggt  420
ggtggcggct cccaatcagt attgacccag ccccttctg tctccgctgc tccagggcaa  480
aaggtcacca tcagttgctc tggtagttcc tctaacattg gtaacaatta cgtcagctgg  540
tatcagcagt taccaggtac tgcaccaaag ctgttgatct acgaccacac caacagaccc  600
gctggtgtcc cagataggtt ttctggatca aaatctggca cttcagctag tcttgctatc  660
```

-continued
```
tctggatttc gttccgagga tgaagccgat tactactgcg cttcatggga ttacactcta    720
tcaggctggg tgtttggcgg aggcactaaa ctgacagtgc tt                       762

SEQ ID NO: 238          moltype = DNA   length = 57
FEATURE                 Location/Qualifiers
misc_feature            1..57
                        note = Synthetic construct
regulatory              1..57
                        note = Synthetic construct
                        regulatory_class = other
source                  1..57
                        mol_type = other DNA
                        organism = synthetic construct
SEQUENCE: 238
atgggctggt ctctgatcct gctgttcctg gtggccgtgg ccacgcgtgt gctgtcc       57

SEQ ID NO: 239          moltype = DNA   length = 258
FEATURE                 Location/Qualifiers
misc_feature            1..258
                        note = Synthetic construct
regulatory              1..258
                        note = Synthetic construct
                        regulatory_class = other
source                  1..258
                        mol_type = other DNA
                        organism = synthetic construct
SEQUENCE: 239
atgatgagat ttccttcaat ttttactgcc gttttattcg cagcatcctc cgcattagct    60
gctccagtca acactacaac agaagatgaa acggcacaaa ttccggctga agctgtcatc    120
ggttactcag atttagaagg ggatttcgat gttgctgttt tgccattttc caacagcaca    180
aataacgggt tattgtttat aaatactact attgccagca ttgctgctaa agaagaaggg    240
gtatctctcg ataaaaga                                                  258

SEQ ID NO: 240          moltype = DNA   length = 255
FEATURE                 Location/Qualifiers
misc_feature            1..255
                        note = Synthetic construct
regulatory              1..255
                        note = Synthetic construct
                        regulatory_class = other
source                  1..255
                        mol_type = other DNA
                        organism = synthetic construct
SEQUENCE: 240
atgagatttc cttcaatttt tacagcagtt ttattcgcag catcctccgc attagccgct    60
ccagccaaca ccacgacaga ggatgaaacg gcacaaattc cggccgaggc tgtcatcgat    120
tactcagatc tagaagggga tttcgatgct gctgctctgc cactttccaa cagcacaaat    180
aacgggttat cgtctacaaa tactactatt gccagcattg ctgctaaaga agaaggggta    240
cagctggata aaaga                                                     255

SEQ ID NO: 241          moltype = DNA   length = 54
FEATURE                 Location/Qualifiers
misc_feature            1..54
                        note = Synthetic construct
regulatory              1..54
                        note = Synthetic construct
                        regulatory_class = other
source                  1..54
                        mol_type = other DNA
                        organism = synthetic construct
SEQUENCE: 241
atgcagttac ttcgctgttt ttcaatattt tctgttattg cttcagtttt agca          54

SEQ ID NO: 242          moltype = DNA   length = 60
FEATURE                 Location/Qualifiers
misc_feature            1..60
                        note = Synthetic construct
regulatory              1..60
                        note = Synthetic construct
                        regulatory_class = other
source                  1..60
                        mol_type = other DNA
                        organism = synthetic construct
SEQUENCE: 242
atgatgcttt tgcaagcctt ccttttcctt ttggctggtt ttgcagccaa aatatctgcg    60

SEQ ID NO: 243          moltype = DNA   length = 114
FEATURE                 Location/Qualifiers
misc_feature            1..114
```

```
                          note = Synthetic construct
regulatory                1..114
                          note = Synthetic construct
                          regulatory_class = other
source                    1..114
                          mol_type = other DNA
                          organism = synthetic construct
SEQUENCE: 243
atgaaagtcc tgattgtgct acttgcgatt ttcgctgcac taccgcttgc gctggcgcag    60
ccagtgatta gcaccactgt aggcagcgct gctgaaggta gcctggataa aaga          114

SEQ ID NO: 244            moltype = AA  length = 85
FEATURE                   Location/Qualifiers
REGION                    1..85
                          note = Synthetic construct
PEPTIDE                   1..85
source                    1..85
                          mol_type = protein
                          organism = synthetic construct
SEQUENCE: 244
MRFPSIFTAV LFAASSALAA PVNTTTEDET AQIPAEAVIG YSDLEGDFDV AVLPFSNSTN     60
NGLLFINTTI ASIAAKEEGV SLEKR                                          85

SEQ ID NO: 245            moltype = DNA  length = 255
FEATURE                   Location/Qualifiers
misc_feature              1..255
                          note = Synthetic construct
regulatory                1..255
                          note = Synthetic construct
                          regulatory_class = other
source                    1..255
                          mol_type = other DNA
                          organism = synthetic construct
SEQUENCE: 245
atgagatttc cttcaatttt tactgctgtt ttattcgcag catcctccgc attagctgct    60
ccagtcaaca ctacaacaga agatgaaacg gcacaaattc cggctgaagc tgtcatcggt   120
tactcagatt tagaagggga tttcgatgtt gctgttttgc catttccaa cagcacaaat    180
aacgggttat tgtttataaa tactactatt gccagcattg ctgctaaaga agaaggggta   240
tctctcgaga aaagg                                                    255

SEQ ID NO: 246            moltype = AA  length = 927
FEATURE                   Location/Qualifiers
REGION                    1..927
                          note = Synthetic construct
source                    1..927
                          mol_type = protein
                          organism = synthetic construct
SEQUENCE: 246
QVQLVQSGAE VKKPGESLKI SCKGSGYSFT SYWIAWVRQM PGKGLEYMGL IYPGDSDTKY     60
SPSFQGQVTI SVDKSVSTAY LQWSSLKPSD SAVYFCARAD VGYCTDRTCA KAPAWLGVWG    120
QGTLVTVSSG GGGSSGGGSG GGGSQSVLTQ PPSVSAAPGQ KVTISCSGSS SNIGNNYVSW    180
YQQLPGTAPK LLIYDHTNRP AGVPDRFSGS KSGTSASLAI SGFRSEDEAD YYCASWDYTL    240
SGWVFGGGTK LTVLGAASDA HKSEVAHRFK DLGEENFKAL VLIAFAQYLQ QSPFEDHVKL    300
VNEVTEFAKT CVADESAENC DKSLHTLFGD KLCTVATLRE TYGEMADCCA KQEPERNECF    360
LQHKDDNPNL PRLVRPEVDV MCTAFHDNEE TFLKKYLYEI ARRHPYFYAP ELLFFAKRYK    420
AAFTECCQAA DKAACLLPKL DELRDEGKAS SAKQRLKCAS LQKFGERAFK AWAVARLSQR    480
FPKAEFAEVS KLVTDLTKVH TECCHGDLLE CADDRADLAK YICENQDSIS SKLKECCEKP    540
LLEKSHCIAE VENDEMPADL PSLAADFVES KDVCKNYAEA KDVFLGMFLY EYARRHPDYS    600
VVLLLRLAKT YETTLEKCCA AADPHECYAK VFDEFKPLVE EPQNLIKQNC ELFEQLGEYK    660
FQNALLVRYT KKVPQVSTPT LVEVSRNLGK VGSKCCKHPE AKRMPCAEDY LSVVLNQLCV    720
LHEKTPVSDR VTKCCTESLV NRRPCFSALE VDETYVPKEF QAETFTFHAD ICTLSEKERQ    780
IKKQTALVEL VKHKPKATKE QLKAVMDDFA AFVEKCCKAD DKETCFAEEG KKLVAASQAA    840
LGLAAALQGP ETLCGAELVD ALQFVCGDRG FYFNKPTGYG SSSRRAPQTG IVDECCFRSC    900
DLRRLEMYCA PLKPAKSAGG SHHHHHH                                        927

SEQ ID NO: 247            moltype = DNA  length = 2787
FEATURE                   Location/Qualifiers
misc_feature              1..2787
                          note = Synthetic construct
source                    1..2787
                          mol_type = other DNA
                          organism = synthetic construct
SEQUENCE: 247
caggtgcagc tcgtccagag cggcgccgag gtgaagaagc caggcgagtc cctgaagatc    60
tcctgtaagg gctccggcta cagcttcacc tcctactgga tcgcttgggt gaggcagatg   120
ccaggaaagg gactggagta catgggcctg atctaccctg gcgactccga caccaagtac   180
tccccatcct tccagggcca ggtgaccatc agcgtggaca gtccgtgtc taccgcctac    240
ctgcaatggt cctccctgaa gccttctgac tctgccgtgt actttttgtgc ccgggccgat   300
gtgggctact gcaccgaccg gacatgtgcc aaggcccccg cgtggctggg agtgtgggga   360
```

```
cagggaacac tggtgacagt gagttctggc ggtggcggct cttccggcgg tggctctggt    420
ggcggcggat ctcagagcgt gctgacacag ccacctagcg tgtccgctgc ccctggccag    480
aaggtgacaa tcagctgctc cggcagctct tccaacatcg gcaacaacta cgtgtcttgg    540
tatcagcagc tgcccggaac agctccaaaa ctgctgatct atgaccacac caatcggcct    600
gccggccgtgc cagatcggtt ctctggctct aagagcggca cctccgccag cctggctatc    660
tctggcttca gatctgagga tgaggctgac tactattgtg cctcctggga ctacaccctg    720
tctggctggg tgttcggcgg tggcaccaag ctgacagtcc tgggcgccgc ctccgacgct    780
cacaagagcg aagtggcaca taggttcaaa gatctgggcg aagagaactt taaggccctc    840
gtcctgatcg ctttcgcaca gtacctccag cagtctccct tgaagatca cgtgaaactg    900
gtcaatgagg tgaccgaatt tgccaagaca tgcgtggctg atgagagtgc agaaaactgt    960
gacaaatcac tgcatactct ctttggagat aagctgtgca ccgtcgccac actcagagag    1020
acttatgggg aaatggctga ctgttgcgca aaacaggagc ctgaacggaa tgagtgtttc    1080
ctccagcaca aggatgacaa cccaaatctg ccccgcctcg tgcgacctga ggtcgatgtg    1140
atgtgcaccg cctttcatga caacgaagag acattcctga agaaatacct gtatgaaatt    1200
gctcgtaggc acccatactt ttatgcccoc gagctcctgt tctttgcaaa gagatacaaa    1260
gctgccttca ctgaatgttg ccaggcagct gataaggccg catgtctcct gcctaaactg    1320
gacgagctcc gggatgaagg taaggcttcc agcgccaaac agcgcctgaa gtgcgcttct    1380
ctccagaagt ttggcgagcg agcattcaaa gcctgggcgt tggcccgtct cagtcagagg    1440
tttccaaagg cagaatttgc tgaggtctca aaactggtga ccgacctcac aaaggtccat    1500
actgagtgtt gccacggaga tctgctggaa tgtgccgacg atagagcaga cctcgctaaa    1560
tatatctgcg agaatcagga ttccattagc tctaagctga agaatgttg cgagaagccc    1620
ctcctggaaa agagtcattg tatcgccgag gtggaaaacg acgagatgcc agcagatctg    1680
ccatcactcg ctgccgactt tgtggaatcc aaagatgtct gcaagaatta cgcagaggct    1740
aaagacgtgt tcctggggat gtttctgtat gagtacgccc ggcgtcaccc cgattatagc    1800
gtcgtgctcc tgctccgact ggcaaagacc tacgaaacaa ctctggagaa atgttgcgct    1860
gccgcagacc ctcatgaatg ttatgctaag gtgttcgatg agtttaagcc actcgtgga    1920
gagccccaga acctgattaa acagaattgc gaactgttcg agcagctcgg tgaatacaag    1980
tttcagaacg ccctgctcgt gcgttatacc aaaaaggtcc ctcaggtgtc tacaccaact    2040
ctggtggagg tcagtaggaa tctgggcaaa gtgggatcaa agtgttgcaa acaccccgag    2100
gcaaagagaa tgccttgtgc tgaagattac ctctccgtcg tgctgaacca gctctgcgtg    2160
ctgcatgaaa agacocccagt cagcgaccgg gtgacaaaat gttgcaccga atctctggtc    2220
aatcgccgac cctgtttcag tgccctcgaa gtggacgaaa cttatgtgcc taaggagttt    2280
caggctgaaa cattcacctt tcacgccgat atctgcactc tgtccgagaa agaaaggcag    2340
attaagaaac agacagcact gtcgagctc gtgaagcata aaccaaaggc taccaaggag    2400
cagctgaaag ccgtcatgga cgatttcgca gcttttgtgg aaaagtgttg caaagccgac    2460
gataaggaga cttgtttcgc agaagagggg aaaaagctcg tggctgccag ccaggcagct    2520
ctgggtctgg ccgcagctct gcagggccca gaaacacttt gtggagccga actggtggat    2580
gctctccaat tcgtttgcgg cgaccgcgga ttctacttta caagcccac cggttacggg    2640
tcttcaagcc ggagggcccc gcagactggc atcgtcgacg agtgctgttt tagaagctgc    2700
gatctgcgac ggttggagat gtattgtgca cctctgaagc ccgcgaaaag tgctggggc    2760
tcccaccatc accatcacca ctagtga                                        2787
```

```
SEQ ID NO: 248          moltype = AA  length = 1032
FEATURE                 Location/Qualifiers
REGION                  1..1032
                        note = Synthetic construct
source                  1..1032
                        mol_type = protein
                        organism = synthetic construct
SEQUENCE: 248
QVQLVQSGAE VKKPGESLKI SCKGSGYSFT SYWIAWVRQM PGKGLEYMGL IYPGDSDTKY    60
SPSFQGQVTI SVDKSVSTAY LQWSSLKPSD SAVYFCARAD VGYCTDRTCA KAPAWLGVWG   120
QGTLVTVSSG GGGSSGGGSG GGGSQSVLTQ PPSVSAAPGQ KVTISCSGSS SNIGNNYVSW   180
YQQLPGTAPK LLIYDHTNRP AGVPDRFSGS KSGTSASLAI SGFRSEDEAD YYCASWDYTL   240
SGWVFGGGTK LTVLGAASDA HKSEVAHRFK DLGEENFKAL VLIAFAQYLQ QSPFEDHVKL   300
VNEVTEFAKT CVADESAENC DKSLHTLFGD KLCTVATLRE TYGEMADCCA KQEPERNECF   360
LQHKDDNPNL PRLVRPEVDV MCTAFHDNEE TFLKKYLYEI ARRHPYFYAP ELLFFAKRYK   420
AAFTECCQAA DKAACLLPKL DELRDEGKAS SAKQRLKCAS LQKFGERAFK AWAVARLSQR   480
FPKAEFAEVS KLVTDLTKVH TECCHGDLLE CADDRADLAK YICENQDSIS SKLKECCEKP   540
LLEKSHCIAE VENDEMPADL PSLAADFVES KDVCKNYAEA KDVFLGMFLY EYARRHPDYS   600
VVLLLRLAKT YETTLEKCCA AADPHECYAK VFDEFKPLVE EPQNLIKQNC ELFEQLGEYK   660
FQNALLVRYT KKVPQVSTPT LVEVSRNLGK VGSKCCKHPE AKRMPCAEDY LSVVLNQLCV   720
LHEKTPVSDR VTKCCTESLV NRRPCFSALE VDETYVPKEF QAETFTFHAD ICTLSEKERQ   780
IKKQTALVEL VKHKPKATKE QLKAVMDDFA AFVEKCCKAD DKETCFAEEG KKLVAASQAA   840
LGLAAALQQR KRRNTIHEFK KSAKTTLIKI DPALKIKTKK VNTADQCANR CTRNKGLPFT   900
CKAFVFDKAR KQCLWFPFNS MSSGVKKEFG HEFDLYENKD YIRNCIIGKG RSYKGTVSIT   960
KSGIKCQPWS SMIPHEHSFL PSSYRGKDLQ ENYCRNPRGE EGGPWCFTSN PEVRYEVCDI  1020
PQCGGSHHHH HH                                                       1032
```

```
SEQ ID NO: 249          moltype = DNA  length = 3102
FEATURE                 Location/Qualifiers
misc_feature            1..3102
                        note = Synthetic construct
source                  1..3102
                        mol_type = other DNA
                        organism = synthetic construct
SEQUENCE: 249
caggtgcagc tcgtccagag cggcgccgag gtgaagaagc caggcgagtc cctgaagatc    60
tcctgtaagg gctccggcta cagcttcacc tcctactgga tcgcttgggt gaggcagatg   120
```

```
ccaggaaagg gactggagta catgggcctg atctaccctg gcgactccga caccaagtac  180
tccccatcct tccagggcca ggtgaccatc agcgtggaca agtccgtgtc taccgcctac  240
ctgcaatggt cctccctgaa gccttctgac tctgccgtgt acttttgtgc ccgggccgat  300
gtgggctact gcaccgaccg gacatgtgcc aaggcccccg cgtggctggg agtgtgggga  360
cagggaacac tggtgacagt gagttctggc ggtggcggct cttccggcgg tggctctggt  420
ggcggcggat ctcagagcgt gctgacacag ccacctagcg tgtccgctgc ccctggccaa  480
aaggtgacaa tcagctgctc cggcagctct tccaacatcg gcaacaacta cgtgtcttgg  540
tatcagcagc tgcccggaac agctccaaaa ctgctgatct atgaccacac caatcggcct  600
gccggcgtgc cagatcggtt ctctggctct aagagcggca cctccgccag cctggctatc  660
tctggcttca gatctgagga tgaggctgac tactattgtg cctcctggga ctacaccctg  720
tctggctggg tgttcggcgg tggcaccaag ctgacagtcc tgggcgccgc ctccgacgct  780
cacaagagcg aagtggcaca taggttcaaa gatctgggcg aagagaactt taaggccctc  840
gtcctgatcg ctttcgcaca gtacctccag cagtctccct ttgaagatca cgtgaaactg  900
gtcaatgagg tgaccgaatt tgccaagaca tgcgtggctg atgagagtgc agaaaactgt  960
gacaaatcac tgcatactct ctttggagat aagctgtgca ccgtcgccac actcagagag  1020
acttatgggg aaatggctga ctgttgcgca aaacaggagc ctgaacggaa tgagtgtttc  1080
ctccagcaca aggatgacaa cccaaatctg ccccgcctcg tgcgacctga ggtcgatgtg  1140
atgtgcaccg cctttcatga caacgaagag acattcctga gaaatacct gtatgaaatt  1200
gctcgtaggc acccatactt ttatgccccc gagctcctgt tctttgcaaa gagatacaaa  1260
gctgccttca ctgaatgttg ccaggcagct gataaggccg catgtctcct gcctaaactg  1320
gacgagctcc gggatgaagg taaggcttcc agcgccaaac agcgcctgaa gtgcgcttct  1380
ctccagaagt ttggcgagcg agcattcaaa gcctgggctg tggcccgtct cagtcagagg  1440
tttccaaagg cagaatttgc tgaggtctca aaactggtga ccgacctcac aaaggtccat  1500
actgagtgtt gccacggaga tctgctggaa tgtgccgacg atagagcaga cctcgctaaa  1560
tatatctgcg agaatcagga ttccattagc tctaagctga agaatgttg cgagaagccc  1620
ctcctggaaa agagtcattg tatcgccgag gtggaaaacg acgagatgcc agcagatctg  1680
ccatcactcg ctgccgactt tgtggaatcc aaagatgtct gcaagaatta cgcagaggct  1740
aaaagacgtgt tcctggggat gtttctgtat gagtacgccc ggcgtcaccc cgattatagc  1800
gtcgtgctcc tgctccgact ggcaaagacc tacgaaacaa ctctggagaa atgttgcgct  1860
gccgcagacc ctcatgaatg ttatgctaag gtgttcgatg agtttaagcc actcgtcgaa  1920
gagccccaga acctgattaa acagaattgc gaactgttcg agcagctcgg tgaatacaag  1980
tttcagaacg ccctgctcgt gcgttatacc aaaaaggtcc ctcaggtgtc tacaccaact  2040
ctggtggagg tcagtaggaa tctgggcaaa gtgggatcaa agtgttgcaa acaccccgag  2100
gcaaagagaa tgccttgtgc tgaagattac ctctccgtcg tgctgaacca gctctgcgtg  2160
ctgcatgaaa agaccccagt cagcgaccgg gtgacaaaat gttgcaccga atctctggtc  2220
aatcgccgac cctgtttcag tgccctcgaa gtggacgaaa cttatgtgcc taaggagttt  2280
caggctgaaa cattcacctt tcacgccgat atctgcactc tgtccgagaa agaaaggcag  2340
attaagaaac agacagcact ggtcgagctc gtgaagcata aaccaaaggc taccaaggag  2400
cagctgaaag ccgtcatgga cgatttcgca gcttttgtgg aaaagtgttg caaagccgac  2460
gataaggaga cttgtttcgc agaagagggg aaaaagctcg tggctgccag ccaggcagct  2520
ctgggtctgg ccgcagctct gcagcagcgg aaaaggagaa acaccattca cgagtttaag  2580
aagtccgcga agaccacact gattaagatt gatcccgccc ttaaaatcaa gacaaagaag  2640
gtgaacacgg ctgaccagtg tgctaatcgc tgcacaagga ataaaggact gccatttact  2700
tgtaaagcct ttgtattcga taaggcacgc aagcagtgcc tctggttccc tttcaattct  2760
atgagcagtg tgttaagaa agagtttggc catgaattcg acttgtacga aaacaaagat  2820
tatatccgga actgcattat cgggaaaggc cggtcttaca aaggcaccgt ctccataacc  2880
aagagtggca tcaaatgtca accctggagc tcaatgatcc cacatgaaca ctccttcctc  2940
ccaagttcat accgggggcaa ggacctgcaa gagaactatt gcagaaatcc gcgaggggaa  3000
gagggagggc cttggtgttt cacttctaat cccgaggtga ggtatgaggt gtgcgacata  3060
cctcagtgcg gtggaagcca ccatcaccac caccattagt ga  3102
```

```
SEQ ID NO: 250          moltype = AA  length = 925
FEATURE                 Location/Qualifiers
REGION                  1..925
                        note = Synthetic construct
source                  1..925
                        mol_type = protein
                        organism = synthetic construct
SEQUENCE: 250
AQVLRGTVTD FPGFDERADA ETLRKAMKGL GTDEESILTL LTSRSNAQRQ EISAAFKTLF  60
GRDLLDDLKS DLTGKFEKLI VALMKPSRLY DAYELKHALK GAGTNEKVLT EIIASRTPEE  120
LRAIKQVYEE EYGSSLEDDV VGNTSGYYQR MLVVLLQANR DPDAGIDEAQ VEQDAQALFQ  180
AGELKWGTDE EKFITIFGTR SVSHLRKVFD KYMTISGFQI EETIDRATSG NLEQLLLAVV  240
KSIRSIPAYL AETLYYAMKG AGTDDHTLIR VMVSRSEIDL FNIRKEFRKN FATSLYSMIK  300
GNTSGDYKKA LLLLCGEDDA SDAHKSEVAH RFKDLGEENF KALVLIAFAQ YLQQSPFEDH  360
VKLVNEVTEF AKTCVADESA ENCDKSLHTL FGDKLCTVAT LRETYGEMAD CCAKQEPERN  420
ECFLQHKDDN PNLPRLVRPE VDVMCTAFHD NEETFLKKYL YEIARRHPYF YAPELLFFAK  480
RYKAAFTECC QAADKAACLL PKLDELRDEG KASSAKQRLK CASLQKFGER APKAWAVARL  540
SQRFPKAEFA EVSKLVTDLT KVHTECCHGD LLECADDRAD LAKYICENQD SISSKLKECC  600
EKPLLEKSHC IAEVENDEMP ADLPSLAADF VESKDVCKNY AEAKDVFLGM FLYEYARRHP  660
DYSVVLLLRL AKTYETTLEK CCAAADPHEC YAKVFDEFKP LVEEPQNLIK QNCELFEQLG  720
EYKFQNALLV RYTKKVPQVS TPTLVEVSRN LGKVGSKCCK HPEAKRMPCA EDYLSVVLNQ  780
LCVLHEKTPV SDRVTKCCTE SLVNRRPCFS ALEVDETYVP KEFQAETFTF HADICTLSEK  840
ERQIKKQTAL VELVKHKPKA TKEQLKAVMD DFAAFVEKCC KADDKETCFA EEGKKLVAAS  900
QAALGLAAAT GGGSGGSGGH HHHH                                          925
```

```
SEQ ID NO: 251          moltype = DNA  length = 2781
FEATURE                 Location/Qualifiers
misc_feature            1..2781
```

```
                        note = Synthetic construct
source                  1..2781
                        mol_type = other DNA
                        organism = synthetic construct
SEQUENCE: 251
gctcaagtgc taaggggaac tgttactgat tttccaggtt ttgatgaaag agcagatgct   60
gagactttaa ggaaagctat gaaaggattg ggtacagacg aggaatccat tttgacacta   120
ttgcatcac gaagtaacgc ccagagacaa gagatctcag cagcttttcaa aaccctgttc   180
ggaagagatt tgcttgacga tttgaagtct gatttgactg gtaagtttga aaaactaata   240
gttgccctga tgaagccttc cagactttat gatgcttacg aacttaagca cgctttgaaa   300
ggggctggaa caaatgaaaa agttttgact gagataatcg catcacgtac ccctgaggaa   360
ctaagagcca ttaagcaggt atatgaagag gaatacggta gttccttaga ggacgacgtc   420
gttggtaaca catctggtta ctatcagagg atgttggttg tcttgttgca agctaatagg   480
gatcctgatg ctggcatcga tgaagcccaa gtagagcagg acgcccaagc cctgtttcaa   540
gcaggcgaat tgaagtgggg aacggacgaa gagaagttta tcaccatctt cggaactcgt   600
tctgtatctc atcttagaaa agtattcgac aaatacatga cgatttctgg tttttcaaatt   660
gaggagacta ttgatagagc tacgtctgga aacttagaac agctttttgct tgccgtcgtt   720
aagtctataa ggagtattcc agcctactta gctgaaacct tgtactacgc catgaagggt   780
gctggaactg atgatcatac cttgatacga gttatggtaa gtcgatcaga gattgatttg   840
tttaacatta ggaaggagtt caggaaaaac tttgctacct cattgtattc catgataaag   900
ggtaacactt caggtgatta caaaaaggct ctgctttttgc tgtgtggcga ggacgatgct   960
agcgatgctc acaaatctga agtcgctcat cgtttcaaag acttgggtga ggaaaacttt   1020
aaggctttag ttctgattgc ttttgcccaa tatcttcaac aatcaccatt cgaagatcat   1080
gtgaaacttg ttaacgaagt taccgaattt gcaaaaacgt gtgtggcaga cgaaagtgcc   1140
gaaaactgtg acaaatcatt acacactttg ttcggtgaca agttatgcac tgttgcaacc   1200
ctacgtgaga catatggaga aatggcagac tgttgcgcca aacaagagcc tgaacgaaac   1260
gaatgctttc tgcagcacaa agacgataat ccaaatcttc cccgattagt tcgtcccgaa   1320
gtagacgtaa tgtgcacagc ctttcatgat aatgaagaga cttttcctgaa aaagtacttg   1380
tacgaaattg caagacgtca cccatacttc tatgctcccg agttactgtt tttcgccaaa   1440
cgatacaagg cagcctttac agaatgttgc caagcagctg acaaggctgc atgtcttttta   1500
cctaagttag atgagttaag agacgaaggt aaggcttcct cagcaaaaca gagacttaag   1560
tgcgcatccc ttcaaaagtt tggtgagaga gctttcaagg cttgggctgt cgccagactg   1620
tctcagagat ttcctaaggc tgaattcgca gaagtctcta agctagtaac tgacttgact   1680
aaagttcata ctgagtgctg tcatgggggat ttgttggaat gcgcagatga tcgtgcagac   1740
ttagcaaagt acatctgcga gaaccaagac tctatttcca gtaagttaaa ggaatgttgc   1800
gaaaagccac tacttgagaa gtcccactgt attgctgaag tcgaaaatga tgaaatgcct   1860
gctgaccttc catctttggc cgctgatttc gttgagtcca aggatgtgtg caaaaactat   1920
gctgaagcaa aagatgtgtt cctagggatg ttcctgtatg aatatgctcg tcgacatccc   1980
gactattccg ttgtccttttt actgagattg gctaagacct gcagagacaac cttggagaag   2040
tgttgtgctg ccgcagatcc tcacgagtgt tacgcaaaag tgtttgatga gttcaaacca   2100
ttggttgaag agccacaaaa tctaatcaag cagaactgtg aactgtttga caattgggc   2160
gaatacaaat tccaaaatgc tctgttagtg agatacacca aaaaggtccc acaagtttcc   2220
accccaactc tagtcgaggt gtccagaaat ctaggaaaga ttggatctaa gtgttgtaaa   2280
catccagaag ctaagaggat gccttgcgct gaggattact tgtctgtggt tttgaaccag   2340
ttatgtgttc tacacgagaa aactcctgtc tccgacagag ttactaagtg ctgcacagag   2400
tctttggtca atagaaggcc ttgtttcagt gccctggaag tcgatgaaac ttatgtgcct   2460
aaagagtttc aagccgaaac gttcacttttt cacgctgaca tttgtactct ttctgagaag   2520
gaacgtcaga tcaaaaagca gacagcattg gtgtgaattgg taaagcataa accaaaggct   2580
acaaaagagc agctgaaggc tgttatggat gattttgcag ctttcgtgga aaagtgttgt   2640
aaagccgatg ataaagagac ttgttttgca gaggagggga aaaagctggt tgctgcatca   2700
caagctgccc taggtcttgc agccgctacc ggtggcggaa gtggcggatc aggtggtcac   2760
caccatcatc accattagtg a                                             2781

SEQ ID NO: 252         moltype = AA  length = 925
FEATURE                Location/Qualifiers
REGION                 1..925
                       note = Synthetic construct
source                 1..925
                       mol_type = protein
                       organism = synthetic construct
SEQUENCE: 252
AQVLRGTVTD FPGFDERADA ETLRKAMKGL GTDEESILTL LTSRSNAQRQ EISAAFKTLF   60
GRDLLDDLKS ELTGKFEKLI VALMKPSRLY DAYELKHALK GAGTNEKVLT EIIASRTPEE   120
LRAIKQVYEE EYGSSLEDDV VGDTSGYYQR MLVVLLQANR DPDAGIDEAQ VEQDAQALFQ   180
AGELKWGTDE EKFITIFGTR SVSHLRKVFD KYMTISGFQI EETIDRETSG NLEQLLLAVV   240
KSIRSIPAYL AETLYYAMKG AGTDDHTLIR VMVSRSEIDL FNIRKEFRKN FATSLYSMIK   300
GDTSGDYKKA LLLLCGEDDA SDAHKSEVAH RFKDLGEENF KALVLIAFAQ YLQQSPFEDH   360
VKLVNEVTEF AKTCVADESA ENCDKSLHTL FGDKLCTVAT LRETYGEMAD CCAKQEPERN   420
ECFLQHKDDN PNLPRLVRPE VDVMCTAFHD NEETFLKKYL YEIARRHPYF YAPELLFFAK   480
RYKAAFTECC QAADKAACLL PKLDELRDEG KASSAKQRLK CASLQKFGER AFKAWAVARL   540
SQRFPKAEFA EVSKLVTDLT KVHTECCHGD LLECADDRAD LAKYICENQD SISSKLKECC   600
EKPLLEKSHC IAEVENDEMP ADLPSLAADF VESKDVCKNY AEAKDVFLGM FLYEYARRHP   660
DYSVVLLLRL AKTYETTLEK CCAAADPHEC YAKVFDEFKP LVEEPQNLIK QNCELFEQLG   720
EYKFQNALLV RYTKKVPQVS TPTLVEVSRN LGKVGSKCCK HPEAKRMPCA EDYLSVVLNQ   780
LCVLHEKTPV SDRVTKCCTE SLVNRRPCFS ALEVDETYVP KEFQAETFTF HADICTLSEK   840
ERQIKKQTAL VELVKHKPKA TKEQLKAVMD DFAAFVEKCC KADDKETCFA EEGKKLVAAS   900
QAALGLAAAT GGGSGGSGGH HHHH                                          925

SEQ ID NO: 253         moltype = DNA  length = 2781
```

-continued

```
FEATURE          Location/Qualifiers
misc_feature     1..2781
                 note = Synthetic construct
source           1..2781
                 mol_type = other DNA
                 organism = synthetic construct
SEQUENCE: 253
gctcaagtgc taaggggaac tgttactgat tttccaggtt ttgatgaaag agcagatgct    60
gagactttaa ggaaagctat gaaaggattg ggtacagacg aggaatccat tttgacacta   120
ttgacatcac gaagtaacgc ccagagacaa gagatctcag cagctttcaa aaccctgttc   180
ggaagagatt tgcttgacga tttgaagtct gagttgactg gtaagtttga aaaactaata   240
gttgccctga tgaagccttc cagactttat gatgcttacg aacttaagca cgcttttgaaa  300
ggggctggaa caaatgaaaa agttttgact gagataatcg catcacgtac ccctgaggaa   360
ctaagagcca ttaagcaggt atatgaagag gaatacggtca gttccttaga ggacgacgtc   420
gttggtgaca catctggtta ctatcagagg atgttggttg tcttgttgca agctaatagg   480
gatcctgatg ctggcatcga tgaagcccaa gtagagcagg acgcccaagc cctgtttcaa   540
gcaggcgaat tgaagtgggg aacggacgaa gagaagttta tcaccatctt cggaactcgt   600
tctgtatctc atcttagaaa agtattcgac aaatacatga cgatttctgg ttttcaaatt   660
gaggagacta ttgatagaga gacgtctgga aacttagaac agcttttgct tgccgtcgtt   720
aagtctataa ggagtattcc agcctactta gctgaaacct tgtactacgc catgaagggt   780
gctggaactg atgatcatac cttgatacga gttatggtaa gtcgatcaga gattgatttg   840
tttaacatta ggaaggagtt caggaaaaac tttgctacct cattgtattc catgataaag   900
ggtgatactt caggtgatta caaaaaggct ctgcttttgc tgtgtggcga ggacgatgct   960
agcgatgctc acaaatctga agtcgctcat cgtttcaaag acttgggtga ggaaaacttt  1020
aaggcttttag ttctgattgc ttttgcccaa tatcttcaac aatcaccatt cgaagatcat  1080
gtgaaacttg ttaacgaagt taccgaattt gcaaaaacgt ggttggcaa gaaaagtgcc  1140
gaaaactgtg acaaatcatt acacactttg ttcggtgaca agttatgcac tgttgcaacc  1200
ctacgtgaga catatggaga aatggcagac tgttgcgcca aacaagagcc tgaacgaaac  1260
gaatgctttc tgcagcacaa agacgataat ccaaatcttc cccgattagt tcgtcccgaa  1320
gtagacgtaa tgtgcacagc ctttcatgat aatgaagaga ctttcctgaa aaagtacttg  1380
tacgaaattg caagacgtca cccatacttc tatgctcccg agttactgtt tttcgccaaa  1440
cgatacaagg cagcctttac agaatgttgc caagcagctg acaaggctgc atgtctttta  1500
cctaagttag atgagttaag agacgaaggt aaggcttcct cagcaaaaca gagacttaag  1560
tgcgcatccc ttcaaaagtt tggtgagaga gctttcaagg cttgggctgt cgcccagactg  1620
tctcagagat ttcctaaggc tgaattcgca gaagtctcca agctagtaac tgacttgact  1680
aaagttcata ctgagtgctg tcatggggat ttgttgaat gcgcagatga tcgtgcagac  1740
ttagcaaagt acatctgcga gaaccaagac tctatttcca gtaagttaaa ggaatgttgc  1800
gaaaagccac tacttgagaa gtcccactgt attgctgaag tcgaaaatga tgaaatgcct  1860
gctgaccttc catctttggc cgctgatttc gttgagtcca aggatgtgtg caaaaactat  1920
gctgaagcaa aagatgtgtt cctagggatg ttcctgtatg aatatgctcg tcgacatccc  1980
gactattccg ttgtcctttt actgagattg gctaagacct acgagacaac cttggagaag  2040
tgttgtgctg ccgcagatcc tcacgagtgt tacgcaaaag tgtttgatga gttcaaacca  2100
ttggttgaag agccacaaaa atctaatcaag cagaactgtg aacttttgaa caattgggc  2160
gaatacaaat tccaaaatgc tctgttagtg agatacacca aaaaggtccc acaagtttcc  2220
accccaactc tagtcgaggt gtccagaaat ctaggaaaag ttggatctaa gtgttgtaag  2280
catccagaag ctaagaggat gccttgcgct gaggattact tgtctgtggt tttgaaccag  2340
ttatgtgttc tacacgagaa aactcctgtc tccgacaagg ttactaagtg ctgcacagag  2400
tctttggtca atagaaggcc ttgtttcagt gccctggaag tcgatgaaac ttatgtgcct  2460
aaagagttcc aagccgaaac gttcacttt cacgctgaca tttgtactct ttctgagaag  2520
gaacgtcaga tcaaaaagca gacagcattg gtggaattgg taaagcataa accaaaggct  2580
acaaaagagc agctgaaggc tgttatggat gattttgacg ctttcgtgga aaagtgttgt  2640
aaagccgatg ataaagagac ttgtttttgca gaggagggga aaaagctggt tgctgcatca  2700
caagctgccc taggtcttgc agccgctacc ggtggcggaa gtggcggatc aggtggtcac  2760
caccatcatc accattagtg a                                           2781

SEQ ID NO: 254       moltype = AA   length = 994
FEATURE              Location/Qualifiers
REGION               1..994
                     note = Synthetic construct
source               1..994
                     mol_type = protein
                     organism = synthetic construct
SEQUENCE: 254
STSHLVKCAE KEKTFCVNGG ECFMVKDLSN PSRYLCKCPN EFTGDRCQNY VMASFYKHLG    60
IEFMEAEELY QKGAASDAHK SEVAHRFKDL GEENFKALVL IAFAQYLQQS PFEDHVKLVN   120
EVTEFAKTCV ADESAENCDK SLHTLFGDKL CTVATLRETY GEMADCCAKQ EPERNECFLQ   180
HKDDNPNLPR LVRPEVDVMC TAFHDNEETF LKKYLYEIAR RHPYFYAPEL LFFAKRYKAA   240
FTECCQAADK AACLLPKLDE LRDEGKASSA KQRLKCASLQ KFGERAFKAW AVARLSQRFP   300
KAEFAEVSKL VTDLTKVHTE CCHGDLLECA DDRADLAKYI CENQDSISSK LKECCEKPLL   360
EKSHCIAEVE NDEMPADLPS LAADFVESKD VCKNYAEAKD VFLGMFLYEY ARRHPDYSVV   420
LLLRLAKTYE TTLEKCCAAA DPHECYAKVF DEFKPLVEEP QNLIKQNCEL FEQLGEYKFQ   480
NALLVRYTKK VPQVSTPTLV EVSRNLGKVG SKCCKHPEAK RMPCAEDYLS VVLNQLCVLH   540
EKTPVSDRVT KCCTESLVNR RPCFSALEVD ETYVPKEFQA ETFTFHADIC TLSEKERQIK   600
KQTALVELVK HKPKATKEQL KAVMDDFAAF VEKCCKADDK ETCFAEEGKK LVAASQAALG   660
LAAATGAQVL RGTVTDFPGF DERADAETLR KAMKGLGTDE ESILTLLTSR SNAQRQEISA   720
APKTLFGRDL LDDLKSDLTG KFEKLIVALM KPSRLYDAYE LKHALGAGT NEKVLTEIIA   780
SRTPEELRAI KQVYEEEYGS SLEDDVVGNT SGYYQRMLVV LLQANRDPDA GIDEAQVEQD   840
AQALFQAGEL KWGTDEEKFI TIFGTRSVSH LRKVFDKYMT ISGFQIEETI DRATSGNLEQ   900
LLLAVVKSIR SIPAYLAETL YYAMKGAGTD DHTLIRVMVS RSEIDLFNIR KEFRKNFATS   960
```

```
LYSMIKGNTS GDYKKALLLL CGEDDGGSHH HHHH                                     994

SEQ ID NO: 255          moltype = DNA   length = 2988
FEATURE                 Location/Qualifiers
misc_feature            1..2988
                        note = Synthetic construct
source                  1..2988
                        mol_type = other DNA
                        organism = synthetic construct
SEQUENCE: 255
tccacttctc atttggtgaa atgcgccgag aaggagaaaa cgttctgcgt gaacggtggt   60
gaatgcttta tggtcaaaga tctgtctaac ccttctcgat atctttgtaa gtgtcccaac   120
gagtttactg gtgatcgatg tcagaactac gttatggctt cctttacaa acacttgggt   180
atagaattca tggaggccga ggagttgtac caaaaaggag ctgcaagtga cgctcataag   240
tctgaagttg ctcacagatt caaagaccta ggtgaagaga actttaaggc tcttgtactt   300
atagcatttg ctcagtatct gcaacagagt cccttcgaag atcatgtcaa gctggtgaat   360
gaggtaaccg aattcgccaa gacttgtgtg gctgatgaat ccgccgaaaa ctgtgacaaa   420
tctttacaca cattgttcgg agataaacta tgcacagtag caacttttacg tgaaacttat   480
ggtgagatgg cagattgttg tgctaaacag gagcctgaga gaaatgaatg cttttttgcaa   540
cacaaggacg acaatcctaa ccttcccaga ttggttagac ccgaggttga cgttatgtgt   600
accgccttcc acgacaatga ggaaacattt ctgaaaaagt acttgtacga aattgcacga   660
cgtcacccat acttctatgc acctgagctt ttgtttttcg caaaagata caaggcagct   720
ttcactgagt gctgtcaagc agccgataag gctgcttgtc tattacctaa acttgatgag   780
cttagagatg agggtaaagc atcctccgct aaacagaggt tgaaatgtgc cagttttgcag   840
aagtttggtg aacgtgcttt caaggcatgg gctgttgcta gattatctca aagatttcct   900
aaggccgaat ttgctgaggt gtcaaagttg gtgacggatt tgactaaggt ccacactgag   960
tgttgccatg gtgatctttt ggaatgtgct gacgatagag ccgacctggc caagtatatc   1020
tgtgaaaacc aagattctat cagtagtaag ctgaaggaat gttgcgaaaa acctctacta   1080
gagaaatctc attgcatcgc agaagttgaa aacgatgaaa tgccagccga cttgcccagt   1140
ctggctgctg atttcgtcga gtcaaaagat gtttgcaaaa actatgccga agcaaaggat   1200
gtcttttttgg gcatgtttct gtacgaatat gctcgtcgtc atcctgacta ttccgttgtc   1260
ctgttgctaa gactagctaa aacgtatgaa acgaccttgg aaaagtgttg cgctgcagct   1320
gatccccacg agtgttatgc aaaagttttc gatgagttta agccacttgt agaagagcca   1380
cagaacttga tcaaacagaa ttgtgagctt ttcgagcaat taggtgagta taagtttcaa   1440
aacgctttgc tggttagata taccaaaaag gtcccacaag tgtcaacccc taccctggta   1500
gaagtgagta gaaatctagg aaaagtcgga tctaagtgct gcaagcatcc agaagctaag   1560
agaatgcctt gcgctgagga ttacttgtca gtagttttga atcagttgtg cgtcctacat   1620
gaaaagacac ccgtttctga tagagtcact aagtgttgta ctgagtctct agtaaacaga   1680
aggccttgtt tctctgcatt agaagtagat gaaacctatg tcccaaagga gttccaagct   1740
gaaaccttta catttcacgc cgacatttgt acgctatctg agaaggagcg tcagatcaaa   1800
aagcaaacag cccttgttga gcttgtgaag cacaagccaa aagctacaaa ggagcaattg   1860
aaagccgtca tggacgattt cgccgcattt gttgagaagt gttgcaaggc agatgataag   1920
gaaacttgtt ttgctgaaga gggcaaaaag cttgttgccg cctctcaagc tgctttggga   1980
ctagccgctg ctaccggtgc tcaagttttg aggggaaccg ttaccgactt cccaggtttt   2040
gacgaaagag ccgacgcaga aacattaagg aaagccatga agggcttagg caccgatgag   2100
gagtccattc tgacactgtt gacttcccga tccaatgccc aaaggcagga gatttcagcc   2160
gctttcaaga ctttgtttgg tagagatctt ctggacgacc tgaaatcaa tctgactgga   2220
aagtttgaga aacttattgt tgctttgatg aagccttcaa gactatatga cgcatacgag   2280
ttgaaacatg cattgaaagg tgcaggaact aatgaaaaag tgttaactga gatcattgct   2340
tccagaacac cagaagagct tcgtgctatc aaacaagtgt atgaagagga atacggatca   2400
agtcggagca atgacgattt tggtaatacc tcagggtatt accaaaggat gcttgtcggt   2460
ctattacaag ctaatcgaga tcctgacgcc ggaatcgatg aagctcaagt tgaacaagat   2520
gctcaggctc ttttttcaagc cggtgaattg aagtgggggga ctgatgagga aaagtttatc   2580
acgatctttg gtactagatc tgttagtcat ttgagaaaag tatttgacaa atacatgacc   2640
atttctggct ttcaaatga agagactatt gatagggcca cttccggtaa cttggaacaa   2700
ctgttgttag ctgtggtcaa gagtataaga tcaattccag cttacttagc tgaaactctg   2760
tattacgcaa tgaaaggagc aggcacagac gatcacacgt tgatccgagt catggtttcc   2820
agatcagaga ttgacttgtt caatatcagg aaggaattca ggaaaaactt tgcaacctct   2880
ttgtactcca tgatcaaagg taatacttcc ggtgattaca aaaaggcttt gttgttgtta   2940
tgtggagagg atgacggagg ttcacatcac catcatcacc attagtga             2988

SEQ ID NO: 256          moltype = AA   length = 925
FEATURE                 Location/Qualifiers
REGION                  1..925
                        note = Synthetic construct
source                  1..925
                        mol_type = protein
                        organism = synthetic construct
SEQUENCE: 256
AQVLRGTVTD FPGFDERADA ETLRKAMKGL GTDEESILTL LTSRSNAQRQ EISAAFKTLF    60
GRDLLDDLKS ELTGKFEKLI VALMKPSRLY DAYELKHALK GAGTNEKVLT EIIASRTPEE    120
LRAIKQVYEE EYGSSLEDDV VGNTSGYYQR MLVVLLQANR DPDAGIDEAQ VEQDAQALFQ    180
AGELKWGTDE EKFITIFGTR SVSHLRKVFD KYMTISGFQI EETIDRATSG NLEQLLLAVV    240
KSIRSIPAYL AETLYYAMKG AGTDDHTLIR VMVSRSEIDL FNIRKEFRKN FATSLYSMIK    300
GDTSGDYKKA LLLLCGEDDA SDAHKSEVAH RFKDLGEENF KALVLIAFAQ YLQQSPFEDH    360
VKLVNEVTEF AKTCVADESA ENCDKSLHTL FGDKLCTVAT LRETYGEMAD CCAKQEPERN    420
ECFLQHKDDN PNLPRLVRPE VDVMCTAFHD NEETFLKKYL YEIARRHPYF YAPELLFFAK    480
RYKAAFTECC QAADKAACLL PKLDELRDEG KASSAKQRLK CASLQKFGER AFKAWAVARL    540
SQRFPKAEFA EVSKLVTDLT KVHTECCHGD LLECADDRAD LAKYICENQD SISSKLKECC    600
```

```
EKPLLEKSHC IAEVENDEMP ADLPSLAADF VESKDVCKNY AEAKDVFLGM FLYEYARRHP  660
DYSVVLLLRL AKTYETTLEK CCAAADPHEC YAKVFDEFKP LVEEPQNLIK QNCELFEQLG  720
EYKFQNALLV RYTKKVPQVS TPTLVEVSRN LGKVGSKCCK HPEAKRMPCA EDYLSVVLNQ  780
LCVLHEKTPV SDRVTKCCTE SLVNRRPCFS ALEVDETYVP KEFQAETFTF HADICTLSEK  840
ERQIKKQTAL VELVKHKPKA TKEQLKAVMD DFAAFVEKCC KADDKETCFA EEGKKLVAAS  900
QAALGLAAAT GGGSGGSGGH HHHH                                         925

SEQ ID NO: 257         moltype = DNA  length = 2781
FEATURE                Location/Qualifiers
misc_feature           1..2781
                       note = Synthetic cocnstruct
source                 1..2781
                       mol_type = other DNA
                       organism = synthetic construct
SEQUENCE: 257
gctcaagtgc taaggggaac tgttactgat tttccaggtt ttgatgaaag agcagatgct  60
gagactttaa ggaaagctat gaaaggattg ggtacagacg aggaatccat tttgacacta  120
ttgacatcac gaagtaacgc ccagacacaa gagatctcag cagctttcaa aacccctgttc  180
ggaagagatt tgcttgacga tttgaagtct gagttgactg gtaagtttga aaaactaata  240
gttgccctga tgaagccttc cagactttat gatgcttacg aacttaagca cgctttgaaa  300
ggggctggaa caaatgaaaa agttttgact gagatataatcg catcacgtac ccctgaggaa  360
ctaagagcca ttaagcaggt atatgaagag gaatacgatca gttccttaga ggacgacgtc  420
gttggtaaca catctggtta ctatcagagg atgttggttg tcttgttgca agctaatagg  480
gatcctgatg ctggcatcga tgaagcccaa gtagagcagg acgcccaagc cctgtttcaa  540
gcaggcgaat tgaagtgggg aacggacgaa gagaagttta tcaccatctt cggaactcgt  600
tctgtatctc atcttagaaa agtattcgac aaatacatga cgatttctgg ttttcaaatt  660
gaggagacta ttgatagagc tacgtctgga aacttagaac agcttttgct tgccgtcgtt  720
aagtctataa ggagtattcc agcctactta gctgaaacct tgtactacgc catgaagggt  780
gctggaactg atgatcatac cttgatacga gttatggtaa gtcgatcaga gattgatttg  840
tttaacatta ggaaggagtt caggaaaaac tttgctacct cattgtattc catgataaag  900
ggtgatactt caggtgatta caaaaaggct ctgcttttgc tgtgtggcga ggacgatgct  960
agcgatgctc acaaatctga agtcgctcat cgtttcaaag acttgggtga ggaaaacttt  1020
aaggctttag ttctgattgc ttttgcccaa tatcttcaac aatcaccatt cgaagatcat  1080
gtgaaacttg ttaacgaagt taccgaattt gcaaaaacgt gtgtggcaga cgaaagtgtc  1140
gaaaactgtg acaaatcatt cacacactttg ttcggtgaca agttatgcac tgttgcaacc  1200
ctacgtgaga catatggaga aatggcgacc tgttgcgcca aacaagagcc tgaacgaaac  1260
gaatgctttc tgcagcacaa agacgataat ccaaatcttc cccgattagt tcgtcccgaa  1320
gtagacgtaa tgtgcacagc ctttcatgat aatgaagaga ctttcctgaa aaagtacttg  1380
tacgaaattg caagacgtca cccatacttc tatgctcccg agttactgtt tttcgccaaa  1440
cgatacaagg cagcctttac agaatgttgc caagcagctg acaaggctgc atgtctttta  1500
cctaagttag atgagttaag agacgaaggt aaggcttcct cagcaaaaca gagacttaag  1560
tgcgcatccc ttcaaaagtt tggtgagaga gctttcaagg cttgggctgt cgccagactg  1620
tctcagagat ttcctaaggc tgaattcgca gaagtctcta agctagtaac tgacttgact  1680
aaagttcata ctgagtgctg tcatggggat ttgttggaat gcgcagatga tcgtgcagac  1740
ttagcaaagt acatctgcga gaaccaagac tctatttcca gtaagttaaa ggaatgttgc  1800
gaaaagccac tacttgagaa gtcccactgt attgctgaag tcgaaatgtg tgaaatgcct  1860
gctgaccttc catctttggc cgctgatttc gttgagtcca aggatgtgtg caaaaactat  1920
gctgaagcaa aagatgtgtt cctagggatg ttcctgtatg aatatgctcg tcgacatccc  1980
gactattccg ttgtcctttt actgagattg gctaagacct acgagacaac cttggagaag  2040
tgttgtgctg ccgcagatcc tcacgagtgt tacgcaaaag tgtttgatga gttcaaacca  2100
ttggttgaag agccacaaaa tctaaatcaag cagaactgtg aactgtttga caattgggc  2160
gaatacaaat tccaaaatgc tctgttagtg agatacacca aaaaggtccc acaagtttcc  2220
accccaactc tagtcgaggt gtccagaaat ctaggaaaag ttggatctaa gtgttgtaag  2280
catccagaag ctaagaggat gccttgcgct gaggattact tgtctgtggt tttgaaccag  2340
ttatgtgttc tacacgagaa aactcctgtc tccgacaaga ttactaagtg ctgcacagag  2400
tctttggtca atagaaggcc ttgtttcagt gccctggaag tcgatgaaac ttatgtgcct  2460
aaagagttcc aagccgaaac gttcactttt cacgctgaca tttgtactct ttctgagaag  2520
gaacgtcaga tcaaaaagca gacagcattg gtggaattgg taaagcataa accaaaggct  2580
acaaaagagc agctgaaggc tgttatggat gattttgcag ctttcgtgga aaagtgttgt  2640
aaagccgatg ataaagagac ttgttttgca gaggagggga aaaagctggt tgctgcatca  2700
caagctgccc taggtcttgc agccgctacc ggtggcggaa gtggcggatc aggtggtcac  2760
caccatcatc accattagtg a                                          2781

SEQ ID NO: 258         moltype = AA  length = 1051
FEATURE                Location/Qualifiers
REGION                 1..1051
                       note = Synthetic construct
source                 1..1051
                       mol_type = protein
                       organism = synthetic construct
SEQUENCE: 258
AQVLRGTVTD FPGFDERADA ETLRKAMKGL GTDEESILTL LTSRSNAQRQ EISAAFKTLF   60
GRDLLDDLKS DLTGKFEKLI VALMKPSRLY DAYELKHALK GAGTNEKVLT EIIASRTPEE  120
LRAIKQVYEE EYGSSLEDDV VGNTSGYYQR MLVVLLQANR DPDAGIDEAQ VEQDAQALFQ  180
AGELKWGTDE EKFITIFGTR SVSHLRKVFD KYMTISGFQI EETIDRATSG NLEQLLLAVV  240
KSIRSIPAYL AETLYYAMKG AGTDDHTLIR VMVSRSEIDL FNIRKEFRKN FATSLYSMIK  300
GNTSGDYKKA LLLLCGEDDA SDAHKSEVAH RFKDLGEENF KALVLIAFAQ YLQQSPFEDH  360
VKLVNEVTEF AKTCVADESA ENCDKSLHTL FGDKLCTVAT LRETYGEMAD CCAKQEPERN  420
ECFLQHKDDN PNLPRLVRPE VDVMCTAFHD NEETFLKKYL YEIARRHPYF YAPELLFFAK  480
```

```
RYKAAFTECC QAADKAACLL PKLDELRDEG KASSAKQRLK CASLQKFGER AFKAWAVARL  540
SQRFPKAEFA EVSKLVTDLT KVHTECCHGD LLECADDRAD LAKYICENQD SISSKLKECC  600
EKPLLEKSHC IAEVENDEMP ADLPSLAADF VESKDVCKNY AEAKDVFLGM FLYEYARRHP  660
DYSVVLLLRL AKTYETTLEK CCAAADPHEC YAKVFDEFKP LVEEPQNLIK QNCELFEQLG  720
EYKFQNALLV RYTKKVPQVS TPTLVEVSRN LGKVGSKCCK HPEAKRMPCA EDYLSVVLNQ  780
LCVLHEKTPV SDRVTKCCTE SLVNRRPCFS ALEVDETYVP KEFQAETFTF HADICTLSEK  840
ERQIKKQTAL VELVKHKPKA TKEQLKAVMD DFAAFVEKCC KADDKETCFA EEGKKLVAAS  900
QAALGLAAT GMSPLLRRLL LAALLQLAPA QAPVSQPDAP GHQRKVVSWI DVYTRATCQP  960
REVVVPLTVE LMGTVAKQLV PSCVTVQRCG GCCPDDGLEC VPTGQHQVRM QILMIRYPSS  1020
QLGEMSLEEH SQCECRPKKK DSGGSHHHHH H                                1051

SEQ ID NO: 259        moltype = DNA   length = 3159
FEATURE               Location/Qualifiers
misc_feature          1..3159
                      note = Synthetic construct
source                1..3159
                      mol_type = other DNA
                      organism = synthetic construct
SEQUENCE: 259
gctcaagtgc taaggggaac tgttactgat tttccaggtt ttgatgaaag agcagatgct  60
gagactttaa ggaaagctat gaaaggattg ggtacagacg aggaatccat tttgacacta  120
ttgacatcac gaagtaacgc ccagacacaa gagatctcag cagcttttcaa aaccctgttc  180
ggaagagatt tgcttgacga tttgaagtct gatttgactg gtaagtttga aaaactaata  240
gttgccctga tgaagccttc cagactttat gatgcttacg aacttaagca cgctttgaaa  300
ggggctggaa caaatgaaaa agttttgact gagataatcg catcacgtac ccctgaggaa  360
ctaagagcca ttaagcaggt atatgaagag gaatacggta gttccttaga ggacgacgtc  420
gttggtaaca catctggtta ctatcagagg atgttggttg tcttgttgca agctaatagg  480
gatcctgatg ctggcatcga tgaagcccaa gtagagcagg acgcccaagc cctgtttcaa  540
gcaggcgaat tgaagtgggg aacggacgaa gagaagttta tcaccatctt cggaactcgt  600
tctgtatctc atcttagaaa agtattcgac aaatacatga cgatttctgg ttttcaaatt  660
gaggagacta ttgatagagc tacgtctgga aacttagaac agctttttgct tgccgtcgtt  720
aagtctataa ggagtattcc agcctactta gctgaaacct tgtactacgc catgaagggt  780
gctggaactg atgatcatac cttgatacga gttatggtaa gtcgatcaga gattgatttg  840
tttaacatta ggaaggagtt caggaaaaac tttgctacct cattgtattc catgataaag  900
ggtaacactt caggtgatta caaaaaggct ctgctttttgc tgtgtggcga ggacgatgct  960
agcgatgctc acaaatctga agtcgctcat cgtttcaaag acttgggtga ggaaaactttt  1020
aaggctttag ttctgattgc ttttgcccaa tatcttcaac aatcaccatt cgaagatcat  1080
gtgaaacttg ttaacgaagt taccgaattt gcaaaaacgt gtgtggcaga cgaaagtgcc  1140
gaaaactgtg acaaatcatt acacactttg ttcggtgaca agttatgcac tgttgcaacc  1200
ctacgtgaga catatggaga aatggcgac tgttgcgcca aacaagagcc tgaacgaaac  1260
gaatgctttc tgcagcacaa agacgataat ccaaatcttc cccgattagt tcgtcccgaa  1320
gtagacgtaa tgtgcacagc ctttcatgat aatgaagaga cttttcctgaa aaagtacttg  1380
tacgaaattg caagacgtca cccatacttc tatgctcccg agttactgtt tttcgccaaa  1440
cgatacaagg cagcctttac agaatgttgc caagcagctg acaaggctgc atgtcttttta  1500
cctaagttag atgagttaag agacgaaggt aaggcttcct cagcaaaaca gagacttaag  1560
tgcgcatccc ttcaaaagtt tggtgagaga gcttttcaagg cttgggctgt cgccagactg  1620
tctcagagat ttcctaaggc tgaattcgca gaagtctcta acagtagtaac tgacttgact  1680
aaagttcata ctgagtgctg tcatggggat ttgttggaat gcgcagatga tcgtgcagac  1740
ttagcaaagt acatctgcga gaaccaagac tctatttcca gtaagttaaa ggaatgttgc  1800
gaaaagccac tacttgagaa gtcccactgt attgctgaag tcgaaatga tgaaatgcct  1860
gctgaccttc catctttggc cgctgattttc gttgagtcca aggatgtgtg caaaaactat  1920
gctgaagcaa aagatgtgtt cctagggatg ttcctgtatg aatatgctcg tcgacatccc  1980
gactattccg ttgtcctttt actgagattg gctaagacct acgagacaac cttggagaag  2040
tgttgtgctg ccgcagatcc tcacgagtgt tacgcaaaag tgtttgatga gttcaaacca  2100
ttggttgaag agccacaaaa tctaatcaag cagaactgtg aactgtttga acaattgggc  2160
gaatacaaat tccaaaatgc tctgttagtg agatacacca aaaaggtccc caagtttcc  2220
accccaactc tagtcgaggt gtccagaaat ctaggaaaag ttggatctaa gtgttgtaag  2280
catccagaag ctaagaggat gccttgcgct gaggattact tgtctgtggt tttgaaccag  2340
ttatgtgttc tacacgagaa aactcctgtc tccgacaaga ttactaagtg ctgcacagag  2400
tctttggtca atagaaggcc ttgtttcagt gccctggaag tcgatgaaac ttatgtgcct  2460
aaagagttcc aagccgaaac gttcactttt cacgctgaca tttgtactct ttctgagaag  2520
gaacgtcaga tcaaaaagca gacagcattg gtggaattgg taaagcataa accaaaggct  2580
acaaaagagc agctgaaggc tgttatggat gattttgcag ctttcgtgga aaagtgttgt  2640
aaagccgatg ataaagagac ttgttttgca gaggagggga aaaagctggt tgctgcatca  2700
caagctgccc taggtcttgc agccgctacc ggtatgagtc ctttgttgag aaggttgcta  2760
ttagctgcat tgttacagtt agctcctgct caggccccag tttctcagcc agacgccct  2820
ggtcatcaac gtaaggttgt gtcttggatt gacgtataca cgagagcaac atgccaacca  2880
agggaagtcg ttgttcccct tactgttgag ttgatgggga ctgtggctaa gcagctggtc  2940
ccttcatgtg tcaccgtaca gagatgtgga ggttgttgcc cagacgatgg actagaatgt  3000
gttccaacag gacaacatca ggtgagaatg caaatactga tgatcagata tccatcttca  3060
caacttggcg aaatgtccct ggaagagcac tctcaatgcg agtgtcgacc caaaaagaaa  3120
gatagtggtg gttcccatca ccaccatcat cattagtga                        3159

SEQ ID NO: 260        moltype = AA   length = 1108
FEATURE               Location/Qualifiers
REGION                1..1108
                      note = Synthetic construct
source                1..1108
                      mol_type = protein
```

```
                              organism = synthetic construct
SEQUENCE: 260
AQVLRGTVTD FPGFDERADA ETLRKAMKGL GTDEESILTL LTSRSNAQRQ EISAAFKTLF   60
GRDLLDDLKS DLTGKFEKLI VALMKPSRLY DAYELKHALK GAGTNEKVLT EIIASRTPEE  120
LRAIKQVYEE EYGSSLEDDV VGNTSGYYQR MLVVLLQANR DPDAGIDEAQ VEQDAQALFQ  180
AGELKWGTDE EKFITIFGTR SVSHLRKVFD KYMTISGFQI EETIDRATSG NLEQLLLAVV  240
KSIRSIPAYL AETLYYAMKG AGTDDHTLIR VMVSRSEIDL FNIRKEFRKN FATSLYSMIK  300
GNTSGDYKKA LLLLCGEDDA SDAHKSEVAH RFKDLGEENF KALVLIAFAQ YLQQSPFEDH  360
VKLVNEVTEF AKTCVADESA ENCDKSLHTL FGDKLCTVAT LRETYGEMAD CCAKQEPERN  420
ECFLQHKDDN PNLPRLVRPE VDVMCTAFHD NEETFLKKYL YEIARRHPYF YAPELLFFAK  480
RYKAAFTECC QAADKAACLL PKLDELRDEG KASSAKQRLK CASLQKFGER AFKAWAVARL  540
SQRFPKAEFA EVSKLVTDLT KVHTECCHGD LLECADDRAD LAKYICENQD SISSKLKECC  600
EKPLLEKSHC IAEVENDEMP ADLPSLAADF VESKDVCKNY AEAKDVFLGM FLYEYARRHP  660
DYSVVLLLRL AKTYETTLEK CCAAADPHEC YAKVFDEFKP LVEEPQNLIK QNCELFEQLG  720
EYKFQNALLV RYTKKVPQVS TPTLVEVSRN LGKVGSKCCK HPEAKRMPCA EDYLSVVLNQ  780
LCVLHEKTPV SDRVTKCCTE SLVNRRPCFS ALEVDETYVP KEFQAETFTF HADICTLSEK  840
ERQIKKQTAL VELVKHKPKA TKEQLKAVMD DFAAFVEKCC KADDKETCFA EEGKKLVAAS  900
QAALGLAAAT GMSPLLRRLL LAALLQLAPA QAPVSQPDAP GHQRKVVSWI DVYTRATCQP  960
REVVVPLTVE LMGTVAKQLV PSCVTVQRCG GCCPDDGLEC VPTGQHQVRM QILMIRYPSS 1020
QLGEMSLEEH SQCECRPKKK DSAVKPDSPR PLCPRCTQHH QRPDPRTCRR RCRRRSFLRC 1080
QGRGLELNPD TCRCRKLRRG GSHHHHHH                                    1108

SEQ ID NO: 261        moltype = DNA   length = 3330
FEATURE               Location/Qualifiers
misc_feature          1..3330
                      note = Synthetic construct
source                1..3330
                      mol_type = other DNA
                      organism = synthetic construct
SEQUENCE: 261
gctcaagtgc taaggggaac tgttactgat tttccaggtt ttgatgaaag agcagatgct   60
gagactttaa ggaaagctat gaaaggattg ggtacagacg aggaatccat tttgacacta  120
ttgacatcac gaagtaacgc ccagagacaa gagatctcag cagctttcaa aaccctgttc  180
ggaagagatt tgcttgacga tttgaagtct gatttgactg gtaagtttga aaaactaata  240
gttgccctga tgaagccttc cagactttat gatgcttacg aacttaagca cgctttgaaa  300
ggggctggaa caaatgaaaa agttttgact gagataatcg catcacgtac ccctgaggaa  360
ctaagagcca ttaagcaggt atatgaagag gaatacggta gttccttaga ggacgacgtc  420
gttggtaaca catctggtta ctatcagagg atgttggttg tcttgttgca agctaatagg  480
gatcctgatg ctggcatcga tgaagcccaa gtagagcagg acgcccaagc cctgtttcaa  540
gcaggcgaat tgaagtgggg aacggacgaa gagaagttta tcaccatctt cggaactcgt  600
tctgtatctc atcttagaaa agtattcgac aaatacatga cgatttctgg ttttcaaatt  660
gaggagacta ttgatagagc tacgtctgga aacttagaac agcttttgct tgccgtcgtt  720
aagtctataa ggagtattcc agcctactta gctgaaacct tgtactacgc catgaagggt  780
gctggaactg atgatcatac cttgatacga gttatggtaa gtcgatcaga gattgatttg  840
tttaacatta ggaaggagtt caggaaaaac tttgctacct cattgtattc catgataaag  900
ggtaacactt caggtgatta caaaaaggct ctgcttttgc tgtgtggcga ggacgatgct  960
agcgatgctc acaaatctga agtcgctcat cgtttcaaag acttgggtga ggaaaacttt 1020
aaggctttag ttctgattgc ttttgcccaa tatcttcaac aatcaccatt cgaagatcat 1080
gtgaaacttg ttaacgaagt taccgaattt gcaaaaacgt gtgtggcaga cgaaagtgcc 1140
gaaaactgtg acaaatcatt acacactttg ttcggtgaca agttatgcac tgttgcaacc 1200
ctacgtgaga catatggaga aatggcagac tgttgcgcaa aacaagagcc tgaacgaaac 1260
gaatgctttc tgcagcacaa agacgataat ccaaatcttc cccgattagt tcgtcccgaa 1320
gtagacgtaa tgtgcacagc ctttcatgat aatgaagaga ctttcctgaa aaagtacttg 1380
tacgaaattg caagacgtca cccatacttc tatgctcccg agttactgtt tttcgccaaa 1440
cgatacaagg cagcctttac agaatgttgc caagcagctg acaaggctgc atgtctttta 1500
cctaagttag atgagttaag agacgaaggt aaggcttcct cagcaaaaca gagacttaag 1560
tgcgcatccc ttcaaaagtt tggtgagaga gctttcaagg cttgggctgt cgccagactg 1620
tctcagagat ttcctaaggc tgaattcgca gaagtctcta agctagtaac tgacttgact 1680
aaagttcata ctgagtgctg tcatgggggat ttgttggaat gcgcagatga tcgtgcagac 1740
ttagcaaagt acatctgcga gaaccaagac tctatttcca gtaagttaaa ggaatgttgc 1800
gaaaagccac tacttgagaa gtcccactgt attgctgaag tcgaaaatga tgaaatgcct 1860
gctgaccttc catctttggc cgctgatttc gttgagtcca aggatgtgtg caaaaactat 1920
gctgaagcaa aagatgtgtt cctagggatg ttcctgtatg aatatgctcg tcgacatccc 1980
gactattccg ttgtcctttt actgagattg gctaagacct acgagacaac cttggagaag 2040
tgttgtgctg ccgcagatcc tcacgagtgt tacgcaaaag tgtttgatga gttcaaacca 2100
ttggttgaag agccacaaaa tctaatcaag cagaactgtg aactgtttga acaattgggc 2160
gaatacaaat tccaaaatgc tctgttagtg agatacacca aaaaggtccc acaagtttcc 2220
accccaactc tagtcgaggt gtccagaaat ctaggaaaag ttggatctaa gtgttgtaag 2280
catccagaag ctaagaggat gccttgcgct gaggattact tgtctgtggt tttgaaccag 2340
ttatgtgttc tacacgagaa aactcctgtc tccgacagag ttactaagtg ctgcacagag 2400
tctttggtca atagaaggcc ttgtttcagt gccctggaag tcgatgaaac ttatgtgcct 2460
aaagagttcc aagccgaaac gttcactttt cacgctgaca tttgtactct ttctgagaag 2520
gaacgtcaga tcaaaaagca gacagcattg gtggaattgg taaagcataa accaaaggct 2580
acaaaagagc agctgaaggc tgttatggat gattttgcag ctttcgtgga gaagtgttgt 2640
aaagccgatg ataaagagac ttgttttgca gaggaggggaa aaaagctggt tgctgcatca 2700
caagctgccc taggtcttgc agccgctacc ggtatgagtc ctttgcttag aaggttgtta 2760
ctggccgcac tgcttcaact tgcaccagct caagcccag tctctcaacc tgacgctccc 2820
ggtcatcaga gaaaggtggt atcatggatt gatgtgtata ctcgtgctac atgccaaccc 2880
cgtgaggttg ttgtaccttt gacagtcgaa ttgatgggaa ccgttgccaa gcagttagtt 2940
```

-continued

```
ccttcctgtg tcacagtgca gagatgtgga ggatgttgtc cagatgatgg tttggagtgt   3000
gtacctactg gccaacatca ggttagaatg cagatcttga tgatacgtta cccatcaagt   3060
caactaggtg aaatgtcttt ggaggaacac tcccagtgcg aatgcagacc caaaaagaaa   3120
gattctgctg ttaaaccaga ctctccaaga ccattatgtc ccagatgcac gcaacaccat   3180
caaagaccag atccaaggac ttgtagacgt agatgcagga ggcgatcctt tttgcgatgc   3240
caaggtagag gcctagagct gaatcctgac acctgtcgat gtcgaaagtt aagacgtggt   3300
gggtcacacc accatcacca tcattagtga                                     3330
```

```
SEQ ID NO: 262          moltype = AA  length = 1095
FEATURE                 Location/Qualifiers
REGION                  1..1095
                        note = Synthetic construct
source                  1..1095
                        mol_type = protein
                        organism = synthetic construct
SEQUENCE: 262
AQVLRGTVTD FPGFDERADA ETLRKAMKGL GTDEESILTL LTSRSNAQRQ EISAAFKTLF   60
GRDLLDDLKS DLTGKFEKLI VALMKPSRLY DAYELKHALK GAGTNEKVLT EIIASRTPEE  120
LRAIKQVYEE EYGSSLEDDV VGNTSGYYQR MLVVLLQANR DPDAGIDEAQ VEQDAQALFQ  180
AGELKWGTDE EKFITIFGTR SVSHLRKVFD KYMTISGFQI EETIDRATSG NLEQLLLAVV  240
KSIRSIPAYL AETLYYAMKG AGTDDHTLIR VMVSRSEIDL FNIRKEFRKN FATSLYSMIK  300
GNTSGDYKKA LLLLCGEDDA SDAHKSEVAH RFKDLGEENF KALVLIAFAQ YLQQSPFEDH  360
VKLVNEVTEF AKTCVADESA ENCDKSLHTL FGDKLCTVAT LRETYGEMAD CCAKQEPERN  420
ECFLQHKDDN PNLPRLVRPE VDVMCTAFHD NEETFLKKYL YEIARRHPYF YAPELLFFAK  480
RYKAAFTECC QAADKAACLL PKLDELRDEG KASSAKQRLK CASLQKFGER AFKAWAVARL  540
SQRFPKAEFA EVSKLVTDLT KVHTECCHGD LLECADDRAD LAKYICENQD SISSKLKECC  600
EKPLLEKSHC IAEVENDEMP ADLPSLAADF VESKDVCKNY AEAKDVFLGM FLYEYARRHP  660
DYSVVLLLRL AKTYETTLEK CCAAADPHEC YAKVFDEFKP LVEEPQNLIK QNCELFEQLG  720
EYKFQNALLV RYTKKVPQVS TPTLVEVSRN LGKVGSKCCK HPEAKRMPCA EDYLSVVLNQ  780
LCVLHEKTPV SDRVTKCCTE SLVNRRPCFS ALEVDETYVP KEFQAETFTF HADICTLSEK  840
ERQIKKQTAL VELVKHKPKA TKEQLKAVMD DFAAFVEKCC KADDKETCFA EEGKKLVAAS  900
QAALGLAAAT GQRKRRNTIH EFKKSAKTTL IKIDPALKIK TKKVNTADQC ANRCTRNKGL  960
PFTCKAFVFD KARKQCLWFP FNSMSSGVKK EFGHEFDLYE NKDYIRNCII GKGRSYKGTV 1020
SITKSGIKCQ PWSSMIPHEH SFLPSSYRGK DLQENYCRNP RGEEGGPWCF TSNPEVRYEV 1080
CDIPQCGGSH HHHHH                                                   1095
```

```
SEQ ID NO: 263          moltype = DNA  length = 3291
FEATURE                 Location/Qualifiers
misc_feature            1..3291
                        note = Synthetic construct
source                  1..3291
                        mol_type = other DNA
                        organism = synthetic construct
SEQUENCE: 263
gctcaagtgc taaggggaac tgttactgat tttccaggtt ttgatgaaag agcagatgct   60
gagacttta ggaaagctat gaaaggattg ggtacagacg aggaatccat tttgacacta  120
ttgacatcac gaagtaacgc ccagagacaa gagatctgaa cagctttcaa aaccctgttc  180
ggaagagatt tgcttgacga tttgaagtct gatttgactg gtaagtttga aaaactaata  240
gttgccctga tgaagccttc cagacttat gatgcttacg aacttaagca cgcttttgaaa  300
ggggctggaa caaatgaaaa agttttgact gagataatcg catcacgtac ccctgaggaa  360
ctaagagcca ttaagcaggt atatgaagag gaatacggta gttccttaga ggacgacgtc  420
gttggtaaca catctggtta ctatcagagg atgttggttg tcttgttgca agctaatagg  480
gatcctgatg ctggcatcga tgaagcccaa gtagagcagg acgcccaagc cctgtttcaa  540
gcaggcgaat tgaagtgggg aacggacgaa gagaagttta tcaccatctt cggaactcgt  600
tctgtatctc atcttagaaa agtattcgac aaatacatga cgatttctgg ttttcaaatt  660
gaggagacta ttgatagagc tacgtctgga aacttagaac agcttttgct tgccgtcgtt  720
aagtctataa ggagtattcc agcctactta gctgaaacct tgtactacgc catgaagggt  780
gctggaactg atgatcatac cttgatacga gttatggtaa gtcgatcaga gattgatttg  840
tttaacatta ggaaggagtt caggaaaaac tttgctacct cattgtattc catgataaag  900
ggtaacactt caggtgatta caaaaaggct ctgcttttgc tgtgtggcga ggacgatgct  960
agcgatgctc acaaatctga agtcgctcat cgtttcaaag acttgggtga ggaaaacttt  1020
aaggctttag ttctgattgc ttttgcccaa tatcttcaac aatcaccatt cgaagatcat  1080
gtgaaacttg ttaacgaagt taccgaattt gcaaaaacgt gtgtggcaga cgaaagtgcc  1140
gaaaactgtg acaaatcatt acacactttg ttcggtgaca agttatgcac tgttgcaacc  1200
ctacgtgaga catatggaga aatggcagac tgttgcgcca aacaagagcc tgaacgaaac  1260
gaatgctttc tgcagcacaa agacgataat ccaaatcttc cccgattagt tcgtcccgaa  1320
gtagacgtaa tgtgcacagc ctttcatgat aatgaagaga cttttcctgaa aaagtacttg  1380
tacgaaattg caagacgtca cccatacttc tatgctcccg agttactgtt tttcgccaaa  1440
cgatacaagg cagcctttac agaatgttgc caagcagctg acaaggctgc atgtctttta  1500
cctaagttag atgagttaag agacgaaggt aaggcttcct cagcaaaaca gagacttaag  1560
tgcgcatccc ttcaaaagtt tggtgagaga gctttcaagg cttgggctgt cgccagactg  1620
tctcagagat ttcctaaggc tgaattcgca gaagtctcta agctagtaac tgacttgact  1680
aaagttcata ctgagtgctg tcatgggat ttgttggaat gcgcagatcg tcgtgcagac  1740
ttagcaaagt acatctgcga gaaccaagac tctatttcga gtaagttaaa ggaatgttgc  1800
gaaaagccac tacttgagaa gtcccactgt attgctgaag tcgaaaatga tgaaatgcct  1860
gctgacctc catctttggc cgctgatttc gttgagtcca aggatgtgtg caaaaactat  1920
gctgaagcaa aagatgtgtt cctagggatg ttcctgtatg aatatgctcg tcgacatccc  1980
gactattccg ttgtccttttt actgagattg gctaagacct acgagacaac cttggagaag  2040
tgttgtgctg ccgcagatcc tcacgagtgt tacgcaaaag tgtttgatga gttcaaacca  2100
```

```
ttggttgaag agccacaaaa tctaatcaag cagaactgtg aactgtttga acaattgggc  2160
gaatacaaat tccaaaatgc tctgttagtg agatacacca aaaaggtccc acaagtttcc  2220
accccaactc tagtcgaggt gtccagaaat ctaggaaaag ttggatctaa gtgttgtaag  2280
catccagaag ctaagaggat gccttgcgct gaggattact tgtctgtggt tttgaaccag  2340
ttatgtgttc tacacgagaa aactcctgtc tccgacagag ttactaagtg ctgcacagag  2400
tctttggtca atagaaggcc ttgtttcagt gccctggaag tcgatgaaac ttatgtgcct  2460
aaagagttcc aagccgaaac gttcactttt cacgctgaca tttgtactct ttctgagaag  2520
gaacgtcaga tcaaaaagca gacagcattg gtggaattgg taaagcataa accaaaggct  2580
acaaaagagc agctgaaggc tgttatggat gattttgcag ctttcgtgga aaagtgttgt  2640
aaagccgatg ataaagagac ttgtttttgca gaggaggggga aaaagctggt tgctgcatca  2700
caagctgccc taggtcttgc agccgctacc ggtcaacgta aaagacgaaa tacaattcat  2760
gagttcaaaa agtcagccaa aactacattg attaagattg atcccgctct gaagataaag  2820
accaaaaagg tcaacacagc tgaccagtgc gccaacaggt gtaccaggaa taagggacta  2880
cctttttactt gtaaagcttt cgtattcgac aaagcaagga agcaatgtct gtggttcccc  2940
tttaactcta tgtcatctgg ggtgaaaaag gaatttggcc atgaatttga tttgtatgaa  3000
aacaaagatt acattagaaa ttgcattatc ggcaagggaa gatcatacaa aggtacggtt  3060
tctattacta agtctggaat caagtgccaa ccatggtcat ccatgatccc tcacgagcac  3120
agtttccttc caagttccta ccgtggtaaa gacttacaag agaactattg ccgaaatcct  3180
agaggtgaag agggaggtcc atggtgtttt acctccaacc ctgaagttag atatgaagtc  3240
tgtgatatac ctcagtgtgg cggttctcat catcaccacc accattagtg a              3291
```

SEQ ID NO: 264          moltype = AA   length = 1066
FEATURE                 Location/Qualifiers
REGION                  1..1066
                        note = Synthetic construct
source                  1..1066
                        mol_type = protein
                        organism = synthetic construct
SEQUENCE: 264

```
AQVLRGTVTD FPGFDERADA ETLRKAMKGL GTDEESILTL LTSRSNAQRQ EISAAFKTLF    60
GRDLLDDLKS DLTGKFEKLI VALMKPSRLY DAYELKHALK GAGTNEKVLT EIIASRTPEE   120
LRAIKQVYEE EYGSSLEDDV VGNTSGYYQR MLVVLLQANR DPDAGIDEAQ VEQDAQALFQ   180
AGELKWGTDE EKFITIFGTR SVSHLRKVFD KYMTISGFQI EETIDRATSG NLEQLLLAVV   240
KSIRSIPAYL AETLYYAMKG AGTDDHTLIR VMVSRSEIDL FNIRKEFRKN FATSLYSMIK   300
GNTSGDYKKA LLLLCGEDDA SDAHKSEVAH RFKDLGEENF KALVLIAFAQ YLQQSPFEDH   360
VKLVNEVTEF AKTCVADESA ENCDKSLHTL FGDKLCTVAT LRETYGEMAD CCAKQEPERN   420
ECFLQHKDDN PNLPRLVRPE VDVMCTAFHD NEETFLKKYL YEIARRHPYF YAPELLFFAK   480
RYKAAFTECC QAADKAACLL PKLDELRDEG KASSAKQRLK CASLQKFGER AFKAWAVARL   540
SQRFPKAEFA EVSKLVTDLT KVHTECCHGD LLECADDRAD LAKYICENQD SISSKLKECC   600
EKPLLEKSHC IAEVENDEMP ADLPSLAADF VESKDVCKNY AEAKDVFLGM FLYEYARRHP   660
DYSVVLLLRL AKTYETTLEK CCAAADPHEC YAKVFDEFKP LVEEPQNLIK QNCELFEQLG   720
EYKFQNALLV RYTKKVPQVS TPTLVEVSRN LGKVGSKCCK HPEAKRMPCA EDYLSVVLNQ   780
LCVLHEKTPV SDRVTKCCTE SLVNRRPCFS ALEVDETYVP KEFQAETFTF HADICTLSEK   840
ERQIKKQTAL VELVKHKPKA TKEQLKAVMD DFAAFVEKCC KADDKETCFA EEGKKLVAAS   900
QAALGLAAAT GPALPEDGGS GAFPPGHFKD PKRLYCKNGG FFLRIHPDGR VDGVREKSDP   960
HIKLQLQAEE RGVVSIKGVC ANRYLAMKED GRLLASKCVT DECFFFERLE SNNYNTYRSR  1020
KYTSWYVALK RTGQYKLGSK TGPGQKAILF LPMSAKSGGS HHHHHH                  1066
```

SEQ ID NO: 265          moltype = DNA   length = 3204
FEATURE                 Location/Qualifiers
misc_feature            1..3204
                        note = Synthetic construct
source                  1..3204
                        mol_type = other DNA
                        organism = synthetic construct
SEQUENCE: 265

```
gctcaagtgc taaggggaac tgttactgat tttccaggtt ttgatgaaag agcagatgct   60
gagactttaa ggaaagctat gaaaggattg ggtacagacg aggaatccat tttgacacta  120
ttgacatcac gaagtaacgc ccagacacaa gagatctcag cagctttcaa aacoctgttc  180
ggaagagatt tgcttgacga tttgaagtct gatttgactg gtaagtttga aaaactaata  240
gttgccctga tgaagccttc cagactttat gatgcttacg aacttaagca cgctttgaaa  300
ggggctggaa caaatgaaaa agttttgact gagataatcg catcacgtac ccctgaggaa  360
ctaagagcca ttaagcaggt atatgaagag gaatacggta gttccttaga ggacgacgtc  420
gttggtaaca catctggtta ctatcagagg atgttggttg tcttgttgca agctaatagg  480
gatcctgatg ctggcatcga tgaagcccaa gtagagcagg acgcccaagc cctgtttcaa  540
gcaggcgaat gaagtggggg aacggacgaa gagaagttta tcaccatctt cggaactcgt  600
tctgtatctc atcttagaaa agtattcgac aaatacatga cgatttctgg ttttcaaatt  660
gaggagacta ttgatagagc tacgtctgga aacttagaac agcttttgct tgccgtcgtt  720
aagtctataa ggagtattcc agcctactta gctgaaacct tgtactacgc catgaagggt  780
gctggaactg atgatcatac cttgatacga gttatggtaa gtcgatcaga gattgatttg  840
tttaacatta ggaaggagtt caggaaaaac tttgctacct cattgtattc catgataaag  900
ggtaacactt caggtgatta caaaaaggct ctgcttttgc tgtgtggcga ggacgatgct  960
agcgatgctc acaaatctga agtcgctcat cgtttcaaag acttgggtga ggaaaacttt  1020
aaggctttag ttctgattgc ttttgcccaa tatcttcaat atcaccatt aggagatcat  1080
gtgaaacttg ttaacgaagt taccgaattt gcaaaaacgt gtgtggcaga cgaaagtgcc  1140
gaaaactgtg acaaatcatt acacactttg ttcggtgaca gttatgcac tgttgcaacc  1200
ctacgtgaga catatggaga aatggcagac tgttgcgcca acaaagagcc tgaacgaaac  1260
gaatgctttc tgcagcacaa agacgataat ccaaatcttc cccgattagt tcgtcccgaa  1320
gtagacgtaa tgtgcacagc ctttcatgat aatgaagaga ctttcctgaa aaagtacttg  1380
```

```
tacgaaattg caagacgtca cccatacttc tatgctcccg agttactgtt tttcgccaaa  1440
cgatacaagg cagcctttac agaatgttgc caagcagctg acaaggctgc atgtctttta  1500
cctaagttag atgagttaag agacgaaggt aaggcttcct cagcaaaaca gagacttaag  1560
tgcgcatccc ttcaaaagtt tggtgagaga gctttcaagg cttgggctgt cgccagactg  1620
tctcagagat ttcctaaggc tgaattcgca gaagtctcta agctagtaac tgacttgact  1680
aaagttcata ctgagtgctg tcatggggat ttgttggaat gcgcagatga tcgtgcagac  1740
ttagcaaagt acatctgcga gaaccaagac tctatttcca gtaagttaaa ggaatgttgc  1800
gaaaagccac tacttgagaa gtcccactgt attgctgaag tcgaaaatga tgaaatgcct  1860
gctgaccttc catctttggc cgctgatttc gttgagtcca aggatgtgtg caaaaactat  1920
gctgaagcaa aagatgtgtt cctagggatg ttcctgtatg aatatgctcg tcgacatccc  1980
gactattccg ttgtcctttt actgagattg gctaagacct acgagacaac cttgagaag  2040
tgttgtgctg ccgcagatcc tcacgagtgt tacgcaaaag tgtttgatga gttcaaacca  2100
ttggttgaag agccacaaaa tctaatcaag cagaactgtg aactgtttga acaattgggc  2160
gaatacaaat tccaaaatgc tctgttagtg agatacacca aaaaggtccc acaagtttcc  2220
accccaactc tagtcgaggt gtccagaaat ctaggaaaag ttggatctaa tgttgtaag  2280
catccagaag ctaagaggat gccttgcgct gaggattact tgtctgtggt tttgaaccag  2340
ttatgtgttc tacacgagaa aactcctgtc tccgacagag ttactaagtg ctgcacagag  2400
tctttggtca atagaaggcc ttgtttcagt gccctgaaag tcgatgaaac ttatgtgcct  2460
aaagagttcc aagccgaaac gttcacttt cacgctgaca tttgtactct ttctgagaag  2520
gaacgtcaga tcaaaaagca gacagcattg gtggaattgg taaagcataa accaaaggct  2580
acaaagagc agctgaaggc tgttatggat gattttgcag ctttcgtgga aaagtgttgt  2640
aaagccgatg ataaagagac ttgtttgca gaggagggca aaaagctggt tgctgcatca  2700
caagctgccc taggtcttgc agccgctacc ggtccagcac tgccagagga tggcggatct  2760
ggtgctttcc cacctggaca cttcaaggat cctaaaaggt tatactgcaa aaacggtggg  2820
ttttttcctta gaattcaccc tgatggcaga gtcgacggtg ttcgtgaaaa gagtgaccca  2880
catatcaagt tacagttaca agccgaagag cgaggagtag tttccatcaa aggcgtctgt  2940
gctaacagat atctagctat gaaggaggat ggaagattgt tggcctctaa gtgtgttacc  3000
gacgaatgct ttttcttga aaggttggag tccaacaatt acaatactta tcgttcacga  3060
aagtatacgt cttggtacgt ggctttgaag agaacaggac agtacaaatt gggttccaaa  3120
actggtcctg gtcaaaaagc tatactttt ctacccatgt ctgcaaaatc aggtgggagt  3180
catcaccacc accatcatta gtga                                          3204
```

```
SEQ ID NO: 266          moltype = AA  length = 918
FEATURE                 Location/Qualifiers
REGION                  1..918
                        note = Synthetic construct
source                  1..918
                        mol_type = protein
                        organism = synthetic construct
SEQUENCE: 266
DAHKSEVAHR FKDLGEENFK ALVLIAFAQY LQQSPFEDHV KLVNEVTEFA KTCVADESAE   60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFQAETFTFH ADICTLSEKE RQIKKQTALV ELVKHKPKAT  540
KEQLKAVMDD FAAFVEKCCK ADDKETCFAE EGKKLVAASQ AALGLAAATG AQVLRGTVTD  600
FPGFDERADA ETLRKAMKGL GTDEESILTL LTSRSNAQRQ EISAAFKTLF GRDLLDDLKS  660
ELTGKFEKLI VALMKPSRLY DAYELKHALK GAGTNEKVLT EIIASRTPEE LRAIKQVYEE  720
EYGSSLEDDV VGDTSGYYQR MLVVLLQANR DPDAGIDEAQ VEQDAQALFQ AGELKWGTDE  780
EKFITIFGTR SVSHLRKVFD KYMTISGFQI EETIDRETSG NLEQLLLAVV KSIRSIPAYL  840
AETLYYAMKG AGTDDHTLIR VMVSRSEIDL FNIRKEFRKN FATSLYSMIK GDTSGDYKKA  900
LLLLCGEDDG GSHHHHHH                                                 918
```

```
SEQ ID NO: 267          moltype = DNA  length = 2760
FEATURE                 Location/Qualifiers
misc_feature            1..2760
                        note = Synthetic construct
source                  1..2760
                        mol_type = other DNA
                        organism = synthetic construct
SEQUENCE: 267
gacgctcata agtctgaagt tgctcacaga ttcaaagact taggtgaaga gaactttaag   60
gctcttgtac ttatagcatt tgctcagtat ctgcaacaga gtcccttcga agatcatgtc  120
aagctggtga atgaggtaac cgaattcgcc aagacttgtg tggctgataa atccgccgaa  180
aactgdaca aatctttaca cacattgttc ggagataaac tatgcacagt agcaactta  240
cgtgaaactt atggtgagat ggcagattgt tgtgctaaac aggagcctga gagaaatgaa  300
tgcttttttgc aacacaagga cgacaatcct aaccttccca gattggttag acccgaggtt  360
gacgttatgt gtaccgcctt ccacgacaat gaggaaacat ttctgaaaaa gtacttgtac  420
gaaattgcac gacgtcaccc atacttctat gcacctgagc ttttgttttt cgccaaagaa  480
tacaaggcag ctttactga gtgctgtcaa gcagccgata aggctgcttg tctattacct  540
aaacttgatg agcttagaga tgaggdtaaa gcatcctccg ctaaacagag gttgaaatgt  600
gccagtttgc agaagtttgg tgaacgtgct ttcaaggcat gggctgttgc tagattatct  660
caaagatttc ctaaggccga atttgctgag gtgtcaaagt tggtgacgga tttgactaag  720
gtccacactg agtgttgcca tggtgatctt ttggaatgtg ctgacgatag agccgacctg  780
gccaagtata tctgtgaaaa ccaagattct atcagtagta agctgaagga atgttgcgaa  840
```

```
aaacctctac tagagaaatc tcattgcatc gcagaagttg aaaacgatga aatgccagcc   900
gacttgccca gtctggctgc tgatttcgtc gagtcaaaag atgtttgcaa aaactatgcc   960
gaagcaaagg atgtcttttt gggcatgttt ctgtacgaat atgctcgtcg tcatcctgac  1020
tattccgttg tcctgttgct aagactagct aaaacgtatg aaacgacctt ggaaaagtgt  1080
tgcgctgcag ctgatcccca cgagtgttat gcaaaagttt tcgatgagtt taagccactt  1140
gtagaagagc cacagaactt gatcaaacag aattgtgagc ttttcgagca attaggtgag  1200
tataagtttc aaaacgcttt gctggttaga tataccaaaa aggtcccaca agtgtcaacc  1260
cctaccctgg tagaagtgag tagaaatcta ggaaaagtcg gatctaagtg ctgcaagcat  1320
ccagaagcta agagaatgcc ttgcgctgag gattacttgt cagtagtttt gaatcagttg  1380
tgcgtcctac atgaaaagac acccgtttct gatagagtca ctaagtgttg tactgagtct  1440
ctagtaaaca gaaggccttg tttctctgca ttagaagtag atgaaaccta tgtcccaaag  1500
gagttccaag ctgaaacctt tacatttcac gccgacattt gtacgctatc tgagaaggag  1560
cgtcagatca aaaagcaaac agcccttgtt gagcttgtga agcacaagcc aaaagctaca  1620
aaggagcaat tgaaagccgt catggacgat ttcgccgcat ttgttgagaa gtgttgcaag  1680
gcagatgata aggaaacttg ttttgctgaa gagggcaaaa agcttgttgc cgcctctcaa  1740
gctgctttgg gactagccgc tgctaccggt gctcaagttt tgaggggaac cgttaccgac  1800
ttcccaggtt ttgacgaaag agccgacgca gaaacattaa ggaaagccat gaagggctta  1860
ggcaccgatg aggagtccat tctgacactg ttgacttccc gatccaatgc ccaaaggcag  1920
gagatttcag ccgctttcaa gactttgttt ggtagagatc ttctggacga cctgaaatca  1980
gaactgactg gaaagtttga gaaacttatt gttgctttga tgaagccttc aagactatat  2040
gacgcatacg agttgaaaca tgcattgaaa ggtgcaggaa ctaatgaaaa agtgttaact  2100
gagatcattg cttccagaac accagaagag cttcgtgcta tcaaacaagt gtatgaagag  2160
gaatacggat caagtctgga agatgacgtt gttggtgata cctcagggta ttaccaaagg  2220
atgcttgtcg ttctattaca agctaatcga gatcctgacg ccggaatcga tgaagctcaa  2280
gttgaacaag atgctcaggc tctttttcaa gccggtgaat tgaagtgggg gactgatgag  2340
gaaaagttta tcacgatctt tggtactaga tctgttagtc atttgagaaa agtatttgac  2400
aaatacatga ccatttctgg ctttcaaata gaagagacta ttgataggga aacttccggt  2460
aacttggaac aactgttgtt agctgtggtc aagagtataa gatcaattcc agcttactta  2520
gctgaaactc tgtattacgc aatgaaagga gcaggcacag acgatcacac gttgatccga  2580
gtcatggttt ccagatcaga gattgacttg ttcaatatca ggaaggaatt caggaaaaac  2640
tttgcaacct ctttgtactc catgatcaaa ggtgatactt ccggtgatta caaaaaggct  2700
ttgttgttgt tatgtggaga ggatgacgga ggttccacatc accatcatca ccattagtga  2760
```

SEQ ID NO: 268          moltype = AA   length = 918
FEATURE                 Location/Qualifiers
REGION                  1..918
                        note = Synthetic construct
source                  1..918
                        mol_type = protein
                        organism = synthetic construct SEQUENCE: 268
```
DAHKSEVAHR FKDLGEENFK ALVLIAFAQY LQQSPFEDHV KLVNEVTEFA KTCVADESAE   60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFQAETFTFH ADICTLSEKE RQIKKQTALV ELVKHKPKAT  540
KEQLKAVMDD FAAFVEKCCK ADDKETCFAE EGKKLVAASQ AALGLAAATG AQVLRGTVTD  600
FPGFDERADA ETLRKAMKGL GTDEESILTL LTSRSNAQRQ EISAAFKTLF GRDLLDDLKS  660
ELTGKFEKLI VALMKPSRLY DAYELKHALK GAGTNEKVLT EIIASRTPEE LRAIKQVYEE  720
EYGSSLEDDV VGNTSGYYQR MLVVLLQANR DPDAGIDEAQ VEQDAQALFQ AGELKWGTDE  780
EKFITIFGTR SVSHLRKVFD KYMTISGFQI EETIDRATSG NLEQLLLAVV KSIRSIPAYL  840
AETLYYAMKG AGTDDHTLIR VMVSRSEIDL FNIRKEFRKN FATSLYSMIK GDTSGDYKKA  900
LLLLCGEDDG GSHHHHHH                                               918
```

SEQ ID NO: 269          moltype = DNA   length = 2760
FEATURE                 Location/Qualifiers
misc_feature            1..2760
                        note = Synthetic construct
source                  1..2760
                        mol_type = other DNA
                        organism = synthetic construct SEQUENCE: 269
```
gacgctcata agtctgaagt tgctcacaga ttcaaagact taggtgaaga gaactttaag   60
gctcttgtac ttatagcatt tgctcagtat ctgcaacaga gtcccttcga agatcatgtc  120
aagctggtga atgaggtaac cgaattcgcc aagacttgtg tggctgatga atccgccgaa  180
aactgtgaca aatctttaca cacattgttc ggagataaac tatgcacagt agcaacttta  240
cgtgaaactt atggtgagat ggcagattgt tgtgctaaac aggagcctga gagaaatgaa  300
tgctttttgc aacacaagga cgacaatcct aaccttccca gattggttag acccgaggtt  360
gacgttatgt gtaccgcctt ccacgacaat gaggaaacat ttctgaaaaa gtacttgtac  420
gaaattgcac gacgtcaccc atacttctat gcacctgaac ttttgttttt cgccaaaaga  480
tacaaggcag ctttcactga gtgctgtcaa gcagccgata aggctgcttg tctattacct  540
aaacttgatg agcttagaga tgagggtaaa gcatcctccg ctaaacagag gttgaaatgt  600
gccagtttgc agaagtttgg tgaacgtgct ttcaaggcat gggctgttgc tagattatct  660
caaagatttc ctaaggccga atttgctgag gtgtcaaagt tggtgacgga tttgactaag  720
gtccacactg agtgttgcca tggtgatctt ttggaatgtg ctgacgatag agccgacctg  780
```

-continued

```
gccaagtata tctgtgaaaa ccaagattct atcagtagta agctgaagga atgttgcgaa   840
aaacctctac tagagaaatc tcattgcatc gcagaagttg aaaacgatga aatgccagcc   900
gacttgccca gtctggctgc tgatttcgtc gagtcaaaag atgtttgcaa aaactatgcc   960
gaagcaaagg atgtcttttt gggcatgttt ctgtacgaat atgctcgtcg tcatcctgac  1020
tattccgttg tcctgttgct aagactagct aaaacgacct ggaaaagtgt  1080
tgcgctgcag ctgatcccca cgagtgttat gcaaaagttt tcgatgagtt taagccactt  1140
gtagaagagc cacagaactt gatcaaacag aattgtgagc ttttcgagca attaggtgag  1200
tataagtttc aaaacgcttt gctggttaga tataccaaaa aggtcccaca agtgtcaacc  1260
cctaccctgg tagaagtgag tagaaatcta ggaaaagtcg gatctaagtg ctgcaagcat  1320
ccagaagcta agagaatgcc ttgcgctgag gattacttgt cagtagtttt gaatcagttg  1380
tgcgtcctac atgaaaagac acccgtttct gatagagtca ctaagtgttg tactgagtct  1440
ctagtaaaca gaaggccttg tttctctgca ttagaagtag atgaaaccta tgtcccaaag  1500
gagttccaag ctgaaacctt tacatttcac gccgacattt gtacgctatc tgagaaggag  1560
cgtcagatca aaaagcaaac agcccttgtt gagcttgtga agcacaagcc aaaagctaca  1620
aaggagcaat tgaaagccgt catggacgat ttcgccgcat ttgttgagaa gtgttgcaag  1680
gcagatgata aggaaacttg ttttgctgaa gagggcaaaa agcttgttgc cgcctctcaa  1740
gctgctttgg gactagccgc tgctaccggt gctcaagttt tgaggggaac cgttaccgac  1800
ttcccaggtt ttgacgaaag agccgacgca gaaacattaa ggaaagccat gaagggctta  1860
ggcaccgatg aggagtccat tctgacactg ttgacttccc gatccaatgc ccaaaggcag  1920
gagatttcag ccgctttcaa gactttgttt ggtagagatc ttctggacga cctgaaatca  1980
gaactgactg gaaagtttga gaaacttatt gttgctttga tgaagccttc aagactatat  2040
gacgcatacg agttgaaaca tgcattgaaa ggtgcaggaa ctaatgaaaa agtgttaact  2100
gagatcattg cttccagaac accagaagag cttcgtgcta tcaaacaagt gtatgaagag  2160
gaatacggat caagtctgga agatgacgtt gttggtaata cctcagggta ttaccaaagg  2220
atgcttgtcg ttctattaca agctaatcga gatcctgacg ccggaatcga tgaagctcaa  2280
gttgaacaag atgctcaggc tctttttcaa gccggtaaat tgaagtgggg gactgatgag  2340
gaaaagttta tcacgatctt tggtactaga tctgttagtc atttgagaaa agtatttgac  2400
aaatacatga ccatttctgg ctttcaaata gaagagacta ttgatagggc cacttccggt  2460
aacttggaac aactgttgtt agctgtggtc aagagtataa gatcaattcc agcttactta  2520
gctgaaactc tgtattacgc aatgaaagga gcaggcacag acgatcacac gttgatccga  2580
gtcatggttt ccagatcaga gattgacttg ttcaatatca ggaaggaatt caggaaaaac  2640
tttgcaacct ctttgtactc catgatcaaa ggtgatactt ccggtgatta caaaaaggct  2700
ttgttgttgt tatgtggaga ggatgacgga ggttcacatc accatcatca ccattagtga  2760
```

SEQ ID NO: 270          moltype = AA  length = 918
FEATURE                 Location/Qualifiers
REGION                  1..918
                        note = Synthetic construct
source                  1..918
                        mol_type = protein
                        organism = synthetic construct
SEQUENCE: 270
DAHKSEVAHR FKDLGEENFK ALVLIAFAQY LQQSPFEDHV KLVNEVTEFA KTCVADESAE   60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFQAETFTFH ADICTLSEKE RQIKKQTALV ELVKHKPKAT  540
KEQLKAVMDD FAAFVEKCCK ADDKETCFAE EGKKLVAASQ AALGLAAATG AQVLRGTVTD  600
FPGFDERADA ETLRKAMKGL GTDEESILTL LTSRSNAQRQ EISAAFKTLF GRDLLDDLKS  660
DLTGKFEKLI VALMKPSRLY DAYELKHALK GAGTNEKVLT EIIASRTPEE LRAIKQVYEE  720
EYGSSLEDDV VGNTSGYYQR MLVVLLQANR DPDAGIDEAQ VEQDAQALFQ AGELKWGTDE  780
EKFITIFGTR SVSHLRKVFD KYMTISGFQI EETIDRATSG NLEQLLLAVV KSIRSIPAYL  840
AETLYYAMKG AGTDDHTLIR VMVSRSEIDL FNIRKEFRKN FATSLYSMIK GNTSGDYKKA  900
LLLLCGEDDG GSHHHHHH                                                918

SEQ ID NO: 271          moltype = DNA  length = 2760
FEATURE                 Location/Qualifiers
misc_feature            1..2760
                        note = Synthetic construct
source                  1..2760
                        mol_type = other DNA
                        organism = synthetic construct
SEQUENCE: 271
gacgctcata agtctgaagt tgctcacaga ttcaaagact taggtgaaga gaactttaag   60
gctcttgtac ttatagcatt tgctcagtat ctgcaacaga gtcccttcga agatcatgtc  120
aagctggtga atgaggtaac cgaattcgcc aagacttgtg tggctgatga atccgccgaa  180
aactgtgaca aatctttaca cacattgttc ggagataaac tatgcacagt agcaacttta  240
cgtgaaactt atggtgagat ggcagattgt tgtgctaaac aggagcctga gagaaatgaa  300
tgcttttttgc aacacaagga cgacaatcct aaccttccca gattggttag acccgaggtt  360
gacgttatgt gtaccgcctt ccacgacaat gaggaaacat tctgaaaaa gtacttgtac  420
gaaattgcac gacgtcaccc atacttctat gcacctgagc ttttgttttt cgccaaaaga  480
tacaaggcag ctttcactga gtgctgtcaa gcagccgata aggctgcttg tctattacct  540
aaacttgatg agcttagaga tgagggtaaa gcatcctccg ctaaacagag gttgaaatgt  600
gccagtttgc agaagtttgg tgaacgtgct ttcaaggcat gggctgttgc tagattatct  660
caaagatttc ctaaggccga atttgctgag gtgtcaaagt tggtgacgga tttgactaag  720
```

-continued

```
gtccacactg agtgttgcca tggtgatctt ttggaatgtg ctgacgatag agccgacctg  780
gccaagtata tctgtgaaaa ccaagattct atcagtagta agctgaagga atgttgcgaa  840
aaacctctac tagagaaatc tcattgcatc gcagaagttg aaaacgatga aatgccagcc  900
gacttgccca gtctggctgc tgatttcgtc gagtcaaaag atgtttgcaa aaactatgcc  960
gaagcaaagg atgtcttttt gggcatgttt ctgtacgaat atgctcgtcg tcatcctgac  1020
tattccgttg tcctgttgct aagactagct aaaacgtatg aaacgacctt ggaaaagtgt  1080
tgcgctgcag ctgatcccca cgagtgttat gcaaaagttt tcgatgagtt taagccactt  1140
gtagaagagc cacagaactt gatcaaacag aattgtgagc ttttcgagca attaggtgag  1200
tataagtttc aaaacgcttt gctggttaga tataccaaaa aggtcccaca agtgtcaacc  1260
cctaccctgg tagaagtgag tagaaatcta ggaaaagtcg gatctaagtg ctgcaagcat  1320
ccagaagcta agagaatgcc ttgcgctgag gattacttgt cagtagtttt gaatcagttg  1380
tgcgtcctac atgaaaagac acccgtttct gatagagtca ctaagtgttg tactgagtct  1440
ctagtaaaca gaaggccttg tttctctgca ttagaagtag atgaaaccta tgtcccaaag  1500
gagttccaag ctgaaacctt tacatttcac gccgacattt gtacgctatc tgagaaggag  1560
cgtcagatca aaaagcaaac agcccttgtt gagcttgtga agcacaagcc aaaagctaca  1620
aaggagcaat tgaaagccgt catggacgat ttcgccgcat ttgttgagaa gtgttgcaag  1680
gcagatgata aggaaacttg ttttgctgaa gagggcaaaa agcttgttgc cgcctctcaa  1740
gctgctttgg gactagccgc tgctaccggt gctcaagttt tgaggggaac cgttaccgac  1800
ttcccaggtt ttgacgaaag agccgacgca gaaacattaa ggaaagccat gaagggctta  1860
ggcaccgatg aggagtccat tctgacactg ttgacttccc gatccaatgc ccaaaggcag  1920
gagatttcag ccgctttcaa gactttgttt ggtagagatc ttctggacga cctgaaatca  1980
gatctgactg gaaagtttga gaaacttatt gttgctttga tgaagccttc aagactatat  2040
gacgcatacg agttgaaaca tgcattgaaa ggtgcaggaa ctaatgaaaa agtgttaact  2100
gagatcattg cttccagaac accagaagag cttcgtgcta tcaaacaagt gtatgaagag  2160
gaatacggat caagtctgga agatgacgtt gttggtaata cctcagggta ttaccaaagg  2220
atgcttgtcg ttctattaca agctaatcga gatcctgacg ccggaatcga tgaagctcaa  2280
gttgaacaag atgctcaggc tcttttttcaa gccggtgaat tgaagtgggg gactgatgag  2340
gaaaagttta tcacgatctt tggtactaga tctgttagtc atttgagaaa agtatttgac  2400
aaatacatga ccatttctgg ctttcaaata gaagagacta ttgatagggc cacttccggt  2460
aacttggaac aactgttgtt agctgtggtc aagagtataa gatcaattcc agcttactta  2520
gctgaaactc tgtattacgc aatgaaagga gcaggcacag acgatcacac gttgatccga  2580
gtcatggttt ccagatcaga gattgacttg ttcaatatca ggaaggaatt caggaaaaac  2640
tttgcaacct ctttgtactc catgatcaaa ggtaatactt ccggtgatta caaaaaggct  2700
ttgttgttgt tatgtggaga ggatgacgga ggttcacatc accatcatca ccattagtga  2760
```

```
SEQ ID NO: 272        moltype = AA  length = 1097
FEATURE               Location/Qualifiers
REGION                1..1097
                      note = Synthetic construct
source                1..1097
                      mol_type = protein
                      organism = synthetic construct
SEQUENCE: 272
QRKRRNTIHE FKKSAKTTLI KIDPALKIKT KKVNTADQCA NRCTRNKGLP FTCKAFVFDK   60
ARKQCLWFPF NSMSSGVKKE FGHEFDLYEN KDYIRNCIIG KGRSYKGTVS ITKSGIKCQP  120
WSSMIPHEHS FLPSSYRGKD LQENYCRNPR GEEGGPWCFT SNPEVRYEVC DIPQCGAASD  180
AHKSEVAHRF KDLGEENFKA LVLIAFAQYL QQSPFEDHVK LVNEVTEFAK TCVADESAEN  240
CDKSLHTLFG DKLCTVATLR ETYGEMADCC AKQEPERNEC FLQHKDDNPN LPRLVRPEVD  300
VMCTAFHDNE ETFLKKYLYE IARRHPYFYA PELLFFAKRY KAAFTECCQA ADKAACLLPK  360
LDELRDEGKA SSAKQRLKCA SLQKFGERAF KAWAVARLSQ RFPKAEFAEV SKLVTDLTKV  420
HTECCHGDLL ECADDRADLA KYICENQDSI SSKLKECCEK PLLEKSHCIA EVENDEMPAD  480
LPSLAADFVE SKDVCKNYAE AKDVFLGMFL YEYARRHPDY SVVLLLRLAK TYETTLEKCC  540
AAADPHECYA KVFDEFKPLV EEPQNLIKQN CELFEQLGEY KFQNALLVRY TKKVPQVSTP  600
TLVEVSRNLG KVGSKCCKHP EAKRMPCAED YLSVVLNQLC VLHEKTPVSD RVTKCCTESL  660
VNRRPCFSAL EVDETYVPKE FQAETFTFHA DICTLSEKER QIKKQTALVE LVKHKPKATK  720
EQLKAVMDDF AAFVEKCCKA DDKETCFAEE GKKLVAASQA ALGLAAATGA QVLRGTVTDF  780
PGFDERADAE TLRKAMKGLG TDEESILTLL TSRSNAQRQE ISAAFKTLFG RDLLDDLKSD  840
LTGKFEKLIV ALMKPSRLYD AYELKHALKG AGTNEKVLTE IIASRTPEEL RAIKQVYEEE  900
YGSSLEDDVV GNTSGYYQRM LVVLLQANRD PDAGIDEAQV EQDAQALFQA GELKWGTDEE  960
KFITIFGTRS VSHLRKVFDK YMTISGFQIE ETIDRATSGN LEQLLLAVVK SIRSIPAYLA  1020
ETLYYAMKGA GTDDHTLIRV MVSRSEIDLF NIRKEFRKNF ATSLYSMIKG NTSGDYKKAL  1080
LLLCGEDDGG SHHHHHH                                                 1097
```

```
SEQ ID NO: 273        moltype = DNA  length = 3297
FEATURE               Location/Qualifiers
misc_feature          1..3297
                      note = Synthetic construct
source                1..3297
                      mol_type = other DNA
                      organism = synthetic construct
SEQUENCE: 273
caacgtaagc gtcgaaacac tatccatgag ttcaaaaagt ctgcaaaaac tactttgata   60
aagatagacc cagctttgaa gataaagacg aaaaaggtca atactgccga ccagtgtgct  120
aatcgatgta ctagaaacaa gggcttaccc tttacttgta aggcttttgt tttcgacaaa  180
gcaaggaagc aatgtttatg gttccccttc aattcaatga gttctggtgt gaaaaaggaa  240
tttggtcatg aatttgattt gtacgagaac aaagattaca ttagaaactg cattatcggc  300
aaaggaagat cttacaaggg gacggtgtct ataacaaaga gtggcataaa gtgtcaacca  360
tggtctagta tgattccaca tgagcactct ttccttccct cctcctatcg aggaaaagac  420
ctacaagaga actattgtcg aaaccctaga ggagaagagg gaggcccttg gtgctttacg  480
```

-continued

```
agtaaccctg aggttagata cgaagtttgt gacattccac aatgcggagc tgcaagtgac   540
gctcataagt ctgaagttgc tcacagattc aaagacctag gtgaagagaa ctttaaggct   600
cttgtactta tagcatttgc tcagtatctg caacagagtc ccttcgaaga tcatgtcaag   660
ctggtgaatg aggtaaccga attcgccaag acttgtgtgg ctgatgaatc cgccgaaaac   720
tgtgacaaat ctttacacac attgttcgga gataaactat gcacagtagc aactttacgt   780
gaaacttatg gtgagatggc agattgttgt gctaaacagg agcctgagag aaatgaatgc   840
tttttgcaac acaaggacga caatcctaac cttcccagat tggttagacc cgaggttgac   900
gttatgtgta ccgccttcca cgacaatgag gaaacatttc tgaaaaagta cttgtacgaa   960
attgcacgac gtcacccata cttctatgca cctgagcttt tgtttttcgc caaaagatac  1020
aaggcagctt tcactgagtg ctgtcaagca gccgataagg ctgcttgtct attacctaaa  1080
cttgatgagc ttagagatga gggtaaagca tcctccgcta aacagaggtt gaaatgtgcc  1140
agtttgcaga agtttggtga acgtgctttc aaggcatggg ctgttgctag attatctcaa  1200
agatttccta aggccgaatt tgctgaggtg tcaaagttgg tgacggattt gactaaggtc  1260
cacactgagt gttgccatgg tgatcttttg gaatgtgctg acgatagagc cgacctggcc  1320
aagtatatct gtgaaaacca agattctatc agtagtaagc tgaaggaatg ttgcgaaaaa  1380
cctctactag agaaatctca ttgcatcgca gaagttgaaa acgatgaaat gccagccgac  1440
ttgcccagtc tggctgctga tttcgtcgag tcaaagatg tttgcaaaaa ctatgccgaa  1500
gcaaaggatg tctttttggg catgtttctg tacgaatatg ctcgtcgtca tcctgactat  1560
tccgttgtcc tgttgctaag actagctaaa acgtatgaaa cgaccttgga aaagtgttgc  1620
gctgcagctg atccccacga gtgttatgca aaagttttcg atgagtttaa gccacttgta  1680
gaagagccac agaacttgat caaacagaat tgtgagcttt tcgagcaatt aggtgagtat  1740
aagtttcaaa acgctttgct ggttagatat accaaaaagt tcccacaagt gtcaacccct  1800
accctggtag aagtgagtag aaatctagga aaagtcggat ctaagtgctg caagcatcca  1860
gaagctaaga gaatgccttg cgctgaggat tacttgtcag tagtttgaa tcagttgtgc  1920
gtcctacatg aaaagacacc cgtttctgat agagtcacta agtgttgtac tgagtctcta  1980
gtaaacagaa ggccttgttt ctctgcatta gaagtagatg aaacctatgt cccaaaggag  2040
ttccaagctg aaacctttac atttcacgcc gacatttgta cgctatctga gaaggagcgt  2100
cagatcaaaa agcaaacagc ccttgttgag cttgtgaagc acaagccaaa agctacaaag  2160
gagcaattga aagccgtcat ggacgatttc gccgcatttg ttgagaagtg ttgcaaggca  2220
gatgataagg aaacttgttt tgctgaagag ggcaaaaagc ttgttgccgc ctctcaagct  2280
gctttgggac tagccgctgc taccggtgct caagttttga ggggaaccgt taccgacttc  2340
ccaggttttg acgaaagagc cgacgcagaa acattaagga aagccatgaa gggcttaggc  2400
accgatgagg agtccattct gacactgttg acttcccgat ccaatgccca aaggcaggag  2460
atttcagccg ctttcaagac tttgtttggt agagatcttc tggacgacct gaaatcagat  2520
ctgactggaa agtttgagaa acttattgtt gctttgatga agccttcaag actatatgac  2580
gcatacgagt tgaaacatgc attgaaaggt gcaggaacta atgaaaaagt gttaactgag  2640
atcattgctt ccagaacacc agaagagctt cgtgctatca acaagtgta tgaagaggaa  2700
tacggatcaa gtctggaaga tgacgttgtt ggtaataacct cagggtatta ccaaaggatg  2760
cttgtcgttc tattacaagc taatcgagat cctgacgccg gaatcgatga agctcaagtt  2820
gaacaagatg ctcaggctct ttttcaagcc ggtgaattga agtgggggac tgatgaggaa  2880
aagtttatca cgatctttgg tactagatct gttagtcatt tgagaaaagt atttgacaaa  2940
tacatgacca tttttctggctt tcaaataaa gagactattg atagggccac ttccggtaac  3000
ttggaacaac tgttgttagc tgtggtcaag agtataagt caattccagc ttacttagct  3060
gaaactctgt attacgcaat gaaaggagca ggcacagacg atcacacgtt gatccgagtc  3120
atggtttcca gatcagagat tgacttgttc aatatcagga aggaattcag gaaaaacttt  3180
gcaacctctt gtgtactccat gatcaaaggt aatacttccg gtgattacaa aaaggctttg  3240
ttgttgttat gtgagagga tgacggaggt tcacatcacc atcatcacca ttagtga      3297
```

SEQ ID NO: 274          moltype = AA  length = 1110
FEATURE                 Location/Qualifiers
REGION                  1..1110
                        note = Synthetic construct
source                  1..1110
                        mol_type = protein
                        organism = synthetic construct
SEQUENCE: 274
```
MSPLLRRLLL AALLQLAPAQ APVSQPDAPG HQRKVVSWID VYTRATCQPR EVVVPLTVEL    60
MGTVAKQLVP SCVTVQRCGG CCPDDGLECV PTGQHQVRMQ ILMIRYPSSQ LGEMSLEEHS   120
QCECRPKKKD SAVKPDSPRP LCPRCTQHHQ RPDPRTCRRR CRRRSFLRCQ GRGLELNPDT   180
CRCRKLRRGA ASDAHKSEVA HRFKDLGEEN FKALVLIAFA QYLQQSPFED HVKLVNEVTE   240
FAKTCVADES AENCDKSLHT LFGDKLCTVA TLRETYGEMA DCCAKQEPER NECFLQHKDD   300
NPNLPRLVRP EVDVMCTAFH DNEETFLKKY LYEIARRHPY FYAPELLFFA KRYKAAFTEC   360
CQAADKAACL LPKLDELRDE GKASSAKQRL KCASLQKFGE RAFKAWAVAR LSQRFPKAEF   420
AEVSKLVTDL TKVHTECCHG DLLECADDRA DLAKYICENQ DSISSKLKEC CEKPLLEKSH   480
CIAEVENDEM PADLPSLAAD FVESKDVCKN YAEAKDVFLG MFLYEYARRH PDYSVVLLLR   540
LAKTYETTLE KCCAAADPHE CYAKVFDEFK PLVEEPQNLI KQNCELFEQL GEYKFQNALL   600
VRYTKKVPQV STPTLVEVSR NLGKVGSKCC KHPEAKRMPC AEDYLSVVLN QLCVLHEKTP   660
VSDRVTKCCT ESLVNRRPCF SALEVDETYV PKEFQAETFT FHADICTLSE KERQIKKQTA   720
LVELVKHKPK ATKEQLKAVM DDFAAFVEKC CKADDKETCF AEEGKKLVAA SQAALGLAAA   780
TGAQVLRGTV TDFPGFDERA DAETLRKAMK GLGTDEESIL TLLTSRSNAQ RQEISAAFKT   840
LFGRDLLDDL KSDLTGKFEK LIVALMKPSR LYDAYELKHA LKGAGTNEKV LTEIIASRTP   900
EELRAIKQVY EEEYGSSLED DVVGNTSGYY QRMLVVLLQA NRDPDAGIDE AQVEQDAQAL   960
FQAGELKWGT DEEKFITIFG TRSVSHLRKV FDKYMTISGF QIEETIDRAT SGNLEQLLLA  1020
VVKSIRSIPA YLAETLYYAM KGAGTDDHTL IRVMVSRSEI DLFNIRKEFR KNFATSLYSM  1080
IKGNTSGDYK KALLLLCGED DGGSHHHHHH                                    1110
```

SEQ ID NO: 275          moltype = DNA  length = 3336
FEATURE                 Location/Qualifiers
misc_feature            1..3336

-continued

```
                      note = Synthetic construct
source                1..3336
                      mol_type = other DNA
                      organism = synthetic construct
SEQUENCE: 275
atgtctcctt tgctgagaag gttactattg gctgcattgt tgcagttagc cccagcccaa  60
gctcccgttt cccaaccaga tgcacctggt catcaacgaa aggtggtttc ctggatcgat  120
gtctacacga gagctacctg tcaaccaagg gaagttgtag ttcccttaac tgtggagctt  180
atgggtacag tagccaagca attagttccc tcatgtgtca ctgttcagcg atgtggaggg  240
tgttgtcctg acgacggcct agagtgcgtc ccaacaggac agcaccaagt gagaatgcaa  300
attctgatga tacgatatcc tagttctcag ttgggtgaaa tgagtttgga ggagcattct  360
caatgcgaat gtagacccaa aaagaaagat tccgctgtca aaccagactc tcctagacca  420
ctatgcccaa gatgcactca acaccaccag cgtcctgatc ctagaacttg taggcgtaga  480
tgtcgtagaa gatcattcct tagatgtcag ggaagagtca ttgaattgaa tccagacacc  540
tgccgatgtc gtaagctgcg tagggggagc gcaagtgacg ctcataagtc tgaagttgct  600
cacagattca aagacctagg tgaagagaac tttaaggctc ttgtacttat agcatttgct  660
cagtatctgc aacagagtcc cttcgaagat catgtcaagc tggtgaatga ggtaaccgaa  720
ttcgccaaga cttgtgtggc tgatgaatcc gccgaaaact gtgacaaatc tttacacaca  780
ttgttcggag ataaactatg cacagtagca actttacgtg aaacttatgg tgagatggca  840
gattgttgtg ctaaacagga gcctgagaga aatgaatgct ttttgcaaca caaggacgac  900
aatcctaacc ttcccagatt ggttagaccc gaggttgacg ttatgtgtac cgccttccac  960
gacaatgagg aaacatttct gaaaaagtac ttgtacgaaa ttgcacgacg tcacccatac  1020
ttctatgcac ctgagctttt gtttttcgcc aaaagataca aggcagcttt cactgagtgc  1080
tgtcaagcag ccgataaggc tgcttgtcta ttacctaaac ttgatgagct tagagatgag  1140
ggtaaagcat cctccgctaa acagaggttg aaatgtgcca gtttgcagaa gtttggtgaa  1200
cgtgctttca aggcatgggc tgttgctaga ttatctcaaa gatttcctaa ggccgaattt  1260
gctgaggtgt caaagttggt gacggatttg actaaggtcc acactgagtg ttgccatggt  1320
gatcttttgg aatgtgctga cgatagagcc gacctggcca agtatatctg tgaaaaccaa  1380
gattctatca gtagtaagct gaaggaatgt tgcgaaaaac tctactaga gaaatctcat  1440
tgcatcgcag aagttgaaaa cgatgaaatg ccagccaatc tgcccagtct ggctgctgat  1500
ttcgtcgagt caaaagatgt ttgcaaaaac atgccgaag caaaggatgt ctttttgggc  1560
atgtttctgt acgaatatgc tcgtcgtcat cctgactatt ccgttgtcct gttgctaaga  1620
ctagctaaaa cgtatgaaac gaccttggaa aagtgttgcg ctgcagctga tccccacgag  1680
tgttatgcaa aagtttttcga tgagtttaag ccacttgtag aagagccaca gaacttgatc  1740
aaacagaatt gtgagctttt cgagcaatta ggtgagtata agtttcaaaa cgctttgctg  1800
gttagatata ccaaaaaggt cccacaagtg tcaacccta ccctggtaga agtgagtaga  1860
aatctaggaa aagtcggatc taagtgctgc aagcatccag aagctaagag aatgccttgc  1920
gctgaggatt acttgtcagt agttttgaat cagttgtgcg tcctacatga aaagacaccg  1980
gtttctgata gagtcactaa gtgttgtact gagtctctaa taaacagaag gccttgtttc  2040
tctgcattag aagtagatga aacctatgtc ccaaaggagt tccaagctga aacctttaca  2100
tttcacgccg acatttgtac gctatctgag aaggagcgtc agatcaaaaa gcaaacagcc  2160
cttgttgagc ttgtgaagca caagccaaaa gctacaaagg agcaattgaa agccgtcatg  2220
gacgatttcg ccgcatttgt tgagaagtgt tgcaaggcag atgataagga aacttgtttt  2280
gctgaagagg gcaaaaagct tgttgccgcc tctcaagctg ctttgggact agccgctgct  2340
accggtgctc aagttttgag gggaaccgtt accgacttcc caggttttga cgaaagagcc  2400
gacgcagaaa cattaaggaa agccatgaag ggcttaggca ccgatgagga gtccattctg  2460
acactgtgta cttcccgatc caatgcccaa aggcaggaga tttcagccgc tttcaagact  2520
ttgtttggta gagatcttct ggacgacctg aaatcagatc tgactggaaa gtttgagaaa  2580
cttattgttg ctttgatgaa gccttcaaga ctatatgacg catacgagtt gaaacatgca  2640
ttgaaaggtc aggaactaa tgaaaaagtg ttaactgaga tcattgcttc cagaacacca  2700
gaagacttc gtgctatcaa acaagtgtat gaagaggaat acggatcaag tctggaagat  2760
gacgttgttg gtaataccctc aggggtattac caaaggatgc ttgtcgttct attacaagct  2820
aatcgagatc ctgacgccgg aatcgatgaa gctcaagttg aacaagatgc tcaggctctt  2880
tttcaagccg gtgaattgaa gtgggggact gatgaggaaa agtttatcac gatctttggt  2940
actagatctg ttagtcatt gagaaaagta tttgacaaat acatgaccat ttctggcttt  3000
caaatagaag agactattga tagggccact tccggtaact tggaacaact gttgttagct  3060
gtggtcaaga gtataagatc aattccagct tacttagctg aaactctgta ttacgcaatg  3120
aaaggagcag gcacagacga tcacacgttg atccgagtca tggtttccag atcagagatt  3180
gacttgttca atatcaggaa ggaattcagg aaaaactttg caacctcttt gtactccatg  3240
atcaaaggta atacttccgg tgattacaaa aaggctttgt tgttgttatg tggagaggat  3300
gacggaggtt cacatcacca tcatcaccat tagtga                            3336

SEQ ID NO: 276        moltype = AA  length = 1053
FEATURE               Location/Qualifiers
REGION                1..1053
                      note = Synthetic construct
source                1..1053
                      mol_type = protein
                      organism = synthetic construct
SEQUENCE: 276
MSPLLRRLLL AALLQLAPAQ APVSQPDAPG HQRKVVSWID VYTRATCQPR EVVVPLTVEL  60
MGTVAKQLVP SCVTVQRCGG CCPDDGLECV PTGQHQVRMQ ILMIRYPSSQ LGEMSLEEHS  120
QCECRPKKKD SGAASDAHKS EVAHRFKDLG EENFKALVLI AFAQYLQQSP FEDHVKLVNE  180
VTEFAKTCVA DESAENCDKS LHTLFGDKLC TVATLRETYG EMADCCAKQE PERNECFLQH  240
KDDNPNLPRL VRPEVDVMCT AFHDNEETFL KKYLYEIARR HPYFYAPELL FFAKRYKAAF  300
TECCQAADKA ACLLPKLDEL RDEGKASSAK QRLKCASLQK FGERAFKAWA VARLSQRFPK  360
AEFAEVSKLV TDLTKVHTEC CHGDLLECAD DRADLAKYIC ENQDSISSKL KECCEKPLLE  420
KSHCIAEVEN DEMPADLPSL AADFVESKDV CKNYAEAKDV FLGMFLYEYA RRHPDYSVVL  480
LLRLAKTYET TLEKCCAAAD PHECYAKVFD EFKPLVEEPQ NLIKQNCELF EQLGEYKFQN  540
```

-continued

```
ALLVRYTKKV PQVSTPTLVE VSRNLGKVGS KCCKHPEAKR MPCAEDYLSV VLNQLCVLHE  600
KTPVSDRVTK CCTESLVNRR PCFSALEVDE TYVPKEFQAE TFTFHADICT LSEKERQIKK  660
QTALVELVKH KPKATKEQLK AVMDDFAAFV EKCCKADDKE TCFAEEGKKL VAASQAALGL  720
AAATGAQVLR GTVTDFPGFD ERADAETLRK AMKGLGTDEE SILTLLTSRS NAQRQEISAA  780
FKTLFGRDLL DDLKSDLTGK FEKLIVALMK PSRLYDAYEL KHALKGAGTN EKVLTEIIAS  840
RTPEELRAIK QVYEEEYGSS LEDDVVGNTS GYYQRMLVVL LQANRDPDAG IDEAQVEQDA  900
QALFQAGELK WGTDEEKFIT IFGTRSVSHL RKVFDKYMTI SGFQIEETID RATSGNLEQL  960
LLAVVKSIRS IPAYLAETLY YAMKGAGTDD HTLIRVMVSR SEIDLFNIRK EFRKNFATSL  1020
YSMIKGNTSG DYKKALLLLC GEDDGGSHHH HHH                             1053

SEQ ID NO: 277         moltype = DNA   length = 3165
FEATURE                Location/Qualifiers
misc_feature           1..3165
                       note = Synthetic construct
source                 1..3165
                       mol_type = other DNA
                       organism = synthetic construct
SEQUENCE: 277
atgagtcctt tgctaagacg tttacttttg gctgccttat tgcagctggc accagcccaa  60
gcaccagtgt cacagccaga tgctcccggt caccagagaa aagtggttag ttggattgat  120
gtttacacga gggctacatg ccaacctaga gaagtagttg tccctctgac agttgaacta  180
atggggaccg ttgctaagca attggtgcct tcctgtgtca ctgttcagcg atgcggagga  240
tgttgtccag acgacggtct ggaatgcgta ccaactggcc aacatcaagt cagaatgcag  300
atcttgatga taagatatcc atcttcccaa ttaggagaaa tgtcacttga ggaacattct  360
caatgtgagt gtaggcccaa aaagaaggat tctggagctg caagtgacgc tcataagtct  420
gaagttgctc acagattcaa agacctaggt gaagagaact ttaaggctct tgtacttata  480
gcatttgctc agtatctgca acagagtccc ttcgaagatc atgtcaagct ggtgaatgag  540
gtaaccgaat tcgccaagac ttgtgtggct gatgaatccg ccgaaaactg tgacaaatct  600
ttacacacat tgttcggaga taaactatgc acagtagcaa ctttacgtga aacttatggt  660
gagatggcag attgttgtgc taaacaggag cctgagagaa atgaatgctt tttgcaacac  720
aaggacgaca atcctaacct tcccagattg gttagacccg aggttgacgt tatgtgtacc  780
gccttccacg acaatgagga aacatttctg aaaaagtact tgtacgaaat tgcacgacgt  840
cacccatact tctatgcacc tgagcttttg tttttcgcca aaagatacaa ggcagctttc  900
actgagtgct gtcaagcagc cgataaggct gcttgtctat tacctaaact tgatgagctt  960
agagatgagg gtaaagcatc ctccgctaaa cagaggttga aatgtgccag tttgcagaag  1020
tttggtgaac gtgctttcaa ggcatgggct gttgctagat tatctcaaag atttcctaag  1080
gccgaatttg ctgaggtgtc aaagttggtg acggatttga ctaaggtcca cactgagtgt  1140
tgccatggtg atcttttgga atgtgctgac gatagagccg acctggccaa gtatatctgt  1200
gaaaaccaag attctatcag tagtaagctg aaggaatgtt gcgaaaaacc tctactagag  1260
aaatctcatt gcatcgcaga agttgaaaac gatgaaatgc cagccgactt gcccagtctg  1320
gctgctgatt tcgtcgagtc aaaagatgtt tgcaaaaact atgccgaagc aaaggatgtc  1380
ttttttgggca tgtttctgta cgaatatgct cgtcgtcatc ctgactattc cgttgtcctg  1440
ttgctaagac tagctaaaac gtatgaaacg accttggaaa agtgttgcgc tgcagctgat  1500
ccccacgagt gttatgcaaa agtttttcgat gagtttaagc cacttgtaga agagccacag  1560
aacttgatca aacagaattg tgagcttttc gagcaattag gtgagtataa gtttcaaaac  1620
gctttgctgg ttagatatac caaaaaggtc ccacaagtgt caacccctac cctggtagaa  1680
gtgagtagaa atctaggaaa agtcggatct aagtgctgca agcatccaga agctaagaga  1740
atgccttgcg ctgaggatta cttgtcagta gttttgaatc agttgtgcgt cctacatgaa  1800
aagacacccg tttctgatag agtcactaag tgttgtactg agtctctagt aaacagaagg  1860
ccttgtttct ctgcattaga agtagatgaa acctatgtcc caaaggagtt ccaagctgaa  1920
acctttacat ttcacgccga catttgtacg ctatctgaga aggagcgtca gatcaaaaag  1980
caaacagccc ttgttgagct tgtgaagcac aagccaaaag ctacaaagga gcaattgaaa  2040
gccgtcatgg acgatttcgc cgcatttgtt gagaagtgtt gcaaggcaga tgataaggaa  2100
acttgtttttg ctgaagaggg caaaaagctt gttgccgcct ctcaagctgc tttgggacta  2160
gccgctgcta ccggtgctca agtttttgagg ggaaccgtta ccgacttccc aggtttttgac  2220
gaaagagccg acgcagaaac attaaggaaa gccatgaagg gcttaggcac cgatgaggag  2280
tccattctga cactgttgac ttcccgatcc aatgcccaaa ggcaggagat ttcagccgct  2340
ttcaagactt tgtttggtag agatcttctg gacgacctga aatcagatct gactggaaag  2400
tttgagaaac ttattgttgc tttgatgaag ccttcaagac tatatgacgc atacgagttg  2460
aaacatgcat tgaaaggtgc aggaactaat gaaaaagtgt taactgagat cattgcttcc  2520
agaacaccag aagagcttcg tgctatcaaa caagtgtatg aagaggaata cggatcaagt  2580
ctggaagatg acgttgttgg taataacctca gggtattacc aaaaggatgct tgtcgttcta  2640
ttacaagcta atcgagatcc tgacgccgga atcgatgaag ctcaagttga acaagatgct  2700
caggctcttt ttcaagccgg tgaattgaag tgggggacgt atgaggaaaa gtttatcacg  2760
atctttggta ctagatctgt tagtcatttg agaaaagtat ttgacaaata catgaccatt  2820
tctggctttc aaatagaaga gactattgat agggccactt ccggtaactt ggaacaactg  2880
ttgttagctg tggtcaagag tataagatca attccagctt acttagctga aactctgtat  2940
tacgcaatga aaggagcagg cacagacgat cacacgttga tccgagtcat ggtttccaga  3000
tcagagattg acttgttcaa tatcaggaag gaattcagga aaaactttgc aacctctttg  3060
tactccatga tcaaaggtaa tacttccggt gattacaaaa aggctttgtt gttgttatgt  3120
ggagaggatg acggaggttc acatcaccat catcaccatt agtga             3165
```

BI-SPECIFIC FUSION PROTEINS

RELATED APPLICATIONS

This application is a continuation of U.S. application Ser. No. 17/212,270, filed Mar. 25, 2021, which is a divisional of U.S. application Ser. No. 16/524,451, filed Jul. 29, 2019, now U.S. Pat. No. 10,988,547, which is a continuation of U.S. application Ser. No. 15/618,478, filed Jun. 9, 2017, now U.S. Pat. No. 10,407,512, which is a continuation of U.S. application Ser. No. 14/967,980, filed Dec. 14, 2015, now U.S. Pat. No. 9,718,892, which is a divisional of U.S. application Ser. No. 13/068,808, filed May 20, 2011, now U.S. Pat. No. 9,238,080, which claims the benefit of and priority to U.S. Provisional Application Ser. No. 61/347,040, filed May 21, 2010, the entire content of each of which is herein incorporated by reference in their entirety. Reference is also made to U.S. application Ser. No. 13/112,907, filed May 20, 2011, now U.S. Pat. No. 8,691,771, which is incorporated herein by reference.

REFERENCE TO SEQUENCE LISTING

This specification includes a sequence listing submitted herewith, which includes the file entitled 132463-010125.xml having the following size: 635,578 bytes which was created Oct. 9, 2023, the contents of which are incorporated by reference herein.

TECHNICAL FIELD

The present invention relates generally to fusion proteins that have therapeutic uses, and more specifically to bi-specific fusion proteins, pharmaceutical compositions comprising such fusion proteins, and methods for using such fusion proteins to repair damaged tissue.

BACKGROUND

Tissue regeneration is a multidisciplinary science in which the goal is to restore biological function of diseased or damaged tissues. Tissue regeneration addresses major clinical problems such as myocardial infarction. Myocardial infarction, commonly known as a heart attack, occurs when coronary artery obstruction cuts off the blood supply to part of the heart. The resulting lack of oxygen causes irreversible tissue damage (necrosis and apoptosis), due to the inability of the heart to sufficiently activate endogenous regeneration programs and self-repair. Such tissue damage is a leading cause of congestive heart failure, a condition in which the heart is no longer capable of effectively pumping blood. In the United States, there are more than a million heart attacks every year, and nearly 5 million people are afflicted with congestive heart failure.

There are no effective treatments for regenerating damaged cardiac tissue. Current therapies for congestive heart failure focus on preventing arrhythmia, progression of arteriosclerosis and recurrent myocardial infarction, but do not address the underlying tissue damage. More than half of patients diagnosed with congestive heart failure die within five years of diagnosis.

Stem cell therapy is a potential new strategy for cardiac repair. In the laboratory, it is possible to generate cardiac muscle cells from stem cells. This suggests that stems cells could be used to repair damaged tissue such as cardiac tissue in a patient; however, no therapeutic treatments based on such an approach are presently available. One difficulty that has been encountered in stem cell therapy is that of targeting sufficient numbers of stem cells to the damaged tissue to result in clinically significant repair.

There is, thus, a need in the art for methods for repairing or regenerating damaged tissues, and for improving the targeting of cells such as stem cells to facilitate tissue repair. The present invention fulfills these needs, and provides other related advantages.

SUMMARY OF THE INVENTION

The present invention provides bi-specific fusion proteins, nucleic acid molecules encoding bi-specific fusion proteins and therapeutic methods that employ such bi-specific fusion proteins. In certain aspects, the present invention provides bi-specific fusion proteins that comprise: (a) a targeting domain having a binding specificity to a target molecule associated with a damaged cell of a tissue, wherein the molecule is intracellular in a viable cell and exposed to the extracellular space in the damaged cell; and (b) an activator domain having a binding specificity to a growth factor receptor associated with a surface of a cell in the tissue, wherein upon exposure of the activator domain to the growth factor receptor, the activator domain binds the growth factor receptor so as to modulate regeneration or survival of the tissue. In some embodiments, the bi-specific protein further comprises a peptide half life modulator.

In certain aspects of the invention, the bi-specific fusion protein comprises (a) a targeting domain having a binding specificity to a target molecule associated with a damaged cell of a tissue, wherein the molecule is intracellular in a viable cell and exposed to the extracellular space in the damaged cell; (b) an activator domain having a binding specificity to a molecule associated with the surface of a cell in the tissue, wherein upon exposure of the activator domain to surface-associated molecule, the activator domain binds the surface-associated molecule so as to modulate regeneration or survival of the tissue; and (c) a half life modulator wherein the half life modulator modulates the half life of the bi-specific fusion protein.

In other aspects of the invention, the bi-specific fusion protein comprises (a) a targeting domain having a binding specificity to a target molecule associated with a tissue; (b) an activator domain having a binding specificity to a molecule associated with the surface of a cell in the tissue, wherein upon exposure of the activator domain to the molecule, the activator domain binds the molecule so as to modulate regeneration or survival of the tissue; and (c) a half life modulator wherein the half life modulator modulates the half life of the bi-specific fusion protein.

In other aspects of the invention, the bi-specific fusion protein comprises (a) a targeting domain having a binding specificity to a target molecule associated with a tissue; (b) a binding domain having a binding specificity to a molecule associated with the surface of a cell in the tissue, wherein upon exposure of the binding domain to the molecule, the binding domain binds the molecule so as to promote regeneration or survival of the tissue; and (c) a half life modulator wherein the half life modulator modulates the half life of the bi-specific fusion protein.

Yet other aspects of the invention relate to a fusion protein comprising (a) at least one targeting domain having a binding specificity to at least one target molecule associated with a tissue; (b) at least one activator domain having a binding specificity to at least one molecule associated with the surface of a cell in the tissue, wherein upon exposure of the activator domain to the molecule, the activator domain binds the molecule so as to promote regeneration or survival of the tissue; and (c) a half life modulator wherein the half life modulator modulates the half life of the fusion protein.

In some embodiments, the activator domain or the binding domain binds specifically to a growth factor receptor, cytokine receptor or stem cell-associated antigen. In some embodiments, the targeting domain does not have a biological activity. The targeting domain and the activator domain can bind different molecules on a same cell or can bind different molecules on different cells.

In some embodiments, the activator domain is selected from the group consisting of: fibroblast growth factor (FGF), epidermal-growth factor (EGF), neuregulin/heregulin (NRG/HRG), insulin-like growth factor (IGF), hepatocyte growth factor (HGF), thymosin, granulocyte colony stimulating factor (G-CSF), stem cell factor (SCF)/mast cell growth factor (MGF), periostin, vascular endothelial growth factor (VEGF), stromal cell-derived factor (SDF), platelet-derived growth factor (PDGF), tetracarcinoma-derived growth factor (TDGF), beta-nerve growth factor (NGF), brain-derived neurotrophic factor (BDNF), neurotrophin-3 (NT-3), thrombopoietin (TPO), bone morphogenic protein (BMP), activin A, betacellulin, beta-catenin, dickkopf homolog 1 (DKK1), erythropoietin (EPO), growth hormone (GH), heparin-binding EGF-like growth factor (HBEGF), insulin, interleukin (IL) leukemia inhibitory factor (LIF), monocyte chemotactic protein 1 (MCP1/CCL2), pleiotrophin (PTN), transforming growth factor (TGF), tumor necrosis factor (TNF), Wnt, an antibody having a specificity for an activator receptor, variants thereof, isoforms thereof, fragments thereof, and combinations thereof. In some embodiments, the activator domain comprises a sequence recited in any one of SEQ ID NOs: 3-9, 32-40, or 50-64.

The targeting domain can be at the amino terminus and the activator domain at the carboxy terminus of the fusion protein. In some embodiments, the targeting domain is at the carboxy terminus and the activator domain is at the amino terminus of the fusion protein. In some embodiments, the targeting domain is at the carboxy terminus and the activator domain is at the amino terminus of the fusion protein.

In some embodiments, the half life modulator is a non-immunogenic protein. The half life modulator can comprise a sequence from one of human serum albumin, domain III of human serum albumin, alpha-fetoprotein, vitamin D-binding protein, transthyretin antibody Fc domain, single-chain version of antibody Fc domain, proline-, alanine-, and/or serine-rich sequences, variants thereof, fragments thereof, and combinations thereof. For example, the half life modulator comprises at least 100 consecutive amino acids that are at least 80% identical to a serum albumin amino acid sequence. In some embodiments, the half life modulator has an amino acid sequence recited in any one of SEQ ID NOs: 10, 12, 14-29, 45-49, 65-71 or 105.

In some embodiments, the targeting domain binds to a target molecule selected from the group of myosin, cardiac myosin, DNA, phosphatidylserine, P-selectin, ICAM-1, c-Met (HGF receptor), variants thereof, fragments thereof, and combinations thereof. In some embodiments, the targeting domain binds to the target molecule with a dissociation constant Kd ranging from $10^{-6}$ M to $10^{-12}$M. The targeting domain can be selected from the group of annexin, synaptotagmin, anti-phosphatidylserine antibody, PS4A7, lactadherin, anti-myosin antibody, anti-DNA antibody, aDNASI1, aDNASI22, variants thereof, fragments thereof, and combinations thereof. In some embodiments, the targeting domain has a sequence recited in any one of SEQ ID NOs: 1-2, 30-31, 72-73, 76-83 or 85-86. In some embodiments, the antibody is a scFv antibody having a sequence recited in any one of SEQ ID NOs: 1, 2, 30, 73, 76-80. In some embodiments, annexin is annexin V and has sequence recited in SEQ ID. NOs 31, 81, 82 or 83. In some embodiments, the targeting domain comprises a sequence recited in any one of SEQ ID NOs: 1, 2, 30, 31 or 72-86.

In some embodiments, the bi-specific fusion protein further comprises a connector linking the half-life modulator to the fusion protein. The bi-specific fusion protein can exhibit an in vivo half-life of between 2 hours and 6 hours, between 6 hours and 24 hours, greater than 24 hours, or greater than one week.

In some embodiments, the fusion protein promotes cell recruitment, inhibition of apoptosis and/or induction of cell proliferation. In some embodiments, the fusion protein prevents cell damage, promotes cell growth, promotes motility of stem cells, and/or promotes differentiation of stem cells. In some embodiments, the fusion protein promotes tissue regeneration. The tissue can be a cardiac tissue, kidney tissue, bone, cartilage, joints, skin, liver tissue, pancreatic tissue, blood cells, lung tissue, or nervous system.

In some embodiments, the fusion protein further comprises a leader polypeptide. The leader polypeptide can comprise a sequence recited in any one of SEQ ID NOs: 41, 42, 87-91 or 244.

In some embodiments, the fusion protein further comprises polypeptide affinity tag. In some embodiments, the affinity tag is at the amino terminus of the fusion protein, at the carboxy terminus of the fusion protein, or in the middle of the fusion protein. In some embodiments, the fusion protein comprises a hexahistidine-comprising polypeptide. The hexahistidine-comprising polypeptide can have a sequence recited in any one of SEQ ID NOs: 43, 44, or 92-94.

The bi-specific binding agents provided herein are not necessarily limited to two binding specificities. In certain embodiments, in addition to the targeting domain, the bi-specific fusion protein comprises two or more activator domains that are linked directly or indirectly via peptide bonds. In certain embodiments, in addition to the activator domain, the bi-specific fusion protein comprises two or more targeting domains that are linked directly or indirectly via peptide bonds.

In other aspects, the present invention provides pharmaceutical compositions, comprising a bi-specific fusion protein as described above in combination with a physiologically acceptable carrier.

Within still further aspects, methods are provided for treating pathological tissue damage in a patient, comprising administering a pharmaceutical composition to a patient suffering from pathological tissue damage, and thereby decreasing pathological tissue damage in the patient.

Aspects of the invention relate to a method of promoting tissue regeneration or survival in a subject, the method comprising (a) providing a bi-specific fusion protein comprising (i) a targeting domain having a binding specificity to a target molecule associated with a damaged cell of a tissue, wherein the molecule is intracellular in a viable cell and exposed to the extracellular space in the damaged cell; and (ii) an activator domain having a binding specificity to growth factor receptor; and (b) administering in a patient in need thereof a therapeutically effective amount of the bi-specific fusion protein whereby the targeting domain specifically binds to the target molecule associated with the damaged cell of the tissue thereby targeting the bi-specific fusion protein to a first cell of the tissue and whereby upon exposure of the activator domain to the growth factor receptor, the activator domain specifically activates the growth factor receptor of a second cell so as to promote tissue regeneration.

In some embodiments, the method of promoting tissue regeneration or survival in a subject comprises (a) providing a bi-specific fusion protein comprising (i) a targeting domain having a binding specificity to a target molecule; (ii) an activator domain having a binding specificity to a receptor; (iii) a half life modulator, wherein the half life modulator modulates the half life of the bi-specific fusion protein; and (b) administering in a patient in need thereof a therapeutically effective amount of the bi-specific fusion protein whereby the targeting domain specifically binds to the target molecule thereby targeting the bi-specific fusion protein to a first cell of a tissue and whereby upon exposure of the activator domain to the growth factor receptor, the activator domain specifically activates the receptor of a second cell of the tissue so as to promote tissue regeneration.

In some embodiments, the first and second cells are the same. Yet in other embodiments, the first and second cells are different. In some embodiments, the first cell is a viable cell and the second cell is a damaged cell. Yet in other embodiments, the first cell is a damaged cell and the second cell is a viable cell. In some embodiments, the method further comprises administering stem cells to the patient.

In certain embodiments, the pathological tissue damage is heart tissue damage associated with myocardial infarction. In other embodiments, the pathological tissue damage is kidney tissue damage. In other embodiments, the pathological tissue damage is in bone, cartilage, joints, skin, liver tissue, pancreatic tissue, blood cells, lung tissue, or nervous system. In certain embodiments, such methods further comprise the administration of stem cells to the patient.

Also provided herein are nucleic acid molecules encoding a bi-specific fusion protein as described above. In certain embodiments, the nucleic acid molecule is DNA, and the DNA further comprises transcriptional and translational regulatory sequences operably linked to the bi-specific fusion protein coding sequence, such that transcription and translation of the coding sequence occurs in at least one eukaryotic cell type.

These and other aspects of the present invention will become apparent upon reference to the following detailed description.

DESCRIPTION OF THE SEQUENCE LISTING

SEQ ID NO:1 is the amino acid sequence of the anti-DNA scFv SI-1.
SEQ ID NO:2 is the amino acid sequence of the anti-DNA scFv SI-22.
SEQ ID NO:3 is the amino acid sequence of a growth factor polypeptide corresponding to wild type human IGF-I (mature form).
SEQ ID NO:4 is the amino acid sequence of a growth factor polypeptide corresponding to human IGF-1 with D12A substitution.
SEQ ID NO:5 is the amino acid sequence of a growth factor polypeptide corresponding to human IGF-1 with E9A substitution.
SEQ ID NO:6 is the amino acid sequence of a growth factor polypeptide corresponding to human HGF alpha chain N-K1 domain.
SEQ ID NO:7 is the amino acid sequence of a growth factor polypeptide corresponding to human HGF alpha chain K1 domain.

SEQ ID NO:8 is the amino acid sequence of a growth factor polypeptide corresponding to human HGF alpha chain N-K2 fusion.
SEQ ID NO:9 is the amino acid sequence of a growth factor polypeptide corresponding to human HGF alpha chain K2 domain.
SEQ ID NO:10 is the amino acid sequence of a human serum albumin (HSA) linker with C34S and N503Q substitutions.
SEQ ID NO:11 is the nucleic acid sequence of an HSA linker with C34S and N503Q substitutions.
SEQ ID NO:12 is the amino acid sequence of HSA.
SEQ ID NO:13 is the nucleic acid sequence of HSA.
SEQ ID NO:14 is the amino acid sequence of an HSA linker with C34S and N503Q substitutions and a polypeptide connector.
SEQ ID NO:15 is the amino acid sequence of an HSA linker with C34S and N503Q substitutions and a polypeptide connector.
SEQ ID NO:16 is the amino acid sequence of an HSA linker with C34S and N503Q substitutions and a polypeptide connector.
SEQ ID NO:17 is the amino acid sequence of an HSA linker with C34S and N503Q substitutions and a polypeptide connector.
SEQ ID NO:18 is the amino acid sequence of an HSA linker with C34S and N503Q substitutions and a polypeptide connector.
SEQ ID NO: 19 is the amino acid sequence of an HSA linker with a polypeptide connector.
SEQ ID NO:20 is the amino acid sequence of an HSA linker with a polypeptide connector.
SEQ ID NO:21 is the amino acid sequence of an HSA linker with a polypeptide connector.
SEQ ID NO:22 is the amino acid sequence of an HSA linker with a polypeptide connector.
SEQ ID NO:23 is the amino acid sequence of an HSA linker with a polypeptide connector.
SEQ ID NO:24 is the amino acid sequence of an HSA linker with C34S substitution, domain I.
SEQ ID NO:25 is the amino acid sequence of an HSA linker, domain II.
SEQ ID NO:26 is the amino acid sequence of an HSA linker with N503Q substitution, domain III.
SEQ ID NO:27 is the amino acid sequence of an HSA linker, domain I.
SEQ ID NO:28 is the amino acid sequence of an HSA linker, domain III.
SEQ ID NO:29 is the amino acid sequence of human alpha-fetoprotein.
SEQ ID NO:30 is the amino acid sequence of the anti-phosphatidylserine scFv PS4A7.
SEQ ID NO:31 is the amino acid sequence of human annexin V (AnxV).
SEQ ID NO:32 is an amino acid sequence of a growth factor polypeptide corresponding to human HGF alpha chain N-K1 domain.
SEQ ID NO:33 is an amino acid sequence of a growth factor polypeptide corresponding to human HGF alpha chain K1 domain.
SEQ ID NO:34 is an amino acid sequence of a growth factor polypeptide corresponding to human HGF alpha chain N-K2 domain.
SEQ ID NO:35 is an amino acid sequence of a growth factor polypeptide corresponding to human HGF alpha chain K2 domain.

SEQ ID NO:36 is an amino acid sequence of a growth factor polypeptide corresponding to human VEGF alpha monomer.

SEQ ID NO:37 is an amino acid sequence of a growth factor polypeptide corresponding to human VEGF alpha dimer.

SEQ ID NO:38 is an amino acid sequence of a growth factor polypeptide corresponding to human FGF2.

SEQ ID NO:39 is an amino acid sequence of a growth factor polypeptide corresponding to human NRG1 alpha, EGF-like domain.

SEQ ID NO:40 is an amino acid sequence of a growth factor polypeptide corresponding to human NRG1 alpha, full sequence.

SEQ ID NO:41 is an amino acid sequence of a bi-specific fusion protein leader polypeptide.

SEQ ID NO:42 is an amino acid sequence of a bi-specific fusion protein leader polypeptide.

SEQ ID NO:43 is an amino acid sequence of a C-terminal hexahistidine-comprising polypeptide.

SEQ ID NO:44 is an amino acid sequence of a C-terminal hexahistidine-comprising polypeptide.

SEQ ID NO:45 is an amino acid sequence of a HSA linker.

SEQ ID NO:46 is an amino acid sequence of a HSA linker with N-terminal and C-terminal short connector polypeptides.

SEQ ID NO:47 is an amino acid sequence of a HSA linker with N-terminal and C-terminal short connector polypeptides.

SEQ ID NO:48 is an amino acid sequence of a HSA linker with N-terminal and C-terminal short connector polypeptides.

SEQ ID NO:49 is an amino acid sequence of a HSA linker with N-terminal and C-terminal short connector polypeptides.

SEQ ID NO: 50 is an amino acid sequence of a variant of a growth factor polypeptide corresponding to human FGF2.

SEQ ID NO: 51 is an amino acid sequence of a growth factor polypeptide corresponding to human HGF alpha chain.

SEQ ID NO: 52 is an amino acid sequence of a growth factor polypeptide corresponding to human HGF alpha chain K1 domain.

SEQ ID NO: 53 is an amino acid sequence of a growth factor polypeptide corresponding to human HGF alpha chain N-K2 domain.

SEQ ID NO: 54 is an amino acid sequence of a growth factor polypeptide corresponding to human HGF alpha chain K2 domain.

SEQ ID NO: 55 is an amino acid sequence of a growth factor polypeptide corresponding to human NRG1 beta extracellular domain.

SEQ ID NO: 56 is an amino acid sequence of a growth factor polypeptide corresponding to human NRG1 beta EGF like domain.

SEQ ID NO: 57 is an amino acid sequence of human full length periostin.

SEQ ID NO: 58 is an amino acid sequence of a region of human periostin.

SEQ ID NO: 59 is an amino acid sequence of a growth factor polypeptide corresponding to human bone morphogenetic protein-2.

SEQ ID NO 60 is an amino acid sequence of a growth factor polypeptide corresponding to a single chain human bone morphogenetic protein-2.

SEQ ID NO 61 is an amino acid sequence of a growth factor polypeptide corresponding to vascular endothelial growth factor B.

SEQ ID NO 62 is an amino acid sequence of part of the human vascular endothelial growth factor B.

SEQ ID NO 63 is an amino acid sequence of part of the human vascular endothelial growth factor B.

SEQ ID NO 64 is an amino acid sequence of part of the human vascular endothelial growth factor B.

SEQ ID NO 65 is an amino sequence of domain III of Human Serum Albumin (HSA).

SEQ ID NO 66 is an amino acid sequence of a modified Vitamin D Binding Protein (mVDBP).

SEQ ID NO 67 is an amino sequence of domain III of a modified Human Serum Albumin.

SEQ ID NO 68 is an amino sequence of human AFP.

SEQ ID NO 69 is an amino sequence of a modified AFP.

SEQ ID NO 70 is an amino acid sequence of the albumin-binding domain human antibody (albudAb).

SEQ ID NO 71 is an amino acid sequence of is a monomeric variant form of Fc, named scFc.

SEQ ID NO 72 is an amino acid sequence of synaptotagmin I.

SEQ ID NO 73 is an amino acid sequence of an anti-DNA scFv antibody.

SEQ ID NO 74 is an amino acid sequence of a non-binding synaptotagmin I variant.

SEQ ID NO 75 is an amino acid sequence of a non-binding scFv variant (DAscFv).

SEQ ID NO 76 is an amino acid sequence of B7scFv anti-myosin scFv antibody.

SEQ ID NO 77 is an amino acid sequence of FD2 anti-myosin scFv antibody.

SEQ ID NO 78 is an amino acid sequence of MCA1 anti-myosin scFv antibody.

SEQ ID NO 79 is an amino acid sequence of MCB11 anti-myosin scFv antibody.

SEQ ID NO 80 is an amino acid sequence of S3F5 anti-myosin scFv antibody.

SEQ ID NO 81 is an amino acid sequence of a variant of human annexin V (AnxVmC315S).

SEQ ID NO 82 is an amino acid sequence of a variant of human annexin V (AnxVm3).

SEQ ID NO 83 is an amino acid sequence of a variant of human annexin V (AnxVm23).

SEQ ID NO 84 is an amino acid sequence of a non-binding variant of human annexin V (AnxVm1234).

SEQ ID NO 85 is an amino acid sequence of a variant of lactadherin.

SEQ ID NO 86 is an amino acid sequence of a variant of lactadherin.

SEQ ID NO 87 is an amino acid sequence of alpha mating factor.

SEQ ID NO 88 is an amino acid sequence of app8 leader polypeptide.

SEQ ID NO 89 is an amino acid sequence aga2 signal peptide.

SEQ ID NO 90 is an amino acid sequence SUC2 signal peptide.

SEQ ID NO 91 is an amino acid sequence a synthetic signal peptide.

SEQ ID NO 92 is an amino acid sequence of a hexahistidine tag.

SEQ ID NO 93 is an amino acid sequence of a hexahistidine tag.

SEQ ID NO 94 is an amino acid sequence of a hexahistidine tag.

SEQ ID NOs 95 to 104, and SEQ ID NO 182 to 184 correspond to amino acid sequence of a polypeptide linker.

SEQ ID NO 105 is an amino acid sequence of the proline-, alanine-, and/or serine-rich sequence.

SEQ ID NO 106 is an amino acid sequence of the aDNASI1_mHSA_IGF1 fusion protein. SEQ ID NO 107 is a nucleic acid sequence of the aDNASI1_mHSA_IGF1 fusion protein.

SEQ ID NO 108 is an amino acid sequence of the aPS4A7_mHSA_IGF1 fusion protein. SEQ ID NO 109 is a nucleic acid sequence of the of the aPS4A7_mHSA_IGF1 fusion protein.

SEQ ID NO 110 is an amino acid sequence of the aDNASI1_mHSA_HGF(NK1) fusion protein. SEQ ID NO 111 is a nucleic acid sequence of the aDNASI1_mHSA_HGF(NK1) fusion protein.

SEQ ID NO 112 is an amino acid sequence of the aPS4A7_mHSA_HGF(NK1) fusion protein. SEQ ID NO 113 is a nucleic acid sequence of the aPS4A7_mHSA_HGF(NK1) fusion protein.

SEQ ID NO 114 is an amino acid sequence of the AnxVm1234_mHSA_IGF1 fusion protein. SEQ ID NO 115 is a nucleic acid sequence of the AnxVm1234_mHSA_IGF1 fusion protein.

SEQ ID NO 116 is an amino acid sequence of the AnxVm1234_mHSA_NRG1b(EGF) fusion protein. SEQ ID NO 117 is a nucleic acid sequence of the AnxVm1234_mHSA_NRG1b(EGF) fusion protein.

SEQ ID NO 118 is an amino acid sequence of the AnxV_mHSA_FGF2 fusion protein. SEQ ID NO 119 is a nucleic acid sequence of the AnxV_mHSA_FGF2 fusion protein.

SEQ ID NO 120 is an amino acid sequence of the AnxV_mHSA_NRG1b(EGF) fusion protein. SEQ ID NO 121 is a nucleic acid sequence of the AnxV_mHSA_NRG1b(EGF) fusion protein.

SEQ ID NO 122 is an amino acid sequence of the FGF2_mHSA_AnxVm1234 fusion protein. SEQ ID NO 123 is a nucleic acid sequence of the FGF2_mHSA_AnxVm1234 fusion protein.

SEQ ID NO 124 is an amino acid sequence of the aDNASI1_mHSA_FGF2 fusion protein. SEQ ID NO 125 is a nucleic acid sequence of the aDNASI1_mHSA_FGF2 fusion protein.

SEQ ID NO 126 is an amino acid sequence of the aDNASI1_mHSA_NRG1b(EGF) fusion protein. SEQ ID NO 127 is a nucleic acid sequence of the aDNASI1_mHSA_NRG1b(EGF) fusion protein.

SEQ ID NO 128 is an amino acid sequence of the AnxV_mHSA_VEGFB(111) fusion protein. SEQ ID NO 129 is a nucleic acid sequence of the AnxV_mHSA_VEGFB(111) fusion protein.

SEQ ID NO 130 is an amino acid sequence of the AnxV_mHSA_VEGFB(167) fusion protein. SEQ ID NO 131 is a nucleic acid sequence of the AnxV_mHSA_VEGFB(167) fusion protein.

SEQ ID NO 132 is an amino acid sequence of the AnxV_mHSA_HGF(NK1) fusion protein. SEQ ID NO 133 is a nucleic acid sequence of the AnxV_mHSA_HGF(NK1) fusion protein.

SEQ ID NO 134 is an amino acid sequence of the AnxV_mHSA_IGF1 fusion protein. SEQ ID NO 135 is a nucleic acid sequence of the AnxV_mHSA_IGF1 fusion protein.

SEQ ID NO 136 is an amino acid sequence of the IGF1_mHSA_AnxV fusion protein. SEQ ID NO 137 is a nucleic acid sequence of the IGF1_mHSA_AnxV fusion protein.

SEQ ID NO 138 is an amino acid sequence of the IGF1_mHSA_AnxVm1234 fusion protein. SEQ ID NO 139 is a nucleic acid sequence of the IGF1_mHSA_AnxVm1234 fusion protein.

SEQ ID NO 140 is an amino acid sequence of the HGF(NK1)_mHSA_AnxV fusion protein. SEQ ID NO 141 is a nucleic acid sequence of the HGF(NK1)_mHSA_AnxV fusion protein.

SEQ ID NO 142 is an amino acid sequence of the NRG1b(EGF)_mHSA_AnxV fusion protein. SEQ ID NO 143 is a nucleic acid sequence of the NRG1b(EGF)_mHSA_AnxV fusion protein.

SEQ ID NO 144 is an amino acid sequence of the FGF2_mHSA_AnxV fusion protein. SEQ ID NO 145 is a nucleic acid sequence of the FGF2_mHSA_AnxV fusion protein.

SEQ ID NO 146 is an amino acid sequence of the VEGFB(167)_mHSA_AnxV fusion protein. SEQ ID NO 14 is a nucleic acid sequence of the VEGFB(167)_mHSA_AnxV fusion protein.

SEQ ID NO 148 is an amino acid sequence of the VEGFB(111)_mHSA_AnxV fusion protein. SEQ ID NO 149 a nucleic acid sequence of the VEGFB(111)_mHSA_AnxV fusion protein.

SEQ ID NO 150 is an amino acid sequence of the IGF1_mHSA_B7scFv fusion protein. SEQ ID NO 151 is a nucleic acid sequence of the IGF1_mHSA_B7scFv fusion protein.

SEQ ID NO 152 is an amino acid sequence of the IGF1_mHSA_Syt1 fusion protein. SEQ ID NO 153 is a nucleic acid sequence of the IGF1_mHSA_Syt1 fusion protein.

SEQ ID NO 154 is an amino acid sequence of the IGF1_mHSA_aDNASI1 fusion protein. SEQ ID NO 155 is a nucleic acid sequence of the IGF1_mHSA_aDNASI1 fusion protein.

SEQ ID NO 156 is an amino acid sequence of the NRG1b(EGF)_mHSA_B7scFv fusion protein. SEQ ID NO 157 is a nucleic acid sequence of the NRG1b(EGF)_mHSA_B7scFv fusion protein.

SEQ ID NO 158 is an amino acid sequence of the NRG1b(EGF)_mHSA_Syt1 fusion protein. SEQ ID NO 159 is a nucleic acid sequence of the NRG1b(EGF)_mHSA_Syt1 fusion protein.

SEQ ID NO 160 is an amino acid sequence of the NRG1b(EGF)_mHSA_aDNASI1 fusion protein. SEQ ID NO 161 is a nucleic acid sequence of the NRG1b(EGF)_mHSA_aDNASI1 fusion protein.

SEQ ID NO 162 is an amino acid sequence of the FGF2_mHSA_B7scFv fusion protein. SEQ ID NO 163 is a nucleic acid sequence of the FGF2_mHSA_B7scFv fusion protein.

SEQ ID NO 164 is an amino acid sequence of the FGF2_mHSA_Syt1 fusion protein. SEQ ID NO 165 is a nucleic acid sequence of the FGF2_mHSA_Syt1 fusion protein.

SEQ ID NO 166 is an amino acid sequence of the FGF2_mHSA_aDNASI1 fusion protein. SEQ ID NO 167 is a nucleic acid sequence of the FGF2_mHSA_aDNASI1 fusion protein.

SEQ ID NO 168 is an amino acid sequence of the B7scFv_mHSA_IGF1 fusion protein. SEQ ID NO 169 is a nucleic acid sequence of the B7scFv_mHSA_IGF1 fusion protein.

SEQ ID NO 170 is an amino acid sequence of the Syt1_mHSA_IGF1 fusion protein. SEQ ID NO 171 is a nucleic acid sequence of the Syt1_mHSA_IGF1 fusion protein.

SEQ ID NO 172 is an amino acid sequence of the aDNASI1_mHSA_IGF1 fusion protein. SEQ ID NO 173 is a nucleic acid sequence of the aDNASI1_mHSA_IGF1 fusion protein.

SEQ ID NO 174 is an amino acid sequence of the B7scFv_mHSA_NRG1b(EGF) fusion protein. SEQ ID NO 175 is a nucleic acid sequence of the B7scFv_mHSA_NRG1b(EGF) fusion protein.

SEQ ID NO 176 is an amino acid sequence of the Syt1_mHSA_NRG1b(EGF) fusion protein. SEQ ID NO 177 is a nucleic acid sequence of the Syt1_mHSA_NRG1b(EGF) fusion protein.

SEQ ID NO 178 is an amino acid sequence of the B7scFv_mHSA_FGF2 fusion protein. SEQ ID NO 179 is a nucleic acid sequence of the B7scFv_mHSA_FGF2 fusion protein.

SEQ ID NO 180 is an amino acid sequence of the Syt1_mHSA_FGF2 fusion protein. SEQ ID NO 181 is a nucleic acid sequence of the Syt1_mHSA_FGF2 fusion protein.

SEQ ID NO 185 is an amino acid sequence of the IGF1_mHSA_DAscFv fusion protein. SEQ ID NO 186 is a nucleic acid sequence of the IGF1_mHSA_DAscFv fusion protein.

SEQ ID NO SEQ ID NOs: 187-190 are the nucleic acid sequences of a growth factor polypeptide corresponding to human FGF2 (SEQ ID NO:38).

SEQ ID NOs 191-94 are the nucleic acid sequences of a growth factor polypeptide corresponding to HGF alpha chain N-K1 domain (SEQ ID NO: 6, SEQ ID NO: 32).

SEQ ID NOs 195-197 are the nucleic acid sequences of a growth factor polypeptide corresponding to wild type human IGF-I (SEQ ID NO 3).

SEQ ID NO 198 is the nucleic acid sequence of a growth factor polypeptide corresponding to human NRG1 alpha, full sequence (SEQ ID NO 40).

SEQ ID NO 199 is the nucleic acid sequence of a growth factor polypeptide corresponding to human NRG1 alpha, EGF-like domain (SEQ ID NO 39).

SEQ ID NOs 200-202 are the nucleic acid sequences of a growth factor polypeptide corresponding to human NRG1 beta EGF like domain (SEQ ID NO 56).

SEQ ID NO 203 is the nucleic acid sequence of a growth factor polypeptide corresponding to a region of human periostin (SEQ ID NO 58).

SEQ ID NO 204 is the nucleic acid sequence of a growth factor polypeptide corresponding to human bone morphogenetic protein-2 (SEQ ID NO 59).

SEQ ID NO 205 is the nucleic acid sequence of a growth factor polypeptide corresponding to a single chain human bone morphogenetic protein-2 (SEQ ID NO 60).

SEQ ID NO 206 is the nucleic acid sequence of a growth factor polypeptide corresponding to a human VEGF alpha monomer (SEQ ID NO 36).

SEQ ID NO 207 is the nucleic acid sequence of a growth factor polypeptide corresponding to human VEGF alpha dimmer (SEQ ID NO 37).

SEQ ID NOs 208-209 are the nucleic acid sequences of a growth factor polypeptide corresponding to vascular endothelial growth factor B (SEQ ID NO 61).

SEQ ID NOs 210-211 are the nucleic acid sequences of a growth factor polypeptide corresponding to the human vascular endothelial growth factor B.

SEQ ID NOs 212-214 are the nucleic acid sequences of a half life modulator corresponding to human serum albumin (HSA) linker with C34S and N503Q substitutions (SEQ ID NO 10).

SEQ ID NO 215 is a nucleic acid sequence of a half life modulator corresponding to the domain III of a modified Human Serum Albumin (SEQ ID NO 67).

SEQ ID NO 216 is a nucleic acid sequence of a half life modulator corresponding to a modified AFP (SEQ ID NO 69).

SEQ ID NO 217 is a nucleic acid sequence of a half life modulator corresponding to the albumin-binding domain human antibody (SEQ ID NO 70).

SEQ ID NO 218 is a nucleic acid sequence of a half life modulator corresponding to monomeric variant form of Fc, named scFc (SEQ ID NO 71).

SEQ ID NO 219 is a nucleic acid sequence of a half life modulator corresponding to a modified Vitamin D Binding Protein, mVDBP (SEQ ID NO 66).

SEQ ID NOs 220-221 are nucleic acid sequences corresponding to anti-DNA scFv antibody (SEQ ID NO 73).

SEQ ID NO 222 is a nucleic acid sequence corresponding to the anti-DNA scFv SI-1 (SEQ ID NO 1).

SEQ ID NO 223 is a nucleic acid sequence corresponding to the B7scFv anti-myosin scFv antibody (SEQ ID NO 76).

SEQ ID NO 224 is a nucleic acid sequence corresponding to the anti-phosphatidylserine scFv PS4A7 (SEQ ID NO 30).

SEQ ID NOs 225-227 are nucleic acid sequences corresponding to human annexin V (SEQ ID NO 31).

SEQ ID NO 228 is a nucleic acid sequence corresponding to a variant of human annexin V (C317S, SEQ ID NO 81).

SEQ ID NOs 229-230 are nucleic acid sequences corresponding to a variant of human annexin V AnxVm3, SEQ ID NO 82).

SEQ ID NOs 231-232 are nucleic acid sequences corresponding to a non-internalizing variant of annexin V (AnxVm23, SEQ ID NO 83).

SEQ ID NOs 233-234 are nucleic acid sequences corresponding to a non-binding variant of annexin V (AnxVm1234, SEQ ID NO 84).

SEQ ID NO 235 is a nucleic acid sequence corresponding to synaptotagmin I (SEQ ID NO 72).

SEQ ID NOs 236-237 are nucleic acid sequences corresponding to non-binding scFv variant (DAscFv; SEQ ID No 75).

SEQ ID NOs 238 is a nucleic acid sequence corresponding to a leader polypeptide.

SEQ ID NO 239 is a nucleic acid sequence corresponding to alpha mating factor.

SEQ ID NO 240 is a nucleic acid sequence corresponding to app8 leader polypeptide.

SEQ ID NO 241 is a nucleic acid sequence corresponding to aga2 signal peptide.

SEQ ID NO 242 is a nucleic acid sequence corresponding to SUC2 signal peptide.

SEQ ID NO 243 is a nucleic acid sequence corresponding to a synthetic signal peptide.

SEQ ID NO: 244 is an amino acid sequence corresponding to the alpha-factor signal sequence. SEQ ID NO 245 is a nucleic acid sequence corresponding to the alpha-factor signal sequence.

SEQ ID NO 246 is an amino acid sequence of the DAscFv_mHSA_IGF1 fusion protein. SEQ ID NO 247 is a nucleic acid sequence corresponding to the DAscFv_mHSA_IGF1 fusion protein.

SEQ ID NO 248 is an amino acid sequence of the DAscFv_mHSA_HGF(NK1) fusion protein. SEQ ID NO 249 is a nucleic acid sequence corresponding to the DAscFv_mHSA_HGF(NK1) fusion protein.

SEQ ID NO 250 is an amino acid sequence of the AnxVm1234_mHSA fusion protein. SEQ ID NO 251 is a nucleic acid sequence corresponding to the AnxVm1234_mHSA fusion protein.

SEQ ID NO 252 is an amino acid sequence of the AnxV_mHSA fusion protein. SEQ ID NO 253 is a nucleic acid sequence corresponding to the AnxV_mHSA fusion protein.

SEQ ID NO 254 is an amino acid sequence of the NRG1b(EGF)_mHSA_AnxVm1234 fusion protein. SEQ ID NO 255 is a nucleic acid sequence corresponding to the NRG1b(EGF)_mHSA_AnxVm1234 fusion protein.

SEQ ID NO 256 is an amino acid sequence of the AnxVm23_mHSA fusion protein. SEQ ID NO 257 is a nucleic acid sequence corresponding to the AnxVm23_mHSA fusion protein.

SEQ ID NO 258 is an amino acid sequence of the AnxVm1234_mHSA_VEGFB(111) fusion protein. SEQ ID NO 259 is a nucleic acid sequence corresponding to the AnxVm1234_mHSA_VEGFB(111) fusion protein.

SEQ ID NO 260 is an amino acid sequence of the AnxVm1234_mHSA_VEGFB(167) fusion protein. SEQ ID NO 261 is a nucleic acid sequence corresponding to the AnxVm1234_mHSA_VEGFB(167) fusion protein.

SEQ ID NO 262 is an amino acid sequence of the AnxVm1234_mHSA_HGF(NK1) fusion protein. SEQ ID NO 263 is a nucleic acid sequence corresponding to the AnxVm1234_mHSA_HGF(NK1) fusion protein.

SEQ ID NO 264 is an amino acid sequence of the AnxVm1234_mHSA_FGF2 fusion protein. SEQ ID NO 265 is a nucleic acid sequence corresponding to the AnxVm1234_mHSA_FGF2 fusion protein.

SEQ ID NO 266 is an amino acid sequence of the mHSA_AnxV fusion protein. SEQ ID NO 267 is a nucleic acid sequence corresponding to the mHSA_AnxV fusion protein.

SEQ ID NO 268 is an amino acid sequence of the mHSA_AnxVm23 fusion protein. SEQ ID NO 269 is a nucleic acid sequence corresponding to the mHSA_AnxVm23 fusion protein.

SEQ ID NO 270 is an amino acid sequence of the mHSA_AnxVm1234 fusion protein. SEQ ID NO 271 is a nucleic acid sequence corresponding to the mHSA_AnxVm1234 fusion protein.

SEQ ID NO 272 is an amino acid sequence of the HGF(NK1)_mHSA_AnxVm1234 fusion protein. SEQ ID NO 273 is a nucleic acid sequence corresponding to the HGF(NK1)_mHSA_AnxVm1234 fusion protein.

SEQ ID NO 274 is an amino acid sequence of VEGFB (167)_mHSA_AnxVm1234 fusion protein. SEQ ID NO 275 is a nucleic acid sequence corresponding to the VEGFB(167)_mHSA_AnxVm1234 fusion protein.

SEQ ID NO 276 is an amino acid sequence of VEGFB (111)_mHSA_AnxVm1234 fusion protein. SEQ ID NO 277 is a nucleic acid sequence corresponding to the VEGFB(111)_mHSA_AnxVm1234 fusion protein.

BRIEF DESCRIPTION OF THE DRAWINGS

FIG. 20A is a graph showing the specific binding of aDNASI1_mHSA_FGF2 to DNA. FIG. 20B is a graph showing the specific binding of aDNASI1_mHSA_NRG1b (EGF) to DNA. FIG. 20C is a graph showing the specific binding of IGF1_mHSA_aDNASI1 to DNA.

FIGS. 30A-30D are representative photomicrographs from immunohistochemical staining of heart sections 24 hr after a mouse was treated with IGF1_mHSA_AnxV.

FIGS. 31A-31D are representative photomicrographs from immunohistochemical staining of heart sections showing infarcted tissue and bordering areas from a mouse treated with IGF1_mHSA_AnxVm1234. Time point was 24 hours after dosing.

FIGS. 33A, 33B, 33C, 33D, 33E, and 33F represent different structures of certain bi-specific fusion proteins according to some embodiments.

DETAILED DESCRIPTION OF THE INVENTION

Figure 1:
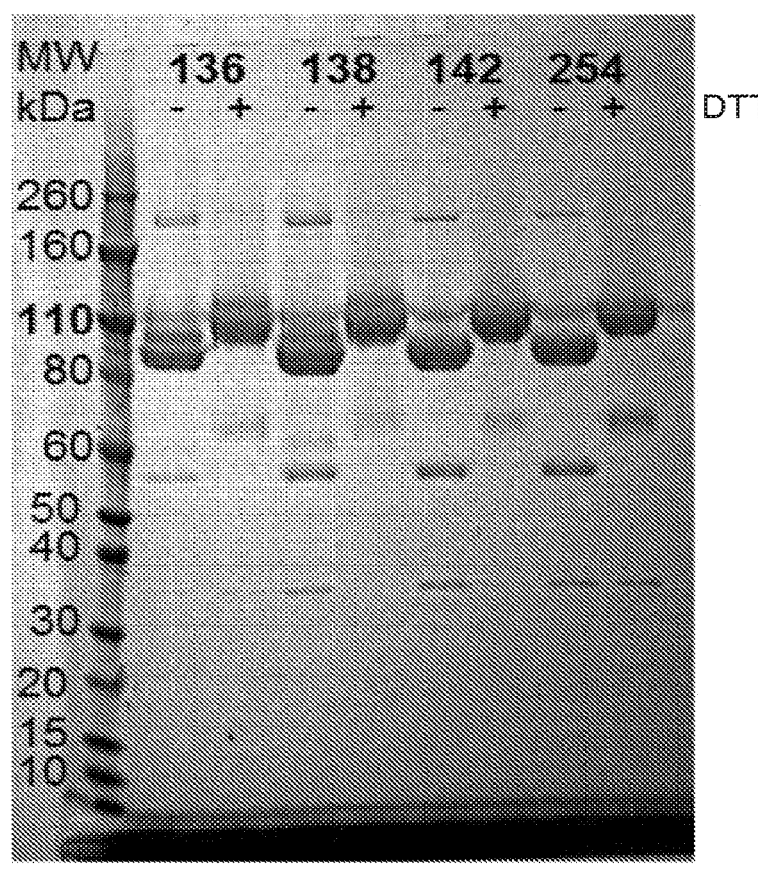
FIG. 1 is a SDS-PAGE of purified IGF1_mHSA_AnxV (136), IGF1_mHSA_AnxVm1234 (138), NRG1b(EGF)_ mHSA_AnxV (142) and NRG1b(EGF)_mH-SA_AnxVm1234 fusion proteins.
Figures 2A, 2B, 2C:
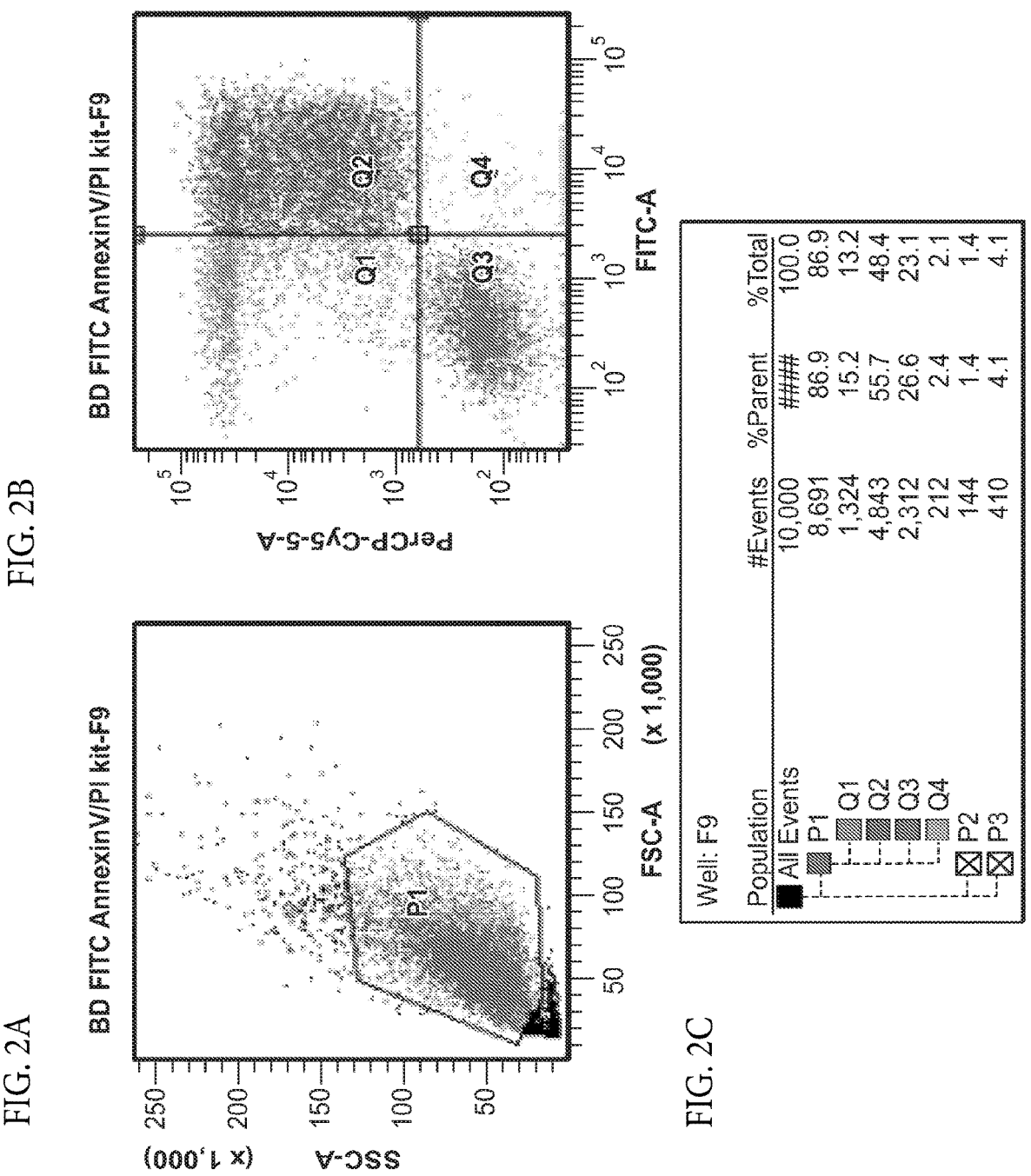
FIGS. 2A-2C represent the data obtained by flow cytometry of Annexin V-FITC plus propidium iodide (PI) apoptosis detection positive control in apoptotic heart cells.
Figure 3A:
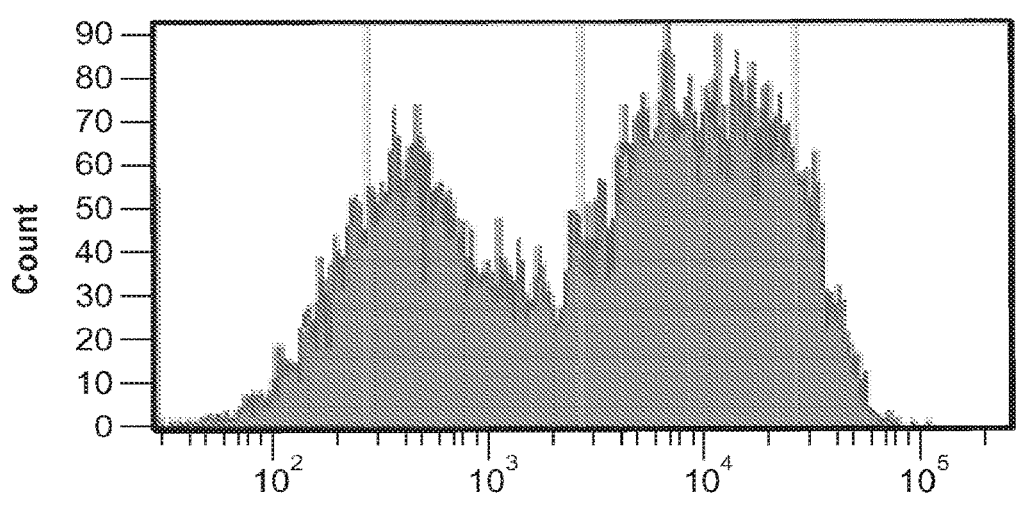
FIGS. 3A-3B are flow cytometry histograms for the FITC and PI channels shown in the FIGS. 2 A-2C.
Figure 3B:
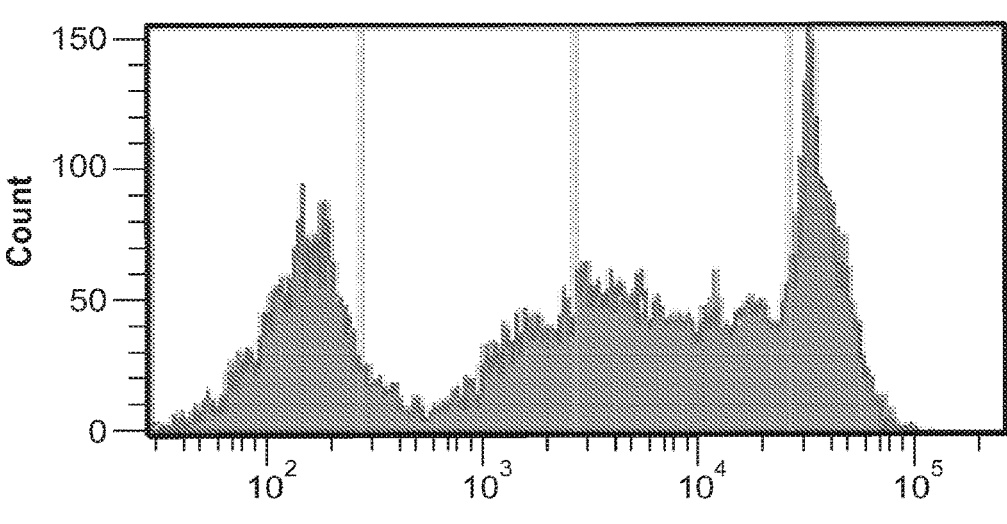
Figures 4A, 4B, 4C:
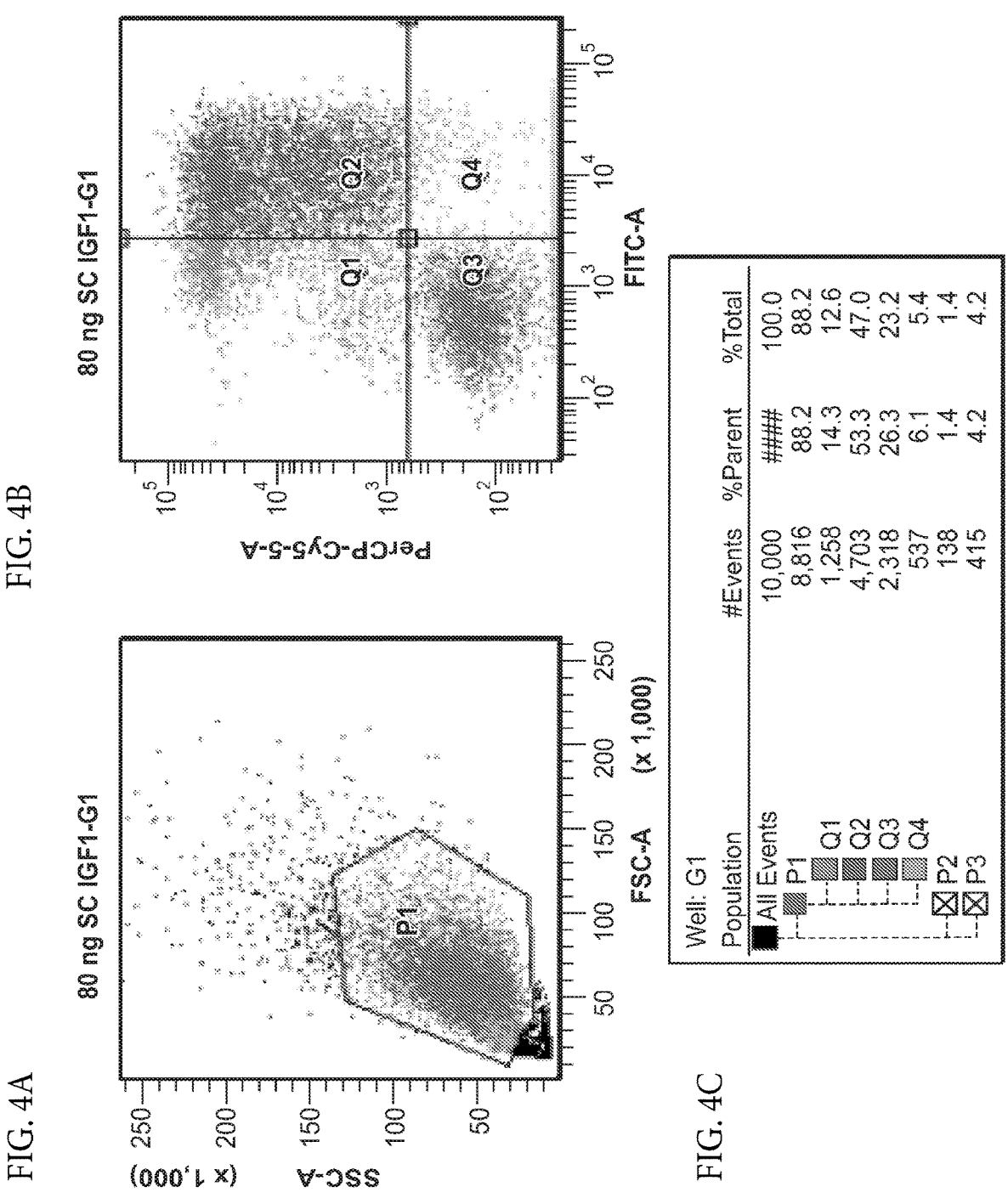
FIGS. 4A-4C represent the data obtained by flow cytometry of IGF1_mHSA_AnxV plus propidium iodide in apoptotic heart cells.
Figures 5A, 5B:
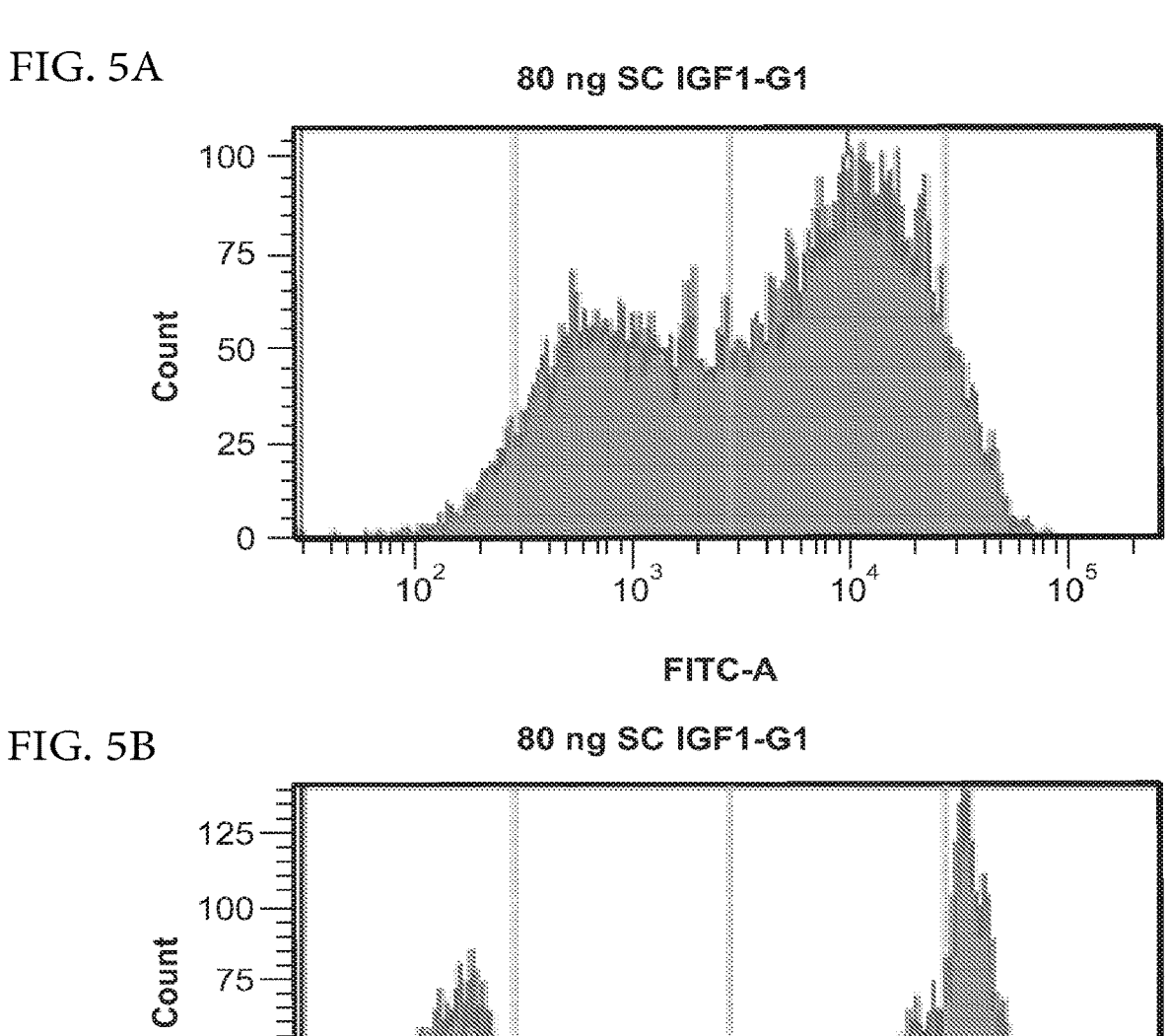
FIGS. 5A-5B are flow cytometry histograms for the FITC and PI channels shown in FIGS. 4 A-4C.
Figures 6A, 6B, 6C:
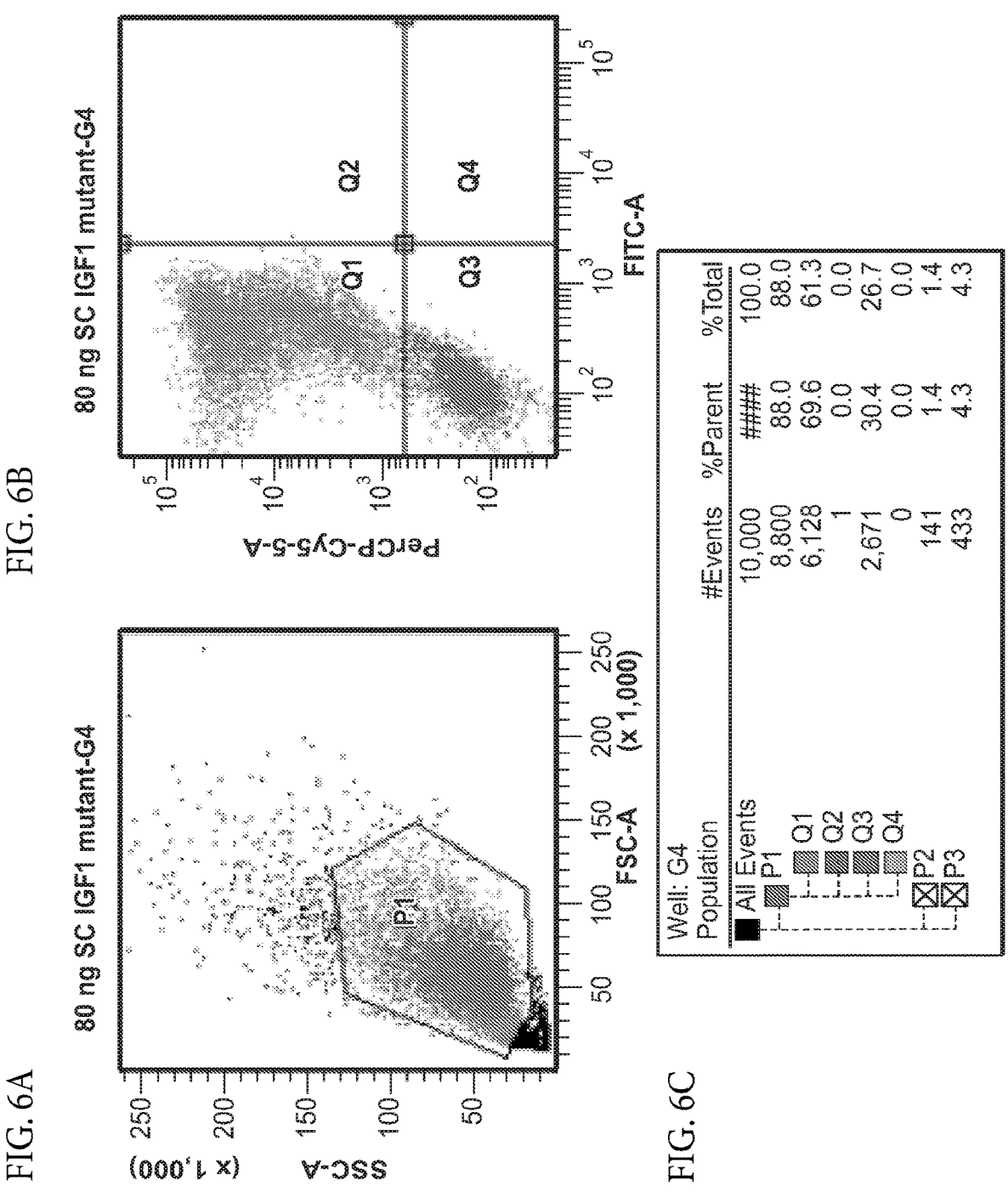
FIGS. 6A-6C represent the data obtained by flow cytometry of IGF1_mHSA_AnxVm1234 plus propidium iodide in apoptotic heart cells.
Figure 7A:
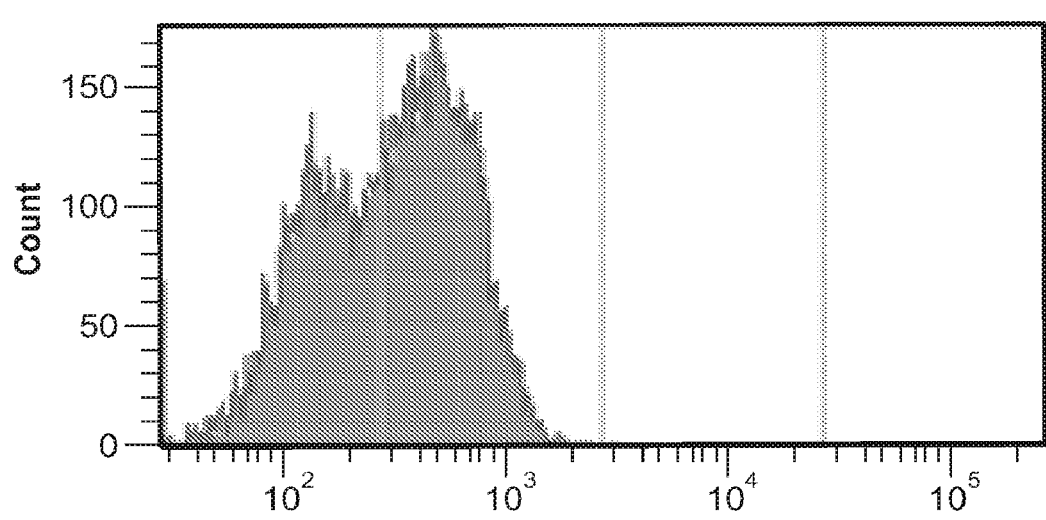
FIGS. 7A-7B are flow cytometry histograms for the FITC and PI channels shown in FIGS. 6A-6C.
Figure 7B:
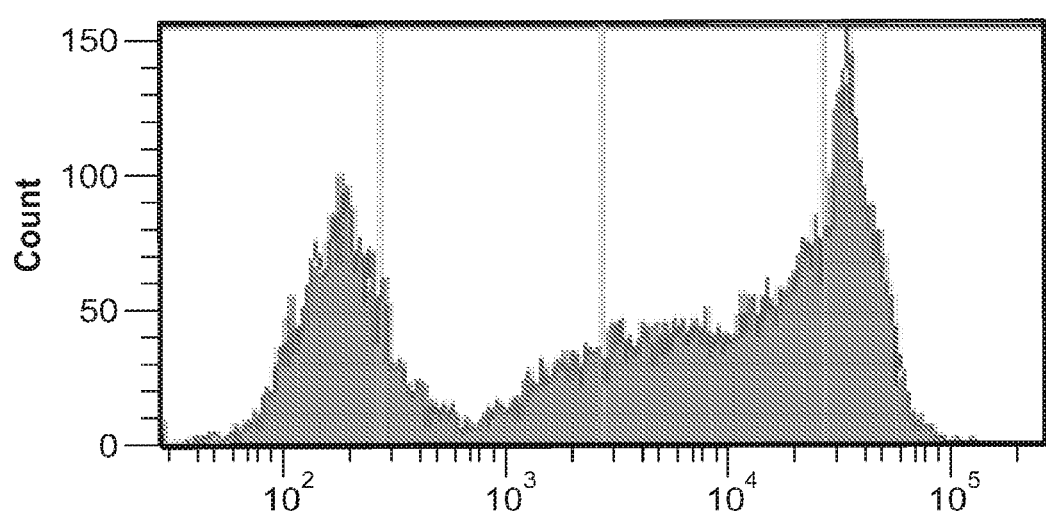
Figures 8A, 8B, 8C:
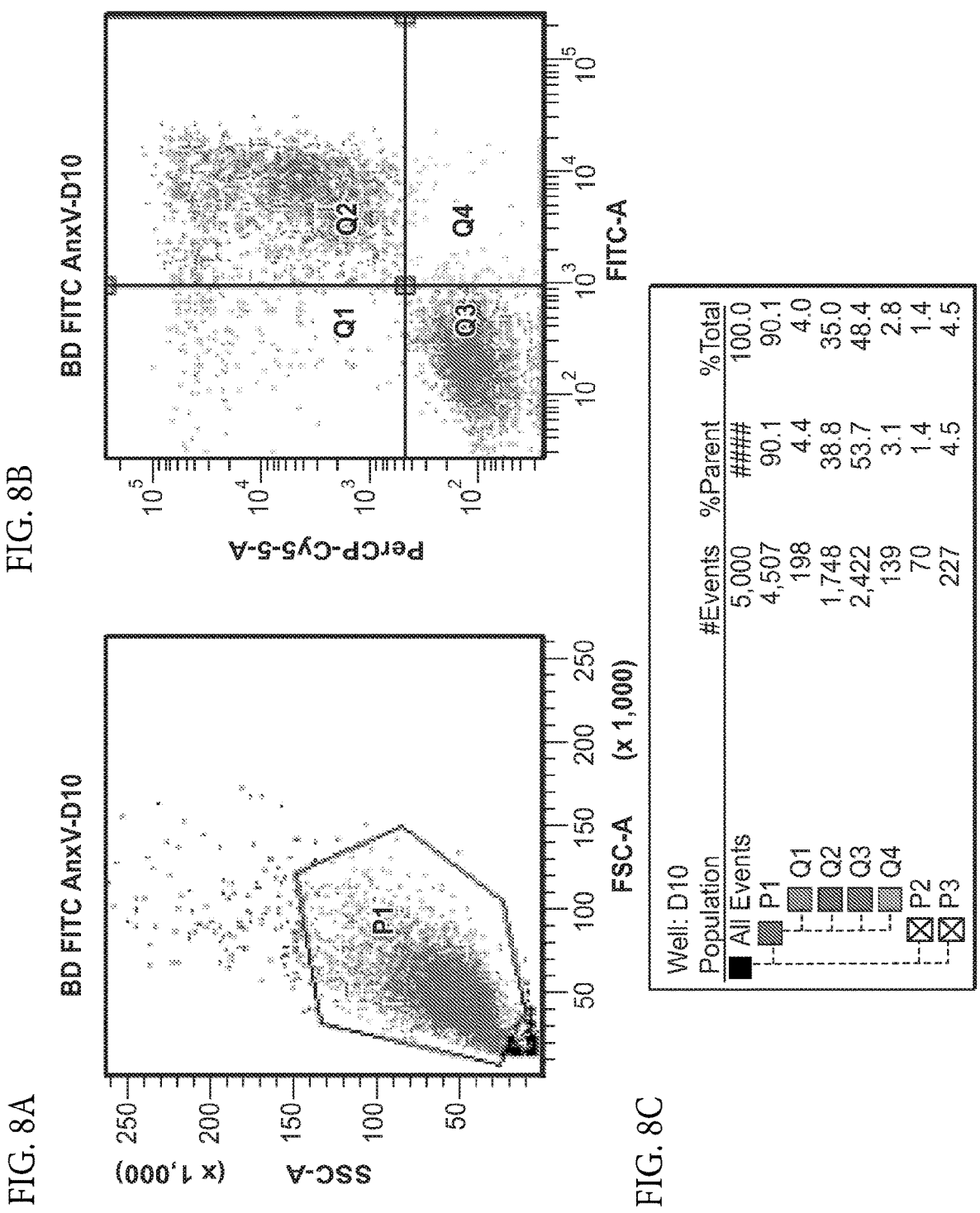
FIGS. 8A-8C represent the data obtained by flow cytometry of Annexin V-FITC plus propidium iodide (PI) apoptosis detection positive control in apoptotic heart cells.
Figure 9A:
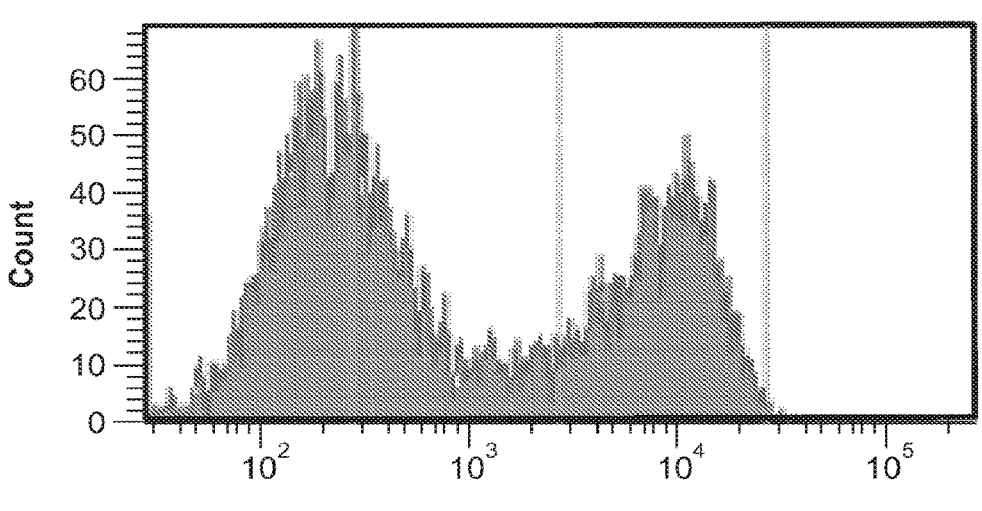
FIGS. 9A-9B are flow cytometry histograms for the FITC and PI channels shown in FIG. 8 A-8C.
Figure 9B:
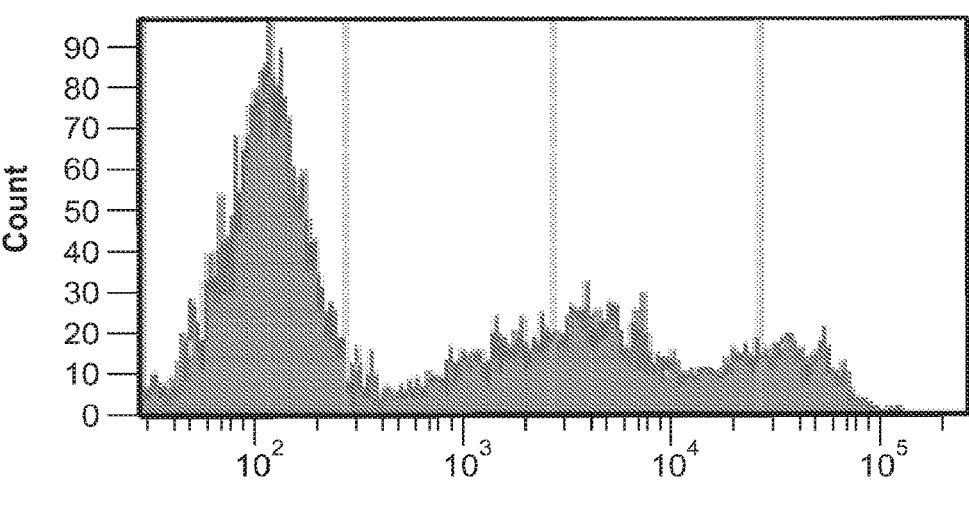
Figures 10A, 10B, 10C:
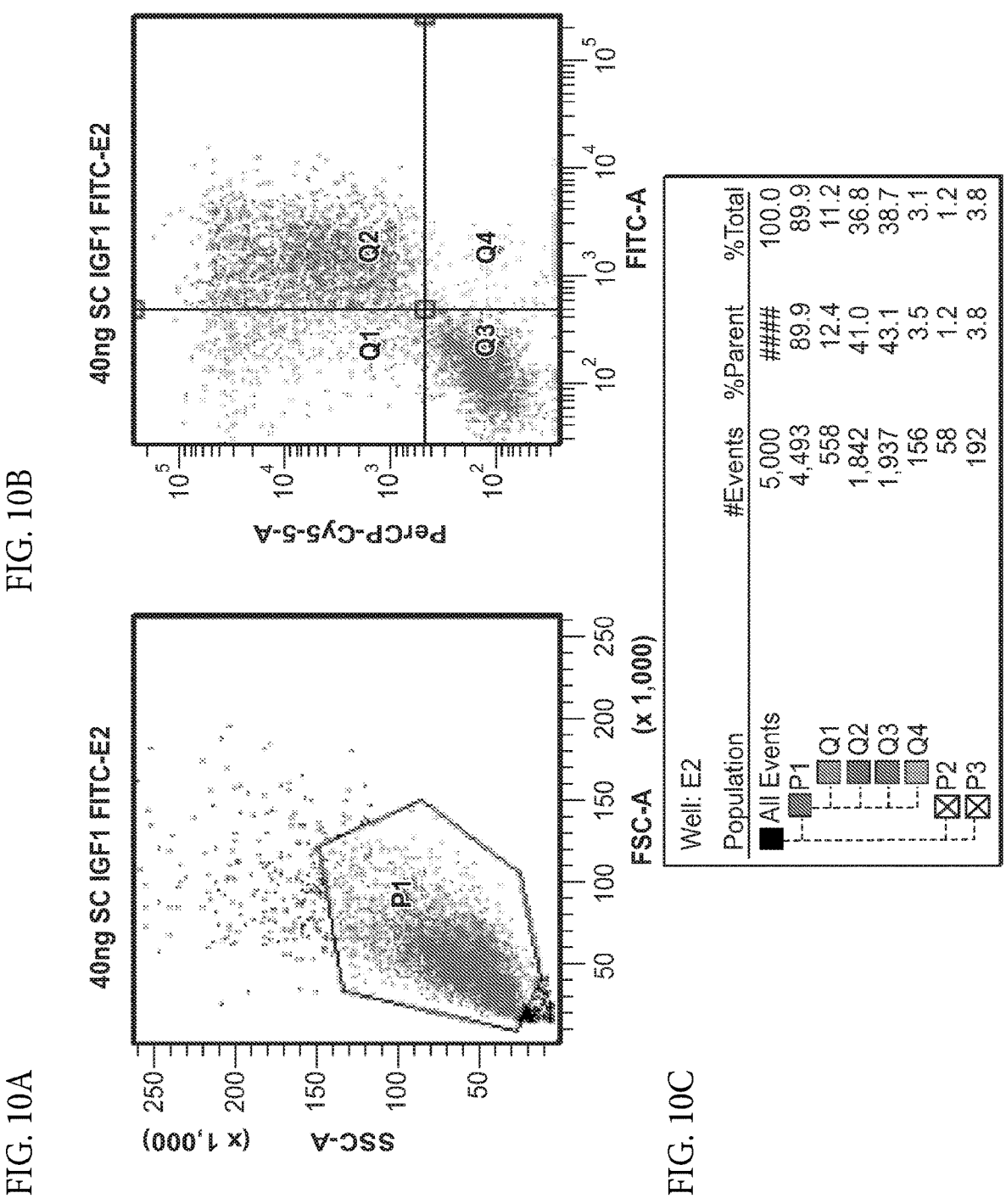
FIGS. 10A-10C represent the data obtained by flow cytometry of IGF1_mHSA_AnxV plus propidium iodide in apoptotic heart cells, without pre-blocking with IGF1.
Figures 11A, 11B:
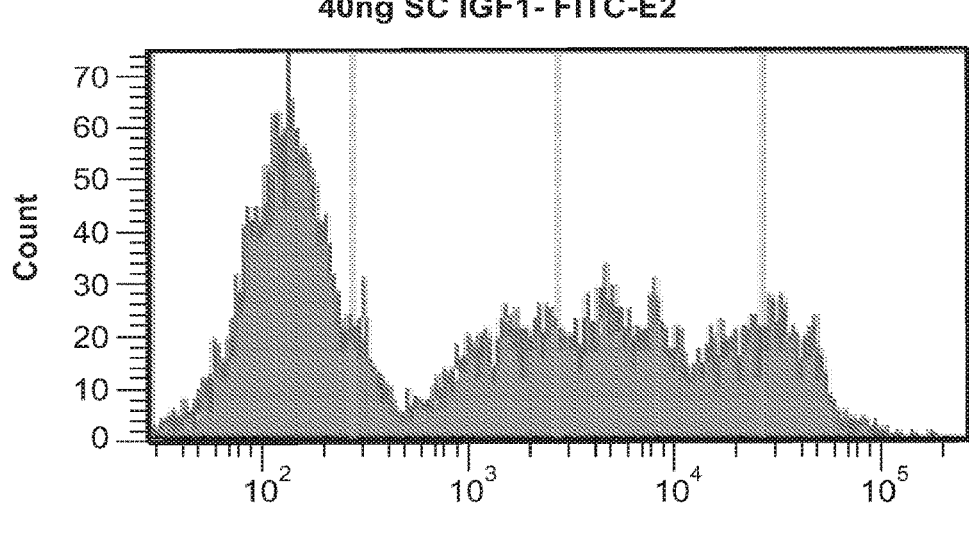
FIGS. 11A-11B are flow cytometry histograms for the FITC and PI channels shown in FIGS. 10A-10C.
Figures 12A, 12B, 12C:
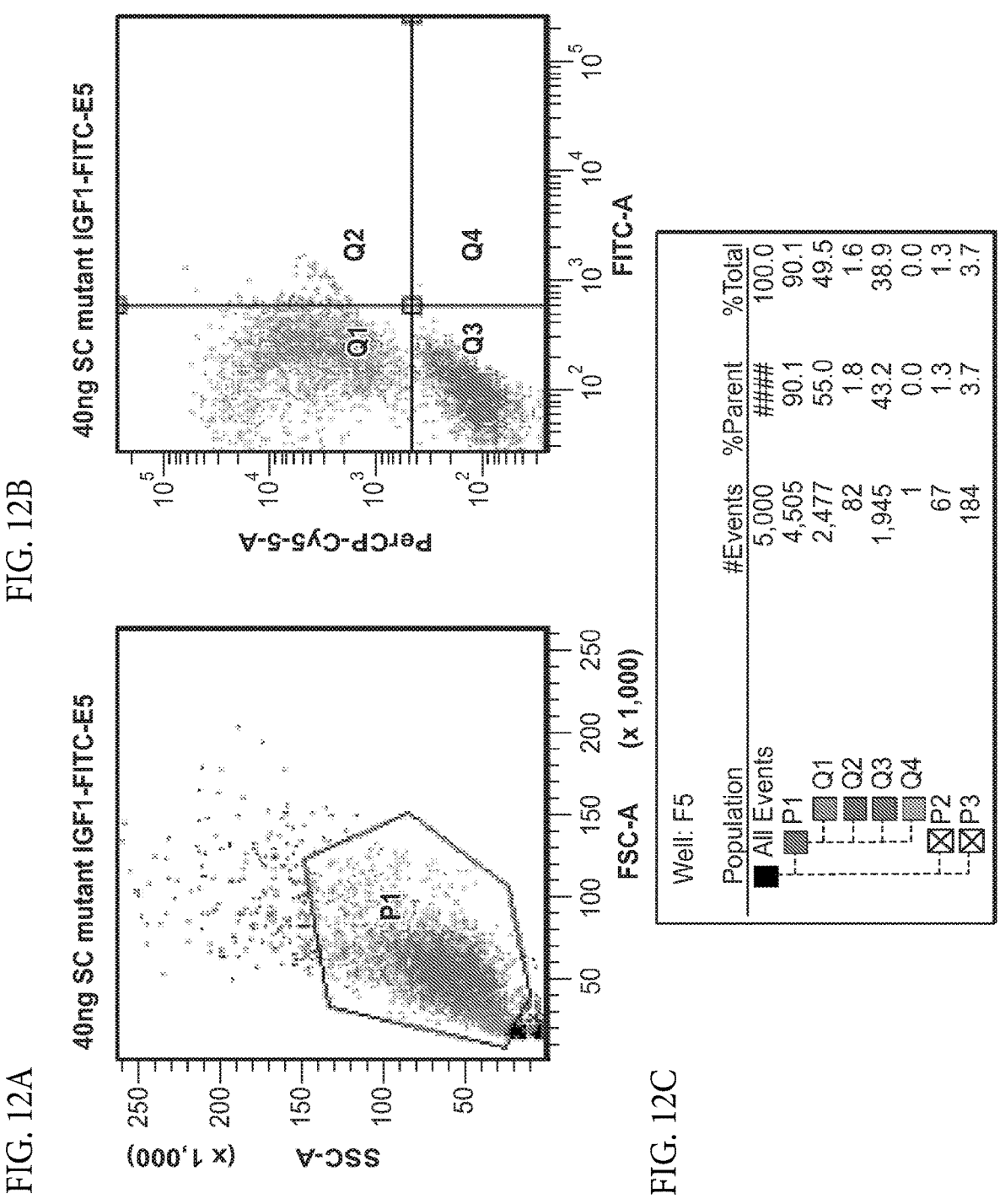
FIGS. 12A-12C represent the data obtained by flow cytometry of IGF1_mHSA_AnxVm1234 plus propidium iodide in apoptotic heart cells, without pre-blocking with IGF1.
Figure 13A:
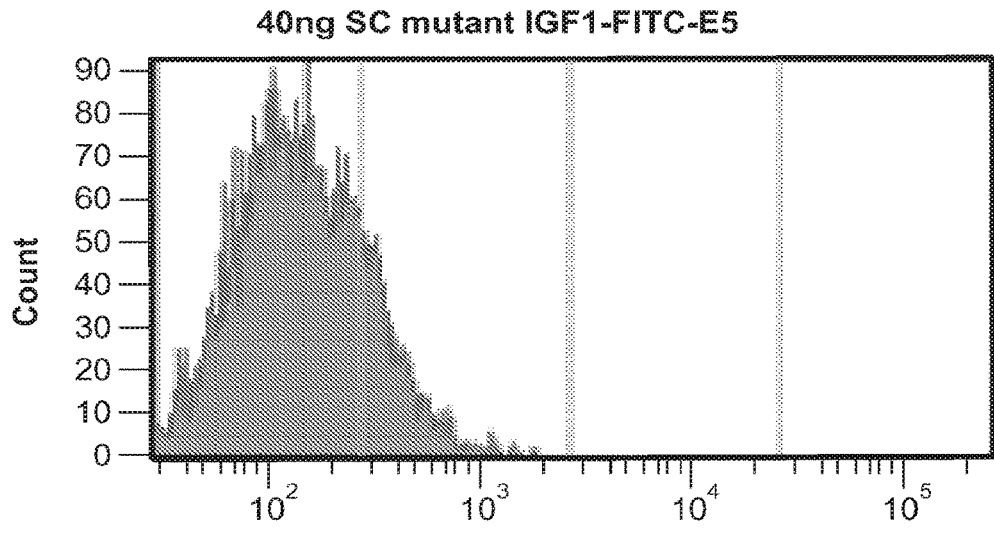
FIGS. 13A-13B are flow cytometry histograms for the FITC and PI channels shown in FIG. 12A-12C.
Figure 13B:
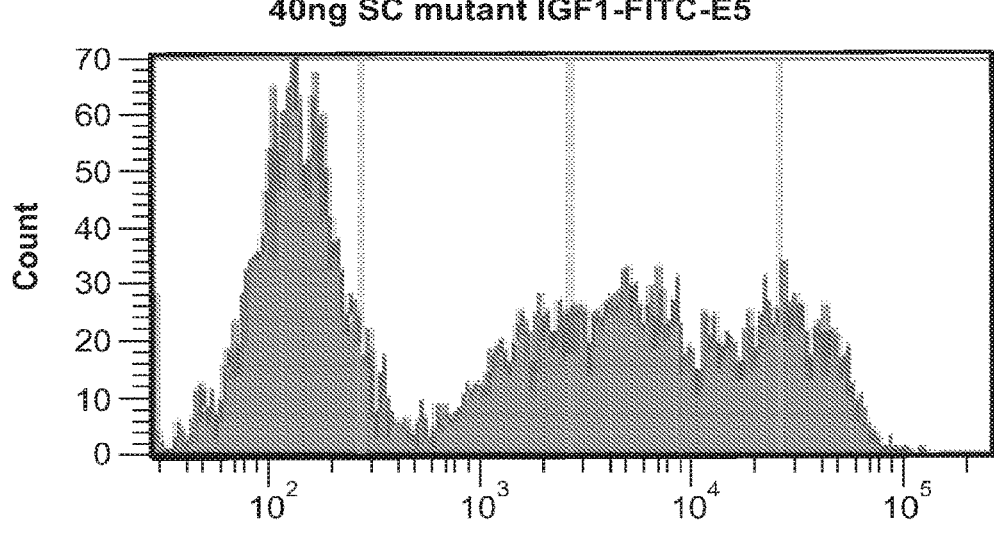
Figures 14A, 14B, 14C:
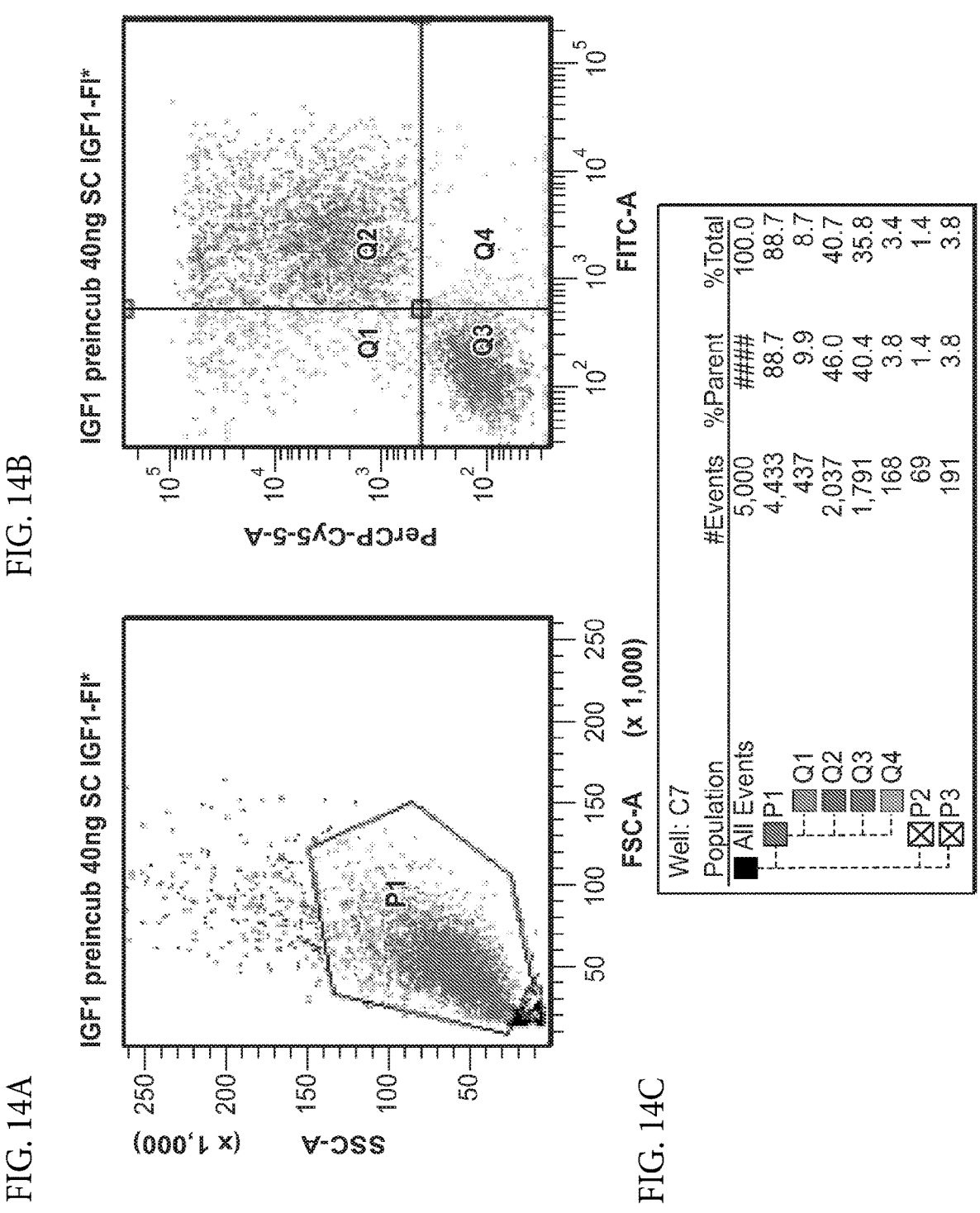
FIGS. 14A-14C represent the data obtained by flow cytometry of IGF1_mHSA_AnxV plus propidium iodide in apoptotic heart cells, with pre-blocking with 10 min, 800 nM IGF1.
Figure 15A:
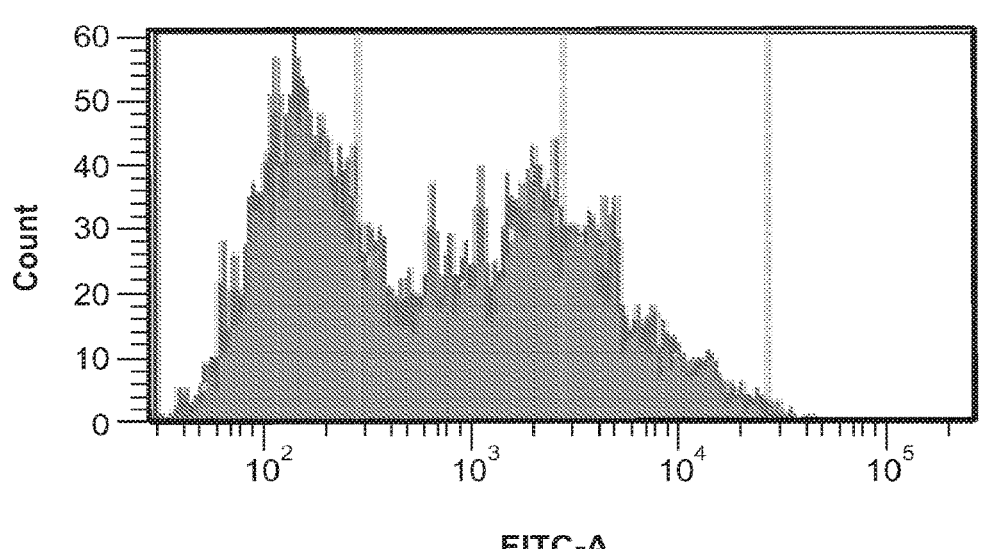
FIGS. 15A-15B are flow cytometry histograms for the FITC and PI channels shown in FIGS. 14 A-14C.
Figure 15B:
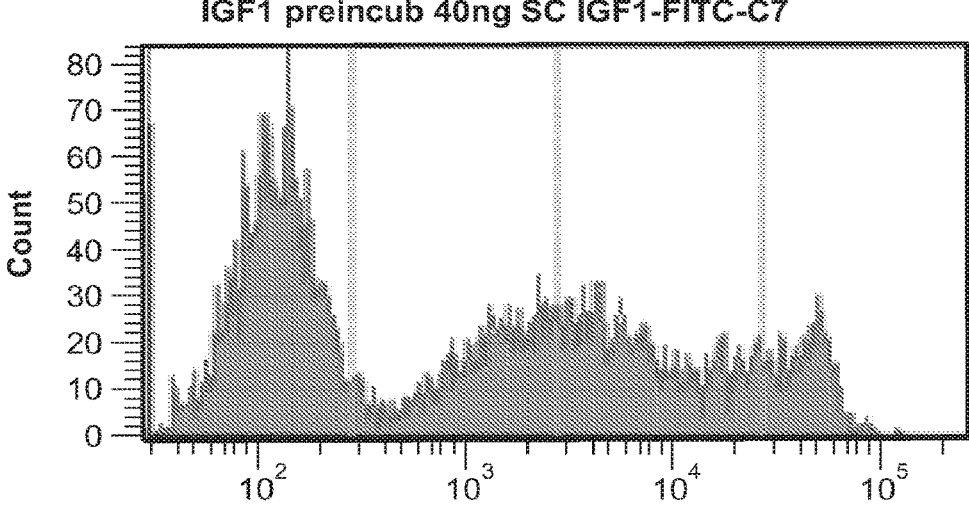

Aspects of the invention are directed to a bi-specific fusion protein that comprises two binding domains, a targeting domain having a binding specificity to a specific target molecule or target cell and an activator domain having a binding specificity to a receptor that modulates tissue regeneration. In some embodiments, the targeting domain serves to target the bi-specific fusion protein to a target cell or tissue while activator domain serves to activate a cell thereby to promote regeneration of the targeted tissue. As used herein a "bi-specific protein" refers to a fusion protein capable of specific binding to two or more specific molecules.

In some embodiments, the bi-specific protein comprises (1) a targeting domain having a binding specificity to a molecule associated with a damaged cell of a tissue, wherein the molecule is intracellular in a viable cell and exposed to the extracellular space in the damaged cell; and (2) an activator domain having a binding specificity to a growth factor receptor or a cytokine receptor of a cell in the tissue, wherein upon exposure of the activator domain to the growth factor receptor or cytokine receptor, the activator domain binds the growth factor receptor or cytokine receptor so as to modulate regeneration or survival of the tissue.

In some embodiments, the bi-specific fusion protein comprises (1) a targeting domain having a binding specificity to a molecule associated with a damaged cell of a tissue, wherein the molecule is intracellular in a viable cell and exposed to the extracellular space in the damaged cell; (2) an activator domain having a binding specificity to a molecule associated with the surface of a cell in the tissue, wherein upon exposure of the activator domain to membrane-associated molecule, the activator domain binds the membrane-associated molecule so as to modulate regeneration of the tissue and (3) a half life modulator wherein the half life modulator modulates the half life of the bi-specific fusion protein.

In some embodiments, the bi-specific proteins comprise: (1) a targeting polypeptide domain that binds to an ischemia-associated molecule; and (2) an activator domain, such as a growth factor polypeptide or a cytokine polypeptide so as to promote tissue regeneration or survival.

In some embodiments, the bi-specific fusion protein comprises (1) a targeting domain having a binding specificity to a target molecule associated with a tissue; (2) a binding domain (e.g. an activator domain) having a binding specificity to a molecule associated with the surface of a cell in the tissue, wherein upon exposure of the binding domain to the molecule, the binding domain binds the molecule so as to promote regeneration or survival of the tissue; and (3) a half life modulator wherein the half life modulator modulates the half life of the bi-specific fusion protein.

In certain embodiments, the bi-specific fusion protein a half life modulator (HLM). In some embodiments, the HLM is a polypeptide. The HLM can have two termini, an N-terminus and a C-terminus, and is joined at one terminus via a peptide bond to the targeting polypeptide domain and is joined at the other terminus via a peptide bond to the activator domain. In other embodiments, the half life modulator is joined at one terminus (N-terminus or C-terminus) to the activator domain or to the targeting domain. Accordingly, the half life modulator can be at the N-terminus or at the C-terminus of the bi-specific fusion protein. The half life modulator may be joined to the targeting domain or the activator domain via peptide bonds.

Other aspects of the invention relate to fusion proteins comprising (1) at least one targeting domain having a binding specificity to at least one target molecule associated with a tissue; (2) at least one binding domain (such as an activator domain) having a binding specificity to at least one molecule associated with the surface of a cell in the tissue, wherein upon exposure of the binding domain to the molecule, the binding domain binds the molecule so as to promote regeneration of the tissue; and (3) optionally a half life modulator wherein the half life modulator modulates the half life of the fusion protein. In some embodiments, the fusion protein comprises two or more targeting domains, each targeting domain having a binding affinity to a target molecule associated with a tissue. Each of the targeting domains may have a same binding specificity (e.g., a binding specificity for the same target molecule) or a different binding specificity (e.g., a binding specificity for a different target molecule). In some embodiments, the fusion protein comprises two or more activator domains. Each of the activator domains may have the same binding specificity (e.g., a binding specificity to the same receptor on the cell) or different binding specificity (e.g., a binding specificity for a different receptor on a cell).

One skilled in the art will appreciate that such bi-specific fusion proteins can find use in tissue regeneration. In some embodiments, bi-specific fusion proteins can be used in diseased cells, following tissue or organ injury or following an event in which the cells of a tissue may be damaged. In some embodiments, the bi-specific fusion proteins can activate cells that express one or more growth factor and/or cytokine (e.g., chemokine) and/or integrin. In other embodiments, the bi-specific fusion proteins find use, for example, in recruiting cells that express one or more growth factor and/or cytokine (e.g., chemokine) receptors and/or integrins (e.g., stem cells, progenitor cells or immune system cells) to tissue following for example, injury, or an event in which the cells of a tissue may be damaged or may become dysfunctional (e.g. beta cell dysfunction in diabetes). Yet, in vivo, the administration of such bi-specific fusion proteins may be used to facilitate repair or regeneration of damaged tissue or organ.

In some embodiments, the bi-specific proteins disclosed herein can find use in modulating tissue survival. For example, the bi-specific proteins can enhance or maintain the viability of a cell. In some embodiments, the bi-specific fusion proteins can activate the pro-survival or the cell survival pathway. In some embodiments, the bi-specific proteins can modulate apoptosis.

In some embodiments, bi-specific proteins can have (a) a targeting polypeptide domain wherein the targeting domain binds to a target molecule thereby targeting the bi-specific fusion protein to a first cell of a tissue and (b) an activator domain having a binding specificity to a receptor. Upon exposure of the activator domain to the receptor, the activator domain can activate the receptor of a second cell so as to promote cell recruitment, inhibition of apoptosis, induction of cell proliferation, activation of the pro-survival pathway, regeneration, survival of the tissue. One skilled in the art will appreciate that the bi-specific fusion protein can bind to a first cell population and act on the same cell population (e.g. in an autocrine manner) or on a different cell population (e.g. in a paracrine manner). In some embodiments, the targeting domain binds specifically to a target molecule associated with a damaged first cell population and the activator domain binds specifically to a receptor of a second cell population of viable cells. Yet in some embodiments, the targeting domain binds specifically to a tissue specific target molecule at the surface of a first cell population and the activator domain acts specifically to a second cell population. The first cell can be a viable cell, or an "at risk" cell. As used herein "at risk" cell refers to a viable cell that has not yet undergone apoptosis or is not damaged but is at risk to be damaged.

In some embodiments, the bi-specific protein has two different binding domains (such targeting domain and activator domain) which bind to different molecule on different cells in a tissue or organ. Yet in other embodiments, the bi-specific protein has two different binding domains which bind to different molecules on the same target cell in a tissue, the targeting domain being selected to bind specifically a target cell and the activator domain selected to promote tissue regeneration.

The term "polypeptide" is used herein to refer to a molecule that consists of multiple amino acid residues linked by peptide bonds. This term carries no implication as to the number of amino acid residues so linked.

The term "bi-specific," as used herein, refers to the ability of the fusion protein to interact with two different ligands: a target molecule (bound by the targeting polypeptide domain) and a receptor for the activator domain. The binding properties of the targeting polypeptide domain and the activator domain are discussed in more detail below.

As used herein the term "target molecule" refers to any molecule that is associated with a tissue (e.g. diseased or damaged tissue). A "target cell" is meant to be a cell to which a bi-specific protein or targeting domain thereof can specifically bind. Preferred target molecules are exposed or enriched on the exterior of a target cell. In some embodiments, the target molecule is associated with a damaged cell, the target molecule being intracellular in a viable or undamaged cell and being exposed to the extracellular space in a damaged cell. Such molecules include, for example, molecules that are exposed in cells that undergo necrosis (such as DNA) or apoptosis (e.g., phosphatidylserine), myosin (including the tissue type-specific subtypes thereof), ICAM-1 or P-selectin. Yet in other embodiments, the target molecule is a molecule that is present or enriched at the surface of a diseased or dysfunctional cell or tissue as compared to the level detected in a healthy or functional cell or tissue.

Cells are bounded by a plasma membrane (or cell membrane) comprising a lipid bilayer. The cell membrane may be considered to have a surface facing the cytosol (cytosolic side or interior of the cell) and a surface facing the exterior of the cell, or the extracellular space. Transbilayer movement of anionic phospholipids from the inner to the outer leaflet of the plasma membrane occurs during apoptosis. The anionic phospholipid-binding protein, such as annexin V, synaptotagmin I or lactadherin can be used to detect the presence of phosphatidylserine on the outer leaflet of the cell membrane. Phosphatidylserine is a phospholipid, that is usually restricted to the cytosolic side of the membrane in viable or undamaged cells, and that becomes exposed on the outer cell surface or to the extracellular space in apoptosis. Phosphatidylserine has been used as a marker in in vivo imaging studies (see Table 2).

In some embodiments, the target molecule is a "ischemia-associated molecule". An "ischemia-associated molecule" is any molecule that is detected at a level that is significantly higher (e.g., at least 2-fold higher) following ischemia or hypoxia. Any suitable binding assay may be used to identify ischemia-associated molecules, including those provided herein. The increased level of molecule that is detected may be the result of upregulation or decreased turnover, or may be due to increased accessibility (e.g., resulting from cell damage). In certain embodiments, the ischemia-associated molecule is detected in a cell of post-ischemic tissue at a significantly higher level (e.g., at least 2-fold higher) than in a cell of the same tissue that has not undergone an ischemic event (i.e., the molecule is specific to or enriched in the post-ischemic tissue). In further embodiments, the ischemia-associated molecule is associated with cell damage (i.e., the molecule is detected at a significantly higher level in cells that are damaged than in undamaged cells of the same type). Certain ischemia-associated molecules are enriched (2-fold or higher) in the heart after an ischemic event (or in a model system that is used to mimic ischemia in the heart). Such molecules include, for example, molecules that are exposed on myocytes or other cardiac cells that undergo necrosis (such as DNA) or apoptosis (e.g., phosphatidylserine) or molecules that are enriched in scarred heart tissue, such as collagen (collagen I, III), myosin (including the cell type-specific subtypes thereof), or other extracellular matrix proteins that are enriched in post ischemic hearts. Such molecules can be identified on the basis of enrichment following ischemia-reperfusion in vivo or in simulated ischemia-reperfusion in vitro, or following exposure to conditions such as hypoxia, decreased ATP, increased reactive oxygen species (ROS) or nitric oxide synthase (NOS) production, or serum starvation of cells cultured in vitro.

The Targeting Polypeptide Domain

Binding to the target molecule associated with a tissue (for example, the ischemia-associated molecule) is mediated by the targeting polypeptide domain. This domain may be any polypeptide sequence that serves this function. Preferably, binding of the targeting domain to the target molecule does not have a biological activity. As used herein, "biological activity" refers to a defined, known activity performed by exposure of a molecule to a domain of the fusion protein.

In some embodiments, the targeting domain is a non-antibody naturally occurring polypeptide having a binding affinity to the target molecule, fragment thereof or variant thereof. Yet in other embodiments, the targeting polypeptide domain comprises one or more antibody variable regions. One skilled in the art will appreciate that any targeting domain capable of binding directly or indirectly to the target molecule is contemplated.

In some embodiments, the targeting domain is annexin V (SEQ ID NO: 31), fragment thereof, or variant thereof (SEQ ID NOs: 81-83). Annexin V binds to phosphatidylserine (PS). In some embodiments, annexin V is modified to substitute cysteine 315 with serine or alanine to reduce dimer formation. In some embodiments, annexin V is modified to reduce internalization of Annexin V while maintaining phosphatidylserine binding affinity. In some embodiments, one or more residues of annexin V may be altered to modify binding to achieve a more favored on-rate of binding to the target molecule, or a more favored off-rate of binding to the target molecule. In some embodiments, variants of annexin V in which D144 was substituted to N, and/or E228 was substituted with A can be used (see Mira, 1997; Kenis, 2004; Kenis 2010 and Ungthum, 2010).

In other embodiments, the targeting domain is synaptotagmin I, fragment thereof, or variant thereof. Synaptotagmin I (SytI) has been shown to bind phosphatidylserine in a Ca(2+)-dependent manner with a binding affinity of about 5 to 40 nM. In some embodiments, one of the two C2 domains of synaptotagmin (e.g., C2B) can be used as the targeting domain. In some embodiments, the targeting domain is a C2 domain of Ca2+-dependent membrane-targeting proteins involved in signal transduction or membrane trafficking (e.g., protein kinase C, blood coagulation factor V and VIII). In some embodiments, the targeting domain has sequence recited in SEQ ID. NO: 72. Lactadherin, also known as milk fat globule-EGF 8, is a 45 kDa phosphatidylserine-binding glycoprotein secreted by macrophages. Lactadherin contains EGF-like domains at the amino terminus and two C-domains at the carboxy terminus. Accordingly, in some embodiments, the targeting domain comprises the C-domain of lactadherin, fragment thereof or variant thereof. In some embodiments, one or more residues of the C2 domain may be altered to modify binding to achieve a more favored on-rate of binding to the target molecule, or to achieve a more favored off-rate of binding to the target molecule. In some embodiments, the targeting domain has sequence recited in SEQ ID. NOs: 85 or 86. In some embodiments, the targeting polypeptide domain comprises a T cell immunoglobulin mucin 1 & 4 (TIM protein). In other embodiments, the targeting polypeptide domain comprises a 3G4 antibody or antibody domain capable of binding indirectly to phosphatidylserine through plasma 2-glycoprotein 1. Yet in other embodiments, the targeting polypeptide domain comprises an anti-phosphatidylserine antibody (e.g. PS4A7, SEQ ID NO. 30) or antibody domain capable of binding phosphatidylserine.

In some embodiments, the targeting polypeptide domain comprises a polypeptide that binds to the target molecule. Representative such polypeptides comprise or have the sequences provided herein as SEQ ID NOs: 31, 72, 81-83 or 85-86. Representative such polypeptides nucleic acid sequences comprise or have the sequences provided herein as SEQ ID NOs: 225-232 or 235.

Native polypeptide can be used as targeting domains. It will be apparent, however, that portions of such native sequences and polypeptides having altered sequences may also be used, provided that such polypeptides retain the ability to bind the target molecule with an appropriate binding affinity (Kd) as described in more details below.

As used herein, an "antibody" is a protein consisting of one or more polypeptides substantially encoded by immunoglobulin genes. A typical antibody is a tetramer that is composed of two identical pairs of polypeptide chains, each pair having one "light" (about 25 kD) and one "heavy" chain (about 50-70 kD). "$V_L$" and $V_H$" refer to these light and heavy chains respectively. An "antibody variable region" is an N-terminal region of an antibody variable chain ($V_L$ or $V_H$) comprising amino acid residues that are primarily responsible for antigen recognition. Those of ordinary skill in the art are readily able to identify an antibody variable region and to determine the minimum size needed to confer antigen recognition. Typically, an antibody variable region comprises at least 70 amino acid residues, and more commonly at least 100 amino acid residues. A polypeptide that comprises an antibody variable region may (but need not) further comprise other light and/or heavy chain sequences, and may (but need not) further comprise sequences that are not antibody-derived. It will be apparent that the sequence of an antibody variable region may be naturally-occurring, or may be modified using standard techniques, provided that the function (antigen recognition) is retained. Certain polypeptides that comprise an antibody variable region are single chain antibodies (antibodies that exist as a single polypeptide chain), more preferably single chain Fv antibodies (scFv) in which a variable heavy chain region and a variable light chain region are joined together (directly or through a peptide linker) to form a continuous polypeptide. The scFv antibody may be chemically synthesized or may be expressed from a nucleic acid including $V_H$- and $V_L$-encoding sequences either joined directly or joined by a peptide-encoding linker.

"Binding" or "specific binding" are used interchangeably herein and indicates that a bi-specific protein exhibits substantial affinity for a specific molecule (e.g., targeting domain exhibits substantial affinity for a target molecule, or an activator domain exhibits substantial affinity for a molecule associated with the surface of a cell such as a receptor) or a cell or tissue bearing the molecule and is said to occur when the fusion protein (or the targeting polypeptide domain thereof or the activator domain thereof) has a substantial affinity for the specific molecule and is selective in that it does not exhibit significant cross-reactivity with other molecules. Preferred substantial binding includes binding with a dissociation constant ($K_d$) of $10^{-6}$, $10^{-7}$, $10^{-1}$, $10^{-9}$, $10^{-10}$, $10^{-11}$, $10^{-12}$ M or better. For example, the $K_d$ of an antibody-antigen interaction indicates the concentration of antibody (expressed as molarity) at which 50% of antibody and antigen molecules are bound together at thermodynamic equilibrium. Thus, at a suitable fixed antigen concentration, 50% of a higher (i.e., stronger) affinity antibody will bind antigen molecules at a lower antibody concentration than would be required to achieve the same percent binding with a lower affinity antibody. $K_d$ is also the ratio of the kinetic on and off rates ($k_{on}$ and $k_{off}$); i.e., $K_d=k_{off}/k_{on}$. Thus, a lower $K_d$ value indicates a higher (stronger) affinity. As used herein, "better" affinities are stronger affinities, and are identified by dissociation constants of lower numeric value than their comparators, with a $K_d$ of $10^{-10}$M being of lower numeric value and therefore representing a better affinity than a $K_d$ of $10^{-9}$M. Affinities better (i.e., with a lower $K_d$ value and therefore stronger) than $10^{-7}$M, preferably better than $10^{-8}$M, are generally preferred. Values intermediate to those set forth herein are also contemplated, and preferred binding affinity can be indicated as a range of dissociation constants, for example preferred binding affinities for antibodies disclosed herein are represented by $K_d$ values ranging from $10^{-6}$ to $10^{-2}$ M (i.e., micromolar to picomolar), preferably $10^{-7}$ to $10^{-2}$ M, more preferably $10^{-1}$ to $10^{-2}$ M or better. An antibody that "does not exhibit significant cross-reactivity" is one that will not appreciably bind to an off-target antigen. For example, in one embodiment, an antibody that specifically and selectively binds to cardiac myosin will exhibit at least a two, and preferably three, or four or more orders of magnitude better binding affinity (i.e., binding exhibiting a two, three, or four or more orders of magnitude lower $K_d$ value) for cardiac myosin than for myosin molecules other than cardiac myosin or for non-myosin proteins or peptides. Binding affinity and selectivity can be determined using any art-recognized methods for determining such characteristics, including, for example, using Scatchard analysis and/or competitive (competition) binding assays.

Binding may be assessed, and $K_d$ values determined, using any of a variety of techniques that are well known in the art. For example, binding to an ischemia-associated DNA molecule is commonly assessed by coating an appropriate solid support (e.g., beads, ELISA plate or BIACORE chip) with target DNA fragments. For a targeting polypeptide domain that binds to any sequence of DNA, DNA fragments (single or double-stranded) of 10 base pairs or larger are immobilized on the solid substrate. For a targeting polypeptide domain that binds to a specific sequence or DNA complex (e.g., DNA-histone complex) the appropriate corresponding target is immobilized. Prior to adding the ischemia-associated molecule, non-specific binding sites for protein are blocked with BSA, milk, or any other appropriate blocker. Uncoated wells or wells coated with a non-target molecule serve as specificity controls. Increasing concentrations of the bi-specific fusion protein (or targeting polypeptide domain) are incubated with target-coated substrate or control substrate. A fusion protein or domain that does not bind to the target is also tested as a specificity control. Target specific, dose-dependent binding of the bi-specific fusion protein (or targeting polypeptide domain) is then assessed by measuring the amount of bi-specific fusion protein (or targeting polypeptide domain) binding to target versus controls as a function of increasing dose using standard protocols corresponding to the solid support and binding technology being used. Representative such protocols include those described in Wassaf et al., *Anal. Biochem.* 351(2):241-53 (2006); Epub 2006 Feb. 10 (BIACORE); and Murray and Brown, *J Immunol. Methods.* 127(1):25-8 (1990) (ELISA). In addition, studies that vary the amount of immobilized target molecule or that include increasing levels of soluble target molecule as a competitor may also be performed to monitor binding and specificity.

The binding affinity and kinetic on and off rates for binding to the target molecule are measured using standard techniques and compared to other negative control molecules (e.g., fusion protein with irrelevant targeting polypeptide or fusion protein lacking a targeting polypeptide or fusion proteins with non-binding targeting polypeptide and positive control molecules (e.g., parental antibody that targets the target molecule, or other antibodies or antibody fragments that are known to bind to the target molecule). For example, the non-binding targeting polypeptide can be a non-binding annexin V variant (SEQ ID NO: 84, nucleic acid sequence SEQ ID NOs 233-234), a non-binding synaptotagmin variant (SEQ ID NO: 74) or a non-binding scFv (SEQ ID NO: 75; nucleic acid sequence SEQ ID NOs 236-237)

In certain embodiments, the $K_d$ is determined using a biosensor (e.g., by surface plasmon resonance (e.g., BIAcore) or resonant mirror analysis (IAsys)). Such determinations may be performed as described by Hefta et al., Measuring Affinity Using Biosensors, in "Antibody Engineering: A Practical Approach," McCafferty et al. (eds), pp. 99-116 (Oxford University Press, 1996), and references cited therein. Briefly, kinetic on and off rates ($k_{on}$ and $k_{off}$) are determined using a sensor chip to which the ischemia-associated molecule has been coupled. To evaluate association ($k_{on}$), solutions of different concentrations of bi-specific fusion protein (or targeting polypeptide domain) flow across the chip while binding is monitored using mass sensitive detection. Using the BIAcore system (GE Healthcare; Piscataway, NJ), $k_{on}$ is the slope of the plot of dR/dt versus R, where R is the signal observed. Following binding, dissociation is observed by passing a buffer solution across the chip, and $k_{off}$ is determined in an analogous fashion. $K_d$ is then calculated using the equation:

$$K_d=k_{off}/k_{on}$$

In the context of the present invention, a bi-specific fusion protein binds to the target molecule if it binds with a $K_d$ of less than $10^{-8}$ M, preferably less than $10^{-7}$ M, $10^{-8}$ M, $10^{-9}$ M or $10^{-10}$ M. In addition, the binding of the bi-specific fusion protein to the target molecule in this assay is significantly higher (e.g., at least 2-, 10- or 100-fold higher) than binding of the bi-specific fusion protein to negative controls. Preferably, binding to the immobilized target can also be competed using excess soluble target.

As noted above, certain target molecules are specific to (or enriched in) damaged cells. Representative target molecules include but are not limited to phosphatidylserine, DNA, myosin, cardiac myosin, c-Met (HGF receptor), phosphatidylserine, P-selectin, and ICAM-1. Binding to damaged cells is conveniently demonstrated in vitro using cultured cells that are exposed to conditions that induce necrosis or apoptosis. For example, necrosis can be induced in cultured cardiomyocytes by simulated ischemia/reperfusion, and monitored using a LDH release assay, or trypan blue assay followed by subtraction of the number of cells undergoing apoptosis, essentially as described in Shan et al., *Am. J Physiol. Cell. Physiol.* 294:833-841 (2008). This assay quantitates the total dead cells and the difference between the total and the number of apoptotic cells is attributed to necrosis, as discussed in more detail below. Conditions that induce apoptosis include exposure to $H_2O_2$, and apoptosis can be monitored using any of a variety of techniques known in the art including, for example, annexin V binding, cleavage of target peptide sequences by known caspases that are activated by apoptosis, or DNA laddering (measured by TUNEL assay, essentially as described in Kuramochi, *J. Biol. Chem.* 279(49): 51141-47 (2004)). Binding to the cells undergoing necrosis or apoptosis may be assessed by adding fluorescently labeled bi-specific fusion protein (or targeting polypeptide domain) or appropriate control proteins to cells following the induction of apoptosis or necrosis. After following ischemia-reperfusion injury. In such a case, demonstration of in vivo targeting may be accomplished by inducing tissue damage, preferably by a method that causes ischemia followed by re-establishment of blood supply. Numerous methods are available to do this in different tissues. For example, blood flow to the hindlimb of the mouse can be transiently blocked with a simple tourniquet. Alternatively, temporary clamp on the artery leading into the kidney can be employed. Ischemia-reperfusion injury can be induced in the heart through temporary blockage of the coronary artery as demonstrated in mice, rats, dogs, and pigs. Representative methods for inducing tissue damage in an animal model are summarized in Table 1.

TABLE 1

| Representative Methods used to Induce Ischemia-Reperfusion Damage | | |
|---|---|---|
| Organ or tissue | Methods used to induce damage | Reference |
| Heart | Mouse: left anterior descending artery (LAD) clamped for up to 30 to minutes followed by reperfusion<br>Rat: coronary artery ligation | Dumont et al., *Circulation* 102(13): 1564-8 (2000)<br>Davis, *Proc. Natl. Acad. Sci. USA* 23: 103(21): 8155-60 (2006) |
| Kidney | Mouse: Renal artery clamped with pediatric suture for 1-6 hrs | Chen et al., *FASEB J.* 4(12): 3033-39 (1990) |
| Liver | Dog: The hepatic pedicle and hepatic artery (close to the celiac artery) were cross-clamped with vascular clamps.<br>Pig: Details in reference | Miranda et al., *Braz. J. Med. Biol. Res.* 40(6): 857-65 (2007)<br>Kobayashi et al., *World J. Gastroenterol.* 13(25): 3487-92 (2007) |
| Hindlimb | | Zbinden et al., *Am. J. Physiol. Heart Circ. Physiol.* 292: H1891-H1897 (2007) | incubation of the proteins with the cells for times ranging from a few minutes to one day, the cells are washed and then the cell-bound fluorescence is measured using immunofluorescence, flow cytometry, or similar techniques. Alternatively, other methods of detecting the bound bi-specific fusion protein (or targeting polypeptide domain) may be used, including radiolabeling or using enzymes conjugated to the bi-specific fusion protein (or targeting polypeptide domain) or to antibodies that bind to the fusion protein (or targeting polypeptide domain), which is common practice in ELISA protocols. The bi-specific fusion protein (or targeting polypeptide domain) binds to target cells if significantly higher (e.g., 2-fold higher) binding to cells following ischemia (e.g., cells undergoing necrosis or apoptosis) is detected, as compared to cells that have not experienced injury (e.g., cells not undergoing apoptosis or necrosis).

In vivo targeting may be demonstrated by inducing, for example, ischemia in an animal model and comparing the level of administered bi-specific fusion protein (or targeting polypeptide domain) in a target tissue before and after ischemia. In vivo targeting to damaged cells may be demonstrated by inducing tissue damage in an animal model, administering the bi-specific fusion protein (or targeting polypeptide domain), and comparing the level of bi-specific fusion protein (or targeting polypeptide domain) in damaged versus undamaged cells. In one embodiment, the bi-specific fusion proteins are designed to target areas of tissue damage Animal models for ischemia-reperfusion injury are further detailed in the following references:

Greenberg et al., Chapter 7. Mouse models of ischemic angiogenesis and ischemia-reperfusion injury. *Methods Enzymol.* 444:159-74 (2008).

Chimenti et al., Myocardial infarction: animal models. *Methods Mol. Med.* 98:217-26 (2004).

Black S C, In vivo models of myocardial ischemia and reperfusion injury: application to drug discovery and evaluation. *J. Pharmacol. Toxicol. Methods* 43(2):153-67 (2000).

The specificity of targeting can be established by comparing the bi-specific fusion protein (or targeting polypeptide domain) deposition in the clamped versus unclamped kidney as shown in Chen et al., *FASEB J.* 4(12): 3033-39 (1990), or in the treated versus untreated hindlimb as shown in Zbinden et al., *Am. J. Physiol. Heart Circ. Physiol.* 292: H1891-H1897 (2007), using radiolabeled bi-specific fusion protein (or targeting polypeptide domain). Alternatively, bi-specific fusion protein (or targeting polypeptide domain) can be detected in homogenized tissue using ELISA, or can be imaged in real time using bi-specific fusion protein (or targeting polypeptide domain) labeled with the appropriate metal for imaging (e.g., Tc99, Y or Gd). Specific deposition in the damaged area of the heart can be measured as described in Dumont et al., *Circulation* 102(13):1564-8 (2000). Representative methods for demonstrating targeting of proteins to damaged tissue are shown in Table 2.

TABLE 2

| Demonstration of Targeting to Damaged Tissue | | |
|---|---|---|
| Damaged organ or tissue targeted | Methods used to demonstrate targeted delivery | Reference |
| Heart | Humans: Tc99 labeling of annexin V followed by imaging in humans using SPECT in patients with myocardial infarction followed by reperfusion attempts via angioplasty or thrombolysis | Hofstra et al., *The Lancet* 356 (9225): 209-12 (2000) |
| Heart | Mouse: Fluorescent labeling of annexin V in murine model of ischemia reperfusion with distribution in the myocardium detected histologically | Dumont et al., *Circulation* 102(13): 1564-8 (2000) |
| Heart | Humans: Tc99 labeling of annexin V followed by imaging in humans using SPECT in patients undergoing cardiac transplant rejection | Hofstra et al., *The Lancet* 356 (9225): 209-12 (2000) |
| Heart | Mouse: Fluorescently-labeled growth factor imaged in heart tissue using confocal microscopy | Urbanek, *Proc. Natl. Acad. Sci. USA* 102 (24): 8692-97 (2005) |
| Damaged kidney targeted using radiolabeled to antibody DNA | Radiographs of clamped versus unclamped kidney Microautoradiographs to show localization to specific cellular structures in the kidney Imaging of whole mouse using I131-labeled antibody to DNA (versus labeled control) Biodistribution of I125-labeled antibody to show deposition in non-target tissues | Chen et al., *FASEB J.* 4(12): 3033-9 (1990) |

As noted above, certain targeting polypeptide domains comprise an antibody that binds to the target molecule (e.g., DNA, myosin, cardiac myosin, c-Met, P-selectin, ICAM-1). In some embodiments, the targeting domain is an anti-myosin antibody (e.g. RI ID-10 against human cardiac myosin, 2G4-sD7 against cardiac myosin heavy chain, 1B2 and 5C2 against human cardiac myosin heavy chain, 2F4 against human cardiac myosin, monoclonal antibodies against myosin, B7 antibody, B7 scFv, or other antibodies known in the art). In some embodiments, the certain targeting polypeptide domains comprise an scFv antibody that binds to the target molecule. For example, the targeting domain can be an anti-DNA S1-1 scFv (aDNAS11, SEQ ID NOs: 1, or 73) an anti-DNA SI-22 scFv (aDNAS122, SEQ ID NO: 2). Representative such antibodies and scFv antibodies comprise or have the sequences provided herein as SEQ ID NOs: 1, 2, 30, 73 and 76-80. In some embodiments, representative such antibodies and scFv antibodies nucleic acid sequences comprise or have the sequences provided herein as SEQ ID NOs 220-224.

It will be apparent that functionally related antibodies may also, or alternatively, be used as a targeting polypeptide domain. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to generate modified antibodies that mimic the properties of an original antibody by combining CDR sequences from one antibody with framework sequences from a different antibody. Such framework sequences can be obtained from public DNA databases that include germline antibody gene sequences.

Thus, one or more CDRs of a targeting polypeptide domain sequence provided herein can be used to create functionally related antibodies that retain the binding characteristics of the original targeting polypeptide domain. In one embodiment, one or more CDR regions selected from SEQ ID NOs: 1, 2, 30, 73 and 76-80 is combined recombinantly with known human framework regions and CDRs to create additional, recombinantly engineered, targeting polypeptide domains. The heavy and light chain variable framework regions can be derived from the same or different antibody sequences. CDR regions are readily identified using alignments with known sequences in databases such as Vbase and IMGT. The resulting targeting polypeptide domains share one or more CDRs with the targeting polypeptide domains of SEQ ID NOs: 1, 2, 30, 73 and 76-80. In certain embodiments, the targeting polypeptide domain comprises at least one CDR of a sequence as recited in SEQ ID NO: 1, 2, 30, 73 and 76-80.

It is well known in the art that antibody heavy and light chain CDR3 domains play a particularly important role in the binding specificity/affinity of an antibody for an antigen. Accordingly, in certain embodiments, antibodies are generated that include the heavy and/or light chain CDR3s of the particular antibodies described herein. The antibodies can further include the heavy and/or light chain CDR1 and/or CDR2s of the antibodies disclosed herein.

The CDR 1, 2, and/or 3 regions of the engineered antibodies described above can comprise the exact amino acid sequence(s) as those disclosed herein. However, the ordinarily skilled artisan will appreciate that some deviation from the exact CDR sequences may be possible, particularly for CDR1 and CDR2 sequences, which can tolerate more variation than CDR3 sequences without altering epitope specificity (such deviations are, e.g., conservative amino acid substitutions). Accordingly, in another embodiment, the engineered antibody may be composed of one or more CDR1s and CDR2s that are, for example, 80%, 90%, 95%, 98%, 99% or 99.5% identical to the corresponding CDRs of an antibody named herein.

In another embodiment, one or more residues of a CDR may be altered to modify binding to achieve a more favored on-rate of binding, or a more favored off-rate of binding. Using this strategy, an antibody having ultra high binding affinity (e.g., $K_d = 10^{-10}$ or less) can be achieved. Affinity maturation techniques, well known in the art, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

Modifications can also be made within one or more of the framework or joining regions (i.e., non-CDR residues) of the heavy and/or the light chain variable regions of an antibody, so long as antigen binding affinity subsequent to these modifications is not substantially diminished.

The Activator Domain

The activator domain is any polypeptide that detectably modulates the activity of a cellular network or recruit cells from one location to another. In some embodiments, the activator domain is capable of activating signal transduction pathways by binding to a receptor at the surface a cell. In some embodiments, certain activator domains are growth factor polypeptides, cytokine polypeptides (e.g., a chemokine polypeptide), or any agonist of the receptor or integrin-binding ligands. It will be apparent that such modulation may be an increase or a decrease in the activity of the cellular network such as induction of proliferation of cells, induction of cell growth, promotion of cell survival and/or inhibition of apoptosis. In some embodiments, the activator domain can recruit other factors or cells (e.g. stem cells).

A growth factor polypeptide detectably modulates activation of a growth factor receptor (such as HGF or IGF receptor). Certain such polypeptides are wild-type hepatocyte growth factor (HGF) or HGF alpha chain (e.g., GEN-BANK accession number P14210), or derivatives thereof that retain at least 10% of wild-type biological activity, as determined by measuring activation of the corresponding growth factor receptor in appropriate target cells. Activation may be assessed, for example, by measuring phosphorylation of receptor kinase or downstream proteins, such as AKT, essentially as described by Nishi et al., *Proc. Natl. Acad. Sci. USA* 95:7018-7023 (1998). MTT and CTG assays known in the art may also be used.

In some embodiments, the activator domain is a growth factor. In some embodiments, the activator domain comprises the foregoing or a variant of the protein. Representative activator domains include but are not limited to fibroblast growth factor (FGF), fibroblast growth factor 1 (FGF1), fibroblast growth factor 2 (FGF2, also known as basic fibroblast growth factor (bFGF)), fibroblast growth factor 2, 146aa (FGF2-146aa), fibroblast growth factor 2, 157aa (FGF2-157aa), fibroblast growth factor 4 (FGF4), fibroblast growth factor 7 (FGF7), epidermal-growth factor (EGF), insulin-like growth factor (IGF), insulin-like growth factor 1 (IGF1), insulin-like growth factor 2 (IGF2), hepatocyte growth factor (HGF), hepatocyte growth factor-NK1 domains (HGF-NK1), hepatocyte growth factor-K1 domain (HGF-K1), hepatocyte growth factor-NK2 domains (HGF-NK2), hepatocyte growth factor-K2 domain (HGF-K2), neuregulin (NRG, also known as heregulin (HRG)), neuregulin-1beta extracellular domain (NRG1beta-ECD), neuregulin-1beta EGF-like domain (NRG1beta-EGF), thymosin, thymosin beta4 (Tbeta4), granulocyte colony-stimulating factor (G-CSF), stem cell factor (SCF, also known as mast cell growth factor (MGF)), periostin, vascular endothelial growth factor (VEGF, also known as vascular endothelial growth factor-A (VEGF-A)), vascular endothelial growth factor-A-121 (VEGF-A-121), vascular endothelial growth factor-A-165 (VEGF-A-165), vascular endothelial growth factor-B (VEGF-B), vascular endothelial growth factor-B-167 (VEGF-B-167), vascular endothelial growth factor-C (VEGF-C), stromal cell-derived factor (SDF), stromal cell-derived factor-1 (SDF-1), stromal cell-derived factor-1alpha (SDF-1alpha), platelet-derived growth factor (PDGF), platelet-derived growth factor-AA (PDGF-AA), platelet-derived growth factor-AB (PDGF-AB), platelet-derived growth factor-BB (PDGF-BB), tetracarcinoma-derived growth factor (TDGF), teratocarcinoma-derived growth factor 1 (TDGF1), nerve growth factor (NGF), beta-nerve growth factor (beta-NGF), brain-derived neurotrophic factor (BDNF), neurotrophin-3 (NT-3), thrombopoietin (TPO), transforming growth factor-beta1 (TGF-beta1), transforming growth factor-beta2 (TGF-beta2), bone morphogenic protein (BMP), bone morphogenetic protein-2 (BMP2), single-chain BMP-2 (scBMP2), bone morphogenic protein 3 (BMP3), bone morphogenic protein 4 (BMP4), activin A, betacellulin, beta-catenin, dickkopf homolog 1 (DKK1), erythropoietin (EPO), growth hormone (GH), heparin-binding EGF-like growth factor (HBEGF), insulin, interleukin (IL), interleukin 6 (IL-6), interleukin 10 (IL-10), interleukin 33 (IL-33), leukemia inhibitory factor (LIF), monocyte chemotactic protein 1 (MCP1, also known as CCL2), pleiotrophin (PTN), tumor necrosis factor-alpha (TNF-alpha), Wnt, Wnt1, Wnt2, Wnt3a, Wnt7a, Wnt8a, Wnt11, or antibody having a specificity for the activator receptor, variant thereof, isoforms thereof, fragment thereof, and combinations thereof. In some embodiments, the activator domain is designed to comprise a single chain of a growth factor or growth factor domain. For example, the activator domain can be designed to comprise two or more copies of a growth factor domain (e.g. BMP-2) linked together via a linker (e.g., GGGGSGGGGSGGGGS (SEQ ID NO: 103).

Representative growth factor polypeptides have a sequence as recited in SEQ ID NO: 3-9 32-40, or 50-64, herein. Representative growth factor can be encoded by the nucleic acid sequences as recited in SEQ ID NOs: 187-211, herein.

As discussed above for CDRs of some of the targeting polypeptide domains, activator domains that share one or more domains, modules, or amino acid sequences with the activator domains or variations of SEQ ID NOs: 3-9, 32-40, or 50-64, are also contemplated. Such domains, modules, or amino acid sequences may be identified and such activator domains may be constructed using well known techniques. Thus, in certain embodiments, the activator domain comprises at least one domain, module, or amino acid sequence or variation of a sequence as recited in SEQ ID NO: 3-9, 32-40, or 50-64. Similarly, a cytokine polypeptide modulates activation of the corresponding cytokine receptor, as determined in the same fashion.

In certain embodiments, the activator domain is a growth factor polypeptide, which binds a growth factor receptor on a cell surface. Representative such growth factor receptors are receptors for epidermal growth factor (EGF), Neregulin/Heregulin (NRG/HRG), fibroblast growth factor (FGF), insulin-like growth factor (e.g., IGF-I), platelet-derived growth factor (PDGF), vascular endothelial growth factor (VEGF) and isoforms thereof (e.g., VEGF-A or VEGF-C), teratocarcinoma-derived growth factor 1 (TDGF1), transforming growth factor alpha (TGF-α), transforming growth factor beta (TGF-β) and isoforms thereof e.g., TGF-β1 or TGF-β2, thrombopoietin (THPO) or periostin. Other such receptors include mast/stem cell growth factor receptor (SCFR), hepatocyte growth factor receptor (HGF receptor, i.e., c-Met), ErbB-2, ErbB-3, ErbB-4, high affinity nerve

29 | 30 growth factor receptor, BDNF/NT-3 growth factors receptor, NT-3 growth factor receptor, or vascular endothelial growth factor receptor 1 (VEGFR-I).

Representative cytokine receptors include, for example, FL cytokine receptor, receptor for cytokine receptor common gamma chain, interleukin-10 receptor alpha chain, interleukin-10 receptor beta chain, interleukin-12 receptor beta-1 chain, interleukin-12 receptor beta-2 chain, interleukin-13 receptor alpha-1 chain, interleukin-13 receptor alpha-2 chain, interleukin-17 receptor; interleukin-17B receptor, interleukin 21 receptor precursor, interleukin-1 receptor type I, interleukin-1 receptor type II, interleukin-2 receptor alpha chain, interleukin-2 receptor beta chain, interleukin-3 receptor alpha chain, interleukin-4 receptor alpha chain, interleukin-5 receptor alpha chain, interleukin-6 receptor alpha chain, interleukin-6 receptor beta chain, interleukin-7 receptor alpha chain, high affinity interleukin-8 receptor A, high affinity interleukin-8 receptor B, interleukin-9 receptor, interleukin-18 receptor 1, interleukin-1 receptor-like 1 precursor, interleukin-1 receptor-like 2, toll-like receptor 1, toll-like receptor 2, toll-like receptor 5, CX3C chemokine receptor 1, C-X-C chemokine receptor type 3, C-X-C chemokine receptor type 4, C-X-C chemokine receptor type 5, C-X-C chemokine receptor type 6, C-C chemokine receptor type 1, C-C chemokine receptor type 2, C-C chemokine receptor type 3, C-C chemokine receptor type 4, C-C chemokine receptor type 6, C-C chemokine receptor type 7 precursor, C-C chemokine receptor type 8, C-C chemokine receptor type 9, C-C chemokine receptor type 10, C-C chemokine receptor type 11, chemokine receptor-like 2, and chemokine XC receptor. Still other activator domains are receptors for solute carrier organic anion transporter family, member 1A2 (SLCO1A2), sphingosine kinase 1 (SPHK1), secreted phosphoprotein 1 (SPP1), also called osteopontin (OPN), tumor protein 53 (TP53), troponin T type 1 (TNNT1), TSPY-like protein 2 (TSPYL2), visfatin, WAP four-disulfide core domain 1 (WFDC1), thymosin beta 4, wingless-type MMTV integration site family, member 11 (WNT11). Representative activator domains include, for example, resistin, stromal cell-derived factor-1 (SDF-1), signal-induced proliferation-associated gene 1 (SIPA1), and any of the other ligands listed above, as well as portions and derivatives of the foregoing that substantially retain the ability to bind to cognate receptors.

Integrins are receptors that mediate attachment of a cell to other cells or tissue surrounding it. Integrins bind cell surface and extracellular matrix components such as fibronectin, vitronectin, collagen and laminin. Representative integrins include for example, $\alpha_1\beta_1$, $\alpha_2\beta_1$, $\alpha_4\beta_1$, $\alpha_5\beta_1$, $\alpha_6\beta_1$ $\alpha_L\beta_2$, $\alpha_M\beta_2$, $\alpha_{IIb}\beta_3$, $\alpha_V\beta_3$, $\alpha_V\beta_5$, $\alpha_V\beta_6$, $\alpha_6\beta_4$.

As an initial test, binding of a bi-specific fusion protein (or activator domain thereof) to the appropriate receptor may be assessed using techniques known in the art. In one representative assay, binding is demonstrated by coating an appropriate solid support with the recombinant ectodomain of the appropriate receptor. An ectodomain from a receptor not recognized by the activator domain of the bi-specific fusion protein is used as a specificity control. A support substrate that does not have any immobilized receptor is also used as a control. Similar to the methods described above for binding to the ischemia-associated molecule, specific, dose-dependent binding to receptor is demonstrated using standard protocols corresponding to the solid support and binding technology being used. In addition, studies that vary the amount of receptor or that include increasing levels of soluble target molecule as a competitor are also performed to monitor binding and specificity. Alternatively, the bi-specific fusion protein is immobilized to a support and the binding of the soluble ectodomain of the corresponding receptor(s) is used to demonstrate dose-dependent, specific binding.

The binding affinity and kinetic on and off rates for binding of the bi-specific fusion protein to the receptor(s) are also measured using standard techniques and compared to other negative control molecules (fusion protein with irrelevant control activator domain, fusion protein lacking an activator domain) and positive control molecules (recombinant wild-type receptor ligand, such as a growth factor or cytokine). The equilibrium and kinetic binding parameters of the bi-specific fusion protein are also compared to the same parameters measured for the un-fused wild-type ligand to determine whether fusion of the ligand to other molecules affects the normal binding of the ligand to its corresponding receptor. Such information may be used to determine the effective dose of the bi-specific fusion protein.

A bi-specific fusion protein binds to immobilized growth factor receptor or cytokine receptor with a significantly higher affinity (e.g., at least 100-fold) than that observed for negative controls. In addition, binding to the immobilized receptor can be competed using excess soluble polypeptide, soluble receptor, or antibodies that bind to polypeptide or receptor and block their interaction. Preferably, the bi-specific fusion protein binds to the growth factor or cytokine receptor with an affinity within 1000-fold of the native ligand binding to its receptor.

A bi-specific fusion protein (and its activator domain) further has the capacity to mediate cognate receptor activation. Such activity may be assessed, for example, using a cellular model of ischemia reperfusion, which uses cultured cardiomyocytes such as neonatal rat ventricular myocytes (NRVM) or cell lines. Simulated ischemia (SI) is generally initiated by metabolic inhibitors (deoxyglucose and dithionite) and metabolites (high potassium, lactate, low pH) or by hypoxia in an anaerobic chamber. Reperfusion is simulated by resuspension in an oxygenated buffer. An in vitro adult cardiomyocyte pellet model of ischemia has been developed that provides the two primary components of ischemia—hypoxia and metabolite accumulation—in the absence of any exogenous metabolic inhibitors or metabolites. Table 3 shows representative methods for demonstrating the ability of a bi-specific fusion protein to prevent damage of cardiomyocytes, promote growth, motility or differentiation of cardiac stem cells and/or promote repair of damaged tissue.

TABLE 3

| Activity Assessment Methods | | |
|---|---|---|
| Aspect | Assay | Reference |
| Localization and retention kinetics | Detection of activator domain in cell lysate by ELISA | Davis, *Proc Natl Acad Sci USA* |

TABLE 3-continued

Activity Assessment Methods

| Aspect | Assay | Reference |
|--------|-------|-----------|
| of activator domain | Detection of activator domain in cells by immunofluorescence (flow cytometry or microscopic) | 103(21): 8155-60 (2006) Urbanek, *Proc. Natl. Acad. Sci. USA* 102 (24): 8692-97 (2005) |
| Signaling by activator domain | Detection of phospho-akt or phospho-ERK in cells by flow cytometry, immunofluorescence, ELISA, phospho-labeling, or Western | Davis, *Proc Natl Acad Sci USA* 103(21): 8155-60 (2006) Urbanek, Proc. *Natl. Acad. Sci. USA* 102 (24): 8692-97 (2005) |
| Protection of cells against apoptosis following hypoxia or other cell stressor | AnnexinV binding by immunofluorescence or flow cytometry Detection of caspase activity TUNEL-assay (reduced number of TUNEL-positive cells) DNA laddering Cell viability Enhancement of cardiomyocyte viability following exposure to $H_2O_2$. Number of rod-shaped cells pPCR assessment of gene expression | |
| Protection of cells against necrosis | Reduced necrotic area by H&E staining | |
| Reduction in scar formation | Reduction in number of fibroblastic cells in infarct area Reduction collagen deposition Reduction in other matrix proteins associated with scar formation | |
| Migration of CSC into the infarct area | Time dependent increase in c-kit+, sca-1+, MDR1+ cell numbers and numbers undergoing transition to small myocytes | Urbanek, *Proc. Natl. Acad. Sci. USA* 102 (24): 8692-97 (2005) |
| Myocyte mechanics and cell fusion: | Frequency of distribution of myocyte sizes Peak shortening Velocity of shortening and relengthening Assessment of cell fusion (number of X chromosomes) | Urbanek, *Proc. Natl. Acad. Sci. USA* 102 (24): 8692-97 (2005) |
| Cardiac functional assessment | Comparison of MI-treated versus MI-untreated animals LVEDP LVDP +dp/dT LV Weight Chamber Volume Diastolic Wall Stress Survival | Urbanek, *Proc. Natl. Acad. Sci. USA* 102 (24): 8692-97 (2005) |
| Myocardial regeneration | Composition of regenerated myocardium Assessment of BrdU+ cells in infarct area in treated versus untreated animals Myosin+ cells in the infarct area in treated versus untreated animals | Urbanek, *Proc. Natl. Acad. Sci. USA* 102 (24): 8692-97 (2005) |
| Cardiac structural | Infarct size Fibrosis Cardiomyocyte hypertrophy | Urbanek, *Proc. Natl. Acad. Sci. USA* 102 (24): 8692-97 (2005) |

Native growth factors and cytokines can be used as activator domains. It will be apparent, however, that portions of such native sequences and polypeptides having altered sequences may also be used, provided that such polypeptides retain the ability to activate the cognate receptor (e.g., using one of the assays discussed below), such polypeptides detectably activate the receptor, and preferably activate the receptor to a degree that is at least 1% (preferably at least 10%) of that observed for the native ligand. Certain activator domains that bind to growth factor receptors are provided herein in SEQ ID NOs: 3-9, 32-40, and 50-64. Activity of fusion proteins comprising such sequences is well known in the art (e.g., Hashino et al., *J. Biochem.* 119(4):604-609 (1996); Nishi et al., *Proc. Natl. Acad. Sci. USA* 95:7018-23 (1998)).

An activator domain for a particular application may be selected based on the desired therapeutic outcome. For example, an activator domain that comprises FGF2, VEGF alpha, or a portion or derivative thereof, that substantially retains the ability to bind to cognate receptor, may generally be used to increase angiogenesis. To increase survival and for stem cell differentiation (regenerative) purposes, activator domains that comprise IGF, HGF or NRG1 (or a portion or derivative thereof) may be used.

In some cases, it may be desirable to assess the activity of both the activator domain and the targeting polypeptide simultaneously. An ELISA may be conveniently used for this purpose.

The substrate of the targeting polypeptide (e.g., DNA) is adsorbed to the ELISA plate, which is then blocked with appropriate BSA containing buffers. The bi-specific fusion protein is then added, followed by addition of recombinant substrate for the activator domain (e.g., if the activator is a growth factor, then the substrate is recombinant cognate receptor or receptor fragment (ectodomain)). This substrate is either fluorescently labeled for detection or detected using a labeled antibody to a region of the receptor that does not significantly affect ligand binding.

The in vivo activity of the bi-specific fusion protein is generally assessed by detecting signaling changes in molecules that are regulated by the activator domain of the bi-specific fusion protein. This typically involves changes in cell surface receptor phosphorylation status or downstream mediators such as phospho-AKT or phospho-ERK as detected by flow cytometry, immunofluorescence, ELISA, phospho-labeling, or Western analysis of treated tissues. Other functional assessments include tests for the number of viable cells by staining and morphological identification, level of apoptosis by annexin V binding (via immunofluorescence) or flow cytometry, detection of caspase activity, TUNEL-assay (reduced number of TUNEL-positive cells) or DNA laddering. In each case, a bi-specific fusion protein functions in vivo if it induces a significant (e.g., at least 2-fold) change in the level, functional activity, or phosphorylation of the regulated molecule detected by the assay. The repair of damaged tissue in a patient can be assessed using any clinically relevant standard. For example, repair of infarcted tissue can be measured by quantitation of cell number, such as the number of myocytes, fibroblast, or amount of scarring, or with functional assays for output or structural aspects of heart function including, LVEDP, LVDP, +dp/dT, LV Weight, Chamber Volume, and Diastolic Wall Stress. Methods for such assessments are well known and amply described in the literature. In general, a bi-specific fusion protein is said to repair damaged tissue if it results in a significant (e.g., at least 2-fold) change in any such clinical assessment.

Half Life Modulator

One skilled in the art would appreciate that bi-specific proteins used in therapeutic applications may not exhibit optimal serum half lives due to their relatively low molecular weight. In some therapeutic applications, it may therefore be desirable to modulate the half life of the bi-specific proteins. In some embodiments, to achieve accumulation of the bi-specific protein to the diseased injured or damaged area of an organ, the bi-specific protein is conjugated with a half-life modulator. Such half-life modulators can increase the in vivo half life of the fusion proteins. For example, the half life of the bi-specific proteins comprising the half life modulator is about 1 hour, 2 hours, 3 hours, 4 hours, 5 hours, 6 hours or greater. In some embodiments, the half life of the bi-specific proteins comprising the half life modulator is about 24 hours, or greater. In some embodiments, the half life of the bi-specific proteins comprising the half life modulator is about a week or greater.

The targeting polypeptide domain and activator domain may be directly joined via a peptide bond. In some embodiments, they may be joined via a half-life modulator. In preferred embodiments, the half-life modulator is a polypeptide. Accordingly, the half-life modulator can have two termini, an N-terminus and a C-terminus. In some embodiments, the half-life modulator is joined at one terminus via a peptide bond to the targeting polypeptide domain and is joined at the other terminus via a peptide bond to the activator domain. In certain embodiments, the linker is joined at the N-terminus to the C-terminus of the targeting polypeptide domain and at the C-terminus to the N-terminus of the activator domain. In other embodiments, the linker is joined at the C-terminus to the targeting polypeptide domain and at the N-terminus to the activator domain. Yet, in other embodiments, the half-life modulator is joined at one of the termini of the bi-specific protein. For example, in some embodiments, the half-life modulator is joined at the C-terminus to the N-terminus of the activator domain. In other embodiments, the half-life modulator is joined at the C-terminus of the targeting domain. In other embodiments, the half-life modulator can be joined at the N-terminus to the C-terminus of the activator domain. Yet in other embodiments, the half-life modulator can be joined at the N-terminus to the C-terminus of the targeting domain.

In some embodiments, the half-life modulator is designed to drive the size of the bi-specific fusion protein beyond about 70 kDa or equivalent radius to minimize renal clearance. In some embodiments, the half-life modulator is designed to extend the half-life of the bi-specific fusion protein through FcRn receptor-mediated recycling or through binding to serum components such as Human Serum Albumin (HSA).

Preferably, the half-life modulator is non-immunogenic in humans. The half-life modulator can be a human serum protein or a derivative thereof that retains at least 50% sequence identity over a region that consists of at least 100 consecutive amino acids. As used herein "sequence identity" means, in the context of comparing a polynucleotide or a polypeptide sequence to a reference sequence, that the polynucleotide or polypeptide sequence is the same or has a specified percentage of nucleotides or residues that are the same at the corresponding locations within the reference sequence when the polynucleotide or polypeptide sequences are optimally aligned.

In some embodiments, the half-life modulator can be modified by glycosylation of one or more glyscosylation site present in the half-life modulator. For example, the following amino acids: asparagine, serine, threonine can be added or removed to alter the glycosylation of the half-life modulator. In some embodiments, glycosylation of the half-life modulator in the bi-specific protein can modulate the half-life of the bi-specific protein. In some embodiments, the half-life modulator sequence is modified to reduce glycosylation. Such modification comprising the substitution of Asn (N) by Gln (Q) or Ala (A), and/or the substitution of Ser (S) or Thr (T) by Ala (A).

Human serum albumin (HSA) has a naturally long serum half life, in part due to its binding to FcRN and recycling. HSA is the most abundant protein in the blood and has a demonstrated safety in humans. In some embodiments, the asparagine at position 503 of HSA, which may be deamidated and decrease half life, can be removed by the N503Q substitution. In some embodiments, the cysteine C34 of HSA may be substituted to serine or alanine (S or A) to remove the free cysteine and minimize alternate disulfide-bond formation. In some embodiments, the half-life modulator is a modified version of the domain III (mHSA_dIII) of a modified HSA with the N503Q substitution and an additional terminal glycine. Such a modified version retains the HSA property of binding to FcRn and increased serum half life. In some embodiments, the half-life modulator comprises at least 100 consecutive amino acids that are at least 70%, 80%, 85%, 90% or 95% identical to a human serum albumin amino acid sequence (SEQ ID NO: 12). In some embodiments, the half-life modulator comprises the sequence recited in SEQ ID NOs: 10, 12, 24-28, 65, or 67. In some embodiments, the half-life modulator nucleic acid sequence comprises the sequence recited in SEQ ID NOs: 212-215.

In some embodiments, the half-life modulator comprises at least 100 consecutive amino acids that are at least 70%, 80%, 85%, 90% or 95% identical to a human alpha-feto-protein (AFP) amino acid sequence (SEQ ID NOs: 29, 68). In some embodiments, the N-linked glycosylation site of the AFP is removed by the N251Q substitution. In some embodiments, the half-life modulator comprises the sequence recited in SEQ ID NOs: 29, 68, or 69. In some embodiments, the half-life modulator nucleic acid sequence comprises the sequence recited in SEQ ID NO: 216.

In some embodiments, the half-life modulator comprises at least 100 consecutive amino acids that are at least 70%, 80%, 85%, 90% or 95% identical a vitamin D-binding protein (VDBP) amino acid sequence. In some embodiments, the N-linked glycosylation site of the VDBP can be removed by the N288Q or N288T substitution. In some embodiments, the half-life modulator comprises the sequence recited in SEQ ID NO: 66. In some embodiments, the half-life modulator nucleic acid sequence comprises the sequence recited in SEQ ID NO: 219.

In some embodiments, the half-life modulator comprises at least 100 consecutive amino acids that are at least 70%, 80%, 85%, 90% or 95% identical to a human transthyretin (TTR) amino acid sequence. In some embodiments, the transthyretin is modified to remove the N118 N-glycosylation site. In some embodiments, the half-life modulator is a monomeric form of TTR.

In some embodiments, the half-life modulator comprises at least 100 consecutive amino acids that are at least 70%, 80%, 85%, 90% or 95% identical to a human Fc amino acid sequence. The Fc domain of an antibody has a natural capability to bind FcRn, resulting in an extended half-life. In some embodiments, the Fc domain of an antibody is engineered not to bind Fc(gamma)R. In an exemplary embodiment, the Fc domain is engineered to substitute N397 with Q (N297Q variant). In some embodiments, the half-life modulator is a monomeric variant form of Fc, named scFc. For example, the subset of IgG heavy chain which naturally dimerizes to form Fc is hinge-CH2-CH3. In some embodiments, the Fc domain is engineered to form a single chain by linking the hinge-CH2-CH3 with a flexible linker such as GGGGSGGGGSGGGGSGGGGS (SEQ ID NO: 104) to create a hinge-CH2-CH3-linker-hinge-CH2-CH3 chain. In an exemplary embodiment, the single chain Fc (scFc) is engineered to substitute N397 with Q and C220 with S (N297Q, C220S). In some embodiment, the scFc comprises a sequence recited in SEQ ID NO: 71. In some embodiments, the half-life modulator nucleic acid sequence comprises the sequence recited in SEQ ID NO: 218.

In some embodiments, the half-life modulator comprises at least 100 consecutive amino acids that are at least 70%, 80%, 85%, 90% or 95% identical to a PASylation amino acid sequence. PASylation are proline-, alanine-, and/or serine-rich sequences that mimic PEGylation (see WO2008/155134). Polypeptide stretches of proline, alanine, and/or serine form semi-structured three-dimensional domains with large hydrodynamic radius, thereby reducing clearance of fusion proteins. In some embodiments, the PASylation amino acid sequence is about 200, 300, 400, 500 or 600 amino acids long. For example, the PASylation is a 20 times repeat of the amino acid sequence ASPAAPAPASPAAPAP-SAPA (SEQ ID NO: 105).

In some embodiments, the half-life modulator comprises at least 100 consecutive amino acids that are at least 70%, 80%, 85%, 90% or 95% identical to an albumin-binding domain human antibody (albudAb) amino acid sequence (SEQ ID NO: 70). Albumin-binding domain antibodies can increase the fusion protein half-life by binding non-covalently to serum albumin (see WO2008/096158). In some embodiments, the albumin-binding domain human antibody is engineered to remove the C-terminal arginine to remove the Lys-Arg Kex2 protease site. In some embodiments, the half-life modulator nucleic acid sequence comprises the sequence recited in SEQ ID NO: 217.

Representative such half-life modulators include those recited in any one of SEQ ID NOs: 10, 12, 14-29, 45-49, 65-71 or 105.

In some embodiments, the half-life modulators can be modified to substitute the cysteine residues to serine or alanine residues to reduce the ability to form disulfide bonds.

The half-life modulator may be incorporated or conjugated into a bi-specific fusion protein alone or using a short (e.g., from 2 to 20 amino acid residues) connector polypeptide. In some embodiments, the connector polypeptide is present at the N-terminus, at the C-terminus or at both the N-terminus and the C-terminus of the half-life modulator at one or both ends. Suitable short connector polypeptides for use at the N-terminal end of the linker include, for example, dipeptides such as -Gly-Ala- (GA) and -Ala-Ser- (AS). Suitable short connector polypeptides for use at the C-terminal end of the linker include, for example, dipeptides such as -Leu-Gln- (LQ) and -Thr-Gly- (TG). In some embodiments, the connectors are longer than 2 amino acids. For example, the connectors are 5, 10, 5, 20, 30, 40, 50, 60, 70, 80, 90, 100 amino acids long. Preferably, such connectors are flexible (for example glycine-rich) or structured (e.g., alpha-helix rich). In some embodiments, the connectors or polypeptide linkers have a sequence recited in SEQ ID NOs: 41-42, 87-91 or 244. In some embodiments, the connectors are based on human proteins such as transthyretin.

SEQ ID NOs: 46-49 recite the half-life modulator of SEQ ID NO: 45 with representative connector dipeptides at both the N- and C-termini. It will be apparent, however, that such short connector polypeptides and connector recited in SEQ ID NOs: 95-104 or 182-184, if present, may be located at either one or both termini of the half-life modulator.

Certain preferred half-life modulators provide a prolonged half-life of the bi-specific fusion protein, as compared to fusion protein without half-life modulator. The effect of a half-life modulator on half-life can be evaluated using an assay that determines stability under physiological conditions. For example, bi-specific fusion protein can be incubated at 37° C. in serum (e.g., human serum) for 120 hours, with samples removed at the start of incubation and every 24 hours thereafter. Binding assays as described above are then performed to detect the level of functional bi-specific fusion protein at each time point. This level is then compared to the level of bi-specific fusion protein constructed without half-life modulator (or using a different half-life modulator) to provide a half-life comparison.

Optional Elements and Representative Bi-Specific Fusion Proteins

It will be apparent that elements in addition to those described above may optionally be included in the bi-specific fusion proteins provided herein. Such elements may be present for a variety of purposes, including to facilitate expression, preparation or purification of the bi-specific fusion protein, or to perform targeting functions. For example, an N-terminal leader polypeptide may be present. Representative leader polypeptides comprise or have a sequence recited in anyone of SEQ ID NOs: 41-42, 87-91, or 244. A bi-specific fusion protein may also, or alternatively, comprise a polyhistidine (e.g., hexahistidine) tag to facilitate purification. Such a tag comprises at least six histidine consecutive amino acid residues, and may be located at the C- or N-terminus. In certain embodiments, a hexahistidine tag is included at the C-terminus of the bi-specific fusion protein. Additional amino acid residues may also be present at the junction of the polyhistidine to the remainder of the bi-specific fusion protein. Certain bi-specific fusion proteins provided herein comprise a C-terminal polyhistidine-comprising polypeptide as recited in SEQ ID NOs: 43, 44, or 92-94.

Certain bi-specific fusion proteins have a general structure that satisfies one of the following structure (shown from N-terminal to C-terminal, left to right) shown in FIGS. 33A, 33B, 33C, 33D, 33E and 33F.

Representative bi-specific fusion proteins comprise (from N-terminal to C-terminal):

(a) a leader polypeptide (e.g., comprising or having a sequence recited in SEQ ID NOs: 41-42, 87-91 or 244);

(b) a targeting polypeptide domain (e.g., comprising or having a sequence recited in SEQ ID NOs: 1, 2, 30, 31, 72, 73, 76-83 or 85-86);

(c) a optional short connector polypeptide;

(d) a half-life modulator (e.g., comprising or having a sequence recited in any one of SEQ ID NOs:10, 12, 14-29, 45-49, 65-71, or 105;

(e) a optional short connector polypeptide;

(f) an activator domain (e.g., comprising or having a sequence recited in any one of SEQ ID NOs:3-9, 32-40, and 50-64); and (g) a polyhistidine-comprising polypeptide (e.g., a hexa-histidine-comprising polypeptide, such as a polypeptide comprising or having a sequence recited in SEQ ID NO:43-44 or 92-94).

For example, certain such bi-specific fusion proteins comprise (N-terminal to C-terminal):

(a) a leader polypeptide (e.g., comprising or having a sequence recited in SEQ ID NOs: 41-42, 87-91 or 244);

(b) a targeting polypeptide domain (e.g., comprising or having a sequence recited in SEQ ID NOs: 1, 2, 30, 31, 72, 73, 76-83 or 85-86);

(c) a half-life modulator (e.g., comprising or having a sequence recited in any one of SEQ ID NOs:10, 12, 14-29, 45-49, 65-71, or 105;

(d) an optional short connector polypeptide;

(e) an activator domain (e.g., comprising or having a sequence recited in any one of SEQ ID NOs:3-9, 32-40, and 50-64); and (f) a polyhistidine-comprising polypeptide (e.g., a hexa-histidine-comprising polypeptide, such as a polypeptide comprising or having a sequence recited in SEQ ID NO:43-44 or 92-94).

Other bi-specific fusion proteins comprise (from N-terminal to C-terminal):

(a) a leader polypeptide (e.g., comprising or having a sequence recited in SEQ ID NOs: 41-42, 87-91 or 244);

(b) an activator domain (e.g., comprising or having a sequence recited in any one of SEQ ID NOs:3-9, 32-40, and 50-64);

(c) an optional short connector polypeptide;

(d) a half-life modulator (e.g., comprising or having a sequence recited in any one of SEQ ID NOs:10, 12, 14-29, 45-49, 65-71, or 105);

(e) an optional short connector polypeptide;

(f) a targeting polypeptide domain (e.g., comprising or having a sequence recited in SEQ ID NOs: 1, 2, 30, 31, 72, 73, 76-83 or 85-86);

(g) a poly-histidine-comprising polypeptide (e.g., a hexa-histidine-comprising polypeptide, such as a polypeptide comprising or having a sequence recited in SEQ ID NO:43-44 or 92-94).

Still further bi-specific fusion proteins comprise (from N-terminal to C-terminal):

(a) a leader polypeptide (e.g., comprising or having a sequence recited in SEQ ID NOs: 41-42, 87-91 or 244);

(b) a half-life modulator (e.g., comprising or having a sequence recited in any one of SEQ ID NOs:10, 12, 14-29, 45-49, 65-71, or 105;

(c) an optional short connector polypeptide;

(d) an activator domain (e.g., comprising or having a sequence recited in any one of SEQ ID NOs:3-9, 32-40, and 50-64);

(e) an optional short connector polypeptide;

(f) a targeting polypeptide domain (e.g., comprising or having a sequence recited in SEQ ID NOs: 1, 2, 30, 31, 72, 73, 76-83 or 85-86);

(g) a poly-histidine-comprising polypeptide (e.g., a hexa-histidine-comprising polypeptide, such as a polypeptide comprising or having a sequence recited in SEQ ID NO:43-44 or 92-94).

Still further bi-specific fusion proteins comprise (from N-terminal to C-terminal):

(a) a leader polypeptide (e.g., comprising or having a sequence recited in SEQ ID NOs: 41-42, 87-91 or 244);

(b) a half-life modulator (e.g., comprising or having a sequence recited in any one of SEQ ID NOs:10, 12, 14-29, 45-49, 65-71, or 105);

(c) an optional short connector polypeptide;

(d) a targeting polypeptide domain (e.g., comprising or having a sequence recited in SEQ ID NOs: 1, 2, 30, 31, 72, 73, 76-83 or 85-86);

(e) an optional short connector polypeptide;

(f) an activator domain (e.g., comprising or having a sequence recited in any one of SEQ ID NOs:3-9, 32-40, and 50-64);

(g) a poly-histidine-comprising polypeptide (e.g., a hexa-histidine-comprising polypeptide, such as a polypeptide comprising or having a sequence recited in SEQ ID NO:43-44 or 92-94).

Still further bi-specific fusion proteins comprise (from N-terminal to C-terminal):

(a) a leader polypeptide (e.g., comprising or having a sequence recited in SEQ ID NOs: 41-42, 87-91 or 244);

(b) a targeting polypeptide domain (e.g., comprising or having a sequence recited in SEQ ID NOs: 1, 2, 30, 31, 72, 73, 76-83 or 85-86);

(c) an optional short connector polypeptide;

(d) an activator domain (e.g., comprising or having a sequence recited in any one of SEQ ID NOs:3-9, 32-40, and 50-64);

(e) an optional short connector polypeptide;

(f) a half-life modulator (e.g., comprising or having a sequence recited in any one of SEQ ID NOs:10, 12, 14-29, 45-49, 65-71, or 105);

(g) a poly-histidine-comprising polypeptide (e.g., a hexa-histidine-comprising polypeptide, such as a polypeptide comprising or having a sequence recited in SEQ ID NO:43-44 or 92-94).

Still further bi-specific fusion proteins comprise (from N-terminal to C-terminal):

(a) a leader polypeptide (e.g., comprising or having a sequence recited in SEQ ID NOs: 41-42, 87-91 or 244);

(b) an activator domain (e.g., comprising or having a sequence recited in any one of SEQ ID NOs:3-9, 32-40, and 50-64);

© a optional short connector polypeptide;

(d) a targeting polypeptide domain (e.g., comprising or having a sequence recited in SEQ ID NOs: 1, 2, 30, 31, 72, 73, 76-83 or 85-86);

(e) a optional short connector polypeptide;

(f) a half-life modulator (e.g., comprising or having a sequence recited in any one of SEQ ID NOs:10, 12, 14-29, 45-49, 65-71, or 105);

(g) a poly-histidine-comprising polypeptide (e.g., a hexa-histidine-comprising polypeptide, such as a polypeptide comprising or having a sequence recited in SEQ ID NO:43-44 or 92-94).

In some embodiments, the short connector polypeptide comprises a sequence recited in SEQ ID NOs: 95-104 or 182-184.

In some embodiments, the optional short connector polypeptide is a dipeptide (Gly-Ala; Ala-Ser; Leu-Gln; Thr-Gly) or polypeptide having an amino acid sequence listed in SEQ ID NOs: 95-104 and 182-184.

Representative bi-specific fusion protein include, but are not limited to, aDNASI1_mHSA_IGF1, aPS4A7_mHSA_IGF1, aDNASI1_mHSA_HGF(NK1), aPS4A7_mHSA_HGF(NK1), AnxV_mHSA_FGF2, AnxV_mHSA_NRG1b(EGF), aDNASI1_mHSA_FGF2, aDNASI1_mHSA_NRG1b(EGF), AnxV_mHSA_VEGFB (111), AnxV_mHSA_VEGFB(167), AnxV_mHSA_HGF (NK1), AnxV_mHSA_IGF1, IGF1_mHSA_AnxV, HGF (NK1)_mHSA_AnxV, NRG1b(EGF)_mHSA_AnxV, FGF2_mHSA_AnxV, VEGFB(167)_mHSA_AnxV, VEGFB(111)_mHSA_AnxV, IGF1_mHSA_B7scFv, IGF1_mHSA_Syt1, IGF1_mHSA_aDNASI1, NRG1b (EGF)_mHSA_B7scFv, NRG1b(EGF)_mHSA_Syt1, NRG1b(EGF)_mHSA_aDNASI1, FGF2_mHSA_B7scFv, FGF2_mHSA_Syt1, FGF2_mHSA_aDNASI1, B7scFv_mHSA_IGF1, Syt1_mHSA_IGF1, aDNASI1_mHSA_IGF1, B7scFv_mHSA_NRG1b(EGF), Syt1_mHSA_NRG1b(EGF), B7scFv_mHSA_FGF2, Syt1_mHSA_FGF2. Representative bi-specific fusion proteins can have a sequence recited in SEQ ID NOs; 106, 108, 110, 112, 118, 120, 124, 126, 128, 130, 132, 134, 136, 140, 142, 144, 146, 148, 150, 152, 154, 156, 158, 160, 162, 164, 166, 168, 170, 172, 174, 176, 178, 180, or can be encoded by the nucleic acid having a sequence recited in SEQ ID NOs: 107, 109, 111, 113, 119, 121, 125, 127, 129, 131, 133, 135, 137, 141, 143, 145, 147, 149, 151, 153, 155, 157, 159, 161, 163, 165, 167, 169, 171, 173, 175, 179, or 181.

Representative bi-specific fusion protein comprising a non-binding targeting polypeptide include, but are not limited to, DAscFv_mHSA_IGF1, DAscFv_mHSA_HGF (NK1), AnxVm1234_mHSA_VEGFB(111), AnxVm1234_mHSA_VEGFB(167), AnxVm1234_mHSA_HGF(NK1), AnxVm1234_mHSA_IGF1, AnxVm1234_mHSA_NRG1b (EGF), AnxVm1234_mHSA_FGF2, HGF(NK1)_mH-SA_AnxVm1234, NRG1b(EGF)_mHSA_AnxVm1234, FGF2_mHSA_AnxVm1234, VEGFB(167)_mH-SA_AnxVm1234, VEGFB(111)_mHSA_AnxVm1234, IGF1_mHSA_DAscFv, NRG1b(EGF)_mHSA_DAscFv, FGF2_mHSA_DAscFv, DAscFv_mHSA_NRG1b(EGF), and DAscFv_mHSA_FGF2. Representative bi-specific fusion proteins can have a sequence recited in SEQ ID NOs 114, 116, 122, 138, 185, 246, 248, 254, 258, 260, 262, 264, 272, 274, 276 or can be encoded by nucleic acid having a sequence recited in SEQ ID NOs: 115, 116, 123, 139, 186, 247, 249, 255, 259, 261, 263, 265, 273, 275 or 277.

Preparation of Bi-Specific Fusion Proteins

Bi-specific fusion proteins may be synthesized using standard techniques, including liquid- and solid-phase peptide synthesis and recombinant DNA techniques. For solid phase synthesis, the C-terminal amino acid of the sequence is attached to an insoluble support, and the remaining amino acids are added in sequence. For polypeptides longer than about 50 amino acids, shorter regions may be synthesized in this fashion and then condensed to form the longer polypeptide. Methods of forming peptide bonds by activation of a carboxyl terminal end (e.g., by the use of the coupling reagent N, N'-dicyclohexylcarbodiimide) are well known in the art.

For recombinant DNA techniques, DNA encoding the bi-specific fusion protein is prepared chemically or by isolating and ligating DNA encoding each portion of the fusion protein. The DNA coding for each segment of the bi-specific fusion protein may be isolated from known genes or synthesized de novo. Methods for direct chemical synthesis of DNA are well known in the art, and such syntheses are routinely performed using an automated synthesizer. Chemical synthesis produces a single stranded polynucleotide, which is converted into double stranded DNA by hybridization with a complementary sequence or using DNA polymerase. While chemical synthesis of DNA is generally limited to sequences that are shorter than the bi-specific fusion protein, it will be apparent that the full bi-specific fusion protein may be obtained by ligation of shorter sequences in frame. Alternatively, DNA sequences encoding the bi-specific fusion protein are prepared by cloning. Cloning techniques are well known in the art, and are amply described, for example, by standard references such as Sambrook et al., Molecular Cloning: A Laboratory Manual (3$^{rd}$ ed.), Cold Spring Harbor Laboratory Press (2001). Portions of the DNA may be ligated together in frame to generate the full length coding sequence.

Once the DNA encoding the bi-specific fusion protein is obtained, the DNA may be cloned into a vector for expression in a prokaryotic or eukaryotic host cell. Techniques for incorporating DNA into such vectors are well known to those of ordinary skill in the art. Within such an expression vector, the DNA encoding the bi-specific fusion protein is operably linked to the nucleotide sequences necessary for expression (e.g., a suitable promoter and, if necessary, a terminating signal). A promoter is a nucleotide sequence (typically located 5' to the coding sequence) that directs the transcription of adjacently linked coding sequences. A terminating signal may be a stop codon to end translation and/or a transcription termination signal. Additional regulatory element(s) (e.g., enhancer elements) may also be present within an expression vector. Such a vector is preferably a plasmid or viral vector. Preferably, an expression vector further comprises a selectable marker, which confers resistance to a selection. This allows cells to stably integrate the vector into their chromosomes and grow to form foci, which in turn can be cloned and expanded into cell lines. A variety of selectable markers are known in the art, including, for example, genes that provide resistance to ampicillin, methotrexate, mycophenolic acid, the aminoglycoside G-418, hygromycin and puromycin. Those of ordinary skill in the art are knowledgeable in the numerous expression systems available for expression of proteins including E. coli, other bacterial hosts, yeast, and various higher eukaryotic cells such as the COS, CHO, HeLa and myeloma cell lines.

Host cells are transformed or transfected with the vector that comprises the DNA encoding the bi-specific fusion protein using standard methods. Expression in the host cell results in transcription of the DNA into the corresponding mRNA, followed by translation of the mRNA to generate the bi-specific fusion protein.

Once expressed, the bi-specific fusion protein can be purified according to standard procedures, including, for example, ammonium sulfate precipitation or affinity column chromatography. Substantially pure compositions of at least about 90 to 95% homogeneity are preferred, and 98 to 99% or more homogeneity is most preferred for pharmaceutical uses. Once purified, partially or to homogeneity as desired, if to be used therapeutically, the polypeptides should be substantially free of endotoxin.

Pharmaceutical Compositions

The present invention also provides pharmaceutical compositions comprising at least one bi-specific fusion protein as described herein, together with at least one physiologically acceptable carrier. Such compositions may be used for treating patients who are suffering from, or at risk for, tissue damage, in order to prevent tissue damage, or to repair or regenerate damaged tissue. Such patients include, for example, patients who have experienced myocardial infarction, kidney damage, and/or ischemic stroke. If desired, other active ingredients may also be included within the pharmaceutical composition, such as stem cells or other agents that facilitate repair of damaged tissue.

As used herein, the term "physiologically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the bi-specific fusion protein is administered. Physiologically acceptable carriers can be sterile liquids, such as water and oils, including those of petroleum, animal, vegetable or synthetic origin (e.g., peanut oil, soybean oil, mineral oil, or sesame oil). Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water and ethanol. The composition, if desired, can also contain minor amounts of wetting or emulsifying agents, or pH buffering agents.

Pharmaceutical compositions may be formulated for any appropriate manner of administration, including, for example, parenteral, intranasal, topical, oral, or local administration, such as by a transdermal means, for prophylactic and/or therapeutic treatment. These compositions can take any of a variety of well known forms that suit the mode of administration, such as solutions, suspensions, emulsions, tablets, pills, capsules, powders, aerosols and sustained-release formulations. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical modes of administration and carriers are described in "Remington: The Science and Practice of Pharmacy," A. R. Gennaro, ed. Lippincott Williams & Wilkins, Philadelphia, PA (21$^{st}$ ed., 2005).

Commonly, the pharmaceutical compositions provided herein are administered parenterally (e.g., by intravenous, intramuscular, or subcutaneous injection), or by oral ingestion or topical application. For parenteral administration, the bi-specific fusion protein can either be suspended or dissolved in the carrier. A sterile aqueous carrier is generally preferred, such as water, buffered water, saline or phosphate-buffered saline. In addition, sterile, fixed oils may be employed as a solvent or suspending medium. For this purpose any bland fixed oil may be employed, including synthetic mono- or diglycerides. In addition, fatty acids such as oleic acid find use in the preparation of injectible compositions. Pharmaceutically acceptable auxiliary substances may also be included to approximate physiological conditions, such as pH adjusting and buffering agents, tonicity adjusting agents, dispersing agents, suspending agents, wetting agents, detergents, preservatives, local anesthetics and buffering agents.

In one preferred embodiment, the pharmaceutical composition is formulated for intravenous administration to a patient (e.g., a human). Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a sealed (e.g., hermetically sealed) container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Compositions intended for oral use may be presented as, for example, tablets, troches, lozenges, aqueous or oily suspensions, dispersible powders or granules, emulsion, hard or soft capsules, or syrups or elixirs. Such compositions may further comprise one or more components such as sweetening agents flavoring agents, coloring agents and preserving agents. Tablets contain the active ingredient in admixture with physiologically acceptable excipients that are suitable for the manufacture of tablets. Such excipients include, for example, inert diluents, granulating and disintegrating agents, binding agents and lubricating agents. Formulations for oral use may also be presented as hard gelatin capsules wherein the active ingredient is mixed with an inert solid diluent, or as soft gelatin capsules wherein the active ingredient is mixed with water or an oil medium. Aqueous suspensions comprise the active materials in admixture with one or more excipients suitable for the manufacture of aqueous suspensions. Such excipients include suspending agents and dispersing or wetting agents. Dispersible powders and granules suitable for preparation of an aqueous suspension by the addition of water provide the active ingredient in admixture with a dispersing or wetting agent, suspending agent and one or more preservatives.

Oily suspensions may be formulated by suspending the active ingredients in a vegetable oil (e.g., arachis oil, olive oil, sesame oil or coconut oil) or in a mineral oil such as liquid paraffin. Pharmaceutical compositions may also be in the form of oil-in-water emulsions. The oily phase may be a vegetable oil or a mineral oil or mixture thereof. Suitable emulsifying agents include, for example, naturally-occurring gums, naturally-occurring phosphatides and anhydrides.

Pharmaceutical compositions may be sterilized by conventional sterilization techniques, or may be sterile filtered. Sterile aqueous solutions may be packaged for use as is, or lyophilized, the lyophilized preparation being combined with a sterile aqueous carrier prior to administration. The pH of an aqueous pharmaceutical composition typically will be between 3 and 11, more preferably between 5 and 9 or between 6 and 8, and most preferably between 7 and 8, such as 7 to 7.5.

Bi-specific fusion proteins provided herein are generally present within a pharmaceutical composition at a concentration such that administration of a single dose to a patient delivers a therapeutically effective amount. A therapeutically effective amount is an amount that results in a discernible patient benefit, such as detectable repair or regeneration of damaged tissue or diminution of symptoms of tissue damage. Therapeutically effective amounts can be approximated from the amounts sufficient to achieve detectable tissue repair or regeneration in one or more animal models exemplified in Table 3. Nonetheless, it will be apparent that a variety of factors will affect the therapeutically effective amount, including the activity of the bi-specific fusion protein employed; the age, body weight, general health, sex and diet of the patient; the time and route of administration; the rate of excretion; any simultaneous treatment, such as a drug combination; and the type and severity of the tissue damage in the patient undergoing treatment. Optimal dosages may be established using routine testing, and procedures that are well known in the art. Dosages generally range from about 0.5 mg to about 400 mg of bi-specific fusion protein per dose (e.g., 0.5 mg, 1 mg, 2 mg, 5 mg, 10 mg, 50 mg, 100 mg, 200 mg, 300 mg, or 400 mg per dose). In general, compositions providing dosage levels ranging from about 0.1 mg to about 100 mg per kilogram of body weight per day are preferred. In certain embodiments, dosage unit forms contain between from about 10 mg to about 100 mg of bi-specific fusion protein.

Pharmaceutical compositions may be packaged for treating or preventing tissue damage (e.g., for treatment of myocardial infarction or kidney damage). Packaged pharmaceutical preparations include a container holding a therapeutically effective amount of at least one pharmaceutical composition as described herein and instructions (e.g., labeling) indicating that the contained composition is to be used for treating tissue damage (such as myocardial infarction or kidney damage) in a patient. Pharmaceutical compositions may be packaged in multiple single dose units, each containing a fixed amount of bi-specific fusion protein in a sealed package. Alternatively, the container may hold multiple doses of the pharmaceutical composition.

Methods of Treatment

The pharmaceutical compositions can be administered to a patient (preferably a mammal such as a cow, pig, horse, chicken, cat, dog, or more preferably a human) to treat pathological tissue damage in the patient. Within the context of the present invention, the term "treatment" encompasses both prophylactic and therapeutic administration. In prophylactic applications, a pharmaceutical composition as described herein is administered to a patient susceptible to or otherwise at risk for developing pathological tissue damage, in order to prevent, delay or reduce the severity of tissue damage. In therapeutic applications, treatment is performed in order to reduce the severity of the pathological tissue damage or regenerate tissue after damage. In some embodiments, the pharmaceutical composition can be administered in combination with other therapeutic compositions.

Representative pathological tissue damage includes heart tissue damage (e.g., damage associated with myocardial infarction), kidney tissue damage and tissue damage following a ischemic stroke (e.g. cerebral ischemia, also known as brain ischemia, critical limb ischemia or other ischemia). In some embodiments, the pharmaceutical composition can be used to protect tissue from damage and/or to regenerate tissue and/or blood supply after tissue or organ damage.

In some embodiments, the pharmaceutical composition can be administered to prevent, delay, reduce or treat autoimmune diseases, for example, Systemic Lupus Erythematosus (SLE), also known as Lupus. SLE is an autoimmune disease where many tissues or systems are attacked and become inflamed, for example, joints, skin, liver, kidneys, blood cells, heart, lungs, nervous system, blood vessels. The immune system produces antibodies against self, particular against nuclear proteins and DNA. In some embodiments, the pharmaceutical compositions can be administered to a subject in need thereof to protect tissue from damage and regenerating tissue after damage. In some embodiments, the pharmaceutical composition can be administered in combination with existing immune-suppression or other treatments.

In some embodiments, the pharmaceutical compositions can be administered to a subject in need thereof to prevent, delay, reduce or treat Type I diabetes. In type I diabetes, the body's own immune system destroys the insulin-producing beta cells in the pancreas. In some embodiments, the pharmaceutical compositions can be administered to a subject in need thereof to regenerate beta cells. In some embodiments, the pharmaceutical compositions can be administered in combination with Type I diabetes treatments known in the art.

In some embodiments, the pharmaceutical compositions can be administered to a subject in need thereof to prevent, delay, reduce or treat tissue or organ degeneration. For example, the pharmaceutical compositions can be used to treat brain, spinal cord or nerve degeneration such as Alzheimer's disease, Parkinson's disease, Multiple sclerosis, or Amyotrophic lateral sclerosis (ALS), also known as Lou Gehrig's disease. In some embodiments, the pharmaceutical compositions can be administered in combination with existing treatments known in the art.

In some embodiments, the pharmaceutical compositions can be administered to a subject in need thereof to prevent, delay, reduce or treat bone and/or cartilage associated disease. In some embodiments, the pharmaceutical compositions can be used to regenerate bone and/or cartilage tissues. The pharmaceutical compositions can be administered in combination with existing treatments known in the art.

Any of a variety of known delivery systems can be used to administer a bi-specific fusion protein including, for example, encapsulation in liposomes, microparticles, microcapsules, recombinant cells capable of expressing the bi-specific fusion protein, receptor-mediated, or a retroviral or other nucleic acid vector. The bi-specific fusion protein may be administered by any convenient route, for example by infusion or bolus injection, by absorption through epithelial or mucocutaneous linings (e.g., oral mucosa, rectal and intestinal mucosa, etc.), and may be administered together with other biologically active agents. Administration can be systemic or local. In addition, it may be desirable to introduce the bi-specific fusion protein into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the bi-specific fusion protein of the invention locally to the area in need of treatment; this may be achieved by, for example, local infusion during surgery, topical application (e.g., in conjunction with a wound dressing after surgery), by injection, by means of a catheter, by means of a suppository, or by means of an implant, said implant being of a porous, non-porous, or gelatinous material, including membranes, such as sialastic membranes, or fibers. In another embodiment, a vesicle, such as a liposome, can be used to deliver the bi-specific fusion protein. In yet another embodiment, the bi-specific fusion protein is delivered in a controlled release system; for example, such a controlled release system may be placed at or near the therapeutic target (e.g., an organ of the body that has experienced or is at risk for tissue damage). The use of such delivery systems is well known to those of ordinary skill in the art.

In some embodiments, the bi-specific fusion proteins provided herein are effective for treating pathological tissue damage at least in part due to their ability to recruit stem cells to the damaged tissue. In certain cases, sufficient stem cells may reside within the patient (e.g., resident cardiac stem cells). In certain embodiments, however, it may be beneficial to co-administer stem cells (e.g., bone marrow-derived autologous stem cells). Such stem cells may be administered before or after the bi-specific fusion protein, or may be administered simultaneously (either in the same pharmaceutical composition or in separate compositions).

In some embodiments, the bi-specific proteins provided herein are effective in enhancing tissue survival. In some embodiments, the bi-specific proteins can be administered and target a specific tissue or organ (e.g heart). The bi-specific proteins can then accumulate in the specific tissue or organ (e.g. heart as opposed to another organ) through binding of the targeting domain to the tissue associated target molecule. Once bound to the target molecule, the bi-specific fusion protein can dissociate from the target molecule, move away and re-associate to a target molecule, a growth factor receptor, or cytokine receptor of a different cell of the tissue in a paracrine-like manner (e.g. a damaged cell or an "at risk" cell).

As noted above, the optimal dose depends on certain factors known in the art, but generally ranges from about 0.5 mg to about 400 mg of bi-specific fusion protein per dose (e.g., 10 mg, 50 mg, 100 mg, 200 mg, 300 mg, or 400 mg per dose). A dose of bi-specific fusion protein (within a pharmaceutical composition as described above) can be administered therapeutically to a patient one or more times per hour, day, week, month, or year (e.g., 2, 4, 5, 6, 7, 8, 9, 10, 11, or 12 times per hour, day, week, month, or year). More commonly, a single dose per day or per week comprising an amount of bi-specific fusion protein ranging from about 0.1 mg to about 100 mg per kilogram of body weight is administered.

In other embodiments, a pharmaceutical composition comprising a bi-specific fusion protein may be administered to a patient in a dosage that ranges from about 0.1 mg per week to about 2500 mg per week, about 0.1 mg per week to about 10 mg per week, about 1 mg per week to about 100 mg per week, about 10 mg per week to about 500 mg per week, about 100 mg per week to about 2500 mg per week, about 10 mg per week to about 100 mg per week, or about 100 mg per week to about 1000 mg per week. Alternatively, a pharmaceutical composition comprising a bi-specific fusion protein may be administered at a dose that ranges from about 0.1 mg every other day to about 500 mg every other day, about 1 mg every other day to about 75 mg every other day, about 10 mg every other day to about 50 mg every other day, or about 20 mg every other day to about 40 mg every other day. A pharmaceutical composition comprising a bi-specific fusion protein may alternatively be administered at a dose that ranges from about 0.1 mg three times per week to about 100 mg three times per week, about 1 mg three times per week to about 75 mg three times per week, about 10 mg three times per week to about 50 mg three times per week, or about 20 mg three times per week to about 40 mg three times per week.

In further embodiments of, a pharmaceutical composition comprising a bi-specific fusion protein is administered to a mammal (e.g., a human) continuously for 1, 2, 3, or 4 hours; 1, 2, 3, or 4 times a day; every other day or every third, fourth, fifth, or sixth day; 1, 2, 3, 4, 5, 6, 7, 8, 9, or 10 times a week; biweekly; 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 times a month; bimonthly; 1, 2, 3, 4, 5, 6, 7, 8, 9, or 10 times every six months; 1, 2, 3, 4, 5, 6, 7, 8, 9, 10, 11, 12, 13, 14, 15, 16, 17, 18, 19, or 20 times a year; or biannually. It will be apparent that a pharmaceutical composition comprising a bi-specific fusion protein may, but need not, be administered at different frequencies during a therapeutic regime.

The following Examples are offered by way of illustration and not by way of limitation. Unless otherwise specified, all reagents and solvents are of standard commercial grade and are used without further purification. Using routine modifications, the procedures provided in the following Examples may be varied by those of ordinary skill in the art to make and use other bi-specific fusion proteins and pharmaceutical compositions within the scope of the present invention.

EXAMPLES

Example 1. Preparation of a Representative Bi-Specific Fusion Protein

A bi-specific fusion protein in which targeting polypeptide domain binds to DNA and the activator domain is NRG1 is prepared. The two domains are joined by a modified human serum albumin (HSA) linker. The NRG1 is recombinantly fused to the amino terminus of the HSA linker incorporating a short connector polypeptide and the anti-DNA scFv is recombinantly fused to the carboxy terminus of the modified HSA linker incorporating an additional short connector polypeptide. The modified HSA linker contains two amino acid substitutions. A cysteine residue at position 34 of native HSA is mutated to serine in order to reduce potential protein heterogeneity due to oxidation at this site. An asparagine residue at amino acid 503 of native HSA, which may be sensitive to deamidation, resulting in decreased pharmacologic half-life, is mutated to glutamine. The modified HSA linker confers an extended circulating half-life on the bi-specific fusion protein.

Example 2. In Vitro Activity of a Bi-Specific Fusion Protein

The activity of both components of the representative bi-specific fusion protein prepared in Example 1 (in which the targeting polypeptide domain binds to DNA and the activator domain is NRG1) are tested using an ELISA designed to give activity only when both arms of the bi-specific fusion protein are bound to their substrates simultaneously. The ELISA is performed essentially as described in Stokes et al., J. Clin. Pathol. 35(5): 566-573 (1982) and Gripenberg et al., Scand. J. Immunol. 1:151-157 (1978). More specifically, 1 to 50 ng/ml solution of the bi-specific fusion protein in PBS is added to the wells of a plate pre-adsorbed with DNA (Anti-DS-DNA antibody ELISA kit (Alpha Diagnostic International, Dist by AutogenBioclear, UK) and incubated and washed according to manufacturer's directions until the step in which the detection antibody is added. At this stage, 100 µl of 1-50 ng/ml solution of Biotinylated goat anti-human NRG1-β1 (R&D Systems BAF377) (antibody to the 'activator arm') in PBS/1% BSA/0.05% Tween is added to all wells and incubated for 1 hr at room temperature, washed in PBS with 0.05% Tween-20. 100 µl of Streptavidin-HRP (1:200 dilutions of stock 2 ug/ml, (R&D Systems 890803)) diluted in PBS is added to each well and incubated 30 min at room temperature. After a final wash in PBS with 0.05% Tween-20, 100 µl of SuperSignal ELISA Pico Chemiluminescent Substrate (as per manufacturer's instructions, Pierce, cat #34077) is added and luminescence (representative of positive signal) is measured on Fusion Microplate reader (Packard) or similar instrument.

The amount of signal detected is significantly higher (at least 100-fold higher) in the wells with bi-specific fusion protein than in wells without DNA or negative controls that contain a dead arm (i.e., does not contain an activator domain or targeting polypeptide domain). In addition, the signal is seen to vary with the amount of bi-specific fusion protein added to the wells.

Example 3. In Vivo Activity of a Bi-Specific Fusion Protein

The in vivo activity of the representative bi-specific fusion protein prepared in Example 1 is determined by detecting signaling changes in a molecule that is regulated by the activator domain of the fusion protein. For the activator domain in this fusion protein NRG1, activity is assessed by detection of increased phosphorylated ErbB-3 in cells of hearts treated with the bi-specific fusion compared to untreated or mock treated hearts. Myocardial infarction is generated in C57BL/6 mice by ligation of the left coronary artery (LCA) following endotracheal intubation, ventilation and thoracotomy. Coronary occlusion is confirmed by acute inspection of color change of the left ventricle wall, and ST elevation on the electrocardiogram before chest closure. Sham-operated mice undergo the same surgical procedure without LCA ligation.

Hearts from normal mice or those following induction of myocardial infarction, from both control and bi-specific fusion protein treated mice, are removed, fixed in 4% paraformaldehyde, embedded, sectioned and mounted as described in Dhein, Mohr and Delmar, Practical Methods in Cardiovascular Research, 2005, p. 473 (Springer, New York). Phospho-ErbB3 antibody (Cell Signaling Technology; Beverly, MA) is used for detection of Phospho-ErbB3 by immunofluorescence. A 2-fold increase or more in phospho-ErbB3 levels in treated versus untreated hearts is observed and is indicative of functional activator. The increase is in either the number (number per field, or percentage of total) of cells exhibiting signal, the intensity of signal per cell, or both.

Example 4. Tissue Damage Repair in Mice Using a Bi-Specific Fusion Protein

A composition comprising the representative bi-specific fusion protein of Example 1 is administered to a mouse following myocardial infarction, induced as described above. Administration is via intravenous injection (e.g., tail vein). Following administration, heart function is assessed as follows. Mice are anesthetized with chloral hydrate (400 mg/kg body weight, i.p.), and the right carotid artery is cannulated with a microtip pressure transducer (model SPR-671, Millar) for the measurements of left ventricular (LV) pressures and LV+ and –dP/dt in the closed-chest preparation. Measurements are compared to those obtained from untreated control mice to confirm that treatment with the bi-specific fusion protein affects heart function. A significant improvement is observed in heart function as assessed using at least one of these measurements.

Example 5. Expression and Purification of Fusion Proteins

Fusion proteins that comprise a targeting domain, a half-life modulator, and an activator domain were designed, expressed, and purified. Various combinations of targeting domains and activator domains were assembled with the mHSA (SEQ ID 10) half-life modulator in different orientations, with different short connecting polypeptide sequences, and with different polypeptide leader sequences. Synthetic DNA sequences were designed for each amino-acid sequence, taking into account the codon usage of the intended expression organism (e.g., CHO or *Pichia pastoris*), the desire to include or avoid particular restriction enzyme recognition sites, and other factors for codon optimization known in the art. DNA sequences were constructed and/or assembled into expression plasmids, the plasmids were transformed into an expression organism, and fusion proteins were overexpressed. Each fusion protein was then purified using a combination of different methods, including Cibacron Blue Sepharose chromatography, Ni affinity chromatography, anion exchange chromatography, and size exclusion chromatography.

DNA encoding complete fusion proteins or parts to be incorporated into fusion proteins (e.g. individual targeting domains, half-life modulation domains, or activator domains) was purchased from commercial sources (BioBasic, DNA 2.0). Amino acid sequences were explicitly defined. Constraints such as codon usage and restriction sites (demanded or prohibited) were conveyed to the vendor. The final DNA sequence encoding the protein of interest was selected from the theoretical pool of iso-coding sequences by the vendor in accordance with those constraints, general strategies to avoid low expression (such as avoidance of high secondary structure at the mRNA level), and vendor preferences. In some cases codon usage was tailored to CHO or *Pichia* alone. In other cases a combined codon usage table that avoids rare codons in distribution of either organism was applied. In some cases full-length fusion proteins were supplied by the vendor in an expression vector. In other cases, subcloning to an expression vector of interest was required. Subcloning manipulations were accomplished using traditional methods employing type II restriction enzymes and DNA ligase (New England Biolabs). Additional molecular cloning to produce fusions proteins with alternative combinations and orientations of targeting, activator, and half-life modulation domains was performed using these techniques as well as polymerase chain reaction (PCR). Fusion proteins were designed with one or more type-II restriction sites located at the junctions between functional domains at the DNA level for the facile replacement or rearrangement of any of the functional domains. When needed, restriction sites or linker regions were added to sequences by incorporating them in the primers used for PCR.

In some cases, proteins were expressed in *Pichia pastoris* using the PichiaPink Expression System (Invitrogen A11151 kit). Genes encoding the protein of interest were cloned in frame with the *Saccharomyces cerevisiae* α-mating factor secretion signal using the pPinkα-HC plasmid to allow for secreted expression of recombinant protein. In other cases, proteins were purified using the Selexis/CHO clonal system. Genes encoding the protein of interest were cloned into Selexis vectors and transfected into polyclonal CHO-K1 cells to allow for expression of recombinant protein. The pPinkα-HC plasmid contains a bacterial origin of replication (pUC) and resistance maker (Ampicillin) for propagation and selection of the circular plasmid in *E. coli*. It also contains the TRP2 gene, used for targeting the integration of the linearized vector during transformation into *Pichia*, and the ADE2 gene, included for complementation of adenine auxotrophy in *Pichia*. The AOX1 promoter ensures high levels of transcription upon methanol induction and the CYC1 sequence ensured efficient transcriptional termination. Integration of the plasmid into ADE2-deficient *Pichia* enabled both viability-driven selection on adenine deficient media as well as screening based on colony color. High copy integrants appeared white, whereas low copy integrants appeared pink or red due to the accumulation of purine precursors in the *Pichia* vacuole. White colonies were selected for protein production and in some cases several colonies were screened for efficiency of protein production on a small scale (milliliters) before production on a large scale (liters). pPinkα-HC plasmid map and details are available from Invitrogen.

In other cases, proteins were purified using the Selexis/CHO clonal system. An exemplary expression vector is pMP 20K (SELEXIS) and an exemplary cell line is CHO-kl-S (SELEXIS). pMP20K employs commonly used genetic elements. Expression is driven by the human GAPD promoter. Genetic elements referred to as Matrix Attachment Regions or MAR elements control the dynamic organization of chromatin, and insulate nearby genes from the effect of surrounding chromatin thereby increasing copy number dependent, position-independent, expression of genes. MAR elements have been shown to improve the probability of isolating a clone exhibiting the desired level of expression for the production of a recombinant protein and to increase the stability of production. In addition to the expression plasmid, antibiotic resistance plasmids (such as pSV2-neo, SELEXIS) were also used to select for stable transformants. Expression plasmids were linearized (e.g., with PvuI) followed by QIAQUICK purification (QIAGEN). Lipofectamine LTX (Invitrogen) was used for transfection into CHO cells in OptiMemI (Gibco). Transfected cells were recovered with F12Hams medium containing 10% FBS for 2 days without selection pressure, then with selection pressure for 4 days, then change to serum-free medium with selection pressure. HyClone® (Thermo Scientific) is used for the HSA-fused BBAs, with HT supplements (GIBCO).

Following expression, proteins were purified by a combination of Cibacron Blue Sepharose chromatography, Ni affinity chromatography, anion exchange chromatography, and size exclusion chromatography in accordance with manufacturer instructions (GE Healthcare). Protein production was monitored by sodium dodecyl sulfate polyacrylamide gel electrophoresis (SDS-PAGE).

Protein Expression in *Pichia pastoris* and Subsequent Purification by Chromatography.

Genes encoding the protein of interest were cloned in frame with the *Saccharomyces cerevisiae* α-mating factor secretion signal (SEQ ID 244, 245) using the pPinkα-HC plasmid (included in Invitrogen A11151 kit) to allow for secreted expression of recombinant protein. In addition, DNA encoding for a His6-tag was added to the 3' end of the gene to allow for the option of purification of the recombinant protein by Ni affinity chromatography. Briefly, plasmids were transformed into chemically competent PichiaPink Strain 2 (Invitrogen, catalog #A11154), and cultures were grown at 30° C. in a shaking incubator in BMGY (buffer complexed glycerol medium=1% yeast extract, 2% peptone, 100 mM potassium phosphate, pH 6.0, 1.34% Yeast Nitrogen Base with Ammonium Sulfate, without amino acids, 0.0004% biotin, 1% glycerol) to an OD600=2-6. At this time, the cells were pelleted, protein expression was induced by replacement of the media with BMMY (buffer complexed methanol medium=1% yeast extract, 2% peptone, 100 mM potassium phosphate, pH 6.0, 1.34% Yeast Nitrogen Base with Ammonium Sulfate, without amino acids, 0.0004% biotin, 0.5-1% methanol) at ⅕ the volume of the original cultures. Cultures were then grown at 20-30° C. in a shaking incubator for an additional 24-48 hours. Every 12-24 hours, additional methanol (to a final concentration of 0.5-1% (v/v)) was added to the cultures. At the time of harvest, cells were pelleted by centrifugation, the supernatant was collected, sterile filtered and stored at 4° C. until purification (typically within 3 days of harvest).

The following fusion proteins were purified according the methods described below IGF1_mHSA_AnxV (SEQ ID 136, 137); IGF1_mHSA_AnxVm1234 (SEQ ID 138, 139); NRG1b(EGF)_mHSA_AnxV (SEQ ID 142, 143); NRG1b (EGF)_mHSA_AnxVm1234 (SEQ ID 254, 255); FGF2 mHSA_AnxV (SEQ ID 144, 145). Recombinant proteins were purified by Ni affinity chromatography using Ni Sepharose 6 Fast Flow resin (GE Healthcare 17-5318-04; 1 mL of resin/50 mL of supernatant) by gravity flow according to the manufacturer's instructions. The flow-throughs from these purifications were then buffer-exchanged into 50 mM NaCl, 20 mM Tris, pH 7.0, using centrifugal concentrators, and loaded onto HiTrap Blue HP 1 mL cartridges (GE Healthcare, 17-0412-01) equilibrated in the same buffer. The proteins were purified according to the manufacturer's instructions using 20 mM Tris, pH 7.0, 50 mM NaCl, 30 mM sodium octanoate as the elution buffer. The eluates from Ni affinity chromatography and Blue Sepharose chromatography were combined and concentrated/buffer-exchanged into PBS (100 mM sodium phosphate, 150 mM NaCl), pH 7.2, using centrifugal concentrators. The samples were then loaded onto a HiPrep 26/60 Sephacryl S-200 High resolution column (GE Healthcare 17-1195-01), and the proteins were eluted in PBS (100 mM sodium phosphate, 150 mM NaCl), pH 7.2, at a flow rate of 1.3 mL/min. Fractions containing the protein of interested, as identified by (SDS-PAGE), were pooled and concentrated using centrifugal concentrators.

Final purity was assessed by SDS-PAGE. FIG. 1 shows a SDS-PAGE of IGF1_mHSA_AnxV (136), IGF1_mHSA_AnxVm1234 (138), NRG1b(EGF)_mHSA_AnxV (142), and NRG1b(EGF)_mHSA_AnxVm1234. Lane 1 corresponds to the protein molecular weight standards. Lanes 2, 4, 6, correspond to the protein samples under non-reducing conditions. Lanes 3, 5, 7, 9 correspond to protein samples under reducing conditions (50 mM dithiothreitol (DTT)). As shown in FIG. 1 showed, the fusion protein (SEQ ID NO 136) run at the correct molecular weight (MW) on SDS-PAGE gel (expected MW=111 kDa). The purity is >80%. In the absence of DTT, some dimer (<10% of total protein) were present, and the protein ran as a double band. Truncation could be the cause of the double band pattern observed. As shown in FIG. 1, the following proteins IGF1_mHSA_AnxVm1234 (SEQ ID NO 138), NRG1b(EGF)_mHSA_AnxV (SEQ ID NO 142), NRG1b (EGF)_mHSA_AnxVm1234 (SEQ ID NO 254) ran at the correct molecular weight (MW) on SDS-PAGE gel (expected MW=111 kDa). The purity of these fusion proteins was superior to 80%. In the absence of DTT, some dimer form of the proteins were present (<10% of total protein) and the dimers were eliminated with the addition of DTT.

After purification, the purity of FGF2_mHSA_AnxV fusion protein (SEQ ID NO 144) was about 50%. The fusion protein ran as a double band, one of which is at the correct MW (120 kDa), and one of which is at a lower MW. This result may suggest that the lower molecular weight band is a truncation product.

The recombinant fusion protein AnxV_mHSA_FGF2 (SEQ ID NO 118) was purified by Ni affinity chromatography using Ni Sepharose 6 Fast Flow resin (GE Healthcare 17-5318-04; 1 mL of resin/50 mL of supernatant) by gravity flow according to the manufacturer's instructions. The Binding/Wash Buffer consisted of 20 mM potassium phosphate, pH 7.4, 500 mM NaCl, 25 mM imidazole, and the Elution Buffer consisted of 20 mM potassium phosphate, pH 7.4, 500 mM NaCl, 450 mM imidazole. Following purification, purity was assessed by SDS-PAGE. The fusion protein ran at the correct MW on the gel (120 kDa) and showed a purity superior to 80%.

AnxV_mHSA_NRG1b(EGF) (SEQ ID 120, 121), AnxVm1234_mHSA_NRG1b(EGF) (SEQ ID 116, 117), AnxV_mHSA_IGF1 (SEQ ID 134, 135), AnxVm1234_mHSA_IGF1 (SEQ ID 114, 115), AnxVm1234_mHSA_FGF2 (SEQ ID 264, 265), IGF1_mHSA_B7scFv (SEQ ID 150, 151), aDNASI1_mHSA_FGF2 (SEQ ID 124, 125), aDNASI1_mHSA_NRG1b(EGF) (SEQ ID 126, 127), IGF1_mHSA_Syt1 (SEQ ID 152, 153), Syt1_mHSA_IGF1 (SEQ ID 170, 171), IGF1_mHSA_aDNASI1 (SEQ ID 154, 155), NRG1b(EGF)_mHSA_B7scFv (SEQ ID 156, 157) were purified according the methods described below. Blue Sepharose 6 Fast Flow resin (GE Healthcare 17-0948-03) was packed into Econo-pac (Bio-Rad 732-1010) columns (1.5 cm inner diameter; 4 mL resin/column) using standard procedures. Chromatography was performed using an 8-channel peristaltic pump. The columns were equilibrated with buffer containing 50 mM NaCl, 20 mM Tris, pH 7.0 (Blue Sepharose Wash Buffer). The conductivity of the protein expression supernatants was adjusted with deionized water to match that of the Blue Sepharose Wash Buffer (as determined using a conductivity meter). The supernatants from each protein expression culture were loaded onto the columns at 4-5 mL/min. Columns were washed with 5-10 column volumes of Blue Sepharose Wash Buffer. Protein was then eluted with 5-10 column volumes of Low Salt (LS) Elution Buffer (20 mM Tris, pH 7.1, 50 mM NaCl, 45 mM Na-Octanoate). In some cases (proteins having SEQ IN Nos 120, 116, 134, 114, 264), this elution step was divided into 5×1.5 mL fractions (A1-5) followed by 7×4 mL fractions (B1-7). Following elution with Low Salt Elution Buffer additional protein was eluted with 5 column volumes of High Salt (HS) Elution Buffer (20 mM Tris, pH 7.1, 1 M NaCl, 45 mM Na-Octanoate). Fractions were analyzed for protein content by SDS-PAGE concentrated by centrifugal ultrafiltration (Sartorius-Stedim, VS2022), and desalted into 0.1M sodium phosphate, 0.15M NaCl, pH 7.2 using PD-10 columns (GE 17-0851-01). Fractions containing the protein of interest were pooled. Fractions of the AnxV_mHSA_NRG1b(EGF) (SEQ ID 120) fusion protein was analyzed by SDS-PAGE. The purified fusion protein was about 50% pure. Analysis of the SDS-PAGE showed a double band on the gel. One of the band was at the expected MW (112 kDa) of the full length fusion protein, and one of the band was characterized by a lower MW which may suggest it was a truncation product. Fractions of the AnxVm1234_mHSA_NRG1b(EGF) (SEQ ID 116) fusion protein was analyzed by SDS-PAGE. SDS-PAGE analysis showed a purity of about 50% and a double band on the gel. One of the band was at the correct MW (112 kDa) of the full length fusion protein, and one of the band was characterized by a lower MW which may suggest it was a truncation product. Fractions of the AnxV_mHSA_IGF1 (SEQ ID 134) fusion protein was analyzed by SDS-PAGE. SDS-PAGE analysis showed a purity of about 50% and a double band on the gel. One of the band was at the correct MW (111 kDa) of the full length fusion protein, and one of the band was characterized by a lower MW which may suggest it was a truncation product. Fractions of the AnxVm1234_mHSA_IGF1 (SEQ ID 114) fusion protein was analyzed by SDS-PAGE. SDS-PAGE analysis showed a purity of about 50% and a double band on the gel. One of the band was at the correct MW (111 kDa) of the full length fusion protein, and one of the band was characterized by a lower MW which may suggest it was a truncation product. Fractions of the AnxVm1234_mHSA_FGF2 (SEQ ID 264) fusion protein was analyzed by SDS-PAGE. SDS-PAGE analysis showed a purity of about 50% and a double band on the gel. One of the band was at the correct MW (120 kDa) of the full length fusion protein, and one of the band was characterized by a lower MW which may suggest it was a truncation product. Fractions of the IGF1_mHSA_B7scFv (SEQ ID 150) fusion protein was analyzed by SDS-PAGE. SDS-PAGE analysis showed a purity of more than 50% and a double band on the gel. One of the band was at the correct MW (102 kDa) of the full length fusion protein, and one of the band was characterized by a lower MW which may suggest it was a truncation product. Fusion protein aDNASI1_mHSA_FGF2 (SEQ ID NO 124) was analyzed on SDS-PAGE and showed a purity of less than 20% with a band corresponding to the correct MW (110 kDa) of the full-length protein. The presence of lower MW bands suggested that the protein may be cleaved or truncated. Fusion protein aDNASI1_mHSA_NRG1b(EGF) (SEQ ID NO 126) was analyzed on SDS-PAGE and showed a purity of less than 50% with a band corresponding to the correct MW (110 kDa) of the full length protein. The presence of lower MW bands suggested that the protein may be cleaved or truncated. Fusion protein IGF1_mHSA_Syt1 (SEQ ID NO 152) was analyzed on SDS-PAGE and showed a purity of about 50% with a band corresponding to the correct MW (91 kDa) of the full-length protein. The presence of lower MW bands suggested that the protein may be cleaved or truncated. Fusion protein Syt1_mHSA_IGF1 (SEQ ID NO 170) was analyzed on SDS-PAGE and showed a purity of less than 50% with a band corresponding to the correct MW (91 kDa) of the full-length protein. The presence of higher and lower MW bands suggested the presence of dimeric products and truncation products. Fusion protein IGF1_mHSA_aDNASI1 (SEQ ID NO 154) was analyzed on SDS-PAGE and showed a purity of about 50% with a band corresponding to the correct MW (102 kDa) of the full-length protein. Fusion protein NRG1b(EGF)_mHSA_B7scFv (SEQ ID NO 156) was analyzed on SDS-PAGE and showed a purity of less than 50% with a band corresponding to the correct MW (102 kDa) of the full length protein and a lower MW band which may correspond to a truncation product.

AnxV_mHSA (SEQ ID 252, 253) and AnxVm1234_mHSA (SEQ ID 250, 251) fusion proteins were purified according to the methods described below. Proteins were precipitated from *Pichia* expression supernatant by Ammonium Sulfate (added to a final concentration of 82%). Precipitate was resuspended in PBS buffer and dialyzed against PBS overnight. Following dialysis, protein was loaded onto a HiPrep 26/60 Sephacryl S-200 High resolution column (GE Healthcare 17-1195-01) equilibrated in 50 mM NaCl, 20 mM potassium phosphate, pH 7.0. Protein was eluted in the same buffer, fractions from the elution were analyzed by SDS-PAGE, and fractions containing the protein of interest were pooled. This pooled eluate was then loaded (at a flow rate of 1 mL/min) onto a 1 mL HiTrap Q Sepharose Fast Flow column (GE Healthcare 17-5053-01) equilibrated in 20 mM potassium phosphate, 50 mM NaCl, pH 7.0. Protein was eluted with Elution Buffer (20 mM potassium phosphate, 500 mM NaCl, pH 7.0) over a gradient of 20 column volumes at 1 mL/min. Fractions were collected and analyzed by SDS-PAGE. Fractions containing protein of interest were pooled. Final purity was assessed by SDS-PAGE in the presence and absence of reductant. Fusion protein AnxV_mHSA (SEQ ID NO 252) was analyzed on SDS-PAGE and showed a purity of more than 90% with a band corresponding to the expected MW (104 kDa) of the full-length protein. Some dimers (<10% of the total protein) were present but were eliminated in the presence of DTT. Fusion protein AnxVm1234_mHSA (SEQ ID NO 252) was analyzed on SDS-PAGE and showed a purity of more than 90% with a band corresponding to the expected MW (104 kDa) of the full-length protein. Some dimers (<10% of the total protein) were present but were eliminated in the presence of DTT.

Protein Expression in Selexis/CHO Expression System and Subsequent Purification by Chromatography.

A stable Selexis CHO cell line expressing the protein of interest was cultured in serum-free media at 37° C., 5-8% CO2 in a shaking incubator. Media used for growth was: 1 L Ex-Cell™ CD CHO Fusion media (Sigma, 14365C-1000ML), 40 mL of 200 mM L-glutamine (Invitrogen, 25030-081), 10 mL 100× HT supplement (Invitrogen, 11067-030). The seeding density for the cells was 0.3-0.5× 106 cells/mL. The culture was diluted once it reached 2-4×106 cells/mL, until the desired culture volume (6 L) was achieved. Cell Boost solution (1 L ddH2O, 35 g Cell Boost 5 (HyClone, 30865.01), 20 g D-glucose, adjust pH to 7.0 with NaOH) was added 3-5 days after seeding the final large culture (amount of Cell Boost=7-12% of the culture). Cell supernatant containing secreted protein of interest was harvested as soon as the culture viability dropped below 90% (~1 week after diluting the culture to its final volume). The cell supernatant was harvested by centrifugation and was sterile filtered. Supernatant was stored at 4° C. if purification was to be performed within a week, otherwise the supernatant was stored at −80° C.

Fusion proteins aDNASI1(L23)_mHSA_HGF(NK1) (SEQ ID 110, 111), DAscFv_mHSA_IGF1 (SEQ ID 246, 247), DAscFv_mHSA_HGF(NK1) (SEQ ID 248, 249) were purified according to the methods described below. Supernatant from Selexis/CHO expression was diluted 1:0.5 with ddH2O and passed over a 5 mL Blue Sepharose column twice. Protein was eluted in buffer containing 45 mM Na Octanoate then dialyzed against PBS. Protein was then diluted 1:1 with ddH2O and loaded onto a 1 mL Q anion exchange column and eluted with shallow gradient (gradient=10% B, where A=1:1 PBS:water, B=1 M NaCl in PBS, PBS=standard Dulbecco's PBS, Mg/Ca free). Fractions containing protein of interest were pooled and frozen in aliquots. Final purity was assessed by SDS-PAGE. All purified proteins showed a purity superior to 90% and ran as a single band on SDS-PAGE. A SDS_PAGE of the aDNASI1(L23)_mHSA_HGF(NK1) (SEQ ID 110) fusion protein showed a single band at the expected MW of 114 kDa. A SDS_PAGE of the DAscFv_mHSA_IGF1 (SEQ ID 246) fusion protein showed a single band at the expected MW of 102 kDa. A SDS_PAGE of the DAscFv_mH-SA_HGF(NK1) (SEQ ID 248) fusion protein showed a single band at the expected MW of 115 kDa.

Example 6. Specific Binding of Bi-Specific Fusion Protein to Damaged Cells

Fusion proteins that comprise a targeting domain, a half-life modulator, and an activator domain were produced, and their ability to specifically bind via their targeting domain to damaged cells in vitro was validated. The targeting domain used was human annexin V (AnxV, SEQ ID 31), which binds to phosphatidylserine which becomes exposed on the outer cell surface during apoptosis. Specific binding was demonstrated for a variety of fusion proteins, including fusion proteins with different activator domains, and fusion proteins in different fusion orientations (e.g., N-terminal activator domain with C-terminal targeting domain, and N-terminal targeting domain with C-terminal activator domain). Specific binding was also demonstrated for binding to damaged cells of different cell types, including cardiac muscle cells and embryonic stem cell-derived (ESC-derived) cardiac cells. In some cases, cells were injured with hydrogen peroxide (H2O2) to induce oxidative stress to mimic the damaged state of cells in vivo after myocardial infarction. Fusion proteins comprising a non-binding variant of annexin V (AnxVm1234, SEQ ID 84), did not bind to damaged cells, demonstrating that binding of fusion proteins was modulated by the annexin V targeting domain. Overall, these data demonstrate the capability of fusion proteins to deliver an activator domain specifically to damaged cells via the specific binding of a fused targeting domain.

Binding of fusion proteins to cells was observed using flow cytometry. Apoptotic cell death was induced by oxidative stress from treatment with hydrogen peroxide (H2O2). Apoptotic or dead cells were identified by labeling with propidium iodide (PI) or by labeling with a fluorescent Annexin V-based commercial apoptosis detection kit. In some cases, fusion proteins were first covalently labeled with a fluorescent dye for later detection. In these cases, specific binding of fusion protein to apoptotic cells was demonstrated by observing cells to be double-positive for both PI and the fusion-protein fluorescence, while equivalent cells incubated with a non-binding variant of the fusion protein were PI positive but negative for fusion-protein fluorescence. In other cases, the fusion proteins were not first covalently labeled, and instead a fluorescently-labeled secondary antibody that binds to the half-life modulator in the protein fusion was used for detecting the fusion protein. In these cases, specific binding of fusion protein to apoptotic cells was demonstrated by showing a strong correlation between the amount of fluorescent signal from the fusion protein secondary antibody to the amount of fluorescent signal from the commercial annexin V-based detection kit.

A. Specific Binding of IGF1 mHSA_AnxV to Apoptotic Heart Cells

The fusion proteins IGF1_mHSA_AnxV (SEQ ID 136) and IGF1_mHSA_AnxVm1234 (SEQ ID 138) were expressed and purified as described in Example 5. Both proteins were covalently labeled with Alexa Fluor 488 (Alexa Fluor 488 microscale protein labeling kit, Invitrogen, A30006) following the manufacturer's instructions. HL-1 cells (William C. Claycomb, Louisiana State University Health Sciences Center), a cardiac muscle cell line with characteristics of adult cardiomyocytes, were seeded in gelatin/fibronectin pre-coated 96-well plates (BD/Falcon, 353072) at 1:3 in complete medium (Claycomb medium (Sigma, 51800C), containing 10% FBS (Sigma, 12103C), 2 mM L-glutamine (Invitrogen/Gibco, 25030), 100 U/mL penicillin+100 ug/mL streptomycin (Invitrogen/Gibco, 15070), and 0.1 mM norepinephrine (Sigma, A0937)) and incubated at 37° C. and 5% CO2. Two days later, the cells were re-fed with 0.1 mL/well of medium supplemented with 400 uM H2O2 (Sigma, H1009), and incubated for 15 min at 37° C. and 5% CO2. Next, the H2O2-supplemented medium was aspirated from each well and replaced with complete medium and the cells were incubated for 20-24 hr at 37° C. and 5% CO2. The next day, medium from each well was transferred into a 96-deepwell v-bottom plate (USA Scientific, 1896-1110) to collect detached cells. The cells were washed once with PBS (Sigma, D8537) and then trypsinized using 40 uL of 0.025% Trypsin-EDTA and placed in a 37° C. incubator. Cell detachment was monitored under a microscope and 100 uL/well of DMEM plus 10% FBS was added to deactivate the trypsin. Cells were washed with cold PBS and resuspended in 100 uL of binding buffer (component of Annexin V-FITC apoptosis detection kit, BD Biosciences, 556547). Alexa Fluor 488-labeled fusion protein was then added and incubated in the dark on ice for 1 hr. Positive-control detection of apoptotic cells was obtained using an Annexin V-FITC apoptosis detection kit (BD Biosciences, 556547). In both cases, 3 uL of propidium iodide (PI) was added for the final 15 min of incubation. Cells were analyzed on a BD FACSCanto II flow cytometer, using appropriate unstained and single-stained controls for calibration.

Apoptotic cells were co-labeled with Annexin V-FITC and propidium iodide (PI) from the BD Biosciences apoptosis detection kit (FIGS. 2A-2D and 3A-3B). 56% of cells were in the double-positive quadrant, indicating late apoptosis or cell death. Positive and negative populations were fairly well separated.

IGF1_mHSA_AnxV (SEQ ID 136) and IGF1_mHSA_AnxVm1234 (SEQ ID 138) were each labeled with Alexa Fluor 488, achieving a degree-of-labeling (DOL) of 7.1 and 8.1 mole dye/mole protein, respectively. Apoptotic cells were also co-labeled with 80 ng (7.1 nM) of IGF1_mHSA_AnxV and PI (FIGS. 4A-4C and 5A-5B), or 80 ng (7.1 nM) of IGF1_mHSA_AnxVm1234 and PI (FIGS. 6A-6C and 7A-7B). The IGF1_mHSA_AnxV-labeled cells displayed a fairly well-separated double-positive peak (53% of cells), very similar to the apoptosis detection-kit positive control, indicating that the fusion protein bound specifically to apoptotic or dead cells. On the other hand, the IGF1_mHSA_AnxVm1234-labeled cells did not display a double-positive peak (0% of cells), indicating that the non-binding targeting arm did not bind to apoptotic or dead cells, as designed. Together, these data showed that a fusion protein comprising annexin V (AnxV) as a targeting domain can bind specifically to apoptotic or dead cardiac cells, and may therefore be used to deliver a fused agent or molecule having a biological (e.g. therapeutic) effect, such as an activator domain, to treat injured or damaged cardiac tissue.

B. Specific Binding of IGF1 mHSA_AnxV to Apoptotic Heart Cells

To verify that the binding to apoptotic heart cells observed in Example 6A was specific to the AnxV targeting domain in the IGF1_mHSA_AnxV fusion protein, and not a result of binding from the IGF1 domain to cell-surface IGF receptors, the experiment was repeated with the inclusion of an IGF1 pre-incubation step to saturate and block any/all IGF1 cell surface receptors. The methods used were the same as in Example 6A, except that the H2O2 concentration was changed to 200 µM. In addition, after resuspension of the cells in binding buffer, but prior to addition of Alexa Fluor 488-labeled fusion protein, 800 nM of IGF1 (Calbiochem, 407240) was added and incubated for 10 min to pre-block any/all IGF1 cell surface receptors with IGF1.

The Annexin V-FITC plus PI positive control in FIGS. 8A-8C and 9A-9B showed that approximately 40% were double-positive, indicating late apoptosis or cell death population. FIGS. 10A-10C and 11A-11B demonstrated binding of IGF1_mHSA_AnxV to apoptotic cells, while the non-binding control fusion, IGF1_mHSA_AnxVm1234, did not bind (FIGS. 12A-12C and 13A-13B), as shown in Example 6A. Next, to demonstrate that IGF1_mHSA_AnxV did not appreciably bind to cells via its IGF1 domain, the assays were repeated with the IGF1 blocking step. FIGS. 14A-14C and 15A-15B_showed the binding of IGF1_mHSA_AnxV to apoptotic cells, even in the presence of, and after incubation with, excess IGF1. These data demonstrated that the AnxV targeting domain was responsible for the specific binding of protein fusions to apoptotic cells.

C. Specific Binding of AnxV_mHSA to Apoptotic ESC-Derived Cardiac Cells

AnxV_mHSA (SEQ ID 252) and AnxVm1234_mHSA (SEQ ID 250) were directly conjugated to Alex Fluor 647 (Alexa Fluor 647 carboxylic acid, succinimidyl ester, Invitrogen, A-20006) following the manufacturer's instructions. Embryonic stem cell-derived (ESC-derived) cardiac cells (Peter Zandstra, University of Toronto) were derived essentially as described in Yang et al (Nature 2008, 453:524-8). Protocol was derived from Bauwens C L, et al. Tissue Eng Part A. 2011 Apr. 25., Geometric Control of Cardiomyogenic Induction in Human Pluripotent Stem Cells." Aggregate-based differentiation of hESCs was carried out using a protocol for serum-free directed differentiation to the cardiac lineage which has been previously described. HESC aggregate size was controlled by forced aggregation of defined cell concentrations in AggreWell™ inserts (STEMCELL Technologies) containing a textured surface of micro-wells. Briefly, a single cell suspension of feeder depleted hESCs was spun down into Aggrewells at a density of 1000 cells/micro-well. Cells were allowed to aggregate in hypoxic conditions over night in StemPro34 supplemented with Glutamax, ascorbic acid, transferrin, pen/strep as base media, with the addition of ROCK inhibitor and 0.5 ng/ml BMP4. On day 1 the media was replaced by base media with 10 ng/ml BMP4, 3 ng/ml Actvin A and 5 ng/ml bFGF. On day 4, cells were removed from the micro-wells, washed with DMEM F12 supplemented with 5% KOSR and transferred to low cluster plates in base media with 10 ng/ml VEGF and 150 ng/ml Dkk1. On day 8 the media was replaced by base media with 10 ng/ml VEGF, 150 ng/ml Dkk1 and 5 ng/ml bFGF. On day 12 the media was replaced again (same cytokines) and cells were transferred to normoxic conditions until day 16.

Figure 16:
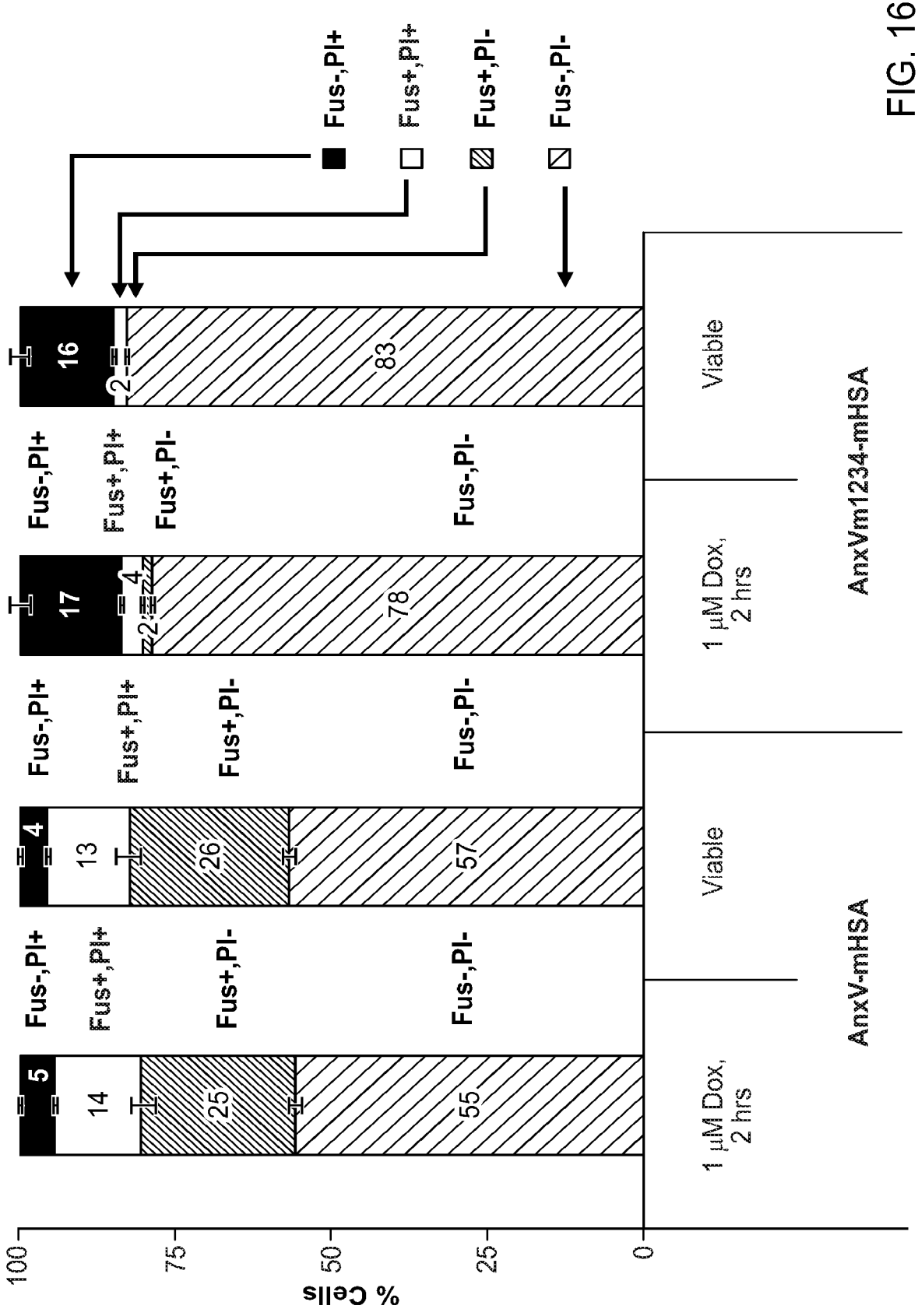
FIG. 16 is a graph showing that ESC-derived cardiac cells exhibit an apoptotic population, with or without doxorubicin treatment. Ann-HSA=AnxV_mHSA. M1234-Ann-HSA=AnxVm1234_mHSA.

Even without H2O2 or doxorubicin treatment, the cardiac cells exhibit a measureable apoptotic population, based on PI labeling and the Annexin V-FITC detection kit (FIG. 16).

Figures 17, 17A:
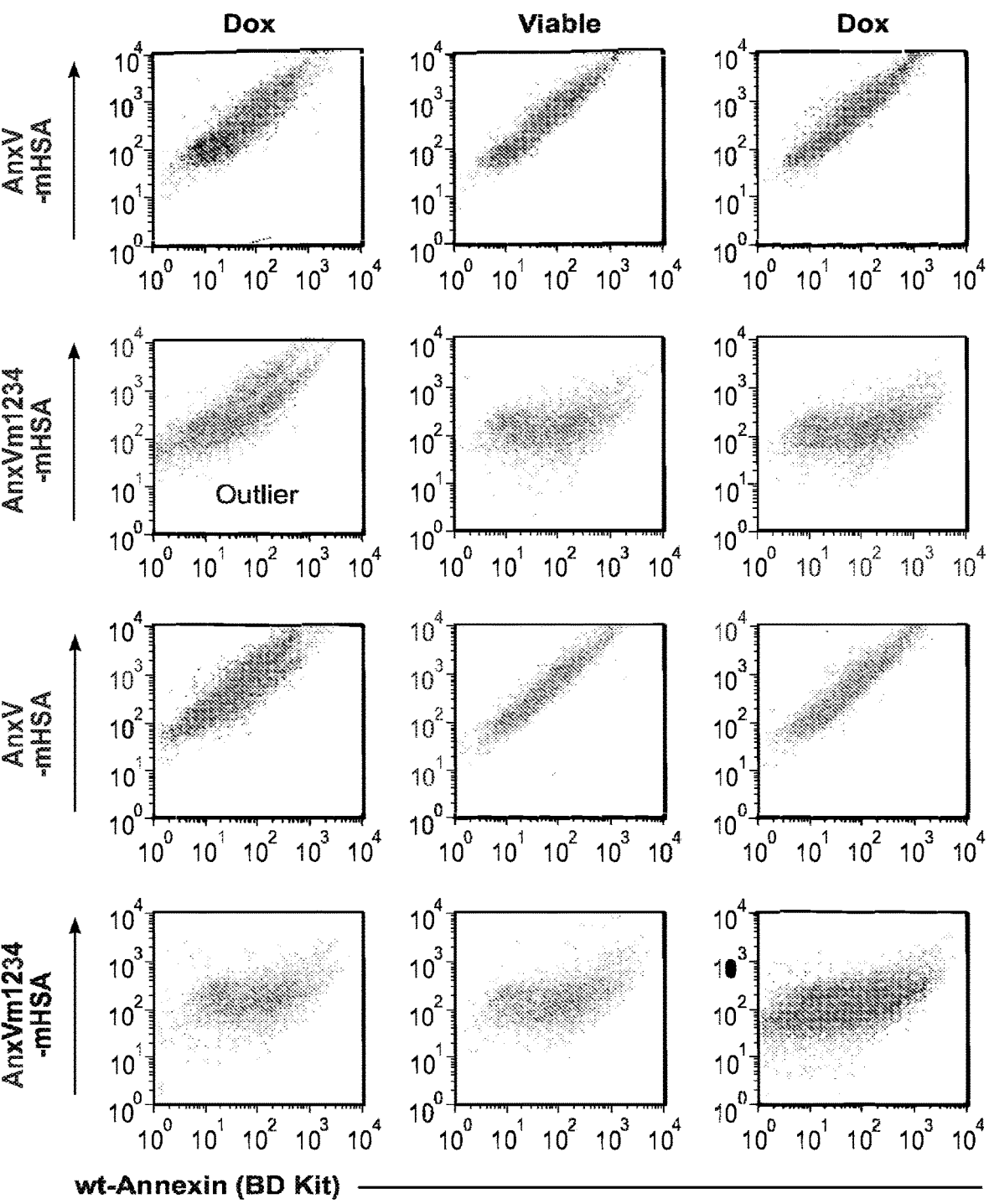
FIGS. 17A-17B represent the data obtained by flow cytometry showing the specific binding of AnxV_mHSA, and not AnxVm1234_mHSA, to apoptotic, ESC-derived cardiac cells.
Figure 17B:
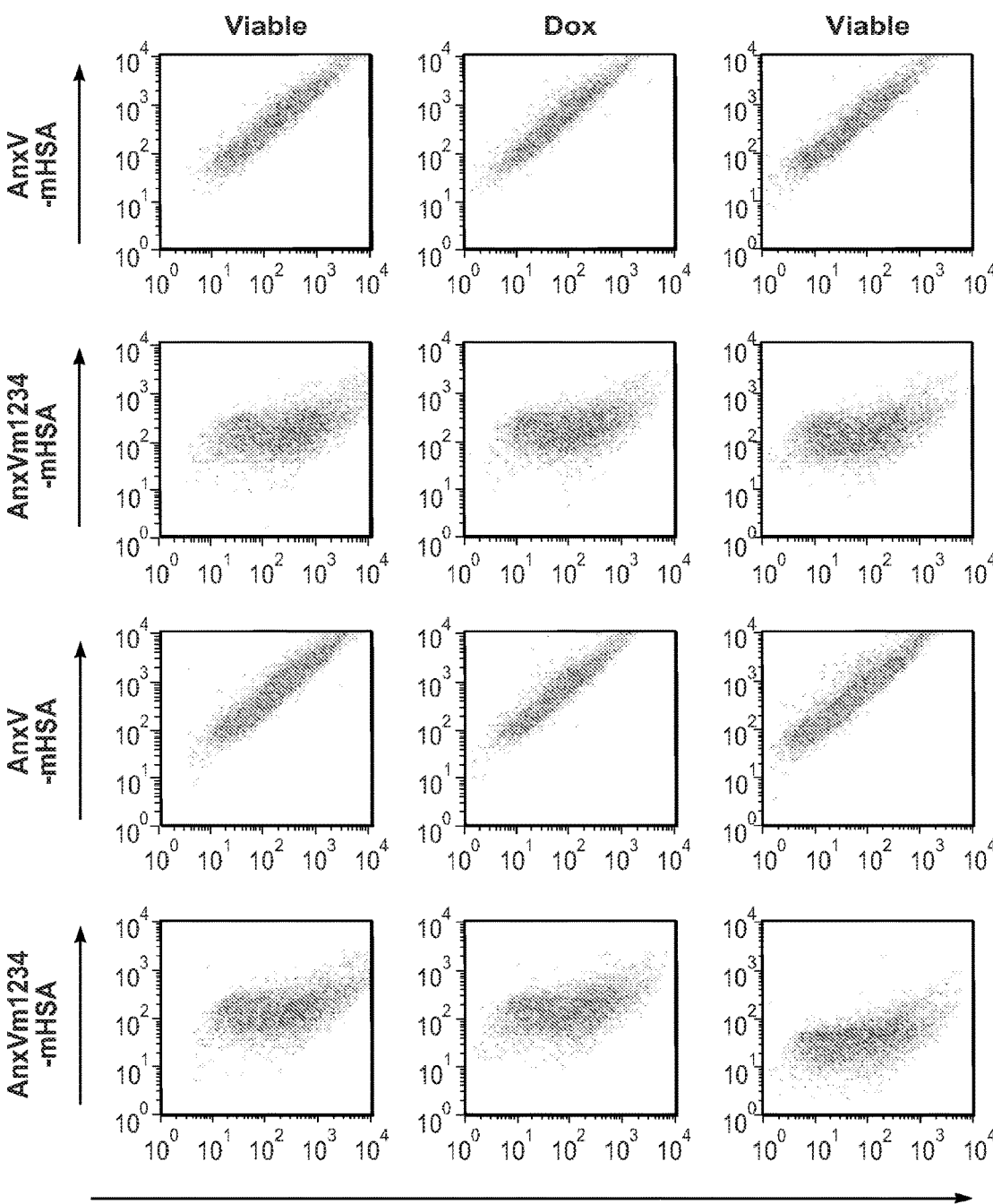

Further addition of doxorubicin did not increase the apoptotic fraction. Nevertheless, apoptotic cell population was sufficient for testing the binding of apoptosis-targeting fusion proteins. The cardiac cell population was incubated with either AnxV_mHSA or AnxVm1234_mHSA, while being co-incubated with the Annexin V-FITC detection kit as well. The fluorescent signal from the Alexa Fluor 647 on the AnxV_mHSA fusion, and not from the AnxVm1234_mHSA fusion, correlated strongly with the FITC signal from the apoptosis detection kit (FIGS. 17A-17B), demonstrating that AnxV_mHSA binds specifically to apoptotic ESC-derived cardiac cells.

Figures 18, 18A, 18B:
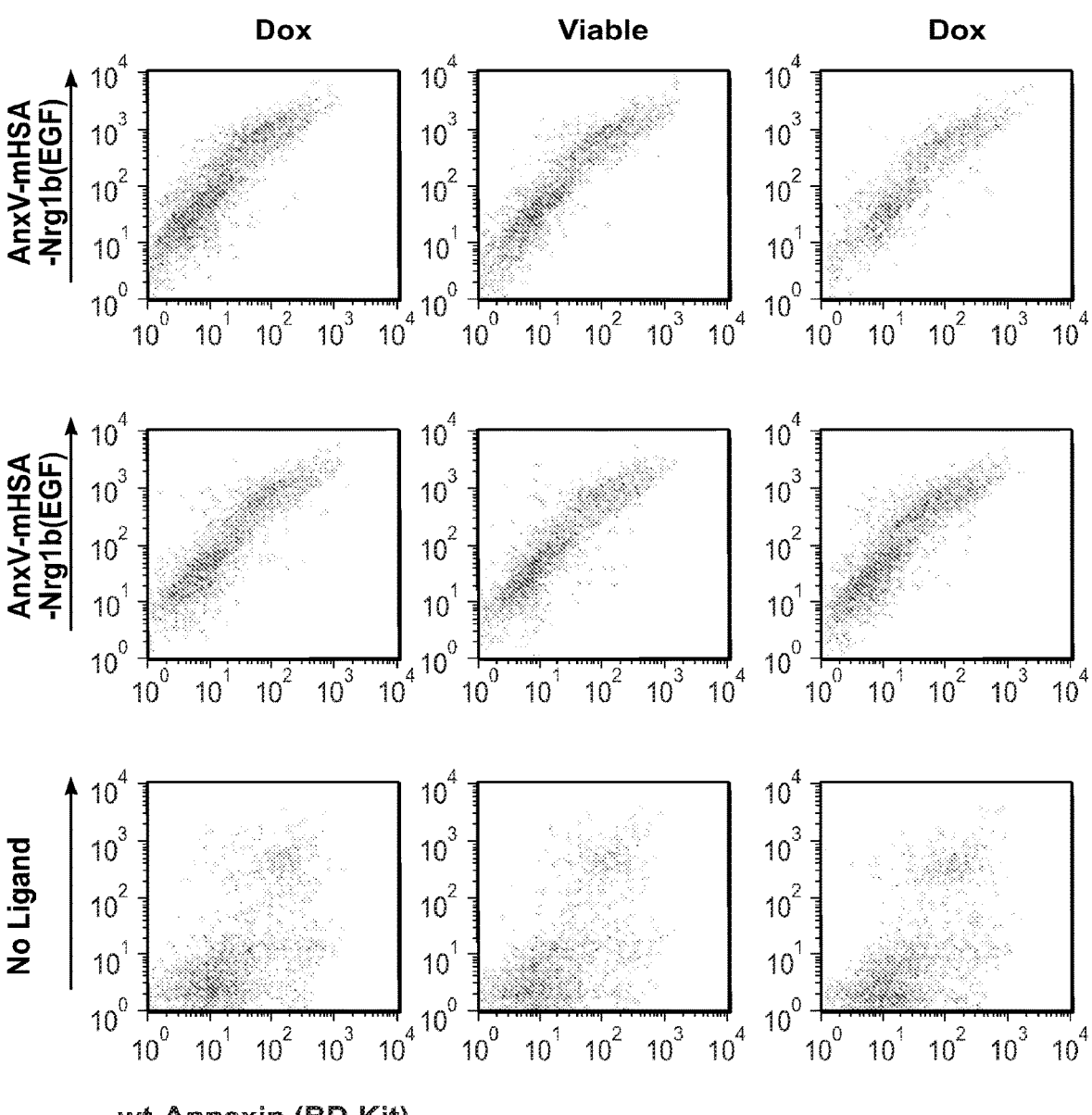
FIGS. 18A-18B represent the data obtained by flow cytometry showing the specific binding of AnxV_mHSA_NRG1b(EGF) to apoptotic ESC-derived cardiac cells.
Figure 18B:
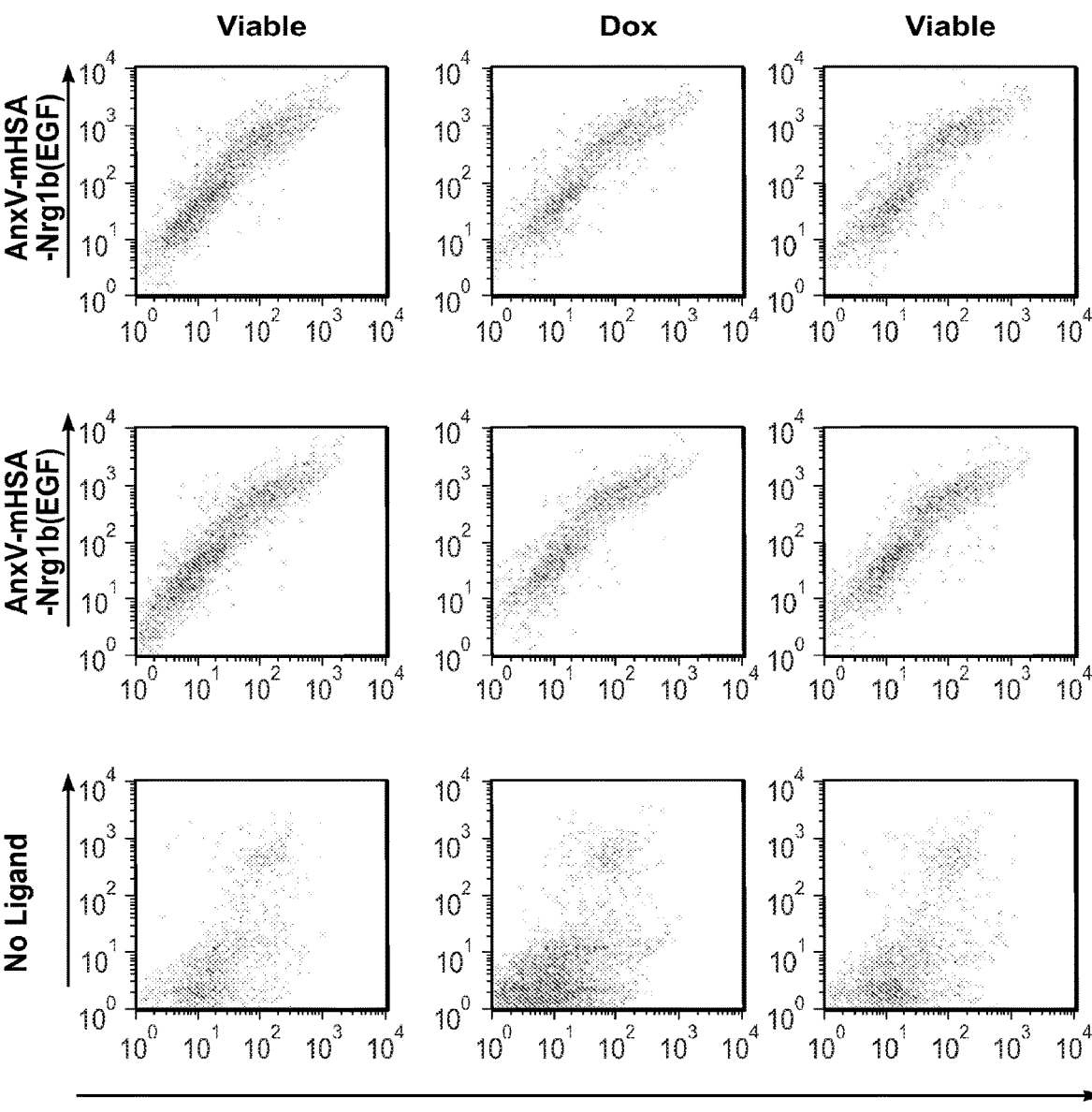

D. Specific Binding of AnxV_mHSA_NRG1b(EGF) to Apoptotic ESC-Derived Cardiac Cells Binding of the fusion protein AnxV_mHSA_NRG1b (SEQ ID 120) to apoptotic ESC-derived cardiac cells was demonstrated using a secondary detection scheme, instead of first altering the fusion protein with a covalently attached fluorophore. The fusion protein was detected using an anti-HSA antibody (goat anti-human albumin antibody affinity purified, Bethyl Labs, A80-129A) that was itself covalently labeled with Alexa Fluor 647 (Alexa Fluor 647 carboxylic acid, succinimidyl ester, Invitrogen, A-20006) following the manufacturer's instructions. Cardiac cells were incubated with AnxV_mHSA_NRG1b(EGF), while being co-incubated with the Annexin V-FITC detection kit as described in Example 6C. The fusion protein was detected by the anti-HSA Alexa Fluor 647 secondary antibody. Fluorescent signal from the Alexa Fluor 647 correlated strongly with the FITC signal from the detection kit (FIGS. 18A-18B). This demonstrated that AnxV_mHSA_NRG1b(EGF) binds to apoptotic ESC-derived cardiac cells. Furthermore, a control experiment that excluded fusion protein ("No Ligand" in FIGS. 18A-18B), but still incubated with secondary detection reagents, did not exhibit any correlation of Alexa Fluor 647 signal to the apoptosis-based FITC signal, demonstrating that the original Alexa Fluor 647 fluorescent signal was due to binding of the fusion protein itself and not due binding of the secondary antibody alone.

Example 7. Specific Binding of Fusion Proteins to their Targets

The process of localizing therapeutics to a disease-related area of the patient can be accomplished by targeting molecular epitopes that are either restricted to, or particularly abundant in, the area of interest. For example, myocardial infarction can expose several target molecules (e.g. DNA, cardiac myosin, and phosphatidylserine) upon tissue damage that can be exploited for this purpose. Several fusion proteins were produced that comprise targeting domains specific for these target molecules. In particular, annexin V and synaptotagmin can be used to target phosphatidylserine, and the SI-1 single-chain variable fragment (aDNASIscFv) can be used to target DNA. However, one skilled in the art will appreciate that the inclusion of a binding domain in a fusion protein may result in the loss or change of properties of each individual domain (e.g. change in binding affinity, change in biological activity). To determine if functionality can be maintained in the fusion proteins disclosed herein, an ELISA-based in vitro binding test was developed and applied. Essentially, the assay showed that targeting-competent fusion proteins were retained in microplate wells, despite stringent washing, due to their interaction with cognate target molecules lining the well surfaces. The presence of fusion protein was quantified immunochemically. In the absence of cognate target molecule, or presence of non-cognate target molecules, retention was not expected, in the absence of unexpected targeting domain cross reactivity. The combination of retention with cognate target molecule, and clearance without, was taken as proof of binding specificity and targeting function.

Microplates (Pierce 15041) were coated with the epitopes of interest. Phosphatidylserine (PS, Avanti Polar Lipids 840032) was deposited by evaporating to dryness 50 μL/well of a 12.5 μg/mL solution in Methanol. DNA (Sigma D3664) was deposited by adding 50 μL of a pre-mixed 1:1 solution of DNA at 10 μg/mL and DNA Coating Reagent (Pierce 17250) to wells. Myosin was deposited by incubating a 10 μg/mL solution in Dublecco's PBS. All coating reactions were performed at room temperature for 2 hours with 200 rpm shaking. After washing, 250 μL/well of protein-free blocking buffer (Pierce 37572) was added and plates incubated at room temperature for 3-4 hours. After further washing, 100 μL of chromatographically purified fusion proteins were added to wells at concentrations ranging from 160 ng/mL-20 μg/mL. Binding proceeded for two hours at room temperature in 10 mM Hepes, 140 mM NaCl, 2.5 mM CaCl2, pH 7.4. After further washing, 100 uL detection antibody (Goat anti-Human Albumin Antibody HRP Conjugated, Bethyl Labs A80-129P) was added to wells at dilutions of either 1:5,000 or 1:50,000 in PBST and incubated for 30-60 minutes. After further washing, 75 μL peroxidase substrate (Pierce TMB Ultra 34028) was applied, and upon the observation of significant color development, the reaction quenched with 75 μL of Stop solution (KPL 50-85-05). Absorbance of wells was read at 450 nm in a plate reader (Tecan M200 Pro). All fusion proteins and antibody combinations were performed in triplicate. All wash steps consisted of four cycles of dispensing and aspirating 250 μL PBST with five second soak and shake steps between cycles using an automated 96 well plate washer (Biotek, Elx405). Mock coated blank wells (solvent, coating reagent, or buffer only) and wells without fusion protein were included as negative controls.

Figure 19A:
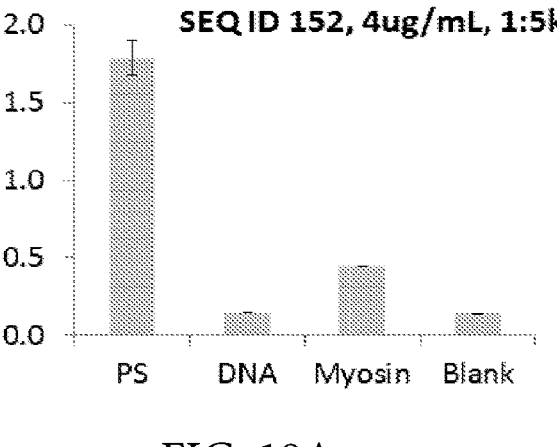
FIGS. 19A-19B are graphs showing the specific binding of IGF1_mHSA_Syt1 and IGF1_mHSA_AnxV to phosphatidylserine.
Figure 19B:
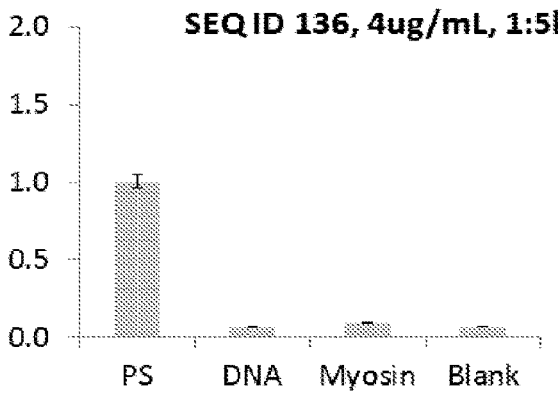

Fusion proteins were produced as detailed in Example 5. IGF1_mHSA_Syt1 (SEQ ID 152) and IGF1_mHSA_AnxV (SEQ ID 136) were shown to specifically bind phosphatidylserine (FIGS. 19A-19B). aDNASI1_mHSA_FGF2 (SEQ ID 124), aDNASI1_mHSA_NRG1b(EGF) (SEQ ID 126), and IGF1_mHSA_aDNASI1 (SEQ ID 154) were shown to bind specifically to DNA (FIGS. 20A-20C).

The fusion proteins were shown to bind specifically to the target molecules demonstrating the retention of functional binding after fusing a targeting domain to a half-life modulator and activator domain and also exemplifying the breadth of targeting domains (as well as target) capable of being fused into fusion proteins. Specific targets, such as phosphatidylserine, may be addressed with a variety of binding domains, such as annexin V and synaptotagmin. Conversely, specific protein classes, like the antibody-derived scFvs, of which aDNASI1 is a member, have a large diversity of members which bind a correspondingly large variety of target molecules or epitopes. The successful incorporation of scFvs into fusion proteins is an indication of the potential for the application of antibody-derived targeting in other fusion proteins. The aDNASI1 domain was further shown to be functional in either N- or C-terminal fusion orientation as well as in fusions that contain a variety of activator domains. Taken together, these results establish that fusion proteins targeting may not be restricted to a specific target epitope, a specific class of targeting domain, a specific translational orientation, or a specific activator domain-containing molecule.

Example 8. Modulation of Cell Activity

The bioactivity of the activator domains of purified fusion proteins was demonstrated in vitro by measuring downstream signaling in stimulated cells. The potency of the fusion proteins was compared to that of wild-type, non-fused activator domains. A variety of fusion proteins with different activator domains, different targeting domains, and different fusion orientations were produced and demonstrated to be bioactive. These data demonstrate that fusion proteins can be produced that are bioactive and capable of signaling cellular pathways such as pro-survival or proliferative pathways.

Each fusion protein was tested alongside a positive-control, commercially obtained, non-fused version of its activator domain. Fusion proteins with active targeting domains (e.g., AnxV) as well as non-binding control targeting domains (e.g., AnxVm1234 or DAscFv) were both used, demonstrating that activity of the activator domain was independent of the identity and function of the targeting domain. Cells to be stimulated were grown, serum starved, and then stimulated with the fusion proteins. Proteins were then washed away, and cell activity was measured by ELISA for either phospho-Akt (pAkt) or phospho-Erk (pErk).

A. Stimulation of AKT Activity in Cancer Cells Using NRG1b(EGF) Fusion Proteins

The fusion proteins NRG1b(EGF)_mHSA_AnxV (SEQ ID 142) and AnxV_mHSA_NRG1b(EGF) (SEQ ID 120) were produced as described in Example 5. Wild-type NRG1b(EGF) was obtained from R&D Systems (396-HB/CF). DU145 cells, a human prostate carcinoma, epithelial-like cell, were seeded in 96-well plates (BD/Falcon, 353072) at 25,000 cells/well in complete medium (RPMI-1640 (Invitrogen/Gibco, 11875) containing 10% FBS (Hyclone, SH30071), 2 mM L-glutamine (Invitrogen/Gibco, 25030), and 50 U/mL penicillin+50 ug/mL streptomycin (Invitrogen/Gibco, 15070)) and incubated overnight at 37° C. and 5% $CO2$. The next day, the media was aspirated, the cells were washed with 0.1 mL/well PBS (without calcium and magnesium, Sigma, D8537), the cells were re-fed with 0.1 mL/well of RPMI-1640+0.5% FBS, and the cells were incubated for 20-24 hr at 37° C. and 5% $CO2$. The next day, cells were stimulated with diluted fusion proteins or control proteins, adding 25 μL/well to the existing 0.1 mL/well, for 10 min at 37° C. and 5% $CO2$. Stimulation was stopped by aspirating media from the wells and washing with 0.2 mL/well cold PBS. Cells were lysed in 25 μL/well complete M-PER lysis buffer (Mammalian protein extraction reagent (Pierce/ThermoScientific, 78501), 150 mM NaCl, protease inhibitor cocktail (Roche complete mini, 04 693 124 001), and phosphatase inhibitors (Roche PhosSTOP, 04 906 837 001)), prepared in advance. Plates were sealed, cells were lysed on an orbital shaker for 30 min at 4° C., and lysates were snap frozen on dry ice and stored at –78° C. 384-well flat, white plates (MaxiSorp, Nunc, 460372) were coated with anti-Akt capture antibody (clone SKB1, Millipore, 05-591), sealed, and stored at room temp overnight.

The next day, the cell lysates were thawed and ELISA plates were washed & blocked. Thawed lysates were pooled, ELISA plates were washed again, Akt standards or pooled lysates were added to the ELISA plates, and plates were incubated for 2 hr at room temp. ELISA plates were washed, anti-phospho Akt detection antibody (biotinylated mouse mAb, Cell Signaling, 5102) was added, and plates were incubated for 1.5 hr at room temp. The plates were washed, streptavidin-horseradish peroxidase (SA-HRP, R&D Systems, 890803) was added, and plates were incubated for 30 min at room temp. Plates were washed again, substrate (SuperSignal ELISA Pico Chemiluminescent, Pierce/ThermoScientific, 37069) was added, and luminescence was read on a plate reader. The pAkt standard curve was fit to a line (log-log scale).

Figure 21:
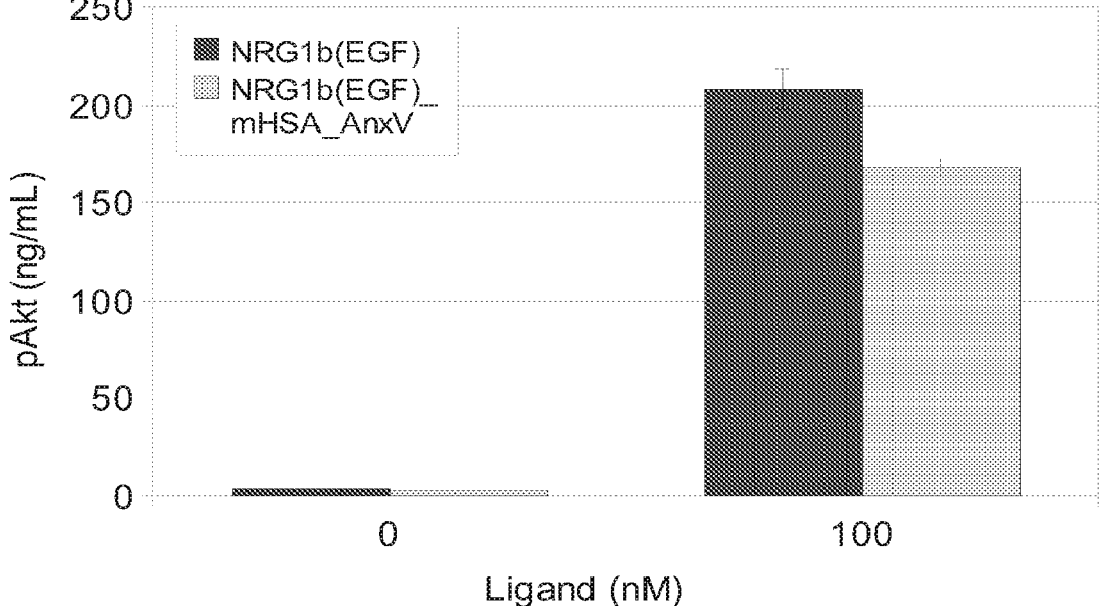
FIG. 21 is a graph showing stimulation of pAkt in DU145 cells by fusion protein, NRG1b(EGF)_mHSA_AnxV, and positive-control, NRG1b(EGF).
Figure 22:
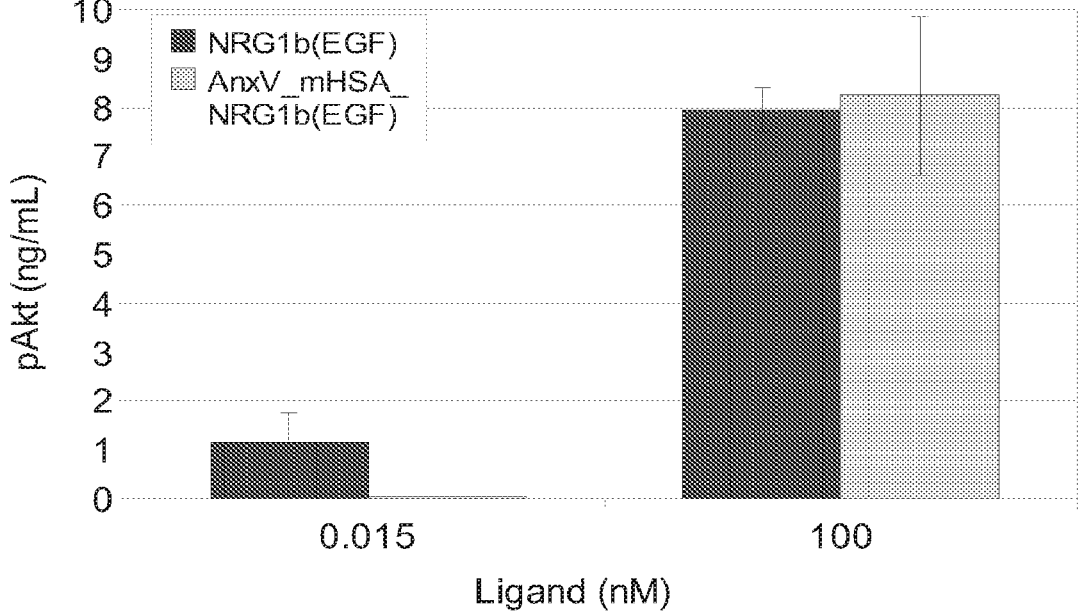
FIG. 22 is a graph showing stimulation of pAkt in DU145 cells by fusion protein, AnxV_mHSA_NRG1b(EGF), and positive-control, NRG1b(EGF).

Activities of NRG1b(EGF) and NRG1b(EGF)_mHSA_AnxV are shown in FIG. 21. Both the commercial wild-type NRG1b(EGF) and the fusion protein were shown to be bioactive, stimulating the pAkt pathway. Similarly, FIG. 22 shows the activities of the wild type and the reverse-orientation fusion protein, AnxV_mHSA_NRG1b (EGF). These results demonstrate that translationally fusing the NRG1b(EGF) activator domain to mHSA and AnxV did not abolish its bioactivity, as the NRG1b(EGF) fusions proteins expressed and purified in Example 5 were bioactive.

B. Stimulation of AKT Activity in Cancer Cells Using IGF1 Fusion Proteins

Figure 23:
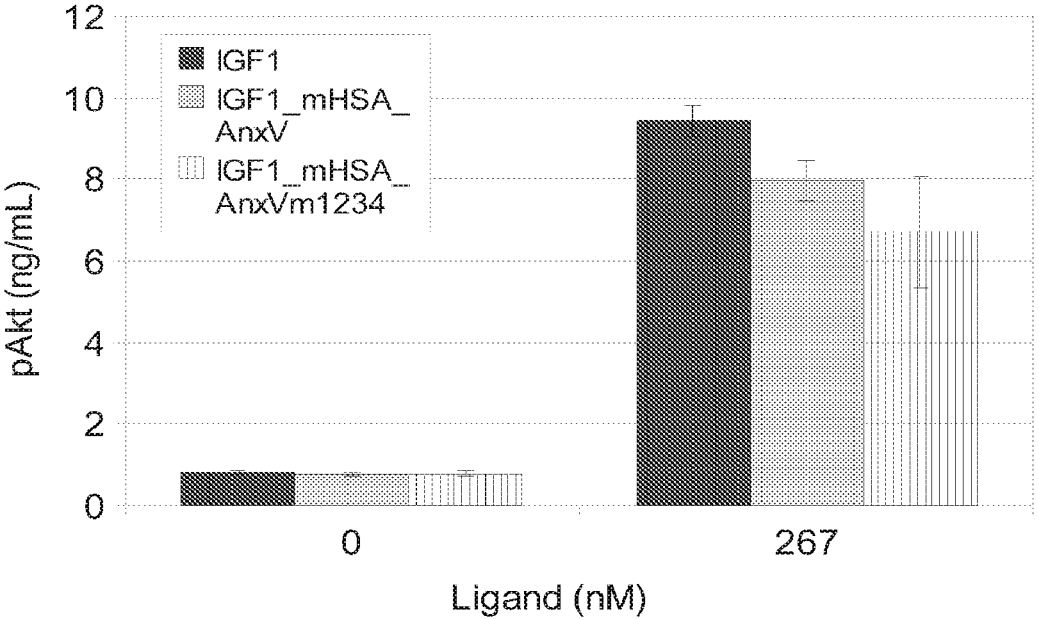
FIG. 23 is a graph showing stimulation of pAkt in DU145 cells by fusion protein IGF1_mHSA_AnxV, fusion protein IGF1_mHSA_AnxVm1234, and positive-control, IGF1.
Figure 24:
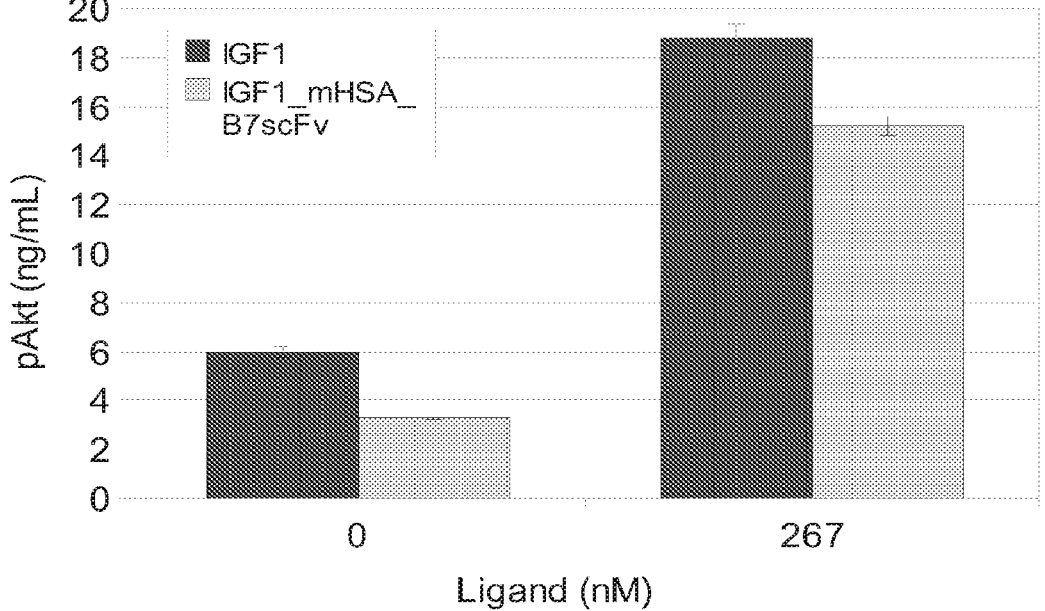
FIG. 24 is a graph showing stimulation of pAkt in DU145 cells by fusion protein IGF1_mHSA_B7scFv, and positive-control, IGF1.

The fusion proteins IGF1_mHSA_AnxV (SEQ ID 136), IGF1_mHSA_AnxVm1234 (SEQ ID 138), and IGF1_mHSA_B7scFv (SEQ ID 150) were produced as described in Example 5. Wild-type IGF1 was obtained from Calbiochem (407240). DU145 cells were grown and stimulated as described in Example 8A. All three IGF1-based protein fusions were shown to be bioactive in the DU145 cancer cells, with similar pAkt stimulation as for wild-type IGF1 (see FIGS. 23-24).

C. Stimulation of AKT Activity in Heart Cells Using IGF1 Fusion Proteins

The fusion protein IGF1_mHSA_AnxV (SEQ ID 136) was produced as described in Example 5. Wild-type IGF1 was obtained from Calbiochem (407240). HL-1 cells (William C. Claycomb, Louisiana State University Health Sciences Center), a cardiac muscle cell line with characteristics of adult cardiomyocytes, were seeded in gelatin/fibronectin pre-coated 96-well plates (BD/Falcon, 353072) at 60,000 cells/well in complete medium (Claycomb medium (Sigma, 51800C), containing 10% FBS (Sigma, 12103C), 2 mM L-glutamine (Invitrogen/Gibco, 25030), 100 U/mL penicillin+100 ug/mL streptomycin (Invitrogen/Gibco, 15070), and 0.1 mM norepinephrine (Sigma, A0937)) and incubated overnight at 37° C. and 5% $CO2$. Cells were washed and subjected to an ELISA protocol as described in Example 8A.

Figure 25:
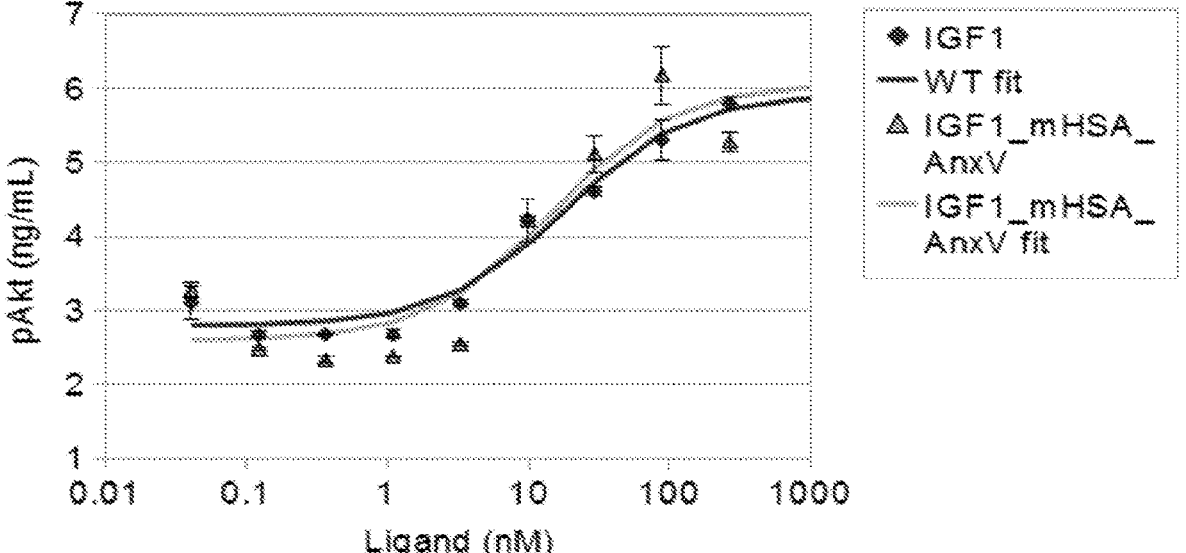
FIG. 25 is a graph showing the dose-response stimulation of pAkt in heart cells by IGF1 and IGF1 mHSA_AnxV.

The IGF1_mHSA_AnxV fusion protein was shown to be bioactive in heart cells, and its potency comparable to wild-type IGF1 (see dose response activities, FIG. 25). These data demonstrate that an activator domain fused to a half-life modulator and a targeting domain can be produced and can retain its ability to potently stimulate cells.

D. FGF2 Fusion Protein Stimulates ERK Activity in Heart Cells

Figure 26:
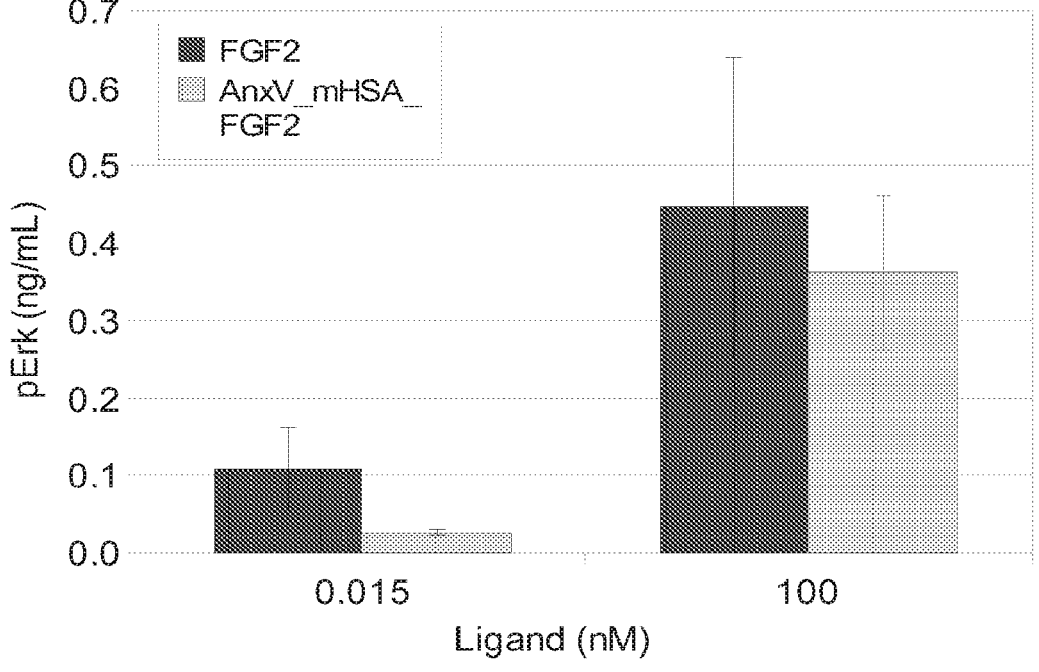
FIG. 26 is a graph showing stimulation of pErk in ESC-derived cardiomyocytes by FGF2 and AnxV_mHSA_FGF2.

Cardiomyocytes derived from embryonic stem cells (ESCs, provided by Peter Zandstra's lab at the University of Toronto) were dissociated and seeded in gelatin pre-coated 96-well plates at 40,000 cells/well in StemPro-34 medium (Invitrogen/Gibco, 10639) supplemented with 38.5× StemPro-34 nutrient supplement (provided with StemPro-34 medium), 2 mM L-glutamine (Invitrogen/Gibco, 25030), 50 U/mL penicillin+50 ug/mL streptomycin (Invitrogen/Gibco, 15070), 0.4 mM monothioglycerol (Sigma, M6145), 50 ug/mL ascorbic acid (Sigma, A4544), 150 ug/mL transferrin (Sigma T8158), 10 ng/mL VEGF (R&D Systems, 293-VE), 150 ng/mL DKK-1 (R&D Systems, 5439-DK), and 5 ng/mL basic FGF (FGF2, PeproTech, 100-18b), and incubated at 37° C. and 5% $CO2$. Twenty-four hours prior to stimulation, the growth medium was changed to StemPro-34 without nutrient supplement and growth factors. Cells were stimulated and lysed as described in Example 8A. For the ELISA, a 96-well high binding black ELISA plate was coated with phospho-Erk1/Erk2 capture antibody (R&D Systems, DYC1018), sealed, and stored overnight at room temperature. The next day, lysates were subjected to the ELISA protocol described in Example 8A, except that instead of Akt standards and an anti-phospho-Akt detection antibody, phospho-Erk1/Erk2 standards (R&D Systems, DYC1018) and a phospho-Erk1/Erk2 detection antibody (R&D Systems, DYC1018) were used to measure activated Erk1/Erk2 levels. The fusion protein AnxV_mHSA_FGF2 (SEQ ID 118) was compared to wild-type FGF2 for stimulation of pERK ESC-derived cardiac cells and was shown to be bioactive (FIG. 26).

Example 9. Accumulation of Fusion Proteins Accumulate with Apoptotic Cells and Stimulation of Cell Activity The ability of fusion proteins to specifically bind to cells via their targeting domain and subsequently stimulate cell signaling pathways via their activator domain was demonstrated in vitro. The targeting domain used was human annexin V (AnxV, SEQ ID 31). AnnV can bind to phosphatidylserine which becomes exposed on the outer cell surface during apoptosis. The activator domain used was IGF1 (SEQ ID 3), which binds to the IGF1 receptor expressed on the cell surface. Once bound, the IGF1 receptor initiates intracellular signaling. Fusion proteins were first bound to apoptotic cardiac cells, which mimic the damaged state of cells in vivo after myocardial infarction. The fusion protein-bound cells were then used to stimulate IGF1 signaling in healthy cardiac cells, mimicking the paracrine effect of the fusion proteins to activate signaling in nearby damaged or healthy cells at or near the infarct zone. Phospho-Akt, a downstream target of IGF1 signaling, was measured by ELISA. Cell-bound fusion protein was able to stimulate Akt signaling in heart cells. Wild type, non-fused IGF1 did not induce Akt signaling indicating that the annexin V targeting domain of the fusion protein was critical for signaling to occur. Likewise, the AnxV_mHSA fusion protein did not stimulate Akt signaling, indicating that the targeting domain itself was not sufficient for signaling. Collectively, these data show that fusion proteins are bi-functional, being capable of specifically target damaged tissue and capable of signaling cellular pathways in a paracrine-like fashion via their activator domains. The results demonstrate a therapeutic role for fusion proteins to accumulate specifically in damaged tissue and not in healthy tissue, to then modulate survival or regeneration through the activator domains.

In a first step, the fusion protein was allowed to accumulate with damaged cells through annexin V-phosphatidylserine binding in HL1 cardiomyocytes undergoing apoptosis. Apoptotic cell death was induced by oxidative stress from treatment with hydrogen peroxide (H2O2). Binding of the fusion protein to damaged cells was carried out by incubating the fusion protein with detached apoptotic cells contained in the growth medium of H2O2 treated cells. In a second step, the bioactivity of the activator domain of cell-bound fusion protein was assessed in vitro by stimulating serum-starved cardiomyocytes with the cell-bound fusion protein. After washing to stop the stimulation, downstream signaling in stimulated cells was measured by ELISA for phospho-Akt (pAkt). The levels of pAkt induced by the fusion protein were compared to that of a commercially obtained, non-fused version of its activator domain as well as that of a fusion protein that contained the annexin V targeting domain but lacked the activator domain.

The fusion protein IGF1_mHSA_AnxV (SEQ ID 136) was expressed and purified as described in Example 5. HL-1 cells (William C. Claycomb, Louisiana State University Health Sciences Center), a cardiac muscle cell line with characteristics of adult cardiomyocytes, were seeded in gelatin/fibronectin pre-coated 96-well plates (BD/Falcon, 353072) at 1:2 in complete medium (Claycomb medium (Sigma, 51800C), containing 10% FBS (Sigma, 12103C), 2 mM L-glutamine (Invitrogen/Gibco, 25030), 100 U/mL penicillin+100 µg/mL streptomycin (Invitrogen/Gibco, 15070), and 0.1 mM norepinephrine (Sigma, A0937)) and incubated at 37° C. and 5% CO2. The following day, the cells were re-fed with 0.1 mL/well of medium supplemented with 400 uM H2O2 (Sigma, H1009), and incubated for 15 min at 37° C. and 5% CO2. Next, the H2O2-supplemented medium was aspirated from each well and replaced with complete medium and the cells were incubated for 20-24 hr at 37° C. and 5% CO2. The next day, medium from the wells was transferred into a 96-deepwell v-bottom plate (USA Scientific, 1896-1110) to collect detached cells. For each sample, medium from 3 wells were pooled into 1 well of the 96-deepwell v-bottom plate. Collected cells were then incubated with fusion proteins in the presence of calcium (binding buffer, a component of Annexin V-FITC apoptosis detection kit, BD Biosciences, 556547) for 15 minutes at 37° C. and 5% CO2. Fusion protein-bound cells were pelleted by centrifugation and washed once with PBS (Sigma, D8537), after which, cells were resuspended in 100 µL/well DMEM containing calcium (binding buffer). HL-1 cells that were seeded in gelatin/fibronectin pre-coated 96-well plates and serum starved in advance were then stimulated with the 100 µL/well resuspended fusion protein-bound cells for 20 minutes. Stimulated cells were then washed and subjected to an ELISA protocol as described in Example 5. Healthy HL-1 cells that were not exposed to H2O2 were also harvested by trypsinization using 40 uL/well of 0.025% Trypsin-EDTA and placed in a 37° C. incubator. Cell detachment was monitored under a microscope and 100 µL/well of DMEM plus 10% FBS was added to deactivate the trypsin. For each sample, trypsinized cells from 3 wells were pooled into 1 well of the 96-deepwell v-bottom plate. Cells were washed with cold PBS, and resuspended in 300 µL of DMEM. Cells were then incubated with fusion proteins in the presence of calcium, processed as described above, and used to stimulate HL-1 cells that were seeded and serum starved in advance. Stimulated cells were washed and subjected to an ELISA protocol as described in Example 8A.

Figure 27:
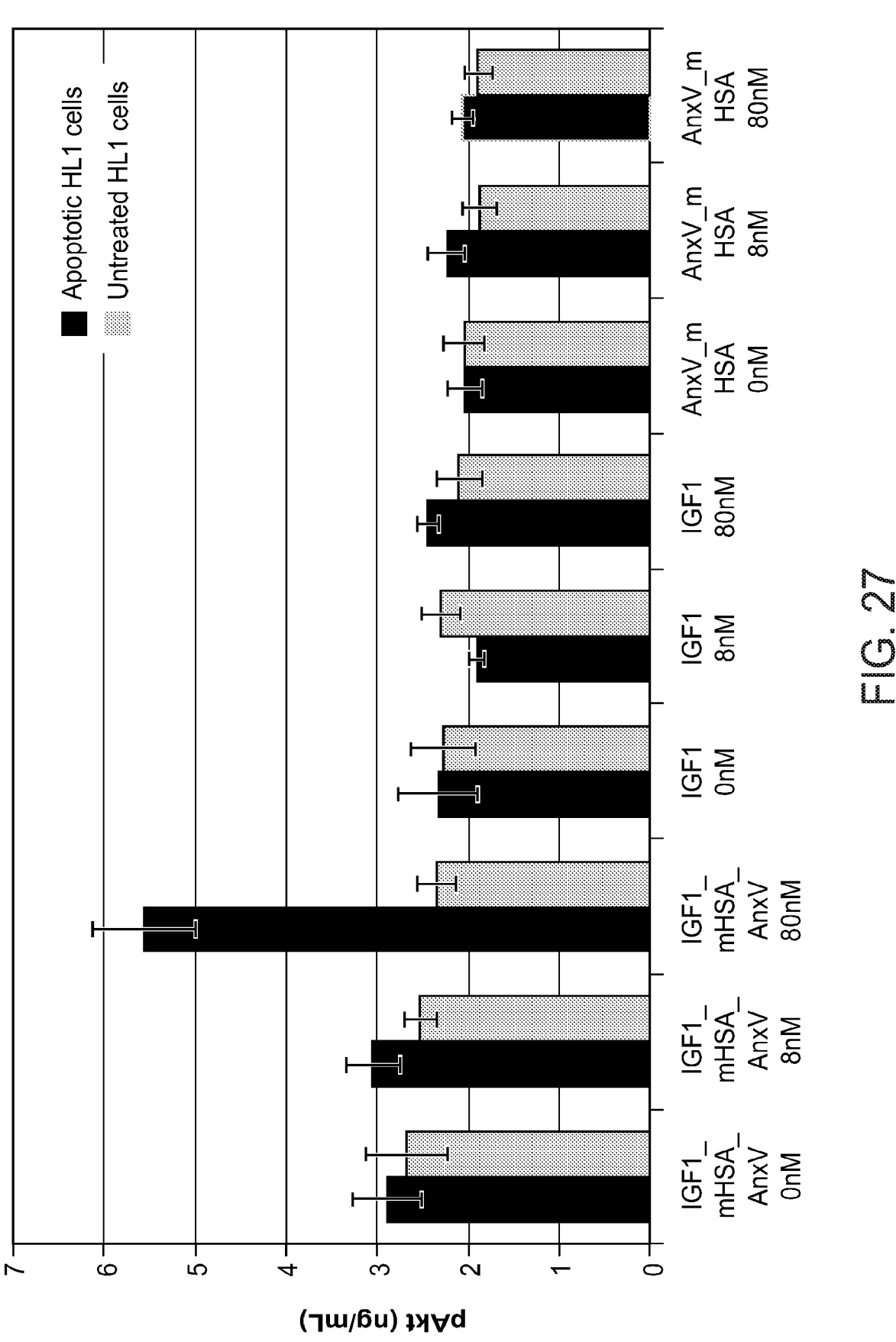
FIG. 27 is a graph showing the pAkt levels induced by proteins pre-mixed with apoptotic HL-1 cells (black bars), and with untreated HL-1 cells (gray bars).

An increase in phospho-Akt levels was observed only in cells stimulated by apoptotically captured fusion protein containing both targeting (AnxV) and activator (IGF1) domains as shown in FIG. 27. Wild type, non-fused IGF1 was unable to stimulate cells, presumably because IGF1 did not bind apoptotic cells and therefore was not captured. Both fusion protein and wild type IGF1 have comparable activities as shown in Example 4C, thus the increase in phospho-Akt levels by captured fusion protein was not caused by differences in their potencies. Although non-fused IGF1 could in theory bind to the IGF1 receptor expressed on the surface of apoptotic cells, there appeared to not be enough growth factor retained to induce signaling, or the growth factor was retained in a signaling-incapable way. Likewise, the AnxV_mHSA fusion protein was unable to stimulate cells. While it was capable of binding apoptotic cells, as shown in Example 6, the AnxV_mHSA fusion protein was not able to signal in a paracrine-like fashion since it lacked the activator domain. Increases in phospho-Akt levels were not detected in cells stimulated by any of the proteins that were premixed with untreated cells, presumably because healthy cells do not have phosphatidylserine exposed on the cell surface for capture of the fusion proteins. Likewise, despite being able to bind IGF1 receptors on the cell surface of healthy cells, the capture of growth factor was not sufficient to stimulate cells. Taken together, the data demonstrate the simultaneous targeting and activating functions of the fusion protein.

Example 10. In Vivo Targeting of Fusion Protein to Damaged Heart Tissue

We tested the hypothesis that the fusion protein IGF1_mHSA_AnxV (SEQ ID: 136), which binds specifically through the AnxV targeting domain to phosphatidylserine on apoptotic and necrotic cells (Example 6), would accumulate more and for longer in damaged heart tissue following myocardial infarction than IGF1_mHSA_AnxVm1234 (SEQ ID: 138) (a variant that does not bind phosphatidylserine). An experimental myocardial infarction (MI) was induced in mice, a test article was injected intravenously (either IGF1_mHSA_AnxV, IGF1_mHSA_AnxVm1234, or vehicle-only control), animals were sacrificed 12, 24, or 72 hours later, and protein accumulation in the infarcted, border zone, and remote (undamaged) areas of the heart was observed by ELISA and immunohistochemistry. The immunohistochemistry demonstrated that IGF1_mHSA_AnxV at 24 hours post-administration is localized in the border zone at the edge of the infarct, while none of the nonbinding variant is seen in the infarct, border zone, or remote (healthy) region. The ELISA data demonstrated that the targeted protein, IGF1_mHSA_AnxV, accumulates to a greater extent and for a longer time in the infarcted and border zones of the heart than the nonbinding variant protein IGF1_mHSA_AnxVm1234. These data demonstrate the capability of IGF1_mHSA_AnxV, a prototypical targeted fusion protein, to specifically accumulate and persist in damaged heart tissue following myocardial infarction, enabling the specific delivery of fused activators domains.

Experimental myocardial infarction (MI) was induced in mice by ligation of the left coronary artery as explained below in detail. After 60 minutes, the ligation was removed, allowing reperfusion of the heart. Dosing of test articles or vehicle control was done at 22 hours post-MI by injection in the tail vein. 15 mice per group were dosed with the following:

Group 1: Vehicle-only control
Group 2: 15 µg IGF1_mHSA_AnxV
Group 3: 15 µg IGF1_mHSA_AnxVm1234

For each group, 5 mice were sacrificed at each of the following times: 12, 24, and 72 hours post-dosing. For each group/time point, 3 animals were prepared for immunohistochemistry and 2 for ELISA, with the goal of identifying anti-HSA signal specific to IGF1_mHSA_AnxV or IGF1_mHSA_AnxVm1234 in or bordering the infarcted area of the heart. Detailed protocols follow.

The animal work was performed by Biotrofix, Inc., in laboratory space leased at ViviSource Inc., Waltham MA. The protocol was reviewed and approved by the ViviSource IACUC, and all animal welfare concerns were addressed and documented. Ninety (90) male C57/B6 12-week-old mice were ordered 7-10 days prior to study (including 15 for pilot studies, Charles River Laboratories). They were allowed free access to food and water. Animals were assigned identification numbers using permanent marker on the tail. The animals were observed the day prior to study, and those appearing to be in poor health were excluded. Animals were housed in rooms provided with filtered air at 21±2° C. and 50%±20% relative humidity. The room was on an automatic timer for a light/dark cycle of 12 hours on and 12 hours off with no twilight. Shepherd's® ¼" premium corn cob was used for bedding and a Bio-Huts™ for Mice (BioServ K3352) or a mouse Runnel™ (BioServ K3322, K3323) was put in each cage. Animals were fed with Lab Diet® 5001 chow. Water was provided ad libitum. The animals were housed 4 to 6 per cage.

On the day of surgery, the mouse was weighed, and anesthesia was induced in a Plexiglas chamber with isoflurane in 100% O2. The mouse was placed on the surgery surface on a self-regulating heating pad. The mouse was secured in place on its dorsum (ventral side up), endotracheally intubated using an appropriate size intracath (22G), and maintained on isoflurane anesthesia at 1.0-2.5% in 100% O2. A surgical level of anesthesia was confirmed by loss of palpebral reflex along with lack of response to toe, heel, and tail pinch.

The thorax (from the lowest aspect of the dorsum to just across to the right side of the sternum) was shaved, fur was removed with vacuum, and the skin was prepped with septisol. A skin incision was made over the left thorax from the sternum to the mid-thorax region parallel with the ribs. The intercostal muscles between ribs 5 and 6 were opened over the left side of the heart and the ribs were retracted. The heart (left ventricle and left atrium) was identified, and the pericardium was opened. The left lung was gently compressed inferiorly to remove it from the field. A 7-0 silk suture was placed around the left coronary artery and ligated over a ~2 mm piece of sterile polyethylene PE-10 tubing, and the heart was observed for pallor (blanching, as evidence of ischemia) posterior to the ligation. The residual ends of the suture were cut, and the ligation was removed by cutting through the PE tubing and silk suture after 60 minutes of ischemia time. The wound was kept moist by covering the opening with a sterile warmed saline moistened gauze sponge. Once the suture was removed, the heart was observed for proper reperfusion of the ischemic area. The left lung was re-inflated using PEEP (positive end expiratory pressure), and the opposing ribs were closed with 6-0 non-absorbable monofilament nylon suture. The muscle layers were closed with 6-0 absorbable suture, followed by skin closure with the 6-0 silk suture in continuous fashion.

Buprenorphine (Bedford Labs™ Lot: 18655303) was injected for analgesia (0.05 mg/kg, subcutaneously), the isoflurane was shut off, and the mouse was extubated once spontaneous respiration occurred, and placed in a clean cage with supplemental heat for recovery. Following surgery, animals remained on a heating pad until they recovered from anesthesia. They were then returned to clean cages. They were observed frequently on the day of surgery (Day 0) and at least once daily thereafter. Animals were weighed before surgery on Day −1 and on Day 0 (day of surgery) and then daily until sacrifice.

10 µL aliquots of test articles at the appropriate concentrations (IGF1 Groups 1-3 defined above; vehicle, IGF1_mHSA_AnxV, or IGF1_mHSA_AnxVm1234 in endotoxin-free PBS) were stored at −80° C. until the day of use. Endotoxin-free PBS was stored at 4° C. Each test article aliquot was thawed right before injection. 200 µL of endotoxin-free PBS (room temperature) was added to the test articles and mixed by pipetting up and down several times and then, using a no-headspace syringe, 200 μL was injected into mice through the tail vein, at 22 (+/−1) hours after the MI.

At designated time points (12, 24, or 72 hours following dosing), the mice were euthanized as follows: The animals were placed under deep ketamine/xylazine anesthesia. For 3 animals per treatment group, the chest was opened and the heart was punctured at the apex. About 0.1 ml of 15% KCl was injected to the left ventricle, and the animal was perfusion-fixed by normal saline followed by zinc formalin. The heart was collected, stored in zinc formalin for 24-48 hours, then transferred to 70% Ethyl Alcohol, and stored at 4° C. The samples were then sent to Mass Histology Services for immunohistochemistry measurements.

Figures 28A, 28B:
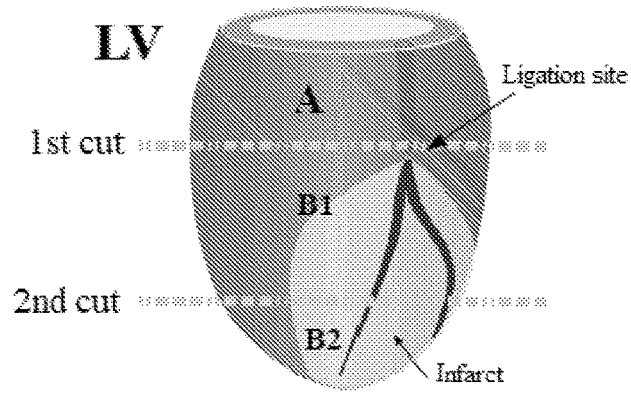
FIG. 28A shows a heart dissection used for preparation of 2 hearts per group for ELISA measurements.
FIG. 28B shows a cross section of section B1. Sections B1-infarct and B2 contain most or all of the infarct and nearby border region, while Sections A and B1-remote contain predominantly healthy tissue. LV: Left ventricle.

For 2 animals per treatment group, the animals were perfused with normal saline. The heart was isolated and the left ventricle was washed with saline. The heart was trimmed down to just the left and right ventricles, and dissected into four pieces as shown FIG. 28A. The pieces were collected, weighed, flash frozen (in liquid Nitrogen), then stored in labeled microcentrifuge tubes (one sample per tube, hence 4 samples per heart) at −80° C. and shipped to Silver Creek Pharmaceuticals on dry ice.

To obtain heart tissue for immunohistochemistry and ELISA control experiments, several additional mice were euthanized as above without surgery, the hearts were excised and rinsed as above, and in some, 2 μg of fusion protein IGF1_mHSA_AnxV in 15 μl was injected directly into the left ventricle wall. Hearts with or without injected protein were fixed as described above in preparation for immunohistochemistry.

Immunohistochemistry Detection of Fusion Proteins

Immunohistochemistry was performed at Mass Histology Service Inc., Worcester, MA, a GLP-compliant histopathology laboratory. Their standard protocols for processing and staining fixed tissues for detection of specific proteins were used. Briefly, the hearts fixed in zinc-formalin were dissected down to the ventricle and routinely processed through a standard series of alcohols and xylene. Each heart was embedded in paraffin, and sections were made on a Leica microtome at approximately 6 microns in thickness each and placed on microscope slides. For each heart, 8 serial transverse sections were made and placed on slides, 100 m was skipped, another 8 sections were made, 100 m was skipped, and this was repeated through the length of the heart.

Two slides from each set of 8 were stained, one with H&E to reveal morphology and the other stained with anti-HSA for HSA-localization, with DAPI counterstaining to show the nuclei of the cells. A traditional process was used for H&E staining. Specifically, the tissue was deparaffinized in xylene, cleared in alcohol, hydrated in water, and stained in Harris hematoxylin. The slide was washed, stained in 1% aqueous eosin, dehydrated in a series of alcohols, cleared in a series of xylenes, and coverslipped. Slides representing sections at various levels of the heart were then viewed with the light microscope to locate sections containing infarcted regions.

For HSA-localization in the heart tissue, sections adjacent to those stained for H&E were washed in xylene, cleared in alcohol, hydrated in water, incubated overnight at 4 C with goat anti-human albumin primary antibody diluted 1:200, and rinsed in PBS. Alexa Fluor 594 donkey anti-goat IgG, the fluorescently labeled antibody against goat anti-HSA antibody, was then used at a dilution of 1:400 for 1 hr at 37 C as the secondary antibody to detect the anti-HSA localization. The slides were rinsed in PBS, and coverslipped using ProLong Gold antifade reagent which also includes a DAPI stain for nuclear visualization.

For positive controls, slides from the hearts directly injected with IGF1_mHSA_AnxV were processed using the anti-HSA protocol as well. In addition, Mass Histology Services stained a sample of human liver tissue, which contains native HSA, as a positive control for the primary detection antibody. Negative controls included directly injected mouse heart that was processed for HSA-localization while leaving out the primary anti-HSA antibody, and a naïve heart (no fusion protein exposure) normally processed for HSA-localization.

ELISA Detection of Fusion Proteins

The four samples per heart (FIG. 28A) were prepared for ELISA as follows. Samples were transferred to Eppendorf safe-lock microcentrifuge tubes and were thawed on ice. To each tube, RIPA buffer including Pierce Halt Protease Inhibitor Cocktail (diluted 100-fold into buffer) in a 1:5 ratio of (mg tissue sample): (uL buffer) was added. At least 100 μL buffer was used for each sample. A 50/50 mix of ZROB05 and ZROB10 beads in a 1:2 ratio of beads:buffer were also added. Tubes were placed in a Bullet Blender tissue homogenizer set to speed 9 and homogenized for 3 minutes; this was repeated if homogenization was not complete. The samples were centrifuged and aliquots were taken to perform the BCA (bicinchoninic acid) protein assay to determine total protein in each sample.

Enzyme-Linked Immunosorbent Assay (ELISA) measurements were done using standard methods. Specifically, on day 1, Reacti-Bind plates were coated overnight, 4° C. with 50 μL/well anti-HSA coating antibody diluted 1:50 in Dulbecco's PBS. On day 2, wells were washed 4× with PBS-T (PBS, 0.05% Tween 20) using a plate washer (program 6). Nonspecific binding was blocked with 200 uL/well protein-free blocking buffer for 2 hr at room temperature and wells were washed 4× with PBS-T (PBS, 0.05% Tween 20) using a plate washer. 50 uL/well (96 well plate) of either standard curve sample or test samples were added to the wells. Test samples were diluted in RIPA buffer (+protease inhibitors) to a final total protein concentration of 8.745 mg/mL. Plates were sealed and incubated overnight at 4° C. On day 3, wells were washed 4× with PBS-T using a plate washer and 100 uL/well goat anti-HSA-HRP detection antibody diluted 1:25,000 in PBS-T was added per well and incubated 30 min at room temperature on a shaker platform at 220 rpm, protected from light. Wells were washed 4× with PBS-T using a plate washer. 100 μL per well of 1-step Ultra TMB ELISA reagent at room temperature was added and plates were incubated at room temperature protected from light for 25 minutes. The reaction was stopped with addition of 100 uL KLP TMB stop reagent. Color changes from blue to yellow. After 5 minutes, absorbance readings were made on a plate reader at a wavelength of A450. Background values for absorbance from tissue with no fusion protein exposure were obtained from naïve heart samples produced using the same procedures as above. The background value was subtracted from all test sample absorbance values to obtain the difference. A standard curve for the concentration-absorbance relationship was generated from samples spiked with a range of known amounts of fusion protein. Then the concentration of protein in each test sample was determined by comparison to the standard concentration-absorbance curve. Two aliquots from each heart test sample were measured to assess measurement variability and these are the basis of the standard deviations included in the ELISA data (FIG. 29).

Fusion proteins used include IGF1_mHSA_AnxV (targeted protein) and IGF1_mHSA_AnxVm1234 (nonbinding variant), produced as described in Example 5. Vehicle control was endotoxin-free PBS (Sigma). Animals were male C57/B6 mice, 12-week-old when ordered, acclimatized 7-10 days before surgery. Stains and antibodies used in immunohistochemistry: primary antibody was goat anti-human albumin (HSA) cross-adsorbed antibody, affinity purified (Bethyl Labs 080-229A lot #3); fluorescently labeled secondary antibody was Alexa Fluor 594 donkey anti-goat IgG (H+L) (Invitrogen, A11058); ProLong Gold antifade reagent with DAPI (Invitrogen, P36931). Reagents used for ELISA included RIPA Lysis and Extraction Buffer (Pierce, 89901); Pierce Halt Protease Inhibitor Cocktail, EDTA-free (Pierce, 78425); Pierce BCA assay kit, 23227; Reacti-Bind plates (Pierce, 15041); Dulbecco's PBS (Thermo, 28374); protein-free blocking buffer (Pierce, 37572); anti-HSA coating antibody (Bethyl labs antibody A80-229A); goat anti-HSA-HRP detection antibody (Bethyl Labs, A80-229P); 1-step Ultra TMB ELISA reagent (Thermo (Pierce), 34028); KLP TMB stop reagent (KLP, 50-85-05); protein-free blocking buffer (Pierce, 37572); tissue homogenization beads (Next Advance, ZROB05 and ZROB10). Materials used in animal surgery included Buprenorphine (Bedford Labs™ Lot: 18655303), isoflurane, ketamine, xylazine, zinc formalin, and 15% KCl.

Figure 29:
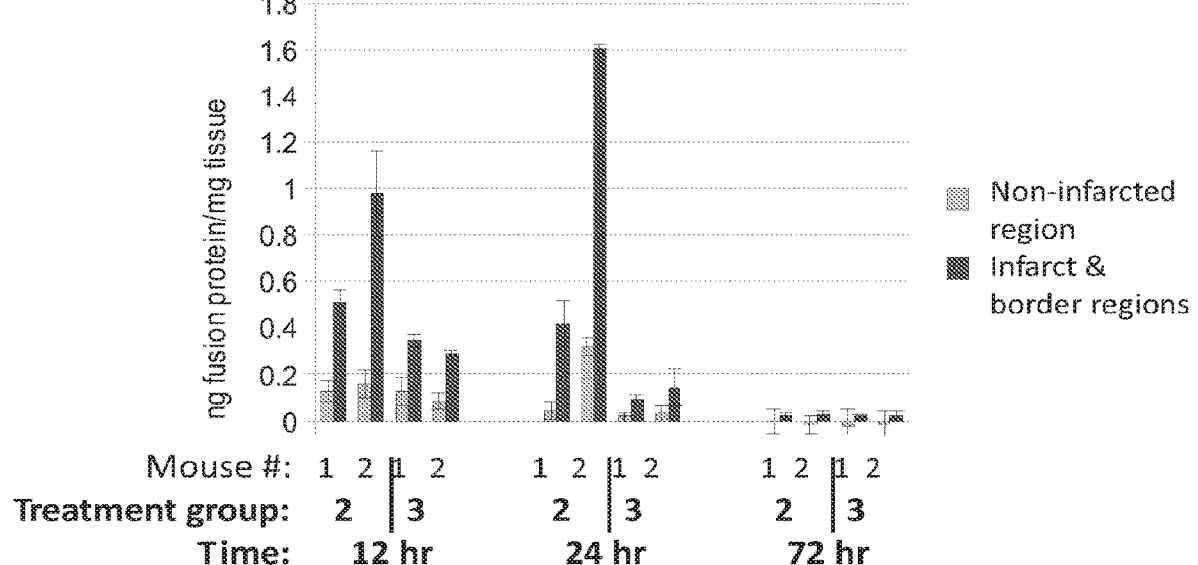
FIG. 29 is a graph showing measurement of IGF1_mHSA_AnxV and nonbinding IGF1_mHSA_AnxVm1234 fusion proteins in heart at three times after dosing. Black bars represent the concentration of protein found in the infarcted plus border regions and gray bars represent the concentration of protein found in the noninfarcted regions. Two mice per group are shown. Group 2 corresponds to the mice dosed with targeting protein IGF1_mHSA_AnxV, Group 3 corresponds to the mice dosed with nonbinding variant IGF1_mHSA_AnxVm1234.
Figures 32A, 32B, 32C, 32D:
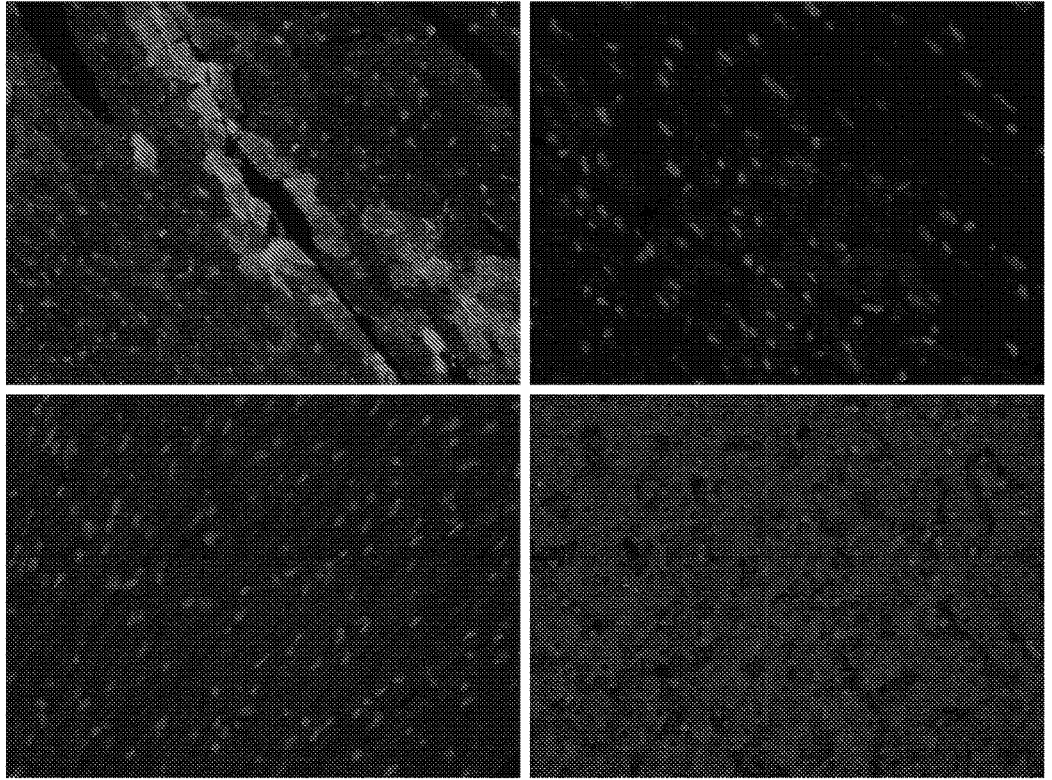
FIGS. 32A-32D are photomicrographs of controls used to demonstrate specificity of staining of HSA-containing protein or HSA-producing tissue by the primary anti-HSA antibody used in mouse experiments.

Detection of targeted and nonbinding variant fusion proteins by ELISA are summarized in FIG. 29. Protein measured in the infarct+border zone was compared to protein in the non-infarcted region of the heart in two mice for each of the targeted (Group 2) and nonbinding variant (Group 3) fusion proteins at three times after dosing (12, 24, and 72 hours). For each heart, the protein measured in samples A and B1-remote (as defined in FIG. 28A) were added, and represent the protein in the non-infarcted regions of the heart. Likewise, the protein measured in samples B1-infarct and B2 were added, and represent the protein in the infarcted region plus surrounding border region of the heart.

As shown in FIG. 29, IGF1_mHSA_AnxV, the targeted fusion protein (Group 2, black bars), was highly elevated in the infarct region at both 12- and 24-hours post-injection, compared to its level in the remote regions of heart (Group 2, gray bars) in the same animals. It is undetectable in both infarcted and noninfarcted regions by 72 hours. In comparison, nonbinding variant protein IGF1_mHSA_AnxVm1234 (Group 3, black bars) were somewhat elevated at 12 hours, decreasing by 24 hours and undetectable at 72 hours. Comparing the targeted to nonbinding protein, at both 12 and 24 hours, the targeted IGF1_mHSA_AnxV was more elevated in the infarct+border zone (black bars, Group 2) than is nonbinding IGF1_mHSA_AnxVm1234 (black bars, Group 3). These results demonstrate that the fusion protein IGF1_mHSA_AnxV, which is targeted to the damaged cardiomyocytes (by actively binding phosphatidylserine associated with apoptotic or necrotic cardiomyocytes), can enter and be retained in the areas of the heart damaged by the experimental MI at higher concentrations and for longer times than the nonbinding variant. In addition, the data showed specific localization of the targeted fusion protein to the damaged areas of the heart, demonstrating efficacy of targeting via the AnxV targeting domain.

Localization of HSA-containing fusion proteins by immunohistochemistry also demonstrated greater accumulation of IGF1_mHSA_AnxV in the infarct and bordering region compared to the nonbinding variant IGF1_mHSA_AnxVm1234 at 24 hours after dosing. FIGS. 30A-30C shows morphology of the infarct and surrounding tissue, as well as positive staining specific for IGF1_mHSA_AnxV at the infarct edge and border region around the infarct. Top left (FIG. 30A): H&E stain showing morphology. The infarcted region is central, with the edge demarcated by the black curve, and viable is in the upper left and lower right. (200× magnification) Top right (FIG. 30B): A serial section of this region stained for HSA-containing proteins at the same magnification. Red indicates HSA localization; blue indicates DAPI staining of cell nuclei. Higher magnification images of the same region are shown in the lower left (400×, FIG. 30C) and lower right (600×, FIG. 30D). There is positive signal in cardiomyocytes (thin arrows) at the edge of infarcted tissue (medium thickness arrows). White boxes in Top left and right are in approximately in the same place in two adjacent 6 um slides, and the Lower left and right images are magnifications near the area of those boxes.

By comparison, FIGS. 31A-31D shows the same information for the nonbinding mutant IGF1_mHSA_AnxVm1234 showing minimal staining specific for it. Top left (FIG. 31A): H&E stain showing morphology. The infarcted region is in the upper central part of the image, with the edge demarcated by the black curve (200× magnification). Top right (FIG. 31B): An adjacent section of this region stained for HSA-containing proteins at the same magnification. Red indicates anti-HSA localization; blue indicates DAPI staining of cell nuclei. Higher magnification images of the same region are shown in the lower left (400×, FIG. 31C) and lower right (600×, FIG. 31D). There is only background signal in cardiomyocytes (thin arrow) and red blood cells (thick arrow) at the edge of infarcted tissue (medium thickness arrows). White boxes in Top left and right are in approximately in the same place in two adjacent 6 um slides, and the Lower left and right images are magnifications near the area of those boxes.

FIG. 32A-32D illustrates the controls used to confirm specificity of the anti-HSA antibody for the HSA-containing fusion proteins. Top left (FIG. 32A): Positive control in a mouse heart in which IF1_mHSA_AnxV had been directly injected as described. Dark red indicates strong localization of HSA-containing fusion protein where it was injected. Top right (FIG. 32B): Negative control in mouse heart. Same preparation as in Top left including injection of IGF1_mHSA_AnxV but staining proceeded without the primary anti-HSA antibody. No specific staining seen. Bottom left (FIG. 32C): Second negative control in mouse heart. No protein was injected in the heart, and it was processed as in the top left. Only faint red background staining can be seen. Bottom right (FIG. 32D): Positive control in human liver. Human liver produces significant amounts of HSA. Staining with the anti-HSA antibody shows specific staining throughout the sample. In all images: Blue staining is DAPI stain indicating cell nuclei.

It is understood that the examples and embodiments described herein are for illustrative purposes only and that various modifications of changes in light thereof are to be included within the spirit and purview of this application and scope of the appended claims. All publication, patents and patent applications cited herein are hereby incorporated by reference in their entirety for all purposes.

The invention claimed is:

1. A method for accumulating an IGF-1 fusion protein in cardiac tissue of a subject having myocardial infarction, the method comprising:

administering an effective amount of the IGF-1 fusion protein to the subject having myocardial infarction, wherein the IGF-1 fusion protein comprises:

(i) a human IGF-1 having at least 98.5% identity with SEQ ID NO: 3;

(ii) a variant of human serum albumin having at least 95% identity with SEQ ID NO: 12, and comprising substitution of the cysteine residue corresponding to C34 to serine or alanine, and/or sub-
stitution of the asparagine residue corresponding
to N503 to glutamine of SEQ ID NO: 12; and (iii) optionally a connector polypeptide, wherein the administering of the effective amount of
the IGF-1 fusion protein to the subject results in
accumulation of the IGF-1 fusion protein in the
cardiac tissue, and wherein the administering of the effective amount of
the IGF-1 fusion protein to the subject results in
reduction of the severity of the myocardial infarc-
tion.

2. The method of claim 1, wherein the IGF-1 is at the
amino terminus of the fusion protein.

3. The method of claim 1, wherein the connector poly-
peptide is from 2 amino acids to 20 amino acids long.

4. The method of claim 1, wherein the connector poly-
peptide is a flexible or a structured polypeptide.

5. A method for accumulating an IGF-1 fusion protein in
cardiac tissue of a subject having myocardial infarction, the
method comprising:

administering an effective amount of the IGF-1 fusion
protein to the subject having myocardial infarction, wherein the IGF-1 fusion protein comprises:

(i) a human IGF-1 having at least 98.5% identity
with SEQ ID NO: 3;

(ii) a fragment of a human serum albumin compris-
ing least at least 95% identity with Domain I
comprising the amino acid sequence of SEQ ID
NO: 27, Domain II comprising the amino acid
sequence of SEQ ID NO: 25 or Domain III having
the amino acid sequence of SEQ ID NO: 28; and (iii) optionally a connector polypeptide, wherein the administering of the effective amount of
the IGF-1 fusion protein to the subject results in
accumulation of the fusion protein in the cardiac
tissue, and wherein the administering of the effective amount of
the IGF-1 fusion protein to the subject results in
reduction of the severity of the myocardial infarc-
tion.

6. The method of claim 5 wherein the fragment of human
serum albumin comprises the amino acid sequence of SEQ
ID NO: 24 or the amino acid sequence of SEQ ID NO: 26.

* * * * *